US011046669B2

(12) United States Patent
Harrison et al.

(10) Patent No.: US 11,046,669 B2
(45) Date of Patent: Jun. 29, 2021

(54) INHIBITORS OF (α-V)(β-6) INTEGRIN

(71) Applicant: Morphic Therapeutic, Inc., Waltham, MA (US)

(72) Inventors: Bryce A. Harrison, Framingham, MA (US); Matthew G. Bursavich, Needham, MA (US); Mark Brewer, Wallingford (GB); Aleksey I. Gerasyuto, Flemington, NJ (US); Kristopher N. Hahn, Medford, MA (US); Kyle D. Konze, Brooklyn, NY (US); Fu-Yang Lin, Sudbury, MA (US); Blaise S. Lippa, Newton, MA (US); Alexey A. Lugovskoy, Belmont, MA (US); Bruce N. Rogers, Belmont, MA (US); Mats A. Svensson, New York, NY (US); Dawn M. Troast, Bedford, MA (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

(21) Appl. No.: 16/453,418

(22) Filed: Jun. 26, 2019

(65) Prior Publication Data

US 2020/0157075 A1 May 21, 2020

Related U.S. Application Data

(63) Continuation of application No. 15/906,745, filed on Feb. 27, 2018, now abandoned.

(60) Provisional application No. 62/464,693, filed on Feb. 28, 2017.

(51) Int. Cl.
| | |
|---|---|
| *C07D 471/04* | (2006.01) |
| *C07D 401/12* | (2006.01) |
| *C07D 519/00* | (2006.01) |
| *C07D 471/08* | (2006.01) |
| *C07D 487/08* | (2006.01) |

(52) U.S. Cl.
CPC ......... *C07D 401/12* (2013.01); *C07D 471/04* (2013.01); *C07D 471/08* (2013.01); *C07D 487/08* (2013.01); *C07D 519/00* (2013.01)

(58) Field of Classification Search
CPC .. C07D 401/12; C07D 471/12; C07D 519/00; A61K 31/4375; A61P 35/00
USPC .......................................... 546/122; 514/300
See application file for complete search history.

(56) References Cited

U.S. PATENT DOCUMENTS

| | | | |
|---|---|---|---|
| 5,952,341 A | 9/1999 | Duggan et al. | |
| 6,017,926 A | 1/2000 | Askew et al. | |
| 6,048,861 A | 4/2000 | Askew et al. | |
| 6,069,143 A | 5/2000 | Ali et al. | |
| 6,232,308 B1 | 5/2001 | Askew | |
| 6,358,970 B1 * | 3/2002 | Duggan ................ A61P 19/10 |
| | | | 514/300 |
| 6,723,711 B2 | 4/2004 | Biediger et al. | |
| 8,716,226 B2 | 5/2014 | Ruminski et al. | |
| 9,572,801 B2 | 2/2017 | Askew et al. | |
| 2001/0034445 A1 | 10/2001 | Ali et al. | |
| 2002/0010176 A1 | 1/2002 | Askew et al. | |
| 2002/0035127 A1 | 3/2002 | Head et al. | |
| 2004/0043988 A1 | 3/2004 | Khanna et al. | |
| 2008/0045521 A1 | 2/2008 | Arnould et al. | |
| 2009/0104116 A1 | 4/2009 | Zischinsky et al. | |
| 2012/0289481 A1 | 11/2012 | O'Neil et al. | |
| 2014/0038910 A1 | 2/2014 | Ruminski et al. | |
| 2014/0051715 A1 | 2/2014 | Ruminski et al. | |
| 2014/0349968 A1 | 11/2014 | O'Neil et al. | |
| 2016/0280705 A1 | 9/2016 | Anderson et al. | |
| 2017/0290817 A1 | 10/2017 | Anderson et al. | |
| 2017/0369490 A1 | 12/2017 | Askew et al. | |
| 2018/0008583 A1 | 1/2018 | Fukunaga et al. | |
| 2018/0093984 A1 | 4/2018 | Jiang et al. | |
| 2018/0244648 A1 | 8/2018 | Harrison et al. | |
| 2019/0248832 A1 | 8/2019 | Almeida et al. | |
| 2019/0276449 A1 | 9/2019 | Cha et al. | |
| 2020/0002334 A1 | 1/2020 | Harrison et al. | |
| 2020/0071322 A1 | 3/2020 | Harrison et al. | |
| 2020/0087299 A1 | 3/2020 | Brewer et al. | |
| 2020/0109141 A1 | 4/2020 | Cha et al. | |
| 2020/0157075 A1 | 5/2020 | Harrison et al. | |
| 2020/0354359 A1 | 11/2020 | Harrison et al. | |
| 2020/0385384 A1 | 12/2020 | Harrison et al. | |

FOREIGN PATENT DOCUMENTS

| | | |
|---|---|---|
| EP | 0537696 A1 | 4/1993 |
| EP | 0623615 A1 | 11/1994 |
| EP | 0796855 A1 | 9/1997 |
| EP | 2221308 A1 | 8/2010 |
| WO | WO-1993/10091 A2 | 5/1993 |
| WO | WO-93/14077 A1 | 7/1993 |
| WO | WO-97/24122 A1 | 7/1997 |
| WO | WO-97/24124 A1 | 7/1997 |
| WO | WO-97/25323 A1 | 7/1997 |
| WO | WO-9726250 A1 | 7/1997 |
| WO | WO-97/36871 A1 | 10/1997 |

(Continued)

OTHER PUBLICATIONS

Bennet et al., "Cecil Textbook of Medicine," 20th Edition, 1:1004-1010 (1996).

(Continued)

*Primary Examiner* — Charanjit Aulakh

(74) *Attorney, Agent, or Firm* — Foley Hoag LLP; Dana M. Gordon; Lawrence P. Tardibono

(57) ABSTRACT

Disclosed are small molecule inhibitors of αvβ6 integrin, and methods of using them to treat a number of diseases and conditions.

35 Claims, 2 Drawing Sheets

(56) References Cited

FOREIGN PATENT DOCUMENTS

| WO | WO-98/08840 A1 | 3/1998 |
|---|---|---|
| WO | WO-98/46220 A1 | 10/1998 |
| WO | WO-1998/044797 A1 | 10/1998 |
| WO | WO-1999/026945 A1 | 6/1999 |
| WO | WO-1999/030713 A1 | 6/1999 |
| WO | WO-1999/031061 A1 | 6/1999 |
| WO | WO-1999/031099 A1 | 6/1999 |
| WO | WO-2000/006169 A1 | 2/2000 |
| WO | WO-2000/031067 A1 | 6/2000 |
| WO | WO-2000/037487 A1 | 6/2000 |
| WO | WO-2000/072801 A2 | 12/2000 |
| WO | WO-2000/073260 A1 | 12/2000 |
| WO | WO-2000/78317 A1 | 12/2000 |
| WO | WO-2001/005810 A2 | 1/2001 |
| WO | WO-2001/023357 A2 | 4/2001 |
| WO | WO-2001/044194 A2 | 6/2001 |
| WO | WO-2001/053262 A1 | 7/2001 |
| WO | WO-2001/053297 A1 | 7/2001 |
| WO | WO-2001/096334 A2 | 12/2001 |
| WO | WO-2002/16328 A1 | 2/2002 |
| WO | WO-2002/022124 A1 | 3/2002 |
| WO | WO-2002/022615 A1 | 3/2002 |
| WO | WO-2002/022616 A2 | 3/2002 |
| WO | WO-02/060438 A1 | 8/2002 |
| WO | WO-2002/074730 A1 | 9/2002 |
| WO | WO-2002/090325 A2 | 11/2002 |
| WO | WO-2003/066594 A2 | 8/2003 |
| WO | WO-2004/020435 A1 | 3/2004 |
| WO | WO-2006/024699 A1 | 3/2006 |
| WO | WO-2008/157162 A1 | 12/2008 |
| WO | WO-2014/015054 A1 | 1/2014 |
| WO | WO-2014/154725 A1 | 10/2014 |
| WO | WO-2014/154809 A1 | 10/2014 |
| WO | WO-2015/103643 A2 | 7/2015 |
| WO | WO-2015/150557 A1 | 10/2015 |
| WO | WO-2015/179823 A2 | 11/2015 |
| WO | WO-2016/022851 A1 | 2/2016 |
| WO | WO-2016/046225 A1 | 3/2016 |
| WO | WO-2016/046226 A1 | 3/2016 |
| WO | WO-2016/046230 A1 | 3/2016 |
| WO | WO-2016/046241 A1 | 3/2016 |
| WO | WO-2016/176532 A1 | 11/2016 |
| WO | WO-2017/117538 A1 | 7/2017 |
| WO | WO-2017/158072 A1 | 9/2017 |
| WO | WO-2017/162570 A1 | 9/2017 |
| WO | WO-2017/162572 A1 | 9/2017 |
| WO | WO-2018/009501 A1 | 1/2018 |
| WO | WO-2018/049068 A1 | 3/2018 |
| WO | WO-2018/085552 A1 | 5/2018 |
| WO | WO-2018/085578 A1 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/119087 A1 | 6/2018 |
| WO | WO-2018/132268 A1 | 7/2018 |
| WO | WO-2018/160521 A2 | 9/2018 |
| WO | WO-2018/160522 A1 | 9/2018 |
| WO | WO-2019/173653 A1 | 9/2019 |
| WO | WO-2020/006315 A1 | 1/2020 |
| WO | WO-2020/009889 A1 | 1/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/076862 A1 | 4/2020 |
| WO | WO-2020/081154 A1 | 4/2020 |
| WO | WO-2020/047207 A8 | 12/2020 |

OTHER PUBLICATIONS

Dermeret et al., "Another Anniversary for the War on Cancer," Bio/Technology, 12:320 (1994).

Freshney et al., "Culture of Animal Cells, a Manual of Basic Technique," 4, (1983).
International Search Report and Written Opinion for International Application No. PCT/US/18/19838 dated Aug. 8, 2018.
International Search Report and Written Opinion for International Application No. PCT/US18/19839 dated Aug. 9, 2018.
Raab-Westphal et al., "Integrins as Therapeutic Targets: Successes and Cancers," Cancers, 9(110):1-28 (2017).
Database Accession No. 1380858-49-0., Database Registry [Online] Chemical Abstracts Service: XP002799454 (2012).
Database Accession No. 1380909-02-3., Database Registry [Online] Chemical Abstracts Service: XP002799455 (2012).
Database Accession No. 1380948-25-3., Database Registry [Online] Chemical Abstracts Service: XP002799456 (2012).
Database Accession No. 1380999-27-8., Database Registry [Online] Chemical Abstracts Service: XP002799457 (2012).
Database Accession No. 1571616-43-7., Database Registry [Online] Chemical Abstracts Service: XP002799458 (2014).
Database Accession No. 1623225-85-3., Database Registry [Online] Chemical Abstracts Service: XP002799459 (2014).
Database Accession No. 1837357-51-3., Database Registry [Online] Chemical Abstracts Service: XP002799460 2015).
Database Accession No. 1838839-35-2., Database Registry [Online] Chemical Abstracts Service: XP002799461 2015).
Database Accession No. 1940788-29-3., Database Registry [Online] Chemical Abstracts Service: XP002799462 (2016).
Database Accession No. 2038980-05-9., Database Registry [Online] Chemical Abstracts Service: XP002799463 (2016).
Extended European Search Report for EP Application No. 18761396.3 dated Jul. 2, 2020.
Extended European Search Report for EP Application No. EP 18760393.1 dated Jul. 14, 2020.
Extended European Search Report for EP Application No. EP 19194490 dated Dec. 10, 2019.
International Search Report and Written Opinion for International Application No. PCT/US2019/048734 dated Mar. 20, 2020.
International Search Report and Written Opinion for International Application No. PCT/US2019/048737 dated Dec. 27, 2019.
International Search Report and Written Opinion for International Application No. PCT/US2019/048738 dated Jan. 7, 2020.
International Search Report and Written Opinion for International Application No. PCT/US2019/048782 dated Dec. 27, 2019.
International Search Report for International Application No. PCT/US2019/055252 dated Jan. 23, 2020.
Invitation to Pay Additional Fees for International Application No. PCT/US2019/048737 dated Oct. 11, 2019.
Invitation to Pay Additional Fees for International Application No. PCT/US2019/048738 dated Oct. 11, 2019.
Invitation to Pay Additional Fees for International Application No. PCT/US2019/048782 dated Oct. 11, 2019.
Meissner et al., "Nonpeptide avß3 antagonists. Part 2: constrained glycyl amides derived from the RGD tripeptide," Bioorganic & Medicinal Chemistry Letters, 12(1): 25-29 (2002).
Written Opinion for International Application No. PCT/US2017/067622 dated Mar. 8, 2018.
Written Opinion for International Application No. PCT/US2019/021243 dated Jul. 5, 2019.
Written Opinion for International Application No. PCT/US2019/039624 dated Sep. 13, 2019.
Written Opinion for International Application No. PCT/US2019/055252 dated Jan. 23, 2020.
Anderson et al., "The discovery of an orally bioavailable pan-#v integrin inhibitor for idiopathic pulmonary fibrosis," J. Med. Chem. Just Accepted Manuscript, (2019).
Brashear et al., "Non-Peptide $\alpha_v\beta_3$ Antagonists. Part 5: Identification of Potent RGD Mimetics Incorporating 2-Aryl β-Amino Acids as Aspartic Acid Replacements," Bioorganic & Medicinal Chemistry Letters 12: 3483-3486 (2002).
Breslin et al., "Nonpeptide $\alpha_v\beta_3$ antagonists. Part 10: In vitro and in vivo evaluation of a potent 7-methyl substituted tetrahydro-[1,8]naphthyridine derivative," Bioorganic & Medicinal Chemistry Letters, 14: 4515-4518 (2004).

(56) References Cited

OTHER PUBLICATIONS

Coleman et al., "Nonpeptide $\alpha_v\beta_3$ Antagonists. Part 11: Discovery and Preclinical Evaluation of Potent $\alpha_v\beta_3$ Antagonists for the Prevention and Treatment of Osteoporosis," J. Med. Chem. 47: 4829-4837 (2004).
Cui et al., "In Vitro and in Vivo Metabolism of a Potent and Selective Integrin $\alpha_v\beta_3$ Antagonist in Rats, Dogs, and Monkeys," Drug Metabolism and Disposition, 32(8): 848-861 (2004).
Duggan et al., "Nonpeptide $\alpha_v\beta_3$ Antagonists. 1. Transformation of a Potent, Integrin-Selective $\alpha_{IIb}\beta_3$ Antagonist into a Potent $\alpha_v\beta_3$ Antagonist," J. Med. Chem. 43: 3736-3745 (2000).
Goodman et al., "Nanomolar Small Molecule Inhibitors for $\alpha_v\beta_6$, $\alpha_v\beta_5$, and $\alpha v\beta 3$ Integrins," J. Med. Chem. 45: 1045-1051 (2002).
Hall et al., "Characterisation of a novel, high affinity and selective $\alpha_v\beta_6$ integrin RGD—mimetic radioligand," Biochemical Pharmacology, 117(1): 88-96 (2016).
Hatley et al., "An αV-RGD integrin inhibitor toolbox: drug discovery insight, challenges and opportunities," Angew. Chem., 57(13): 3298-3321 (2017).
Hutchinson et al., "Nonpeptide $\alpha 6 2_3$ Antagonists. 8. In Vitro and in Vivo Evaluation of a Potent $\alpha_v\beta_3$ Antagonist for the Prevention and Treatment of Osteoporosis," J. Med. Chem. 46: 4790-4798 (2003).
International Preliminary Report on Patentability for International Application No. PCT/EP00/06188 dated May 31, 2001.
International Preliminary Report on Patentability for International Application No. PCT/EP02/01836 dated Oct. 14, 2002.
International Preliminary Report on Patentability for International Application No. PCT/EP2003/000327 dated Dec. 3, 2003.
International Preliminary Report on Patentability for International Application No. PCT/EP2014/056167 dated Sep. 29, 2015.
International Preliminary Report on Patentability for International Application No. PCT/EP99/09842 dated Jan. 12, 2001.
International Preliminary Report on Patentability for International Application No. PCT/FI2005/050305 dated Feb. 28, 2007.
International Preliminary Report on Patentability for International Application No. PCT/GB00/02020 dated Sep. 19, 2001.
International Preliminary Report on Patentability for International Application No. PCT/GB00/04831 dated Oct. 1, 2002.
International Preliminary Report on Patentability for International Application No. PCT/US00/14901 dated Mar. 28, 2001.
International Preliminary Report on Patentability for International Application No. PCT/US00/16849 dated Jun. 29, 2001.
International Preliminary Report on Patentability for International Application No. PCT/US00/26537 dated Jan. 1, 2002.
International Preliminary Report on Patentability for International Application No. PCT/US01/01298 dated Oct. 8, 2001.
International Preliminary Report on Patentability for International Application No. PCT/US01/01953 dated Sep. 8, 2001.
International Preliminary Report on Patentability for International Application No. PCT/US01/28238 dated Jul. 31, 2002.
International Preliminary Report on Patentability for International Application No. PCT/US01/28404 dated Apr. 25, 2002.
International Preliminary Report on Patentability for International Application No. PCT/US01/42146 dated Sep. 5, 2002.
International Preliminary Report on Patentability for International Application No. PCT/US02/13457 dated Jul. 22, 2003.
Kinney el al., "Suzuki-Miyaura Approach to JNJ-26076713, an Orally Active Tetrahydroquinoline-Containing $\alpha_v\beta_3/\alpha_v\beta_5$ Integrin Antagonist. Enantioselective Synthesis and Stereochemical Studies," J. Org. Chem., 73: 2302-2310 (2008).

Macdonald et al., "Passing on the medicinal chemistry baton: training undergraduates to be industry-ready through research projects between the University of Nottingham and GlaxoSmithKline," Drug Discovery Today, 21(6): 880-887 (2016).
Peng et al., "Integrin $\alpha_v\beta_6$ Critically Regulates Hepatic Progenitor Cell Function and Promotes Ductular Reaction, Fibrosis, and Tumorigenesis," Hepatology 63(1): 217-232 (2016).
Perkins et al., "Non-peptide $\alpha_v\beta_3$ Antagonists: Identification of Potent, Chain-Shortened RGD Mimetics that Incorporate a Central Pyrrolidinone Constraint," Bioorganic & Medicinal Chemistry Letters 13: 4285-4288 (2003).
Procopiou et al., "Discovery of (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic Acid, a Nonpeptidic $\alpha_v\beta_6$ Integrin Inhibitor for the Inhaled Treatment of Idiopathic Pulmonary Fibrosis," Journal of Medicinal Chemistry, 61(18): 8417-8443 (2018).
Prueksaritanont et al., "Disposition of a novel and potent $\alpha_v\beta_3$ antagonist in animals, and extrapolation to man," Xenobiotica 34(1):103-115 (2004).
Prueksaritanont et al., "Renal elimination of a novel and potent $\alpha_v\beta_3$ integrin antagonist in animals," Xenobiotica 34(11/12):1059-1074 (2004).
Rosenthal et al., "Evaluation of the safety, pharmacokinetics and treatment effects of an $\alpha_v\beta_3$ integrin inhibitor on bone turnover and disease activity in men with hormone-refractory prostate cancer and bone metastases," Journal of Clinical Oncology 6: 42-48 (2010).
Rosenthal et al., "Evaluation of the safety, pharmacokinetics and treatment effects of an $\alpha_v\beta_3$ integrin inhibitor on bone turnover and disease activity in men with hormone-refractory prostate cancer and bone metastases," Asia-Pac J Clin Oncol 6:42-48 (2010).
Rubtsov et al., "RGD-based Therapy: Principles of Selectivity," Current Pharmaceutical Design, 22: 925-932 (2016).
Santulli et al., "Studies with an Orally Bioavailable $\alpha_v$ Integrin Antagonist in Animal Models of Ocular Vasculopathy: Retinal Neovascularization in Mice and Retinal Vascular Permeability in Diabetic Rats," Journal of Pharmacology and Experimental Therapeutics, 324(3): 894-901 (2008).
Tipping et al., Relative Binding Affinities of Integrin Antagonists by Equilibrium Dialysis and Liquid Chromatography—Mass Spectrometry, Medicinal Chemistry Letters, 6(2): 221-224 (2015).
Wang et al., "Non-peptide $\alpha_v\beta_3$ antagonists. Part 7: 3-Substituted tetrahydro-[1,8]naphthyridine derivatives," Bioorganic & Medicinal Chemistry Letters, 14: 1049-1052 (2004).
Whilding et al., "The integrin $\alpha_v\beta_6$: a novel target for CAR T-cell immunotherapy?," Biochem. Soc. Trans., 44: 349-355 (2016).
Whitman et al., "Nonpeptide αvβ3 antagonists. Part 9: Improved pharmacokinetic profile through the use of an aliphatic, des-amide backbone," Bioorganic & Medicinal Chemistry Letters, 14: 4411-4415 (2004).
Zhou et al., "An integrin antagonist (MK-0429) decreases proteinuria and renal fibrosis in the ZSF1 rat diabetic nephropathy model," Pharmacology Research & Perspectives, 5(5): 1-14 (2017).
Database Registry, Chemical Abstracts Services, CAS Registry No. 1155165-04-0 (Entered STN: Oct. 6, 2009).
Extended European Search Report for EP Application No. 20190341.6 dated Sep. 28, 2020.
Pickarski et al., "Orally active avß3 integrin inhibitor MK-0429 reduces melanoma metastasis," Oncology Reports, 33: 2737-2745 (2015).
Search Report and Written Opinion for Singaporean Application No. 11201907820S dated Nov. 3, 2020.

\* cited by examiner

Figure 1

| Compound | αvβ6 IC$_{50}$ | Compound | αvβ6 IC$_{50}$ | Compound | αvβ6 IC$_{50}$ |
|---|---|---|---|---|---|
| 3 | A | 43 | B | 72 | C |
| 4 | B | 44-E1 | C | 73 | C |
| 5 | B | 44-E2 | C | 74 | C |
| 6 | C | 45-E1 | B | 75 | C |
| 7-E2 | C | 45-E2 | C | 77 | B |
| 8-E1 | B | 46-E1 | C | 78 | B |
| 9 | C | 46-E2 | C | 79 | C |
| 10-E1 | B | 47 | C | 80 | C |
| 10-E2 | C | 48-E1 | B | 82 | C |
| 11-E1 | A | 50-E1 | C | 83 | C |
| 11-E2 | C | 50-E2 | C | 85 | C |
| 12-E1 | B | 51-E1 | C | 86 | C |
| 12-E2 | C | 51-E2 | C | 88 | C |
| 13-E1 | B | 52 | B | 90 | C |
| 13-E2 | A | 53-E2 | C | 91 | B |
| 14 | A | 54-E1 | B | 92 | C |
| 15 | A | 54-E2 | B | 93 | C |
| 16 | B | 55-E1 | C | 94 | B |
| 17 | B | 56-E1 | C | 95 | B |
| 18 | B | 56-E2 | B | 97 | C |
| 19 | B | 57 | C | 99 | C |
| 20 | B | 60 | C | 101 | C |
| 21 | B | 61 | B | 102 | B |
| 22 | A | 62-E1 | B | 103 | C |
| 23-E1 | C | 62-E2 | B | 107 | C |
| 23-E2 | C | 63 | C | 110 | C |
| 24-E1 | B | 64 | C | 111 | B |
| 24-E2 | B | 65 | B | 112 | B |
| 25 | A | 66 | C | 113 | B |
| 26 | C | 67 | B | 118 | C |
| 27 | B | 68 | B | 121 | C |
| 28 | B | 69 | C | 123 | C |
| 41 | C | 70 | B | 125 | C |
| 42 | C | 71 | C | | |

| Compound | αvβ6 IC$_{50}$ | Compound | αvβ6 IC$_{50}$ | Compound | αvβ6 IC$_{50}$ |
|---|---|---|---|---|---|
| 129-E1 | A | 154-E1 | A | 178-E2 | B |
| 129-E2 | C | 154-E2 | B | 179 | B |
| 130-E2 | B | 155-E1 | B | 180 | B |
| 131-E1 | A | 155-E2 | A | 181-E1 | B |
| 131-E2 | C | 156-E1 | A | 181-E2 | C |
| 132-E1 | B | 156-E2 | C | 182-E1 | A |
| 132-E2 | B | 157-E1 | A | 182-E2 | B |
| 133 | A | 157-E2 | C | 183-E1 | B |
| 134-E1 | C | 158-E1 | C | 183-E2 | A |
| 134-E2 | B | 158-E2 | B | 184-E1 | A |
| 135-E1 | A | 159-E1 | B | 184-E2 | A |
| 135-E2 | C | 160-E1 | A | 185-E1 | B |
| 136-E1 | A | 160-E2 | C | 185-E2 | A |
| 136-E2 | B | 161-E1 | C | 186-E1 | C |
| 137-E1 | A | 161-E2 | A | 186-E2 | A |
| 137-E2 | C | 162-E1 | C | 187-E1 | B |
| 138-E1 | A | 162-E2 | A | 187-E2 | A |
| 138-E2 | C | 163-E1 | C | 188-E1 | A |
| 139-E1 | B | 163-E2 | A | 188-E2 | B |
| 139-E2 | C | 164-E1 | B | 189-E1 | C |
| 140-E1 | B | 164-E2 | C | 189-E2 | A |
| 140-E2 | C | 165-E1 | A | 190-E1 | C |
| 141-E1 | C | 165-E2 | C | 190-E2 | B |
| 141-E2 | B | 166-E1 | B | 191-E1 | A |
| 142 | B | 166-E2 | A | 191-E2 | A |
| 143 | B | 167-E1 | A | 192-E1 | C |
| 144-E1 | C | 167-E2 | B | 192-E2 | B |
| 144-E2 | B | 168 | A | 193-E1 | B |
| 145 | A | 169 | A | 193-E2 | B |
| 146-E1 | A | 170-E1 | A | 194-E1 | A |
| 146-E2 | C | 170-E2 | A | 194-E2 | C |
| 147-E1 | A | 171-E1 | B | 195-E1 | A |
| 147-E2 | C | 171-E2 | A | 195-E2 | B |
| 148-E1 | C | 172-E1 | B | 196-E1 | A |
| 148-E2 | B | 172-E2 | A | 196-E2 | C |
| 149-E1 | A | 173-E1 | A | 197-E1 | A |
| 149-E2 | A | 173-E2 | C | 197-E2 | B |
| 150 | A | 174 | A | 198-E1 | C |
| 151-E1 | A | 175-E1 | C | 198-E2 | A |
| 151-E2 | B | 175-E2 | A | 199-E1 | C |
| 152-E1 | A | 176-E2 | B | 199-E2 | A |
| 152-E2 | B | 177-E1 | B | 200-E2 | B |
| 153-E1 | A | 177-E2 | A | 201-E1 | B |
| 153-E2 | C | 178-E1 | B | 201-E2 | C |

αvβ6 IC$_{50}$'s: A: IC$_{50}$ <0.1 μM; B: 0.1 μM < IC$_{50}$ <1 μM; C: 1 μM < IC$_{50}$ <10 μM.

INHIBITORS OF (α-V)(β-6) INTEGRIN

RELATED APPLICATIONS

This application is a continuation of U.S. application Ser. No. 15/906,745, filed Feb. 27, 2018, which claims the benefit of priority to U.S. Provisional Patent Application No. 62/464,693, filed Feb. 28, 2017.

BACKGROUND OF THE INVENTION

The heterodimeric integrin family of receptors modulate cellular shape and cell adhesion to the extracellular matrix in response to extrinsic and intrinsic cues.

Integrin signaling controls cell survival, cell cycle progression, cell differentiation, and cell migration.

The integrin receptor exclusively can signal a cell bi-directionally, both "inside-out" and "outside-in." Thus, they mediate cell migration by transmitting forces from the extracellular matrix to the cytoskeleton and regulate cytoskeletal organization to achieve shape changes needed during cell migration. RGD-binding integrins can bind to and activate TGF-β, and have recently been implicated in fibrotic disease.

Integrins are expressed on the surface of most of human cells. Their pathology contributes to a diverse set of human diseases, including platelet disorders, atherosclerosis, cancer, osteoporosis, fibrosis, diabetic neuropathy of the kidney, macular degeneration and various autoimmune and chronic inflammation diseases.

The role of integrins as drug targets has long been recognized, and a total of six injectable integrin inhibitors have been approved by the Food and Drug Administration for the treatment of various therapeutic indications: inflammatory bowel disease (Entyvio®, Tysabri®), multiple sclerosis (Tysabri®), psoriasis (Raptiva®), and acute coronary syndrome (Reopro®, Aggrastat®, Integrilin®). However, there has been a notable absence of therapeutic success with orally bioavailable integrin inhibitors.

Of the 24 known integrin heterodimers, as least half have relevance in inflammation, fibrosis, oncology and vascular disease. There exists a need for new classes of integrin inhibitors.

SUMMARY OF THE INVENTION

In certain embodiments, the invention relates to a compound of Formula I:

A-B—C        (I)

wherein:
A is

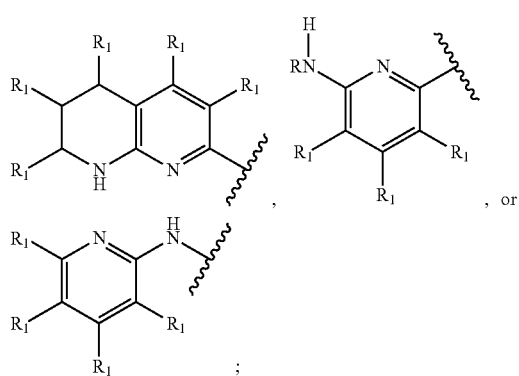

, or

B is alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO$_2$—, -alkylene-(aryl)-, -alkylene-(heterocyclyl)-, alkylene-(heterocyclyl)-alkylene-, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O-heterocyclyl-; -alkylene-O—; -heterocyclyl-C(O)—; cycloalkylene; or clycloalkylene-O—;

C is

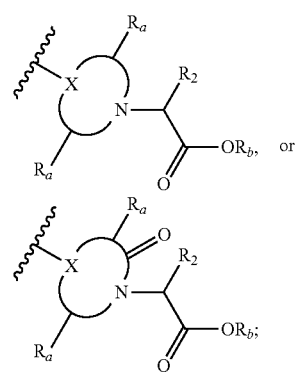

R is H, alkyl, or aryl;

R$_1$ is independently H, alkyl, halide, alkoxy, CF$_3$, OH, alkylene-OH, NO$_2$, —N(H)R, or NH$_2$;

R$_2$ is H, alkyl, substituted or unsubstituted aryl, substituted or unsubstituted heteroaryl, cycloalkyl, -, alkylene-aryl, or heterocycloalkyl;

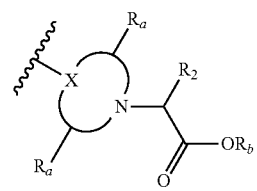

is a 3-12 membered heterocycloalkylene unsubstituted or substituted by one or more instance of R$_1$;

X is C(R$_c$), or N;

both instances of R$_a$ are H, or taken together form a bond, or a (C$_1$-C$_4$)alkylene bridge;

R$_b$ is H, or (C$_1$-C$_6$)alkyl; and

R$_c$ is H, alkyl, aryl, OH, or halide;

or a pharmaceutically acceptable salt thereof;

provided that the compound is not

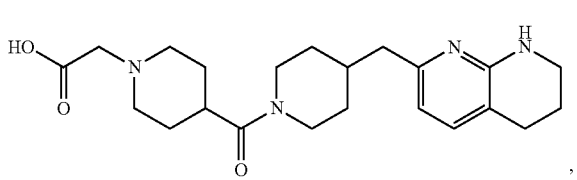

,

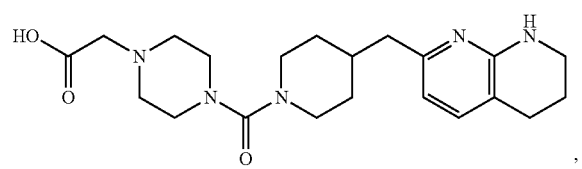
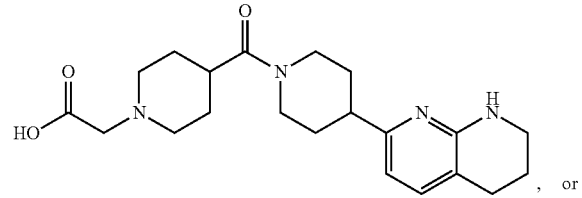
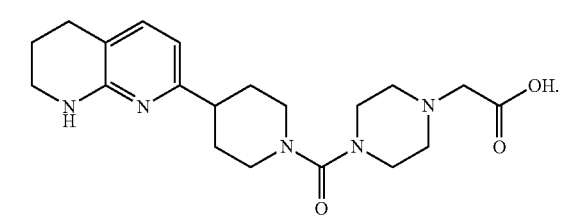
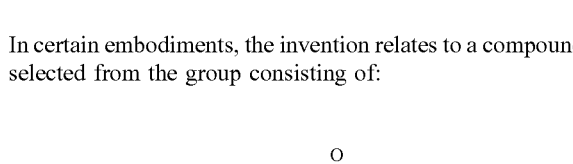
, or
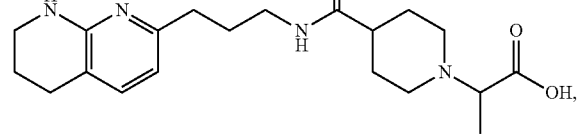
In certain embodiments, the invention relates to a compound selected from the group consisting of:
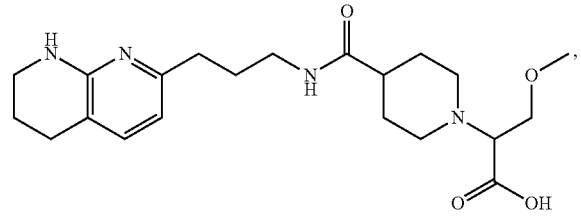
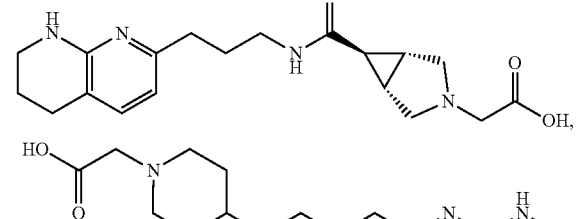

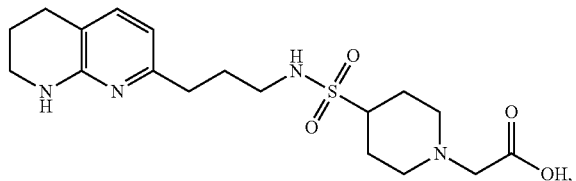
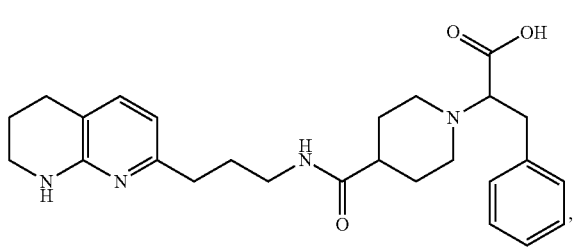
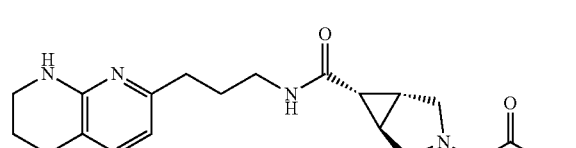
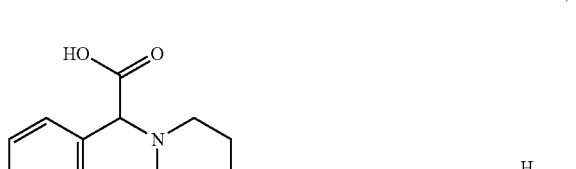
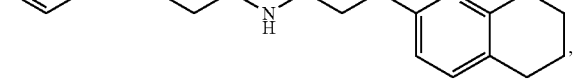
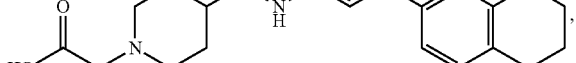
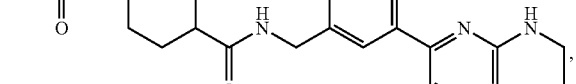
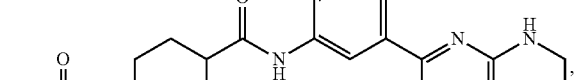

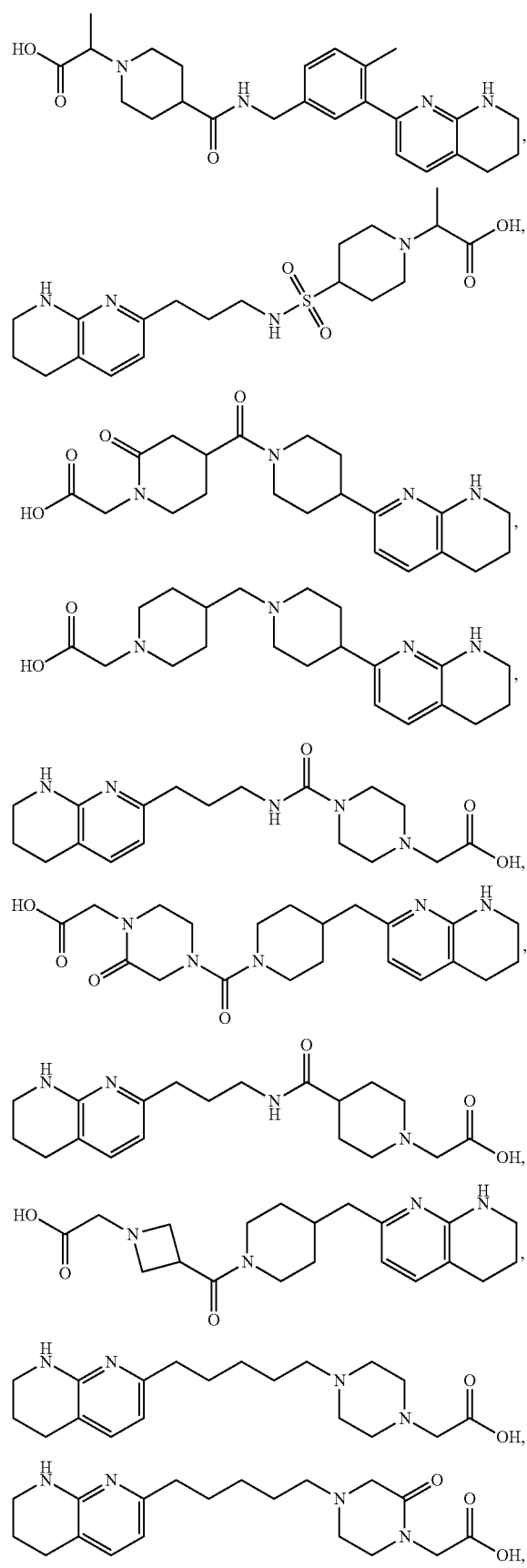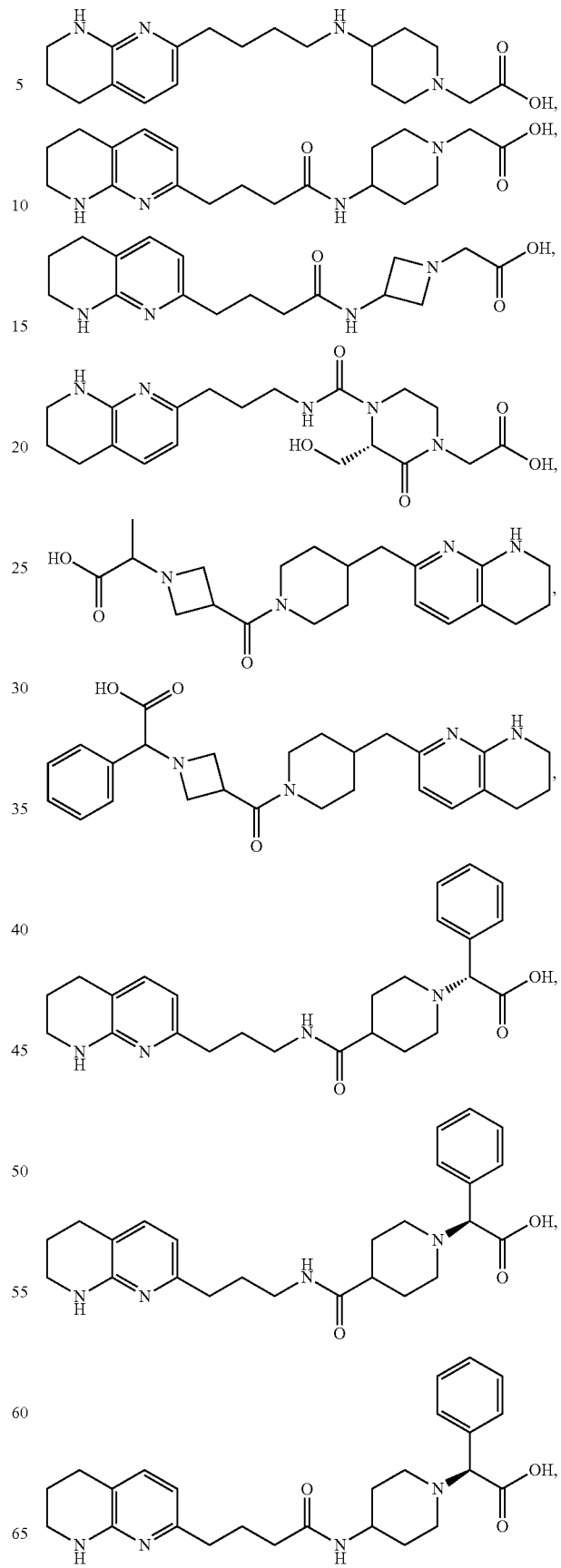

-continued
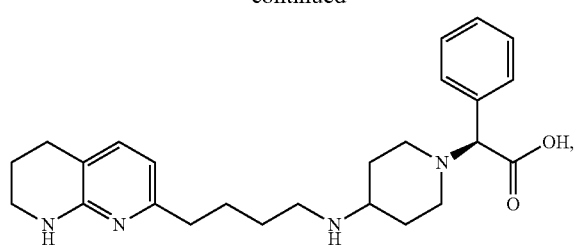
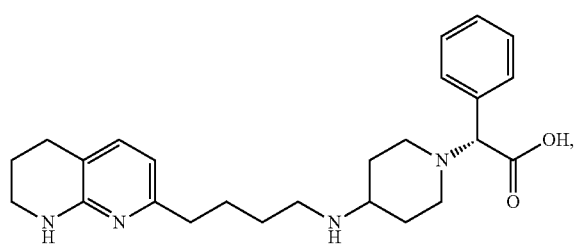
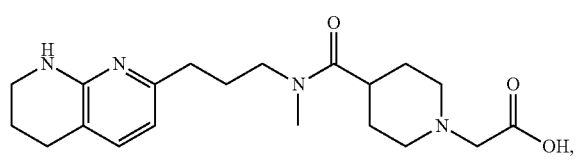
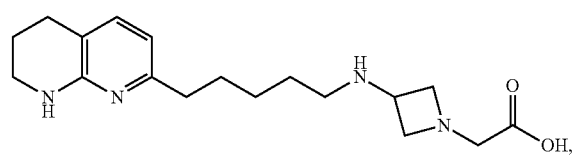
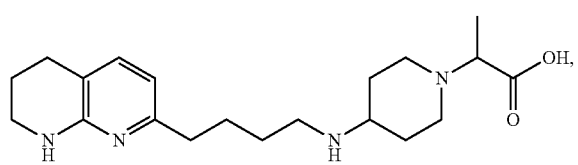
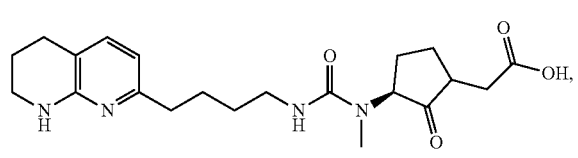
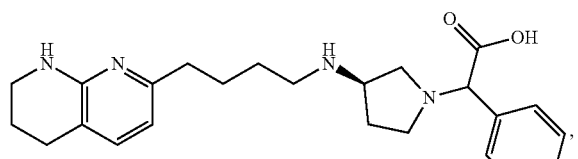
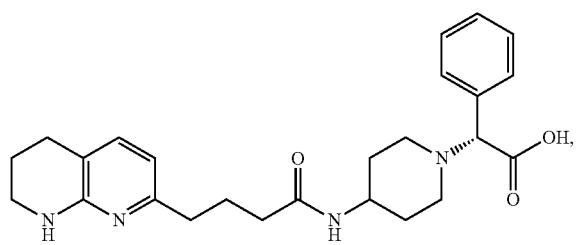
-continued
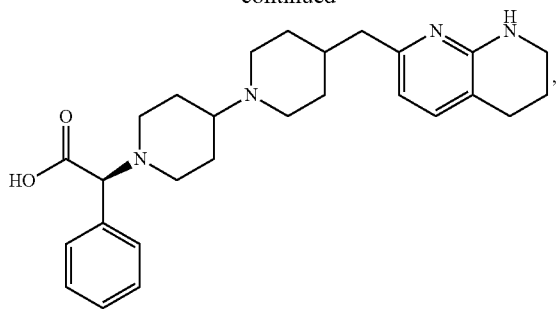
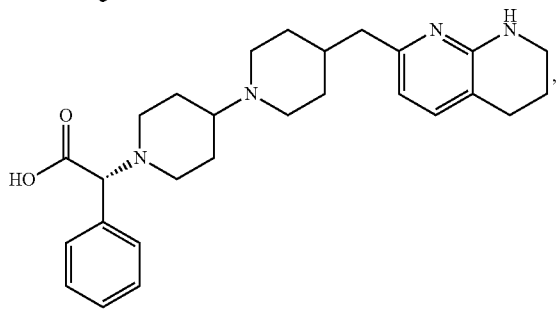
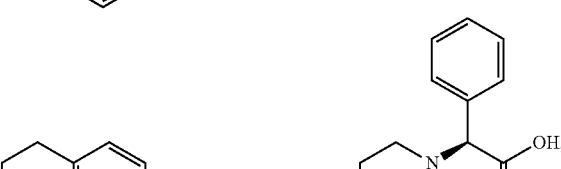
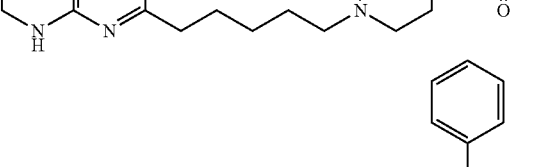
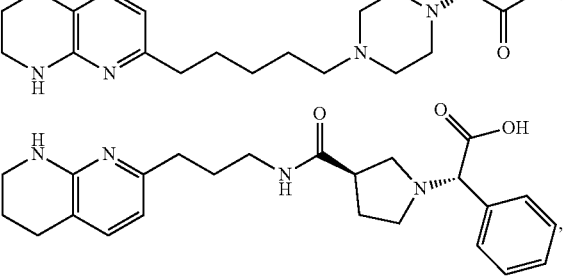
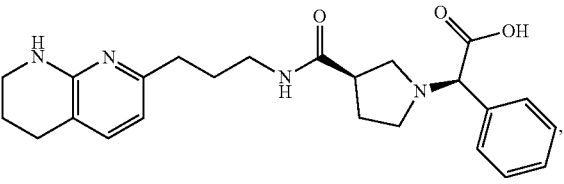
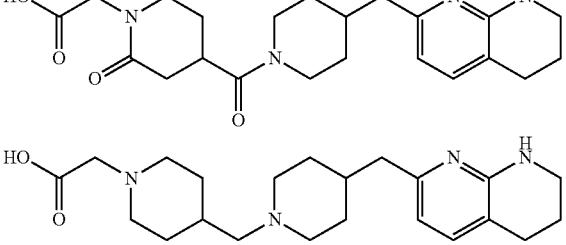

-continued
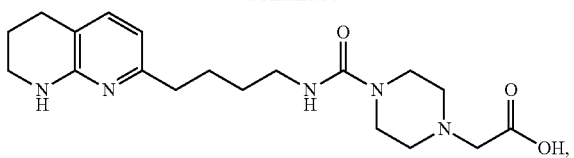
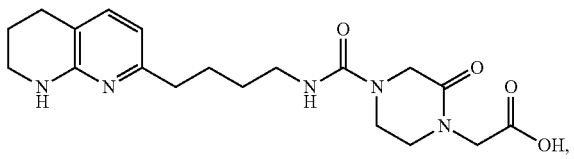
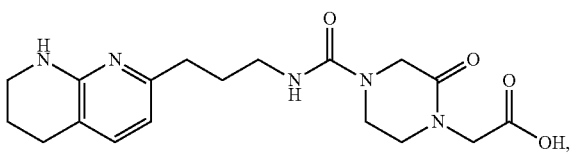
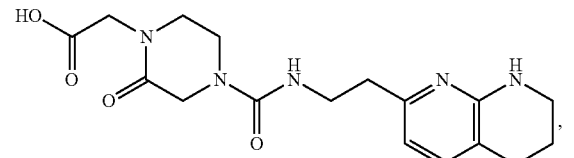
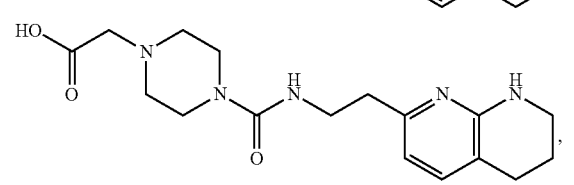

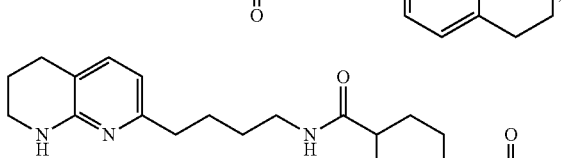
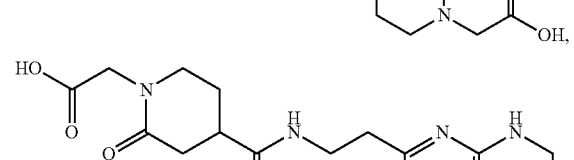
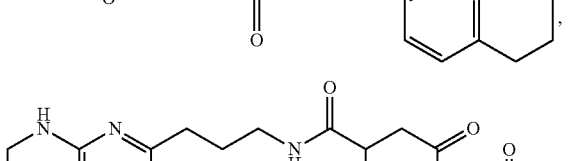
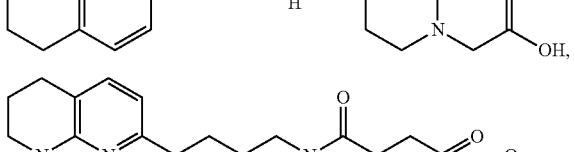
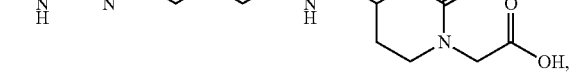
-continued
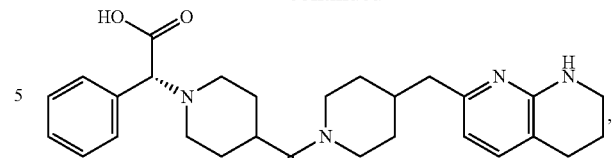
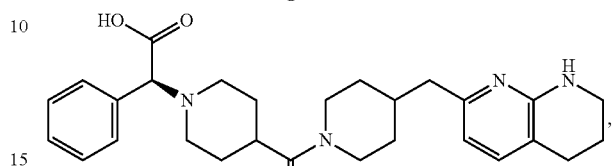
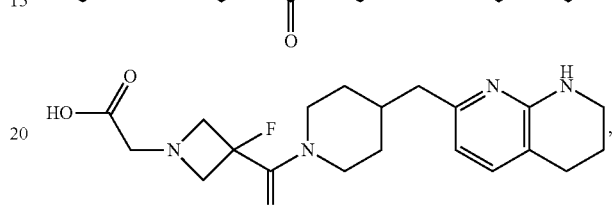
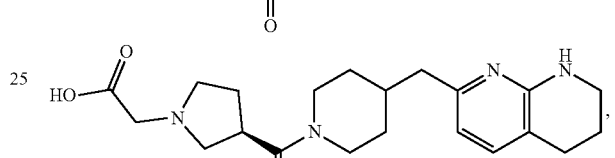
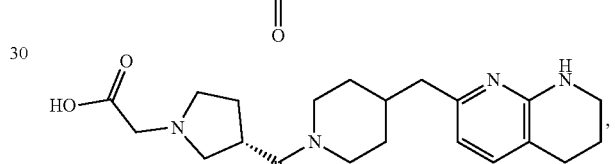
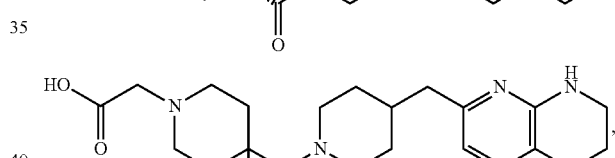
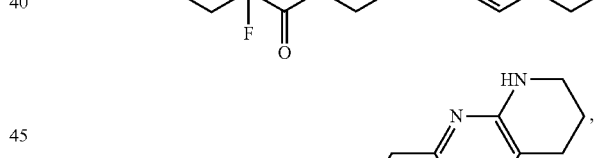
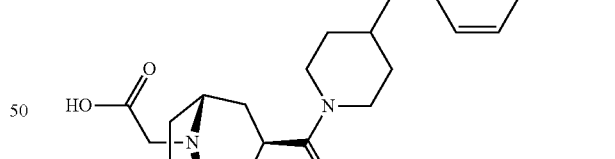
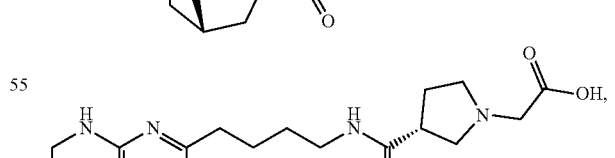
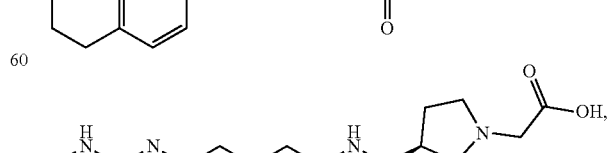
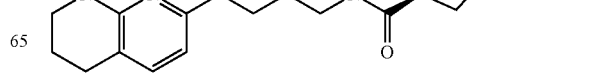

11
-continued
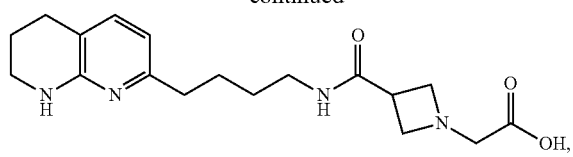
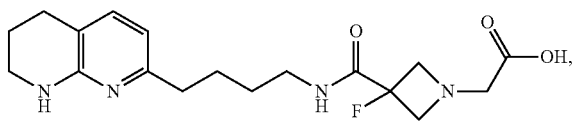
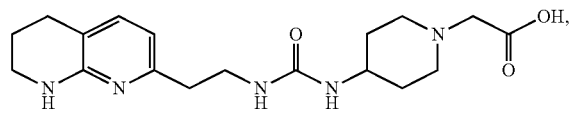
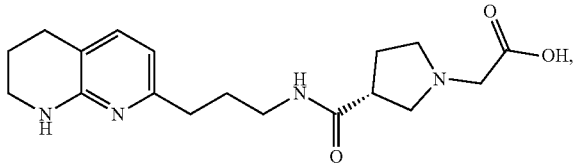
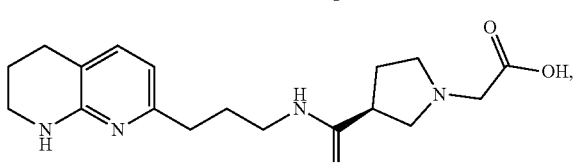
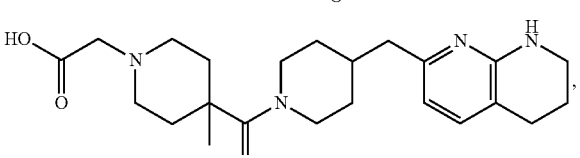
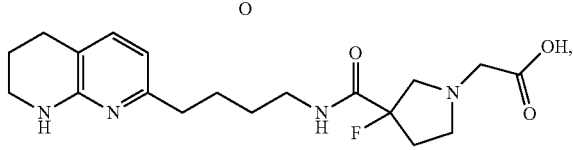
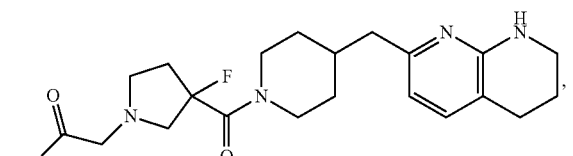
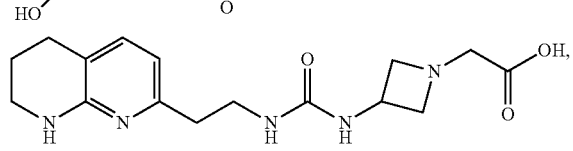
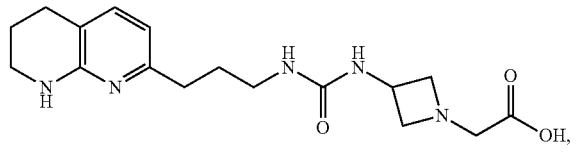
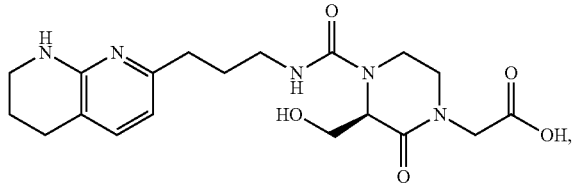
12
-continued
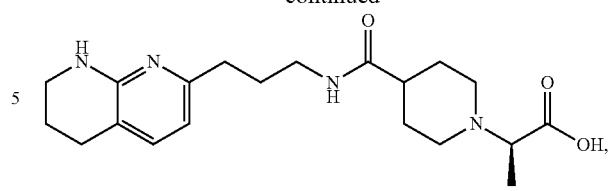
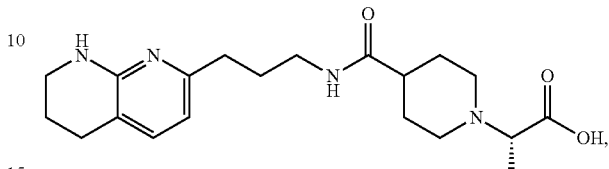
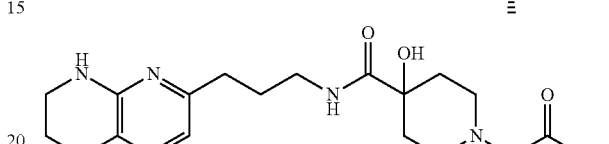
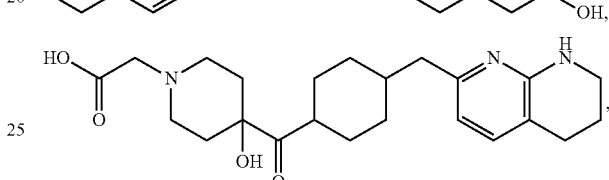
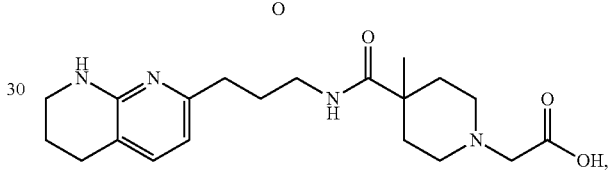
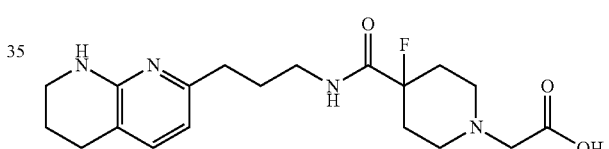
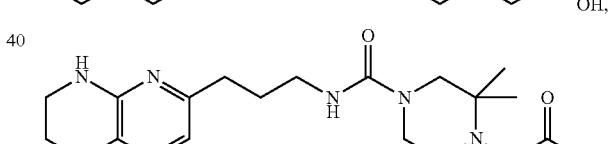
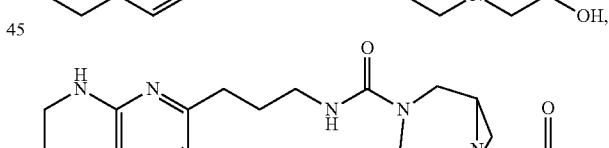
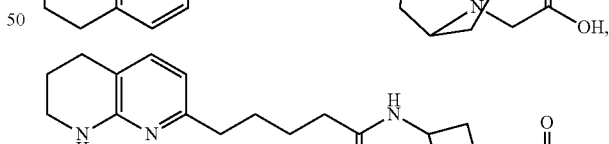
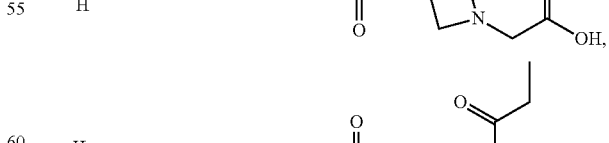
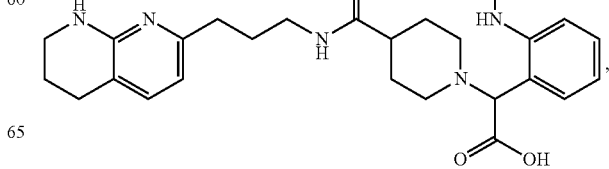

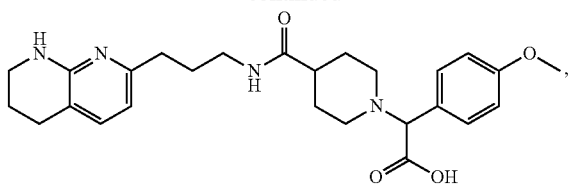
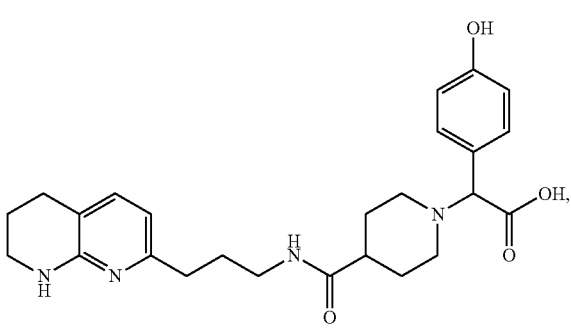
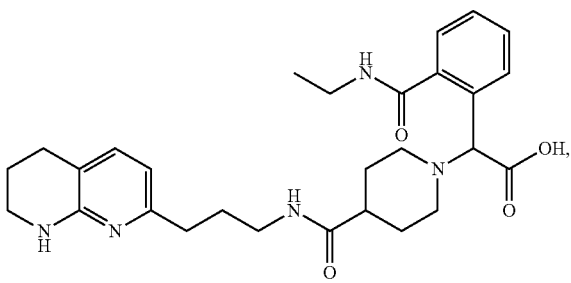
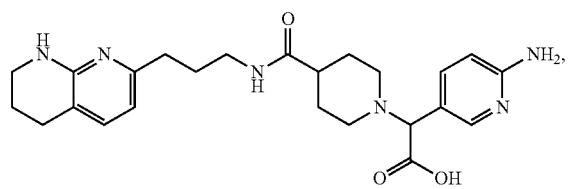
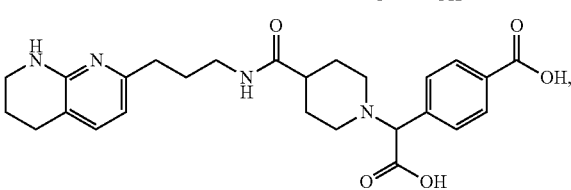
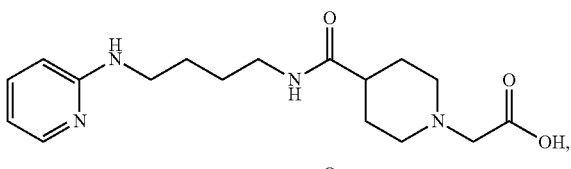
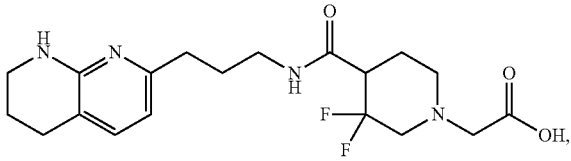
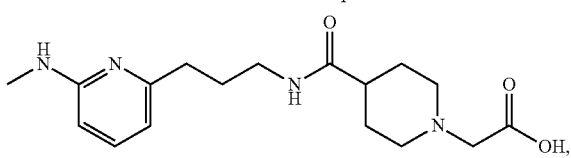
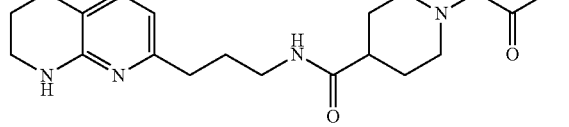
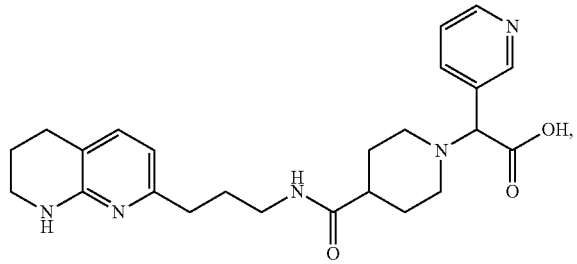
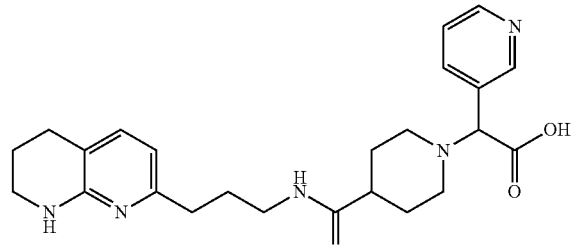
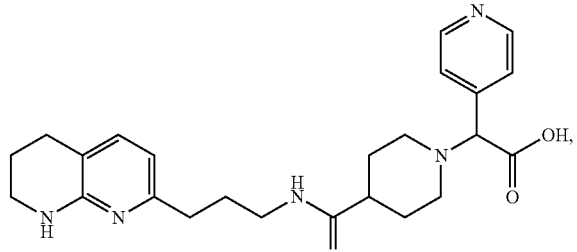
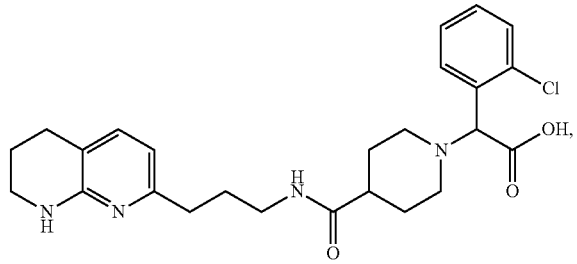
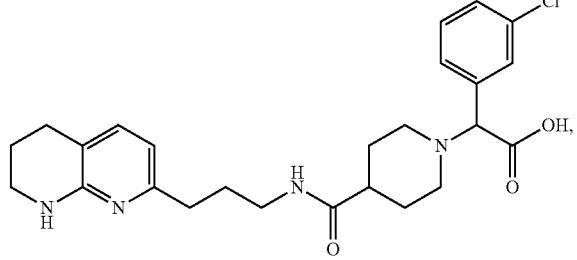

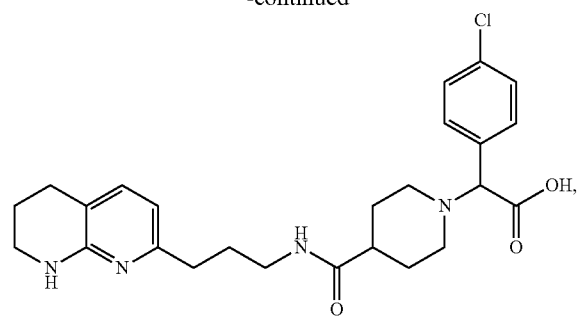
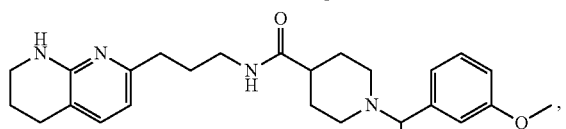
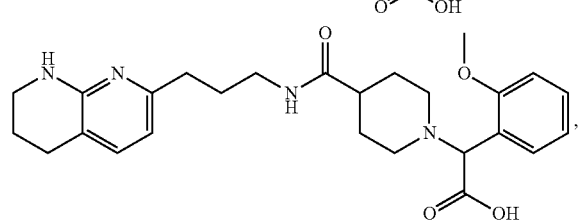
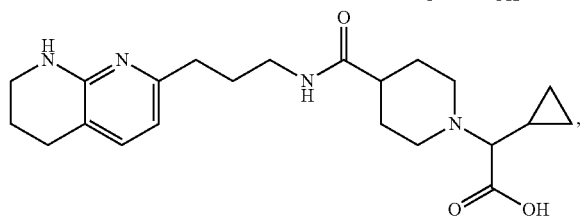
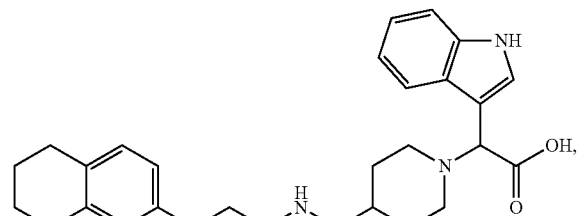
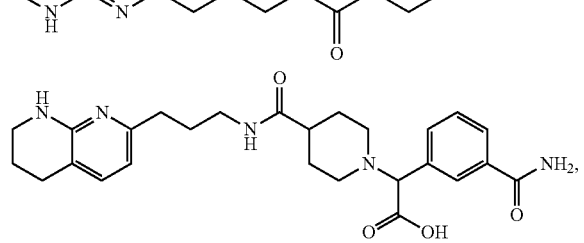
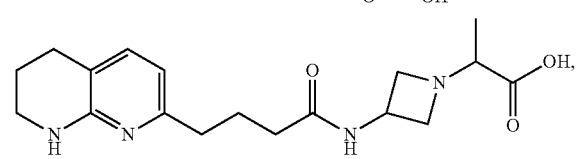
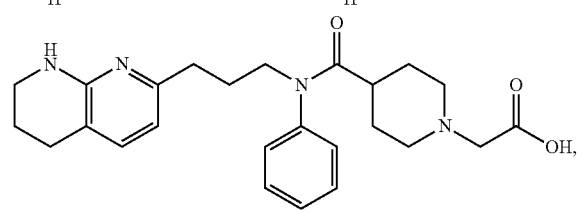
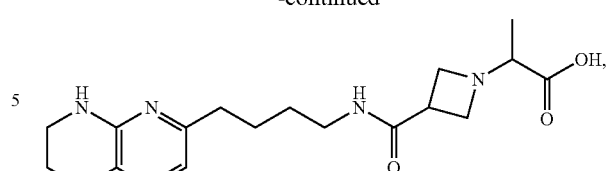
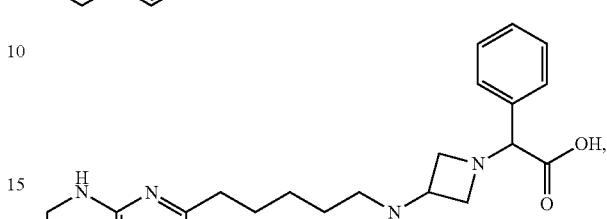
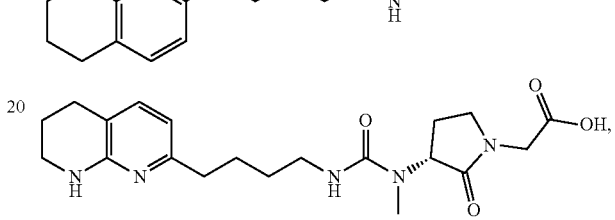
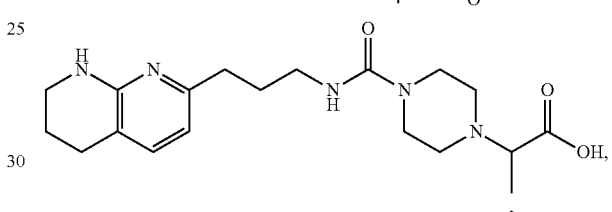
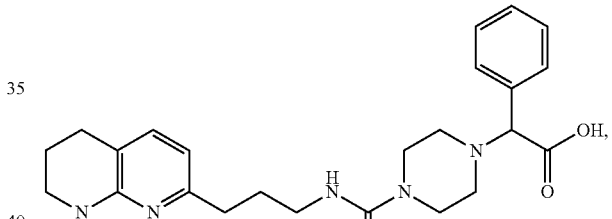
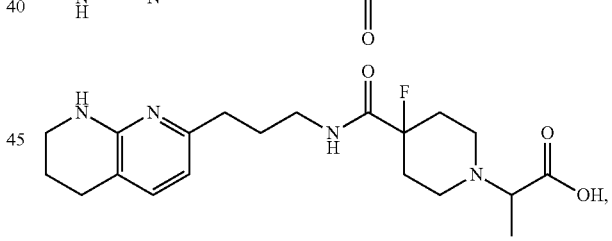
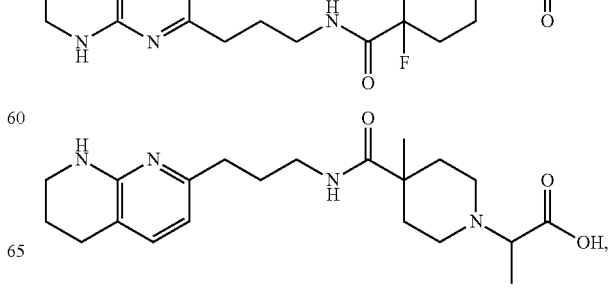

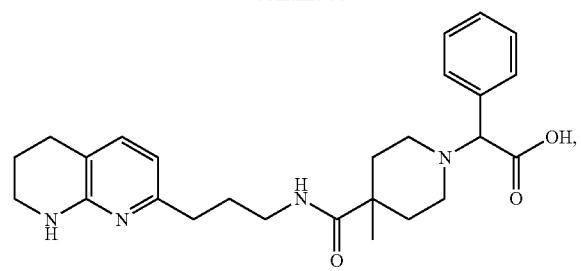
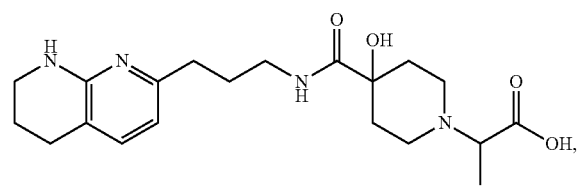
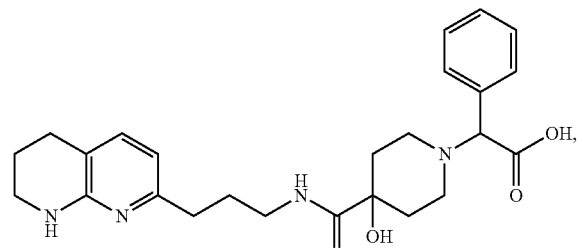
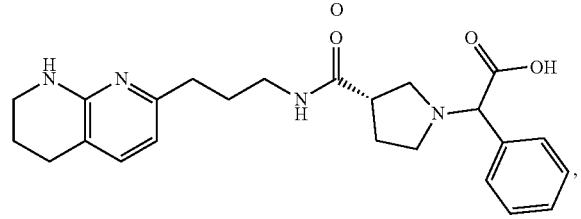
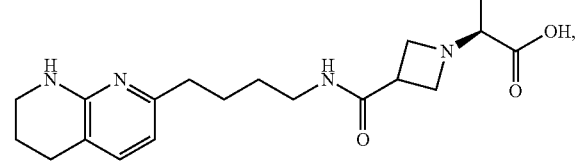
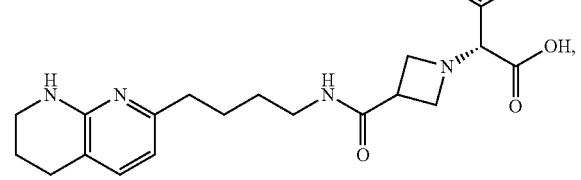
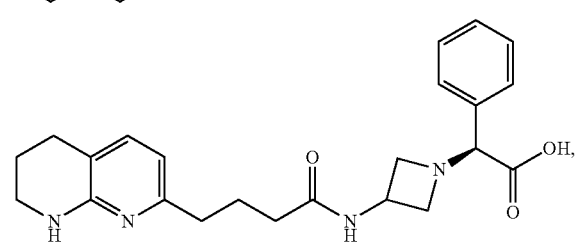
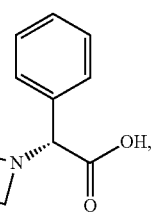
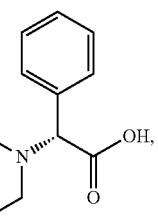
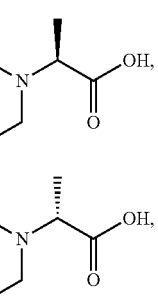
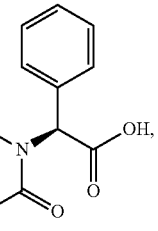
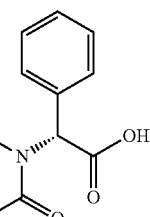
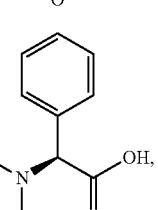
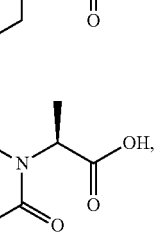

-continued
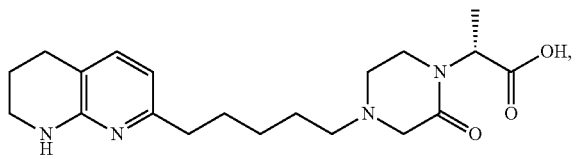
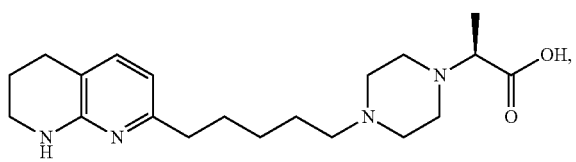
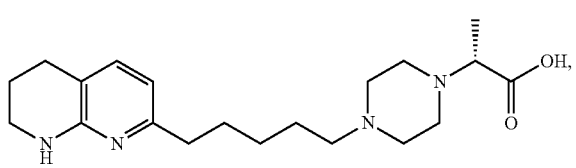
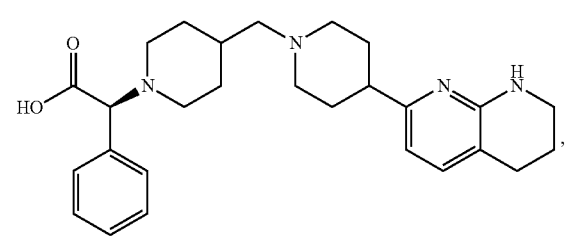
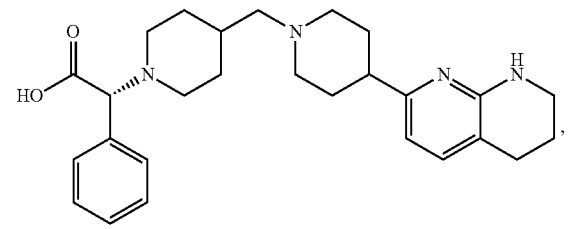
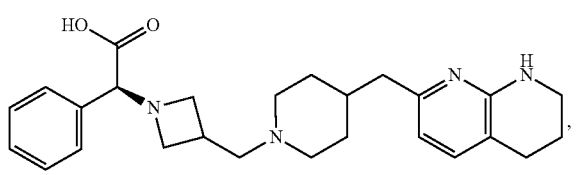
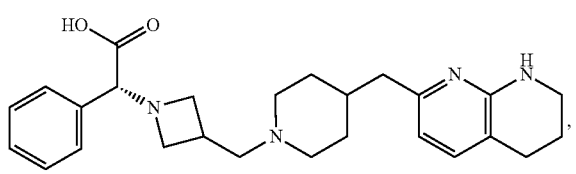
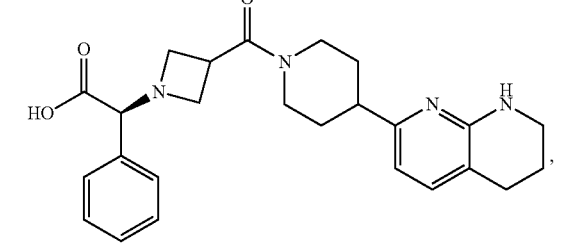
-continued
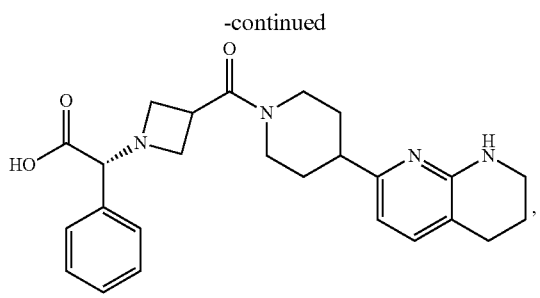
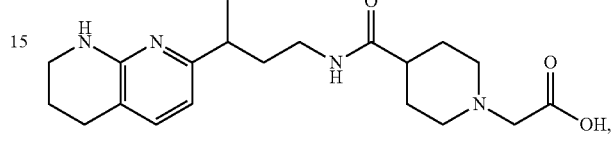
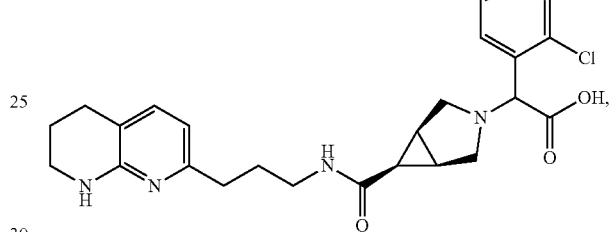
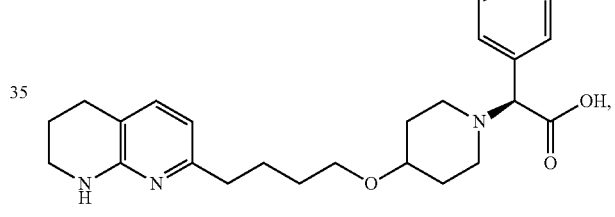
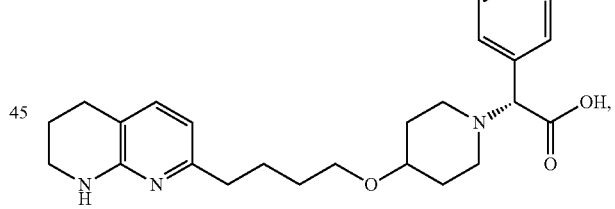
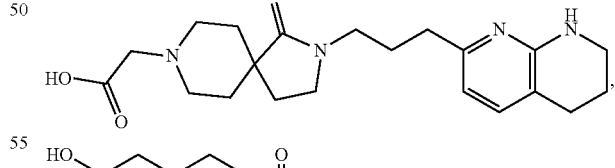
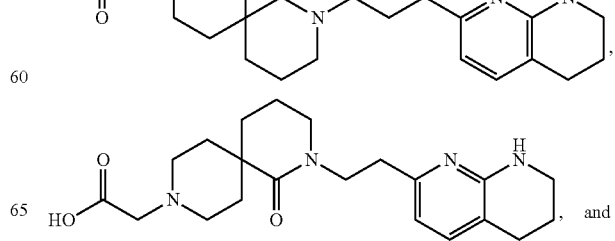
, and -continued

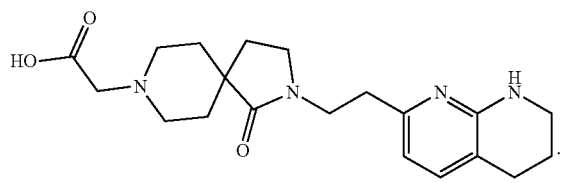

In certain embodiments, the invention relates to a compound selected from the group consisting of:

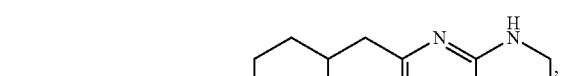

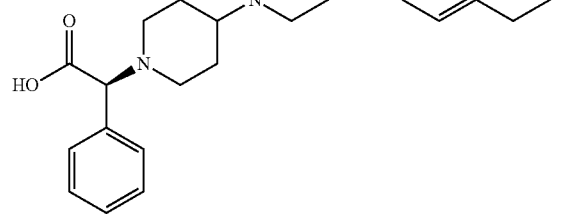

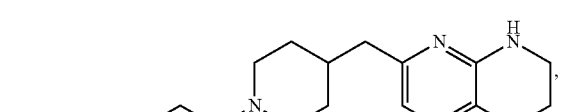

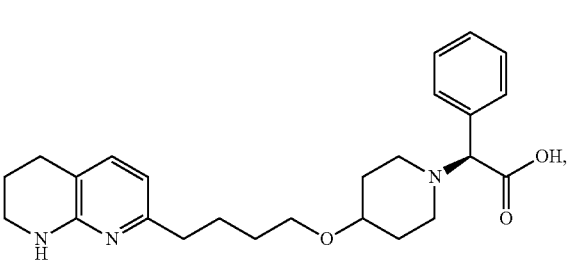

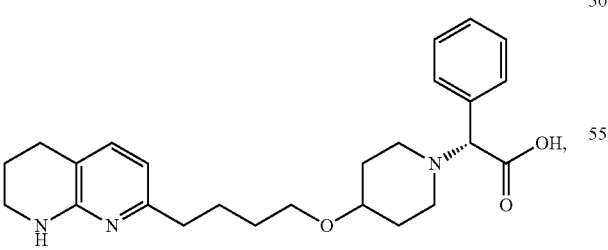

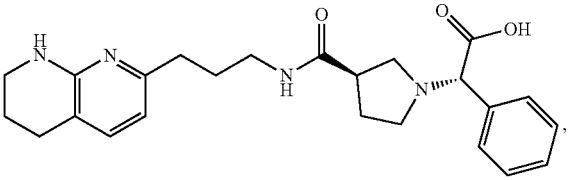

-continued

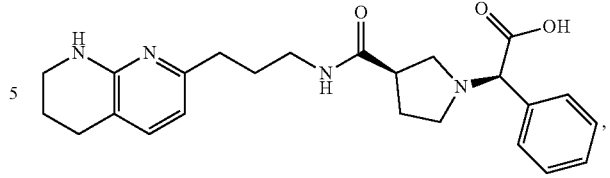

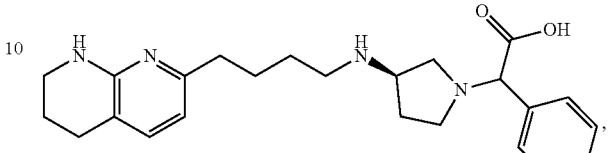

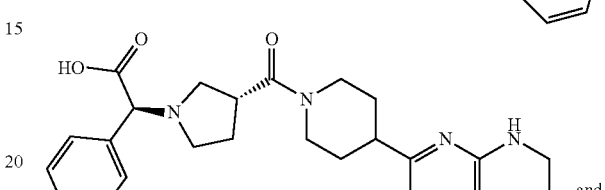

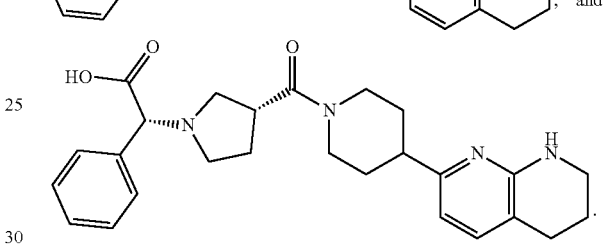

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis comprising the step of: administering to a subject in need thereof a therapeutically effective amount of any one of the compounds described herein.

BRIEF DESCRIPTION OF THE FIGURES

FIG. 1 depicts a table summarizing inhibition of αvβ6 integrin by example compounds in fluorescence polarization assay.

DETAILED DESCRIPTION OF THE INVENTION

In certain embodiments, the invention relates to compounds that inhibit αvβ6 integrin. In certain embodiments, the compounds are selective for αvβ6 integrin.

The compounds will be useful for the treatment of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, or cardiac fibrosis.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)-$(CH_2)_m$—$R^1$, wherein m and $R^1$ are defined below. Representative alkylthio groups include methylthio, ethylthio, and the like. The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_{10}$, where m and $R_{10}$ are described below.

The terms "amine" and "amino" are art-recognized and refer to both unsubstituted and substituted amines, e.g., a moiety that can be represented by the formulae:

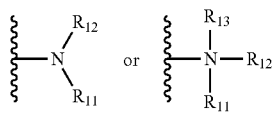

wherein $R_{11}$, $R_{12}$ and $R_{13}$ each independently represent a hydrogen, an alkyl, an alkenyl, —$(CH_2)_m$—$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In certain embodiments, only one of $R_{11}$ or $R_{12}$ can be a carbonyl, e.g., $R_{11}$, $R_{12}$, and the nitrogen together do not form an imide. In even more certain embodiments, $R_{11}$ and $R_{12}$ (and optionally $R_{13}$) each independently represent a hydrogen, an alkyl, an alkenyl, or —$(CH_2)_m$—$R_{10}$. Thus, the term "alkylamine" as used herein means an amine group, as defined above, having a substituted or unsubstituted alkyl attached thereto, i.e., at least one of $R_{11}$ and $R_{12}$ is an alkyl group. In certain embodiments, an amino group or an alkylamine is basic, meaning it has a conjugate acid with a $pK_a > 7.00$, i.e., the protonated forms of these functional groups have $pK_a$s relative to water above about 7.00.

The term "amide", as used herein, refers to a group

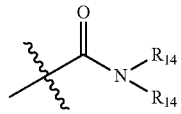

wherein each $R_{14}$ independently represent a hydrogen or hydrocarbyl group, or two $R_{14}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

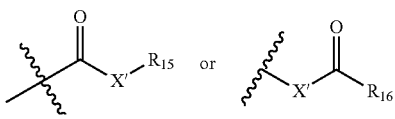

wherein X' is a bond or represents an oxygen or a sulfur, and $R_{15}$ represents a hydrogen, an alkyl, an alkenyl, —$(CH_2)_m$—$R_{10}$ or a pharmaceutically acceptable salt, $R_{16}$ represents a hydrogen, an alkyl, an alkenyl or —$(CH_2)_m$—$R_{10}$, where m and $R_{10}$ are as defined above. Where X' is an oxygen and $R_{15}$ or $R_{16}$ is not hydrogen, the formula represents an "ester." Where X' is an oxygen, and $R_{15}$ is as defined above, the moiety is referred to herein as a carboxyl group, and particularly when $R_{15}$ is a hydrogen, the formula represents a "carboxylic acid". Where X' is an oxygen, and $R_{16}$ is a hydrogen, the formula represents a "formate." In general, where the oxygen atom of the above formula is replaced by a sulfur, the formula represents a "thiocarbonyl" group. Where X' is a sulfur and $R_{15}$ or $R_{16}$ is not hydrogen, the formula represents a "thioester" group. Where X' is a sulfur and $R_{15}$ is a hydrogen, the formula represents a "thiocarboxylic acid" group. Where X' is a sulfur and $R_{16}$ is a hydrogen, the formula represents a "thioformate" group. On the other hand, where X' is a bond, and $R_{15}$ is not hydrogen, the above formula represents a "ketone" group. Where X' is a bond, and $R_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —$NO_2$; the term "halogen" designates —F, —Cl, —Br, or —I; the term "sulfhydryl" means —SH; the term "hydroxyl" means —OH; the term "sulfonyl" means —$SO_2$—; the term "azido" means —$N_3$; the term "cyano" means —CN; the term "isocyanato" means —NCO; the term "thiocyanato" means —SCN; the term "isothiocyanato" means —NCS; and the term "cyanato" means —OCN.

The term "sulfamoyl" is art-recognized and includes a moiety that can be represented by the formula:

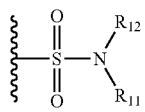

in which $R_{11}$ and $R_{12}$ are as defined above.

The term "sulfate" is art recognized and includes a moiety that can be represented by the formula:

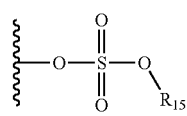

in which $R_{15}$ is as defined above.

The term "sulfonamide" is art recognized and includes a moiety that can be represented by the formula:

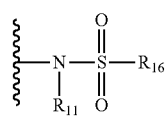

in which $R_{11}$ and $R_{16}$ are as defined above.

The term "sulfonate" is art-recognized and includes a moiety that can be represented by the formula:

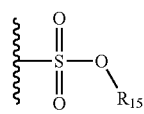

in which $R_{54}$ is an electron pair, hydrogen, alkyl, cycloalkyl, or aryl.

The terms "sulfoxido" or "sulfinyl", as used herein, refers to a moiety that can be represented by the formula:

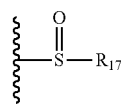

in which $R_{17}$ is selected from the group consisting of the group consisting of hydrogen, alkyl, alkenyl, alkynyl, cycloalkyl, heterocyclyl, aralkyl, or aryl.

The term "urea" is art-recognized and may be represented by the general formula

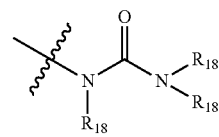

wherein each $R_{18}$ independently represents hydrogen or a hydrocarbyl, such as alkyl, or any occurrence of $R_{18}$ taken together with another and the intervening atom(s) complete a heterocycle having from 4 to 8 atoms in the ring structure.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover.

Exemplary Compounds of the Invention

In certain embodiments, the invention relates to a compound of Formula I:

A-B—C  (I)

wherein:

A is

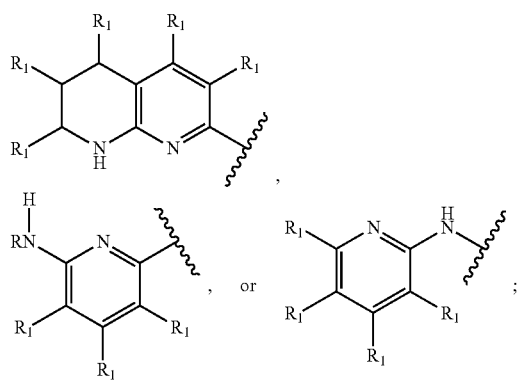

B is alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO$_2$—, -alkylene-(aryl)-, -alkylene-(heterocyclyl)-, -alkylene-(heterocyclyl)-alkylene-, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O-heterocyclyl-; -alkylene-O—; -heterocyclyl-C(O)—; cycloalkylene; or clycloalkylene-O—;

C is

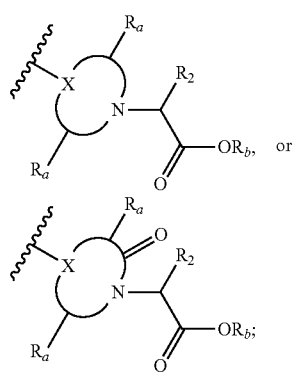

R is H, alkyl, or aryl;

R$_1$ is independently H, alkyl, halide, alkoxy, CF$_3$, OH, NO$_2$, —N(H)R, or NH$_2$;

R$_2$ is H, alkyl, substituted or unsubstituted aryl, substituted or unsubstituted heteroaryl, cycloalkyl, -alkylene-alkoxy, alkylene-aryl, or heterocycloalkyl;

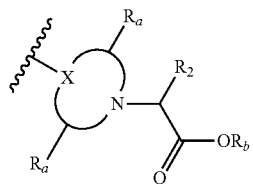

is a 3-12 membered heterocycloalkylene unsubstituted or substituted by one or more instance of R$_1$;

X is C(R$_c$) or N;

both instances of R$_a$ are H, or taken together form a bond, or a (C$_1$-C$_4$)alkylene bridge; and R$_c$ is H, alkyl, aryl, OH, or halide;

or a pharmaceutically acceptable salt thereof;

provided that the compound is not

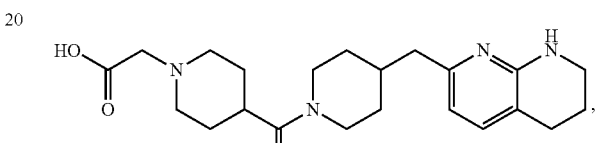

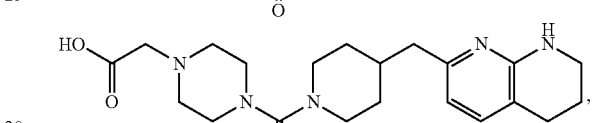

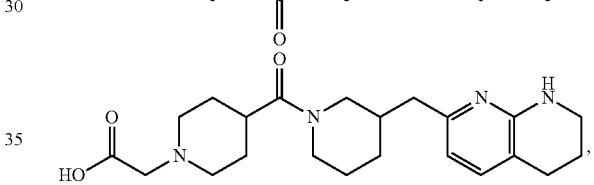

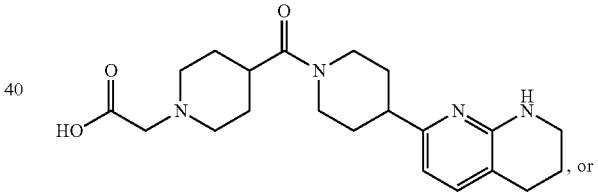

, or

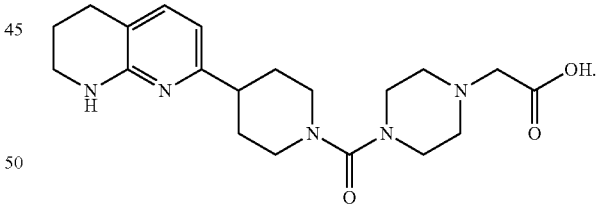

In certain embodiments, the invention relates to any one of the aforementioned compounds, wherein A is

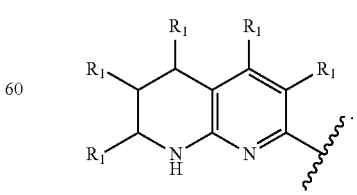

In certain embodiments, the invention relates to any one of the aforementioned compounds, wherein A is In certain embodiments, the invention relates to any one of the aforementioned compounds, wherein A is

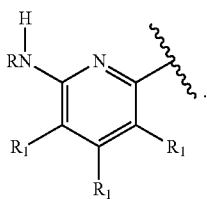

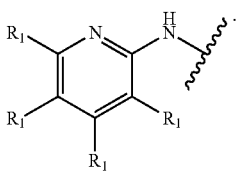

In certain embodiments, the invention relates to any one of the aforementioned compounds, wherein

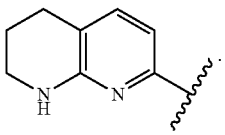 [SMILES: *c1ccc2c(n1)NCCC2]

In certain embodiments, the invention relates to any one of the aforementioned compounds, wherein $R_1$ is independently H, alkyl, halide, alkoxy, $CF_3$, OH, alkylene-OH, $NO_2$, —N(H)R, or $NH_2$. In certain embodiments, the invention relates to any one of the aforementioned compounds, wherein $R_1$ is independently alkyl, halide, alkoxy, $CF_3$, OH, alkylene-OH, $NO_2$, or $NH_2$. In certain embodiments, the invention relates to any one of the aforementioned compounds, wherein $R_1$ is alkyl, halide, OMe, OH, alkylene-OH, or $NH_2$. In certain embodiments, the invention relates to any one of the aforementioned compounds, wherein at least one instance of $R_1$ is alkyl. In certain embodiments, the invention relates to any one of the aforementioned compounds, wherein at least one instance of $R_1$ is methyl. certain embodiments, the invention relates to any one of the aforementioned compounds, wherein at least one instance of $R_1$ is alkylene-OH. In certain embodiments, the invention relates to any one of the aforementioned compounds, wherein at least one instance of $R_1$ is $CH_2OH$. In certain embodiments, the invention relates to any one of the aforementioned compounds, wherein at least one instance of $R_1$ is H. In certain embodiments, the invention relates to any one of the aforementioned compounds, wherein at least one instance $R_1$ is halide. In certain embodiments, the invention relates to any one of the aforementioned compounds, wherein at least one instance $R_1$ is iodo, bromo, chloro, or fluoro. In certain embodiments, the invention relates to any one of the aforementioned compounds, wherein at least one instance of $R_1$ is iodo, bromo, chloro, or fluoro, and the other instances of $R_1$ are hydrogen. In certain embodiments, the invention relates to any one of the aforementioned compounds, wherein all instances of $R_1$ are H.

In certain embodiments, the invention relates to any one of the aforementioned compounds, wherein R is H, alkyl, or aryl. In certain embodiments, the invention relates to any one of the aforementioned compounds, wherein R is H. In certain embodiments, the invention relates to any one of the aforementioned compounds, wherein R is methyl. In certain embodiments, the invention relates to any one of the aforementioned compounds, wherein R is phenyl.

In certain embodiments, the invention relates to any one of the aforementioned compounds, wherein B is alkylene, -alkylene-(O); -alkylene-N(R)C(O)—, -alkylene-(heterocyclyl)-C(O)—, -alkylene-C(O)N(R)—, -alkylene-C(O)—, -alkylene-N(R)—, -alkylene-N(R)C(O)N(R)—, -alkylene-N(R)SO$_2$—, -alkylene-(aryl)-, -alkylene-(heterocyclyl)-, -alkylene-(heterocyclyl)-alkylene, -aryl-alkylene-N(R)C(O)—; -aryl-C(O)N(R)—, -aryl-N(R)C(O)—, -(heterocyclyl)-alkylene-, -heterocyclyl-alkylene-N(R)C(O)—; -heterocyclyl-C(O)N(R)—, —O— heterocyclyl-; -alkylene-O—; -heterocyclyl-C(O)—; cycloalkylene; or clycloalkylene-O—.

In certain embodiments, the invention relates to any one of the aforementioned compounds, wherein B is selected from the group consisting of:

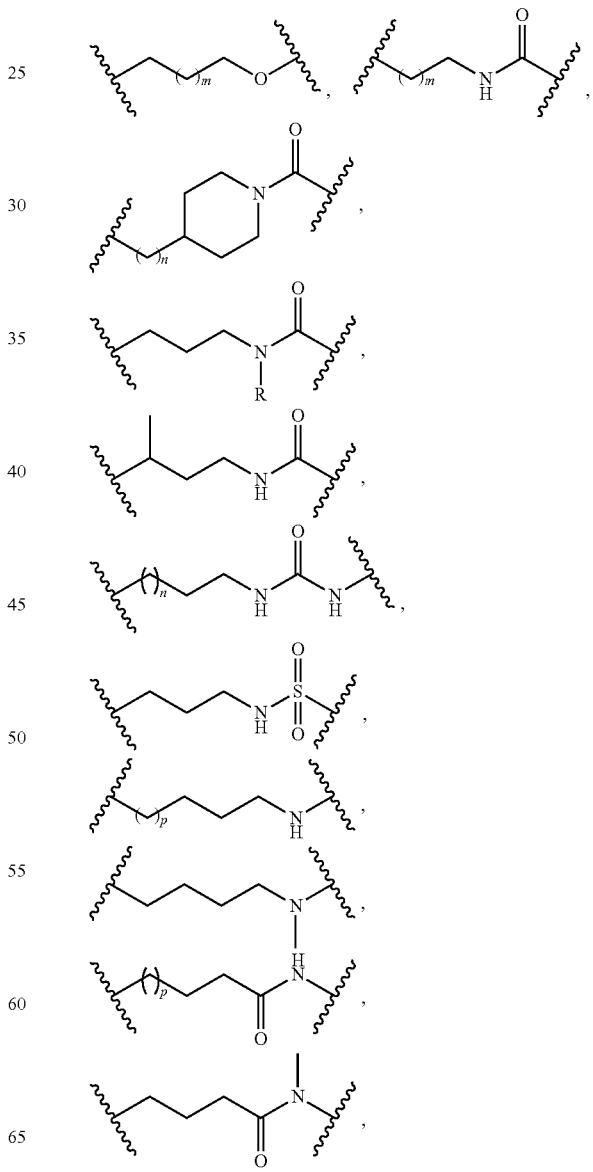

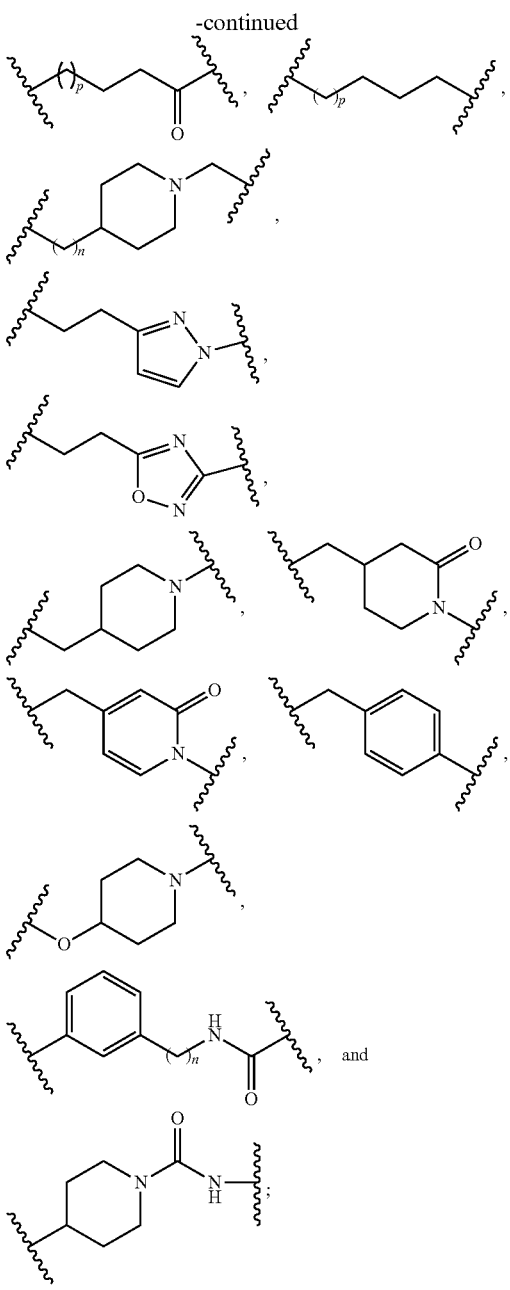

m is 0, 1, 2, or 3; n is 0, or 1; and p is 0, 1, or 2.

In certain embodiments, the invention relates to any one of the aforementioned compounds, wherein

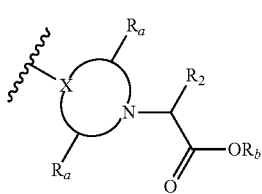

is a 3-12 membered heterocycloalkylene substituted with one or more instances of $R_1$.

In certain embodiments, the invention relates to any one of the aforementioned compounds, wherein

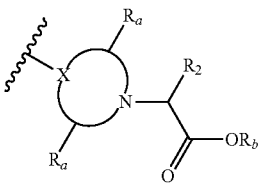

is an unsubstituted 3-12 membered heterocycloalkylene. In certain embodiments, the invention relates to any one of the aforementioned compounds, wherein is a 3-12 membered heterocycloalkylene substituted with one or more instances of $R_1$, wherein $R_1$ is.

In certain embodiments, the invention relates to any one of the aforementioned compounds, wherein X is N.

In certain embodiments, the invention relates to any one of the aforementioned compounds, wherein both instances of $R_a$ are H.

In certain embodiments, the invention relates to any on of the aforementioned compounds, wherein $R_b$ is H. In certain embodiments, the invention relates to any on of the aforementioned compounds, wherein $R_b$ is $(C_1$-$C_6)$alkyl. In certain embodiments, the invention relates to any on of the aforementioned compounds, wherein $R_b$ is methyl. In certain embodiments, the invention relates to any on of the aforementioned compounds, wherein $R_b$ is ethyl.

In certain embodiments, the invention relates to any one of the aforementioned compounds, wherein C is selected from the group consisting of:

In certain embodiments, the invention relates to any one of the aforementioned compounds, wherein X is $C(R_c)$.

In certain embodiments, the invention relates to any one of the aforementioned compounds, wherein $R_c$ is H, alkyl, aryl, OH, or halide. In certain embodiments, the invention relates to any one of the aforementioned compounds, wherein $R_R$ is H.

In certain embodiments, the invention relates to any one of the aforementioned compounds, wherein both instances of $R_a$ are taken together form a bond, or a ($C_1$-$C_4$)-alkylene bridge.

In certain embodiments, the invention relates to any one of the aforementioned compounds, wherein C is

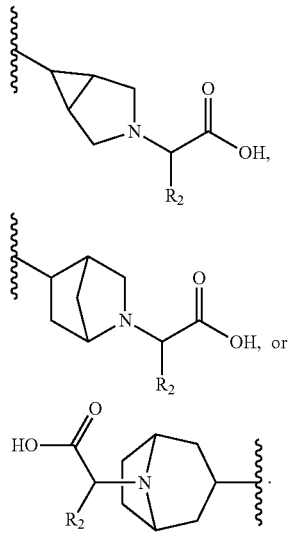

In certain embodiments, the invention relates to any one of the aforementioned compounds, wherein C represents

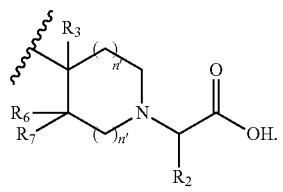

In certain embodiments, the invention relates to any one of the aforementioned compounds, wherein C represents

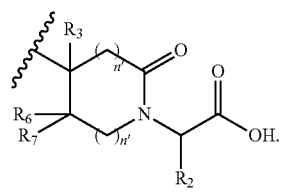

In certain embodiments, the invention relates to any one of the aforementioned compounds, wherein $R_2$ is H, alkyl, substituted or unsubstituted aryl, substituted or unsubstituted heteroaryl, cycloalkyl, -alkylene-alkoxy, alkylene-aryl, or heterocycloalkyl.

In certain embodiments, the invention relates to any one of the aforementioned compounds, wherein $R_2$ is H, ($C_1$-$C_4$)alkyl, cyclopropyl, $CH_2OMe$, phenyl, —$CH_2Ph$, pyridinyl, or indolyl.

In certain embodiments, the invention relates to any one of the aforementioned compounds, wherein $R_2$ is H. In certain embodiments, the invention relates to any one of the aforementioned compounds, wherein $R_2$ is Me. In certain embodiments, the invention relates to any one of the aforementioned compounds, wherein $R_2$ is unsubstituted phenyl. In certain embodiments, the invention relates to any one of the aforementioned compounds, wherein $R_2$ is substituted phenyl. In certain embodiments, the invention relates to any one of the aforementioned compounds, wherein the substituted phenyl is substituted with one or more independent instances of alkoxy, halide, —$C(O)NH_2$, or —$C(O)$alkyl. In certain embodiments, the invention relates to any one of the aforementioned compounds, wherein the substituted phenyl is substituted with at least one halide. In certain embodiments, the invention relates to any one of the aforementioned compounds, wherein the halide is Cl. In certain embodiments, the invention relates to any one of the aforementioned compounds, wherein $R_2$ is unsubstituted pyridinyl. In certain embodiments, the invention relates to any one of the aforementioned compounds, wherein $R_2$ is substituted pyridinyl. In certain embodiments, the invention relates to any one of the aforementioned compounds, wherein the substituted pyridinyl is substituted with $NH_2$, or OH. In certain embodiments, the invention relates to any one of the aforementioned compounds, wherein $R_2$ is

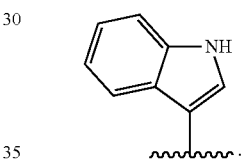

In certain embodiments, the invention relates to any one of the aforementioned compounds, wherein $R_3$ is H, halide, $CF_3$, alkyl, alkylene-alkoxy, aryl, hydroxyl, or alkoxy.

In certain embodiments, the invention relates to any one of the aforementioned compounds, wherein $R_3$ is H, halide, Me, OMe, or Ph. In certain embodiments, the invention relates to any one of the aforementioned compounds, wherein $R_3$ is iodo, bromo, chloro, or fluoro. In certain embodiments, the invention relates to any one of the aforementioned compounds, wherein $R_3$ is H.

In certain embodiments, the invention relates to any one of the aforementioned compounds, wherein $R_6$ is H, halide, $CF_3$, alkyl, alkylene-alkoxy, aryl, hydroxyl, or alkoxy. In certain embodiments, the invention relates to any one of the aforementioned compounds, wherein $R_6$ is H. In certain embodiments, the invention relates to any one of the aforementioned compounds, wherein $R_6$ is OMe. In certain embodiments, the invention relates to any one of the aforementioned compounds, wherein $R_6$ is Me.

In certain embodiments, the invention relates to any one of the aforementioned compounds, wherein $R_7$ is H, halide, $CF_3$, alkyl, alkylene-alkoxy, aryl, hydroxyl, or alkoxy.

In certain embodiments, the invention relates to any one of the aforementioned compounds, wherein $R_7$ is H. In certain embodiments, the invention relates to any one of the aforementioned compounds, wherein $R_7$ is OMe. In certain embodiments, the invention relates to any one of the aforementioned compounds, wherein $R_7$ is Me. In certain embodiments, the invention relates to any one of the aforementioned compounds, wherein $R_7$ is $CH_2OH$.

In certain embodiments, the invention relates to any one of the aforementioned compounds, wherein $R_3$ is H or F, $R_6$ is H, and $R_7$ is H or $CH_2OH$.

In certain embodiments, the invention relates to any one of the aforementioned compounds, wherein only one instance of n' is 0. In certain embodiments, the invention relates to any one of the aforementioned compounds, wherein at least one instance of n' is 0. In certain embodiments, the invention relates to any one of the aforementioned compounds, wherein both instances of n' is 0. In certain embodiments, the invention relates to any one of the aforementioned compounds, wherein only one instance of n' is 1. In certain embodiments, the invention relates to any one of the aforementioned compounds, wherein at least one instance of n' is 1. In certain embodiments, the invention relates to any one of the aforementioned compounds, wherein both instances of n' is 1. In certain embodiments, the invention relates to any one of the aforementioned compounds, wherein only one instance of n' is 2. In certain embodiments, the invention relates to any one of the aforementioned compounds, wherein at least one instance of n' is 2. In certain embodiments, the invention relates to any one of the aforementioned compounds, wherein both instances of n' is 2. In certain embodiments, the invention relates to any one of the aforementioned compounds, wherein one instance of n' is 0, and one instance of n' is 1.

In certain embodiments, the invention relates to any one of the aforementioned compounds, wherein C is selected from the group consisting of:

In certain embodiments, the invention relates to any one of the aforementioned compounds, wherein the optional substituent, when present, is selected from the group consisting of alkoxy, alkyl ester, alkylcarbonyl, hydroxyalkyl, cyano, halo, amino, amido, cycloalkyl, aryl, haloalkyl, nitro, hydroxy, alkoxy, aryloxy, alkyl, alkylthio, and cyanoalkyl.

In certain embodiments, the invention relates to any one of the aforementioned compounds, wherein the compound is a pharmaceutically acceptable salt.

In certain embodiments, the invention relates to a compound selected from the group consisting of:

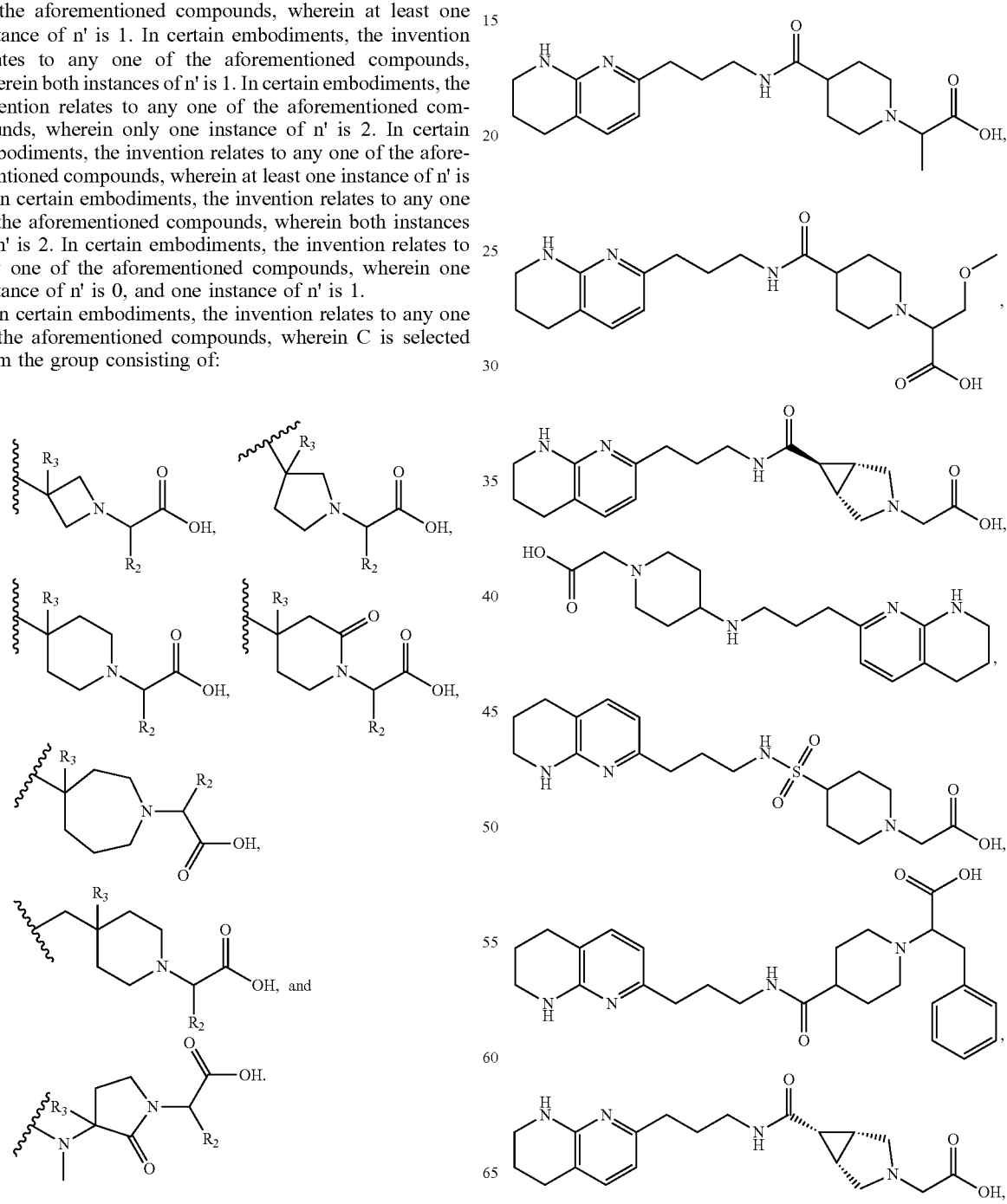

41
-continued
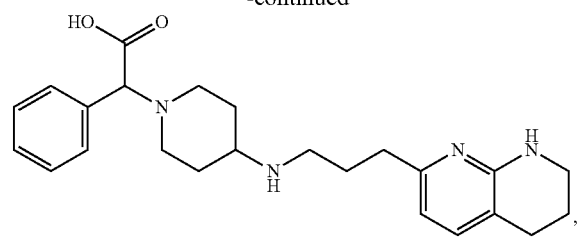
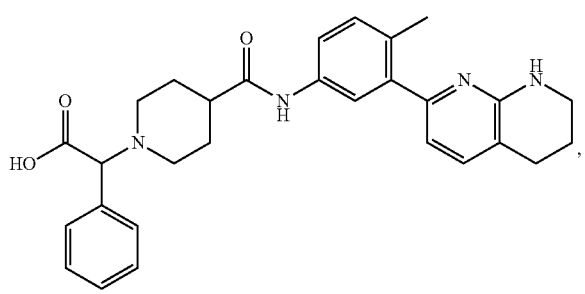
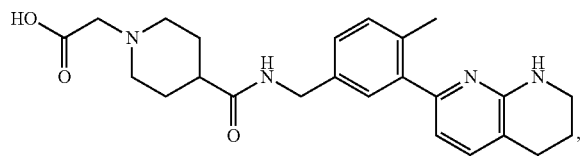
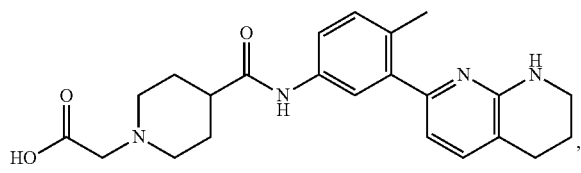
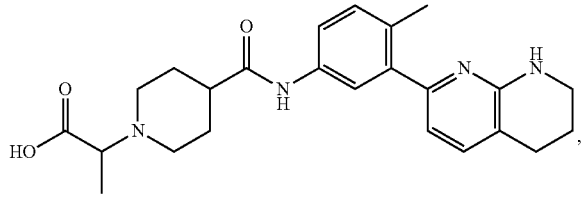
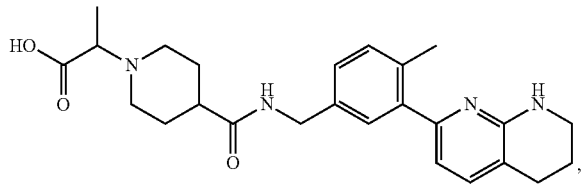
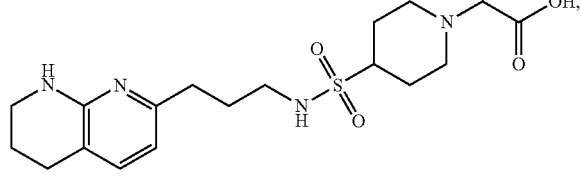
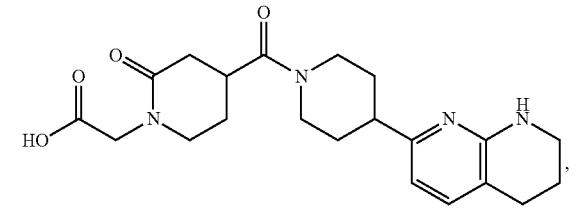
42
-continued
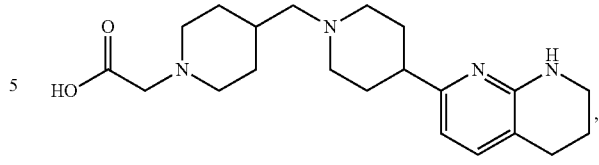
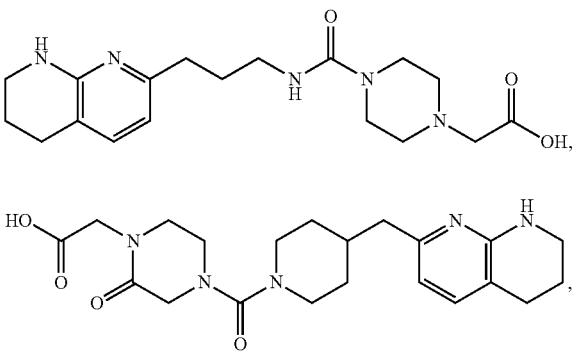
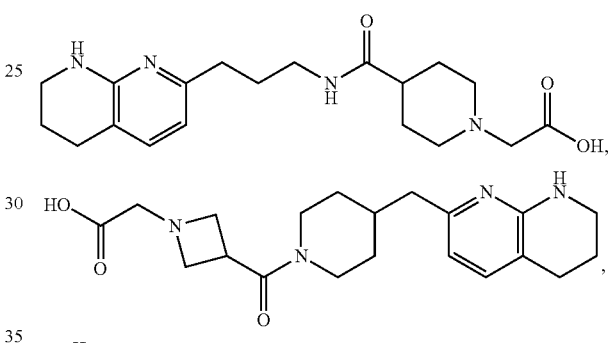
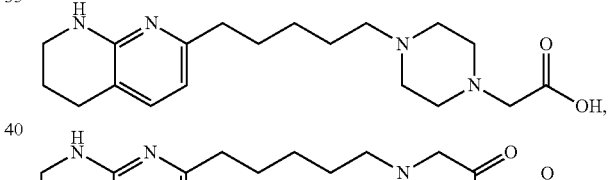
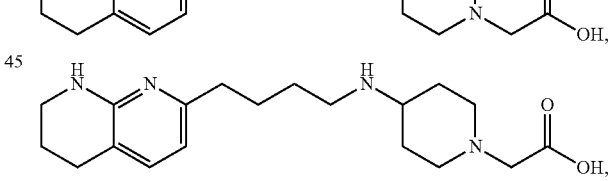
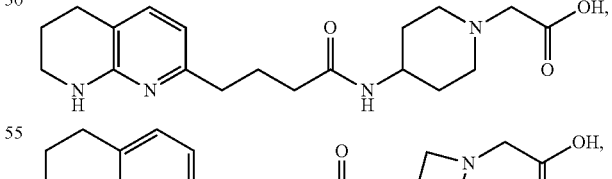
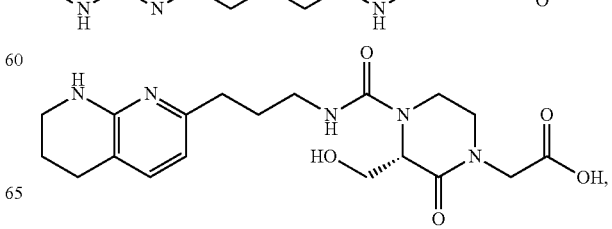

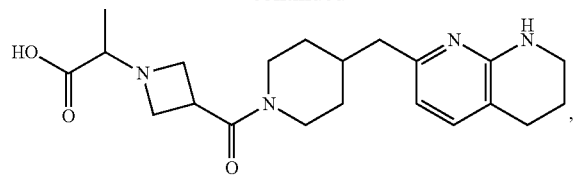
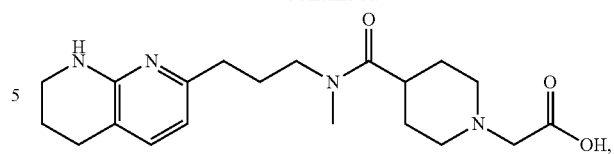
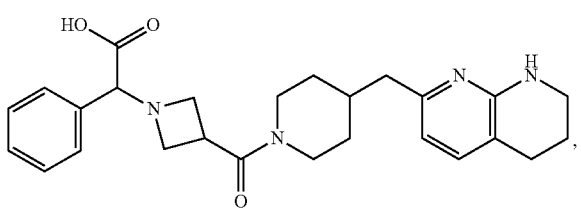
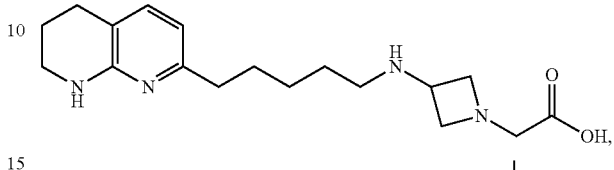
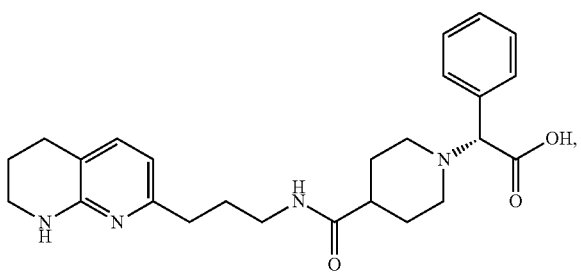
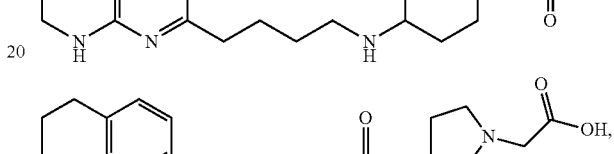
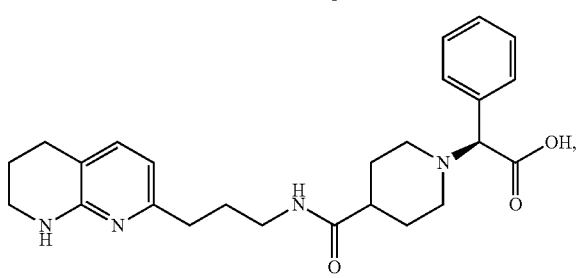
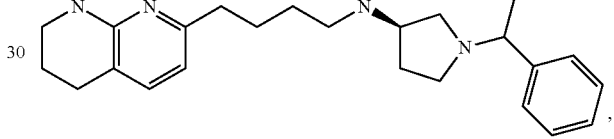
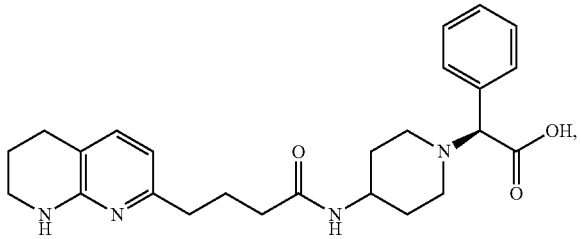
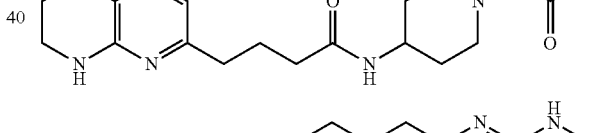
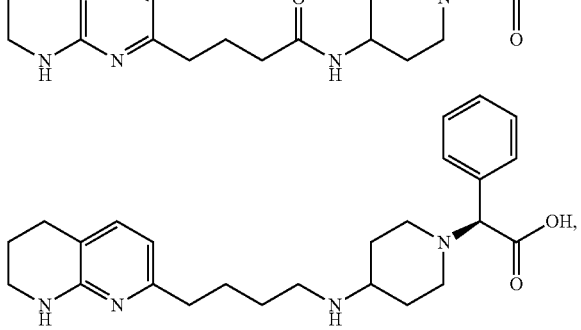
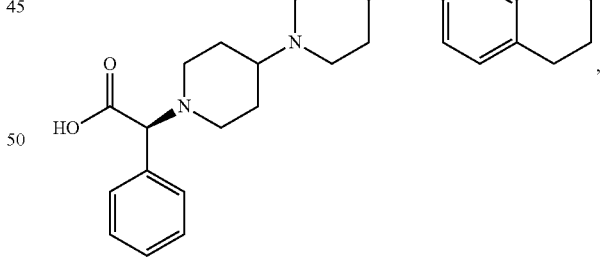
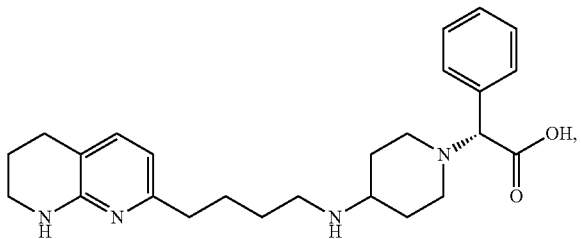
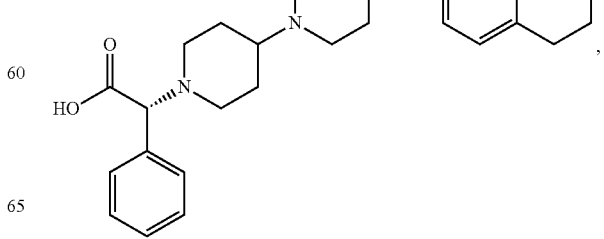

-continued
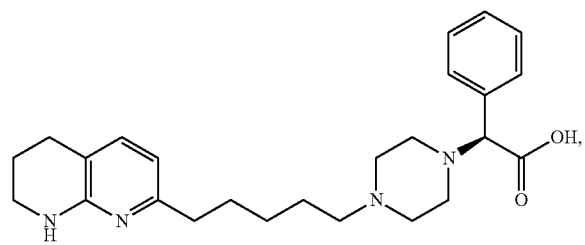
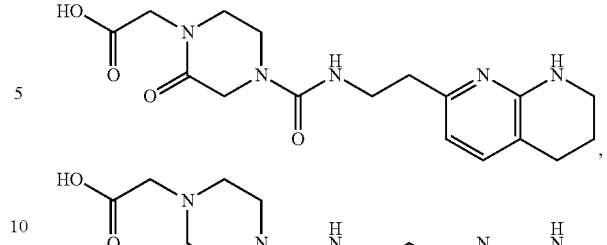
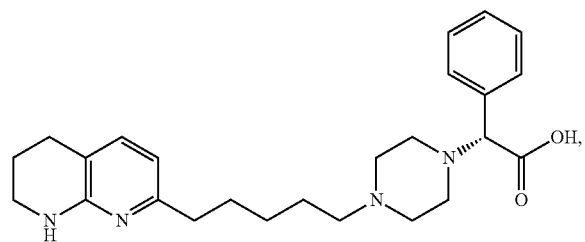
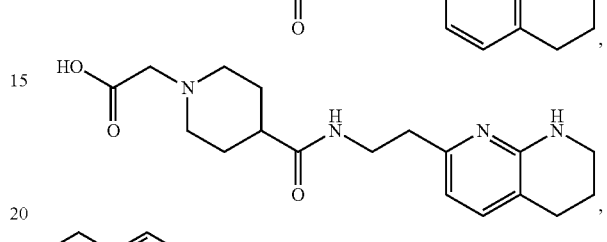
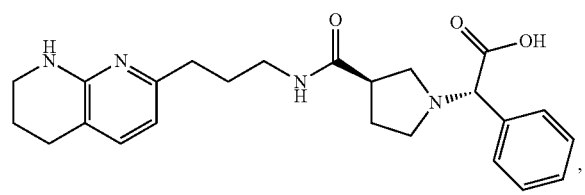
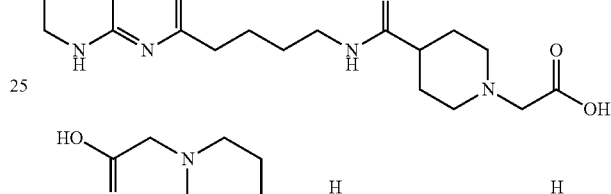
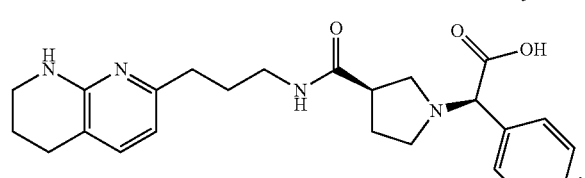
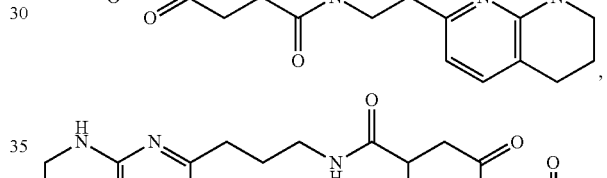
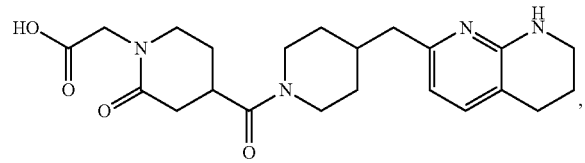
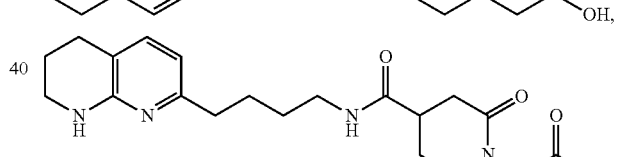
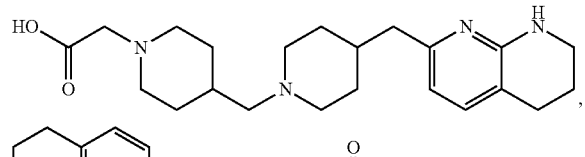
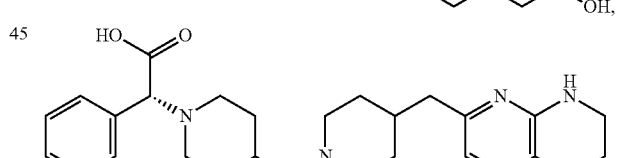
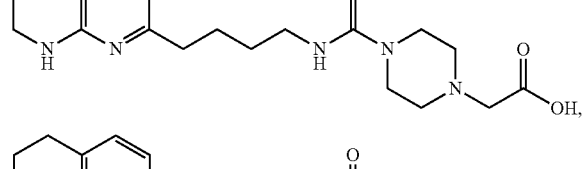
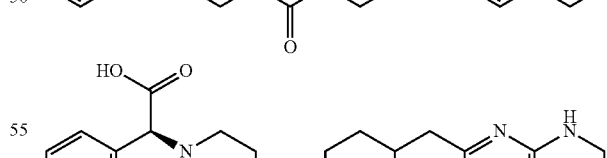
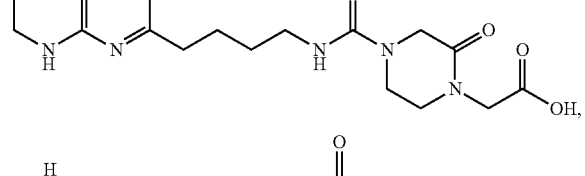
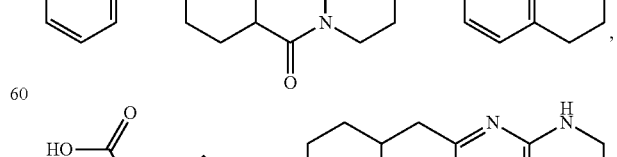
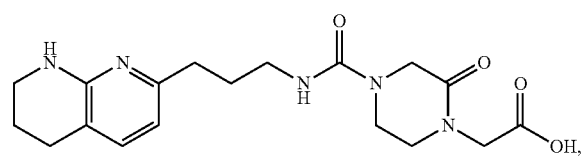
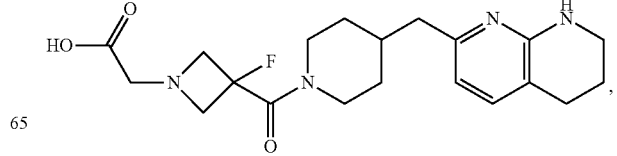

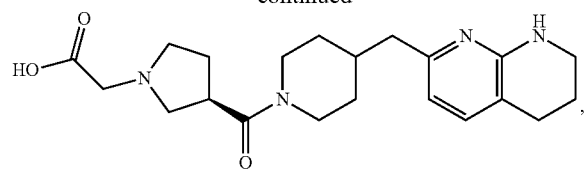
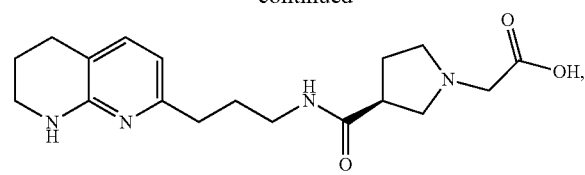
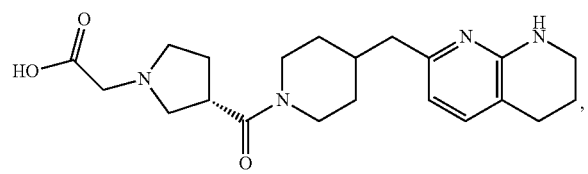
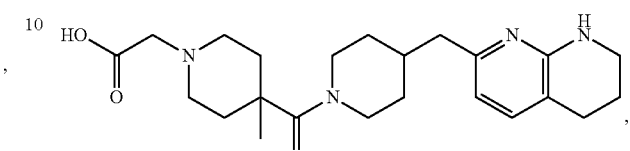
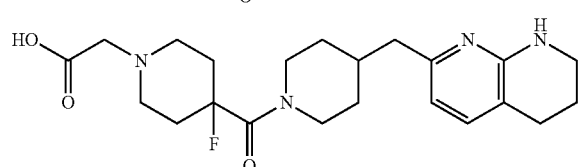
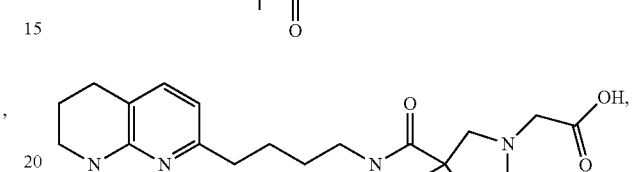
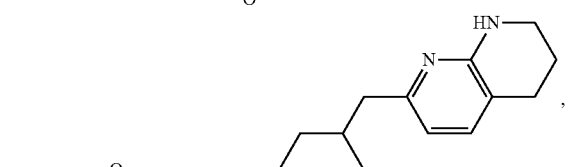
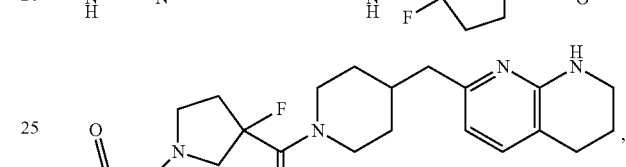
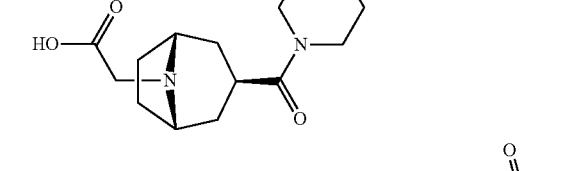
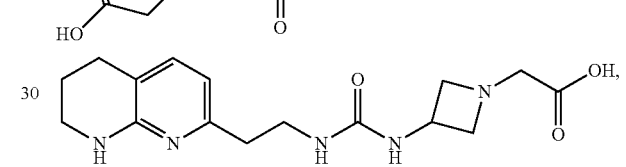
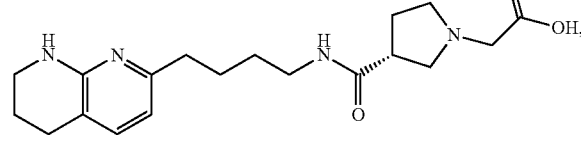
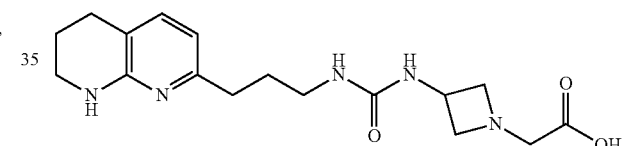
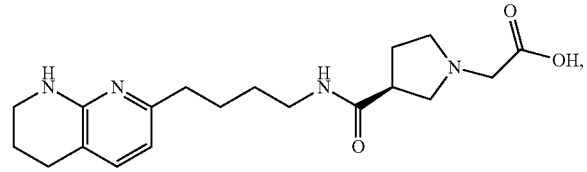
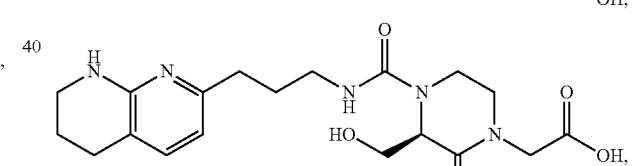
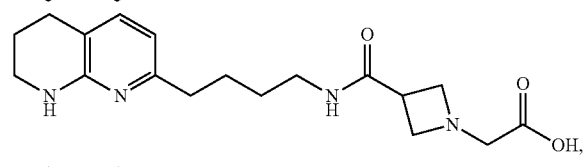
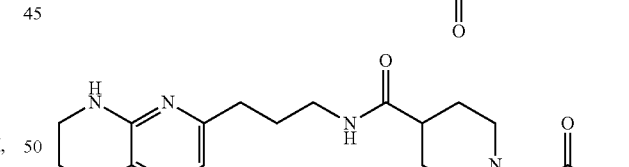
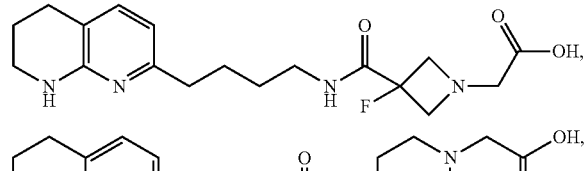
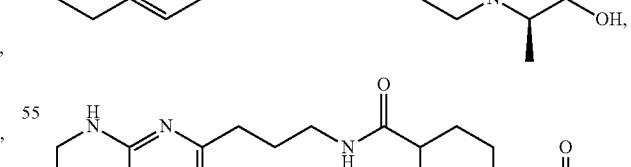
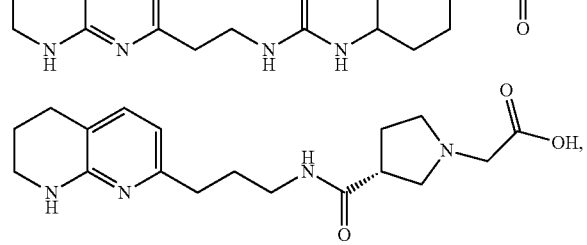
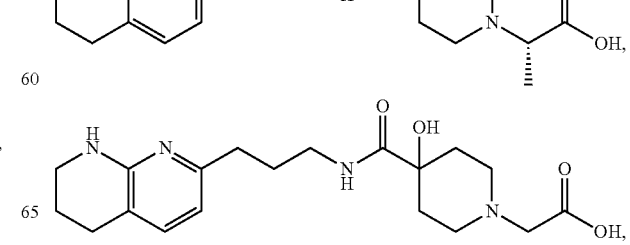

49
-continued
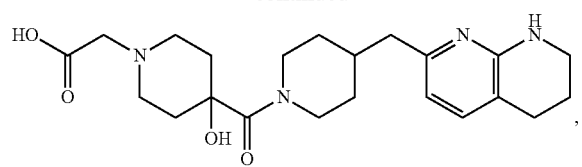
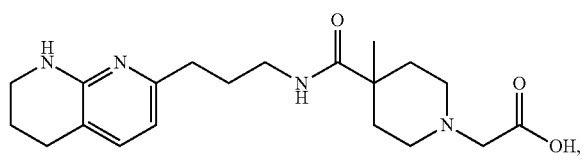
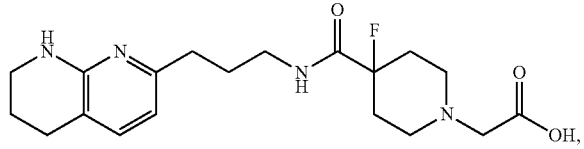
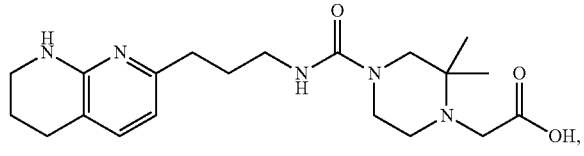
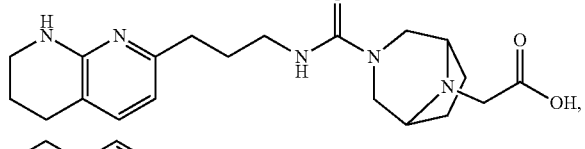
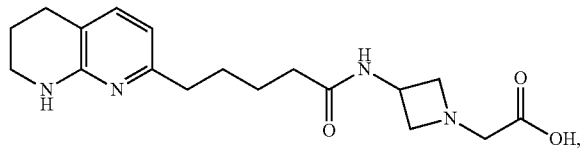
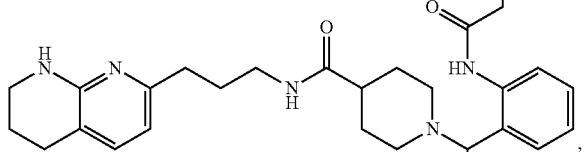
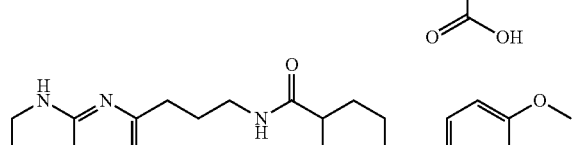
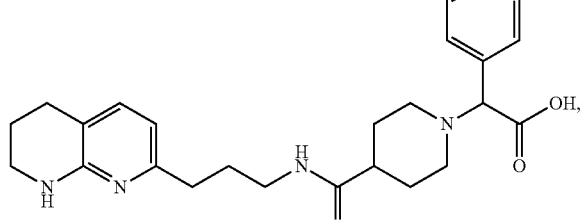
50
-continued
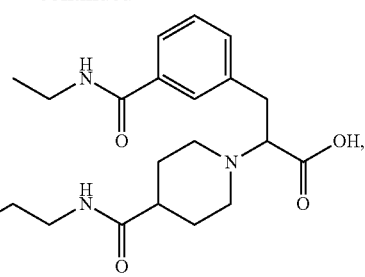
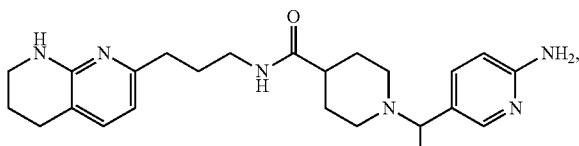
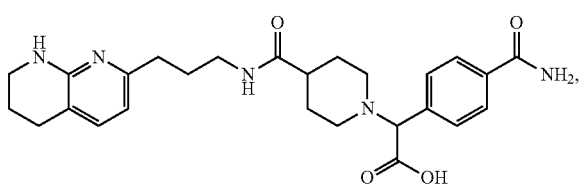
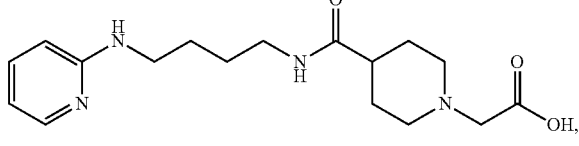
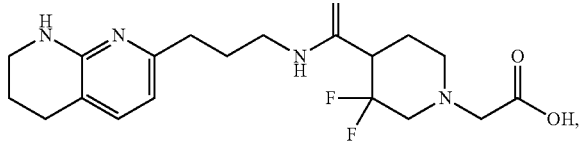
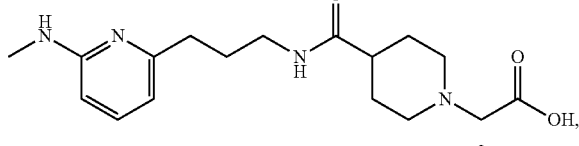
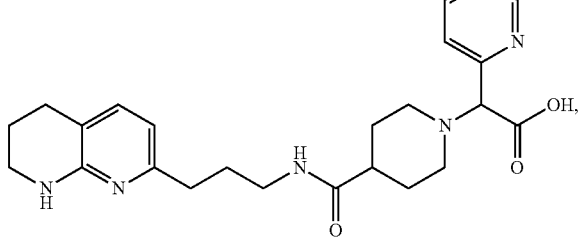
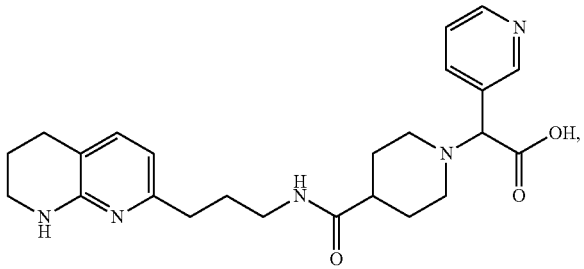

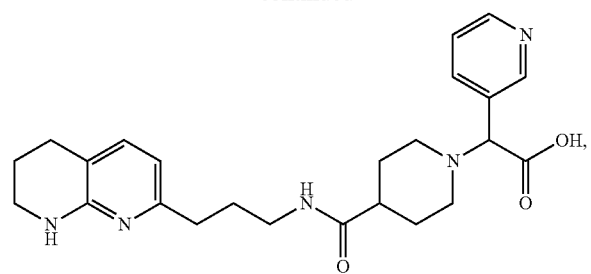
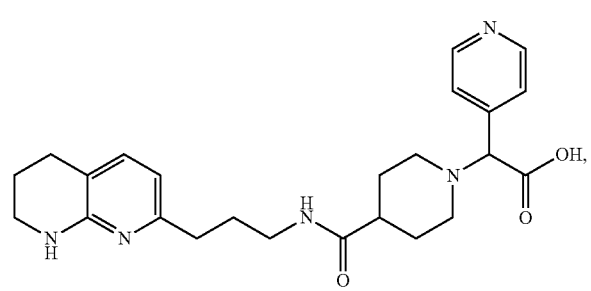
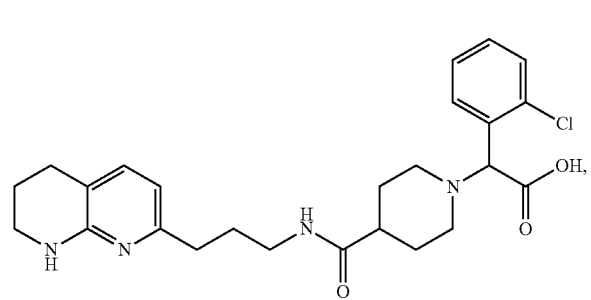
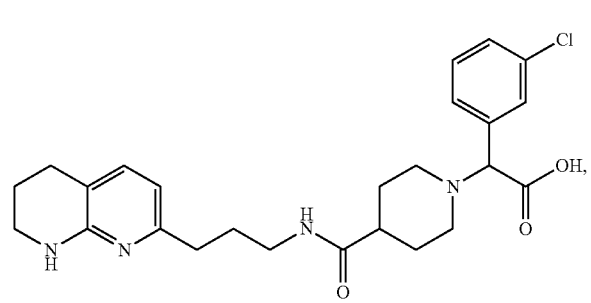
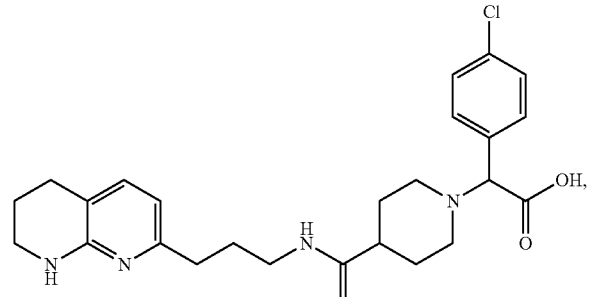
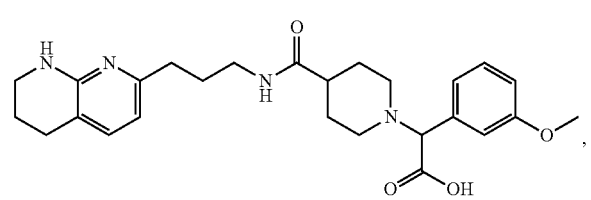
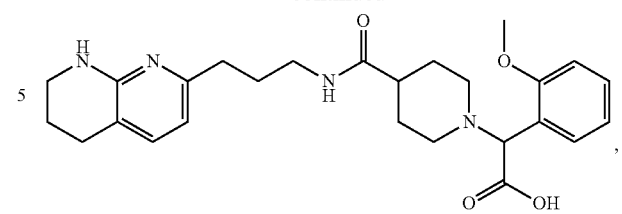
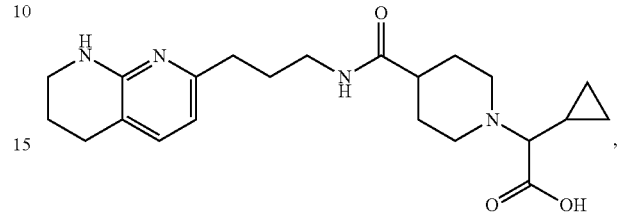
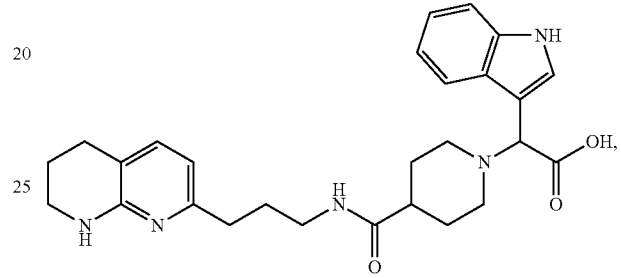
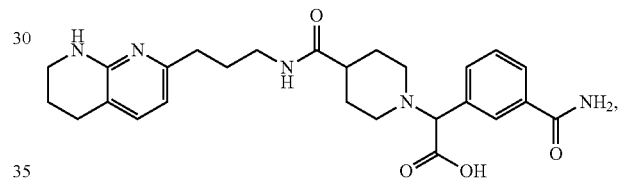
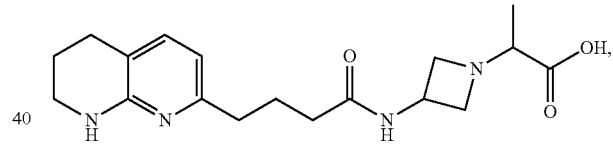
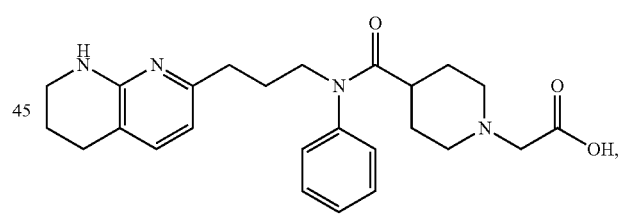
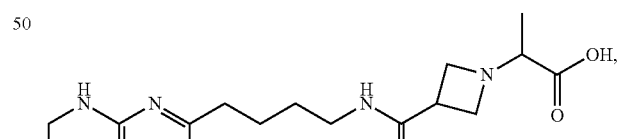
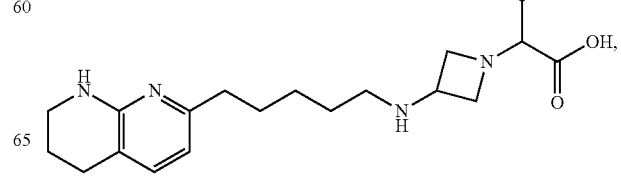

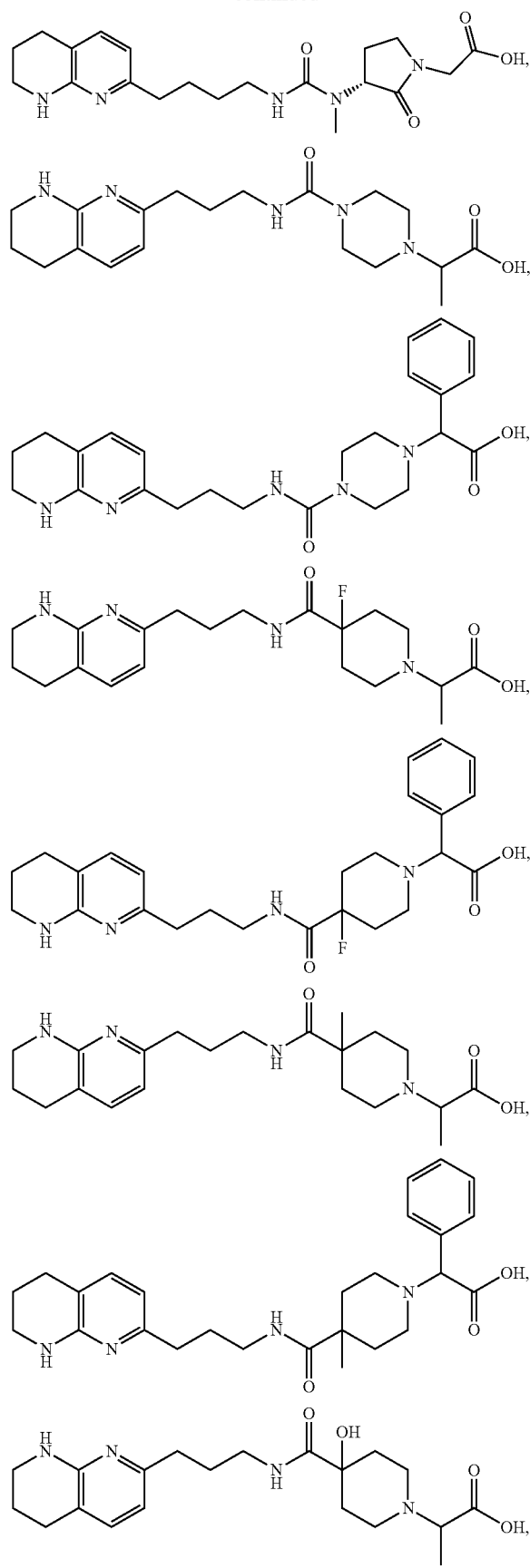
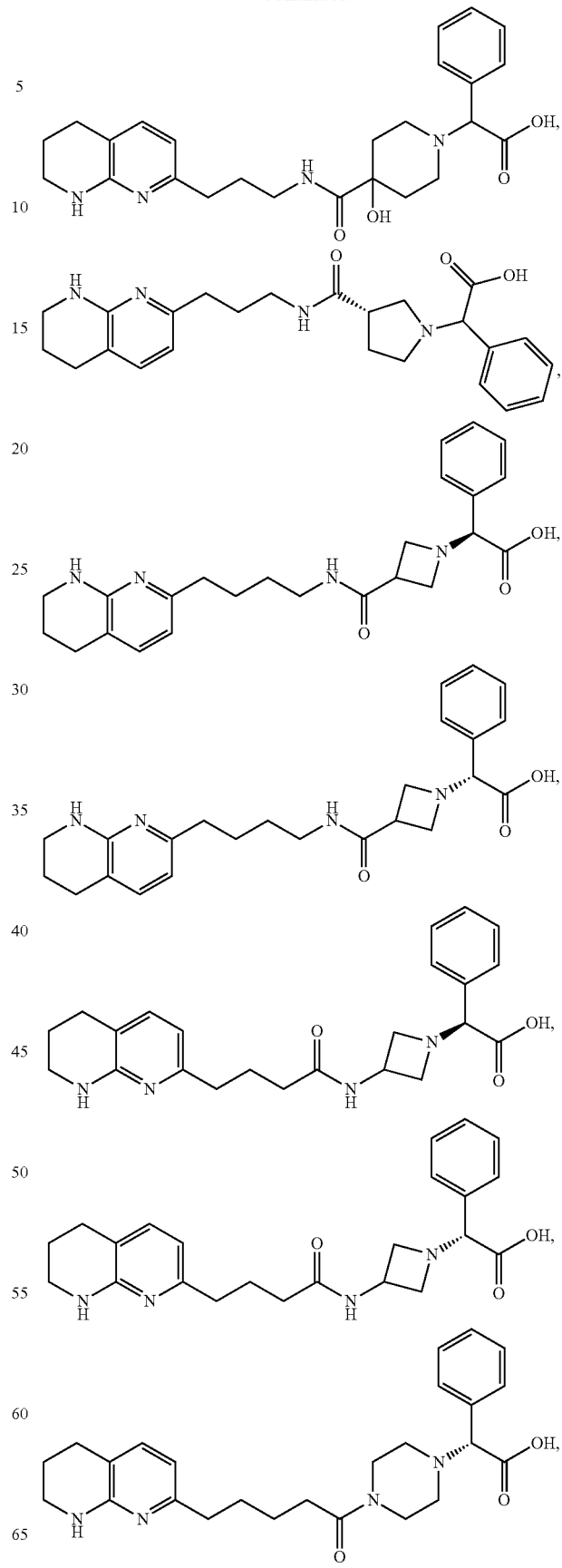

55
-continued
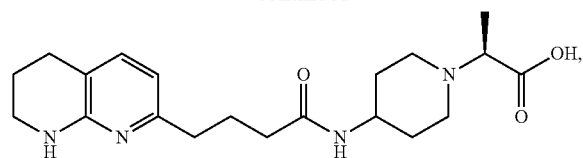
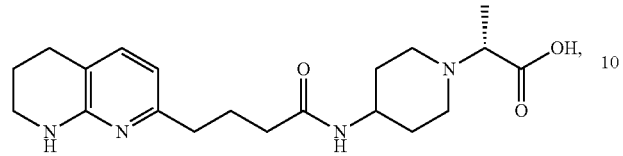
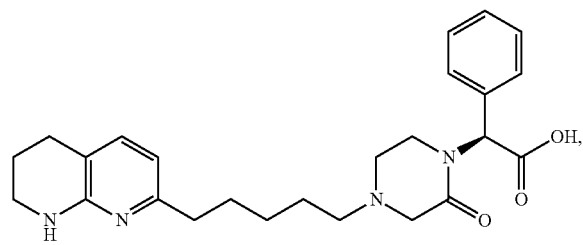
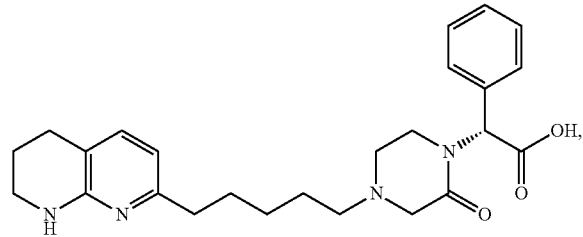
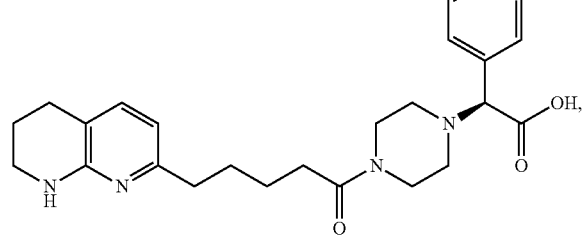
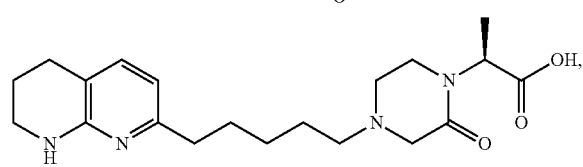
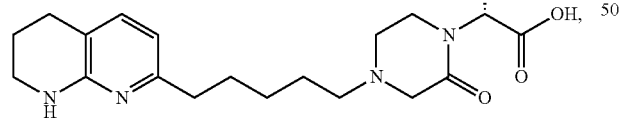
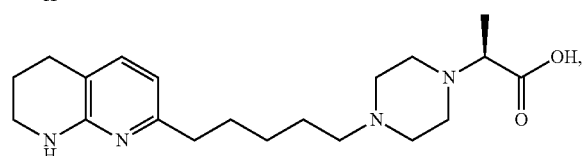
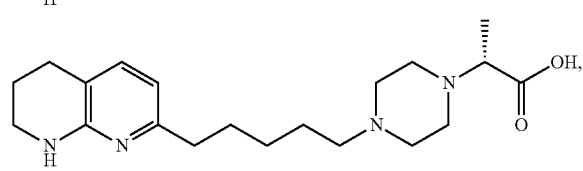
56
-continued
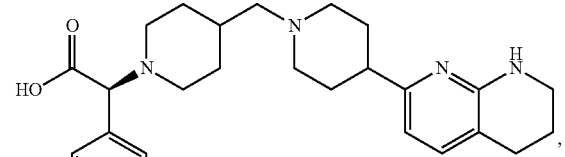
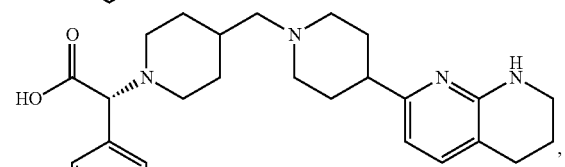
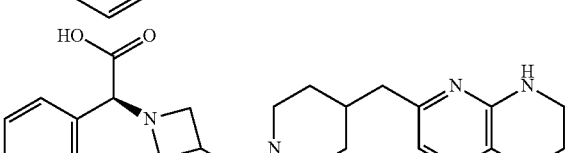
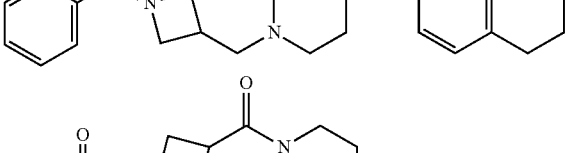
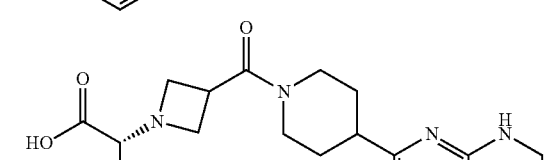
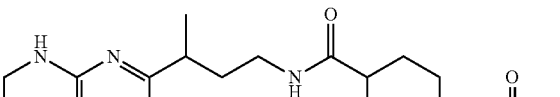
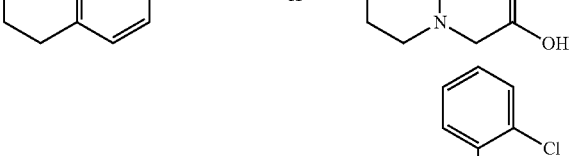
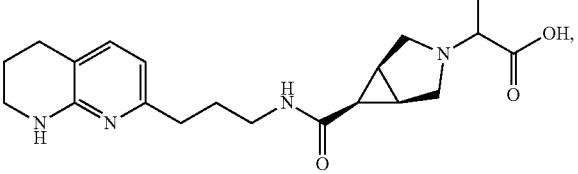

In certain embodiments, the invention relates to a compound selected from the group consisting of:

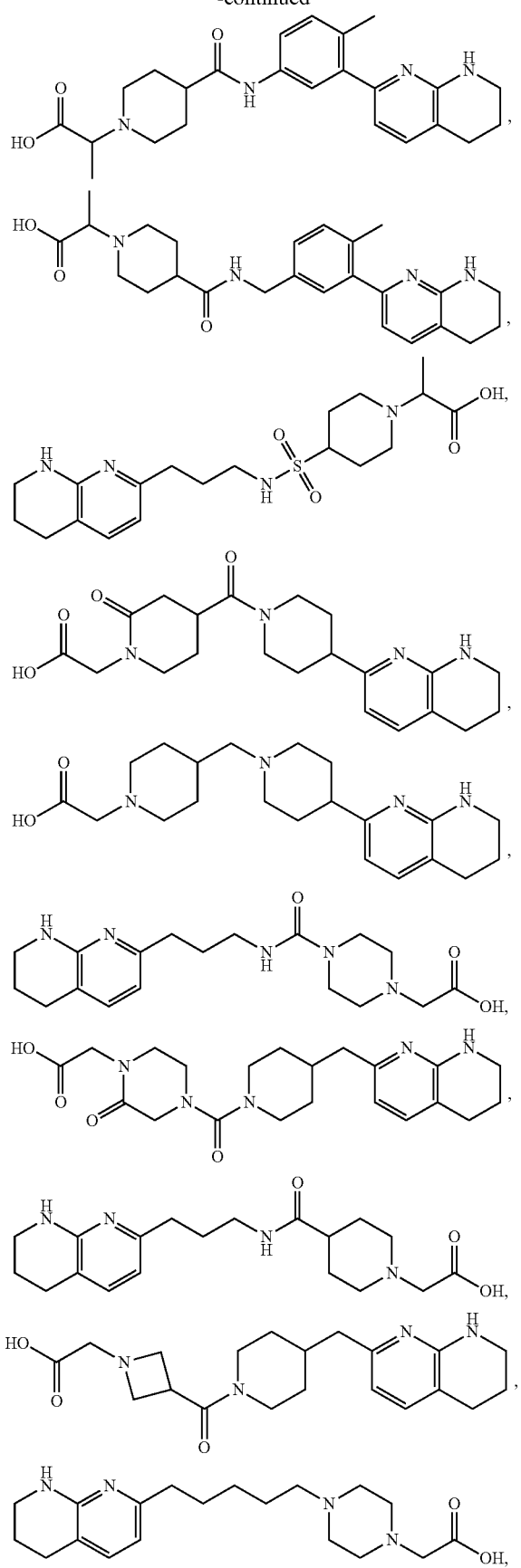
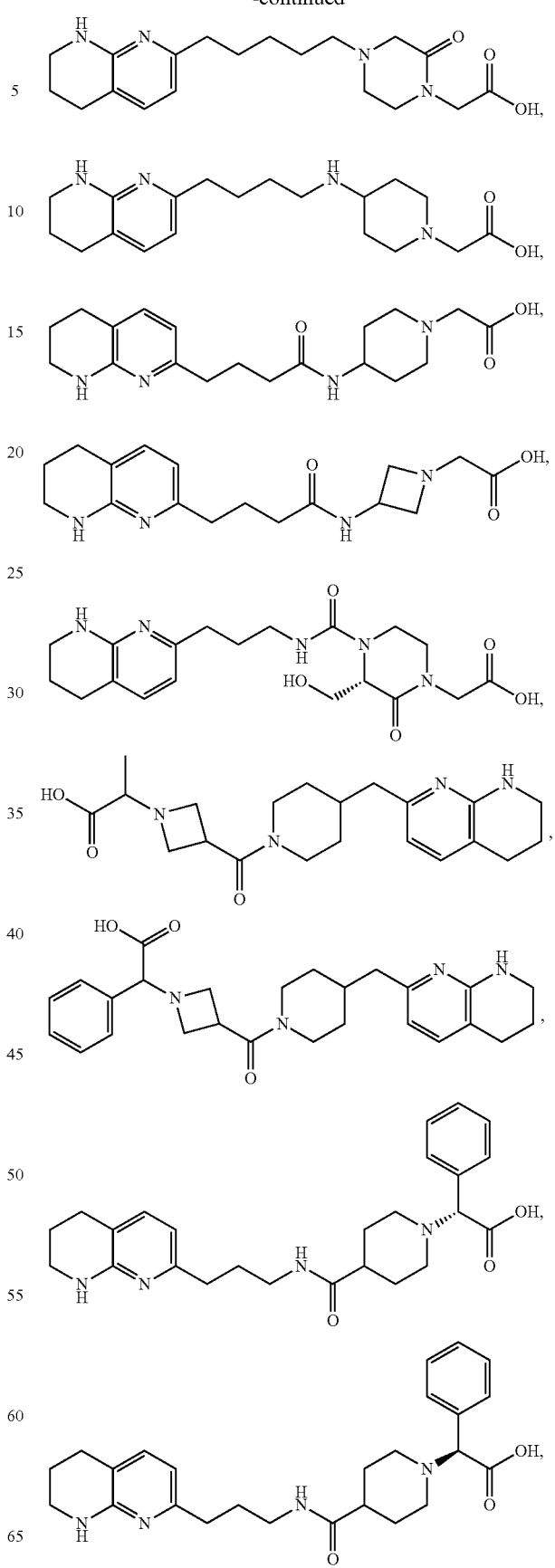

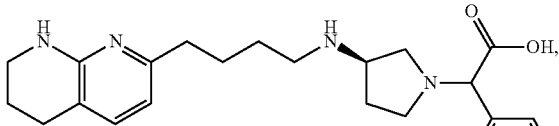
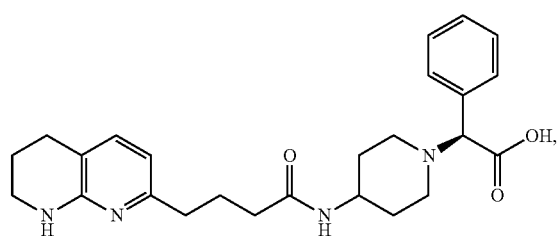
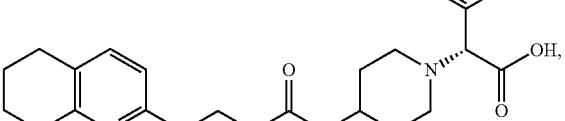
and
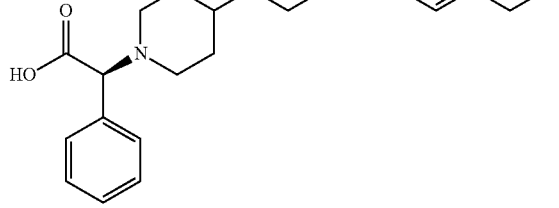
In certain embodiments, the invention relates to a compound selected from the group consisting of:
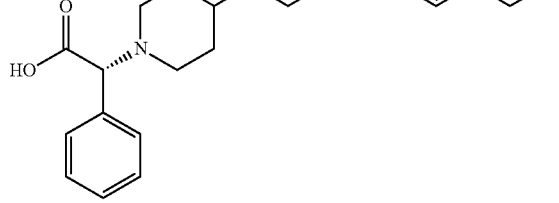
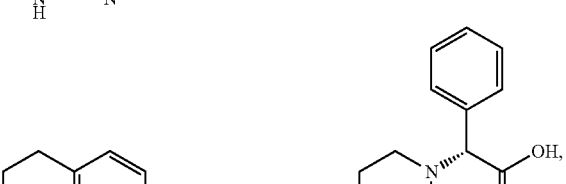
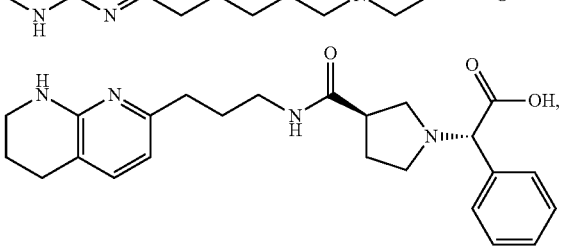

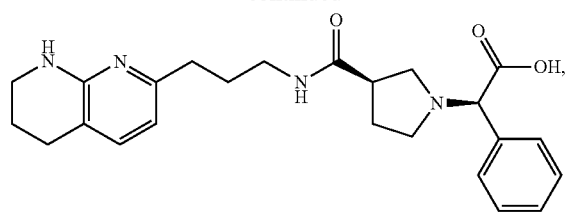
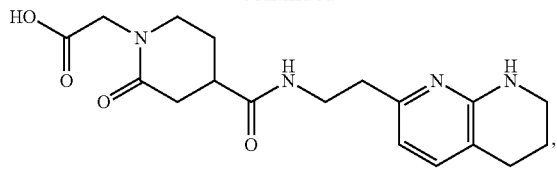
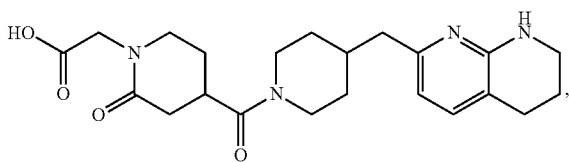
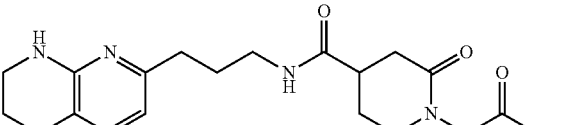
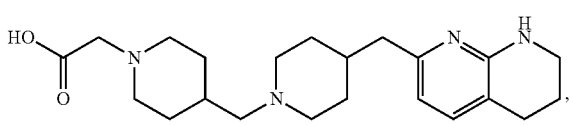
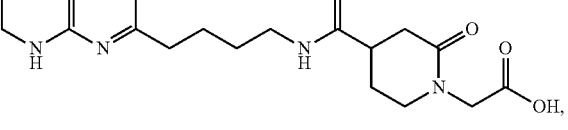
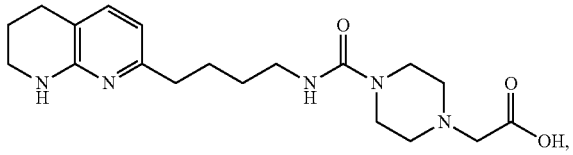
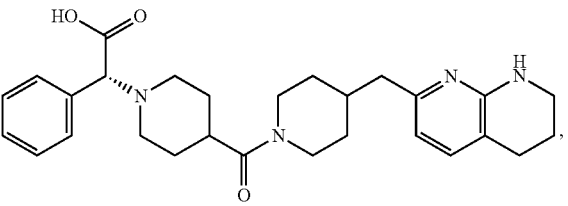
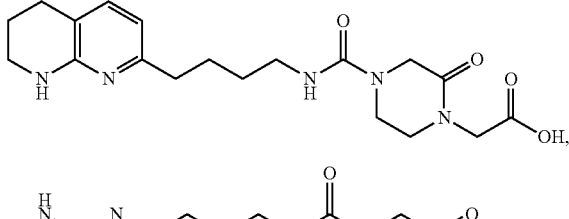
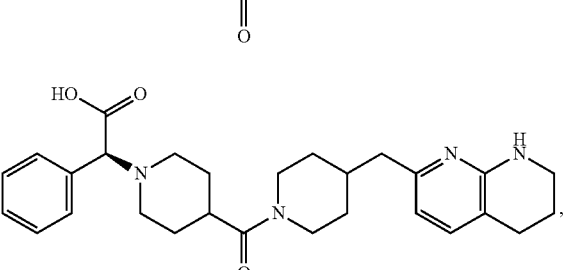
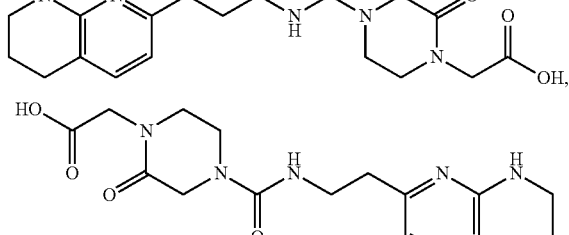
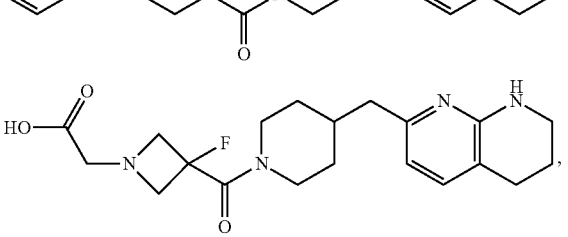
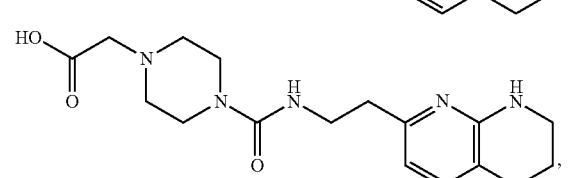
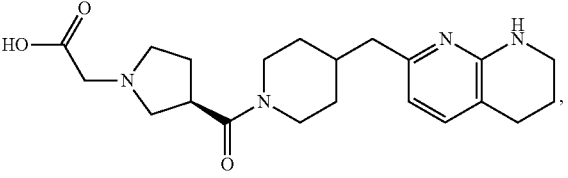
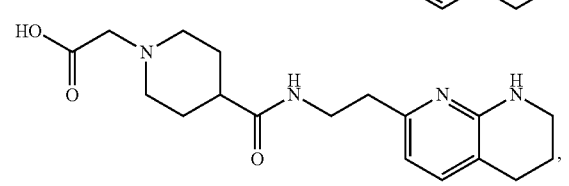
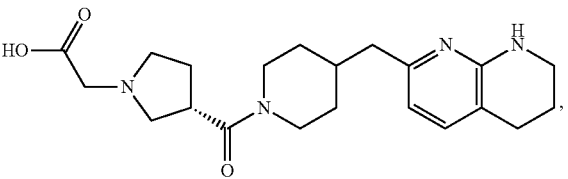
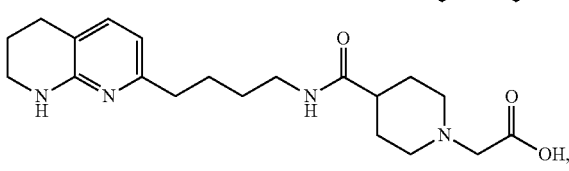
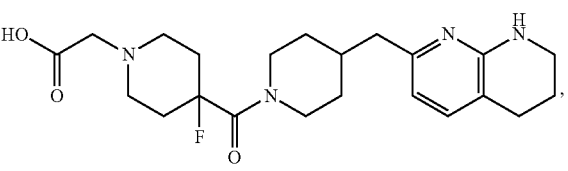

65
-continued
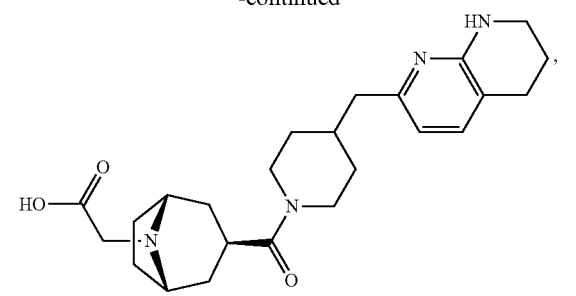
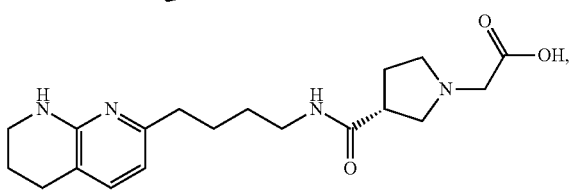
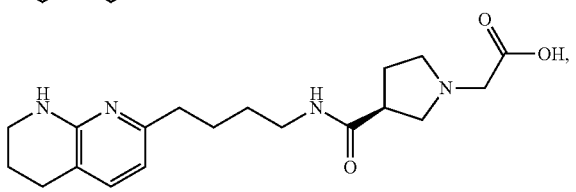
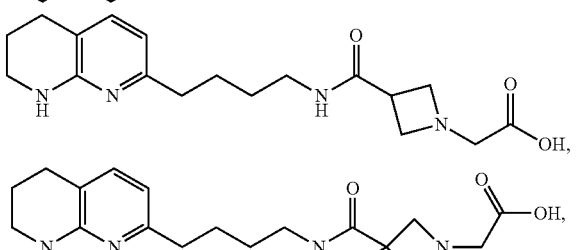
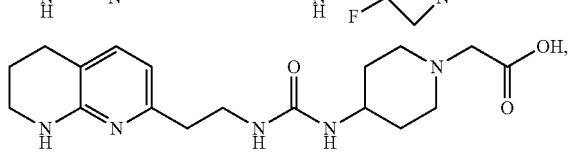
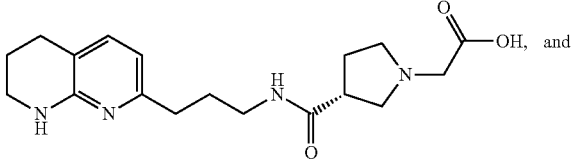
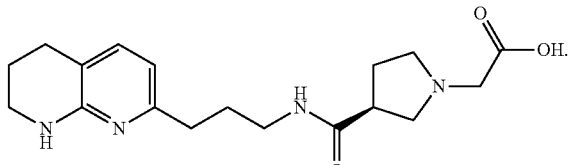
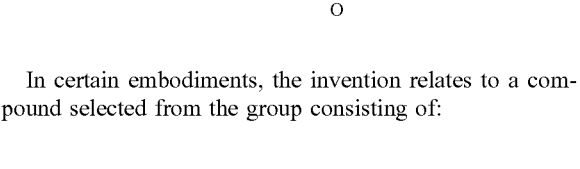
In certain embodiments, the invention relates to a compound selected from the group consisting of:
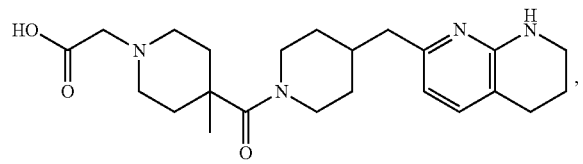
66
-continued
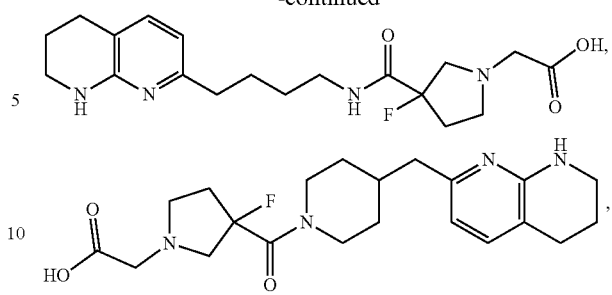
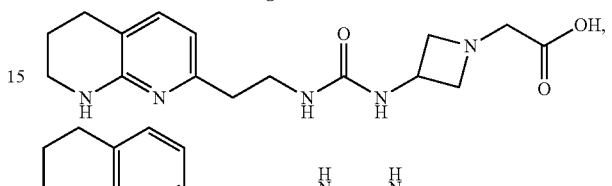
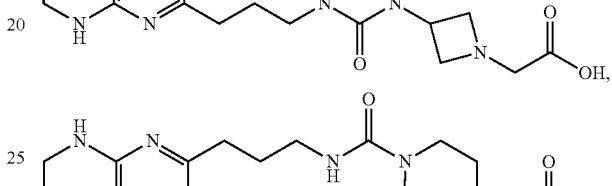
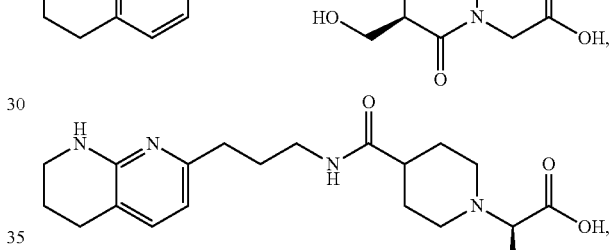
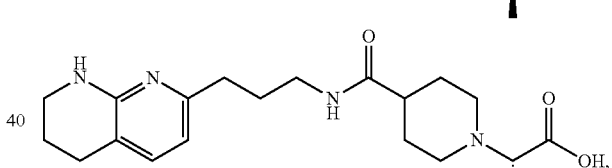
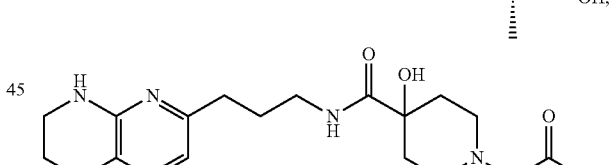
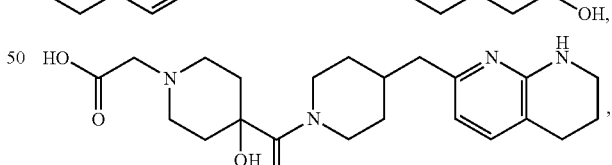
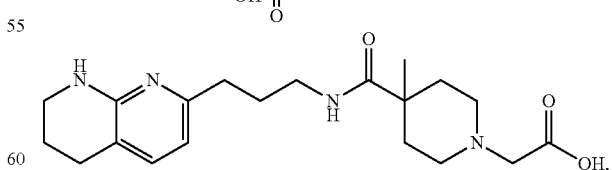
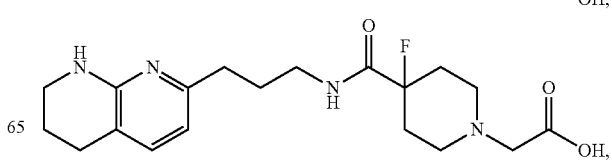

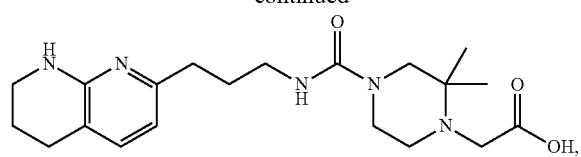
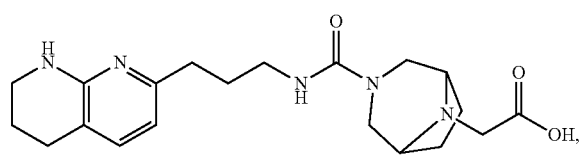
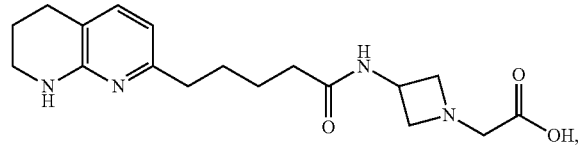
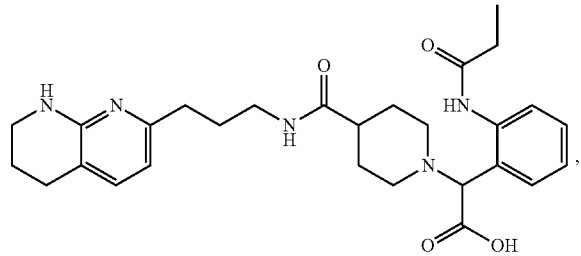
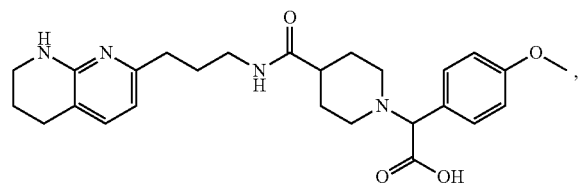
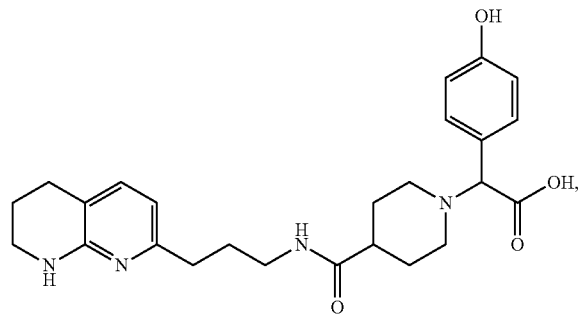
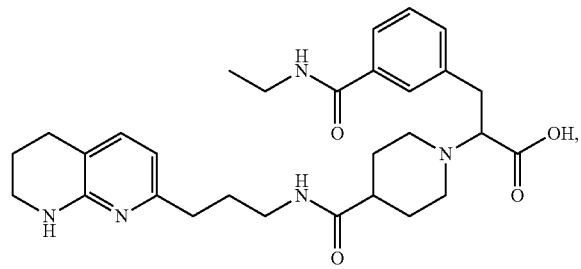
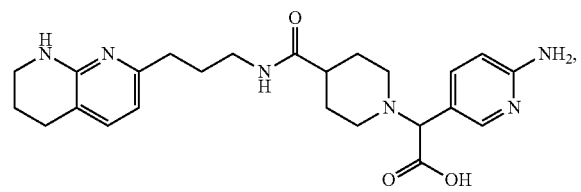
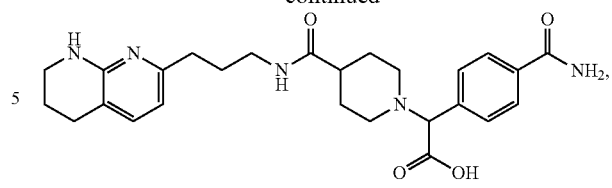
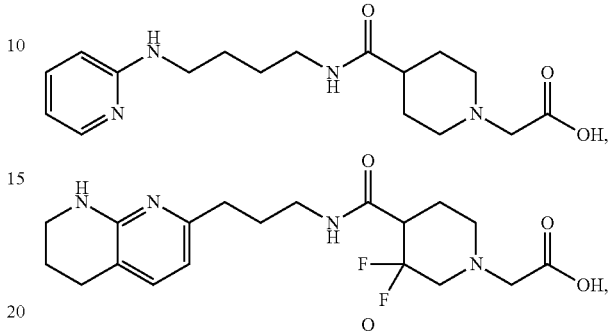
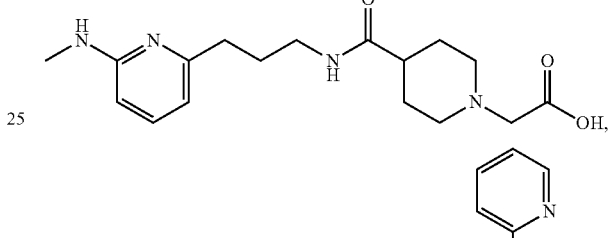
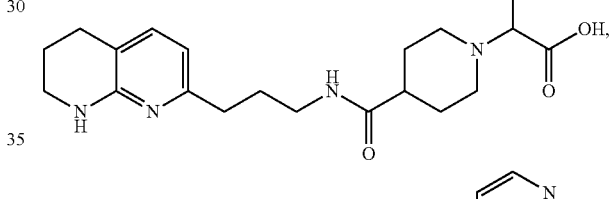
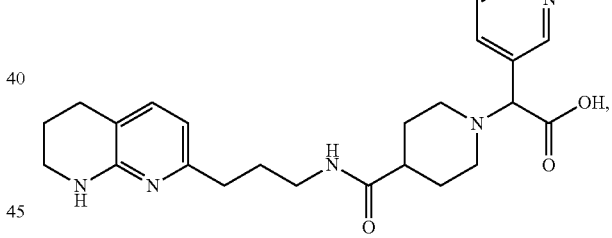
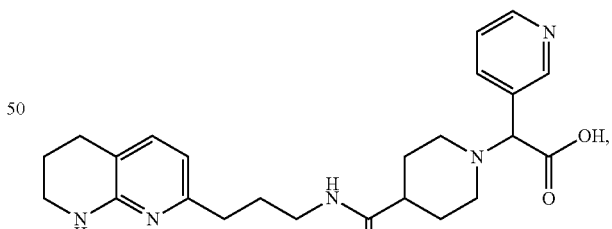
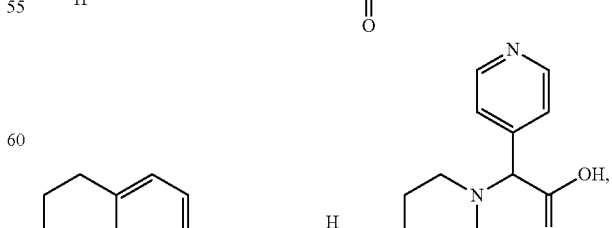
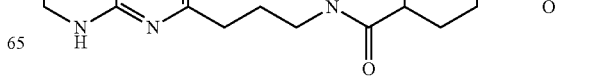

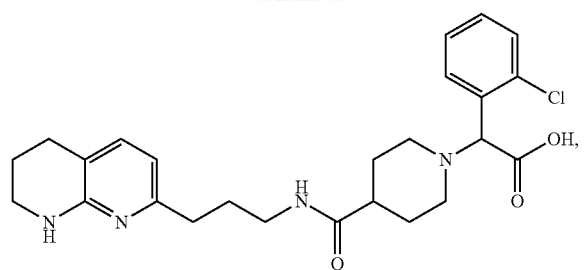
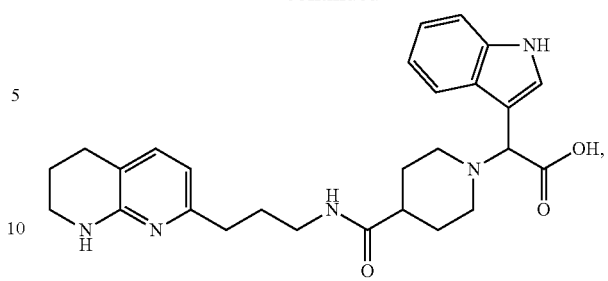
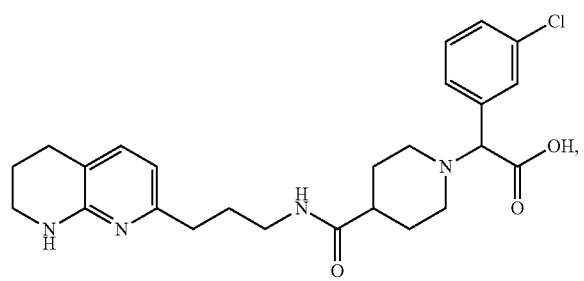
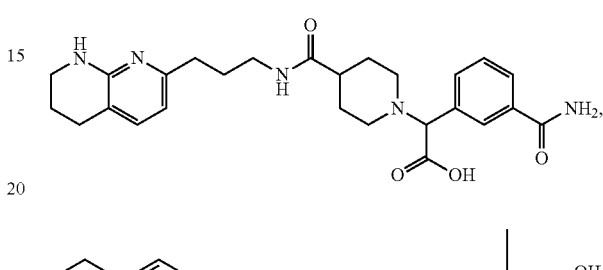
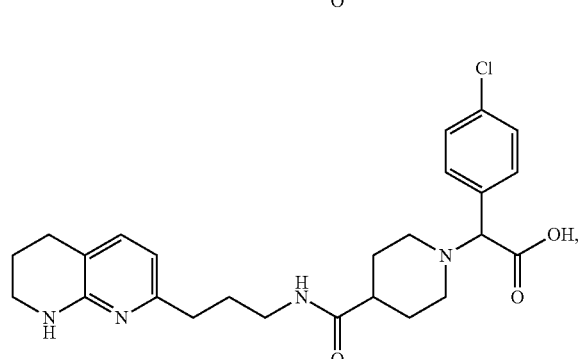
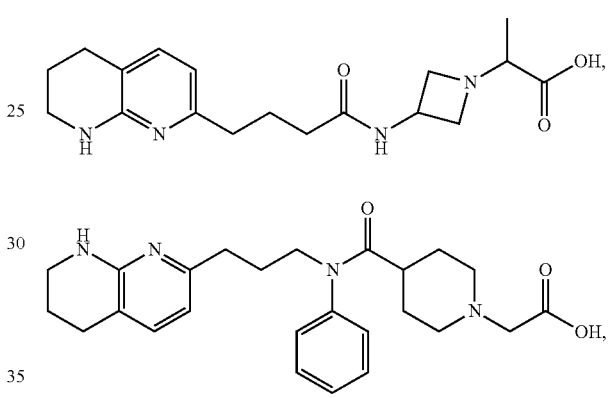
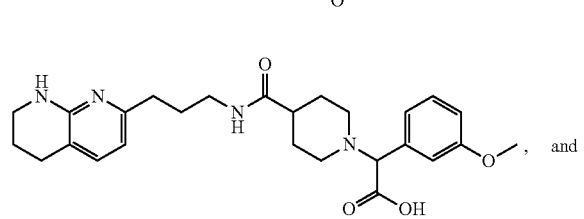, and
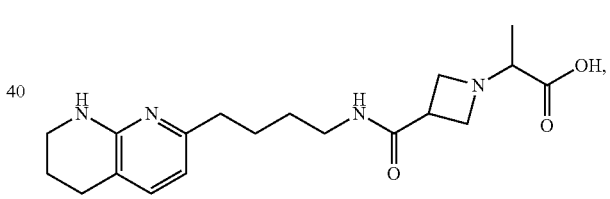
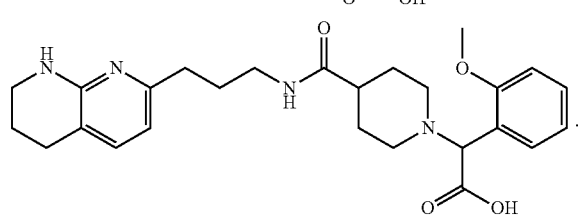
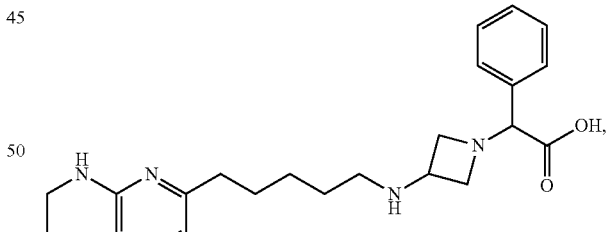
In certain embodiments, the invention relates to a compound selected from the group consisting of:
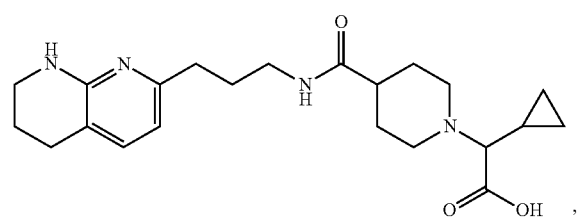
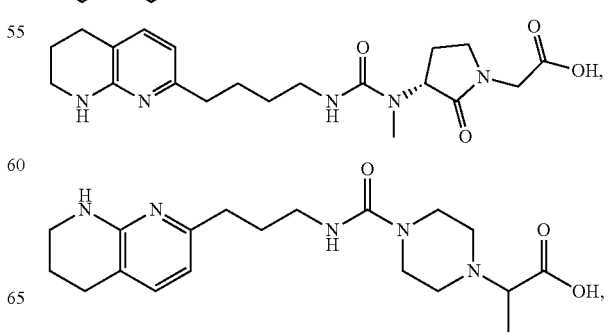

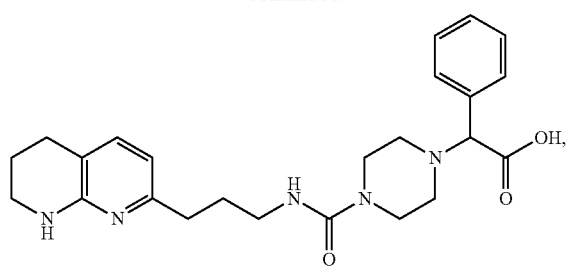
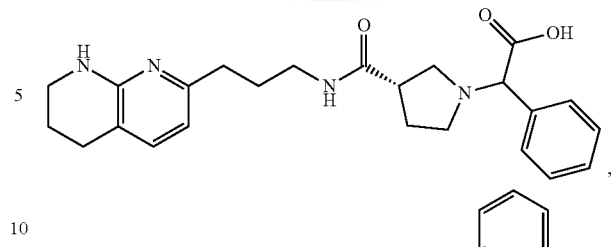
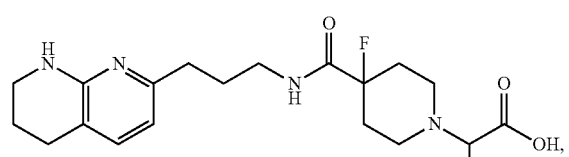
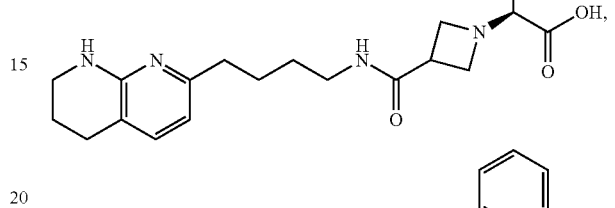
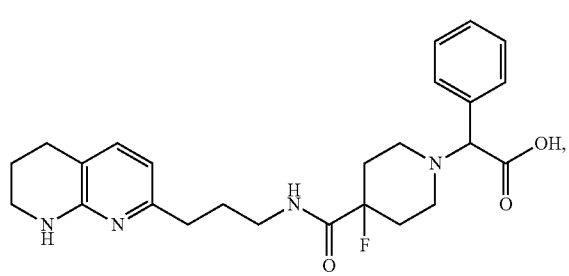
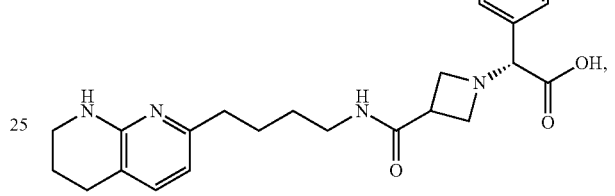
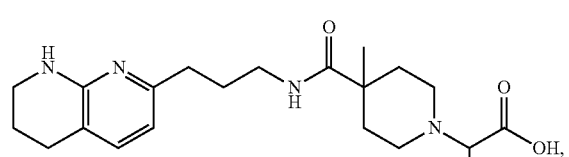
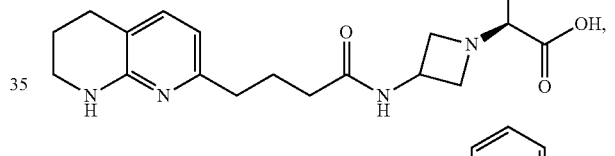
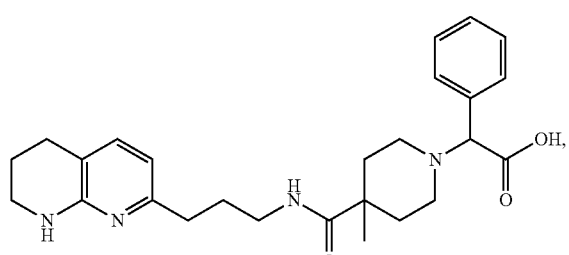
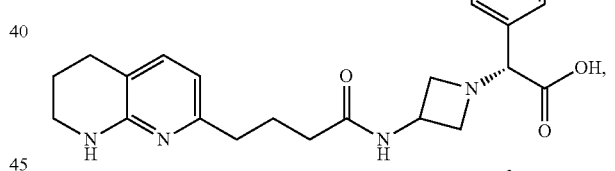
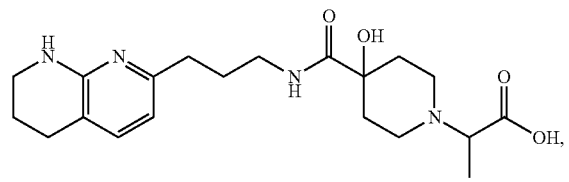
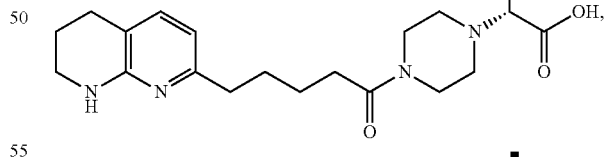
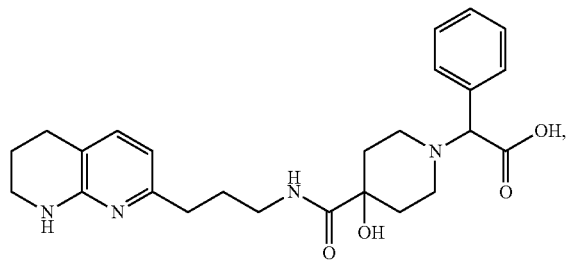
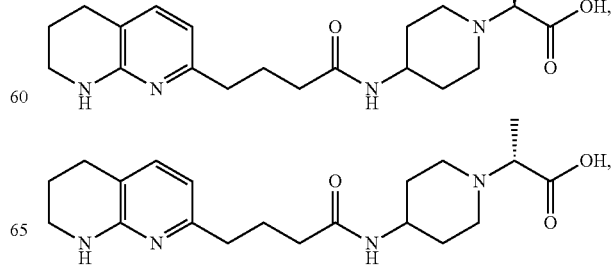

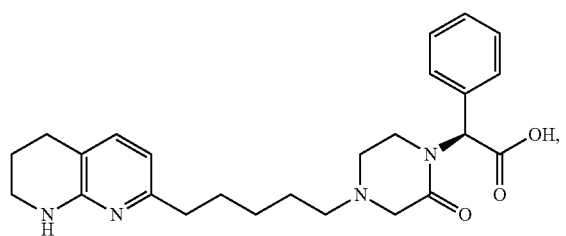
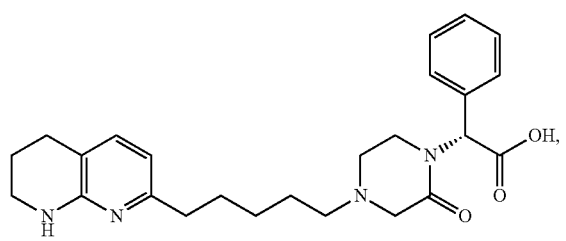
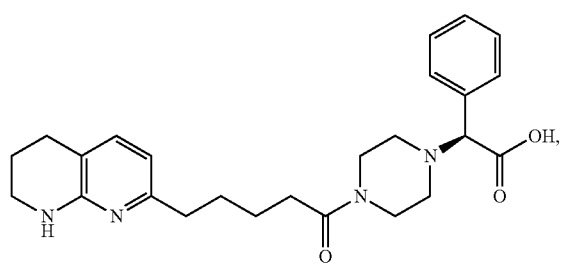
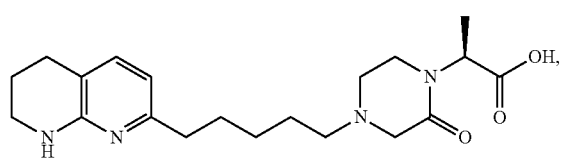
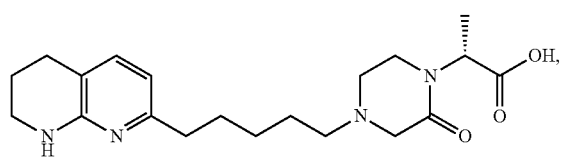
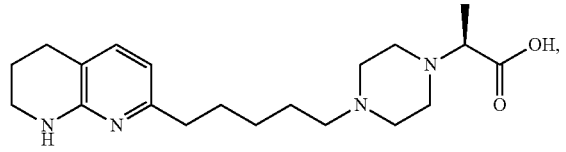
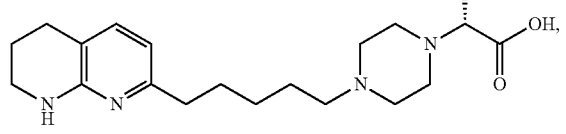
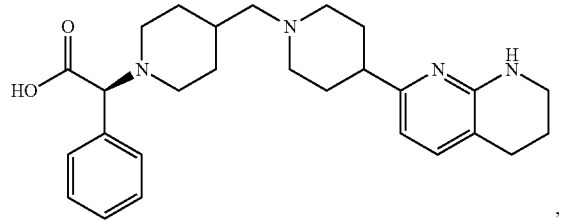
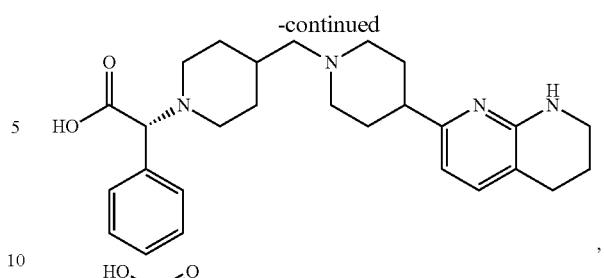
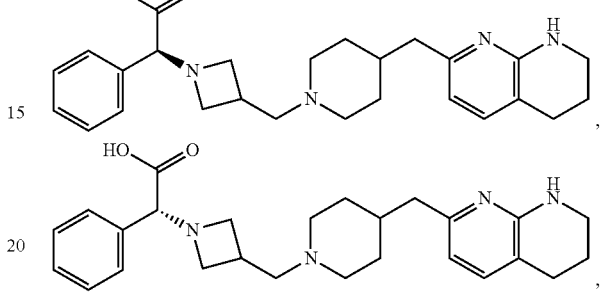
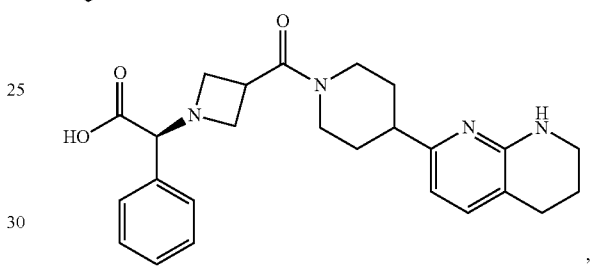
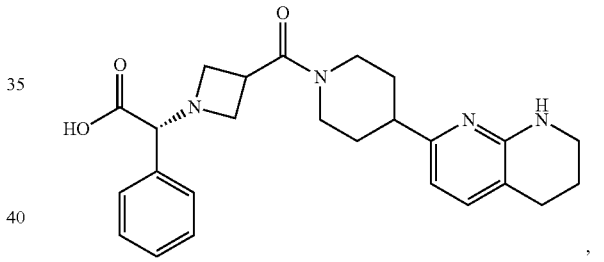
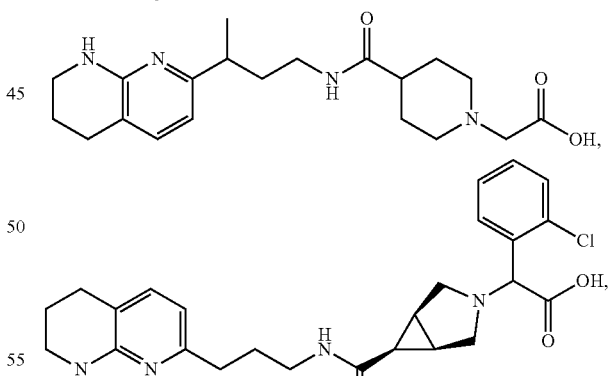
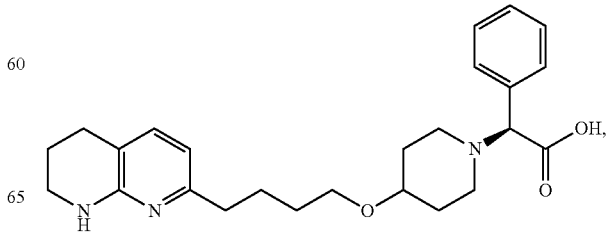

-continued
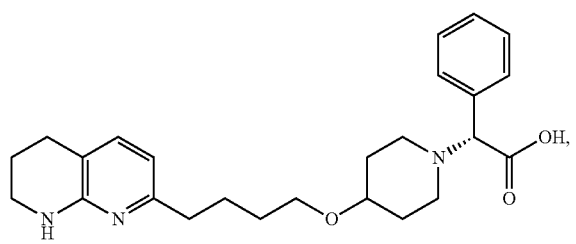
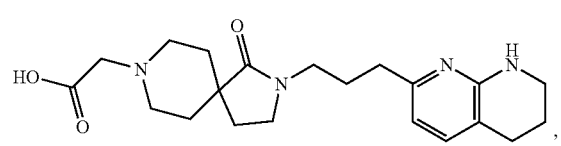
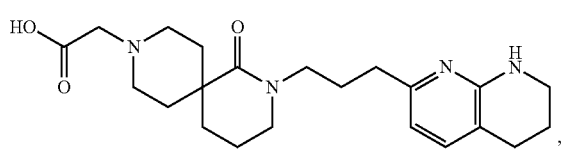
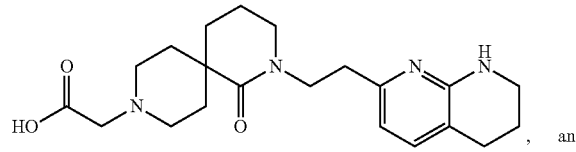
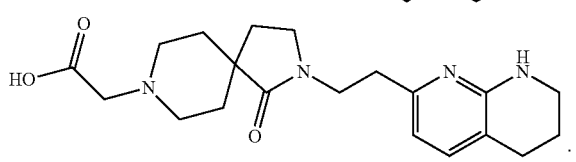
-continued
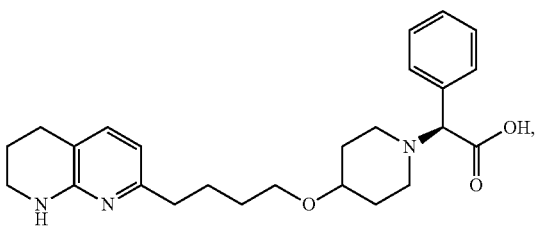
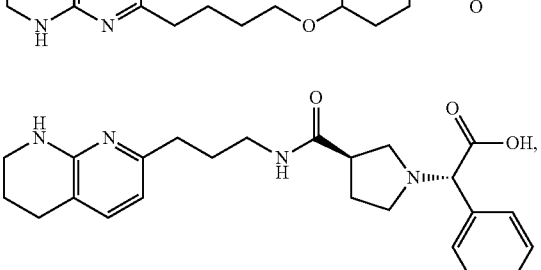
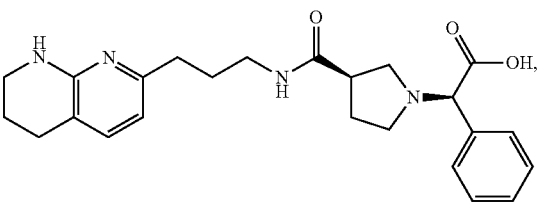
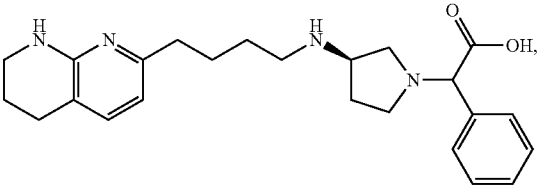
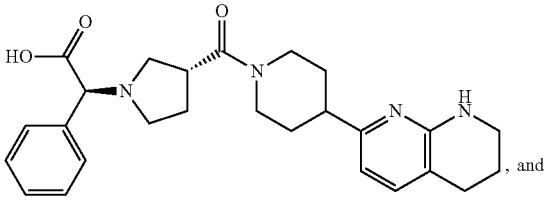
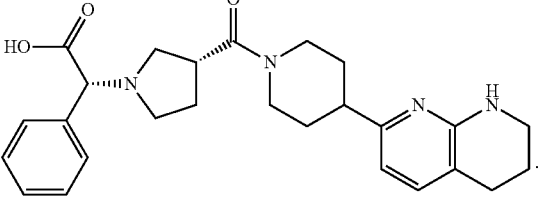
In certain embodiments, the invention relates to a compound selected from the group consisting of:
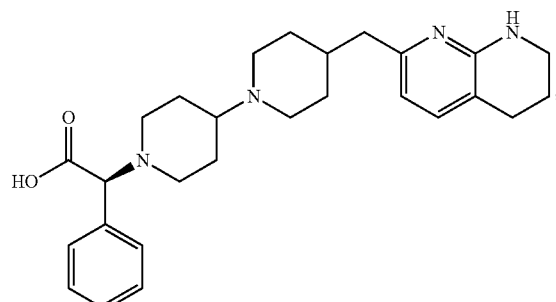
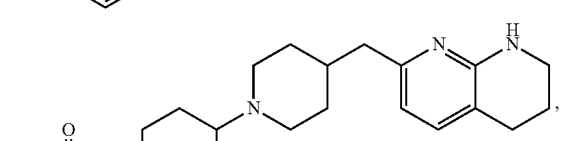
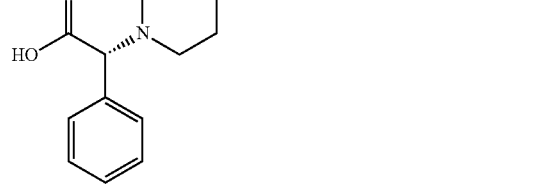
, and
.
In certain embodiments, the invention relates to a compound selected from the group consisting of:

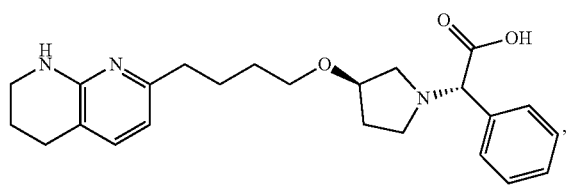
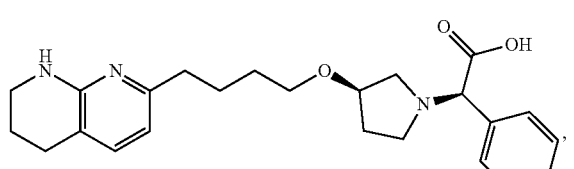
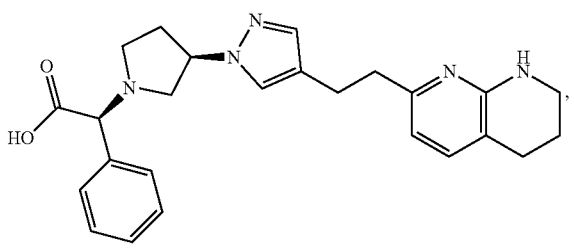
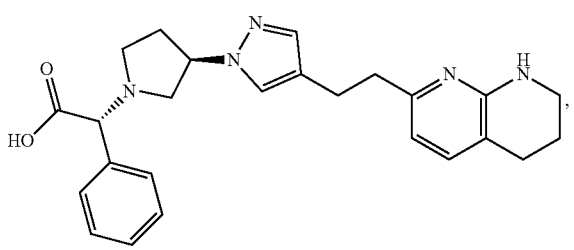
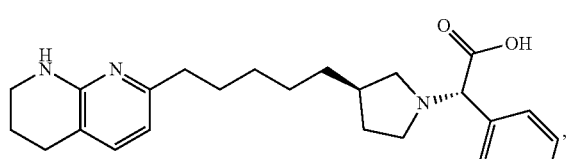
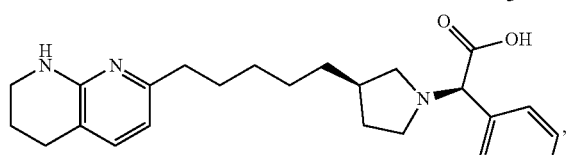
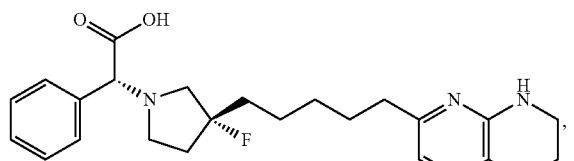
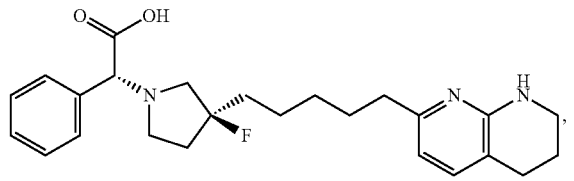
-continued
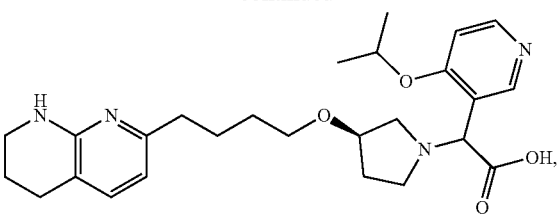
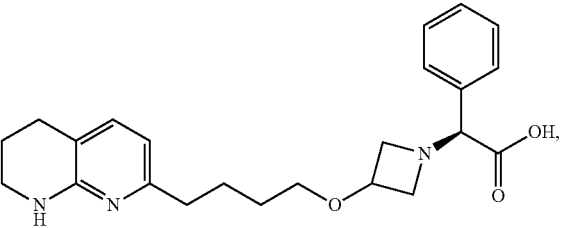
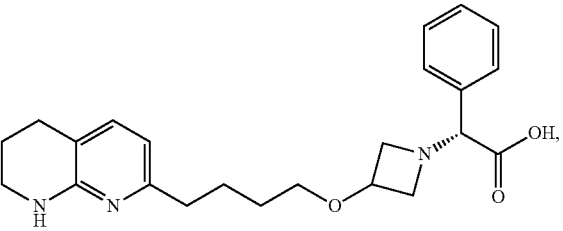
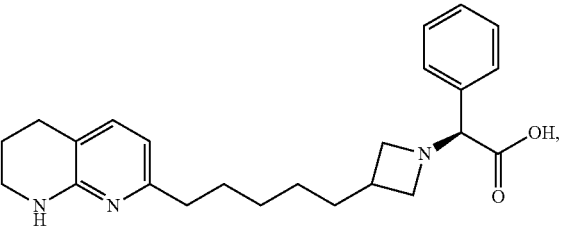
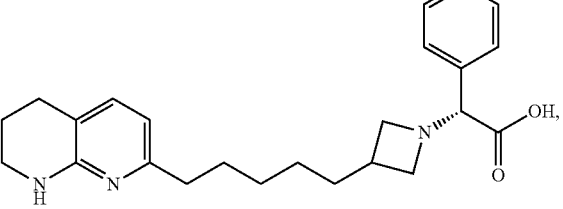
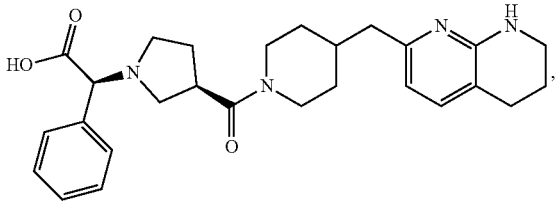
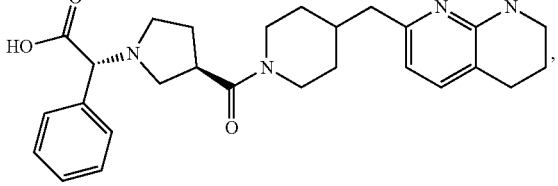

79
-continued
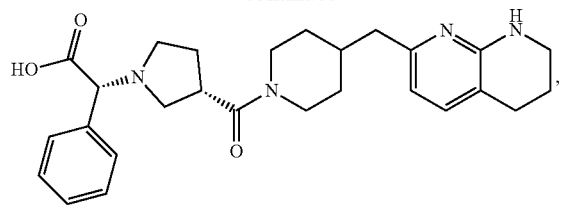
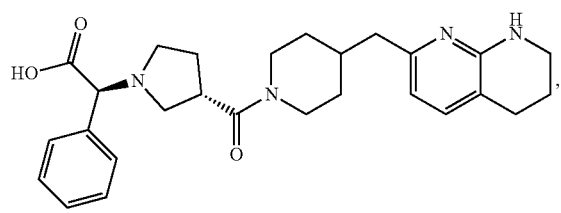
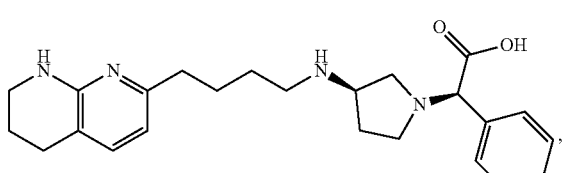
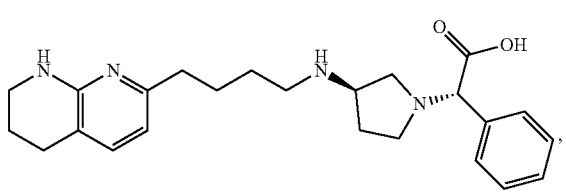
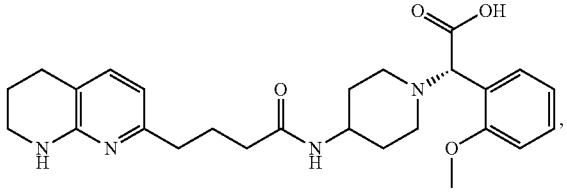
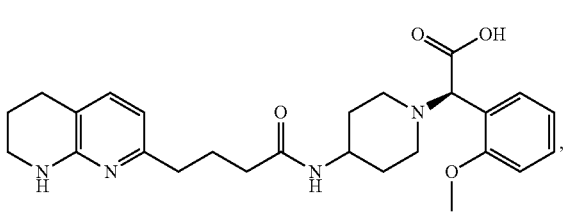
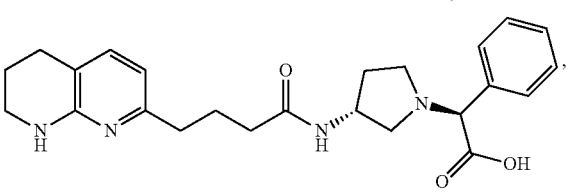
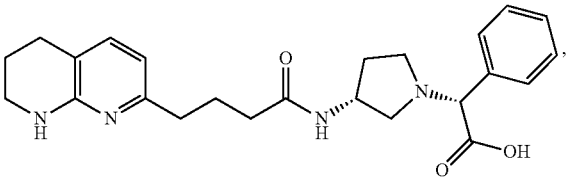
80
-continued
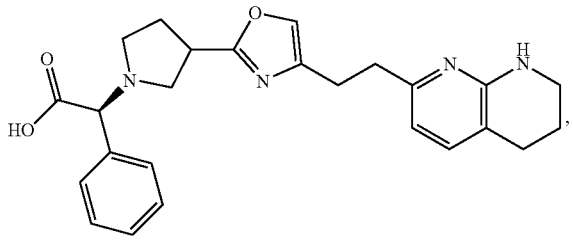
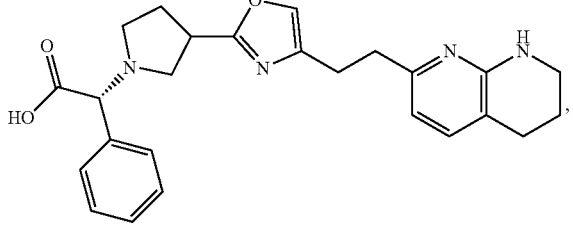
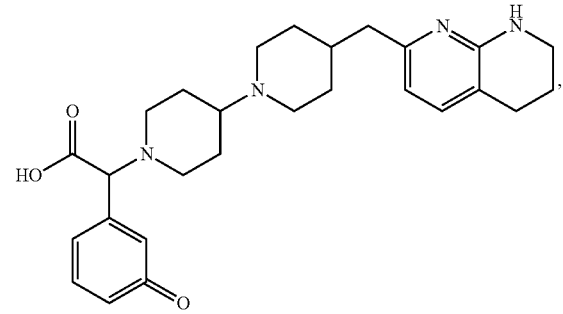
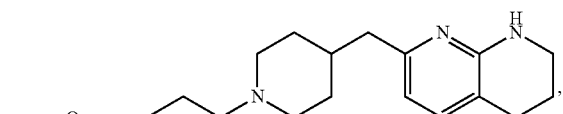
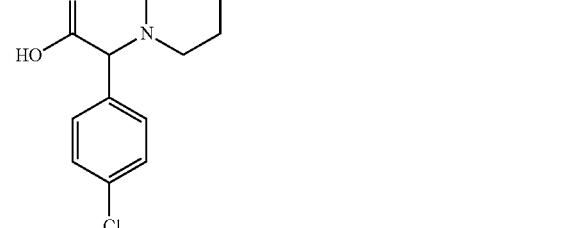
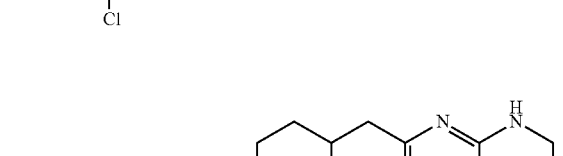
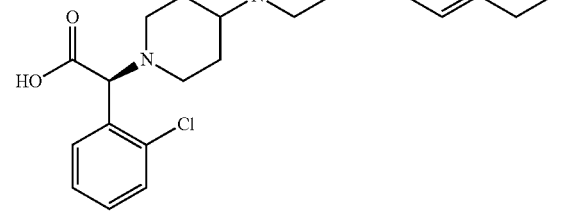

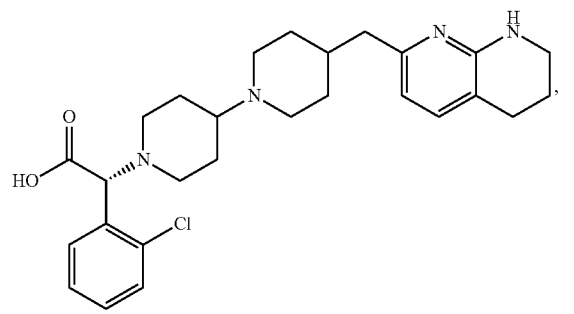
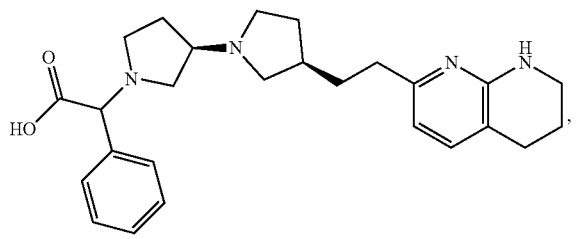
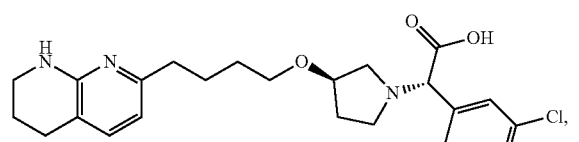
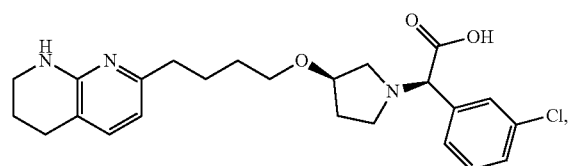
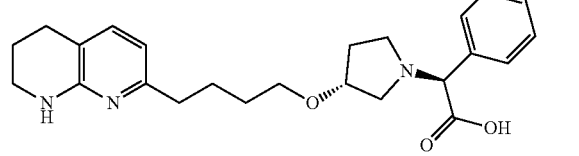
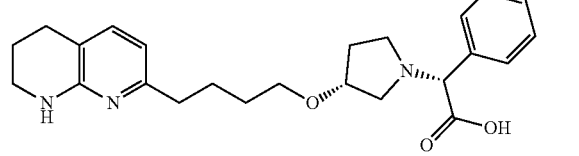
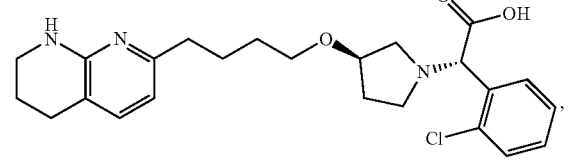
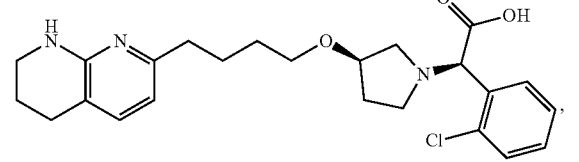
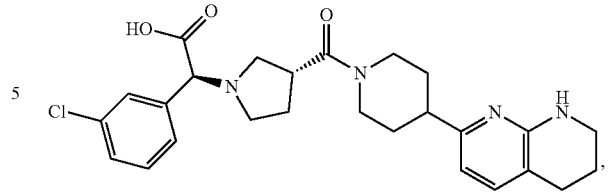
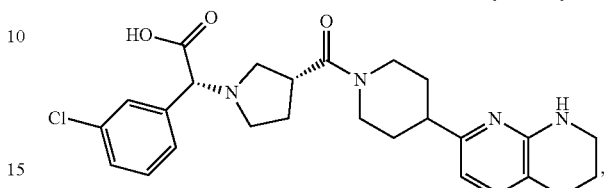
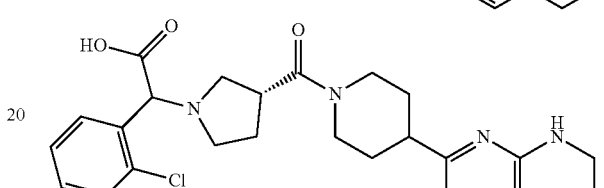
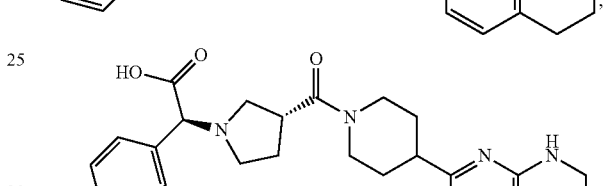
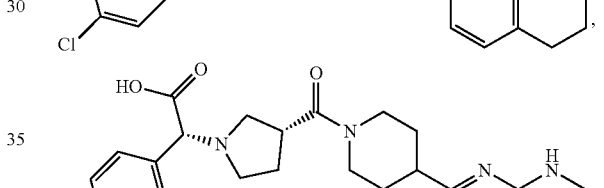
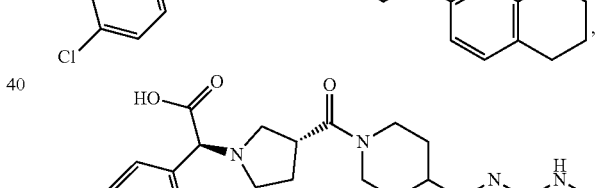
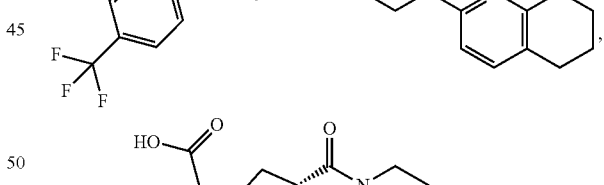
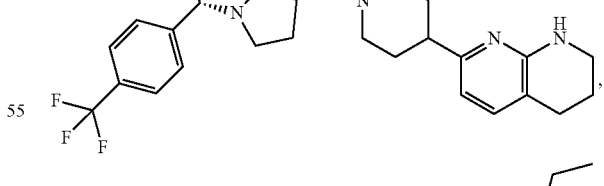
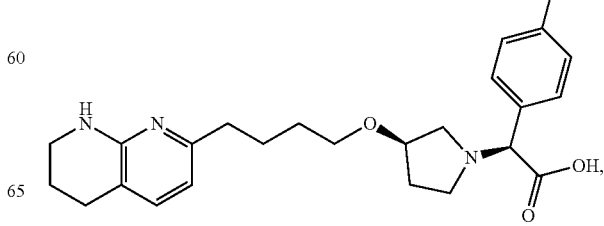

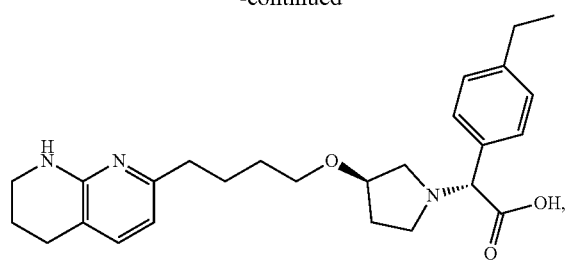
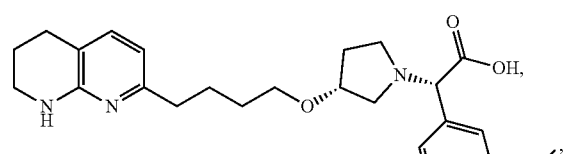
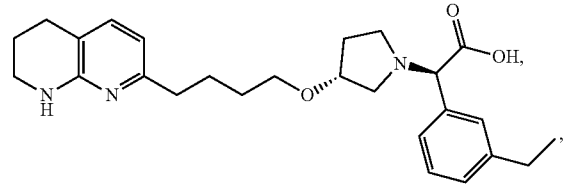
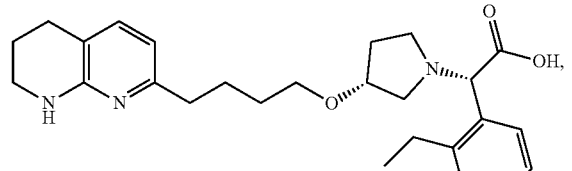
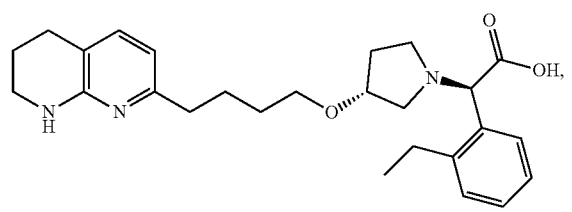
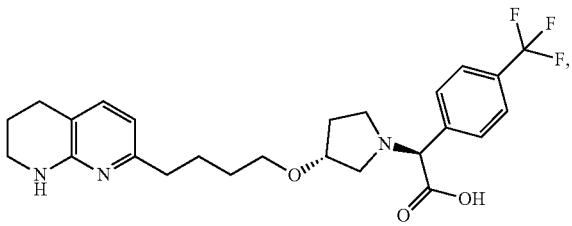
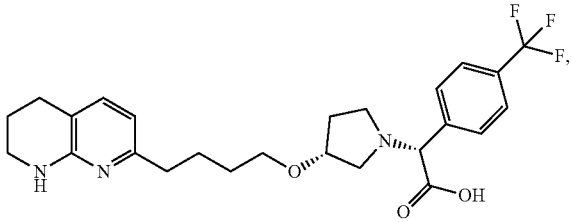
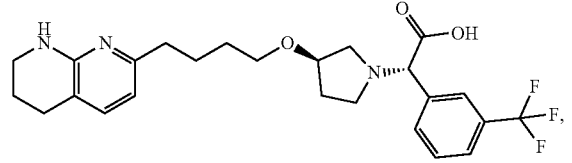
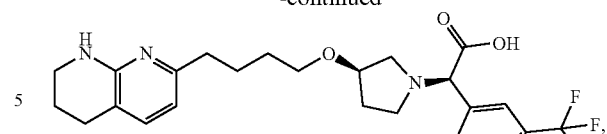
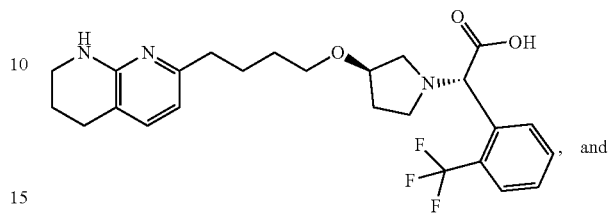
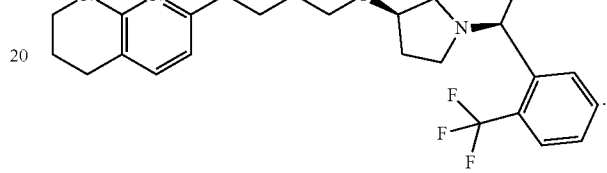, and
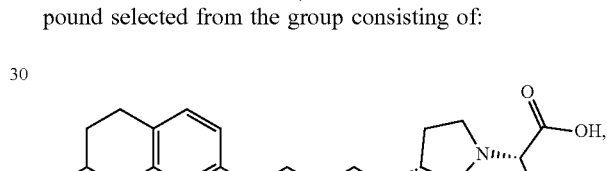.
In certain embodiments, the invention relates to a compound selected from the group consisting of:
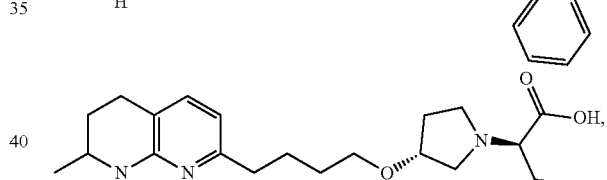
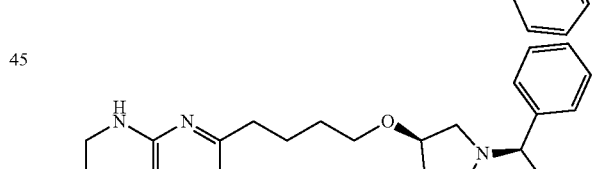
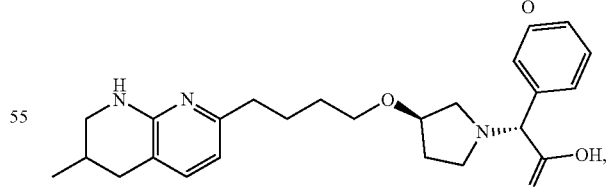
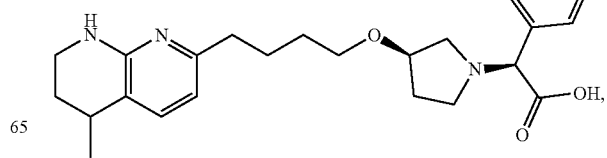

85
-continued
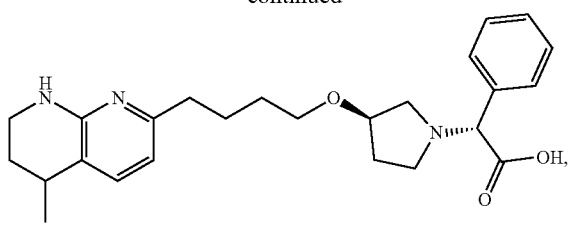
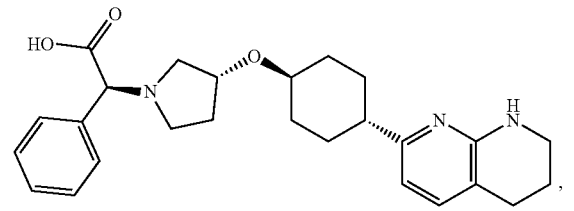
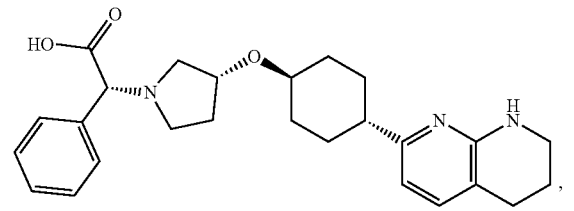
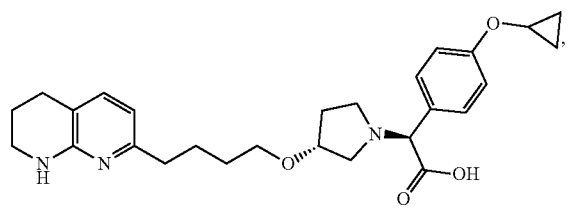
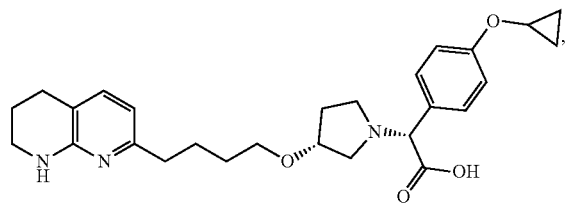
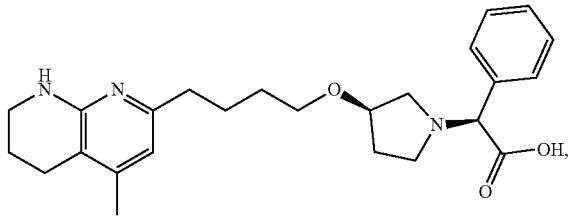
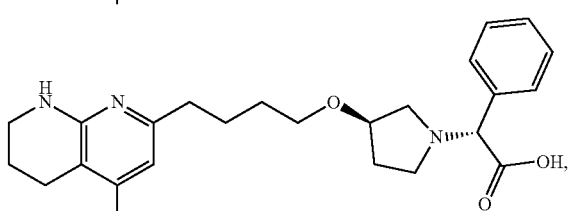
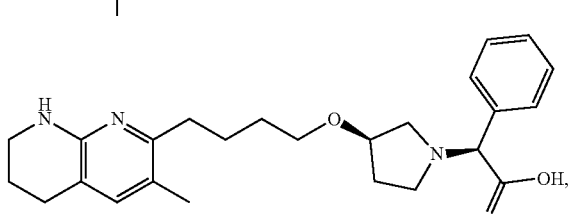
86
-continued
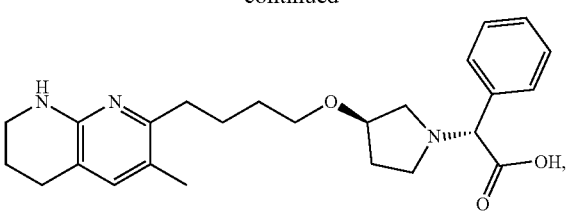
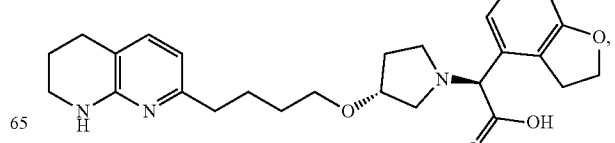

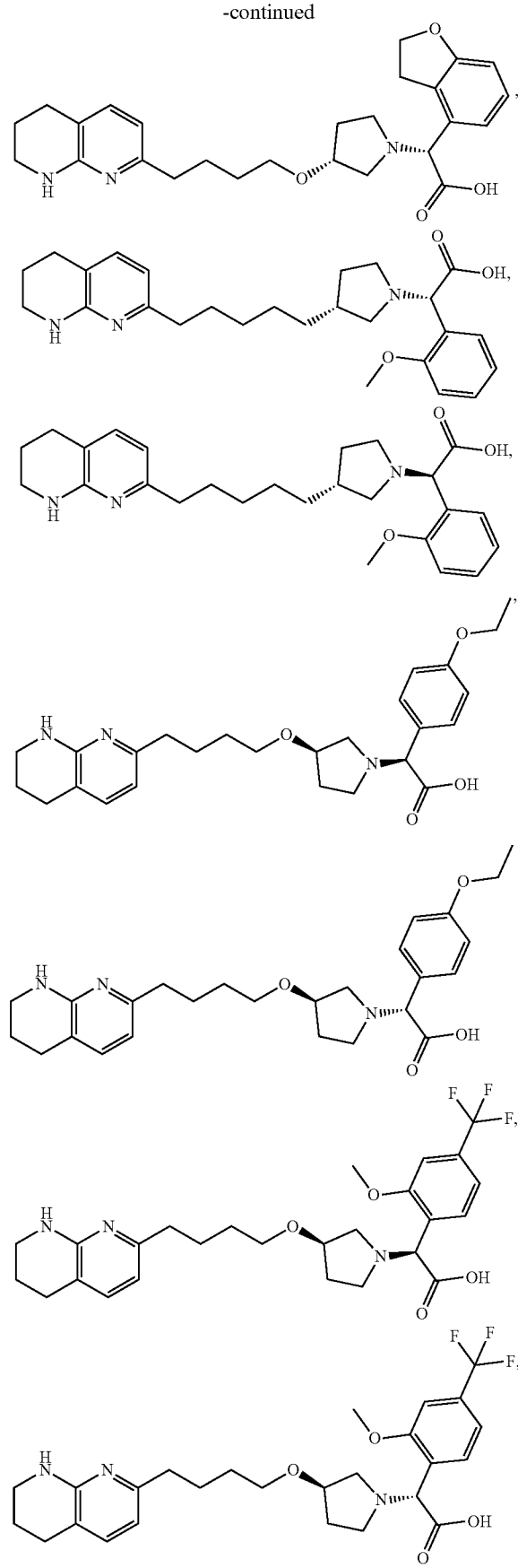
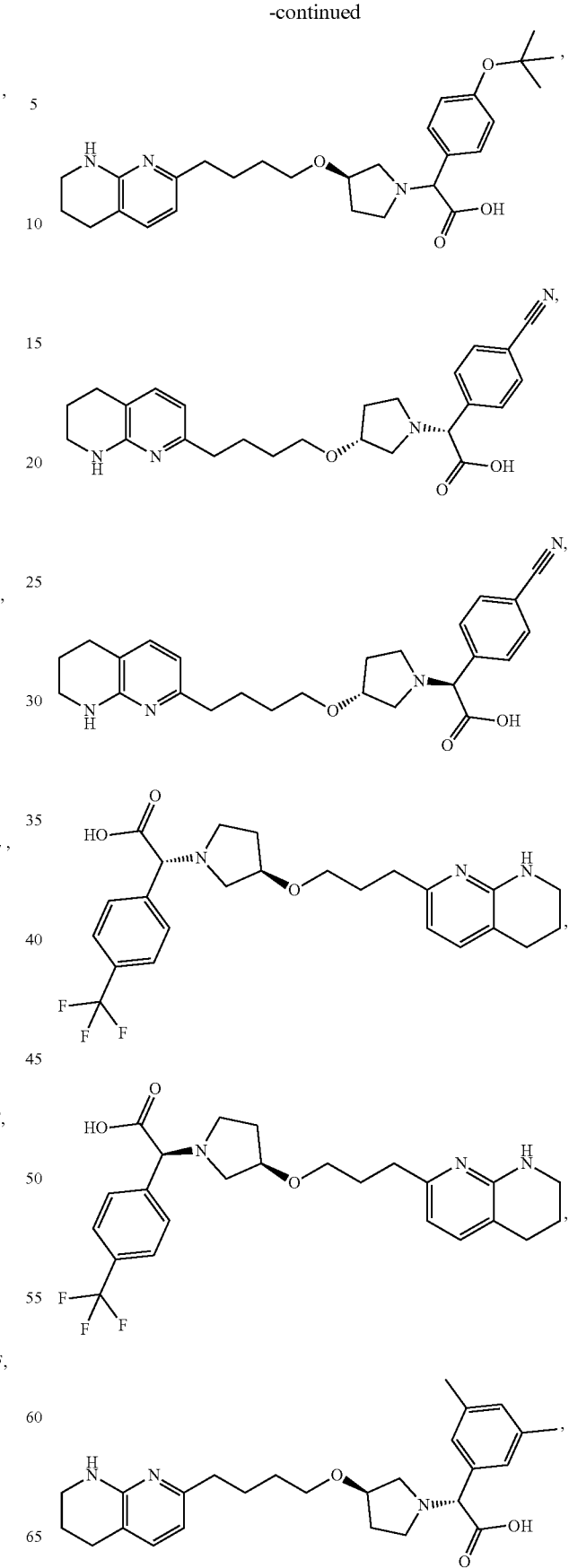

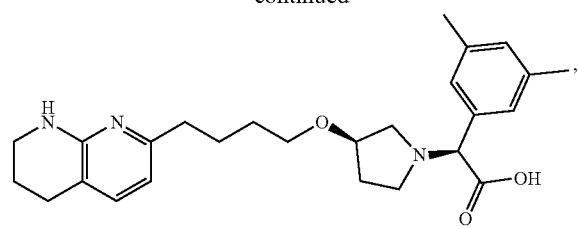
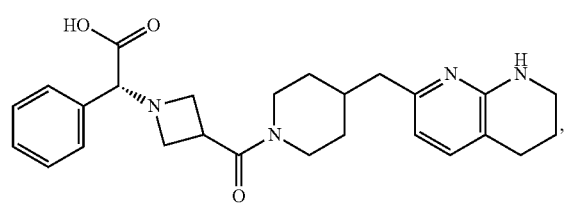
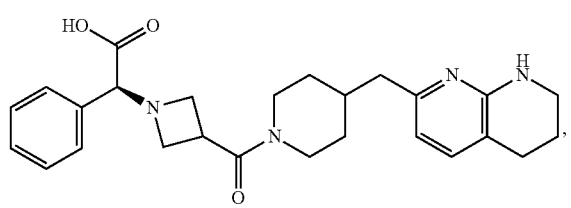
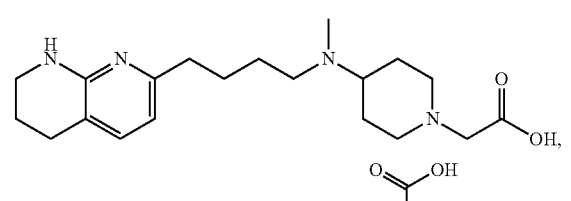
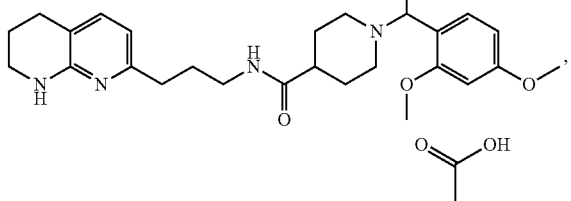
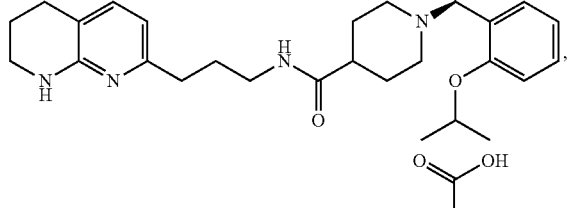
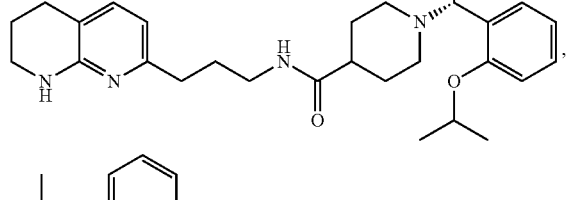
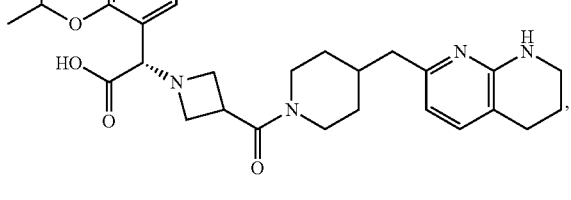
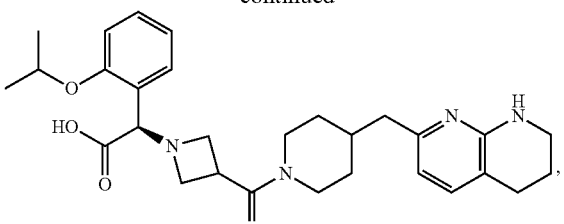
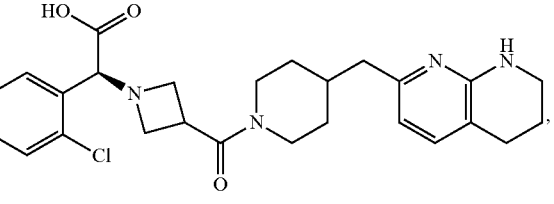
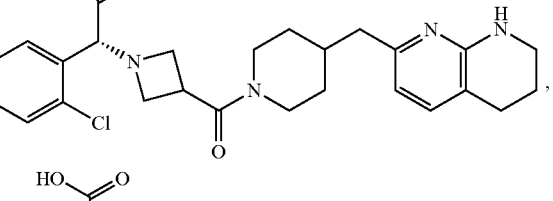
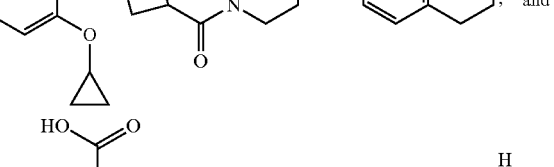
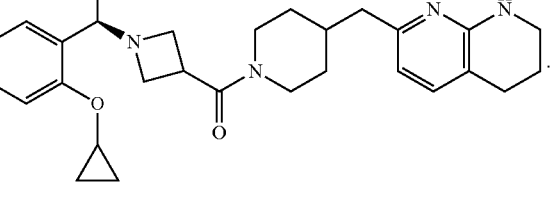
In certain embodiments, the invention relates to a compound selected from the group consisting of:
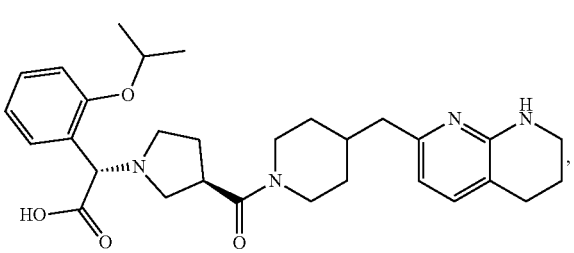
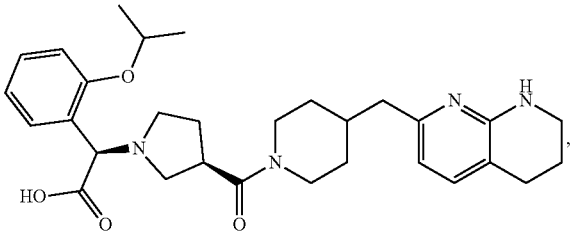

91
-continued
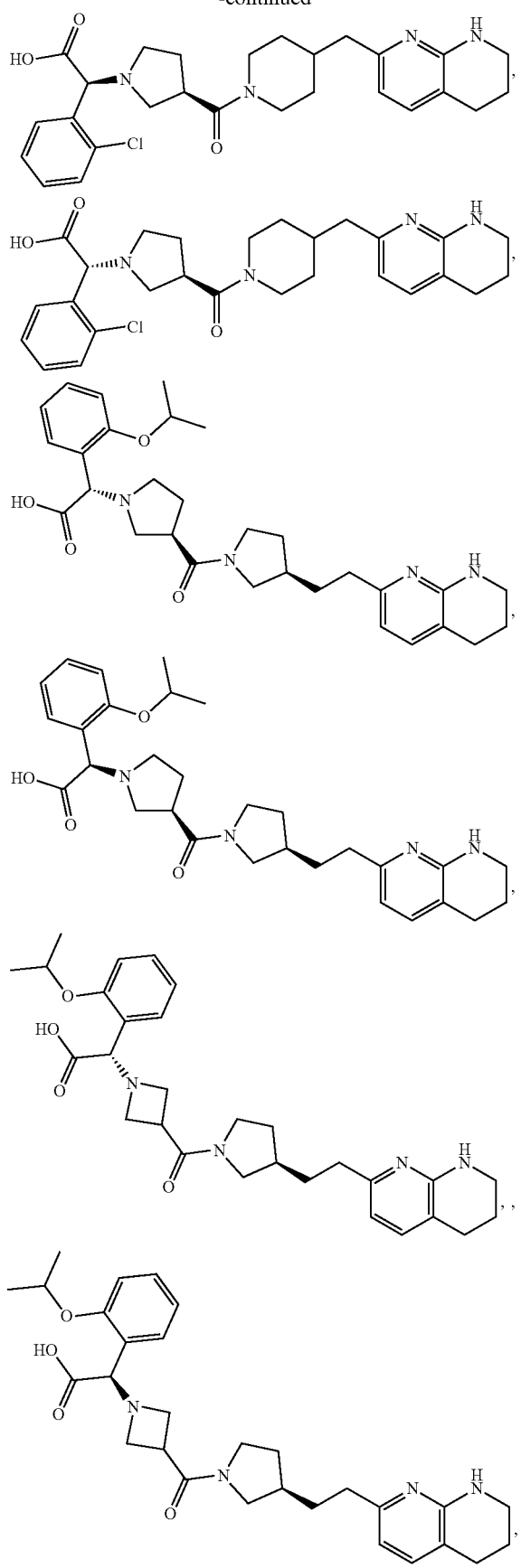
92
-continued
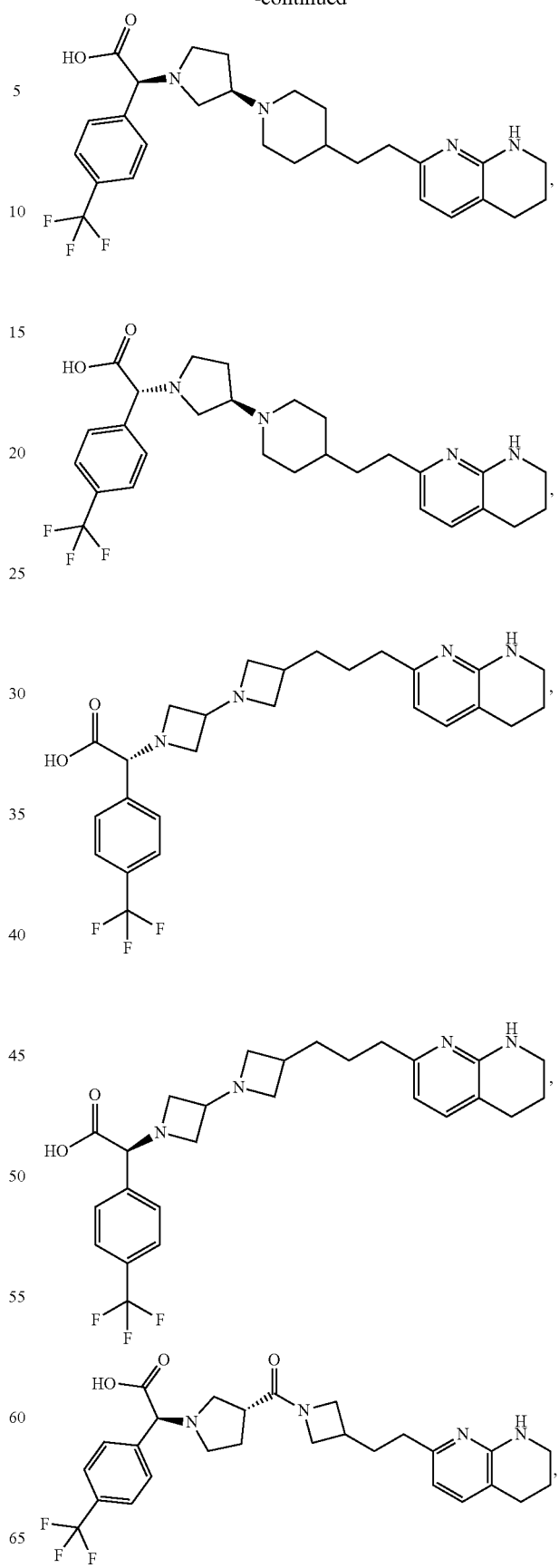

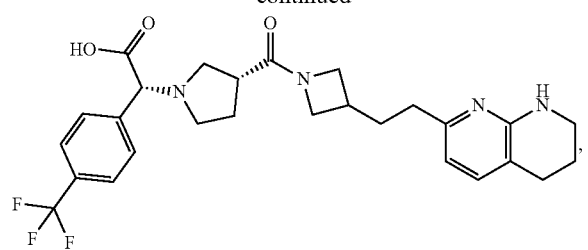
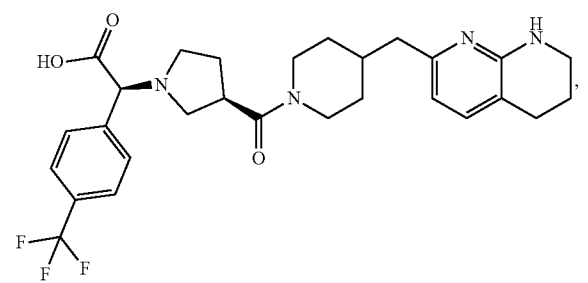
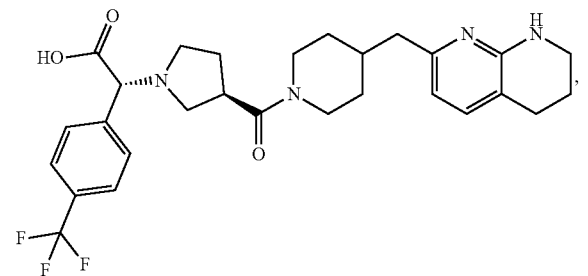
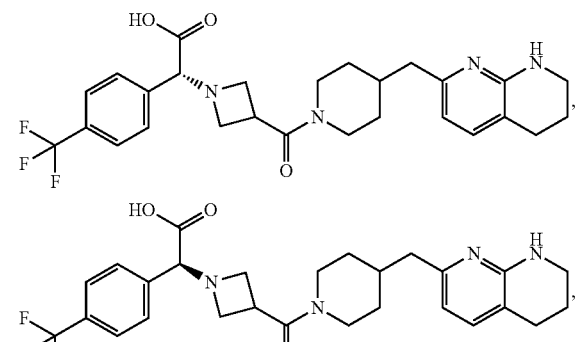
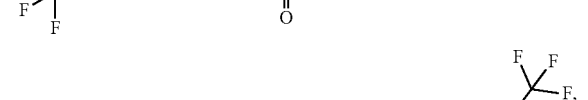
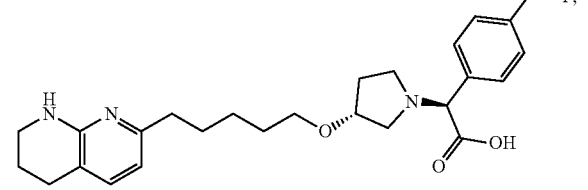
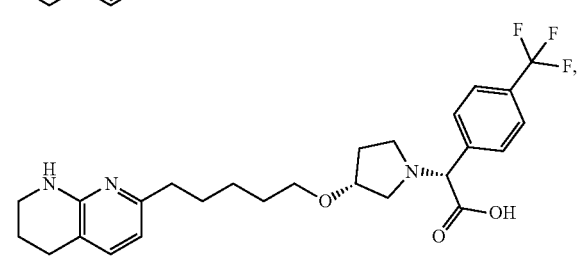
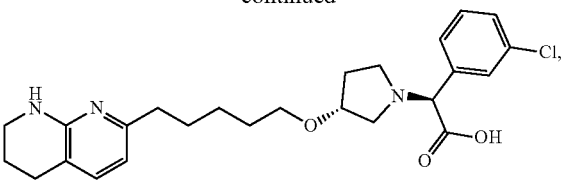
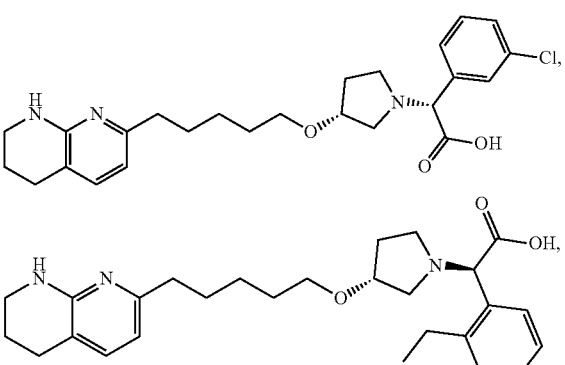
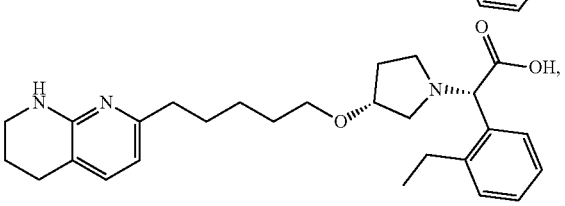
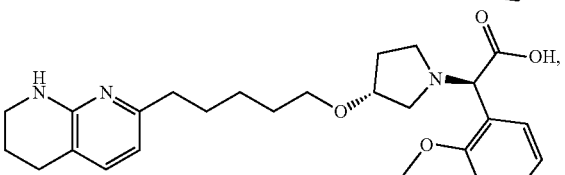
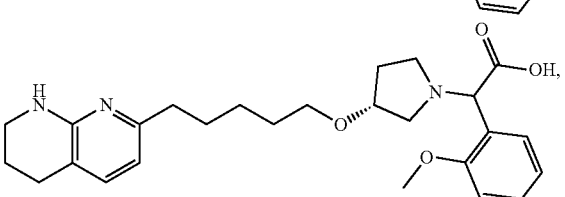
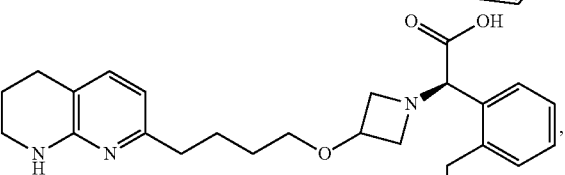
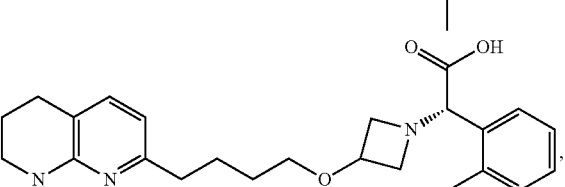
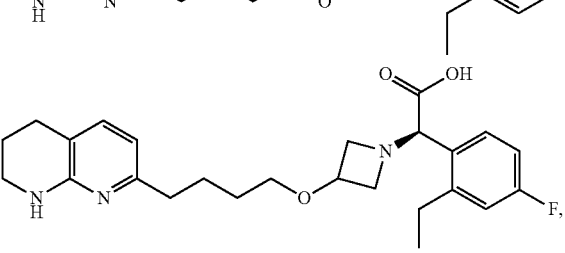
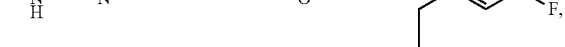

-continued

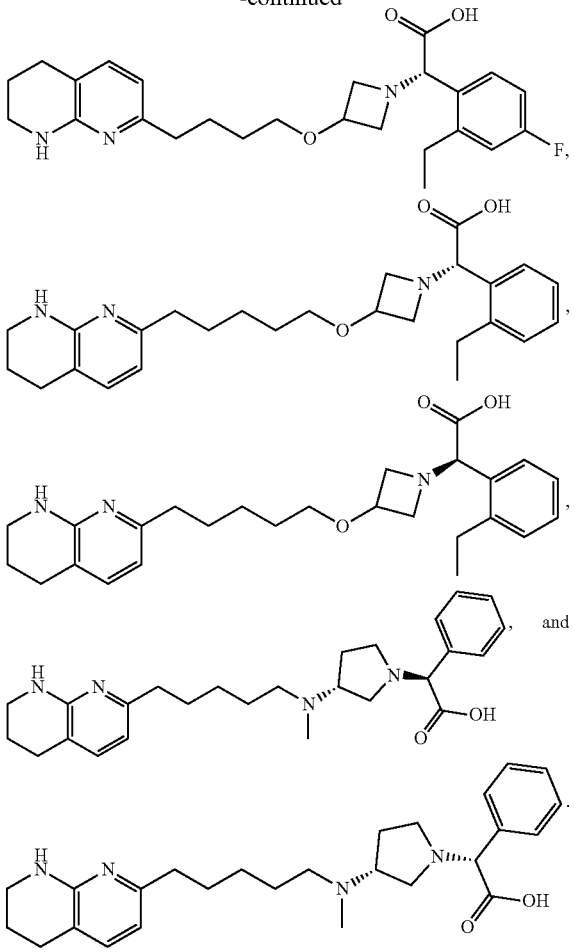

Exemplary Pharmaceutical Compositions

In certain embodiments, the invention relates to a pharmaceutical composition comprising any one of the aforementioned compounds and a pharmaceutically acceptable carrier.

Patients, including but not limited to humans, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In certain embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

EXEMPLARY METHODS OF THE INVENTION

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis comprising the step of: administering to a subject in need thereof a therapeutically effective amount of any one of the aforementioned compounds.

In certain embodiments, the compound administered is selected from the group consisting of:

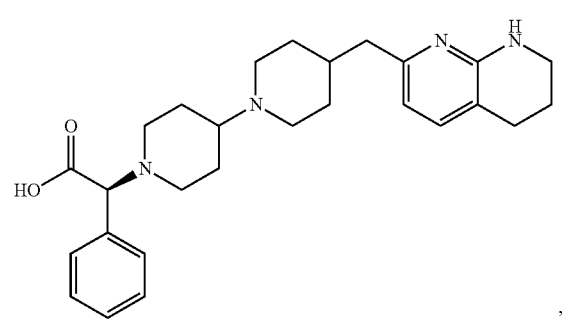

,

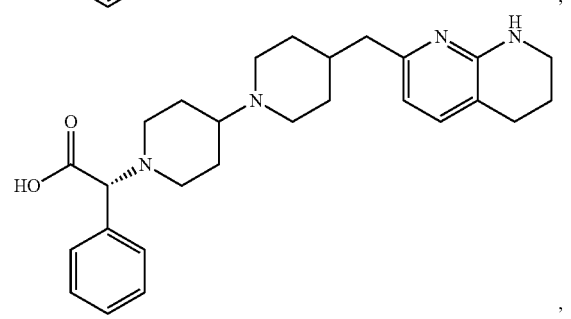

,

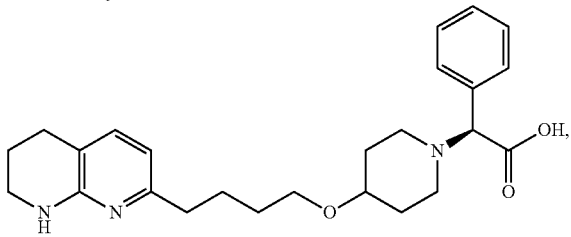

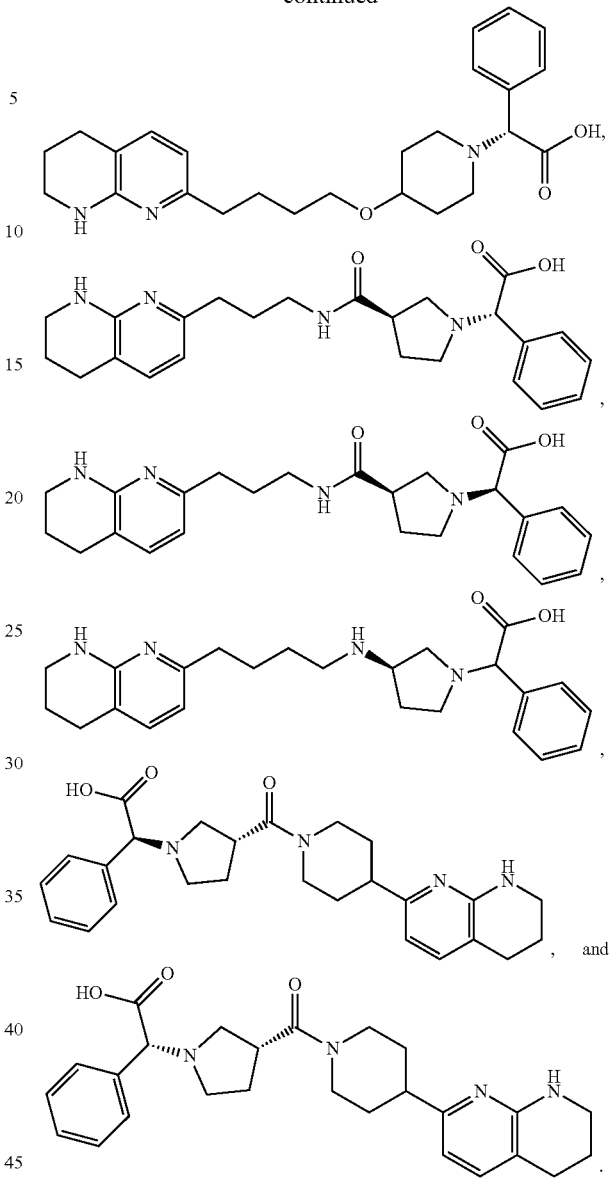

In certain embodiments, the invention relates to any one of the aforementioned methods, wherein the disease or condition is a solid tumor (sarcomas, carcinomas, and lymphomas). Exemplary tumors that may be treated in accordance with the invention include e.g., Ewing's sarcoma, rhabdomyosarcoma, osteosarcoma, myelosarcoma, chondrosarcoma, liposarcoma, leiomyosarcoma, soft tissue sarcoma, non-small cell lung cancer, small cell lung cancer, bronchus cancer, prostate cancer, breast cancer, pancreatic cancer, gastrointestinal cancer, colon cancer, rectum cancer, colon carcinoma, colorectal adenoma, thyroid cancer, liver cancer, intrahepatic bile duct cancer, hepatocellular cancer, adrenal gland cancer, stomach cancer, gastric cancer, glioma (e.g., adult, childhood brain stem, childhood cerebral astrocytoma, childhood visual pathway and hypothalamic), glioblastoma, endometrial cancer, melanoma, kidney cancer, renal pelvis cancer, urinary bladder cancer, uterine corpus, uterine cervical cancer, vaginal cancer, ovarian cancer, multiple myeloma, esophageal cancer, brain cancer (e.g., brain stem glioma, cerebellar astrocytoma, cerebral astrocytoma/ malignant glioma, ependymoma, meduloblastoma, supratentorial primitive neuroectodermal tumors, visual pathway and hypothalamic glioma), lip and oral cavity and pharynx, larynx, small intestine, melanoma, villous colon adenoma, a neoplasia, a neoplasia of epithelial character, lymphomas (e.g., AIDS-related, Burkitt's, cutaneous T-cell, Hodgkin, non-Hodgkin, and primary central nervous system), a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, Waldenstrom's macroglobulinemia, adrenocortical carcinoma, AIDS-related cancers, childhood cerebellar astrocytoma, childhood cerebellar astrocytoma, basal cell carcinoma, extrahepatic bile duct cancer, malignant fibrous histiocytoma bone cancer, bronchial adenomas/carcinoids, carcinoid tumor, gastrointestinal carcinoid tumor, primary central nervous system, cerebellar astrocytoma, childhood cancers, ependymoma, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors (e.g., extracranial, extragonadal, and ovarian), gestational trophoblastic tumor, hepatocellular cancer, hypopharyngeal cancer, hypothalamic and visual pathway glioma, islet cell carcinoma (endocrine pancreas), laryngeal cancer, malignant fibroushistiocytoma of bone/osteosarcoma, medulloblastoma, mesothelioma, metastatic squamous neck cancer with occult primary, multiple endocrine neoplasia syndrome, multiple myeloma/plasma cell neoplasm, mycosis fungoides, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary syndrome, non-melanoma skin cancer, Merkel cell carcinoma, squamous cell carcinoma, testicular cancer, thymoma, gestational trophoblastic tumor, and Wilms' tumor.

In certain embodiments, the invention relates to any one of the aforementioned methods, wherein the disease is disease or condition is a hematological tumor. Exemplary homatological tumors that may be treated in accordance with the invention include e.g., acute lymphocytic leukemia, acute myelogenous leukemia, chronic lymphocytic leukemia, chronic myelogenous leukemia, Hodgkin lymphoma, non-Hodgkin lymphoma, and multiple myeloma.

In certain embodiments, the invention relates to any one of the aforementioned methods, wherein the disease or condition is selected from the group consisting of idiopathic pulmonary fibrosis, systemic sclerosis associated interstitial lung disease, myositis associated interstitial lung disease, systemic lupus erythematosus associated interstitial lung disease, rheumatoid arthritis, and associated interstitial lung disease.

In certain embodiments, the invention relates to any one of the aforementioned methods, wherein the disease or condition is selected from the group consisting of diabetic nephropathy, focal segmental glomerulosclerosis, and chronic kidney disease.

In certain embodiments, the invention relates to any one of the aforementioned methods, wherein the disease or condition is selected from the group consisting of nonalcoholic steatohepatitis, primary biliary cholangitis, and primary sclerosing cholangitis.

In certain embodiments, the invention relates to any one of the aforementioned methods, wherein the subject is a mammal. In certain embodiments, the invention relates to any one of the aforementioned methods, wherein the subject is human.

Exemplification

The invention now being generally described, it will be more readily understood by reference to the following examples, which are included merely for purposes of illustration of certain aspects and embodiments of the present invention, and are not intended to limit the invention.

General Schemes and Procedures for the Preparation of Compounds of the Invention The moieties R and $R_1$ are appropriate ester protecting groups; $R_2$, $R_3$, $R_4$, $R_5$ and $R_6$ are H or an appropriate substituent; and L is an appropriate linker.

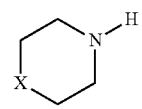

represents an appropriate optionally substituted 3-12 membered heterocycloalkylene, including piperidines, piperazines, piperazinones, pyrrolidines and azetidines.

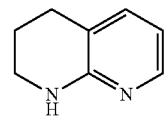

represents an appropriate optionally substituted tetrahydronaphthyridine or 2-aminopyridine.

General Schemes for the Synthesis of αvβ6 Inhibitors

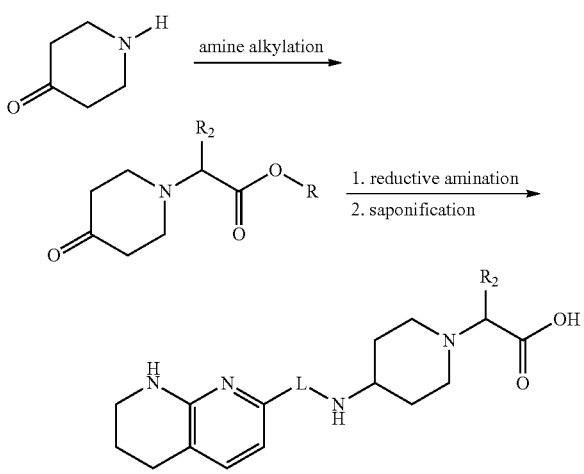

101
-continued
102
-continued
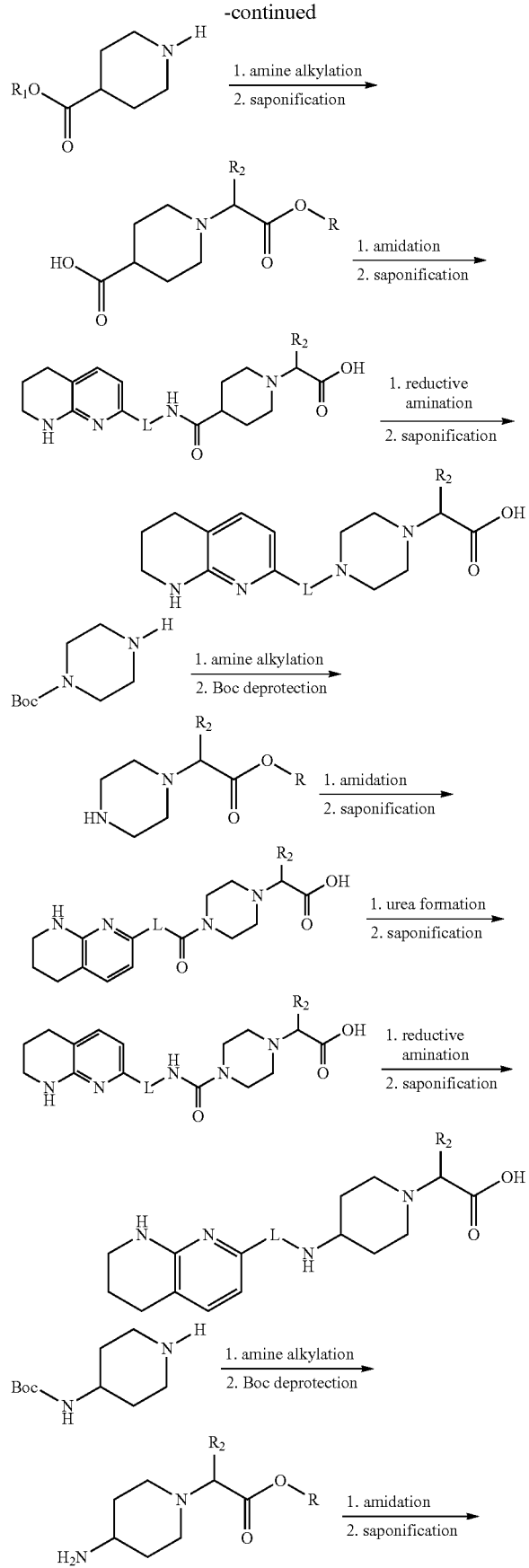
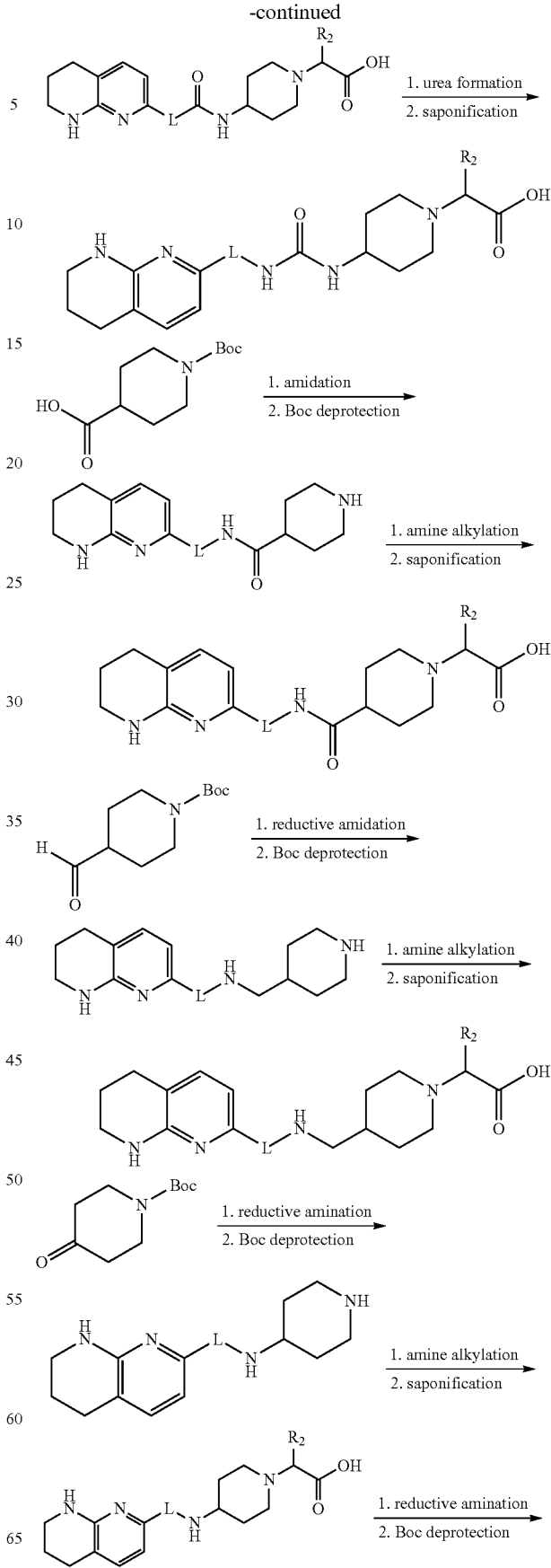

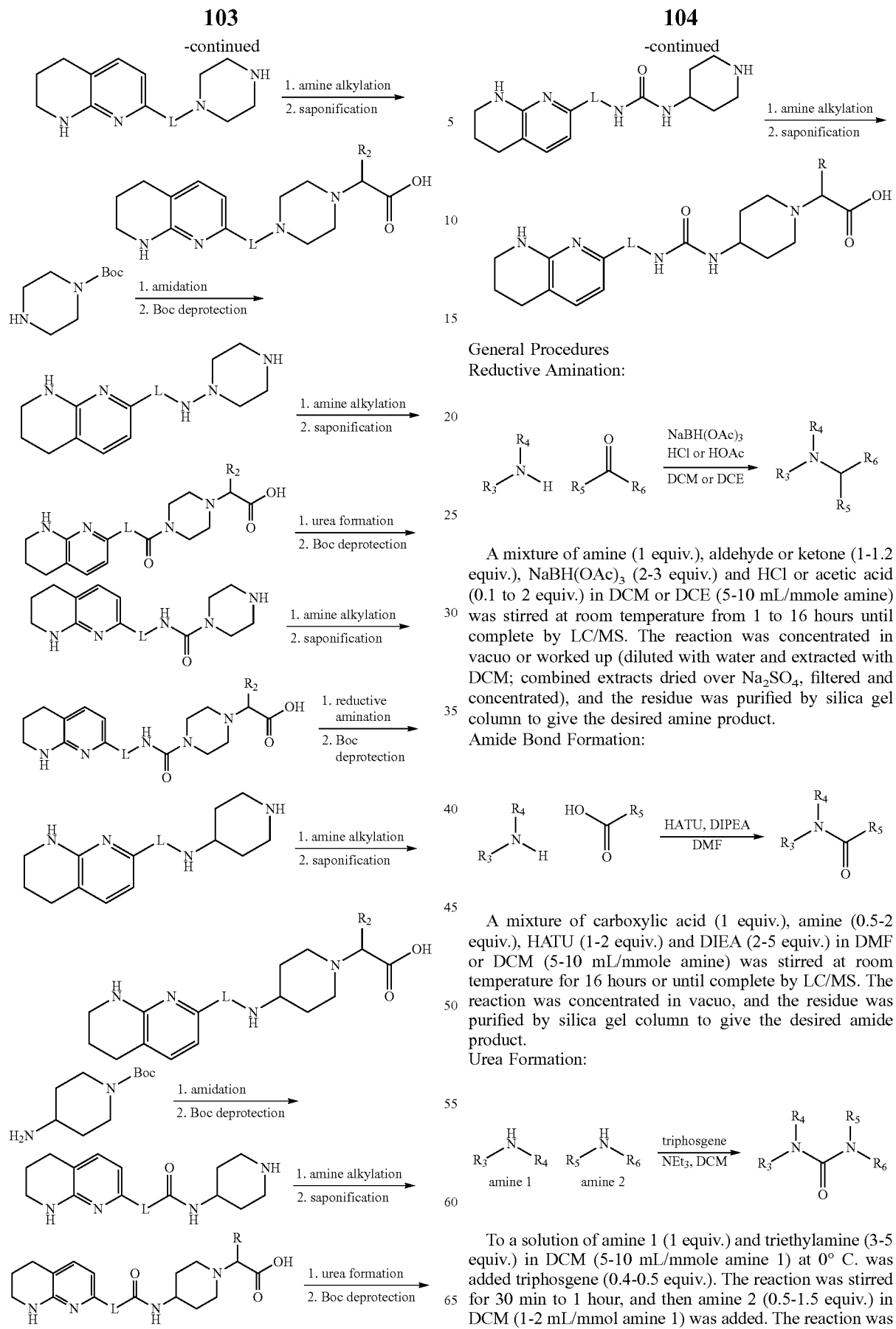

General Procedures
Reductive Amination:

A mixture of amine (1 equiv.), aldehyde or ketone (1-1.2 equiv.), NaBH(OAc)$_3$ (2-3 equiv.) and HCl or acetic acid (0.1 to 2 equiv.) in DCM or DCE (5-10 mL/mmole amine) was stirred at room temperature from 1 to 16 hours until complete by LC/MS. The reaction was concentrated in vacuo or worked up (diluted with water and extracted with DCM; combined extracts dried over Na$_2$SO$_4$, filtered and concentrated), and the residue was purified by silica gel column to give the desired amine product.

Amide Bond Formation:

A mixture of carboxylic acid (1 equiv.), amine (0.5-2 equiv.), HATU (1-2 equiv.) and DIEA (2-5 equiv.) in DMF or DCM (5-10 mL/mmole amine) was stirred at room temperature for 16 hours or until complete by LC/MS. The reaction was concentrated in vacuo, and the residue was purified by silica gel column to give the desired amide product.

Urea Formation:

To a solution of amine 1 (1 equiv.) and triethylamine (3-5 equiv.) in DCM (5-10 mL/mmole amine 1) at 0° C. was added triphosgene (0.4-0.5 equiv.). The reaction was stirred for 30 min to 1 hour, and then amine 2 (0.5-1.5 equiv.) in DCM (1-2 mL/mmol amine 1) was added. The reaction was stirred at room temperature for 2-16 hours, then concentrated under vacuum. The residue was purified by silica gel column to give the desired urea.

Boc Deprotection:

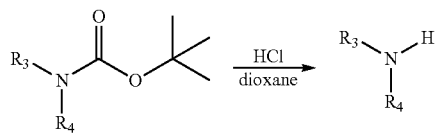

Boc-protected amine (1 equiv.) was treated with HCl (5-20 equiv.) in dioxane (5-20 mL/mmol amine) at room temperature for 1-4 hours. The reaction was concentrated in vacuo, and the amine product was used crude or after purification by silica gel column.

Amine Alkylation:

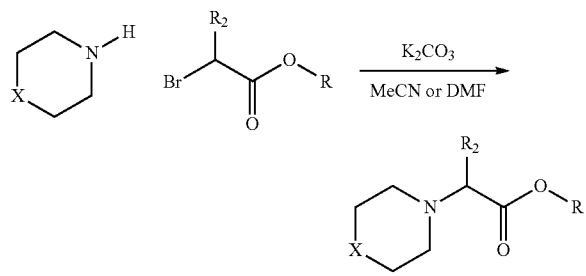

A mixture of amine (1 equiv.) bromoacetate (1-1.5 equiv.) and $K_2CO_3$ (2-5 equiv.) in MeCN or DMF (3-10 mL/mmole amine) was stirred at room temperature for 4-16 hours. The reaction was concentrated in vacuo, and the residue was purified by silica gel column to give the desired amino acetic acid.

Saponification:

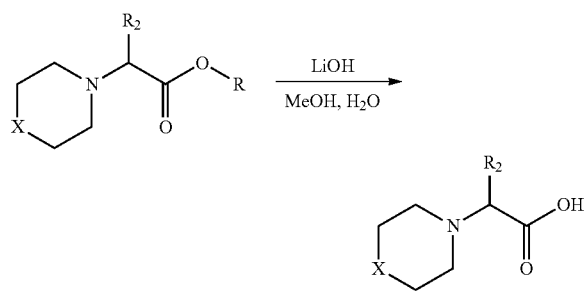

The ester (1 equiv.) was treated with LiOH—$H_2O$ (3-5 equiv.) in MeOH (3-10 mL/mmol ester) and water (3-10 mL/mmol ester) at room temperature for 1-16 hours. The reaction was concentrated in vacuo, and the residue was purified by prep HPLC to give the desired carboxylic acid product.

Petasis Reaction:

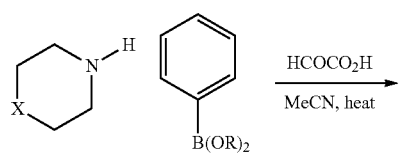

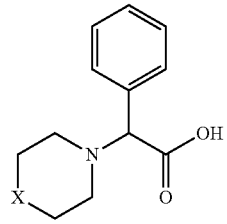

As an alternative to the amine alkylation/saponification sequence, a Petasis reaction can be used to prepare certain aryl analogs: A mixture of amine (1 eq.) aryl boronic acid or aryl boronate ester (1-1.5 eq.) and 2-oxoacetic acid (1.5-2 equiv.) in MeCN or DMF (2-10 mL/mmole amine) was stirred at 50-80° C. for 2-16 hours. The reaction was concentrated in vacuo, and the residue was purified by prep HPLC to give the desired amino acetic acid.

Analytical Methods

LCMS Analytical Methods

Final compounds were analyzed using LC/MS conditions, with UV detector monitoring at 214 nm and 254 nm, and mass spectrometry scanning 110-800 amu in ESI+ ionization mode. LC/MS A: column: XBridge C18, 4.6×50 mm, 3.5 μm; mobile phase: A water (10 mM ammonium hydrogen carbonate), B $CH_3CN$; gradient: 5%-95% B in 1.4 min, then 1.6 min hold; flow rate: 1.8 mL/min; oven temperature 50° C.

LC/MS B: column: SunFire C18, 4.6×50 mm, 3.5 m; mobile phase: A water (0.01% TFA), B $CH_3CN$; gradient: 5%-95% B in 1.5 min, then 1.5 min hold; flow rate: 2.0 mL/min; oven temperature 50° C.

LC/MS C: column: XBridge C18, 4.6×50 mm, 3.5 m; mobile phase: A water (10 mM ammonium hydrogen carbonate), B $CH_3CN$; gradient: 5%-95% B in 1.5 min, then 1.5 min hold; flow rate: 1.8 mL/min; oven temperature 50° C.

LC/MS D: column: Poroshell 120 EC-C138, 4.6×30 mm, 2.7 m; mobile phase: A water (0.01% TFA), B $CH_3CN$ (0.01% TFA); gradient: 5%-95% B in 1.2 min, then 1.8 min hold; flow rate: 2.2 mL/min; oven temperature 50° C.

LC/MS E: column: XBridge C18, 3.0×30 mm, 2.5 μm; mobile phase: A water (10 mM ammonium hydrogen carbonate), B $CH_3CN$; gradient: 5%-95% B in 1.5 min, then 0.6 min hold; flow rate: 1.5 mL/min; oven temperature 50° C.

LC/MS F: column: Agilent poroshell 120 EC-C18, 4.6×50 mm, 2.7 m: A water (0.1% formic acid), B $CH_3CN$ (0.1% formic acid); gradient 5%-95% B in 4.0 min, then 6.0 min hold; flow rate 0.95 mL/min; oven temp 50° C.

Prep-HPLC Methods

Crude samples were dissolved in MeOH and purified by prep HPLC using a Gilson 215 instrument, detection wavelength 214 nm:

Prep HPLC A: column: XBridge C18, 21.2*250 mm, 10 μm; mobile phase: A water (10 mM ammonium hydrogen carbonate), B $CH_3CN$; gradient elution as in text; flow rate: 20 mL/min.

Prep HPLC B: column: XBridge C18, 21.2*250 mm, 10 μm; mobile phase: A water (10 mM formic acid), B $CH_3CN$; gradient elution as in text; flow rate: 20 mL/min.

Prep HPLC C: column: XBridge OBD C18, 19*100 mm, 5 m; mobile phase: A water, B $CH_3CN$; gradient elution as in text; flow rate: 20 mL/min.

Prep Chiral SFC Methods

Racemic products were separated to individual enantiomers by chiral Prep SFC using an SFC-80 (Thar, Waters) instrument, detection wavelength 214 nm:

Prep chiral SFC A: column: (R,R)-Whelk-O1, 20*250 mm, 5 μm (Decial), column temperature: 35° C., mobile phase: CO2/methanol (0.2% methanol ammonia)=60/40, flow rate: 80 g/min, back pressure: 100 bar.

Prep chiral SFC B: column: AD 20*250 mm, 10 μm (Daicel), column temperature: 35° C., mobile phase: CO2/methanol (0.2% methanol ammonia)=60/40, flow rate: 80 g/min, back pressure: 100 bar.

Prep chiral SFC C: column: AS 20*250 mm, 10 μm (Daicel), column temperature: 35° C., mobile phase: CO2/methanol (0.2% methanol ammonia)=60/40, flow rate: 80 g/min, back pressure: 100 bar.

Analytical Chiral SFC Methods

Chiral products were analyzed by chiral SFC using an SFC-80 (Thar, Waters) instrument, detection wavelength 214 nm:

Chiral SFC A: column: (R,R)-Whelk-O1, 4.6*100 mm, 5 μm (Decial), column temperature: 40° C., mobile phase: CO2/methanol (0.2% methanol ammonia), isocratic elution as in text, flow rate: 4 g/min, back pressure: 120 bar.

Chiral SFC B: column: AD 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC C: column: AS 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC D: column: OD 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC E: column: Cellulose-SC 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC F: column: OZ 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC G: column: IC 4.6*100 mm, 5 μm (Daicel), column temperature: 40° C., mobile phase: CO2/methanol (0.2% methanol ammonia), isocratic elution as in text, flow rate: 4 g/min, back pressure: 120 bar.

Chiral SFC H: column: AD 4.6*250 mm, 5 μm (SHIMADZU), column temperature: 40° C., mobile phase: n-Hexane (0.1% DEA):EtOH (0.1% DEA), isocratic elution as in text, flow rate: 1 mL/min.

Chiral SFC I: column: IC 4.6*250 mm, 5 μm (SHIMADZU), column temperature: 40° C., mobile phase: n-Hexane (0.1% DEA):EtOH (0.1% DEA), isocratic elution as in text, flow rate: 1 mL/min.

Chiral SFC J: column: (S,S)-Whelk-O1 4.6*250 mm, 5 μm (SHIMADZU), column temperature: 40° C., mobile phase: n-Hexane (0.1% DEA):EtOH (0.1% DEA), isocratic elution as in text, flow rate: 1 mL/min.

Chiral SFC K: column: OZ—H 4.6*250 mm, 5 μm (SHIMADZU), column temperature: 40° C., mobile phase: n-Hexane (0.1% DEA):EtOH (0.1% DEA), isocratic elution as in text, flow rate: 1 mL/min.

Chiral SFC L: column: chiral PAK IG 4.6*250 mm, 5 μm (SHIMADZU), column temperature: 35° C., mobile phase: n-Hexane (0.1% DEA):EtOH (0.1% DEA), isocratic elution as in text, flow rate: 1 mL/min.

Example 1: Preparation of 2-(4-((4-(5,6,7,8-tetrahydro-1,8-naphthyridin-2-yl)piperidin-1-yl)methyl)piperidin-1-yl)acetic acid (Compound 1)

Step 1: tert-butyl 4-(1,8-naphthyridin-2-yl)piperidine-1-carboxylate

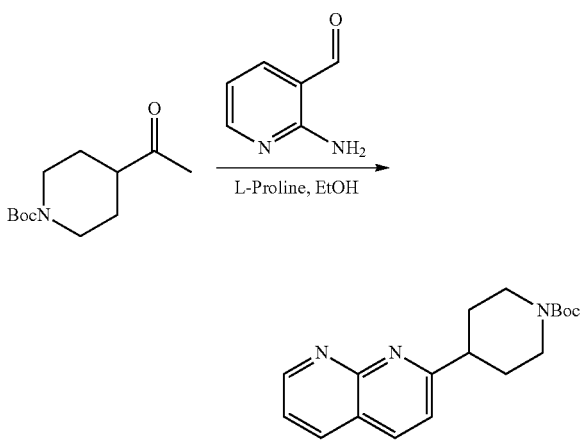

A mixture of tert-butyl 4-acetylpiperidine-1-carboxylate (2.0 g, 8.80 mmol), 2-aminonicotinaldehyde (1.1 g, 8.80 mmol) and L-proline (2.0 g, 17.60 mmol) in EtOH (20 mL) was heated to reflux overnight. Solvent was removed in vacuo, and the residue was purified by silica gel column (pet ether:EtOAc=1:1) to give tert-butyl 4-(1,8-naphthyridin-2-yl)piperidine-1-carboxylate as a colorless oil (0.8 g). Yield 30% (100% purity, UV=214 nm, ESI 314.2 (M+H)$^+$).

Step 2: tert-butyl 4-(5,6,7,8-tetrahydro-1,8-naphthyridin-2-yl)piperidine-1-carboxylate

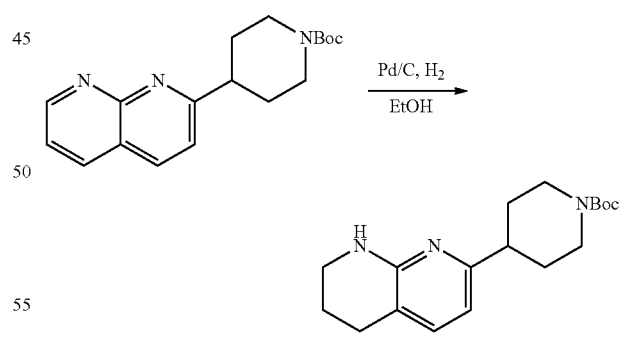

Tert-butyl 4-(1,8-naphthyridin-2-yl)piperidine-1-carboxylate (0.8 g, 2.56 mmol) was hydrogenated over Pd—C (100 mg, 10% on activated carbon) under balloon hydrogen in EtOH (20 mL) at room temperature overnight. The reaction was filtered through Celite and concentrated to give crude tert-butyl 4-(5,6,7,8-tetrahydro-1,8-naphthyridin-2-yl)piperidine-1-carboxylate as a colorless oil (800 mg), which was used directly in the next step. Yield 98% (95% purity, UV=214 nm, ESI 318.2 (M+H)$^+$).

Step 3: 7-(piperidin-4-yl)-1,2,3,4-tetrahydro-1,8-naphthyridine dihydrochloride

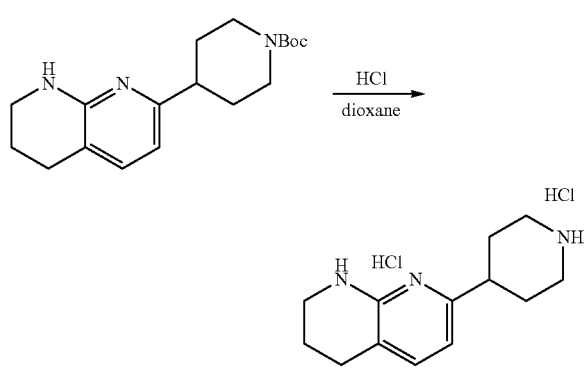

7-(piperidin-4-yl)-1,2,3,4-tetrahydro-1,8-naphthyridine dihydrochloride (800 mg, 2.52 mmol) was treated with HCl in 1,4-dioxane (4N, 4 mL) at room temperature for 2 hours. Solvent was removed in vacuo to give the crude 7-(piperidin-4-yl)-1,2,3,4-tetrahydro-1,8-naphthyridine dihydrochloride as a white solid (750 mg). Yield 95% (100% purity, UV=214 nm, ESI 218.2 (M+H)$^+$). The crude product was used for the next step directly.

Step 4: tert-butyl 4-((4-(5,6,7,8-tetrahydro-1,8-naphthyridin-2-yl)piperidin-1-yl)methyl)piperidine-1-carboxylate

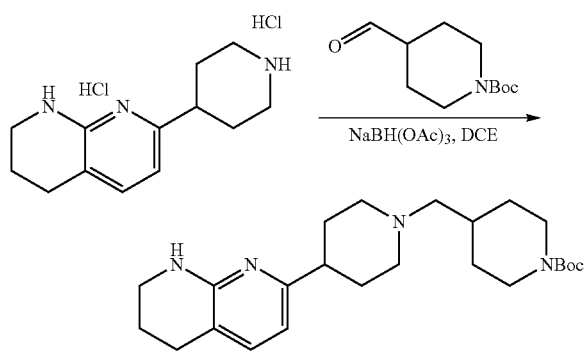

A mixture of 7-(piperidin-4-yl)-1,2,3,4-tetrahydro-1,8-naphthyridine dihydrochloride (300 mg, 1.04 mmol) and tert-butyl 4-formylpiperidine-1-carboxylate (220.6 mg, 1.03 mmol) in DCE (5 mL) under nitrogen atmosphere was stirred at room temperature for 15 min. NaBH(OAc)$_3$ (437 mg, 2.06 mmol) was added at room temperature. The reaction mixture was stirred for another 1 h, diluted with water (10 mL), and extracted with DCM (20 mL×2). The combined organic layers were washed with water (10 mL) and brine (10 mL), dried over Na$_2$SO$_4$, filtered and concentrated under reduced pressure. The residue was purified by Prep-TLC to give tert-butyl 4-((4-(5,6,7,8-tetrahydro-1,8-naphthyridin-2-yl)piperidin-1-yl)methyl)piperidine-1-carboxylate (148 mg, yield: 35%) as colorless oil (90% purity, UV=214 nm, ESI 415.1 (M+H)$^+$).

Step 5: 7-(1-(piperidin-4-ylmethyl)piperidin-4-yl)-1,2,3,4-tetrahydro-1,8-naphthyridine dihydrochloride

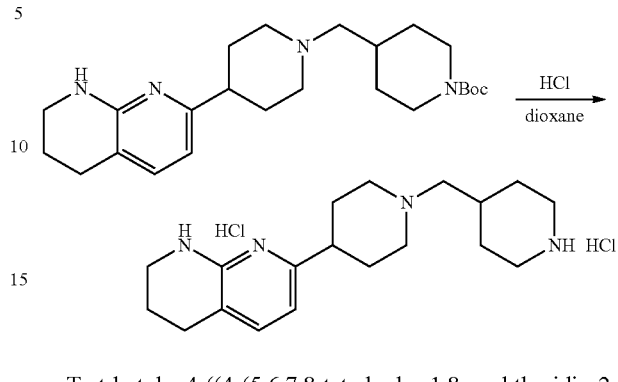

Tert-butyl 4-((4-(5,6,7,8-tetrahydro-1,8-naphthyridin-2-yl)piperidin-1-yl)methyl)piperidine-1-carboxylate (148 mg, 0.36 mmol) was treated with a solution of HCl in 1,4-dioxane (4N, 2 mL) at room temperature for 2 hours. Solvent was removed in vacuo to give the crude 7-(1-(piperidin-4-ylmethyl)piperidin-4-yl)-1,2,3,4-tetrahydro-1,8-naphthyridine dihydrochloride (135 mg crude) as a white solid. Yield 95% (ESI 315.2 (M+H)$^+$). The crude product was used for next step directly.

Step 6: methyl 2-(4-((4-(5,6,7,8-tetrahydro-1,8-naphthyridin-2-yl)piperidin-1-yl)methyl)piperidin-1-yl)acetate

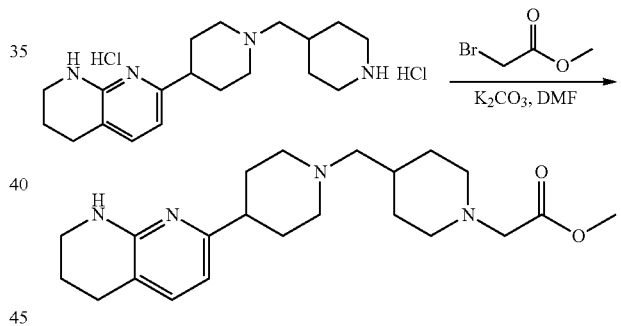

A mixture of 7-(1-(piperidin-4-ylmethyl)piperidin-4-yl)-1,2,3,4-tetrahydro-1,8-naphthyridine dihydrochloride (135 mg crude), methyl 2-bromoacetate (64 mg, 0.42 mmol) and K$_2$CO$_3$ (138 mg, 1.0 mmol) in anhydrous DMF (5 mL) was stirred at room temperature for 5 hours. The reaction was filtered and concentrated in vacuo. The residue was purified by Prep-HPLC A (33-65% MeCN) to give methyl 2-(4-((4-(5,6,7,8-tetrahydro-1,8-naphthyridin-2-yl)piperidin-1-yl)methyl)piperidin-1-yl)acetate (54 mg, 52% yield) as a white solid. (91% purity, UV=254 nm, ESI 387.2 (M+H)$^+$)

Step 7: 2-(4-((4-(5,6,7,8-tetrahydro-1,8-naphthyridin-2-yl)piperidin-1-yl)methyl)piperidin-1-yl)acetic acid (Compound 1)

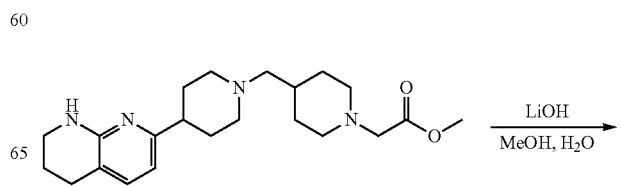

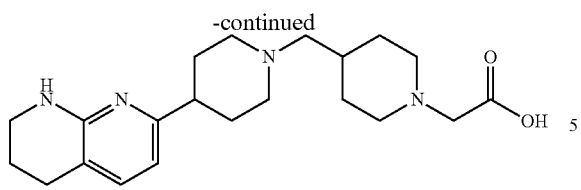

Methyl 2-(4-((4-(5,6,7,8-tetrahydro-1,8-naphthyridin-2-yl)piperidin-1-yl)methyl)piperidin-1-yl)acetate (54 mg, 0.14 mmol) was treated with LiOH (21 mg, 0.5 mmol) in MeOH (3 mL) and H$_2$O (1 mL) at room temperature for 2 hours. Solvent was removed in vacuo, and the residue was purified by Prep-HPLC A (33-65% MeCN) to give compound 1 as a white solid (15 mg, 29% yield). LC/MS D: 100% purity, UV=214 nm, Rt=0.38 min, ESI 373.3 (M+H)$^+$. $^1$H NMR (500 MHz, MeOD) δ 7.43 (d, J=7.4 Hz, 1H), 6.55 (d, J=7.4 Hz, 1H), 3.75-3.61 (m, 4H), 3.53 (d, J=11.9 Hz, 2H), 3.49-3.42 (m, 2H), 3.06 (t, J=11.8 Hz, 2H), 2.92 (d, J=6.5 Hz, 2H), 2.85 (s, 3H), 2.79 (t, J=6.2 Hz, 2H), 2.08-2.01 (m, 7H), 1.98-1.90 (m, 2H), 1.68 (d, J=12.2 Hz, 2H).

Example 2: Preparation of 2-(2-oxo-4-((5,6,7,8-tetrahydro-1,8-naphthyridin-2-yl)methyl) piperidine-1-carbonyl)piperazin-1-yl)acetic acid (Compound 2)

Step 1: tert-butyl 4-(2-methoxy-2-oxoethyl)-3-oxopiperazine-1-carboxylate

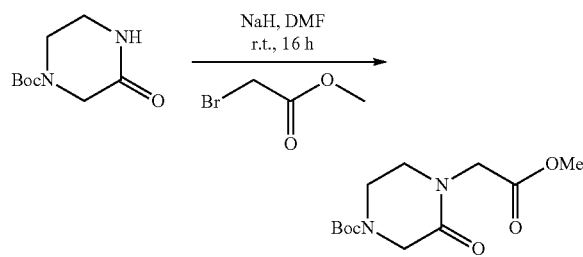

To a solution of tert-butyl 3-oxopiperazine-1-carboxylate (5.00 g, 25.0 mmol) in DMF (50 mL) at 0° C. was added NaH (60% in mineral oil, 1.20 g, 30.0 mmol). The mixture was stirred for 30 min, and then methyl 2-bromoacetate (2.60 mL, 27.5 mmol) was added. The reaction was stirred at room temperate for 16 hours, then quenched with H$_2$O (50 mL) and extracted with EtOAc (50 mL×3). The combined organic extracts were washed with brine, dried over Na$_2$SO$_4$, filtered and concentrated in vacuo. The residue was purified by silica gel column (pet ether:EtOAc 5:1 to 2:1) to afford the desired compound as a colorless oil (4.0 g). Yield 59% (86% purity, UV=214 nm, ESI 217.0 (M+H)$^+$.

Step 2: methyl 2-(2-oxopiperazin-1-yl)acetate

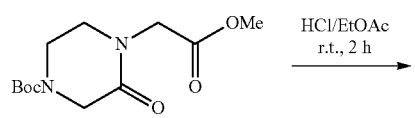

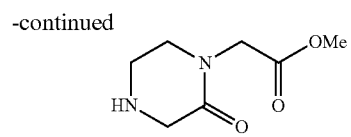

Tert-butyl 4-(2-methoxy-2-oxoethyl)-3-oxopiperazine-1-carboxylate (2.50 g, 9.18 mmol) was treated with a solution of HCl/EtOAc (4.0 M, 20 mL) at room temperate for 2 hours. Solvent was removed in vacuo to give the desired product methyl 2-(2-oxopiperazin-1-yl)acetate as an off-white solid (1.50 g). Yield 98% (88% purity, UV=214 nm, ESI 173.1 (M+H)$^+$.

Step 3: methyl 2-(2-oxo-4-(4-((5,6,7,8-tetrahydro-1,8-naphthyridin-2-yl)methyl)piperidine-1-carbonyl)piperazin-1-yl)acetate

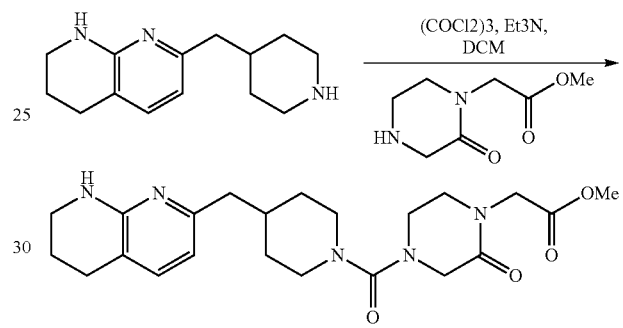

To a mixture of 7-(piperidin-4-ylmethyl)-1,2,3,4-tetrahydro-1,8-naphthyridine (200 mg, 0.75 mmol) and triethylamine (300 mg, 2.96 mmol) in DCM (10 mL) at 0° C. was added triphosgene (111 mg, 0.37 mmol). The mixture was stirred for 30 min, and then methyl 2-(2-oxopiperazin-1-yl)acetate (187 mg, 0.90 mmol) in DCM (5.0 mL) was added. The mixture was stirred at room temperature for 16 hours. Solvent was removed in vacuo, and the residue was purified by silica gel column (DCM:MeOH 20:1) to give the desired product as an off-white solid (300 mg). Yield 93% (81% purity, UV=214 nm, ESI 430.3 (M+H)$^+$.

Step 4: 2-(2-oxo-4-(4-((5,6,7,8-tetrahydro-1,8-naphthyridin-2-yl)methyl)piperidine-1-carbonyl)piperazin-1-yl)acetic acid (Compound 2)

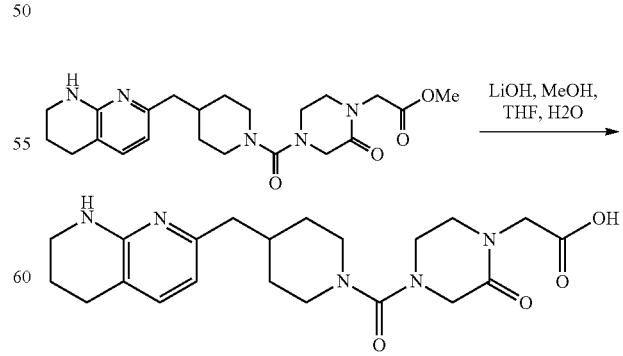

Methyl 2-(2-oxo-4-(4-((5,6,7,8-tetrahydro-1,8-naphthyridin-2-yl)methyl)piperidine-1-carbonyl)piperazin-1-yl)acetate (300 mg, 0.70 mmol) was treated with LiOH—H$_2$O (117 mg, 2.79 mmol) in THF/MeOH/water (5 mL/5 mL/5 mL) for 16 hours at room temperature. Solvent was removed in vacuo, and the residue was purified by Prep-HPLC B (30-55% MeCN) to give compound 2 as a white solid (88 mg), Yield 23%. LC/MS D: 100% purity, UV=214 nm, Rt=0.939 min, ESI 416.1 (M+H)$^+$). 1H NMR (400 MHz, DMSO-d6) δ 8.15 (0.25H, HCOOH), 7.05 (d, J=7.2 Hz, 1H), 6.55 (s, 1H), 6.24 (d, J=7.2 Hz, 1H), 4.00 (s, 2H), 3.78 (s, 2H), 3.58-3.54 (m, 2H), 3.39-3.38 (m, 4H), 3.24 (s, 2H), 2.71-2.65 (m, 2H), 2.62-2.59 (m, 2H), 2.37-2.39 (m, 2H), 1.80-1.73 (m, 3H), 1.56-1.53 (m, 2H), 1.15-1.06 (m, 2H).

Example 3: Preparation of 2-(2-oxo-4-(4-(5,6,7,8-tetrahydro-1,8-naphthyridin-2-yl)piperidine-1-carbonyl)piperidin-1-yl)acetic acid (Compound 3)

Step 1: methyl 1-(2-tert-butoxy-2-oxoethyl)-2-oxopiperidine-4-carboxylate

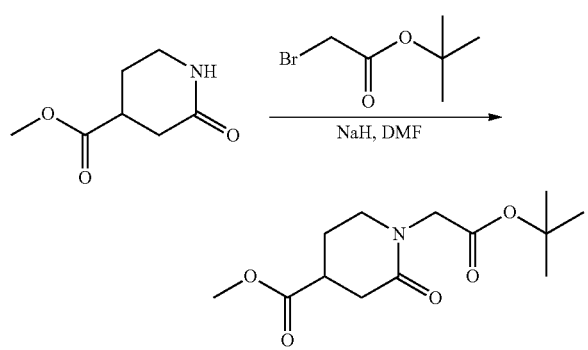

To a solution of methyl 2-oxopiperidine-4-carboxylate (2.90 g, 18.4 mmol) in DMF (30 mL) at 0° C. was added NaH (60% in mineral oil, 886 mg, 22.1 mmol). The mixture was stirred for 30 min, and then tert-butyl 2-bromoacetate (4.32 g, 22.1 mmol) was added. The reaction was stirred at room temperature for 16 hours, then quenched with water (20 mL), and extracted with EtOAc (50 mL×5). The combined organic extracts were washed with brine, dried over Na$_2$SO$_4$, filtered and concentrated in vacuo. The residue was purified by silica gel column (pet ether:EtOAc 4:1) to give methyl 1-(2-tert-butoxy-2-oxoethyl)-2-oxopiperidine-4-carboxylate as a colorless oil (1.5 g). Yield 30% (90% purity, UV=214 nm, ESI 216.1 (M+H)$^+$).

Step 2: 1-(2-tert-butoxy-2-oxoethyl)-2-oxopiperidine-4-carboxylic acid

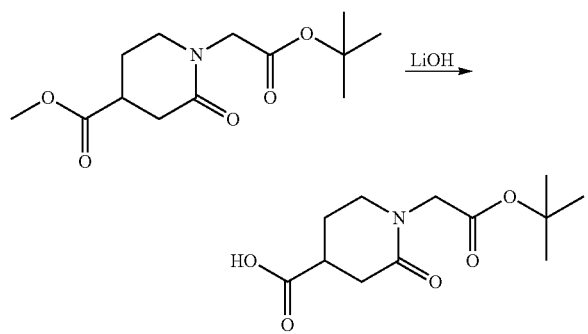

Methyl 1-(2-tert-butoxy-2-oxoethyl)-2-oxopiperidine-4-carboxylate (1.00 g, 3.68 mmol) was treated with LiOH—H$_2$O (201 mg, 4.79 mmol) in THF/MeOH/water (20 mL/20 mL/20 mL) at room temperature for 16 hours. The mixture was adjusted to pH-5 with aqueous HCl (3.0 M, 10 mL) and extracted with EtOAc (50 mL×3). The combined organic extracts were washed with brine, dried over Na$_2$SO$_4$, filtered and concentrated in vacuo to give the desired product 1-(2-tert-butoxy-2-oxoethyl)-2-oxopiperidine-4-carboxylic acid as a pale yellow oil (900 mg). Yield 95% (85% purity, UV=214 nm, ESI 202.0 (M+H)$^+$).

Step 3: tert-butyl 2-(2-oxo-4-(4-(5,6,7,8-tetrahydro-1,8-naphthyridin-2-yl)piperidine-1-carbonyl)piperidin-1-yl)acetate

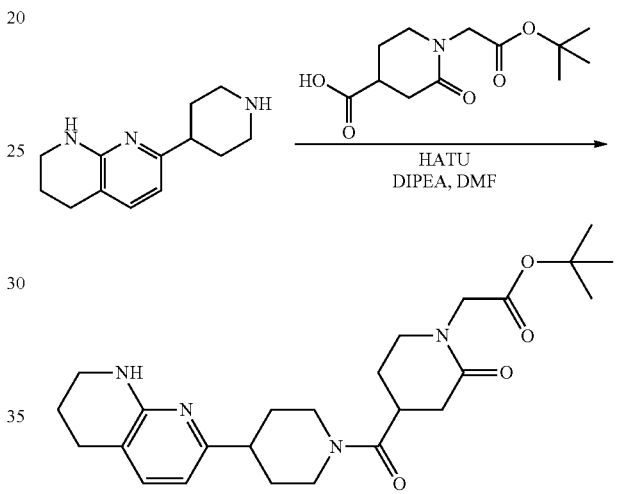

A mixture of 1-(2-tert-butoxy-2-oxoethyl)-2-oxopiperidine-4-carboxylic acid (150 mg, 0.58 mmol) and 7-(piperidin-4-yl)-1,2,3,4-tetrahydro-1,8-naphthyridine (178 mg, 0.70 mmol), DIEA (500 mg, 3.87 mmol) and HATU (450 mg, 1.18 mmol) in DMF (5.0 mL) was stirred at 50° C. for 2 hours. The mixture was concentrated in vacuo, and the residue was purified by silica gel column (DCM:MeOH 20:1) to give the desired product as a pale yellow oil (150 mg). Yield 56% (86% purity, UV=214 nm, ESI 457.4 (M+H)$^+$).

Step 4: 2-(2-oxo-4-(4-(5,6,7,8-tetrahydro-1,8-naphthyridin-2-yl)piperidine-1-carbonyl)piperidin-1-yl)acetic acid (Compound 3)

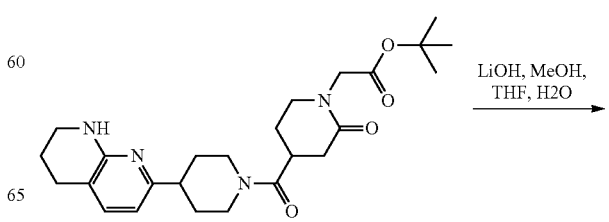

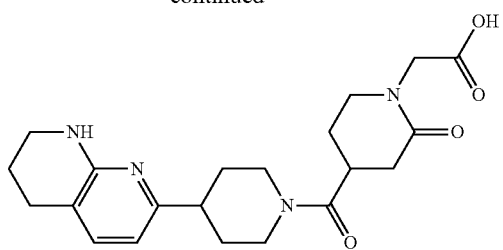

Tert-butyl 2-(2-oxo-4-(4-(5,6,7,8-tetrahydro-1,8-naphthyridin-2-yl)piperidine-1-carbonyl)piperidin-1-yl)acetate (150 mg, 0.33 mmol) was treated with LiOH—H₂O (69 mg, 1.64 mmol) in THF/MeOH/water (5 mL/5 mL/5 mL) at room temperature for 16 hours. Solvent was removed in vacuo, and the residue was purified by Prep-HPLC B (33-50% MeCN) to give the desired product compound 3 as a white solid (20 mg, 15% yield. LC/MS D: 96% purity, UV=214 nm, Rt=1.373 min, ESI 401.1 (M+H)+. 1H NMR (400 MHz, DMSO-d6) δ 8.14 (0.15H, HCOOH), 7.10 (d, J=7.2 Hz, 1H), 6.38-6.36 (m, 1H), 6.31 (d, J=7.2 Hz, 1H), 4.51-4.48 (m, 1H), 4.11-4.04 (m, 2H), 3.87-3.83 (m, 1H), 3.43-3.40 (m, 2H), 3.29-3.24 (m, 5H), 3.13-3.06 (m, 1H), 2.69-2.57 (m, 4H), 2.40-2.26 (m, 2H), 1.91-1.88 (m, 1H), 1.78-1.73 (m, 5H), 1.61-1.55 (m, 1H), 1.47-1.44 (m, 1H).

Example 4: Preparation of 2-(4-(3-(5,6,7,8-tetrahydro-1,8-naphthyridin-2-yl)propylcarbamoyl)piperidin-1-yl)acetic acid (Compound 4)

Step 1: methyl 1-(2-tert-butoxy-2-oxoethyl)piperidine-4-carboxylate

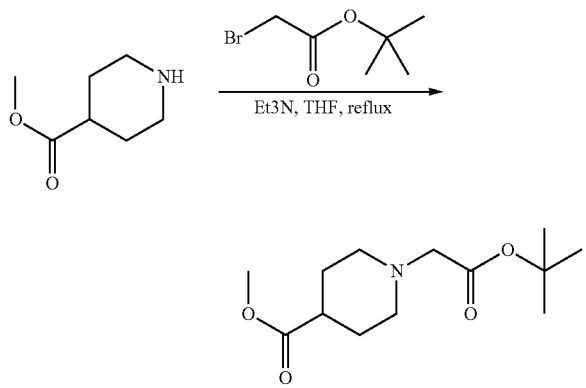

To a solution of piperidine-4-carboxylic acid methyl ester (1.43 g, 1 mmol) and triethylamine (2.02 g, 2 mmol) in THF (20 mL) was added bromo-acetic acid tert-butyl ester (1.95 g, 1 mmol). The resulting mixture was heated at reflux overnight. Solvent was removed in vacuo, and the residue was purified by silica gel column (pet ether:EtOAc 1:1) to give the desired product methyl 1-(2-tert-butoxy-2-oxoethyl)piperidine-4-carboxylate as a colorless oil (0.77 g) Yield 30%. 1H NMR (400 MHz, CDCl3) δ 3.68 (s, 3H), 3.11 (s, 2H), 2.95-2.87 (m, 2H), 2.33-2.21 (m, 3H), 1.94-1.77 (m, 4H), 1.46 (s, 9H).

Step 2: 1-(2-tert-butoxy-2-oxoethyl)piperidine-4-carboxylic acid

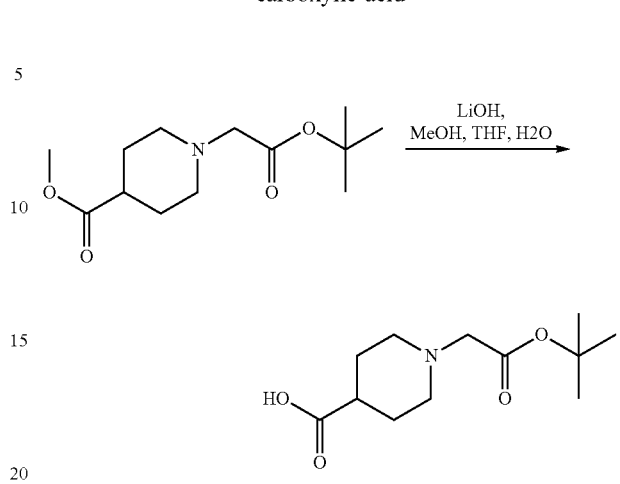

A mixture of methyl 1-(2-tert-butoxy-2-oxoethyl)piperidine-4-carboxylate (0.77 g, 3.0 mmol) was treated with LiOH—H₂O (126 mg, 3.0 mmol) in MeOH (10 mL), THF (5 mL) and H₂O (5 mL) at room temperature overnight. Organic solvent was removed in vacuo; then aqueous HCl (1N) was added to pH-5. The mixture was extracted with EtOAc (10 mL×3). The combined organic layer was washed with brine, dried over anhydrous sodium sulfate, filtered and concentrated in vacuo to give the desired product 1-(2-tert-butoxy-2-oxoethyl)piperidine-4-carboxylic acid as a colorless oil (590 mg). Yield 81% (ESI 244 (M+H)+).

Step 3: butyl 2-(4-(3-(5,6,7,8-tetrahydro-1,8-naphthyridin-2-yl)propylcarbamoyl) piperidin-1-yl)acetate

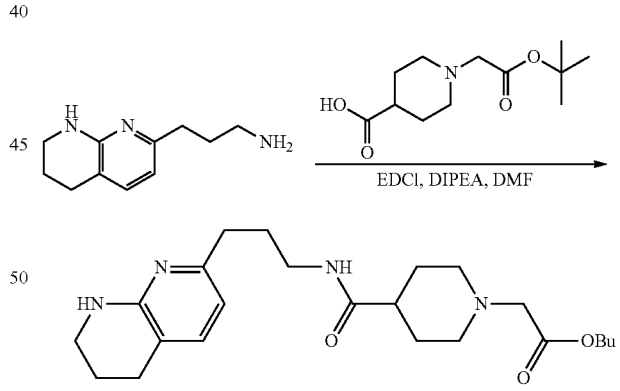

A mixture of 3-(5,6,7,8-tetrahydro-1,8-naphthyridin-2-yl)propan-1-amine hydrochloride (140 mg, 0.62 mmol), 1-(2-tert-butoxy-2-oxoethyl)piperidine-4-carboxylic acid (100 mg, 0.41 mmol), EDCI (118 mg, 0.62 mmol) and DIPEA (159 mg, 1.23 mmol) in DMF (4 mL) was stirred at 50° C. overnight. Solvent was removed in vacuo, and the residue was purified by silica gel column (DCM:MeOH 20:1) to give the desired product butyl 2-(4-(3-(5,6,7,8-tetrahydro-1,8-naphthyridin-2-yl)propylcarbamoyl)piperidin-1-yl)acetate as a yellow oil (120 mg). Yield 70% (95% purity, UV=254 nm, ESI 417.2 (M+H)+).

Step 4: 2-(4-(3-(5,6,7,8-tetrahydro-1,8-naphthyridin-2-yl)propylcarbamoyl) piperidin-1-yl)acetic acid (Compound 4)

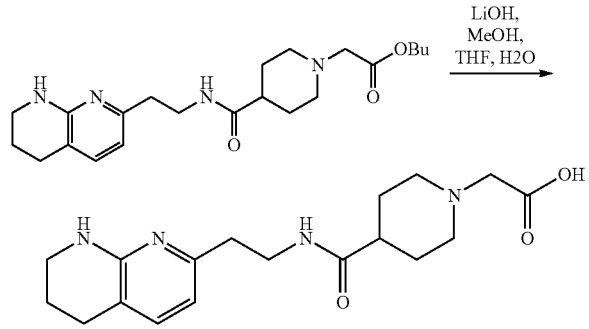

Butyl 2-(4-(2-(5,6,7,8-tetrahydro-1,8-naphthyridin-2-yl)ethylcarbamoyl)piperidin-1-yl)acetate (120 mg, 0.29 mmol) was treated with LiOH—H$_2$O (59 mg, 1.40 mmol) in MeOH (4 mL), THF (2 mL) and H$_2$O (2 mL) at 40° C. for 2 hours. Solvent was removed in vacuo, and the residue was purified by Prep-HPLC A (30-65% MeCN) to give compound 4 as a white solid (40 mg, 39% yield). LC/MS C: 100% purity, UV=214 nm, Rt=1.36 min, ESI 361 (M+H)$^+$. 1H NMR (500 MHz, CD3OD) δ 7.16 (d, J=7.0 Hz, 1H), 6.39 (d, J=7.0 Hz, 1H), 3.66-3.55 (m, 4H), 3.39 (t, J=5.5 Hz, 2H), 3.22 (t, J=7.0 Hz, 2H), 3.04-2.96 (m, 2H), 2.72 (t, J=6.5 Hz, 2H), 2.58-2.43 (m, 3H), 2.05-1.98 (m, 4H), 1.92-1.80 (m, 4H).

Example 5: Preparation of 2-(4-(3-(5,6,7,8-tetrahydro-1,8-naphthyridin-2-yl) propylcarbamoyl)piperazin-1-yl)acetic acid (Compound 5)

Step 1: ethyl 2-(4-(3-(5,6,7,8-tetrahydro-1,8-naphthyridin-2-yl)propylcarbamoyl) piperazin-1-yl)acetate

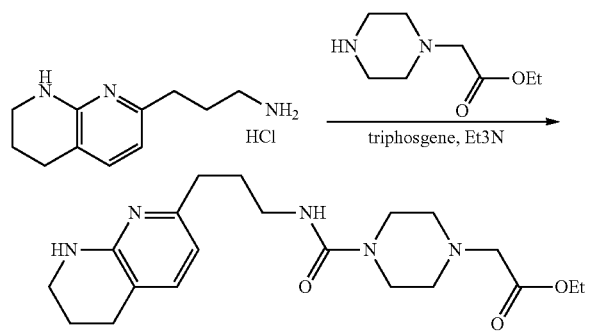

To a mixture of 3-(5,6,7,8-tetrahydro-1,8-naphthyridin-2-yl)propan-1-amine hydrochloride (200 mg, 0.88 mmol) and triethylamine (177 mg, 1.75 mmol) in DCM (6 mL) at 0° C. was added triphosgene (157 mg, 0.52 mmol). The mixture was stirred for 30 min, and then ethyl 2-(piperazin-1-yl)acetate (151 mg, 0.88 mmol) in DCM (2 mL) was added. The mixture was stirred at room temperature overnight. Solvent was removed in vacuo, and the residue was purified by silica gel column (DCM:MeOH 10:1) to give the desired product as a white solid (226 mg). Yield 66% (ESI 390.1 (M+H)+).

Step 2: 2-(4-(3-(5,6,7,8-tetrahydro-1,8-naphthyridin-2-yl)propylcarbamoyl) piperazin-1-yl)acetic acid (Compound 5)

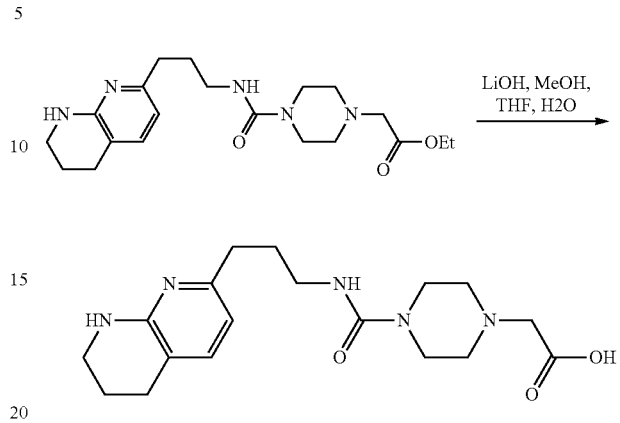

ethyl 2-(4-(3-(5,6,7,8-tetrahydro-1,8-naphthyridin-2-yl)propylcarbamoyl)piperazin-1-yl)acetate (200 mg, 0.51 mmol) was treated with LiOH—H$_2$O (100 mg, 2.38 mmol) in MeOH (4 mL), THF (2 mL) and H$_2$O (2 mL) at room temperature overnight. Solvent was removed in vacuo, and the residue was purified by Prep-HPLC A (30-65% MeCN) to give compound 5 (MRT-A0034) as a white solid (45 mg), Yield 24%. LC/MS B: 100% purity, UV=214 nm, Rt=0.794 min, ESI 362.1 (M+H)+). 1H NMR (400 MHz, CD3OD) δ 7.18 (d, J=7.2 Hz, 1H), 6.41 (d, J=7.2 Hz, 1H), 3.48-3.41 (m, 4H), 3.39 (t, J=5.6 Hz, 2H), 3.19 (t, J=6.8 Hz, 2H), 3.12 (s, 2H), 2.75-2.65 (m, 6H), 2.56 (t, J=7.6 Hz, 2H), 1.91-1.80 (m, 4H).

Example 6: Preparation of (S)-2-(3-(hydroxymethyl)-2-oxo-4-(3-(5,6,7,8-tetrahydro-1,8-naphthyridin-2-yl)propylcarbamoyl)piperazin-1-yl)acetic acid (Compound 6)

Step 1: ethyl 2-(2,2-dimethoxyethylamino)acetate

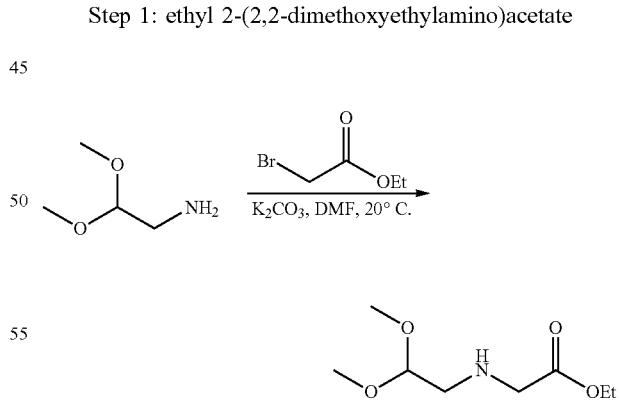

A mixture of 2,2-dimethoxyethanamine (5.0 g, 47.55 mmol), ethyl 2-bromoacetate (7.9 g, 47.30 mmol) and K$_2$CO$_3$ (6.64 g, 48.04 mmol) in DMF (40 mL) was stirred at room temperature overnight. Solvent was removed in vacuo, and the residue was purified by silica gel column (DCM: MeOH 20:1) to give the desired product ethyl 2-(2,2-dimethoxyethylamino)acetate as a colorless oil (6.5 g). Yield 71% (ESI 191.0 (M+H)+).

Step 2: (S)-ethyl 2-(3-(benzyloxy)-2-(tert-butoxycarbonylamino)-N-(2,2-dimethoxyethyl)propanamido)acetate

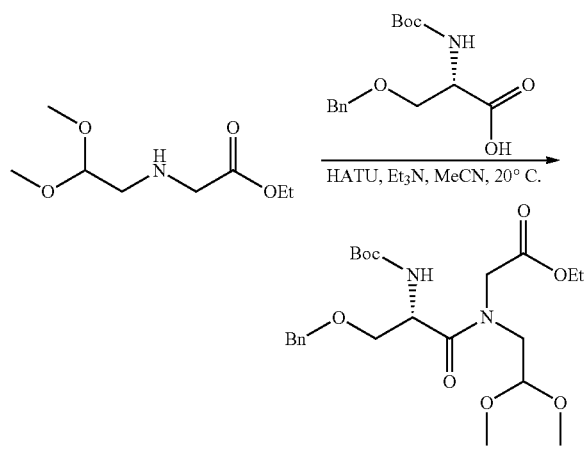

A mixture of ethyl 2-(2,2-dimethoxyethylamino)acetate (1.0 g, 5.23 mmol), (S)-3-(benzyloxy)-2-(tert-butoxycarbonylamino)propanoic acid (1.54 g, 5.23 mmol), HATU (2.98 g, 7.84 mmol) and DIEA (2.02 g, 15.68 mmol) in MeCN (10 mL) was stirred at room temperature overnight. Solvent was removed in vacuo, and the residue was purified by silica gel column (pet ether:EtOAc 1:1) to give the desired product (S)-ethyl 2-(3-(benzyloxy)-2-(tert-butoxycarbonylamino)-N-(2,2-dimethoxyethyl)propanamido)acetate as a colorless oil (1.9 g). Yield 77% (ESI 468 (M+H)$^+$).

Step 3: (S)-tert-butyl-2-(benzyloxymethyl)-4-(2-ethoxy-2-oxoethyl)-3-oxo-3,4-dihydropyrazine-1(2H)-carboxylate

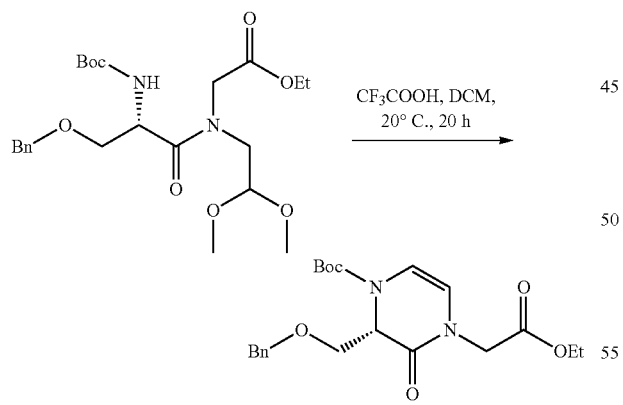

A mixture of (S)-ethyl 2-(3-(benzyloxy)-2-(tert-butoxycarbonylamino)-N-(2,2-dimethoxyethyl)propanamido)acetate (1.5 g, 3.2 mmol) and CF$_3$COOH (1.09 g, 9.6 mmol) in DCM (10 mL) was stirred at room temperature overnight. Solvent was removed in vacuo, and the residue was purified by silica gel column (pet ether:EtOAc 1:1) to give the desired product (S)-tert-butyl 2-(benzyloxymethyl)-4-(2-ethoxy-2-oxoethyl)-3-oxo-3,4-dihydropyrazine-1(2H)-carboxylate as a colorless oil (700 mg). Yield 72% (ESI 404 (M+H)+). 1H NMR (500 MHz, CD3OD) δ 7.20 (d, J=3.8 Hz, 6H), 6.36-6.13 (m, 1H), 5.63 (dd, J=49.5, 6.0 Hz, 1H), 4.92-4.81 (m, 1H), 4.51-4.33 (m, 3H), 4.17 (d, J=4.8 Hz, 2H), 4.12-4.02 (m, 2H), 3.72-3.62 (m, 1H), 3.57-3.46 (m, 1H), 1.41-1.32 (m, 10H), 1.15 (t, J=7.1 Hz, 4H).

Step 4: (S)-tert-butyl 4-(2-ethoxy-2-oxoethyl)-2-(hydroxymethyl)-3-oxopiperazine-1-carboxylate

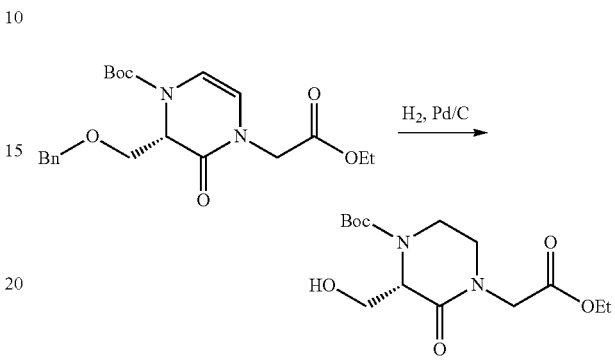

A mixture of (S)-tert-butyl-2-(benzyloxymethyl)-4-(2-ethoxy-2-oxoethyl)-3-oxo-3,4-dihydropyrazine-1(2H)-carboxylate (700 mg, 2.3 mmol) and Pd/C (140 mg, 20 wt %) in MeOH (10 mL) was stirred under H$_2$ balloon at room temperature overnight. The suspension was filtered through a pad of Celite and the filter cake was washed with MeOH (10 mL×2). The combined filtrates were concentrated in vacuo, and the residue was purified by silica gel column (pet ether:EtOAc 1:1) to give the desired product (S)-tert-butyl 4-(2-ethoxy-2-oxoethyl)-2-(hydroxymethyl)-3-oxopiperazine-1-carboxylate as a colorless oil (540 mg). Yield 99% (ESI 316 (M+H)+).

Step 5: (S)-ethyl-2-(3-(hydroxymethyl)-2-oxo-4-(3-(5,6,7,8-tetrahydro-1,8-naphthyridin-2-yl)propylcarbamoyl)piperazin-1-yl)acetate

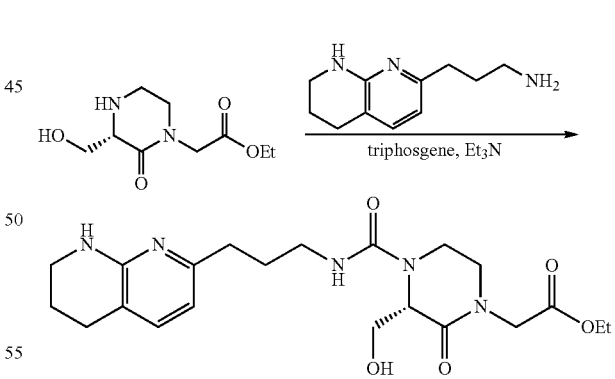

A mixture of 3-(5,6,7,8-tetrahydro-1,8-naphthyridin-2-yl)propan-1-amine (212 mg, 1.11 mmol), triphosgene (137 mg, 0.46 mmol) and triethylamine (562 mg, 5.55 mmol) in DCM (8 mL) was stirred at 0° C. for 1 hour. A solution of (S)-tert-butyl 4-(2-ethoxy-2-oxoethyl)-2-(hydroxymethyl)-3-oxopiperazine-1-carboxylate (200 mg, 0.93 mmol) in DCM (2 mL) was added dropwise by syringe at 0° C. The reaction mixture was stirred at room temperature overnight. Solvent was removed in vacuo, and the residue was purified by silica gel column (DCM:CH$_3$OH 20:1) to give the desired product (S)-ethyl 2-(3-(hydroxymethyl)-2-oxo-4-(3-(5,6,7,8-tetrahydro-1,8-naphthyridin-2-yl)propylcarbamoyl)piperazin-1-yl)acetate as a colorless oil (250 mg). Yield 63% (ESI 433 (M+H)+).

Step 6: (S)-2-(3-(hydroxymethyl)-2-oxo-4-(3-(5,6,7,8-tetrahydro-1,8-naphthyridin-2-yl)propylcarbamoyl)piperazin-1-yl)acetic acid (Compound 6)

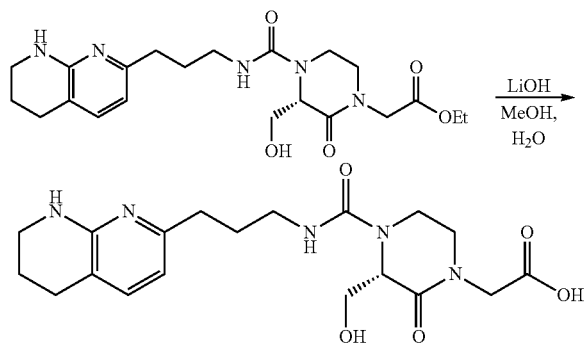

(S)-ethyl 2-(3-(hydroxymethyl)-2-oxo-4-(3-(5,6,7,8-tetrahydro-1,8-naphthyridin-2-yl)propylcarbamoyl)piperazin-1-yl)acetate (250 mg, 0.58 mmol) was treated with LiOH—H$_2$O (97 mg, 2.31 mmol) in MeOH (4 mL) and H$_2$O (1 mL) at room temperature for 2 hours. Solvent was removed in vacuo, and the residue was purified by Prep-HPLC A (30-65% MeCN) to give compound 6 as a white solid (25 mg, 11% yield). LC/MS B: 100% purity, UV=214 nm, Rt=0.58 min, ESI 405.5 (M+H)+. 1H NMR (500 MHz, MeOD) δ 7.49 (d, J=7.3 Hz, 1H), 6.55 (d, J=7.4 Hz, 1H), 4.59 (d, J=16.6 Hz, 2H), 4.09 (dd, J=11.5, 7.1 Hz, 2H), 3.92 (dd, J=11.6, 3.5 Hz, 1H), 3.78 (dd, J=11.7, 4.1 Hz, 1H), 3.68 (d, J=11.6 Hz, 1H), 3.49-3.35 (m, 4H), 3.20 (d, J=8.1 Hz, 2H), 2.80-2.60 (m, 4H), 1.97-1.70 (m, 4H).

Example 7: Preparation of 2-(3-(1-methyl-3-(4-(5,6,7,8-tetrahydro-1,8-naphthyridin-2-yl)butyl)ureido)-2-oxopyrrolidin-1-yl)acetic acid (Compounds 7-E1 and 7-E2)

Step 1: (R)-1-benzyl 4-methyl 2-(tert-butoxycarbonylamino)succinate

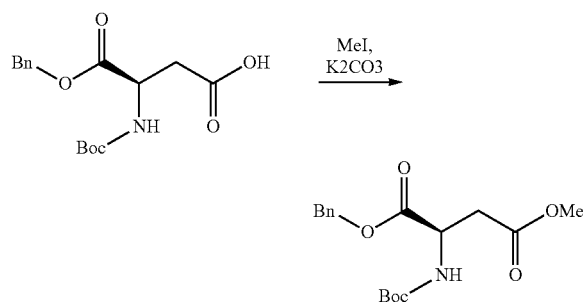

A mixture of (R)-4-(benzyloxy)-3-(tert-butoxycarbonylamino)-4-oxobutanoic acid (11.0 g, 34.0 mmol), K$_2$CO$_3$ (17.0 g, 123 mmol) and MeI (6.50 mL, 104 mmol) in acetone (500 mL) was stirred at room temperature for 16 hours. The mixture was concentrated, diluted with water and extracted with EtOAc (200 mL×5). The combined organic extracts were washed with brine and dried over Na$_2$SO$_4$, filtered and concentrated in vacuo to give (R)-1-benzyl 4-methyl 2-(tert-butoxycarbonylamino)succinate as an yellow solid (11.0 g). Yield 98% (94% purity, UV=214 nm, ESI 238.1 (M+H)+).

Step 2: (R)-1-benzyl 4-methyl 2-(tert-butoxycarbonyl(methyl)amino)succinate

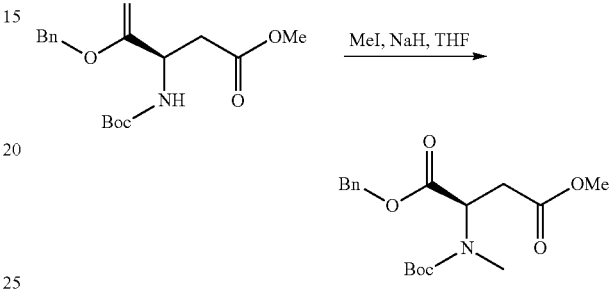

To a solution of (R)-1-benzyl 4-methyl 2-(tert-butoxycarbonylamino)succinate (3.00 g, 8.89 mmol) and MeI (1.50 mL, 24.1 mmol) in DMF (30 mL) at 0° C. was added NaH (60% in mineral oil, 533 mg, 13.3 mmol). The mixture was stirred at room temperature for 1 hour, then diluted with water (20 mL) and extracted with EtOAc (50 mL×5). The combined organic extracts were washed with brine and dried over Na$_2$SO$_4$, filtered and concentrated in vacuo to give (R)-1-benzyl 4-methyl 2-(tert-butoxycarbonyl(methyl)amino)succinate as an yellow oil (3.00 g). Yield 98% (88% purity, UV=214 nm, ESI 252.3 (M+H)+).

Step 3: (R)-benzyl 2-(tert-butoxycarbonyl(methyl)amino)-4-oxobutanoate

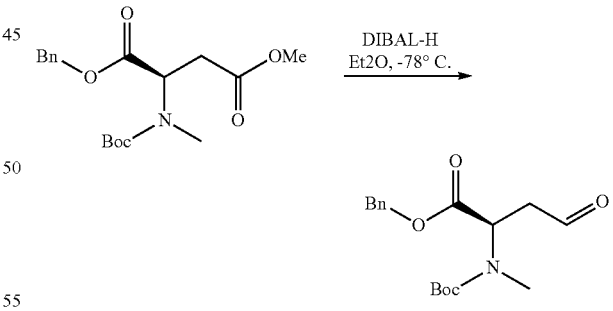

To a solution of (R)-1-benzyl 4-methyl 2-(tert-butoxycarbonyl(methyl)amino)succinate (3.00 g, 8.54 mmol) in anhydrous Et$_2$O (150 mL) at −78° C. was added dropwise DIBAL-H (1.0 M, 17.0 mL). The mixture was stirred at −78° C. for 1 hour, then quenched with sat aqueous NH$_4$Cl (20 mL). The mixture was stirred at room temperature for 1 h, then filtered and extracted with EtOAc (50 mL×3). The combined organic extracts were washed with brine, dried over Na$_2$SO$_4$, filtered and concentrated in vacuo to give the desired product as a pale yellow oil (2.5 g). Yield 92% (80% purity, UV=214 nm, ESI 222.4 (M+H)+).

Step 4: ethyl 2-(3-(tert-butoxycarbonyl(methyl)amino)-2-oxopyrrolidin-1-yl)acetate

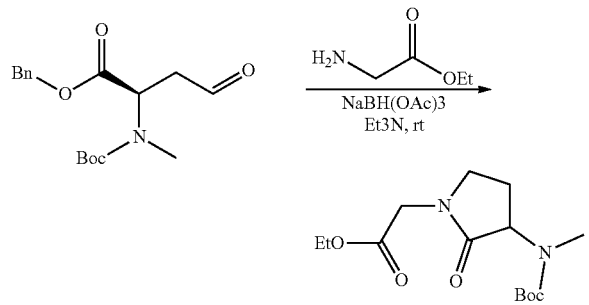

A mixture of ethyl 2-aminoacetate (4.42 g, 31.7 mmol), triethylamine (7.5 mL, 54.1 mmol), NaBH(OAc)₃ (4.00 g, 18.8 mmol), acetic acid (cat) and (R)-benzyl 2-(tert-butoxycarbonyl(methyl)amino)-4-oxobutanoate (1.61 g, 5.01 mmol) in DCM (100 mL) was stirred at room temperature for 16 hours. The reaction was quenched with water (20 mL) and extracted with DCM (50 mL×3). The combined organic extracts were concentrated in vacuo, and the residue was purified by reverse phase C18 column (35%-50% MeCN in H₂O (0.5% NH4HCO3)) to give the desired product as a pale yellow oil (410 mg). Yield 18% (95% purity, UV=214 nm, ESI 201.3 (M+H)+).

Step 5: ethyl 2-(3-(methylamino)-2-oxopyrrolidin-1-yl)acetate

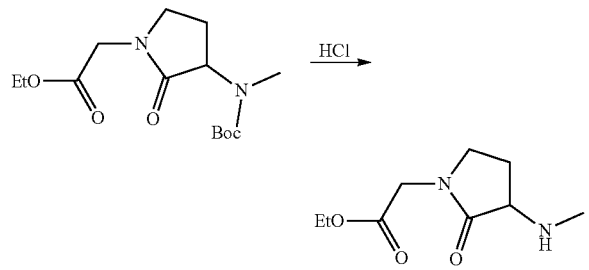

Ethyl 2-(3-(tert-butoxycarbonyl(methyl)amino)-2-oxopyrrolidin-1-yl)acetate (410 mg, 1.36 mmol) was treated with a solution of HCl in dioxane (4.0 M, 10 mL) at room temperature for 2 hours. The reaction was concentrated in vacuo to give the desired product as a pale yellow solid (340 mg). Yield 95% (95% purity, UV=214 nm, ESI 201.3 (M+H)+).

Step 6: ethyl 2-(3-(1-methyl-3-(4-(5,6,7,8-tetrahydro-1,8-naphthyridin-2-yl)butyl)ureido)-2-oxopyrrolidin-1-yl)acetate

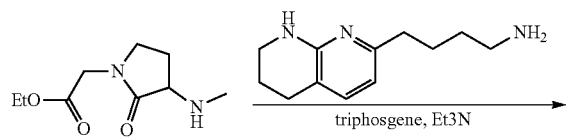

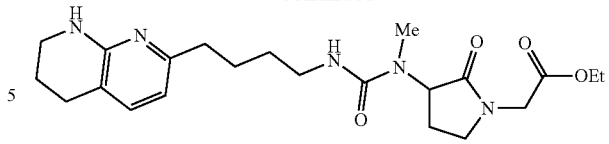

To a mixture of 4-(5,6,7,8-tetrahydro-1,8-naphthyridin-2-yl)butan-1-amine (375 mg, 1.55 mmol) and triethylamine (1.00 mL) in DCM (20 mL) at 0° C. was added triphosgene (250 mg, 0.85 mmol). The mixture was stirred for 30 min, and then ethyl 2-(3-(methylamino)-2-oxopyrrolidin-1-yl)acetate (340 mg, 1.68 mmol) in DCM (5 mL) was added. The mixture was stirred at room temperature for 16 hours. Solvent was removed in vacuo, and the residue was purified by silica gel column (DCM:MeOH 20:1) to give the desired product ethyl 2-(3-(1-methyl-3-(4-(5,6,7,8-tetrahydro-1,8-naphthyridin-2-yl)butyl)ureido)-2-oxopyrrolidin-1-yl)acetate as a pale yellow solid (300 mg). Yield 45% (82% purity, UV=214 nm, ESI 432.4 (M+H)+).

Step 7: 2-(3-(1-methyl-3-(4-(5,6,7,8-tetrahydro-1,8-naphthyridin-2-yl)butyl)ureido)-2-oxopyrrolidin-1-yl)acetic acid (Compounds 7-E1 and 7-E2)

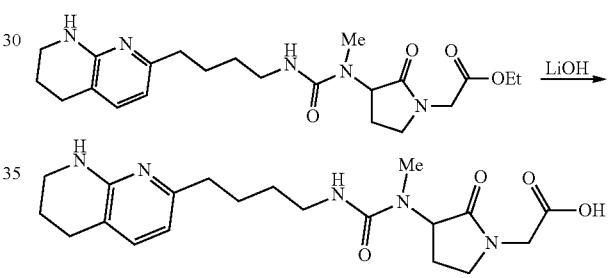

Ethyl 2-(3-(1-methyl-3-(4-(5,6,7,8-tetrahydro-1,8-naphthyridin-2-yl)butyl)ureido)-2-oxopyrrolidin-1-yl)acetate (300 mg, 0.70 mmol) was treated with LiOH—H₂O (292 mg, 6.95 mmol) in MeOH (7.5 mL) and water (2.5 mL) at room temperature for 2 hours. Solvent was removed in vacuo, and the residue was purified by Prep-HPLC A (35-65% MeCN) to give the racemic compound 7 as a white solid (245 mg, 85% yield). The racemic product was separated by prep chiral SFC A to give enantiomeric products compound 7-E1 (118 mg) and compound 7-E2 (95 mg) as white solids.

Compound 7-E1 LC/MS A: 96% purity, UV=214 nm, Rt=1.376 min, ESI 404.3 (M+H)+. 1H NMR (400 MHz, D2O) δ 7.02 (d, J=6.8 Hz, 1H), 6.38 (m, 2), 6.25 (d, J=7.2 Hz, 1H), 4.90 (m, 1H), 3.94-3.81 (m, 2H), 3.22 (m, 4H), 3.02-2.97 (m, 2H), 2.60 (m, 4H), 2.43-2.40 (m, 3H), 2.14-2.08 (m, 1H), 1.89-1.84 (m, 1H), 1.75-1.71 (m, 2H), 1.56-1.53 (m, 2H), 1.41-1.40 (m, 2H). Chiral SFC A (40% MeOH): ee 100%, Rt=1.91 min.

Compound 7-E2 LC/MS A: 99.5% purity, UV=214 nm, Rt=1.37 min, ESI 404.4 (M+H)+. 1H NMR (400 MHz, CD3OD) δ 7.02 (d, J=6.8 Hz, 1H), 6.38 (m, 2), 6.25 (d, J=7.2 Hz, 1H), 4.90 (m, 1H), 3.94-3.81 (m, 2H), 3.22 (m, 4H), 3.02-2.97 (m, 2H), 2.60 (m, 4H), 2.43-2.40 (m, 3H), 2.14-2.08 (m, 1H), 1.89-1.84 (m, 1H), 1.75-1.71 (m, 2H), 1.56-1.53 (m, 2H), 1.41-1.40 (m, 2H). Chiral SFC A (40% MeOH): ee 100%, Rt=4.02 min.

Example 8: Preparation of 2-phenyl-2-(4-(4-(5,6,7,8-tetrahydro-1,8-naphthyridin-2-yl)butanamido)piperidin-1-yl)acetic acid (Compounds 8-E1 and 8-E2)

Step 1: tert-butyl 4-(4-(5,6,7,8-tetrahydro-1,8-naphthyridin-2-yl)butanamido)piperidine-1-carboxylate

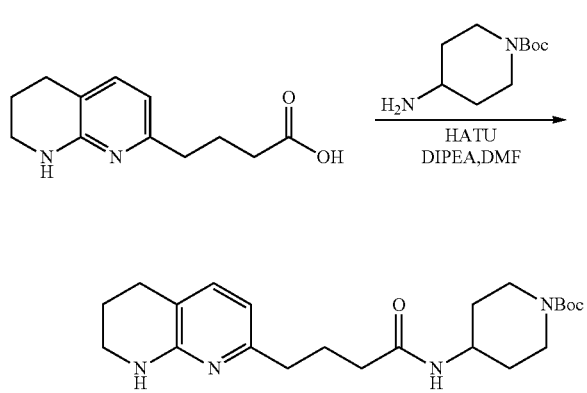

A mixture of 4-(5,6,7,8-tetrahydro-1,8-naphthyridin-2-yl) butanoic acid (500 mg, 2.27 mmol), tert-butyl 4-aminopiperidine-1-carboxylate (454 mg, 2.27 mmol), HATU (1296 mg, 3.41 mmol) and DIEA (879 mg, 6.81 mmol) in DMF (6 mL) was stirred at room temperature overnight. Solvent was removed in vacuo, and the residue was purified by silica gel column (pet ether:EtOAc 2:1) to give the desired product tert-butyl 4-(4-(5,6,7,8-tetrahydro-1,8-naphthyridin-2-yl) butanamido)piperidine-1-carboxylate as a yellow oil (620 mg). Yield 68% (98% purity, UV=214 nm, ESI 402.0 (M+H)$^+$).

Step 2: N-(piperidin-4-yl)-4-(5,6,7,8-tetrahydro-1,8-naphthyridin-2-yl)butanamide

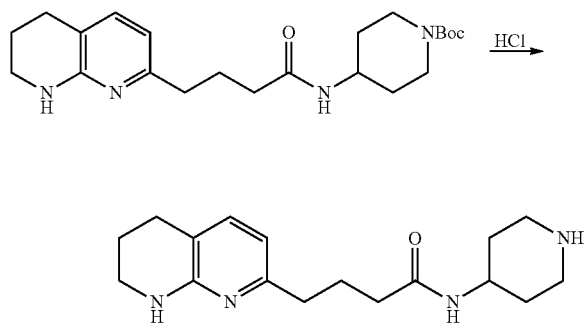

Tert-butyl 4-(4-(5,6,7,8-tetrahydro-1,8-naphthyridin-2-yl)butanamido)piperidine-1-carboxylate (620 mg, 1.54 mmol) was treated with HCl (4 mL, 15.4 mmol) in 1,4-dioxane (5 mL) at room temperature overnight. Solvent was removed in vacuo, and the residue was purified by silica gel column (DCM:MeOH 40:1) to give the desired product N-(piperidin-4-yl)-4-(5,6,7,8-tetrahydro-1,8-naphthyridin-2-yl)butanamide as a yellow oil (440 mg). Yield 95% (100% purity, UV=214 nm, ESI 302 (M+H)$^+$).

Step 3: ethyl 2-phenyl-2-(4-(4-(5,6,7,8-tetrahydro-1,8-naphthyridin-2-yl)butanamido)piperidin-1-yl)acetate

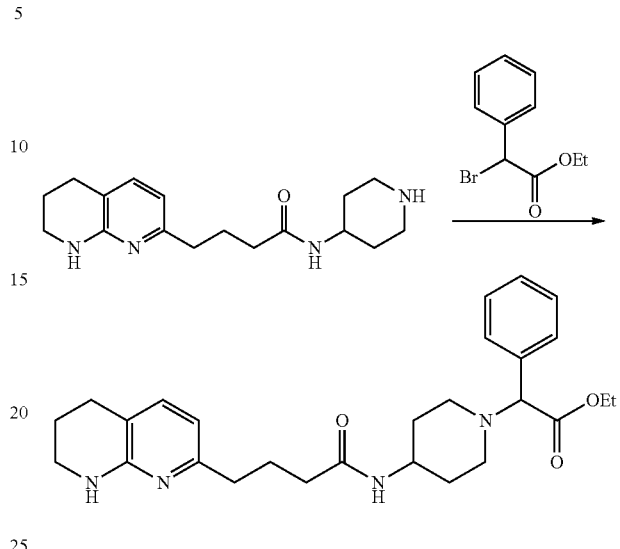

A mixture of N-(piperidin-4-yl)-4-(5,6,7,8-tetrahydro-1,8-naphthyridin-2-yl)butanamide (200 mg, 0.66 mmol), ethyl 2-bromo-2-phenylacetate (192 mg, 0.79 mmol), DIEA (255 mg, 1.98 mmol) and K$_2$CO$_3$ (273 mg, 1.98 mmol) in MeCN (4 mL) was stirred at 50° C. for 3 hours. Solvent was removed in vacuo, and the residue was purified by silica gel column (DCM:MeOH 20:1) to give the desired product ethyl 2-phenyl-2-(4-(4-(5,6,7,8-tetrahydro-1,8-naphthyridin-2-yl)butanamido)piperidin-1-yl)acetate as a yellow oil (160 mg). Yield 52% (100% purity, UV=214 nm, ESI 464 (M+H)$^+$).

Step 4: 2-phenyl-2-(4-(4-(5,6,7,8-tetrahydro-1,8-naphthyridin-2-yl)butanamido)piperidin-1-yl)acetic acid (Compounds 8-E1 and 8-E2)

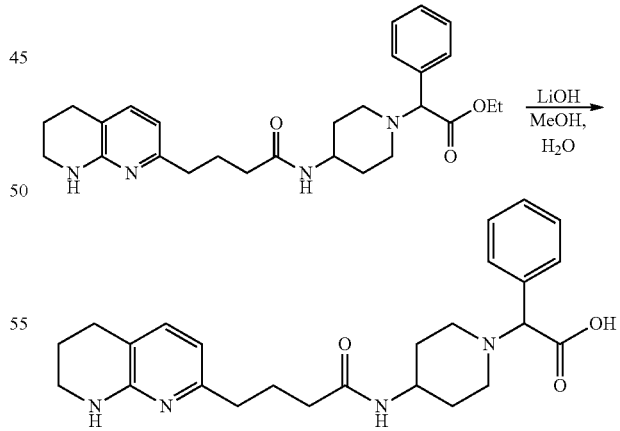

Ethyl 2-phenyl-2-(4-(4-(5,6,7,8-tetrahydro-1,8-naphthyridin-2-yl)butanamido)piperidin-1-yl)acetate (160 mg, 0.34 mmol) was treated with LiOH—H$_2$O (58 mg, 1.38 mmol) in MeOH (4 mL) and H$_2$O (1 mL) for 2 hours at room temperature. Solvent was removed in vacuo, and the residue was purified by Prep-HPLC A (33-65% MeCN) to give the racemic compound 8 as a white solid (65 mg, 44% yield).

The racemic product was separated by prep chiral SFC A to give enantiomeric products compound 8-E1 (32 mg) and compound 8-E2 (31 mg) as white solids.

Compound 8-E1 LC/MS A: 95% purity, UV=214 nm, Rt=1.44 min, ESI 436 (M+H)+. 1H NMR (400 MHz, CD3OD) δ 7.59-7.58 (m, 2H), 7.42-7.41 (m, 3H), 7.19 (d, J=7.0 Hz, 1H), 6.39 (d, J=7.5 Hz, 1H), 4.33 (s, 1H), 3.82 (m, 1H), 3.39-3.32 (m, 4H), 2.96-2.69 (m, 6H), 2.56 (t, J=7.5 Hz, 2H), 2.20 (t, J=7.5 Hz, 2H), 1.86-1.28 (m, 6H). Chiral SFC A (45% MeOH): ee 100%, Rt=2.09 min.

Compound 8-E2 LC/MS A: 95.8% purity, UV=214 nm, Rt=1.45 min, ESI 436 (M+H)+. 1H NMR (400 MHz, CD3OD) δ 7.59-7.58 (m, 2H), 7.42-7.41 (m, 3H), 7.19 (d, J=7.0 Hz, 1H), 6.39 (d, J=7.5 Hz, 1H), 4.33 (s, 1H), 3.82 (m, 1H), 3.39-3.32 (m, 4H), 2.96-2.69 (m, 6H), 2.56 (t, J=7.5 Hz, 2H), 2.20 (t, J=7.5 Hz, 2H), 1.86-1.28 (m, 6H). Chiral SFC A (45% MeOH): ee 100%, Rt=3.8 min.

Example 9: Preparation of 2-(4-(4-(5,6,7,8-tetrahydro-1,8-naphthyridin-2-yl)butylamino)piperidin-1-yl)propanoic acid (Compound 9)

Step 1: methyl 2-(4-oxopiperidin-1-yl)propanoate

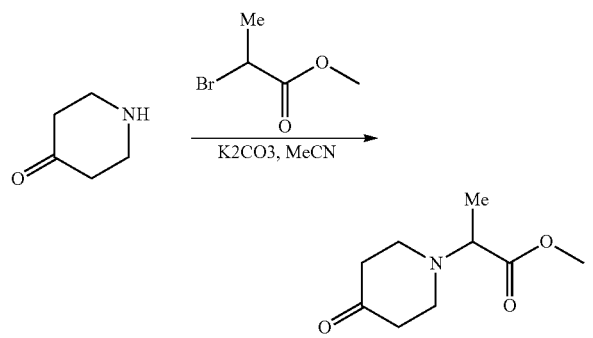

A mixture of piperidin-4-one hydrochloride (1.0 g, 7.38 mmol), methyl 2-bromopropanoate (1.85 g, 11.06 mmol) and K₂CO₃ (3.06 g, 22.13 mmol) in MeCN (20 mL) was stirred at room temperature for 4 hours. Solvent was removed in vacuo, and the residue was purified by silica gel column (pet ether:EtOAc 2:1) to give the desired product as a colorless oil (1.2 g). Yield 88% (80% purity, UV=214 nm, ESI 186.1 (M+H)+).

Step 2: methyl 2-(4-(4-(5,6,7,8-tetrahydro-1,8-naphthyridin-2-yl)butylamino)piperidin-1-yl)propanoate

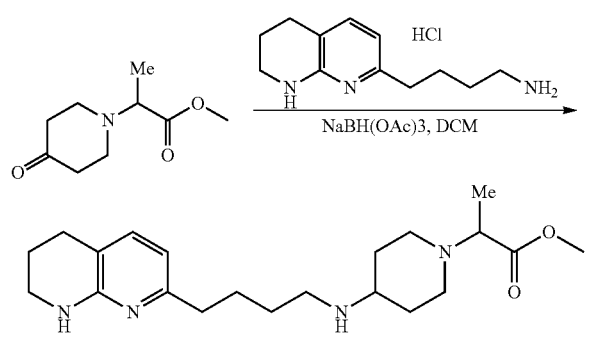

To a solution of 4-(5,6,7,8-tetrahydro-1,8-naphthyridin-2-yl)butan-1-amine hydrochloride (200 mg, 0.72 mmol) in DCM (5 mL) was added triethylamine (145 mg, 1.44 mmol) at room temperature. The mixture was stirred for 10 min, and then methyl 2-(4-oxopiperidin-1-yl)propanoate (213 mg, 0.86 mmol), NaBH(OAc)₃ (457 mg, 2.16 mmol) and one drop of HOAc were added. The mixture was stirred at room temperature overnight. Solvent was removed in vacuo, and the residue was purified by silica gel column (DCM:MeOH 20:1) to give the desired product as a colorless oil (240 mg). Yield 89% (100% purity, UV=254 nm, ESI 375.3 (M+H)+).

Step 3: 2-(4-(4-(5,6,7,8-tetrahydro-1,8-naphthyridin-2-yl)butylamino)piperidin-1-yl)propanoic acid (Compound 9)

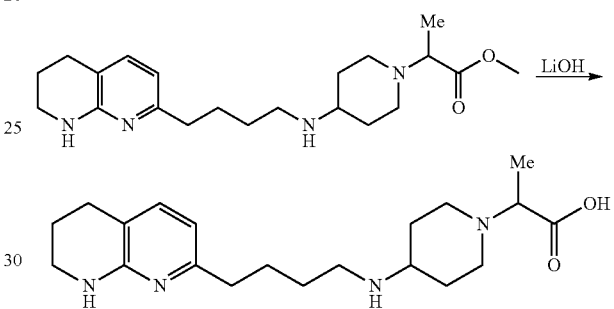

Methyl 2-(4-(4-(5,6,7,8-tetrahydro-1,8-naphthyridin-2-yl)butylamino)piperidin-1-yl)propanoate (100 mg, 0.27 mmol) was treated with LiOH—H₂O (42 mg, 1.0 mmol) in MeOH (4 mL) and H₂O (1 mL) for 2 hours at room temperature. Solvent was removed in vacuo, and the residue was purified by Prep-HPLC A (30-65% MeCN) to give compound 9 (as a white solid (35 mg, yield 36%). LC/MS C: 97.2% purity, UV=214 nm, Rt=1.166 min, ESI 361.4 (M+H)+). 1H NMR (400 MHz, CD3OD) δ 7.14 (d, J=7.2 Hz, 1H), 6.38 (d, J=7.6 Hz, 1H), 3.39-3.18 (m, 4H), 2.91-2.83 (m, 3H), 2.72-2.53 (m, 6H), 2.15-2.02 (m, 2H), 1.89-1.84 (m, 2H), 1.75-1.59 (m, 6H), 1.36 (d, J=6.8 Hz, 3H).

Example 10: Preparation of 2-phenyl-2-(4-(5-(5,6,7,8-tetrahydro-1,8-naphthyridin-2-yl)pentyl)piperazin-1-yl)acetic acid (Compounds 10-E1 and 10-E2)

Step 1: tert-butyl 4-(2-methoxy-2-oxo-1-phenylethyl)piperazine-1-carboxylate

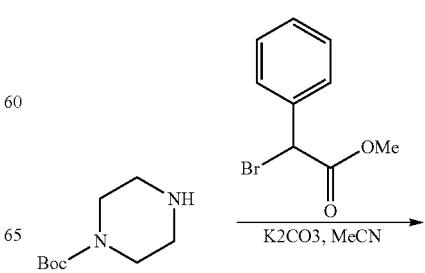

-continued

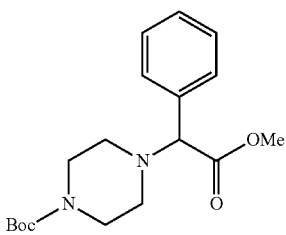

A mixture of tert-butyl piperazine-1-carboxylate (1.5 g, 8.05 mmol), methyl 2-bromo-2-phenylacetate (2.21 g, 9.66 mmol) and K₂CO₃ (3.33 g, 24.15 mmol) in MeCN (30 mL) was stirred at room temperature overnight. Solvent was removed in vacuo, and the residue was purified by silica gel column (pet ether:EtOAc 1:2) to give the desired product as a colorless oil (1.6 g). Yield 60% (ESI 235 (M+H-100)⁺).

Step 2: methyl 2-phenyl-2-(piperazin-1-yl)acetate hydrochloride

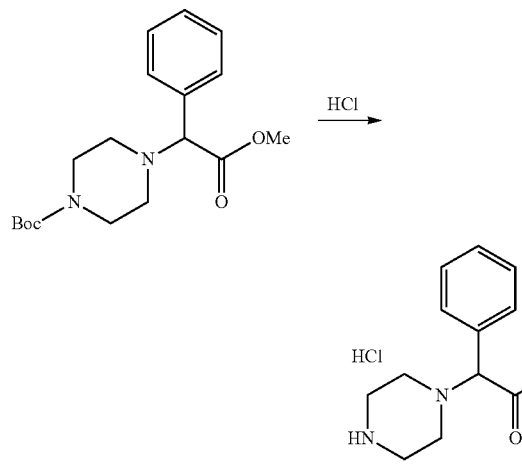

Tert-butyl 4-(2-methoxy-2-oxo-1-phenylethyl)piperazine-1-carboxylate (500 mg, 1.50 mmol) was treated with a solution of HCl/dioxane (2.0 M, 10 mL) at room temperature for 2 hours, then concentrated in vacuo to give the desired product as a white solid (389 mg). Yield 96% (ESI 235 (M+H)+).

Step 3: methyl 2-phenyl-2-(4-(5-(5,6,7,8-tetrahydro-1,8-naphthyridin-2-yl)pentyl)piperazin-1-yl)acetate

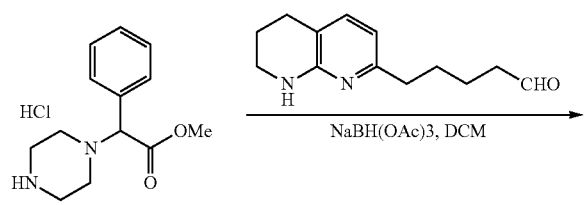

-continued

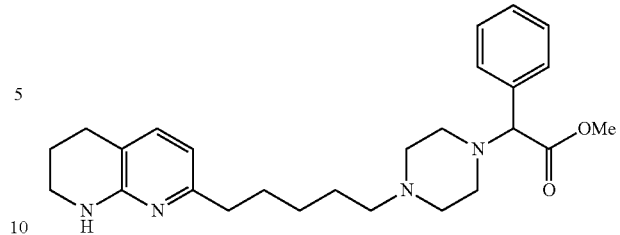

To a solution of methyl 2-phenyl-2-(piperazin-1-yl)acetate hydrochloride (150 mg, 0.55 mmol) in DCM (5 mL) was added triethylamine (112 mg, 1.11 mmol) at room temperature. The mixture was stirred for 10 min, and then 5-(5,6,7,8-tetrahydro-1,8-naphthyridin-2-yl)pentanal (120 mg, 0.55 mmol), NaBH(OAc)₃ (350 mg, 1.65 mmol) and one drop of HOAc was added. The mixture was stirred at room temperature overnight. Solvent was removed in vacuo, and the residue was purified by silica gel column (DCM:MeOH 10:1) to give the desired product as a colorless oil (130 mg). Yield 54% (100% purity, UV=254 nm, ESI 437.3 (M+H)+).

Step 4: 2-phenyl-2-(4-(5-(5,6,7,8-tetrahydro-1,8-naphthyridin-2-yl)pentyl)piperazin-1-yl)acetic acid (Compounds 10-E1 and 10-E2)

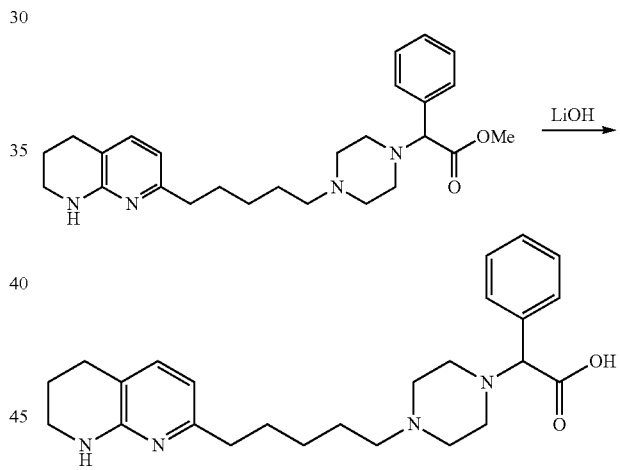

Methyl 2-phenyl-2-(4-(5-(5,6,7,8-tetrahydro-1,8-naphthyridin-2-yl)pentyl)piperazin-1-yl)acetate (130 mg, 0.30 mmol) was treated with LiOH—H₂O (63 mg, 1.50 mmol) in MeOH (5.0 mL) and H₂O (1.0 mL) at room temperature for 2 hours. Solvent was removed in vacuo, and the residue was purified by Prep-HPLC A (30-65% MeCN) to give racemic compound 10 as a white solid (70 mg, 55% yield). The racemic product was separated by prep chiral SFC A to give enantiomeric products compound 10-E1 (21 mg) and compound 10-E2 (18 mg) as white solids.

Compound 10-E1 LC/MS A: 95% purity, UV=214 nm, Rt=1.53 min, ESI 423.4 (M+H)+. 1H NMR (400 MHz, CD3OD) δ 7.43-7.41 (m, 2H), 7.24-7.18 (m, 3H), 7.05 (d, J=7.6 Hz, 1H), 6.26 (d, J=7.2 Hz, 1H), 3.76 (s, 1H), 3.27-3.24 (m, 2H), 2.86-2.39 (m, 14H), 1.80-1.72 (m, 2H), 1.60-1.43 (m, 4H), 1.29-1.17 (m, 2H). Chiral SFC A (45% MeOH): ee 100%, Rt=1.93 min.

Compound 10-E2 LC/MS A: 95% purity, UV=214 nm, Rt=1.53 min, ESI 423.4 (M+H)+. 1H NMR (400 MHz, CD3OD) δ 7.43-7.41 (m, 2H), 7.24-7.18 (m, 3H), 7.05 (d, J=7.6 Hz, 1H), 6.26 (d, J=7.2 Hz, 1H), 3.76 (s, 1H), 3.27-3.24 (m, 2H), 2.86-2.39 (m, 14H), 1.80-1.72 (m, 2H), 1.60-1.43 (m, 4H), 1.29-1.17 (m, 2H). Chiral SFC A (45% MeOH): ee 95%, Rt=2.72 min.

Example 11: Preparation of 2-phenyl-2-(4-((5,6,7,8-tetrahydro-1,8-naphthyridin-2-yl)methyl)-1,4'-bipiperidin-1'-yl)acetic acid (Compounds 11-E1 and 11-E2)

Step 1: methyl 2-(4-oxopiperidin-1-yl)-2-phenylacetate

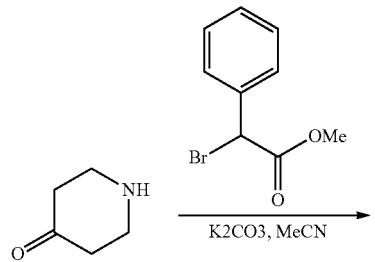

A mixture of piperidin-4-one hydrochloride (1.0 g, 7.38 mmol), methyl 2-bromo-2-phenylacetate (2.53 g, 11.06 mmol) and K$_2$CO$_3$ (3.06 g, 22.13 mmol) in MeCN (30 mL) was stirred at room temperature overnight. Solvent was removed in vacuo, and the residue was purified by silica gel column (pet ether:EtOAc 2:1) to give the desired product methyl 2-(4-oxopiperidin-1-yl)-2-phenylacetate as a colorless oil (1.3 g). Yield 71% (98% purity, UV=214 nm, ESI 248.0 (M+H)$^+$).

Step 2: methyl 2-phenyl-2-(4-((5,6,7,8-tetrahydro-1,8-naphthyridin-2-yl)methyl)-1,4'-bipiperidin-1'-yl)acetate

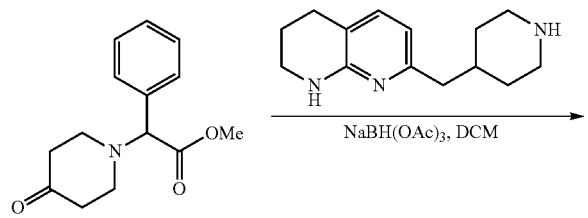

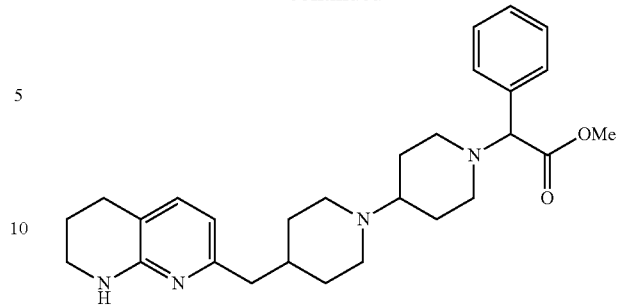

A mixture of 7-(piperidin-4-ylmethyl)-1,2,3,4-tetrahydro-1,8-naphthyridine (152 mg, 0.66 mmol), methyl 2-(4-oxopiperidin-1-yl)-2-phenylacetate (195 mg, 0.79 mmol) and NaBH(OAc)$_3$ (418 mg, 1.97 mmol) in DCM (5 mL) was stirred at room temperature overnight. Solvent was removed in vacuo, and the residue was purified by silica gel column (DCM:MeOH 20:1) to give the desired product methyl 2-phenyl-2-(4-((5,6,7,8-tetrahydro-1,8-naphthyridin-2-yl)methyl)-1,4'-bipiperidin-1'-yl)acetate as a colorless oil (110 mg). Yield 36% (100% purity, UV=214 nm, ESI 463 (M+H)$^+$).

Step 3: 2-phenyl-2-(4-((5,6,7,8-tetrahydro-1,8-naphthyridin-2-yl)methyl)-1,4'-bipiperidin-1'-yl)acetic acid (Compounds 11-E1 and 11-E2)

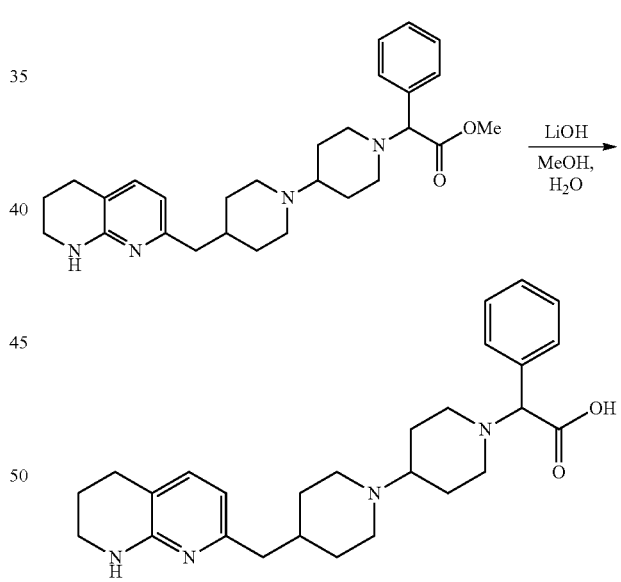

Methyl 2-phenyl-2-(4-((5,6,7,8-tetrahydro-1,8-naphthyridin-2-yl)methyl)-1,4'-bipiperidin-1'-yl)acetate (110 mg, 0.24 mmol) was treated with LiOH—H$_2$O (42 mg, 1.0 mmol) in MeOH (4 mL) and H$_2$O (1 mL) at room temperature for 2 hours. Solvent was removed in vacuo, and the residue was purified by Prep-HPLC A (33-65% MeCN) to give racemic compound 11 as a white solid (55 mg, 52% yield). The racemic product was separated by Prep chiral SFC A to give enantiomeric products compound 11-E1 (12 mg) and compound 11-E2 (15 mg) as white solids.

Compound 11-E1 LC/MS A: 100% purity, UV=214 nm, Rt=1.5 min, ESI 449.5 (M+H)+. 1H NMR (400 MHz, CD3OD) δ 7.54-7.52 (m, 2H), 7.34-7.32 (m, 3H), 7.13 (d, J=7.2 Hz, 1H), 6.35 (d, J=7.2 Hz, 1H), 3.92 (br, 1H), 3.58-3.20 (m, 5H), 2.90-2.32 (m, 9H), 2.22-1.64 (m, 10H), 1.44-1.25 (m, 2H). Chiral SFC A (40% MeOH): ee 100%, Rt=2.98 min Compound 11-E2 LC/MS A: 100% purity, UV=214 nm, Rt=1.5 min, ESI 449.5 (M+H)+. 1H NMR (400 MHz, CD3OD) δ 7.54-7.52 (m, 2H), 7.34-7.32 (m, 3H), 7.13 (d, J=7.2 Hz, 1H), 6.35 (d, J=7.2 Hz, 1H), 3.95 (br, 1H), 3.58-3.20 (m, 5H), 2.90-2.32 (m, 9H), 2.22-1.64 (m, 10H), 1.44-1.25 (m, 2H). Chiral SFC A (40% MeOH): ee 100%, Rt=4.15 min Example 12: Preparation of 2-phenyl-2-(4-(4-(5,6,7,8-tetrahydro-1,8-naphthyridin-2-yl)butoxy)piperidin-1-yl)acetic acid (Compounds 12-E1 and 12-E2)

Step 1: 6-bromohexan-2-one

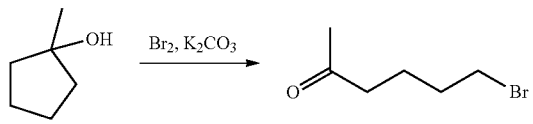

A mixture of 1-methylcyclopentanol (4.00 g, 39.94 mmol) and K₂CO₃ (33.11 g, 239.6 mmol) in CHCl₃ (130 mL) was stirred at 0° C. for 15 min., and then bromine (10.23 mL, 199.7 mmol) was then added. The reaction mixture was stirred at 0° C. for 2.5 hours, then poured slowly into an ice-chilled saturated aqueous Na₂S₂O₃ solution (100 mL). The organic layer was separated, washed with water (2×100 mL), dried over MgSO₄, filtered and concentrated in vacuo. The residue was purified by silica gel column (pet ether: EtOAc 3:1) give the desired product 6-bromohexan-2-one as a colorless oil (4 g). Yield 56% (98% purity, UV=214 nm, ESI no found). ¹H-NMR (400 MHz, CDCl₃) δ 1.66-1.80 (m, 2H), 1.82-1.93 (m, 2H), 2.15 (s, 3H), 2.48 (t, J=7.3 Hz, 2H), 3.41 (t, J=6.5 Hz, 2H).

Step 2: 2-(4-bromobutyl)-2-methyl-1,3-dioxolane

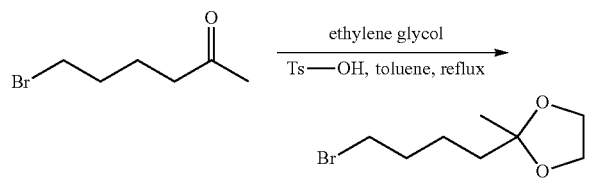

In a flame dried round-bottomed flask equipped with a magnetic stir bar and a Dean-Stark under N₂, a solution of 6-bromo-hexan-2-one (2.0 g, 11.17 mmol), ethylene glycol (6.93 g, 111.7 mmol) and TsOH (384 mg, 0.22 mmol) in toluene (40 mL) was heated to reflux for 3 h. The reaction was allowed to cool to room temperature, and sat. aq. NaHCO₃ (60 mL) and ethyl acetate (100 mL.) were added. The organic layer was separated, washed with water (2×100 mL), dried over MgSO₄, filtered and concentrated in vacuo. The residue was purified by silica gel column (pet ether: EtOAc 4:1) to give the desired product 2-(4-bromobutyl)-2-methyl-1,3-dioxolane as a colorless oil (1.6 g). Yield 64% (98% purity, UV=214 nm, ESI no found). 1H-NMR (400 MHz, CDCl₃) δ 1.34 (s, 3H), 1.50-1.65 (m, 2H), 1.65-1.75 (m, 2H), 1.84-1.98 (m, 2H), 3.43 (t, J=6.8 Hz, 2H), 3.90-4.04 (m, 4H).

Step 3: tert-butyl 4-(4-(2-methyl-1,3-dioxolan-2-yl)butoxy)piperidine-1-carboxylate

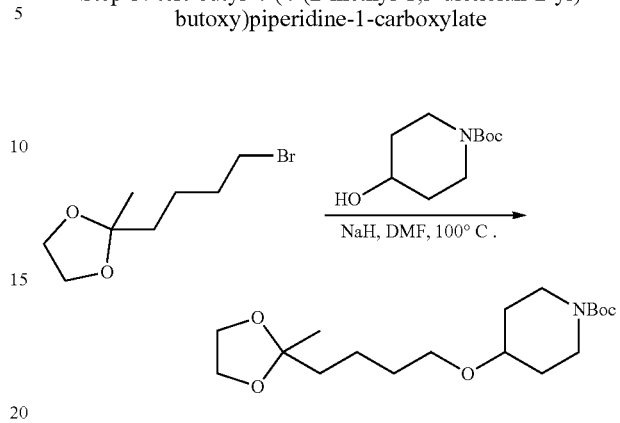

A mixture of tert-butyl 4-hydroxypiperidine-1-carboxylate (866 mg, 4.31 mmol) and NaH (287 mg, 7.18 mmol) in DMF (10 mL) was stirred at 0° C. for 1 hour. A solution of 2-(4-bromobutyl)-2-methyl-1,3-dioxolane (800 mg, 3.59 mmol) in DMF (5 mL) was added dropwise to the above mixture at 0° C., and the reaction mixture was stirred at 100° C. overnight. Solvent was removed in vacuo, and the residue was purified by silica gel column (pet ether:EtOAc 1:1) to give the desired product tert-butyl 4-(4-(2-methyl-1,3-dioxolan-2-yl)butoxy)piperidine-1-carboxylate as a colorless oil (420 mg). Yield 36% (98% purity, UV=214 nm, ESI 243 (M+H)⁺).

Step 4: 6-(piperidin-4-yloxy)hexan-2-one

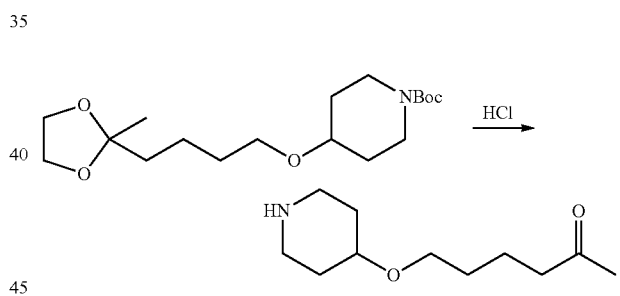

Tert-butyl 4-(4-(2-methyl-1,3-dioxolan-2-yl)butoxy)piperidine-1-carboxylate (420 mg, 1.22 mmol) was treated with 4 M HCl (3.1 mL, 12.2 mmol) in 1,4-dioxane (10 mL) at room temperature for 2 hours. Solvent was removed in vacuo, and the residue was purified by silica gel column (pet ether:EtOAc 1:2) to give the desired product 6-(piperidin-4-yloxy)hexan-2-one as a colorless oil (290 mg). Yield 97% (98% purity, UV=214 nm, ESI 243 (M+H)⁺).

Step 5: methyl 2-(4-(5-oxohexyloxy)piperidin-1-yl)-2-phenylacetate

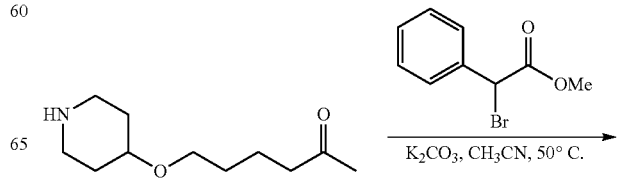

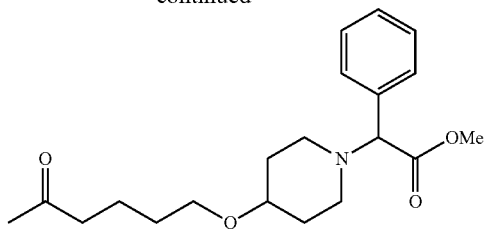
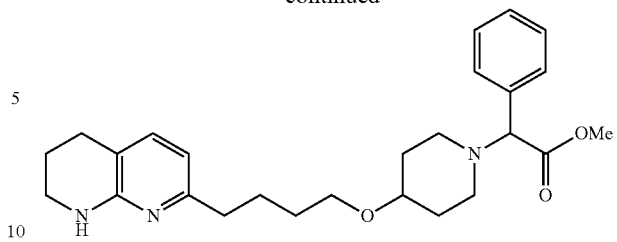

A mixture of 6-(piperidin-4-yloxy)hexan-2-one (290 mg, 1.19 mmol), K₂CO₃ (493 mg, 3.57 mmol) and methyl 2-bromo-2-phenylacetate (409 mg, 1.79 mmol) in acetonitrile (8 mL) was stirred at 50° C. for 3 hours. Solvent was removed in vacuo, and the residue was purified by silica gel column (pet ether:EtOAc 1:2) to give the desired product methyl 2-(4-(5-oxohexyloxy)piperidin-1-yl)-2-phenylacetate a colorless oil (340 mg). Yield 82% (98% purity, UV=214 nm, ESI 347 (M+H)⁺).

Step 6: methyl 2-(4-(4-(1,8-naphthyridin-2-yl)butoxy)piperidin-1-yl)-2-phenylacetate A mixture of methyl 2-(4-(4-(1,8-naphthyridin-2-yl)butoxy)piperidin-1-yl)-2-phenylacetate (220 mg, 0.51 mmol) and Pd/C (10%, 20 mg) in EtOAc (30 mL) was stirred under balloon hydrogen at room temperature for 16 hours. The mixture was filtered and concentrated to give the desired product as a colorless oil (220 mg). Yield 99% (92% purity, UV=214 nm, ESI 438.4 (M+H)⁺).

Step 8: 2-phenyl-2-(4-(4-(5,6,7,8-tetrahydro-1,8-naphthyridin-2-yl)butoxy)piperidin-1-yl)acetic acid (Compounds 12-E1 and 12-E2) (MRT-B0103)

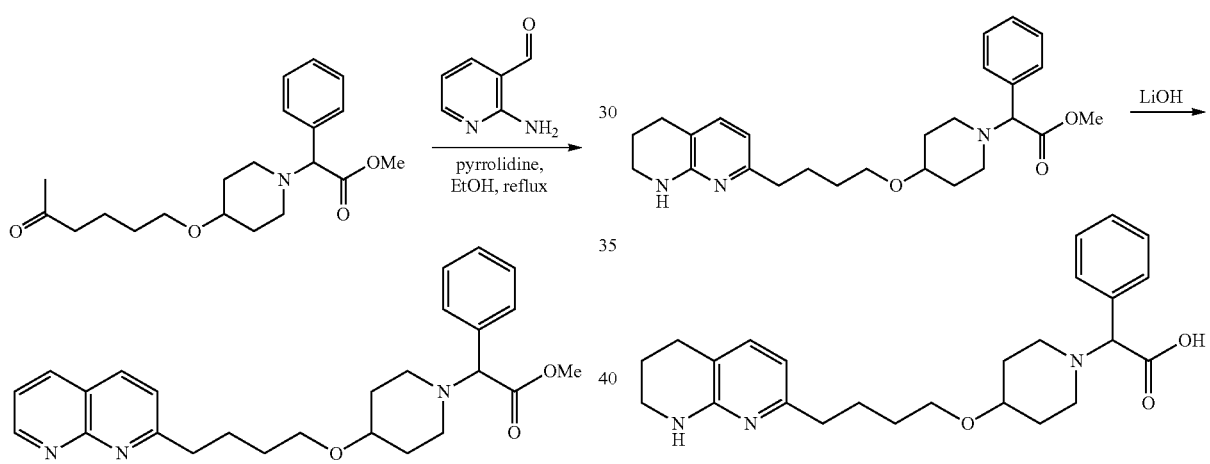

A mixture of 2-(4-(5-oxohexyloxy)piperidin-1-yl)-2-phenylacetate (340 mg, 0.98 mmol), 2-aminonicotinaldehyde (155 mg, 1.27 mmol) and pyrrolidine (90 mg, 1.27 mmol) in ethanol (8 mL) was refluxed overnight. Solvent was removed in vacuo, and the residue was purified by silica gel column (DCM:MeOH 40:1) to give the desired product methyl 2-(4-(4-(1,8-naphthyridin-2-yl)butoxy)piperidin-1-yl)-2-phenylacetate a colorless oil (220 mg). Yield 51% (98% purity, UV=254 nm, ESI 434.5 (M+H)⁺).

Step 7: methyl 2-phenyl-2-(4-(4-(5,6,7,8-tetrahydro-1,8-naphthyridin-2-yl)butoxy)piperidin-1-yl)acetate

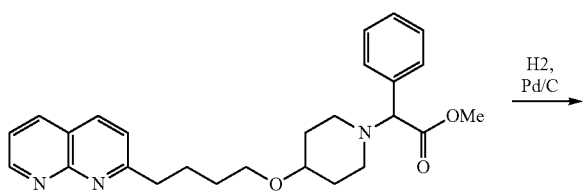

Methyl 2-(4-(4-(1,8-naphthyridin-2-yl)butoxy)piperidin-1-yl)-2-phenylacetate (220 mg, 0.51 mmol) was treated with LiOH—H₂O (86 mg, 2.04 mmol) in MeOH (4 mL) and H₂O (1 mL) at room temperature for 2 hours. Solvent was removed in vacuo, and the residue was purified by Prep-HPLC A (33-65% MeCN) to give racemic compound 12 as a white solid (42 mg, 19% yield). The racemic product was separated by prep chiral SFC A to give enantiomeric products compound 12-E1 (17 mg) and compound 12-E2 (20 mg) as white solids.

Compound 12-E1 LC/MS A: 98% purity, UV=214 nm, Rt=1.61 min, ESI 423.5 (M+H)+. 1H-NMR (400 MHz, MeOD) δ 7.61-7.50 (m, 2H), 7.48-7.38 (m, 3H), 7.14 (d, J=7.3 Hz, 1H), 6.36 (d, J=7.3 Hz, 1H), 4.46 (s, 1H), 3.57 (s, 1H), 3.46 (t, J=6.2 Hz, 2H), 3.41-3.35 (m, 2H), 3.14 (s, 1H), 2.85 (s, 1H), 2.71 (t, J=6.2 Hz, 2H), 2.53 (t, J=7.5 Hz, 2H), 2.19-1.79 (m, 7H), 1.56-1.63 (m, 5H). Chiral SFC A (45% MeOH): ee 96.2%, Rt=1.88 min.

Compound 12-E2 LC/MS A: 97% purity, UV=214 nm, Rt=1.61 min, ESI 423.5 (M+H)+. 1H-NMR (400 MHz, MeOD) δ 7.61-7.50 (m, 2H), 7.48-7.38 (m, 3H), 7.14 (d, J=7.3 Hz, 1H), 6.36 (d, J=7.3 Hz, 1H), 4.46 (s, 1H), 3.57 (s, 1H), 3.46 (t, J=6.2 Hz, 2H), 3.41-3.35 (m, 2H), 3.14 (s, 1H), 2.85 (s, 1H), 2.71 (t, J=6.2 Hz, 2H), 2.53 (t, J=7.5 Hz, 2H), 2.19-1.79 (m, 7H), 1.56-1.63 (m, 5H). Chiral SFC A (45% MeOH): ee 99.6%, Rt=3.05 min.

Example 13: Preparation of 2-phenyl-2-((R)-3-(3-(5,6,7,8-tetrahydro-1,8-naphthyridin-2-yl)propylcarbamoyl)pyrrolidin-1-yl)acetic acid (Compounds 13-E1 and 13-E2)

Step 1: (R)-tert-butyl 3-(3-(5,6,7,8-tetrahydro-1,8-naphthyridin-2-yl)propylcarbamoyl)pyrrolidine-1-carboxylate

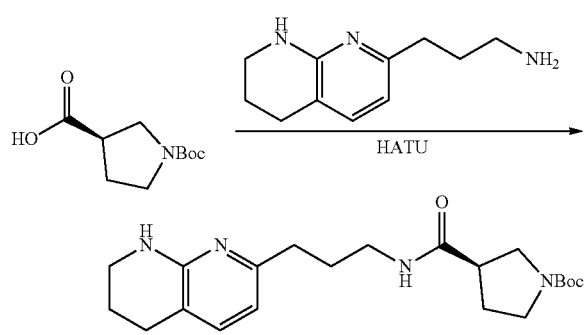

A mixture of (R)-1-(tert-butoxycarbonyl)pyrrolidine-3-carboxylic acid (124.7 mg, 0.58 mmol), 3-(5,6,7,8-tetrahydro-1,8-naphthyridin-2-yl)propan-1-amine (100 mg, 0.52 mmol), HATU (331 mg, 0.87 mmol) and DIPEA (374 mg, 2.9 mmol) in DMF (5.0 mL) was stirred at room temperature for 2 hours. Solvent was removed in vacuo, and the residue was purified by silica gel column (DCM:MeOH 10:1) to give the desired product (R)-tert-butyl 3-(3-(5,6,7,8-tetrahydro-1,8-naphthyridin-2-yl)propylcarbamoyl)pyrrolidine-1-carboxylate as a yellow oil (110 mg). Yield 49% (ESI 389 (M+H)$^+$).

Step 2: (R)—N-(3-(5,6,7,8-tetrahydro-1,8-naphthyridin-2-yl)propyl)pyrrolidine-3-carboxamide

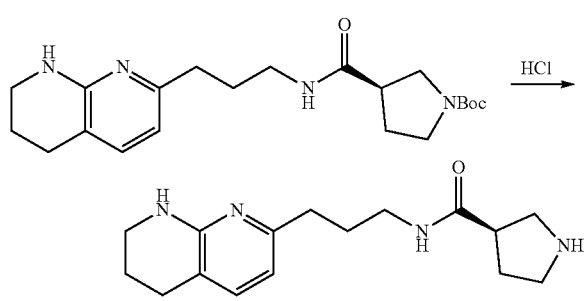

(R)-tert-butyl 3-(3-(5,6,7,8-tetrahydro-1,8-naphthyridin-2-yl)propylcarbamoyl)pyrrolidine-1-carboxylate (110 mg, 0.29 mmol) was treated with a solution of HCl/dioxane (4.0 M, 2 mL) at room temperate for 2 hours. The solvent was removed in vacuo to give the desired product as a brown oil (80 mg). Yield 98% (ESI 289.2 (M+H)$^+$).

Step 3: ethyl 2-phenyl-2-((R)-3-(3-(5,6,7,8-tetrahydro-1,8-naphthyridin-2-yl)propylcarbamoyl)pyrrolidin-1-yl)acetate

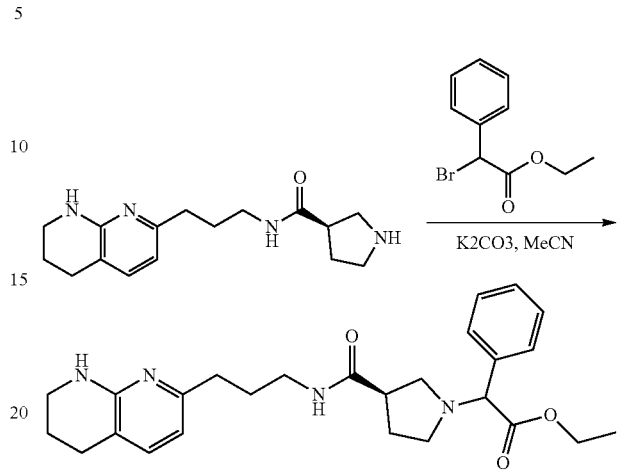

A mixture of (R)—N-(3-(5,6,7,8-tetrahydro-1,8-naphthyridin-2-yl)propyl)pyrrolidine-3-carboxamide (80 mg, 0.28 mmol), ethyl 2-bromo-2-phenylacetate (68.6 mg, 0.28 mmol) and K$_2$CO$_3$ (116 mg, 0.84 mmol) in MeCN (2.5 mL) was stirred at room temperature overnight. Solvent was removed in vacuo, and the residue was purified by silica gel column (pet ether:EtOAc 2:1) to give the desired product ethyl 2-phenyl-2-((R)-3-(3-(5,6,7,8-tetrahydro-1,8-naphthyridin-2-yl)propylcarbamoyl)pyrrolidin-1-yl)acetate as a colorless oil (70 mg). Yield 71% (ESI 451.3 (M+H)$^+$).

Step 4: 2-phenyl-2-((R)-3-(3-(5,6,7,8-tetrahydro-1,8-naphthyridin-2-yl)propylcarbamoyl)pyrrolidin-1-yl)acetic acid (Compounds 13-E1 and 13-E2)

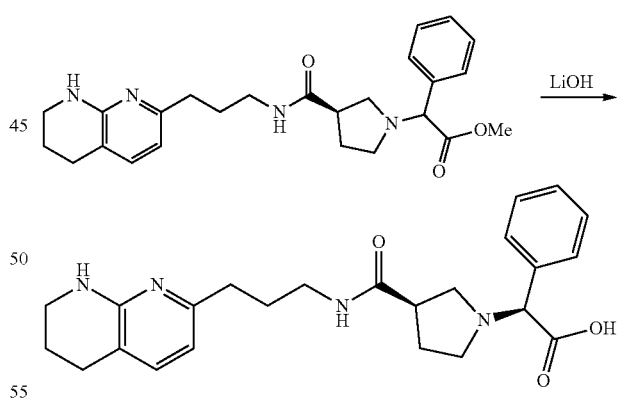

Ethyl 2-phenyl-2-((R)-3-(3-(5,6,7,8-tetrahydro-1,8-naphthyridin-2-yl)propylcarbamoyl)pyrrolidin-1-yl)acetate (70 mg, 0.16 mmol) was treated with LiOH—H$_2$O (65.1 mg, 1.55 mmol) in MeOH (2.0 mL) and H$_2$O (0.5 mL) at room temperature for 2 hours.

Solvent was removed in vacuo, and the residue was purified by Prep-HPLC A (30-65% MeCN) to give two diastereomers compound 13-E1 (6.1 mg) and compound 13-E2 (6.5 mg) as white solids.

Compound 13-E1 LC/MS B: 100% purity, UV=214 nm, Rt=1.23 min, ESI 423.7 (M+H)+. 1H NMR (400 MHz, MeOD) δ 7.55-7.46 (m, 2H), 7.45-7.29 (m, 3H), 7.24 (d, J=7.2 Hz, 1H), 6.42 (d, J=7.2 Hz, 1H), 4.17 (s, 1H), 3.43-3.37 (m, 3H), 3.25-3.12 (m, 2H), 2.97-2.50 (m, 8H), 2.31-2.19 (m, 1H), 2.05-1.73 (m, 5H).

Compound 13-E2 LC/MS B: 97% purity, UV=214 nm, Rt=1.23 min, ESI 423.7 (M+H)+. 1H NMR (400 MHz, MeOD) δ 7.54-7.53 (m, 2H), 7.39-7.24 (m, 3H), 7.16 (d, J=7.3 Hz, 1H), 6.39 (d, J=7.3 Hz, 1H), 4.04 (s, 1H), 3.38 (t, J=5.6 Hz, 2H), 3.28-3.18 (m, 2H), 3.05-2.83 (m, 4H), 2.71 (t, J=6.2 Hz, 2H), 2.58-2.52 (m, 3H), 2.09-1.87 (m, 6H).

Example 14: 2-phenyl-2-((R)-3-(4-(5,6,7,8-tetrahydro-1,8-naphthyridin-2-yl)butylamino)pyrrolidin-1-yl)acetic acid (Compound 14)

Step 1: ethyl 2-((R)-3-(tert-butoxycarbonylamino)pyrrolidin-1-yl)-2-phenylacetate

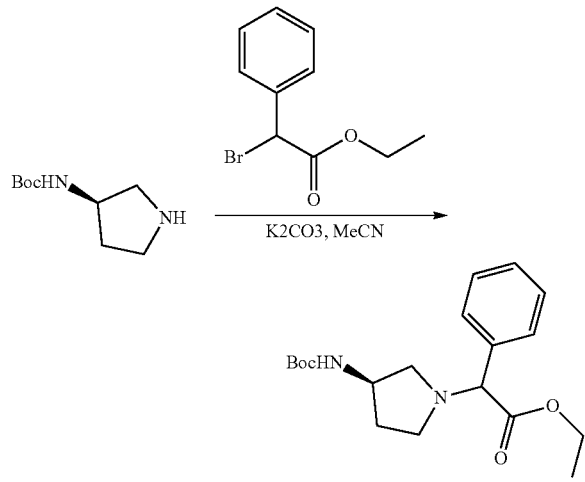

A mixture of (R)-tert-butyl pyrrolidin-3-ylcarbamate (200 mg, 1.07 mmol), ethyl 2-bromo-2-phenylacetate (390 mg, 1.60 mmol) and K₂CO₃ (445 mg, 3.22 mmol) in MeCN (5 mL) was stirred at room temperature overnight. Solvent was removed in vacuo, and the residue was purified by silica gel column (pet ether:EtOAc 3:1) to give the desired product ethyl 2-((R)-3-(tert-butoxycarbonylamino)pyrrolidin-1-yl)-2-phenylacetate as a yellow oil (335 mg). Yield 89% (ESI 349.0 (M+H)⁺).

Step 2: ethyl 2-((R)-3-aminopyrrolidin-1-yl)-2-phenylacetate

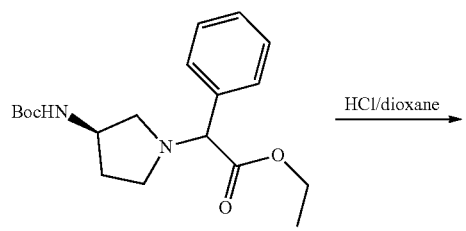

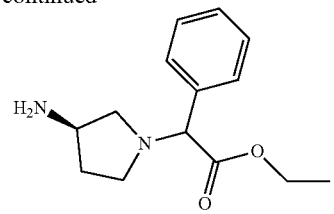

Ethyl 2-((R)-3-(tert-butoxycarbonylamino)pyrrolidin-1-yl)-2-phenylacetate (335 mg, 0.96 mmol) was treated with a solution of HCl/dioxane (4.0 M, 4 mL) at room temperate for 2 hours, then the solvent was removed in vacuo to give the desired product ethyl 2-((R)-3-aminopyrrolidin-1-yl)-2-phenylacetate as a brown oil (234 mg). Yield 98% (ESI 249.2 (M+H)+).

Step 3: ethyl 2-phenyl-2-((R)-3-(4-(5,6,7,8-tetrahydro-1,8-naphthyridin-2-yl)butylamino)pyrrolidin-1-yl)acetate

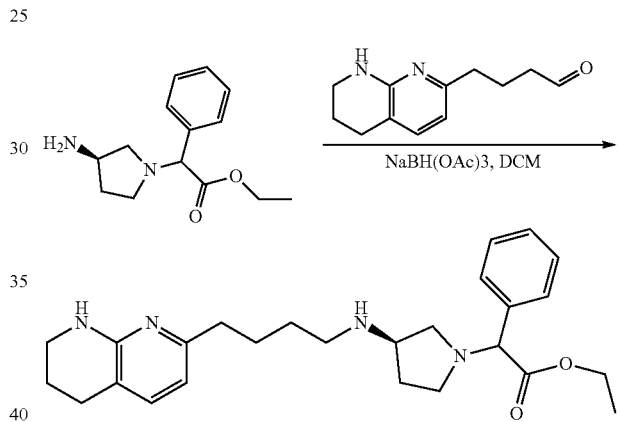

A mixture of ethyl 2-((R)-3-aminopyrrolidin-1-yl)-2-phenylacetate (234 mg, 0.94 mmol), 4-(5,6,7,8-tetrahydro-1,8-naphthyridin-2-yl)butanal (191 mg, 0.94 mmol) and NaBH(OAc)₃ (598 mg, 2.82 mmol) in DCM (5 mL) was stirred at room temperature overnight. Solvent was removed in vacuo, and the residue was purified by silica gel column (DCM:MeOH 15:1) to give the desired ethyl 2-phenyl-2-((R)-3-(4-(5,6,7,8-tetrahydro-1,8-naphthyridin-2-yl)butylamino)pyrrolidin-1-yl)acetate as a colorless oil (180 mg). Yield 44% (ESI 437 (M+H)+).

Step 4: 2-phenyl-2-((R)-3-(4-(5,6,7,8-tetrahydro-1,8-naphthyridin-2-yl)butylamino)pyrrolidin-1-yl)acetic acid (Compound 14)

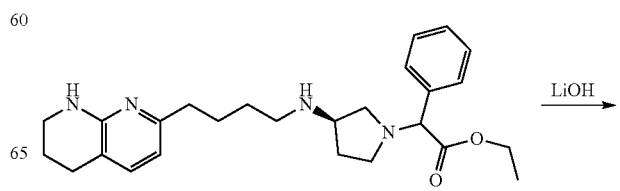

-continued

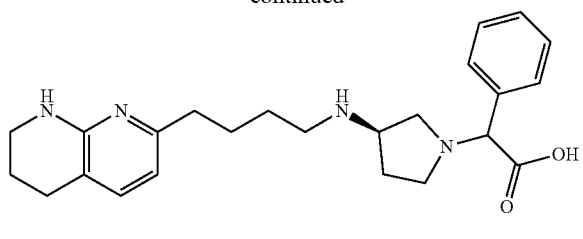

Ethyl 2-phenyl-2-((R)-3-(4-(5,6,7,8-tetrahydro-1,8-naphthyridin-2-yl)butylamino) pyrrolidin-1-yl)acetate (180 mg, 0.41 mmol) was treated with LiOH—H$_2$O (86 mg, 2.05 mmol) in MeOH (5.0 mL) and H$_2$O (1.0 mL) at room temperature for 2 hours. Solvent was removed in vacuo, and the residue was purified by Prep-HPLC A (30-65% MeCN) to give compound 14 (52 mg) as a yellow solid. LC/MS E: 98% purity, UV=214 nm, Rt=1.03 min, ESI 409.2 (M+H)+. 1H NMR (400 MHz, MeOD) δ 7.61-7.54 (m, 2H), 7.54-7.20 (m, 3H), 7.15 (d, J=7.3 Hz, 1H), 6.42-6.38 (m, 1H), 3.81-3.77 (m, 1H), 3.62-3.51 (m, 1H), 3.43-3.34 (m, 2H), 3.24-3.20 (m, 1H), 2.94-2.20 (m, 9H), 1.88-1.57 (m, 8H).

Example 15: Preparation of 2-(3-(4-((5,6,7,8-tetrahydro-1,8-naphthyridin-2-yl)methyl)piperidine-1-carbonyl)azetidin-1-yl)acetic acid (Compound 15)

Step 1: tert-butyl 3-(4-((5,6,7,8-tetrahydro-1,8-naphthyridin-2-yl)methyl)piperidine-1-carbonyl)azetidine-1-carboxylate

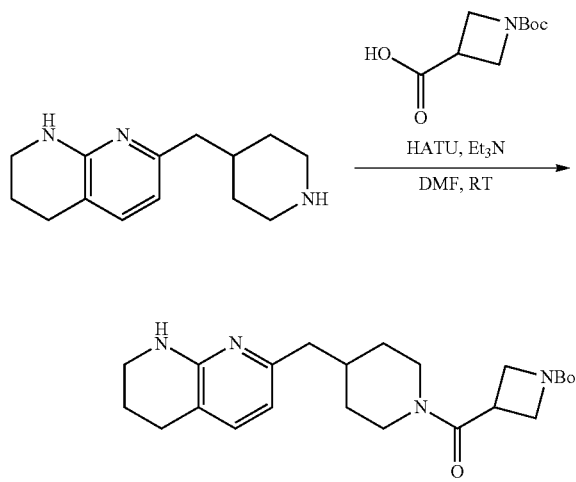

A mixture of 1-(tert-butoxycarbonyl)azetidine-3-carboxylic acid (132 mg, 0.66 mmol), HATU (251 mg, 0.66 mmol), 7-(piperidin-4-ylmethyl)-1,2,3,4-tetrahydro-1,8-naphthyridine hydrochloride (200 mg, 0.66 mmol) and triethylamine (0.4 mL, 2.64 mmol) in DMF (2 mL) was stirred overnight. Solvent was removed in vacuo, and the residue was purified by silica gel column (pet ether:EtOAc 0:100) to give tert-butyl 3-(4-((5,6,7,8-tetrahydro-1,8-naphthyridin-2-yl)methyl)piperidine-1-carbonyl)azetidine-1-carboxylate as a light yellow solid (210 mg). Yield 77% (100% purity, UV=214 nm, ESI 415 (M+H)$^+$).

Step 2: azetidin-3-yl(4-((5,6,7,8-tetrahydro-1,8-naphthyridin-2-yl)methyl)piperidin-1-yl)methanone

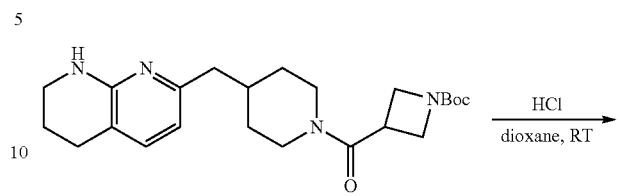

Tert-butyl 3-(4-((5,6,7,8-tetrahydro-1,8-naphthyridin-2-yl)methyl)piperidine-1-carbonyl)azetidine-1-carboxylate (210 mg, 0.51 mmol) was treated with HCl (2 mL, 8 mmol) in dioxane (2 mL) at room temperature overnight. Solvent was removed in vacuo to give azetidin-3-yl(4-((5,6,7,8-tetrahydro-1,8-naphthyridin-2-yl)methyl)piperidin-1-yl) methanone as light yellow solid (189 mg). Yield 100% (100% purity, UV=214 nm, ESI 315 (M+H)$^+$).

Step 3: ethyl 2-(3-(4-((5,6,7,8-tetrahydro-1,8-naphthyridin-2-yl)methyl)piperidine-1-carbonyl)azetidin-1-yl)acetate

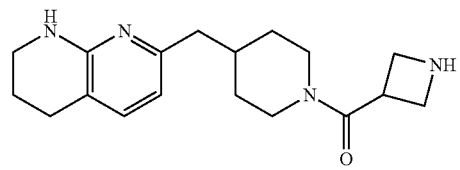

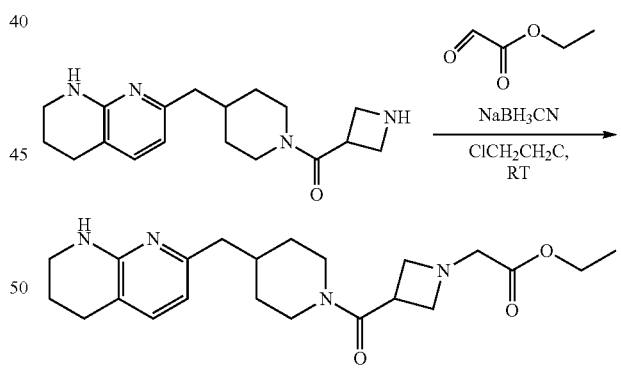

NaBH$_3$CN (103 mg, 6.63 mmol) was added to a stirred mixture of azetidin-3-yl(4-((5,6,7,8-tetrahydro-1,8-naphthyridin-2-yl)methyl)piperidin-1-yl)methanone (158 mg, 0.41 mmol) and ethyl 2-oxoacetate (0.1 mL, 0.12 mmol) in DCE at room temperature. The resulting mixture was stirred for 2 h, then diluted with water (20 mL) and extracted with DCM (3×20 mL). The combined organic extracts were washed with water, brine, dried and concentrated to give ethyl 2-(3-(4-((5,6,7,8-tetrahydro-1,8-naphthyridin-2-yl)methyl) piperidine-1-carbonyl)azetidin-1-yl)acetate as a light yellow oil (150 mg). Yield 92% (100% purity, UV=214 nm, ESI 401 (M+H)$^+$).

Step 4: 2-(3-(4-((5,6,7,8-tetrahydro-1,8-naphthyridin-2-yl)methyl)piperidine-1-carbonyl)azetidin-1-yl)acetic acid (Compound 15)

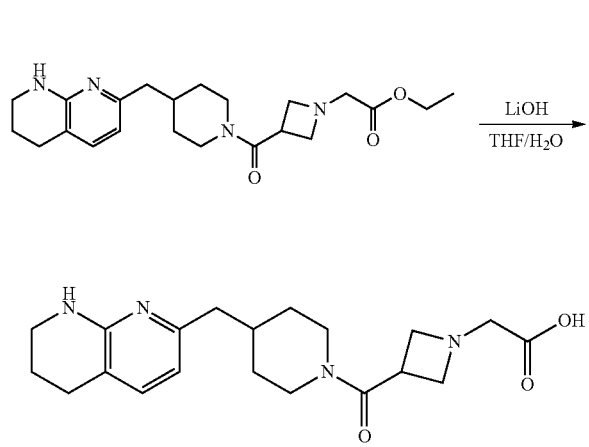

Ethyl 2-(3-(4-((5,6,7,8-tetrahydro-1,8-naphthyridin-2-yl)methyl)piperidine-1-carbonyl)azetidin-1-yl)acetate (163 mg, 0.41 mmol) was treated with LiOH—H$_2$O (34 mg, 0.81 mmol) in THF (4 mL) and H$_2$O (2 mL) for 2 hrs at room temperature. Solvent was removed in vacuo, and the residue was purified by Prep-HPLC A (33-65% MeCN) to give compound 15 as a white solid (15 mg). Yield 10% (LC/MS A: 100% purity, UV=214 nm, Rt=1.44 min, ESI 373 (M+H)$^+$). $^1$H NMR (500 MHz, MeOD) δ 7.05 (d, J=7.2 Hz, 1H), 6.25 (d, J=7.2 Hz, 1H), 4.36 (d, J=13.1 Hz, 1H), 4.21-4.03 (m, 3H), 3.88-3.77 (m, 1H), 3.63 (s, 2H), 3.48 (d, J=13.2 Hz, 1H), 3.32-3.24 (m, 2H), 2.90 (t, J=13.1 Hz, 1H), 2.63-2.49 (m, 3H), 2.36 (d, J=7.2 Hz, 2H), 1.78 (m, 3H), 1.58 (d, J=13.1 Hz, 2H), 1.05 (m, 2H).

Example 16: Preparation of 2-(4-(5-(5,6,7,8-tetrahydro-1,8-naphthyridin-2-yl)pentyl)piperazin-1-yl)acetic acid (Compound 16)

Step 1: methyl 6-oxoheptanoate

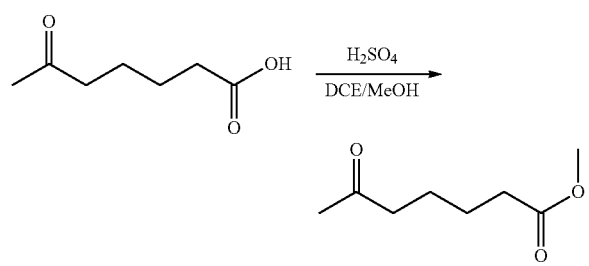

Concentrated H$_2$SO$_4$ (0.2 mL) was added to a stirred solution of 6-oxoheptanoic acid (10 g, 69 mmol) in DCE/MeOH (50 mL/20 mL). The mixture was stirred at 90° C. overnight. The solution was cooled to room temperature and concentrated. The residue was diluted with DCM (200 mL), washed with saturated NaHCO$_3$ solution, water, brine, dried and concentrated to give methyl 6-oxoheptanoate as light yellow liquid (8.4 g) Yield 76% (100% purity, UV=214 nm, ESI 159 (M+H)$^+$).

Step 2: methyl 5-(1,8-naphthyridin-2-yl)pentanoate

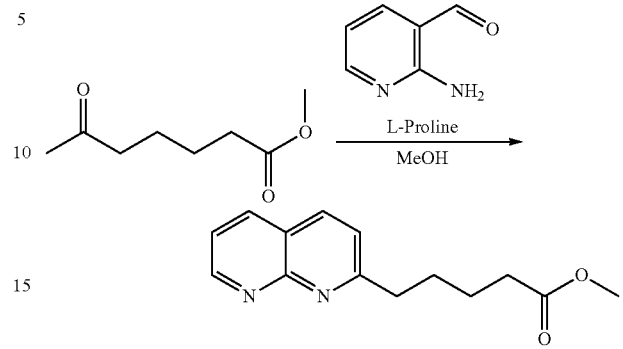

A mixture of methyl 6-oxoheptanoate (11 g, 69.53 mmol), 2-aminonicotinaldehyde (8.5 g, 69.53 mmol) and L-proline (4 g, 34.77 mmol) in MeOH (100 mL) was stirred at 90° C. overnight. The mixture was cooled to room temperature and concentrated. The crude product was purified by silica gel column (EtOAc) to give methyl 5-(1,8-naphthyridin-2-yl)pentanoate as light yellow solid (7 g). Yield 65% (100% purity, UV=214 nm, ESI 245 (M+H)$^+$). $^1$H NMR (400 MHz, CDCl$_3$) δ 9.08 (dd, J=4.2, 1.9 Hz, 1H), 8.16 (dd, J=8.1, 1.9 Hz, 1H), 8.10 (d, J=8.3 Hz, 1H), 7.44 (dd, J=8.1, 4.3 Hz, 1H), 7.39 (d, J=8.3 Hz, 1H), 3.66 (s, 3H), 3.11-3.02 (m, 2H), 2.39 (m, 2H), 1.96 (m, 2H), 1.81-1.70 (m, 2H).

Step 3: methyl 5-(5,6,7,8-tetrahydro-1,8-naphthyridin-2-yl)pentanoate

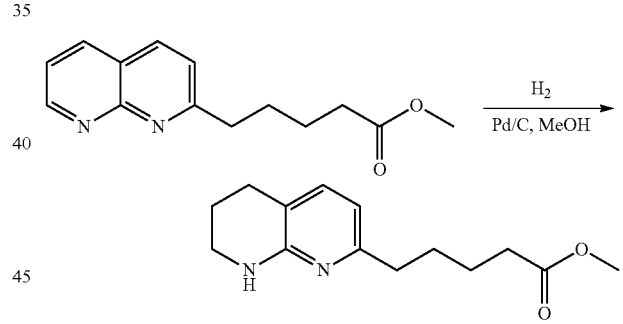

A mixture of methyl 5-(1,8-naphthyridin-2-yl)pentanoate (5 g, 20.47 mmol), and Pd/C (500 mg) in MeOH (50 mL) was stirred at room temperature under balloon H$_2$ overnight. The mixture was filtered and concentrated to give methyl 5-(5,6,7,8-tetrahydro-1,8-naphthyridin-2-yl)pentanoate as a light brown oil (4.2 g). Yield 83% (100% purity, UV=214 nm, ESI 249 (M+H)$^+$).

Step 4: tert-butyl 7-(5-methoxy-5-oxopentyl)-3,4-dihydro-1,8-naphthyridine-1(2H)-carboxylate

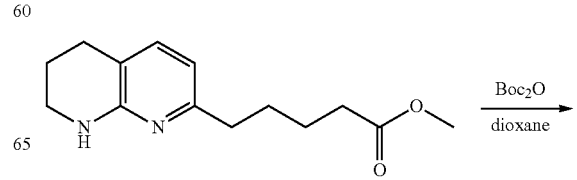

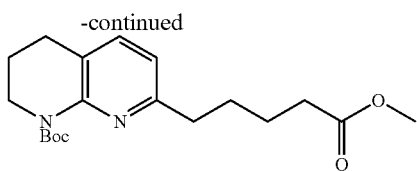

A mixture of methyl 5-(5,6,7,8-tetrahydro-1,8-naphthyridin-2-yl)pentanoate (2.4 g, 9.7 mmol) and Boc₂O (11 g, 48 mmol) in dioxane (20 mL) was stirred at 80° C. for 16 hrs. The mixture was concentrated, and the residue was purified by silica gel column chromatography (pet ether:EtOAc 1:1) to give tert-butyl 7-(5-methoxy-5-oxopentyl)-3,4-dihydro-1,8-naphthyridine-1(2H)-carboxylate as light yellow oil (1.8 g), Yield 53% (100% purity, UV=214 nm, ESI 349 (M+H)⁺).

Step 5: tert-butyl 7-(5-hydroxypentyl)-3,4-dihydro-1,8-naphthyridine-1(2H)-carboxylate

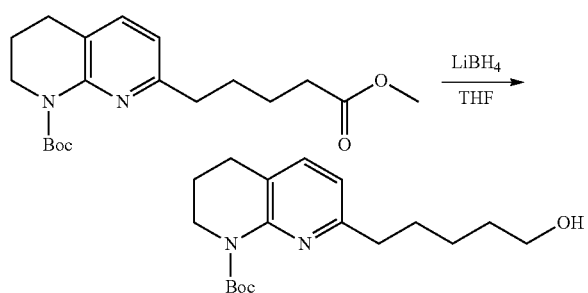

A mixture of tert-butyl 7-(5-methoxy-5-oxopentyl)-3,4-dihydro-1,8-naphthyridine-1 (2H)-carboxylate (740 mg, 2.12 mmol) and LiBH₄ (93 mg, 4.24 mmol) in THF (10 mL) was stirred at 75° C. for 2 hrs. The solution was cooled to room temperature and concentrated, diluted with EtOAc (20 mL), washed with water and brine, dried and concentrated to give tert-butyl 7-(5-hydroxypentyl)-3,4-dihydro-1,8-naphthyridine-1(2H)-carboxylate as a light yellow oil (500 mg). Yield 73% (100% purity, UV=214 nm, ESI 321 (M+H)⁺).

Step 6: tert-butyl 7-(5-oxopentyl)-3,4-dihydro-1,8-naphthyridine-1(2H)-carboxylate

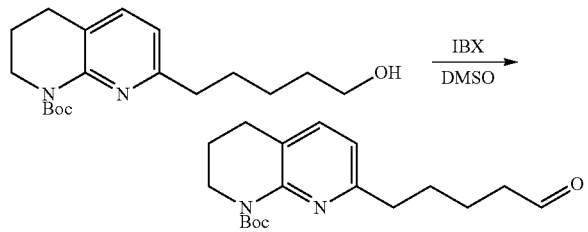

IBX (1.22 g, 4.36 mmol) was added to DMSO (15 mL) and stirred until the solution became clear. tert-butyl 7-(5-hydroxypentyl)-3,4-dihydro-1,8-naphthyridine-1(2H)-carboxylate (700 mg, 2.18 mmol) in DMSO 5 mL) was added dropwise to the solution, and the resulting mixture was stirred at room temperature for 16 hrs, then diluted with water (80 mL) and extracted with DCM (300 mL). The combined organic extracts were washed with water and brine, dried and concentrated. The residue was purified by silica gel column chromatography (pet ether:EtOAc 1:1) to give tert-butyl 7-(5-oxopentyl)-3,4-dihydro-1,8-naphthyridine-1(2H)-carboxylate as light yellow oil (498 mg) Yield 72% (100% purity, UV=214 nm, ESI 319 (M+H)⁺).

Step 7: tert-butyl 7-(5-(4-(2-ethoxy-2-oxoethyl)piperazin-1-yl)pentyl)-3,4-dihydro-1,8-naphthyridine-1(2H)-carboxylate

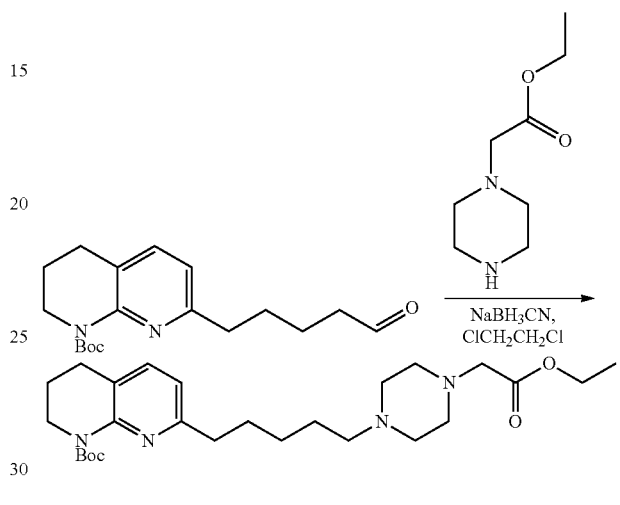

NaBH₃CN (79 mg, 1.26 mmol) was added to a stirred mixture of tert-butyl 7-(5-oxopentyl)-3,4-dihydro-1,8-naphthyridine-1(2H)-carboxylate (100 mg, 0.31 mmol) and ethyl 2-(piperazin-1-yl)acetate (81 mL, 0.47 mmol) in DCE at room temperature. The resulting mixture was stirred for 2 hours, then diluted with water (20 mL) and extracted with DCM (3×20 mL). The combined organic extracts were washed with water and brine, dried and concentrated to give tert-butyl 7-(5-(4-(2-ethoxy-2-oxoethyl)piperazin-1-yl)pentyl)-3,4-dihydro-1,8-naphthyridine-1(2H)-carboxylate as a light yellow oil (98 mg) Yield 65% (100% purity, UV=214 nm, ESI 475 (M+H)⁺).

Step 8: ethyl 2-(4-(5-(5,6,7,8-tetrahydro-1,8-naphthyridin-2-yl)pentyl)piperazin-1-yl)acetate

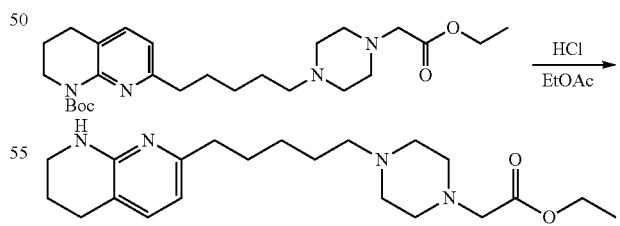

Tert-butyl 7-(5-(4-(2-ethoxy-2-oxoethyl)piperazin-1-yl)pentyl)-3,4-dihydro-1,8-naphthyridine-1(2H)-carboxylate (20 mg, 0.04 mmol) was treated with HCl (3 mL, 9 mmol) in dioxane (2 mL) at room temperature overnight. Solvent was removed in vacuo to give ethyl 2-(4-(5-(5,6,7,8-tetrahydro-1,8-naphthyridin-2-yl)pentyl)piperazin-1-yl)acetate as a light yellow solid (10 mg). Yield 63% (100% purity, UV=214 nm, ESI 375 (M+H)⁺).

Step 9: 2-(4-(5-(5,6,7,8-tetrahydro-1,8-naphthyridin-2-yl)pentyl)piperazin-1-yl)acetic acid (Compound 16)

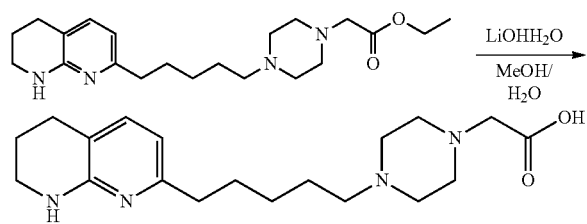

Ethyl 2-(4-(5-(5,6,7,8-tetrahydro-1,8-naphthyridin-2-yl)pentyl)piperazin-1-yl)acetate (10 mg, 0.03 mmol) was treated with LiOH—H$_2$O (3.4 mg, 0.09 mmol) in THF (4 mL) and H$_2$O (2 mL) for 2 hours at room temperature. Solvent was removed in vacuo, and the residue was purified by Prep-HPLC A (30-65% MeCN) to give compound 16 as a white solid (5 mg) Yield 54% (LC/MS A: 100% purity, UV=214 nm, Rt=1.45 min, ESI 347 (M+H)$^+$). $^1$H NMR (500 MHz, MeOD) δ 7.14 (d, J=7.3 Hz, 1H), 6.38 (d, J=7.3 Hz, 1H), 3.42-3.36 (m, 2H), 3.10 (s, 2H), 2.81-2.56 (m, 10H), 2.53 (t, J=7.6 Hz, 2H), 2.46-2.40 (m, 2H), 1.92-1.83 (m, 2H), 1.71-1.62 (m, 2H), 1.61-1.51 (m, 2H), 1.40-1.30 (m, 2H).

Example 17: 2-(2-oxo-4-(5-(5,6,7,8-tetrahydro-1,8-naphthyridin-2-yl)pentyl) piperazin-1-yl)acetic acid (Compound 17)

Step 1: tert-butyl 7-(5-(4-(2-ethoxy-2-oxoethyl)-3-oxopiperazin-1-yl)pentyl)-3,4-dihydro-1,8-naphthyridine-1(2H)-carboxylate

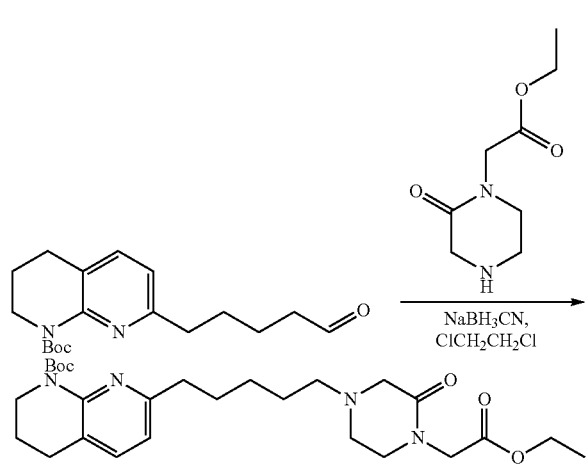

NaBH$_3$CN (79 mg, 1.24 mmol) was added to a stirred mixture of tert-butyl 7-(5-oxopentyl)-3,4-dihydro-1,8-naphthyridine-1(2H)-carboxylate (100 mg, 0.31 mmol) and ethyl 2-(2-oxopiperazin-1-yl)acetate (175 mg, 0.93 mmol) in DCE at room temperature. The resulting mixture was stirred for 2 hrs, then diluted with water (20 mL) and extracted with DCM (3×20 mL). The combined organic extracts were washed with water and brine, dried and concentrated to give tert-butyl 7-(5-(4-(2-ethoxy-2-oxoethyl)-3-oxopiperazin-1-yl)pentyl)-3,4-dihydro-1,8-naphthyridine-1(2H)-carboxylate as light yellow oil (50 mg). Yield 32% (100% purity, UV=214 nm, ESI 489 (M+H)$^+$).

Step 2: methyl 2-(2-oxo-4-(5-(5,6,7,8-tetrahydro-1,8-naphthyridin-2-yl)pentyl) piperazin-1-yl)acetate

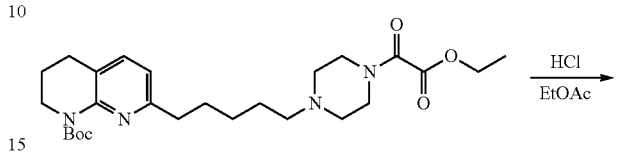

Tert-butyl 7-(5-(4-(2-methoxy-2-oxoethyl)-3-oxopiperazin-1-yl)pentyl)-3,4-dihydro-1,8-naphthyridine-1(2H)-carboxylate (50 mg, 0.11 mmol) was treated with HCl (3 mL, 9 mmol) in dioxane (2 mL) at room temperature overnight. Solvent was removed in vacuo to give methyl 2-(2-oxo-4-(5-(5,6,7,8-tetrahydro-1,8-naphthyridin-2-yl)pentyl)piperazin-1-yl)acetate as light yellow solid (34 mg). Yield 87% (100% purity, UV=214 nm, ESI 389 (M+H)$^+$).

Step 3: 2-(2-oxo-4-(5-(5,6,7,8-tetrahydro-1,8-naphthyridin-2-yl)pentyl)piperazin-1-yl)acetic acid (Compound 17)

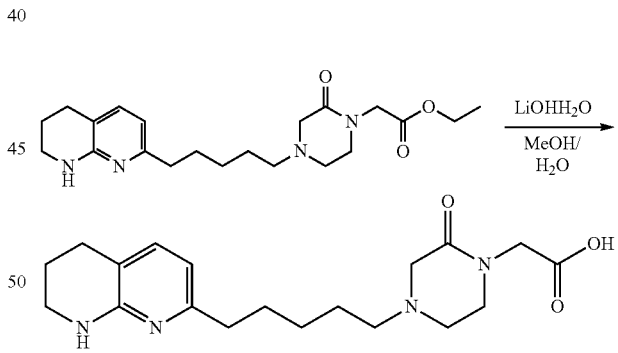

Methyl 2-(2-oxo-4-(5-(5,6,7,8-tetrahydro-1,8-naphthyridin-2-yl)pentyl)piperazin-1-yl)acetate (38 mg, 0.10 mmol) was treated with LiOH—H$_2$O (13 mg, 0.30 mmol) in THF (4 mL) and H$_2$O (2 mL) for 2 hours at room temperature. Solvent was removed in vacuo, and the residue was purified by Prep-HPLC A (33-65% MeCN) to give compound 17 as a white solid (18 mg). Yield 48% (LC/MS A: 100% purity, UV=214 nm, Rt=0.95 min, ESI 361 (M+H)$^+$). $^1$H NMR (500 MHz, MeOD) δ 7.46 (d, J=7.3 Hz, 1H), 6.52 (d, J=7.3 Hz, 1H), 3.98 (s, 2H), 3.52 (t, J=5.7 Hz, 2H), 3.49-3.43 (m, 1H), 3.30 (s, 2H), 3.00 (t, J=5.7 Hz, 2H), 2.79 (t, J=6.1 Hz, 2H), 2.77-2.70 (m, 2H), 2.69-2.61 (m, 2H), 1.98-1.87 (m, 2H), 1.77-1.67 (m, 2H), 1.67-1.58 (m, 2H), 1.54 (m, 2H).

Example 18: Preparation of 2-(4-(4-(5,6,7,8-tetrahydro-1,8-naphthyridin-2-yl)butylamino)piperidin-1-yl)acetic acid (Compound 18)

Step 1: ethyl 2-(4-oxopiperidin-1-yl)acetate

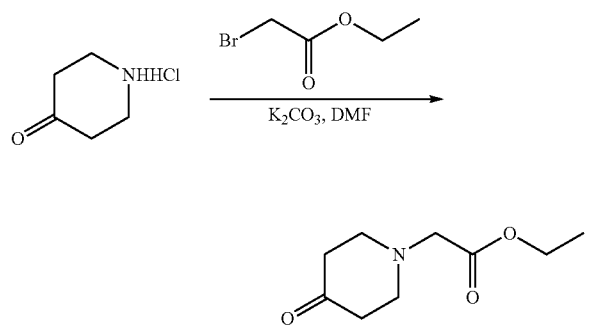

A mixture of piperidin-4-one hydrochloride (120 mg, 0.88 mmol), $K_2CO_3$ (245 mg, 1.76 mmol) and ethyl 2-bromoacetate (147 mg, 0.88 mmol) in DMF (4 mL) was stirred at room temperature for 2 h. The reaction mixture was diluted with water (20 mL) and extracted with EtOAc (15 mL×3). The combined organic extracts were washed with brine, dried over $Na_2SO_4$ and concentrated to give ethyl 2-(4-oxopiperidin-1-yl)acetate (140 mg, 85% yield) as yellow oil. (89% purity, UV=214 nm, ESI 186.2 $(M+H)^+$).

Step 2: ethyl 2-(4-(4-(5,6,7,8-tetrahydro-1,8-naphthyridin-2-yl)butylamino)piperidin-1-yl)acetate

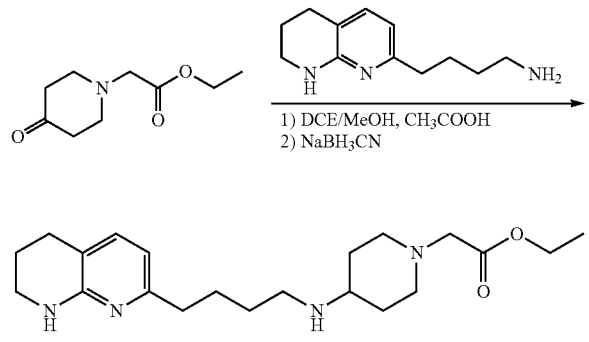

To a solution of ethyl 2-(4-oxopiperidin-1-yl)acetate (140 mg, 0.75 mmol) in DCE (2 mL) and MeOH (2 mL) was added 4-(5,6,7,8-tetrahydro-1,8-naphthyridin-2-yl)butan-1-amine (155 mg, 0.75 mmol) and acetic acid (1 drop). The reaction mixture was stirred at room temperature for 1 h. Then $NaBH_3CN$ (190 mg, 3 mmol) was added, and the reaction mixture was stirred at room temperature for 2 h. The reaction mixture was concenrated in vacuo, and the residue was purified by silica gel column (MeOH:EtOAc=1:5) to give ethyl 2-(4-(4-(5,6,7,8-tetrahydro-1,8-naphthyridin-2-yl)butylamino)piperidin-1-yl)acetate (120 mg, 42% yield) as a yellow oil. (100% purity, UV=214 nm, ESI=375.3 $(M+H)^+$).

Step 3: 2-(4-(4-(5,6,7,8-tetrahydro-1,8-naphthyridin-2-yl)butylamino)piperidin-1-yl)acetic acid (Compound 18)

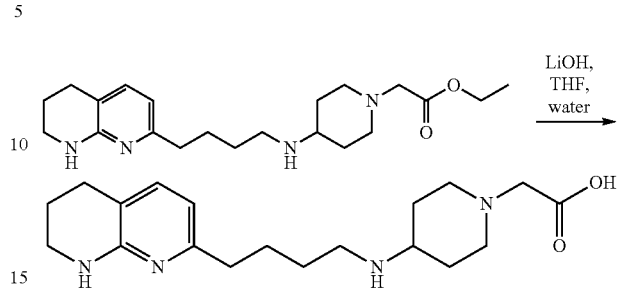

Ethyl 2-(4-(4-(5,6,7,8-tetrahydro-1,8-naphthyridin-2-yl)butylamino)piperidin-1-yl)acetate (120 mg, 0.32 mmol) was treated with LiOH (23 mg, 0.96 mmol) in THF (4 mL) and water (2 mL) for 2 h at room temperature. The reaction mixture was neutralized with 6 N HCl and concentrated in vacuo, and the residue was purified by prep HPLC A (35-69% MeCN) to give compound 18 as a white solid (57 mg). LC/MS A: 100% purity, UV=214 nm, Rt=1.47 min, ESI 347.3 $(M+H)^+$. 1H NMR (500 MHz, CD3OD) δ 7.18 (d, J=7.2 Hz, 1H), 6.42 (d, J=7.2 Hz, 1H), 3.38-3.33 (m, 2H), 3.33-3.32 (m, 4H), 3.01-2.96 (m, 3H), 2.69 (t, J=6 Hz, 2H), 2.56 (t, J=7.2 Hz, 2H), 2.46 (t, J=11.6 Hz, 2H), 2.08 (m, 2H), 1.86 (m, 2H), 1.67 (m, 6H)

Example 19: Preparation of 2-(4-(4-(5,6,7,8-tetrahydro-1,8-naphthyridin-2-yl)butanamido)piperidin-1-yl)acetic acid (Compound 19)

Step 1: tert-butyl 4-(4-(5,6,7,8-tetrahydro-1,8-naphthyridin-2-yl)butanamido)piperidine-1-carboxylate

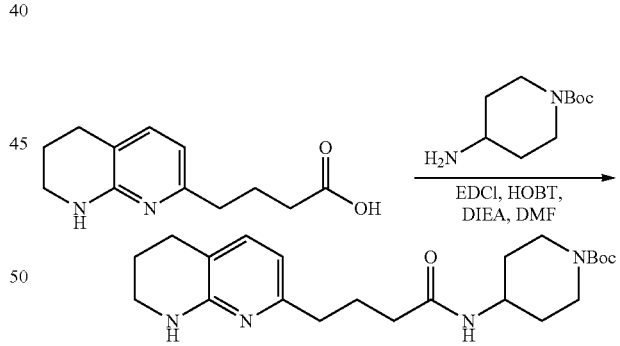

To a solution of 4-(5,6,7,8-tetrahydro-1,8-naphthyridin-2-yl)butanoic acid (100 mg, 0.46 mmol) in DMF (4 mL) was added tert-butyl 4-aminopiperidine-1-carboxylate (110 mg, 0.55 mmol), EDCI (104 mg, 0.55 mmol), HOBT (73 mg, 0.55 mmol) and DIEA (117 mg, 0.92 mmol). The reaction mixture was stirred at room temperature for 2 h. The reaction mixture was diluted with water (25 mL) and extracted with EtOAc (15 mL for 3 times). The combined organic phase was washed with brine, dried over $Na_2SO_4$ and concentrated in vacuo to give tert-butyl 4-(4-(5,6,7,8-tetrahydro-1,8-naphthyridin-2-yl)butanamido)piperidine-1-carboxylate (120 mg, 66% yield) as a yellow oil. (80% purity, UV=254 nm, ESI 403.2 $(M+H)^+$).

Step 2: N-(piperidin-4-yl)-4-(5,6,7,8-tetrahydro-1,8-naphthyrin-2-ylbutanamide

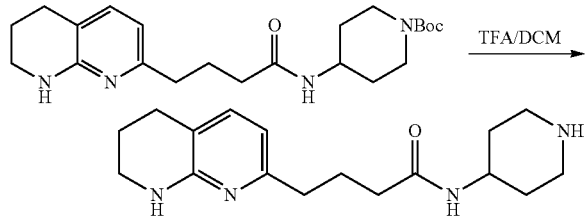

To a solution of tert-butyl 4-(4-(5,6,7,8-tetrahydro-1,8-naphthyridin-2-yl)butanamido)piperidine-1-carboxylate (120 mg, 0.29 mmol) in DCM (4 mL) was added TFA (4 mL). The reaction mixture was stirred at room temperature for 2 h. The reaction was concentrated in vacuo, and the residue was purified by prep HPLC A (30-60% MeCN) to give N-(piperidin-4-yl)-4-(5,6,7,8-tetrahydro-1,8-naphthyridin-2-yl)butanamide (87 mg, 98% yield) as yellow oil. (100% purity, UV=254 nm, ESI 303.3 (M+H)$^+$).

Step 3: ethyl 2-(4-(4-(5,6,7,8-tetrahydro-1,8-naphthyridin-2-yl)butanamido)piperidin-1-yl)acetate

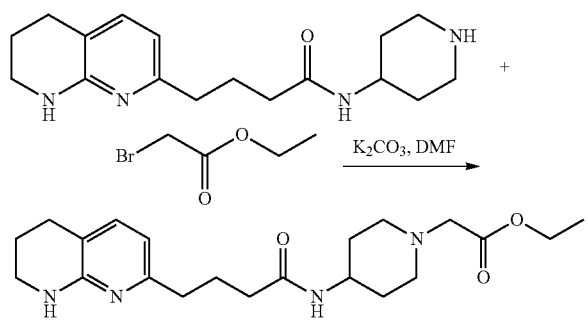

A mixture of N-(piperidin-4-yl)-4-(5,6,7,8-tetrahydro-1,8-naphthyridin-2-yl)butanamide (87 mg, 0.29 mmol), ethyl 2-bromoacetate (52 mg, 0.32 mmol) and K$_2$CO$_3$ (47 mg, 0.32 mmol) in DMF (3 mL) was stirred at room temperature for 2 h. The reaction mixture was diluted with water (30 mL) and extracted with EtOAc (15 mL 3×). The combined organic phase was washed with brine, dried over Na$_2$SO$_4$ and concentrated in vacuo, and the residue was purified by silica gel column (MeOH:EtOAc=5:1) to give ethyl 2-(4-(4-(5,6,7,8-tetrahydro-1,8-naphthyridin-2-yl)butanamido)piperidin-1-yl)acetate (70 mg, 62% yield) as yellow oil. (100% purity, UV=254 nm, ESI 389.1 (M+H)$^+$).

Step 4: 2-(4-(4-(5,6,7,8-tetrahydro-1,8-naphthyridin-2-yl)butanamido)piperidin-1-yl)acetic acid (Compound 19)

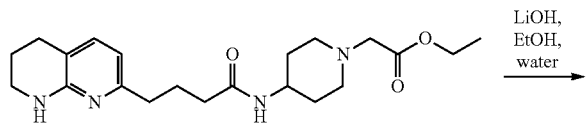

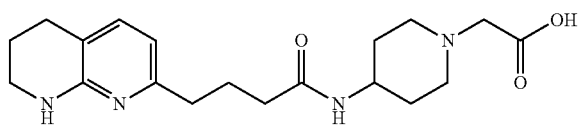

Ethyl 2-(4-(4-(5,6,7,8-tetrahydro-1,8-naphthyridin-2-yl)butanamido)piperidin-1-yl)acetate (70 mg, 0.18 mmol) was treated with LiOH (21 mg, 0.9 mmol) in EtOH (4 mL) and water (2 mL) at room temperature for 2 h. The reaction mixture was neutralized with 6 N HCl. The resultant mixture was concentrated in vacuo, and the residue was purified by prep HPLC A (35-69% MeCN) to give compound 19 as a white solid (47.3 mg). LC/MS A: 100% purity, UV=214 nm, Rt=1.47 min, ESI 361.3 (M+H)+. 1H NMR (500 MHz, MeOD) δ 7.18 (d, J=7.3 Hz, 1H), 6.40 (d, J=7.3 Hz, 1H), 3.99-3.85 (m, 1H), 3.61-3.49 (m, 4H), 3.41 (dd, J=14.9, 9.4 Hz, 2H), 3.10 (t, J=11.0 Hz, 2H), 2.73-2.70 (m, 2H), 2.56 (t, J=7.6 Hz, 2H), 2.32-2.18 (m, 2H), 2.10-2.07 (m, 2H), 2.00-1.74 (m, 6H).

Example 20: Preparation of 2-(1-oxo-2-(3-(5,6,7,8-tetrahydro-1,8-naphthyridin-2-yl)propyl)-2,8-diazaspiro[4.5]decan-8-yl)acetic acid (Compound 20)

Step 1: 1-tert-butyl 4-ethyl 4-allylpiperidine-1,4-dicarboxylate

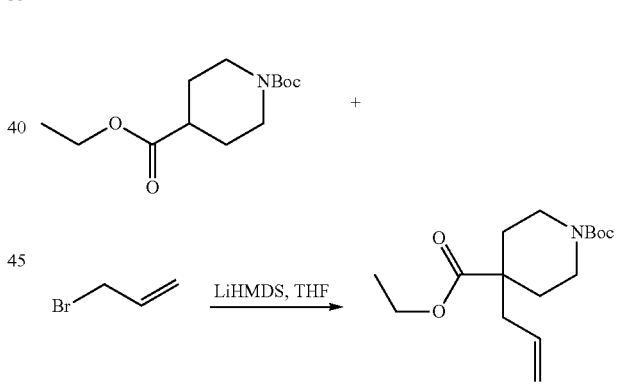

To a solution of 1-tert-butyl 4-ethyl piperidine-1,4-dicarboxylate (5 g, 19.5 mmol) in THF (50 mL) was added LiHMDS (25.3 mL, 1 M/L in THF, 25.3 mmol) at −78° C. The reaction mixture was stirred at −78° C. for 1 h. Then 3-bromoprop-1-ene (3.5 g, 29.3 mmol) was added at −78° C., and the reaction mixture was stirred at room temperature for 16 h. The reaction mixture was diluted with water (30 mL) and extracted with EtOAc (50 mL). The organic phase was concentrated in vacuo, and the residue was purified by silica gel column (pet ether:EtOAc=10:1) to give 1-tert-butyl 4-ethyl 4-allylpiperidine-1,4-dicarboxylate (5 g, 86% yield) as colorless oil. (86% purity, UV=214 nm, ESI 242.2 (M−55)$^+$).

Step 2: 1-tert-butyl 4-ethyl 4-(2-oxoethyl)piperidine-1,4-dicarboxylate

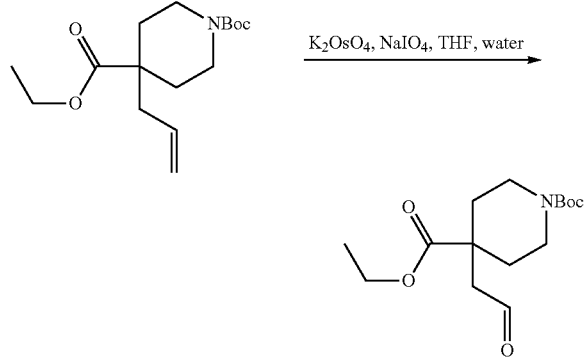

To a solution of 1-tert-butyl 4-ethyl 4-allylpiperidine-1,4-dicarboxylate (1 g, 3.36 mmol) in THF (20 mL) and water (10 mL) was added a solution of K₂OsO₄ (60 mg, 0.17 mmol) in water (2 mL). The reaction mixture was stirred at room temperature for 1 h. Then a solution of NaIO₄ (1.44 g, 6.72 mmol) in water (8 mL) was added, and the reaction mixture was stirred at room temperature for 2 h. The reaction was extracted with DCM (3×20 mL). The combined organic phase was washed with brine, dried over Na₂SO₄ and concentrated in vacuo to give 1-tert-butyl 4-ethyl 4-(2-oxoethyl)piperidine-1,4-dicarboxylate (1 g, 100% crude yield) as a black oil. (36% purity, UV=214 nm, ESI 200.2 (M−99)⁺).

Step 3: tert-butyl 1-oxo-2-(3-(5,6,7,8-tetrahydro-1,8-naphthyridin-2-yl)propyl)-2,8-diazaspiro[4.5]decane-8-carboxylate

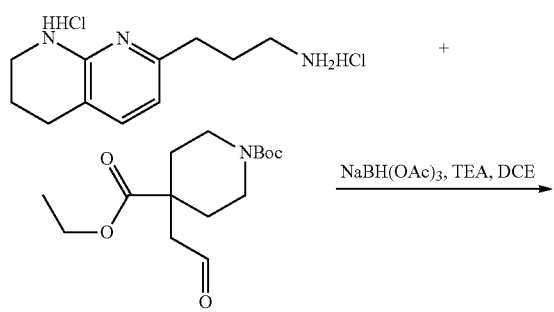

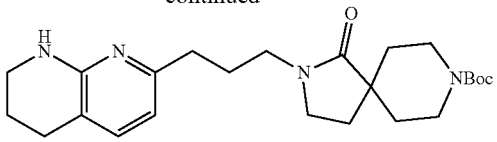

To a suspension of 3-(5,6,7,8-tetrahydro-1,8-naphthyridin-2-yl)propan-1-amine dihydrochloride (400 mg, 1.52 mmol) in DCE (10 mL) was added triethylamine (383 mg, 3.8 mmol) and 1-tert-butyl 4-ethyl 4-(2-oxoethyl)piperidine-1,4-dicarboxylate (454 mg, 1.52 mmol). The reaction mixture was stirred at room temperature for 1 h. Then NaBH(OAc)₃ (644 mg, 3.04 mmol) was added, and the reaction mixture was stirred at room temperature for 48 h. The reaction mixture was concentrated in vacuo, and the residue was purified by silica gel column (EtOAc:MeOH=4:1) to give tert-butyl 1-oxo-2-(3-(5,6,7,8-tetrahydro-1,8-naphthyridin-2-yl)propyl)-2,8-diazaspiro[4.5]decane-8-carboxylate (300 mg, 46% yield) as a yellow oil. (60% purity, UV=254 nm, ESI 429.3 (M+H)⁺).

Step 4: 2-(3-(5,6,7,8-tetrahydro-1,8-naphthyridin-2-yl)propyl)-2,8-diazaspiro[4.5]decan-1-one dihydrochloride

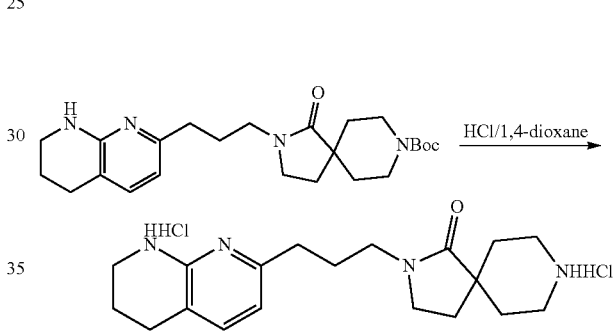

To a solution of tert-butyl 1-oxo-2-(3-(5,6,7,8-tetrahydro-1,8-naphthyridin-2-yl)propyl)-2,8-diazaspiro[4.5]decane-8-carboxylate (300 mg, 0.7 mmol) in 1,4-dioxane (4 mL) was added HCl in 1,4-dioxane (6 mL, 4 M, 24 mmol) at 0° C. The reaction mixture was stirred at room temperature for 16 h. The reaction was concentrated in vacuo to give 2-(3-(5,6,7,8-tetrahydro-1,8-naphthyridin-2-yl)propyl)-2,8-diazaspiro[4.5]decan-1-one dihydrochloride (400 mg, 100% yield) as a yellow oil. (83% purity, UV=254 nm, ESI 329.4 (M+H)⁺).

Step 5: ethyl 2-(1-oxo-2-(3-(5,6,7,8-tetrahydro-1,8-naphthyridin-2-yl)propyl)-2,8-diazaspiro[4.5]decan-8-yl)acetate

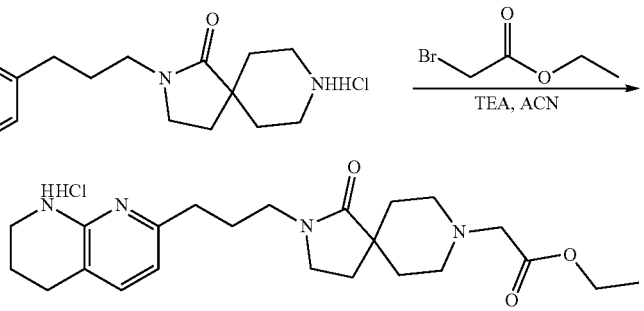

To a solution of 2-(3-(5,6,7,8-tetrahydro-1,8-naphthyridin-2-yl)propyl)-2,8-diazaspiro[4.5]decan-1-one dihydrochloride (400 mg, 1 mmol) in ACN (7 mL) was added triethylamine (300 mg, 3 mmol) and ethyl 2-bromoacetate (193 mg, 0.75 mmol). The reaction mixture was stirred at room temperature for 2 h. The reaction mixture was concentrated in vacuo, and the residue was separated by silica gel column (MeOH:EtOAc=1:5) to give ethyl 2-(1-oxo-2-(3-(5,6,7,8-tetrahydro-1,8-naphthyridin-2-yl)propyl)-2,8-diazaspiro[4.5]decan-8-yl)acetate as yellow solid (180 mg, Yield 45%) as yellow oil. (75% purity, UV=254 nm, ESI 415.4 (M+H)$^+$).

Step 6: 2-(1-oxo-2-(3-(5,6,7,8-tetrahydro-1,8-naphthyridin-2-yl)propyl)-2,8-diazaspiro[4.5]decan-8-yl)acetic acid (Compound 20)

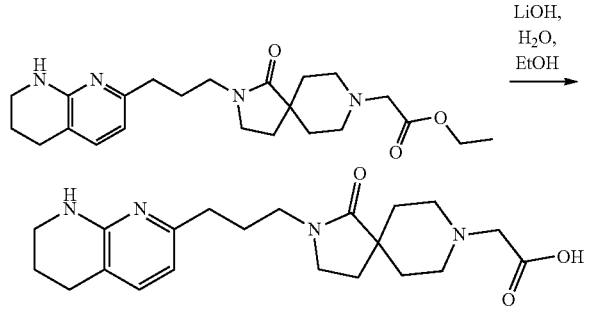

Ethyl 2-(1-oxo-2-(3-(5,6,7,8-tetrahydro-1,8-naphthyridin-2-yl)propyl)-2,8-diazaspiro[4.5]decan-8-yl)acetate (180 mg, 0.43 mmol) was treated with LiOH (92 mg, 2.17 mmol) in EtOH (4 mL) and water (2 mL) at room temperature for 2 h. The reaction was neutralized with 2 N HCl and concentrated in vacuo, and the residue was purified by prep HPLC A (35-65% MeCN) to give compound 20 as a white solid (70 mg). LC/MS A: 100% purity, UV=214 nm, Rt=1.45 min, ESI 387.4 (M+H)$^+$. 1H NMR (500 MHz, CD3OD) δ 7.14 (d, J=7 Hz, 1H), 6.39 (d, J=7 Hz, 1H), 3.50-3.33 (m, 10H), 3.01 (br, 2H), 2.71 (t, J=6.5 Hz, 2H), 2.51 (t, J=7 Hz, 2H), 2.09-2.01 (m, 4H), 1.91-1.86 (m, 4H), 1.69 (d, J=13 Hz, 2H).

Example 21: Preparation of 2-(3-(4-(5,6,7,8-tetrahydro-1,8-naphthyridin-2-yl)butanamido)azetidin-1-yl)acetic acid (Compound 21)

Step 1: tert-butyl 3-(4-(5,6,7,8-tetrahydro-1,8-naphthyridin-2-yl)butanamido)azetidine-1-carboxylate

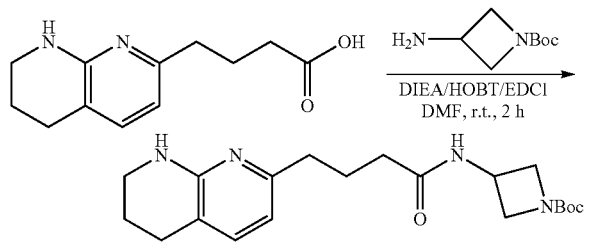

A mixture of 4-(5,6,7,8-tetrahydro-1,8-naphthyridin-2-yl)butanoic acid (100 mg, 0.45 mmol), tert-butyl 3-aminoazetidine-1-carboxylate 78.2 mg, 0.45 mmol), EDCI (123 mg, 0.72 mmol), HOBT (48.6 mg, 0.36 mmol) and DIEA (290 mg, 2.25 mmol) in DMF (2 mL) was stirred at room temperature overnight. Solvent was removed in vacuo, and the residue was purified by silica gel column (MeOH:EtOAc 1:10) to give the desired product tert-butyl 3-(4-(5,6,7,8-tetrahydro-1,8-naphthyridin-2-yl)butanamido)azetidine-1-carboxylate as a yellow oil (80 mg). Yield 47% (98% purity, UV=214 nm, ESI 375 (M+H)$^+$).

Step 2: N-(azetidin-3-yl)-4-(5,6,7,8-tetrahydro-1,8-naphthyridin-2-yl)butanamide

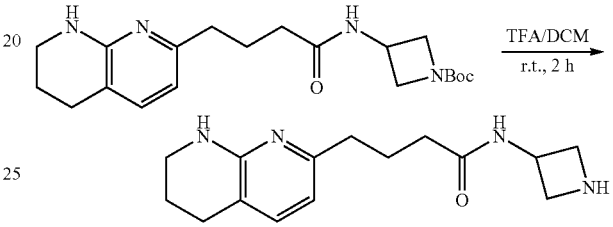

Tert-butyl 3-(4-(5,6,7,8-tetrahydro-1,8-naphthyridin-2-yl)butanamido)azetidine-1-carboxylate (80 mg, 0.21 mmol) was treated with TFA (3 mL, 1.06 mmol) in DCM (3 mL) at room temperature overnight. Solvent was removed in vacuo, and the residue was purified by silica gel column (DCM:MeOH 40:1) to give the desired product N-(azetidin-3-yl)-4-(5,6,7,8-tetrahydro-1,8-naphthyridin-2-yl)butanamide as a yellow oil (205 mg). Yield 98% (98% purity, UV=214 nm, ESI 275 (M+H)$^+$).

Step 3: ethyl 2-(3-(4-(5,6,7,8-tetrahydro-1,8-naphthyridin-2-yl)butanamido) azetidin-1-yl)acetate

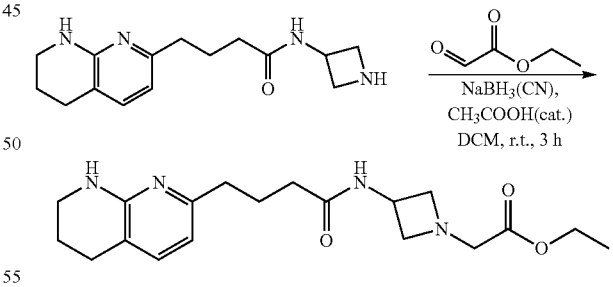

A mixture of N-(azetidin-3-yl)-4-(5,6,7,8-tetrahydro-1,8-naphthyridin-2-yl)butanamide (60 mg, 0.20 mmol), ethyl 2-oxoacetate (82 mg, 0.80 mmol), acetic acid (0.12 mg, 0.002 mmol) and NaBH(OAc)$_3$ (127.2 mg, 0.60 mmol) in DCM (5 mL) was stirred at room temperature overnight. Solvent was removed in vacuo, and the residue was purified by silica gel column (DCM:MeOH 20:1) to give the desired product methyl ethyl 2-(3-(4-(5,6,7,8-tetrahydro-1,8-naphthyridin-2-yl)butanamido)azetidin-1-yl)acetate as a colorless oil (30 mg). Yield 38% (98% purity, UV=214 nm, ESI 361 (M+H)$^+$).

Step 4: 2-(3-(4-(5,6,7,8-tetrahydro-1,8-naphthyridin-2-yl)butanamido)azetidin-1-yl)acetic acid (Compound 21)

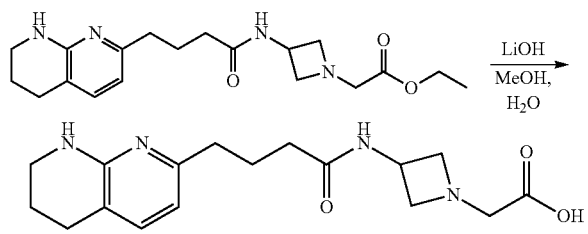

Ethyl 2-(3-(4-(5,6,7,8-tetrahydro-1,8-naphthyridin-2-yl)butanamido) azetidin-1-yl)acetate (30 mg, 0.083 mmol) was treated with LiOH—H$_2$O (14 mg, 0.33 mmol) in MeOH (1 mL) and H$_2$O (1 mL) for 2 hours at room temperature. Solvent was removed in vacuo, and the residue was purified by Prep-HPLC A (33-65% MeCN) to give compound 21 as a white solid (10 mg). Yield 33%. LC/MS A: 98% purity, Rt=1.46 min, ESI 333 (M+H)$^+$). $^1$H NMR (500 MHz, MeOD) δ 7.16 (d, J=7.3 Hz, 1H), 6.39 (d, J=7.3 Hz, 1H), 4.55 (p, J=7.3 Hz, 1H), 4.23-4.15 (m, 2H), 3.78 (dd, J=10.4, 7.0 Hz, 2H), 3.43-3.37 (m, 2H), 2.72 (t, J=6.2 Hz, 2H), 2.56 (t, J=7.5 Hz, 2H), 2.24 (t, J=7.5 Hz, 2H), 2.00-1.85 (m, 4H).

Example 22: 2-(3-(5-(5,6,7,8-tetrahydro-1,8-naphthyridin-2-yl)pentylamino) azetidin-1-yl)acetic acid (Compound 22)

Step 1: tert-butyl 7-(5-(1-(2-ethoxy-2-oxoethyl)azetidin-3-ylamino)pentyl)-3,4-dihydro-1,8-naphthyridine-1(2H)-carboxylate

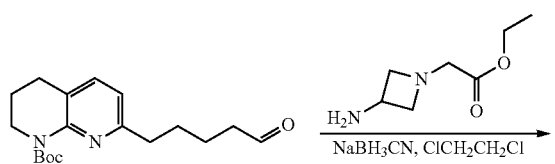

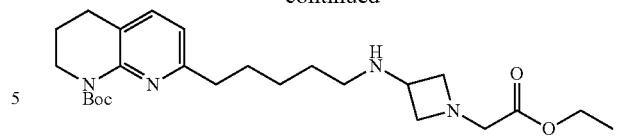

NaBH$_3$CN (59 mg, 0.94 mmol) was added to a stirred mixture of tert-butyl 7-(5-oxopentyl)-3,4-dihydro-1,8-naphthyridine-1(2H)-carboxylate (100 mg, 0.31 mmol) and ethyl 2-(3-aminoazetidin-1-yl)acetate hydrochloride (73 mg, 0.38 mmol) in DCE at room temperature. The resulting mixture was stirred at room temperature for 2 hours, then diluted with water (20 mL) and extracted with DCM (3×20 mL). The combined organic extracts were washed with water and brine, dried and concentrated to give tert-butyl 7-(5-(1-(2-ethoxy-2-oxoethyl)azetidin-3-ylamino)pentyl)-3,4-dihydro-1,8-naphthyridine-1 (2H)-carboxylate as a light yellow oil (102 mg). Yield 71% (100% purity, UV=214 nm, ESI 461 (M+H)$^+$).

Step 2: ethyl 2-(3-(5-(5,6,7,8-tetrahydro-1,8-naphthyridin-2-yl)pentylamino)azetidin-1-yl)acetate

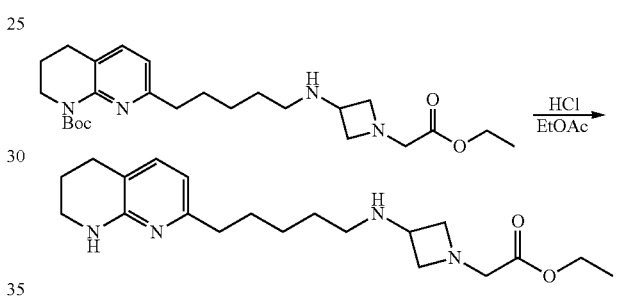

Tert-butyl 7-(5-(1-(2-ethoxy-2-oxoethyl)azetidin-3-ylamino)pentyl)-3,4-dihydro-1,8-naphthyridine-1(2H)-carboxylate (35 mg, 0.08 mmol) was treated with HCl (3 mL, 9 mmol) in dioxane (2 mL) at room temperature overnight. Solvent was removed in vacuo to give ethyl 2-(3-(5-(5,6,7,8-tetrahydro-1,8-naphthyridin-2-yl)pentylamino)azetidin-1-yl)acetate as a light yellow solid (20 mg). Yield 73% (100% purity, UV=214 nm, ESI 361 (M+H)$^+$).

Step 3: 2-(3-(5-(5,6,7,8-tetrahydro-1,8-naphthyridin-2-yl)pentylamino)azetidin-1-yl)acetic acid (Compound 22)

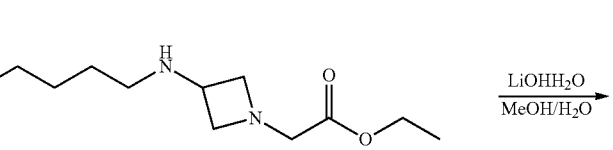

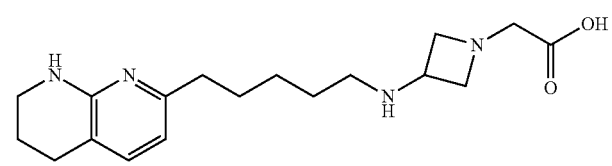

Ethyl 2-(3-(5-(5,6,7,8-tetrahydro-1,8-naphthyridin-2-yl)pentylamino)azetidin-1-yl)acetate (25 mg, 0.07 mmol) was treated with LiOH—H$_2$O (9 mg, 0.21 mmol) in THF (2 mL) and H$_2$O (2 mL) for 2 hours at room temperature. Solvent was removed in vacuo, and the residue was purified by Prep-HPLC B (33-65% MeCN) to give compound 22 as a white solid (5 mg) Yield 26% (LC/MS A: 100% purity, UV=214 nm, Rt=1.47 min, ESI 333 (M+H)$^+$). $^1$H NMR (500 MHz, MeOD) δ 8.45 (s, 2H), 7.52 (d, J=7.3 Hz, 1H), 6.56 (d, J=7.3 Hz, 1H), 4.37-4.21 (m, 2H), 4.00-3.91 (m, 2H), 3.88 (m, 1H), 3.78 (s, 2H), 3.52-3.41 (m, 2H), 2.81 (t, J=6.1 Hz, 2H), 2.70 (dd, J=16.0, 8.2 Hz, 4H), 2.03-1.87 (m, 2H), 1.81-1.65 (m, 2H), 1.67-1.52 (m, 2H), 1.51-1.37 (m, 2H).

Example 23: 2-phenyl-2-(4-(3-(5,6,7,8-tetrahydro-1,8-naphthyridin-2-yl)propylcarbamoyl)piperidin-1-yl) acetic acid (Compounds 23-E1 and 23-E2)

Step 1: tert-butyl 4-(3-(5,6,7,8-tetrahydro-1,8-naphthyridin-2-yl)propylcarbamoyl) piperidine-1-carboxylate

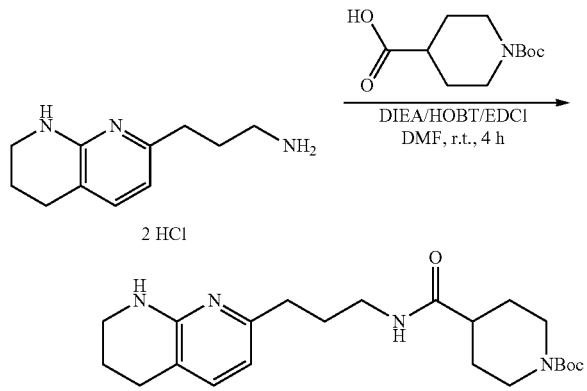

A mixture of 3-(5,6,7,8-tetrahydro-1,8-naphthyridin-2-yl)propan-1-amine (200 mg, 0.76 mmol), 1-(tert-butoxycarbonyl)piperidine-4-carboxylic acid (173 mg, 0.76 mmol), EDCI (234.2 mg, 1.22 mmol), HOBT (82.1 mg, 0.61 mmol) and DIEA (490.2 mg, 3.8 mmol) in DMF (4 mL) was stirred at room temperature overnight. Solvent was removed in vacuo, and the residue was purified by silica gel column (MeOH:EtOAc 1:10) to give the desired product tert-butyl 4-(3-(5,6,7,8-tetrahydro-1,8-naphthyridin-2-yl)propylcarbamoyl) piperidine-1-carboxylate as a yellow oil (133 mg). Yield 43% (98% purity, UV=214 nm, ESI 403.0 (M+H)$^+$).

Step 2: N-(3-(5,6,7,8-tetrahydro-1,8-naphthyridin-2-yl)propyl)piperidine-4-carboxamide

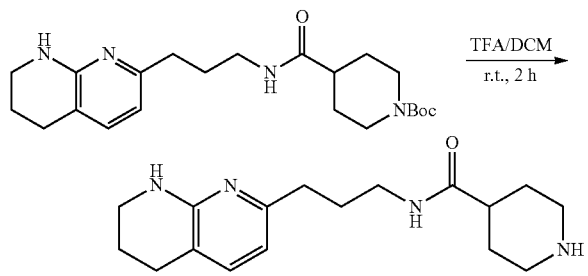

Tert-butyl 4-(3-(5,6,7,8-tetrahydro-1,8-naphthyridin-2-yl)propylcarbamoyl) piperidine-1-carboxylate (133 mg, 0.33 mmol) was treated with TFA (5 mL, 1.65 mmol) in DCM (5 mL) at room temperature overnight. Solvent was removed in vacuo, and the residue was purified by silica gel column (DCM:MeOH 40:1) to give the desired product N-(3-(5,6,7,8-tetrahydro-1,8-naphthyridin-2-yl)propyl)piperidine-4-carboxamide as a yellow oil (100 mg). Yield 99% (98% purity, UV=214 nm, ESI 303 (M+H)$^+$).

Step 3: ethyl 2-phenyl-2-(4-(3-(5,6,7,8-tetrahydro-1,8-naphthyridin-2-yl) propylcarbamoyl) piperidin-1-yl)acetate

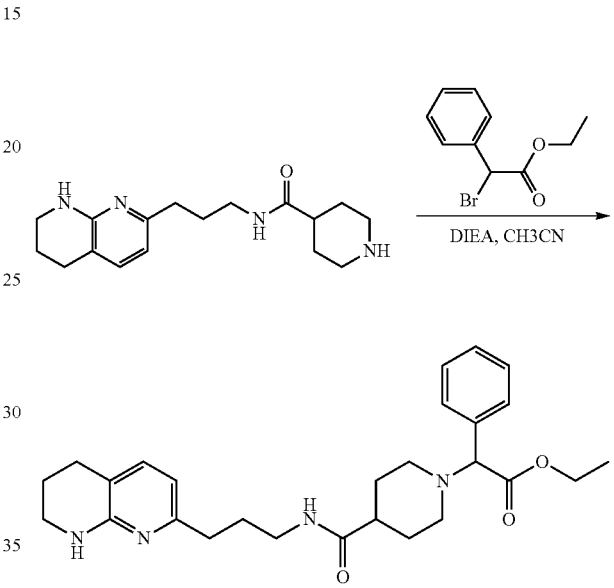

A mixture of N-(3-(5,6,7,8-tetrahydro-1,8-naphthyridin-2-yl)propyl)piperidine-4-carboxamide (200 mg, 0.66 mmol), ethyl 2-bromo-2-phenylacetate (192 mg, 0.79 mmol) and DIEA (255 mg, 1.98 mmol) in MeCN (4 mL) was stirred at room temperature for 3 hours. Solvent was removed in vacuo, and the residue was purified by silica gel column (DCM: MeOH 20:1) to give the desired product ethyl 2-phenyl-2-(4-(3-(5,6,7,8-tetrahydro-1,8-naphthyridin-2-yl)propylcarbamoyl)piperidin-1-yl)acetate as a yellow oil (200 mg). Yield 65% (98% purity, UV=214 nm, ESI 465 (M+H)$^+$).

Step 4: 2-phenyl-2-(4-(3-(5,6,7,8-tetrahydro-1,8-naphthyridin-2-yl)propylcarbamoyl)piperidin-1-yl) acetic acid (Compounds 23-E1 and 23-E2) (MRT-C0123)

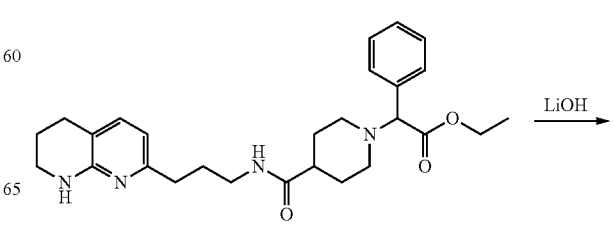

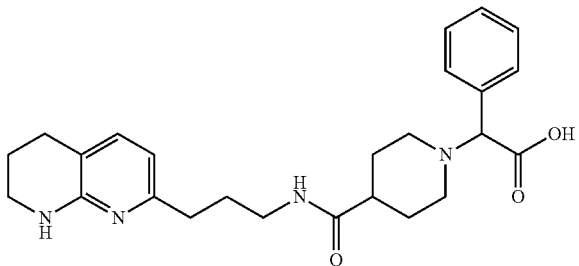

Ethyl 2-phenyl-2-(4-(3-(5,6,7,8-tetrahydro-1,8-naphthyridin-2-yl) propylcarbamoyl) piperidin-1-yl)acetate (200 mg, 0.43 mmol) was treated with LiOH—H₂O (88.3 mg, 2.15 mmol) in MeOH (4 mL) and H₂O (2 mL) at 50° C. for 3 hours. Solvent was removed in vacuo, and the residue was purified by Prep-HPLC A (30-65% MeCN) to give racemic compound 23 as a white solid (150 mg, 44% yield). The racemic product was separated by prep chiral SFC A to give enantiomeric products compound 23-E1 (40 mg) and compound 23-E2 (44 mg) as white solids.

Compound 23-E1 LC/MS A: 98% purity, UV=214 nm, Rt=1.48 min, ESI 437 (M+H)⁺. ¹H NMR (500 MHz, MeOD) δ 7.59 (dd, J=6.5, 2.8 Hz, 2H), 7.49-7.41 (m, 3H), 7.16 (d, J=7.3 Hz, 1H), 6.39 (d, J=7.3 Hz, 1H), 4.43 (s, 1H), 3.77 (s, 1H), 3.41-3.36 (m, 2H), 3.20 (t, J=6.9 Hz, 2H), 3.06 (s, 1H), 2.95 (t, J=10.0 Hz, 1H), 2.82 (s, 1H), 2.70 (dd, J=13.8, 7.5 Hz, 2H), 2.57-2.51 (m, 2H), 2.48-2.38 (m, 1H), 2.10-1.93 (m, 3H), 1.92-1.79 (m, 5H). Chiral S,S-Whelk-O1 A (45% MeOH): ee 100%, Rt=2.17 min.

Compound 23-E2 LC/MS A: 98% purity, UV=214 nm, Rt=1.48 min, ESI 437 (M+H)⁺. ¹H NMR (500 MHz, MeOD) δ 7.59 (dd, J=6.4, 2.8 Hz, 2H), 7.48-7.41 (m, 3H), 7.17 (d, J=7.3 Hz, 1H), 6.39 (d, J=7.3 Hz, 1H), 4.43 (s, 1H), 3.76 (s, 1H), 3.42-3.36 (m, 2H), 3.20 (t, J=6.9 Hz, 2H), 3.06 (d, J=11.6 Hz, 1H), 2.94 (t, J=10.5 Hz, 1H), 2.80 (s, 1H), 2.71 (t, J=6.2 Hz, 2H), 2.58-2.51 (m, 2H), 2.48-2.38 (m, 1H), 2.01 (tt, J=22.5, 11.2 Hz, 3H), 1.92-1.79 (m, 5H). Chiral S,S-Whelk-O1 A (45% MeOH): ee 100%, Rt=3.04 min.

Example 24: Preparation of 2-phenyl-2-(4-(4-(5,6,7,8-tetrahydro-1,8-naphthyridin-2-yl)butylamino)piperidin-1-yl)acetic acid (Compounds 24-E1 and 24-E2)

Step 1: ethyl 2-(4-oxopiperidin-1-yl)-2-phenylacetate

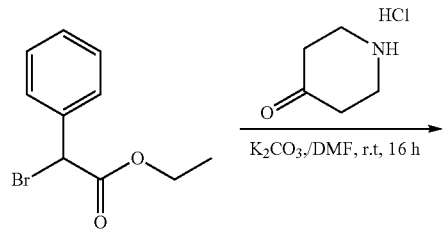

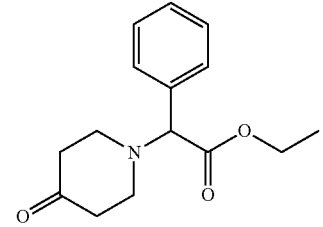

A mixture of piperidin-4-one hydrochloride (1.0 g, 7.38 mmol), ethyl 2-bromo-2-phenylacetate (2.53 g, 11.06 mmol) and K₂CO₃ (3.06 g, 22.13 mmol) in DMF (30 mL) was stirred at room temperature overnight. Solvent was removed in vacuo, and the residue was purified by silica gel column (pet ether:EtOAc 2:1) to give the desired product ethyl 2-(4-oxopiperidin-1-yl)-2-phenylacetate as a colorless oil (1.0 g). Yield 92% (98% purity, UV=214 nm, ESI 262.0 (M+H)⁺).

Step 2: ethyl 2-phenyl-2-(4-(4-(5,6,7,8-tetrahydro-1,8-naphthyridin-2-yl)butylamino)piperidin-1-yl)acetate

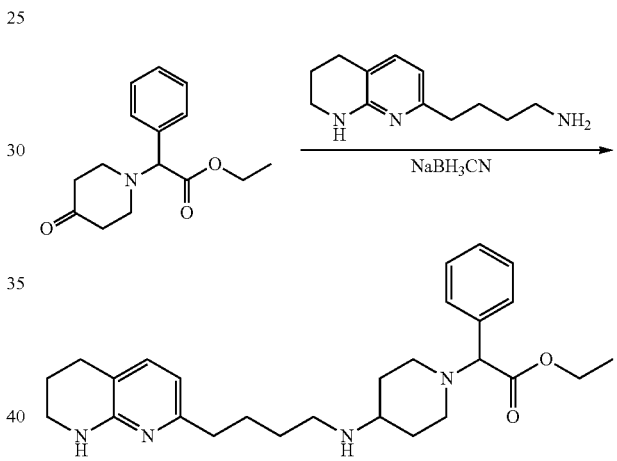

A mixture of 4-(5,6,7,8-tetrahydro-1,8-naphthyridin-2-yl) butan-1-amine (261 mg, 1.28 mmol), ethyl 2-(4-oxopiperidin-1-yl)-2-phenylacetate phenylacetate (400 mg, 1.5 mmol) and NaBH₃CN (245 mg, 3.84 mmol) in DCM (10 mL) was stirred at room temperature overnight.

Solvent was removed in vacuo, and the residue was purified by silica gel column (DCM: MeOH 20:1) to give the desired product ethyl 2-phenyl-2-(4-(4-(5,6,7,8-tetrahydro-1,8-naphthyridin-2-yl)butylamino)piperidin-1-yl)acetate as a colorless oil (180 mg). Yield 45% (98% purity, UV=214 nm, ESI 451 (M+H)⁺).

Step 3: 2-phenyl-2-(4-(4-(5,6,7,8-tetrahydro-1,8-naphthyridin-2-yl)butylamino)piperidin-1-yl)acetic acid (Compounds 24-E1 and 24-E2)

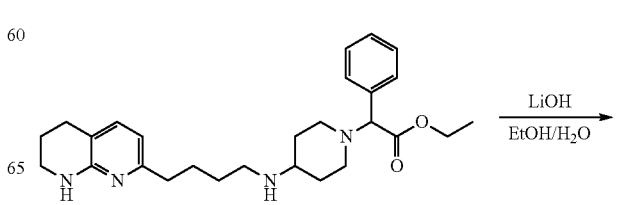

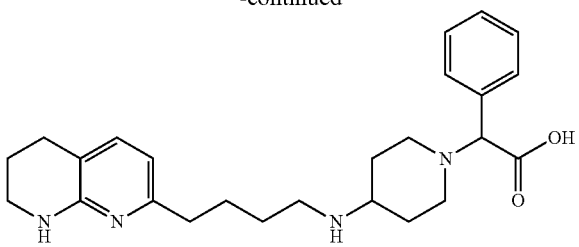

Ethyl 2-phenyl-2-(4-(4-(5,6,7,8-tetrahydro-1,8-naphthyridin-2-yl)butylamino)piperidin-1-yl)acetate (50 mg, 0.11 mmol) was treated with LiOH—H₂O (23.4 mg, 0.56 mmol) in EtOH (2 mL) and H₂O (1 mL) at room temperature for 2 hours. Solvent was removed in vacuo, and the residue was purified by Prep-HPLC A (30-65% MeCN) to give compound 24 as a white solid (30 mg, 60% yield). The racemic product was separated by Prep chiral SFC B to give enantiomeric products compound 24-E1 (2.2 mg) and compound 24-E2 (5.7 mg) as white solids.

Compound 24-E1 LC/MS A: 100% purity, UV=214 nm, Rt=1.623 min, ESI423 (M+H)+¹H NMR (500 MHz, MeOD) δ 7.52 (d, J=7.0 Hz, 2H), 7.34 (dt, J=14.1, 7.1 Hz, 3H), 7.18 (d, J=7.3 Hz, 1H), 6.42 (d, J=7.3 Hz, 1H), 3.80 (s, 1H), 3.38-3.34 (m, 3H), 3.04-2.91 (m, 3H), 2.78 (s, 1H), 2.69 (t, J=6.2 Hz, 2H), 2.56 (t, J=7.0 Hz, 2H), 2.25 (s, 1H), 2.08-1.63 (m, 11H). Chiral AD-H A (40% MeOH): ee 22.5%, Rt=2.49 min Compound 24-E2 LC/MS A: 100% purity, UV=214 nm, Rt=1.51 min, ESI423 (M+H)+¹H NMR (500 MHz, MeOD) δ 7.53 (d, J=7.0 Hz, 2H), 7.32 (dt, J=21.7, 7.0 Hz, 3H), 7.17 (d, J=7.3 Hz, 1H), 6.42 (d, J=7.3 Hz, 1H), 3.80 (s, 1H), 3.41-3.34 (m, 3H), 3.05-2.88 (m, 3H), 2.79 (d, J=11.1 Hz, 1H), 2.69 (t, J=6.2 Hz, 2H), 2.56 (t, J=7.1 Hz, 2H), 2.25 (t, J=11.1 Hz, 1H), 2.08-1.61 (m, 11H). Chiral AD-H A (40% MeOH): ee 36.3%, Rt=0.84 min Example 25: 2-phenyl-2-(3-(4-((5,6,7,8-tetrahydro-1,8-naphthyridin-2-yl)methyl) piperidine-1-carbonyl)azetidin-1-yl)acetic acid (Compound 25)

Step 1: tert-butyl 3-(4-((5,6,7,8-tetrahydro-1,8-naphthyridin-2-yl)methyl)piperidine-1-carbonyl)azetidine-1-carboxylate

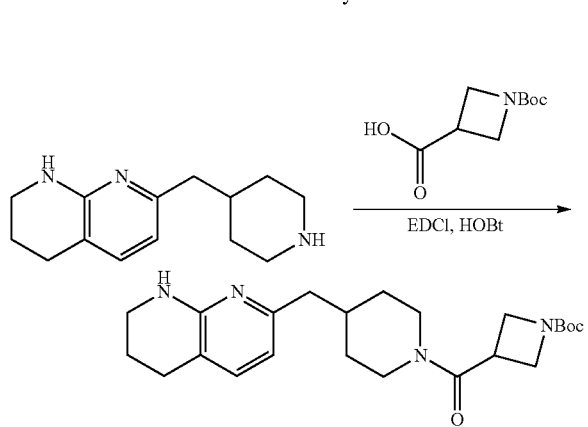

A mixture of 7-(piperidin-4-ylmethyl)-1,2,3,4-tetrahydro-1,8-naphthyridine (300 mg, 0.99 mmol), 1-(tert-butoxycarbonyl)azetidine-3-carboxylic acid (200 mg, 0.99 mmol), EDCI (228 mg, 3.41 mmol), HOBt (135 mg, 0.99 mmol) and DIEA (255 mg, 1.98 mmol) in DMF (3 mL) was stirred at room temperature overnight. Solvent was removed in vacuo, and the residue was purified by silica gel column (pet ether:EtOAc 2:1) to give the desired product tert-butyl 3-(4-((5,6,7,8-tetrahydro-1,8-naphthyridin-2-yl)methyl)piperidine-1-carbonyl)azetidine-1-carboxylate as a yellow oil (295 mg). Yield 63% (ESI 415 (M+H)+).

Step 2: azetidin-3-yl(4-((5,6,7,8-tetrahydro-1,8-naphthyridin-2-yl)methyl)piperidin-1-yl)methanone

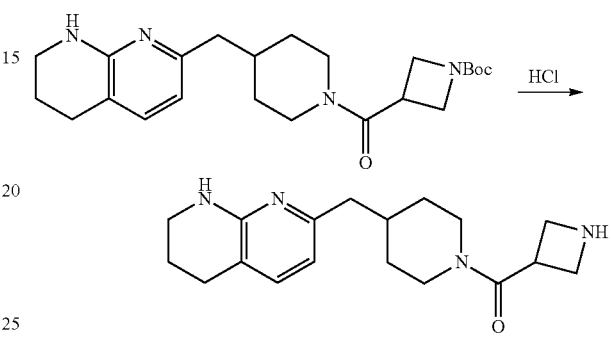

Tert-butyl 3-(4-((5,6,7,8-tetrahydro-1,8-naphthyridin-2-yl)methyl)piperidine-1-carbonyl)azetidine-1-carboxylate (295 mg, 0.71 mmol) was treated with HCl (4 mL, 15.4 mmol) in 1,4-dioxane (5 mL) at room temperature overnight. Solvent was removed in vacuo, and the residue was purified by silica gel column (DCM:MeOH 40:1) to give the desired product azetidin-3-yl(4-((5,6,7,8-tetrahydro-1,8-naphthyridin-2-yl)methyl)piperidin-1-yl)methanone as a yellow oil (140 mg). Yield 62% (ESI 315 (M+H)+).

Step 3: ethyl 2-phenyl-2-(3-(4-((5,6,7,8-tetrahydro-1,8-naphthyridin-2-yl)methyl)piperidine-1-carbonyl)azetidin-1-yl)acetate

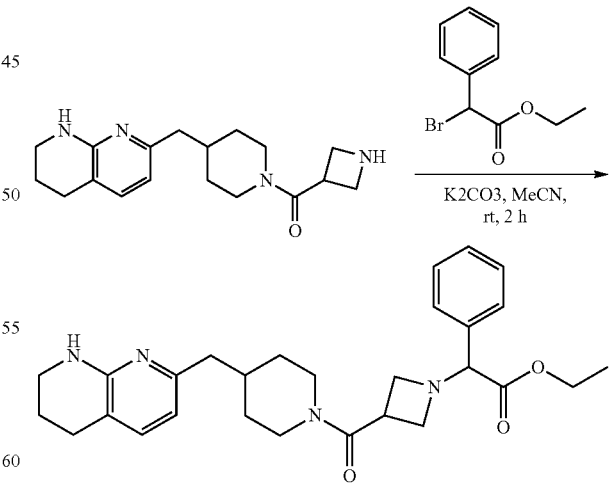

A mixture of piperidin-4-one hydrochloride (140 mg, 0.45 mmol), ethyl 2-bromo-2-phenylacetate (130 mg, 0.54 mmol) and K₂CO₃ (150 mg, 1.1 mmol) in MeCN (5 mL) was stirred at room temperature overnight. Solvent was removed in vacuo, and the residue was purified by silica gel column (pet ether:EtOAc 2:1) to give the desired product ethyl 2-phenyl-2-(3-(4-((5,6,7,8-tetrahydro-1,8-naphthyridin-2-yl)methyl)piperidine-1-carbonyl)azetidin-1-yl)acetate as a colorless oil (130 mg). Yield 71% (ESI 477 (M+H)$^+$).

Step 4: 2-phenyl-2-(3-(4-((5,6,7,8-tetrahydro-1,8-naphthyridin-2-yl)methyl) piperidine-1-carbonyl)azetidin-1-yl)acetic acid (Compound 25)

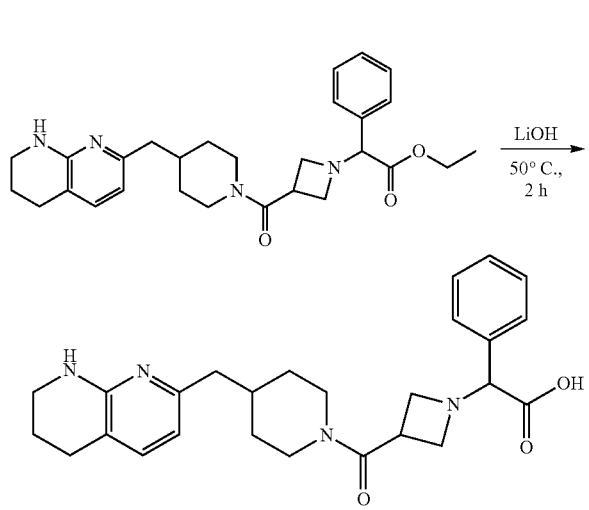

Ethyl 2-phenyl-2-(3-(4-((5,6,7,8-tetrahydro-1,8-naphthyridin-2-yl)methyl)piperidine-1-carbonyl)azetidin-1-yl)acetate (130 mg, 0.27 mmol) was treated with LiOH—H$_2$O (57 mg, 1.4 mmol) in EtOH (4 mL) and H$_2$O (1 mL) at 50° C. for 2 hours. Solvent was removed in vacuo, and the residue was purified by Prep-HPLC A (33-65% MeCN) to give racemic compound 25 as a white solid (42 mg). Yield 34% (ESI 449 (M+H)$^+$).

Compound 25 LC/MS B: Rt=1.08 min, ESI 449 (M+H)$^+$. $^1$H NMR (500 MHz, CD3OD) δ 7.51 (s, 2H), 7.44 (s, 3H), 7.17 (d, J=7.2 Hz, 1H), 6.36 (d, J=7.2 Hz, 1H), 4.69 (s, 1H), 4.47 (d, J=13.7 Hz, 1H), 4.32 (s, 1H), 4.16 (s, 1H), 4.04 (d, J=26.8 Hz, 1H), 3.88 (s, 2H), 3.56 (d, J=13.6 Hz, 1H), 3.43-3.37 (m, 2H), 3.00 (t, J=12.5 Hz, 1H), 2.72 (t, J=6.2 Hz, 2H), 2.66 (t, J=12.3 Hz, 1H), 2.47 (d, J=7.1 Hz, 2H), 1.98-1.85 (m, 3H), 1.69 (d, J=13.1 Hz, 2H), 1.14 (d, J=9.0 Hz, 2H).

Example 26: Preparation of 2-(4-((3-(6-(methylamino)pyridin-2-yl)propyl) carbamoyl)piperidin-1-yl)acetic acid (Compound 26)

Step 1: benzyl piperidine-4-carboxylate

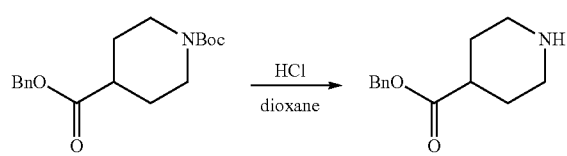 [SMILES: CC(C)(C)OC(=O)N1CCC(C(=O)OCc2ccccc2)CC1 ; Cl ; O=C(OCc1ccccc1)C1CCNCC1]

4-benzyl 1-tert-butyl piperidine-1,4-dicarboxylate (5 g, 15.6 mmol) was treated with 4N HCl/dioxane (20 mL) at room temperature overnight. Solvent was removed in vacuo to give the desired product benzyl piperidine-4-carboxylate as a white solid (4 g). Yield 100% (100% purity, UV=214 nm, ESI 220 (M+H)$^+$).

Step 2: benzyl 1-(2-tert-butoxy-2-oxoethyl)piperidine-4-carboxylate

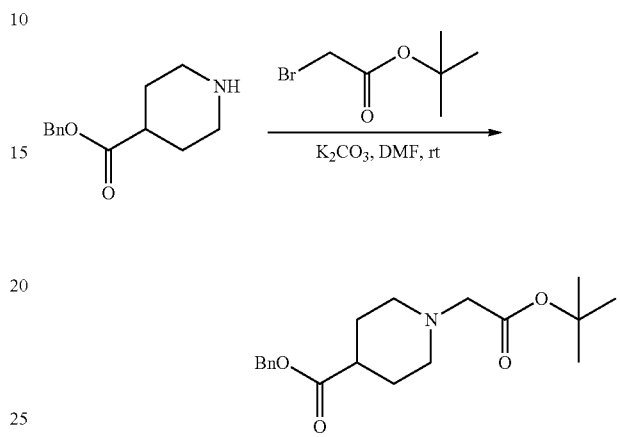

A mixture of benzyl piperidine-4-carboxylate (4 g, 15 mmol), tert-butyl 2-bromoacetate (4.3 g, 22.5 mmol) and K$_2$CO$_3$ (6.1 g, 45 mmol) in DMF (20 mL) was stirred at room temperature overnight. Solvent was removed in vacuo, and the residue was purified by silica gel column (pet ether:EtOAc 2:1) to give the desired product benzyl 1-(2-tert-butoxy-2-oxoethyl)piperidine-4-carboxylate as a colorless oil (3.5 g). Yield 67% (95% purity, UV=214 nm, ESI 334 (M+H)$^+$).

Step 3: 1-(2-tert-butoxy-2-oxoethyl)piperidine-4-carboxylic acid

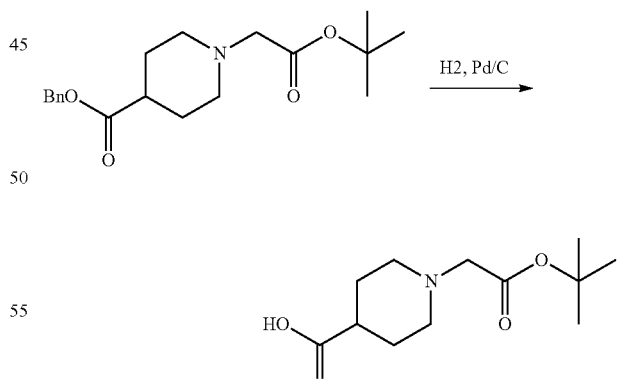

A mixture of benzyl 1-(2-tert-butoxy-2-oxoethyl)piperidine-4-carboxylate (3.2 g, 9.6 mmol) and Pd/C (400 mg) in EtOAc (50 mL) was stirred under balloon hydrogen at room temperature for 18 hours. The mixture was filtered and concentrated in vacuo to give 1-(2-tert-butoxy-2-oxoethyl)piperidine-4-carboxylic acid as a white solid (2.1 g). Yield 79% (100% purity, UV=214 nm, ESI 244 (M+H)$^+$).

Step 4: tert-butyl 3-(6-(methylamino)pyridin-2-yl) prop-2-ynylcarbamate

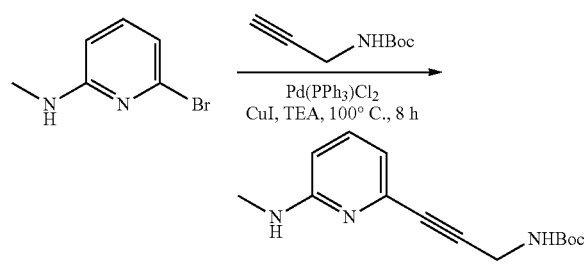

A mixture of 6-bromo-N-methylpyridin-2-amine (600 mg, 3.2 mmol), Pd(PPh₃)₂Cl₂ (141 mg, 0.3 mmol), CuI (121 mg, 0.64 mmol), triethylamine (970 mg, 9.6 mmol) and tert-butyl prop-2-ynylcarbamate (990 mg, 6.4 mmol) in DMF (30 mL) was stirred under nitrogen atmosphere at 100° C. for 8 hours. The mixture was concentrated in vacuo, and the residue was purified by silica gel column (MeOH:DCM 1:15) to give the desired product tert-butyl 3-(6-(methylamino)pyridin-2-yl)prop-2-ynylcarbamate as a colorless oil (500 mg). Yield 60% (98% purity, UV=214 nm, ESI 262 (M+H)⁺).

Step 5: tert-butyl 3-(6-(methylamino)pyridin-2-yl)propylcarbamate

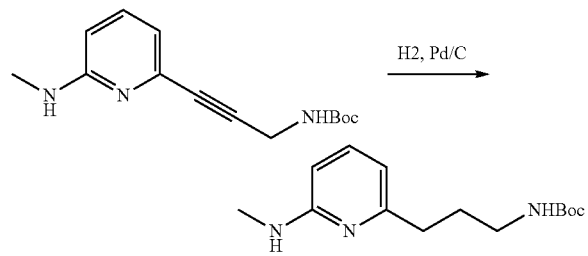

A mixture of tert-butyl 3-(6-(methylamino)pyridin-2-yl) prop-2-ynylcarbamate (500 mg, 1.91 mmol) and Pd/C (50 mg) in EtOAc (15 mL) was stirred under balloon hydrogen at room temperature for 18 hours. The mixture was filtered and concentrated in vacuo to give tert-butyl 3-(6-(methylamino)pyridin-2-yl)propylcarbamate as a yellow oil (460 mg). Yield 91% (100% purity, UV=214 nm, ESI 266 (M+H)⁺).

Step 6: 6-(3-aminopropyl)-N-methylpyridin-2-amine

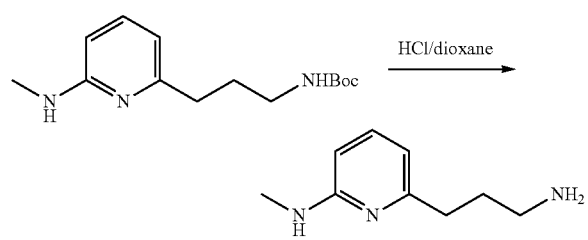

Tert-butyl 3-(6-(methylamino)pyridin-2-yl)propylcarbamate (460 mg, 1.73 mmol) was treated with 4N HCl/dioxane (10 mL) at room temperature for 14 hours. Solvent was removed in vacuo, and the residue was purified by silica gel column (DCM:MeOH 7:1) to give the desired product 6-(3-aminopropyl)-N-methylpyridin-2-amine as a yellow oil (280 mg). Yield 90% (98% purity, UV=214 nm, ESI 166 (M+H)⁺).

Step 7: tert-butyl 2-(4-(3-(6-(methylamino)pyridin-2-yl)propylcarbamoyl)piperidin-1-yl)acetate

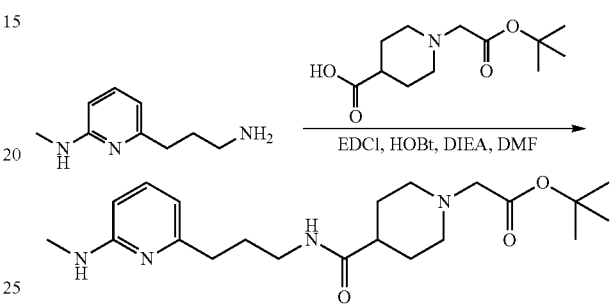

A mixture of 6-(3-aminopropyl)-N-methylpyridin-2-amine (120 mg, 0.73 mmol), 1-(2-tert-butoxy-2-oxoethyl) piperidine-4-carboxylic acid (176.7 mg, 0.73 mmol), EDCI (210 mg, 1.1 mmol), HOBt (78.8 mg, 0.58 mmol) and DIPEA (283 mg, 2.19 mmol) in DMF (4 mL) was stirred at room temperature for 2 hours. Solvent was removed in vacuo, and the residue was purified by silica gel column (MeOH:EtOAc 1:10) to give the desired product tert-butyl 2-(4-(3-(6-(methylamino)pyridin-2-yl)propylcarbamoyl)piperidin-1-yl)acetate as a yellow oil (110 mg). Yield 39% (98% purity, UV=214 nm, ESI 391 (M+H)⁺).

Step 8: 2-(4-(3-(6-(methylamino)pyridin-2-yl)propylcarbamoyl)piperidin-1-yl)acetic acid (Compound 26)

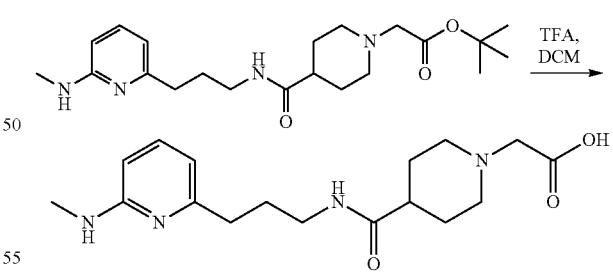

Tert-butyl 2-(4-(3-(6-(methylamino)pyridin-2-yl)propylcarbamoyl)piperidin-1-yl)acetate (110 mg, 0.28 mmol) was treated with TFA (3 mL) in DCM (5 mL) at room temperature for 4 hours. Solvent was removed in vacuo, and the residue was purified by Prep-HPLC A (30-70% MeCN) to give compound 26 as a white solid. (35.5 mg, yield 37.9%). LC/MS A: 100% purity, UV=214 nm, Rt=1.30 min, ESI 335 (M+H)⁺. ¹H NMR (500 MHz, MeOD) δ 7.40 (dd, J=8.2, 7.5 Hz, 1H), 6.46 (d, J=7.2 Hz, 1H), 6.34 (d, J=8.4 Hz, 1H), 3.65 (d, J=12.3 Hz, 2H), 3.59 (s, 2H), 3.24 (t, J=7.0 Hz, 2H), 3.03

(td, J=11.9, 4.2 Hz, 2H), 2.87 (s, 3H), 2.62 (t, J=8.0 Hz, 2H), 2.51-2.46 (m, 1H), 2.09-1.98 (m, 4H), 1.92-1.84 (m, 2H).

Example 27: 2-(4-(methyl(3-(5,6,7,8-tetrahydro-1,8-naphthyridin-2-yl)propyl)carbamoyl)piperidin-1-yl) acetic acid (Compound 27)

Step 1: tert-butyl 3-(1,8-naphthyridin-2-yl)propyl(methyl)carbamate

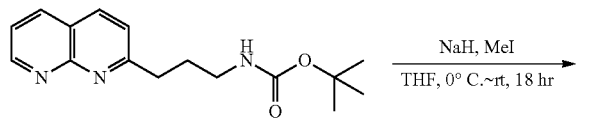

To a mixture of tert-butyl 3-(1,8-naphthyridin-2-yl)propylcarbamate (1 g, 3.5 mmol) in dry THF (30 mL) at 0° C. was added portionwise NaH (60% in mineral oil, 0.7 g, 17.5 mmol). The mixture was stirred at 0° C. for 30 min, and then methyliodide (600 mg, 4.2 mmol) was added. The mixture was stirred at room temperature for 18 hours, then quenched with water, concentrated and purified by Prep-HPLC A to get the desired product tert-butyl 3-(1,8-naphthyridin-2-yl)propyl(methyl)carbamate as a oil (180 mg). Yield 17% (98% purity, UV=214 nm, ESI 302.2 (M+H)$^+$).

Step 2: N-methyl-3-(1,8-naphthyridin-2-yl)propan-1-amine

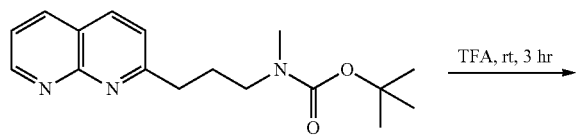

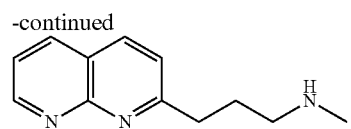

3-(1,8-naphthyridin-2-yl)propyl(methyl)carbamate (180 mg, 0.60 mmol) was treated with TFA (5 mL) at room temperature for 3 hr. Solvent was removed in vacuo, and the residue was purified by silica gel column (DCM:MeOH 20:1) to give the desired product N-methyl-3-(1,8-naphthyridin-2-yl)propan-1-amine as a yellow oil (110 mg). Yield 92% (93% purity, UV 20=214 nm, ESI 202.2 (M+H)$^+$).

Step 3: tert-butyl 2-(4-((3-(1,8-naphthyridin-2-yl)propyl)(methyl)carbamoyl)piperidin-1-yl)acetate

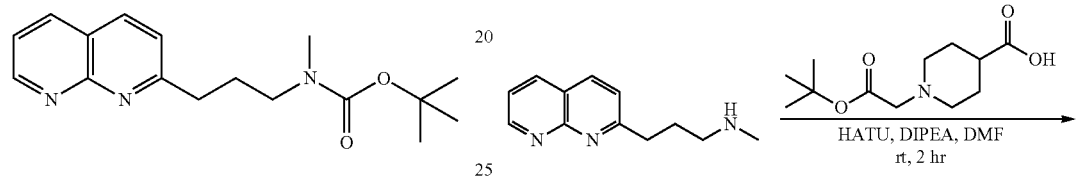

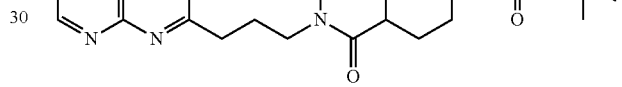

A mixture of N-methyl-3-(1,8-naphthyridin-2-yl)propan-1-amine (110 mg, 0.55 mmol), 1-(2-tert-butoxy-2-oxoethyl)piperidine-4-carboxylic acid (134 mg, 0.55 mmol), HATU (420 mg, 1.1 mmol) and DIPEA (280 mg, 2.2 mmol) in DMF (4 mL) was stirred at room temperature for 2 hr. Solvent was removed in vacuo, and the residue was purified by silica gel column (MeOH:EtOAc 1:10) to give the desired product tert-butyl 2-(4-((3-(1,8-naphthyridin-2-yl)propyl)(methyl)carbamoyl)piperidin-1-yl)acetate as a yellow oil (120 mg). Yield 52% (98% purity, UV=214 nm, ESI 427.0 (M+H)$^+$).

Step 4: tert-butyl 2-(4-(methyl(3-(5,6,7,8-tetrahydro-1,8-naphthyridin-2-yl)propyl)carbamoyl)piperidin-1-yl)acetate

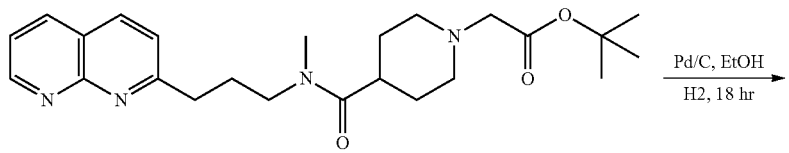

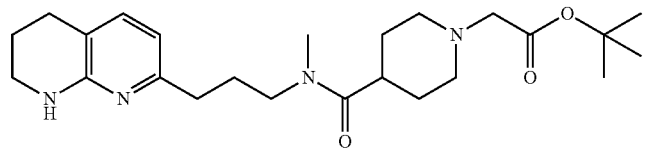

A mixture of tert-butyl 2-(4-((3-(1,8-naphthyridin-2-yl)propyl)(methyl)carbamoyl)piperidin-1-yl)acetate (120 mg, 0.28 mmol) and Pd/C (25 mg) in EtOH (15 mL) was stirred at room temperature under H₂ (1 atm, 1 L) for 18 hr. The mixture was filtered and concentrated in vacuo to get tert-butyl 2-(4-(methyl(3-(5,6,7,8-tetrahydro-1,8-naphthyridin-2-yl)propyl)carbamoyl)piperidin-1-yl)acetate as an oil (100 mg). Yield 83% (100% purity, UV=214 nm, ESI 431.1 (M+H)⁺)

Step 5: 2-(4-(methyl(3-(5,6,7,8-tetrahydro-1,8-naphthyridin-2-yl)propyl)carbamoyl)piperidin-1-yl)acetic acid (Compound 27)

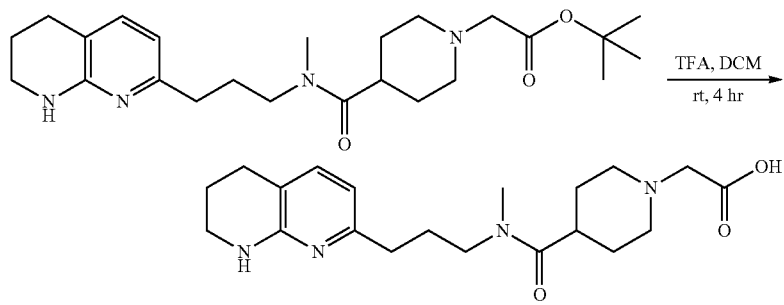

2-(4-(methyl(3-(5,6,7,8-tetrahydro-1,8-naphthyridin-2-yl)propyl)carbamoyl)piperidin-1-yl)acetate (100 mg, 0.28 mmol) was treated with TFA (3 mL) in DCM (5 mL) at room temperature for 4 hours. The solvent was remove in vacuo, and the residue was purified by Prep-HPLC A (30-65% MeCN) to give compound 27 as a white solid. (9 mg, yield 10%). LC/MS A: 99% purity, UV=214 nm, Rt=1.41 min, ESI 375.1 (M+H)⁺. ¹H NMR (500 MHz, MeOD) δ 8.33 (s, 1H), 7.38 (d, J=7.1 Hz, 1H), 6.49 (d, J=7.4 Hz, 1H), 3.61 (d, J=11.2 Hz, 2H), 3.55 (s, 2H), 3.38 (dd, J=13.8, 6.8 Hz, 4H), 3.11-2.80 (m, 6H), 2.70 (dd, J=14.2, 8.1 Hz, 2H), 2.55 (t, J=7.6 Hz, 2H), 2.02-1.76 (m, 8H).

Example 28: 2-(3-(4-((5,6,7,8-tetrahydro-1,8-naphthyridin-2-yl)methyl)piperidine-1-carbonyl)azetidin-1-yl)propanoic acid (Compound 28)

Step 1: tert-butyl 3-(4-((5,6,7,8-tetrahydro-1,8-naphthyridin-2-yl)methyl)piperidine-1-carbonyl)azetidine-1-carboxylate

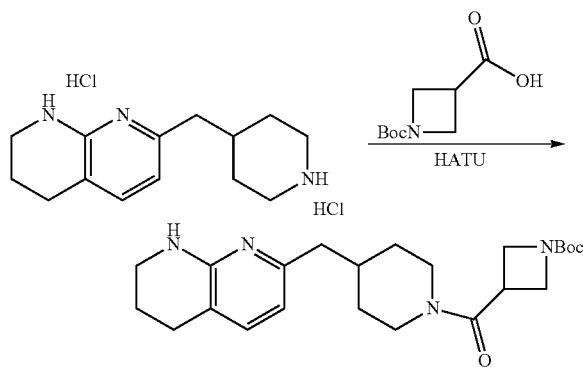

A mixture of 7-(piperidin-4-ylmethyl)-1,2,3,4-tetrahydro-1,8-naphthyridine (100 mg crude), 1-(tert-butoxycarbonyl)azetidine-3-carboxylic acid (79 mg, 0.394 mmol), HATU (149 mg, 0.394 mmol) and DIEA (127 mg, 0.986 mmol) in DMF (5 mL) was stirred at room temperature overnight. Solvent was removed in vacuo, and the residue was purified by silica gel column (pet ether:EtOAc 2:1) to give the desired product tert-butyl 3-(4-((5,6,7,8-tetrahydro-1,8-naphthyridin-2-yl)methyl)piperidine-1-carbonyl)azetidine-1-carboxylate as a yellow oil (90 mg). Yield 61% (93% purity, UV=214 nm, ESI 415.2 (M+H)⁺).

Step 2: azetidin-3-yl(4-((5,6,7,8-tetrahydro-1,8-naphthyridin-2-yl)methyl)piperidin-1-yl)methanone

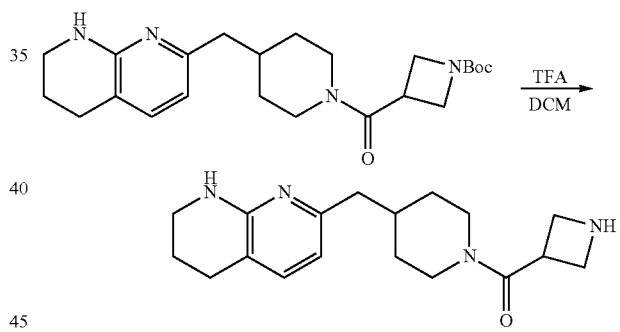

Tert-butyl 3-(4-((5,6,7,8-tetrahydro-1,8-naphthyridin-2-yl)methyl)piperidine-1-carbonyl)azetidine-1-carboxylate (90 mg, 0.217 mmol) was treated with TFA in DCM (3 mL) at room temperature for 2 hours. Solvent was removed in vacuo to give the crude azetidin-3-yl(4-((5,6,7,8-tetrahydro-1,8-naphthyridin-2-yl)methyl)piperidin-1-yl)methanone as a yellow oil (70 mg). Yield 68.7% (100% purity, UV=214 nm, ESI 315.2 (M+H)⁺). The crude product was used for the next step directly.

Step 3: methyl 2-(3-(4-((5,6,7,8-tetrahydro-1,8-naphthyridin-2-yl)methyl)piperidine-1-carbonyl)azetidin-1-yl)propanoate

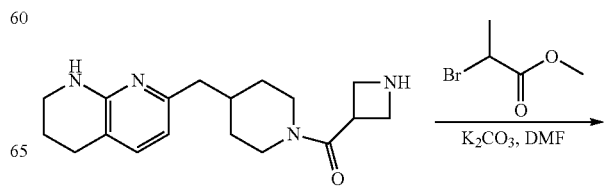

-continued

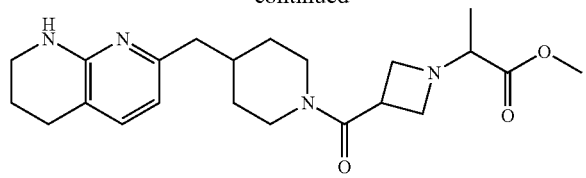

A mixture of azetidin-3-yl(4-((5,6,7,8-tetrahydro-1,8-naphthyridin-2-yl)methyl)piperidin-1-yl)methanone (70 mg crude), methyl 2-bromopropanoate (55 mg, 0.333 mmol) and K₂CO₃ (92 mg, 0.667 mmol) in anhydrous DMF (2 mL) was stirred at room temperature for 5 hours. The reaction was filtered and concentrated in vacuo. The residue was purified by Prep-HPLC A (33-65% MeCN) to give methyl 2-(3-(4-((5,6,7,8-tetrahydro-1,8-naphthyridin-2-yl)methyl)piperidine-1-carbonyl)azetidin-1-yl)propanoate (49 mg, 29% yield) as a white solid. (91% purity, UV=254 nm, ESI 401.2 (M+H)⁺)

Step 4: 2-(3-(4-((5,6,7,8-tetrahydro-1,8-naphthyridin-2-yl)methyl)piperidine-1-carbonyl)azetidin-1-yl)propanoic acid (Compound 28)

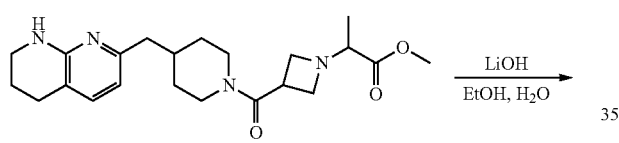

Methyl 2-(3-(4-((5,6,7,8-tetrahydro-1,8-naphthyridin-2-yl)methyl)piperidine-1-carbonyl)azetidin-1-yl)propanoate (49 mg, 0.12 mmol) was treated with LiOH (10 mg, 0.25 mmol) in EtOH (3 mL) and H₂O (1 mL) at room temperature for 2 hours. Solvent was removed in vacuo, and the residue was purified by Prep-HPLC A (33-65% MeCN) to give compound 28 as a white solid (27 mg, 57% yield). LC/MS A: 100% purity, UV=214 nm, Rt=1.45 min, ESI 387.3 (M+H)⁺. ¹H NMR (500 MHz, MeOD) δ 7.15 (d, J=7.3 Hz, 1H), 6.36 (d, J=7.3 Hz, 1H), 4.48 (d, J=13.2 Hz, 1H), 4.33-4.04 (m, 4H), 3.87 (t, J=8.4 Hz, 1H), 3.63 (dd, J=20.6, 11.3 Hz, 2H), 3.43-3.36 (m, 2H), 3.02 (t, J=12.8 Hz, 1H), 2.75-2.63 (m, 3H), 2.47 (d, J=7.1 Hz, 2H), 1.97-1.87 (m, 3H), 1.69 (d, J=7.8 Hz, 2H), 1.39 (d, J=8.1 Hz, 3H), 1.16 (d, J=9.6 Hz, 2H).

Example 29: Preparation of 2-phenyl-2-((R)-3-(4-(5,6,7,8-tetrahydro-1,8-naphthyridin-2-yl)butoxy)pyrrolidin-1-yl)acetic acid (Compounds 129-E1 and 129-E2)

Step 1: tert-butyl (R)-3-(4-(2-methyl-1,3-dioxolan-2-yl)butoxy)pyrrolidine-1-carboxylate

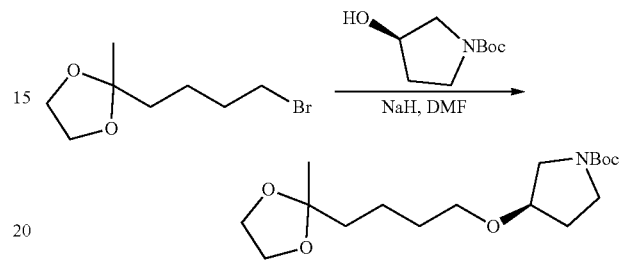

A mixture of (R)-tert-butyl 3-hydroxypyrrolidine-1-carboxylate (1.09 g, 5.41 mmol), 2-(4-bromobutyl)-2-methyl-1,3-dioxolane (1.2 g, 5.41 mmol) and sodium hydride (260 mg, 10.82 mmol) in DMF (5 mL) was stirred at 100° C. for 6 h. Solvent was removed in vacuo, and the residue was purified by silica gel column (pet ether:EtOAc 10:1) to give the desired product (R)-tert-butyl 3-(4-(2-methyl-1,3-dioxolan-2-yl)butoxy)pyrrolidine-1-carboxylate as a colorless oil (380 mg). Yield 21% (ESI 330.2 (M+H)⁺).

Step 2: (R)-tert-butyl 3-(5-oxohexyloxy)pyrrolidine-1-carboxylate

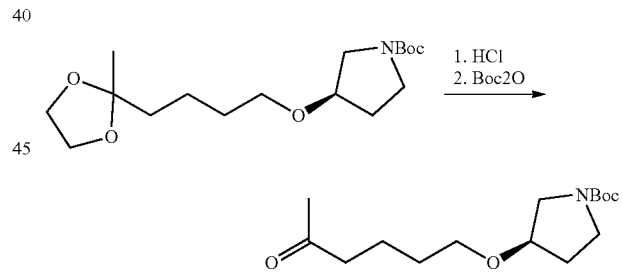

(R)-tert-butyl 3-(4-(2-methyl-1,3-dioxolan-2-yl)butoxy)pyrrolidine-1-carboxylate (1.3 g, 3.95 mmol) was treated with a solution of HCl/dioxane (4.0 M, 10 mL) at room temperature for 2 hours. The solvent was removed in vacuo, and the residue was diluted with acetone (10 mL) and H₂O (1 mL). Potassium carbonate was added to adjust the pH to 8-9, followed by Boc₂O (1.24 g 5.69 mmol). The reaction was stirred at room temperature for 3 h, then filtered and concentrated under vacuum. The residue was purified by silica gel column (pet ether:EtOAc 15:1) to give the desired product (R)-tert-butyl 3-(5-oxohexyloxy)pyrrolidine-1-carboxylate as a colorless oil (820 mg). Yield 73% (ESI 186 (M–100), 230 (M–56)⁺).

Step 3: (R)-tert-butyl 3-(4-(1,8-naphthyridin-2-yl)butoxy)pyrrolidine-1-carboxylate

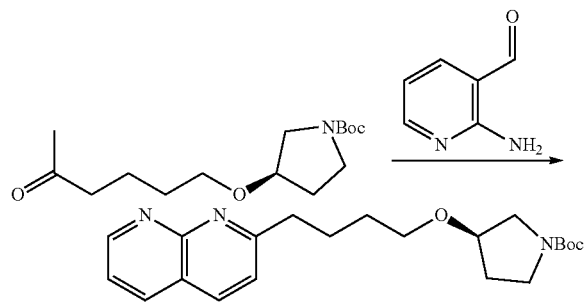

A mixture of (R)-tert-butyl 3-(5-oxohexyloxy)pyrrolidine-1-carboxylate (820 mg, 2.88 mmol), 2-aminonicotinaldehyde (456 mg, 3.77 mmol) and pyrrolidine (265 mg, 3.77 mmol) in DMF (5 mL) was stirred at 85° C. for 4 h. Solvent was removed in vacuo, and the residue was purified by silica gel column (DCM:MeOH 15:1) to give the desired product (R)-tert-butyl 3-(4-(1,8-naphthyridin-2-yl)butoxy)pyrrolidine-1-carboxylate as a colorless oil (750 mg). Yield 70% (ESI 372.2 (M+H)$^+$).

Step 4: (R)-7-(4-(pyrrolidin-3-yloxy)butyl)-1,2,3,4-tetrahydro-1,8-naphthyridine

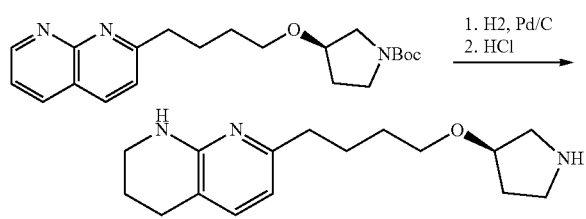

A mixture of (R)-tert-butyl 3-(4-(1,8-naphthyridin-2-yl)butoxy)pyrrolidine-1-carboxylate (750 mg, 2.02 mmol), Pd/C (10%, 500 mg) in EtOAc (10 mL) was stirred at 60° C. for 6 hours under hydrogen. The reaction was filtered and concentrated in vacuo. The residue was treated with a solution of HCl/dioxane (4.0 M, 4 mL) at room temperate for 2 hours, and the solvent was removed in vacuo to give the desired product (R)-7-(4-(pyrrolidin-3-yloxy)butyl)-1,2,3,4-tetrahydro-1,8-naphthyridine as a white solid (600 mg). Yield 96% (ESI 276.2 (M+H)$^+$).

Step 5: methyl 2-phenyl-2-((R)-3-(4-(5,6,7,8-tetrahydro-1,8-naphthyridin-2-yl)butoxy)pyrrolidin-1-yl)acetate

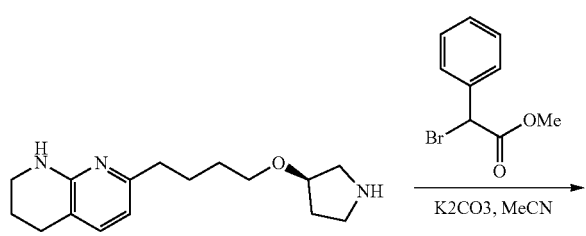

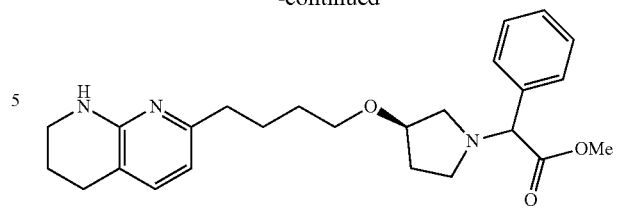

A mixture of (R)-7-(4-(pyrrolidin-3-yloxy)butyl)-1,2,3,4-tetrahydro-1,8-naphthyridine (200 mg, 0.576 mmol), methyl 2-bromo-2-phenylacetate (140 mg, 0.576 mmol) and K$_2$CO$_3$ (240 mg, 1.73 mmol) in MeCN (3 mL) was stirred at room temperature overnight. Solvent was removed in vacuo, and the residue was used into the next step directly. (ESI 424.0 (M+H)$^+$).

Step 6: 2-phenyl-2-((R)-3-(4-(5,6,7,8-tetrahydro-1,8-naphthyridin-2-yl)butoxy)pyrrolidin-1-yl)acetic acid (Compounds 129-E1 and 129-E2)

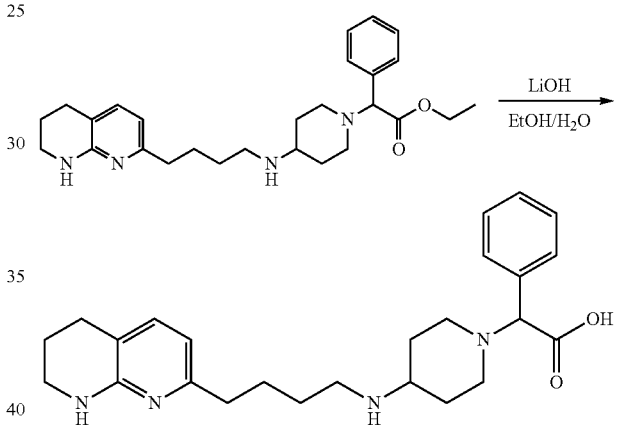

Methyl 2-phenyl-2-((R)-3-(4-(5,6,7,8-tetrahydro-1,8-naphthyridin-2-yl)butoxy)pyrrolidin-1-yl)acetate (180 mg, 0.426 mmol) was treated with LiOH—H$_2$O (126 mg, 3.0 mmol) in EtOH (4 mL) and H$_2$O (1 mL) at room temperature for 2 hours. Solvent was removed in vacuo, and the residue was purified by Prep-HPLC A (30-65% MeCN) to give compound 129 as a white solid (105 mg, 60% yield). The racemic product was separated by prep chiral SFC A to give enantiomeric products compound 129-E1 (38.7 mg) and compound 129-E2 (37.5 mg) as white solids.

Compound 129-E1 LC/MS ESI 410 (M+H)$^+$ $^1$H NMR (400 MHz, MeOD) δ 7.55-7.53 (m, 2H), 7.43-7.41 (m, 3H), 7.17 (d, J=7.2 Hz, 1H), 6.39 (d, J=7.6 Hz, 1H), 4.49 (s, 1H), 4.18 (s, 1H), 3.48-3.43 (m, 3H), 3.39-3.36 (t, J=11.5 Hz, 2H), 3.13 (d, J=10.8 Hz, 1H), 3.01 (m, 1H), 2.72-2.69 (t, J=12.4 Hz, 2H), 2.56-2.52 (t, J=15.4 Hz, 2H), 2.11 (s, 2H), 1.89-1.86 (m, 2H), 1.74-1.59 (m, 5H). Chiral SFC A (40% MeOH): ee 89.9%, Rt=2.14 min.

Compound 129-E2 LC/MS ESI 410 (M+H)$^+$ $^1$H NMR (400 MHz, MeOD) δ 7.56-7.53 (m, 2H), 7.42-7.41 (m, 3H), 7.16 (d, J=7.2 Hz, 1H), 6.39 (d, J=7.2 Hz, 1H), 4.48 (s, 1H), 4.17 (m, 1H), 3.47-3.35 (m, 6H), 3.17-3.12 (m, 2H), 2.70 (t, J=12.4 Hz, 2H), 2.57-2.53 (t, J=10.8 Hz, 2H), 2.21-2.17 (m, 2H), 1.90-1.84 (m, 2H), 1.73-1.58 (m, 4H). Chiral SFC A (40% MeOH): ee 94.4%, Rt=3.46 min.

Example 30: Preparation of 2-phenyl-2-((R)-3-(4-(2-(5,6,7,8-tetrahydro-1,8-naphthyridin-2-yl)ethyl)-1H-pyrazol-1-yl)pyrrolidin-1-yl)acetic acid (Compounds 130-E1 and 130-E2)

Step 1: (R)-tert-butyl 3-(4-formyl-1H-pyrazol-1-yl)pyrrolidine-1-carboxylate

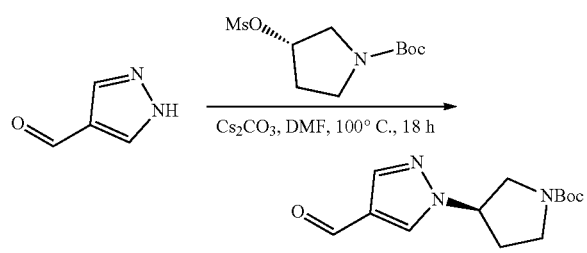

A mixture of 1H-pyrazole-4-carbaldehyde (400 mg, 4.17 mmol), (S)-tert-butyl 3-(methylsulfonyloxy)pyrrolidine-1-carboxylate (1.21 g, 4.58 mmol) and Cs$_2$CO$_3$ (4.08 g, 12.51 mmol) in DMF (30 mL) was stirred at 100° C. for 18 hours. Solvent was removed in vacuo, and the residue was purified by silica gel column (pet ether:EtOAc 2:1) to give the desired product (R)-tert-butyl 3-(4-formyl-1H-pyrazol-1-yl)pyrrolidine-1-carboxylate as a colorless oil (1.0 g). Yield 91% (ESI 266.0 (M+H)$^+$).

Step 2: (R)-tert-butyl 3-(4-(3-oxobut-1-enyl)-1H-pyrazol-1-yl)pyrrolidine-1-carboxylate

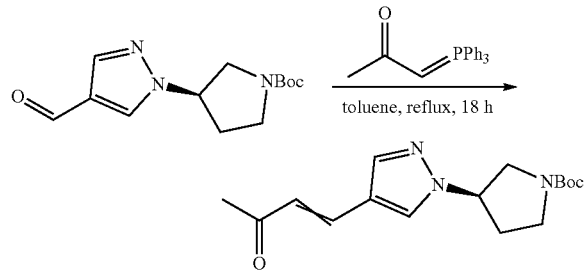

A mixture of (R)-tert-butyl 3-(4-formyl-1H-pyrazol-1-yl)pyrrolidine-1-carboxylate (1 g, 3.77 mmol) and 1-(triphenyl-phosphanylidene)propan-2-one (1.2 g, 5.66 mmol) in toluene (40 mL) was stirred at 110° C. for 18 hours. Solvent was removed in vacuo, and the residue was purified by silica gel column (pet ether:EtOAc 1:1) to give the desired product (R)-tert-butyl 3-(4-(3-oxobut-1-enyl)-1H-pyrazol-1-yl)pyrrolidine-1-carboxylate as a colorless oil (920 mg). Yield 80% (ESI 306.0 (M+H)$^+$).

Step 3: (R)-tert-butyl 3-(4-(3-oxobutyl)-1H-pyrazol-1-yl)pyrrolidine-1-carboxylate

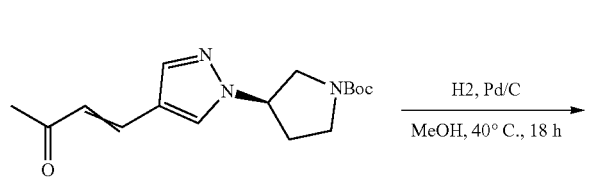

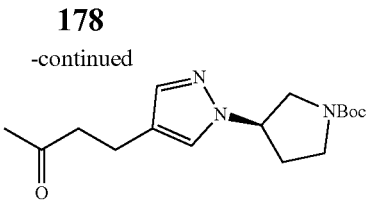

A mixture of (R)-tert-butyl 3-(4-(3-oxobut-1-enyl)-1H-pyrazol-1-yl)pyrrolidine-1-carboxylate (920 mg, 3.02 mmol) and 10% Pd/C (184 mg) in MeOH (20 mL) was stirred under H$_2$ at 40° C. for 18 hours. The mixture was filtered, and the solvent was removed in vacuo to give the desired product (R)-tert-butyl 3-(4-(3-oxobutyl)-1H-pyrazol-1-yl)pyrrolidine-1-carboxylate as a colorless oil (900 mg). Yield 97% (ESI 308.0 (M+H)$^+$).

Step 4: (R)-tert-butyl 3-(4-(3-oxobutyl)-1H-pyrazol-1-yl)pyrrolidine-1-carboxylate

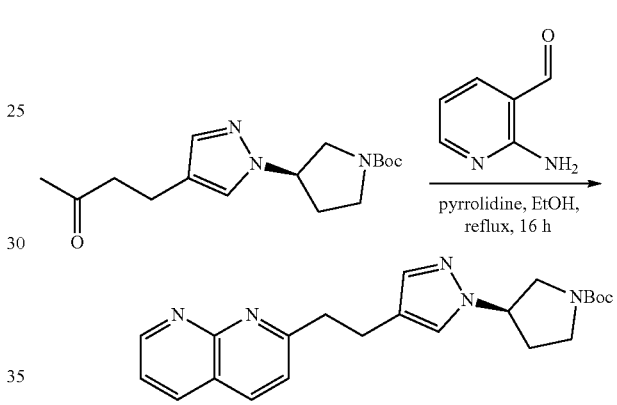

A mixture of ((R)-tert-butyl 3-(4-(3-oxobutyl)-1H-pyrazol-1-yl)pyrrolidine-1-carboxylate (900 mg, 2.93 mmol)), 2-aminonicotinaldehyde (465 mg, 3.81 mmol) and pyrrolidine (270 mg, 3.81 mmol) in EtOH (30 mL) was stirred at 80° C. for 16 hours. Solvent was removed in vacuo, and the residue was purified by silica gel column (DCM:MeOH 20:1) to give the desired product (R)-tert-butyl 3-(4-(3-oxobutyl)-1H-pyrazol-1-yl)pyrrolidine-1-carboxylate as a yellow oil (650 mg). Yield 56% (ESI 394.0 (M+H)$^+$).

Step 5: (R)-tert-butyl 3-(4-(2-(5,6,7,8-tetrahydro-1,8-naphthyridin-2-yl)ethyl)-1H-pyrazol-1-yl)pyrrolidine-1-carboxylate

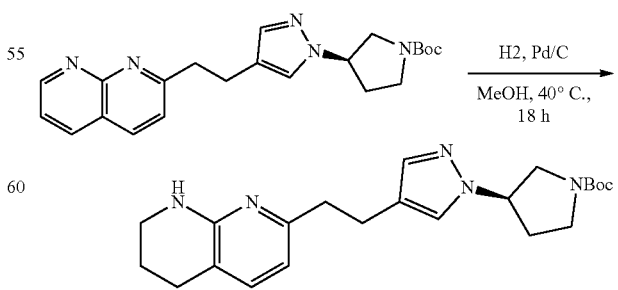

A mixture of (R)-tert-butyl 3-(4-(3-oxobutyl)-1H-pyrazol-1-yl)pyrrolidine-1-carboxylate (650 mg, 1.65 mmol) and 10% Pd/C (130 mg) in MeOH (20 mL) was stirred at 40° C. for 15 hours. The mixture was filtered and the solvent was removed in vacuo to give the desired product (R)-tert-butyl 3-(4-(2-(5,6,7,8-tetrahydro-1,8-naphthyridin-2-yl)ethyl)-1H-pyrazol-1-yl)pyrrolidine-1-carboxylate as a yellow oil (610 mg). Yield 93% (ESI 398.0 (M+H)+).

Step 6: (R)-7-(2-(1-(pyrrolidin-3-yl)-1H-pyrazol-4-yl)ethyl)-1,2,3,4-tetrahydro-1,8-naphthyridine

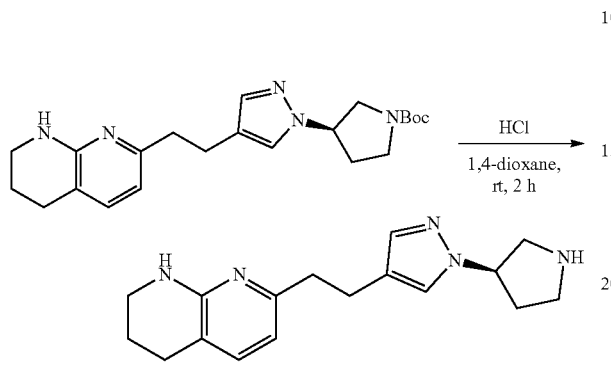

((R)-tert-butyl 3-(4-(2-(5,6,7,8-tetrahydro-1,8-naphthyridin-2-yl)ethyl)-1H-pyrazol-1-yl)pyrrolidine-1-carboxylate (610 mg, 1.54 mmol) was treated with HCl (4M in 1,4-dixoane, 3.9 mL, 15.4 mmol) at 25° C. for 2 hours. Solvent was removed in vacuo to give the desired product (R)-7-(2-(1-(pyrrolidin-3-yl)-1H-pyrazol-4-yl)ethyl)-1,2,3,4-tetrahydro-1,8-naphthyridine as a yellow oil (450 mg). Yield 98% (ESI 298.0 (M+H)+).

Step 7: methyl 2-phenyl-2-((R)-3-(4-(2-(5,6,7,8-tetrahydro-1,8-naphthyridin-2-yl)ethyl)-1H-pyrazol-1-yl)pyrrolidin-1-yl)acetate

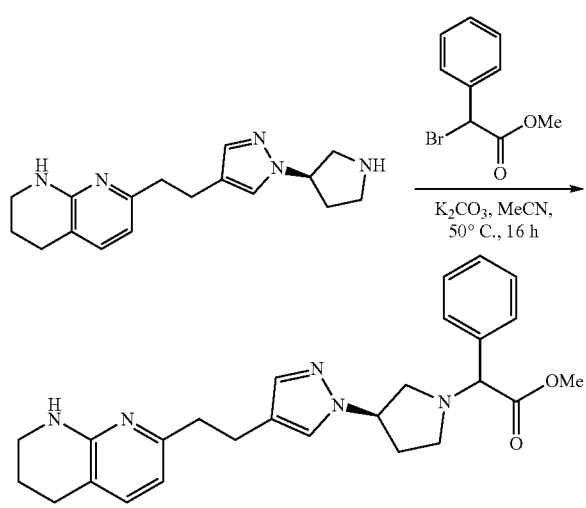

A mixture of (R)-7-(2-(1-(pyrrolidin-3-yl)-1H-pyrazol-4-yl)ethyl)-1,2,3,4-tetrahydro-1,8-naphthyridine (450 mg, 1.51 mmol)), methyl 2-bromo-2-phenylacetate (415 mg, 1.81 mmol) and K$_2$CO$_3$ (625 mg, 4.53 mmol) in MeCN (20 mL) was stirred at 50° C. for 16 hours. Solvent was removed in vacuo, and the residue was purified by silica gel column (DCM:MeOH 20:1) to give the desired product methyl 2-phenyl-2-((R)-3-(4-(2-(5,6,7,8-tetrahydro-1,8-naphthyridin-2-yl)ethyl)-1H-pyrazol-1-yl)pyrrolidin-1-yl)acetate as a yellow oil (120 mg). Yield 19% (ESI 446.0 (M+H)+).

Step 8: 2-phenyl-2-((R)-3-(4-(2-(5,6,7,8-tetrahydro-1,8-naphthyridin-2-yl)ethyl)-1H-pyrazol-1-yl)pyrrolidin-1-yl)acetic acid (Compounds 130-E1 and 130-E2)

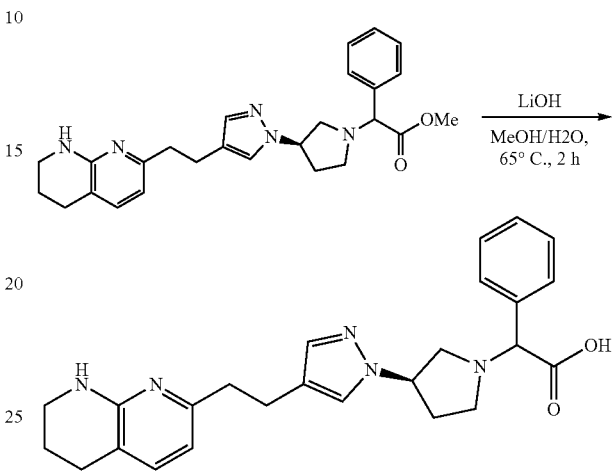

Methyl 2-phenyl-2-((R)-3-(4-(2-(5,6,7,8-tetrahydro-1,8-naphthyridin-2-yl)ethyl)-1H-pyrazol-1-yl)pyrrolidin-1-yl) acetate (120 mg, 0.27 mmol) was treated with LiOH—H$_2$O (45.4 mg, 1.08 mmol) in MeOH (4 mL) and H$_2$O (1 mL) at 65° C. for 2 hours. Solvent was removed in vacuo, and the residue was purified by Prep-HPLC A (30-65% MeCN) to give compound 130 as a white solid (60 mg, 52% yield). The racemic product was separated by prep chiral SFC B to give enantiomeric products compound 130-E1 (46 mg) and compound 130-E2 (27 mg) as white solids.

Compound 130-E1 LC/MS ESI 432 (M+H)+ 1H NMR (400 MHz, MeOD) δ 7.59-7.56 (m, 3H), 7.39-7.21 (m, 5H), 6.39 (d, J=7.3 Hz, 1H), 4.97 (s, 1H), 4.44 (s, 1H), 3.44-3.36 (m, 4H), 3.32-3.15 (m, 2H), 2.81-2.79 (m, 4H), 2.71 (t, J=6.0 Hz, 2H), 2.50-2.45 (m, 1H), 2.25-2.20 (m, 1H), 1.88-1.85 (m, 2H). Chiral SFC B (40% MeOH): ee 100%, Rt=1.34 min.

Compound 130-E2 LC/MS ESI 432 (M+H)+ 1H NMR (400 MHz, MeOD) δ 7.59-7.56 (m, 3H), 7.39-7.21 (m, 5H), 6.39 (d, J=7.3 Hz, 1H), 4.87 (s, 1H), 4.07 (s, 1H), 3.44-3.26 (m, 4H), 2.92-2.51 (m, 8H), 2.50-2.40 (m, 1H), 2.20-2.10 (m, 1H), 1.88-1.85 (m, 2H). Chiral SFC B (40% MeOH): ee 99.5%, Rt=2.89 min.

Example 31: Preparation of 2-phenyl-2-((R)-3-(5-(5,6,7,8-tetrahydro-1,8-naphthyridin-2-yl)pentyl) pyrrolidin-1-yl)acetic acid (Compounds 131-E1 and 131-E2)

Step 1: (R)-tert-butyl 3-(iodomethyl)pyrrolidine-1-carboxylate

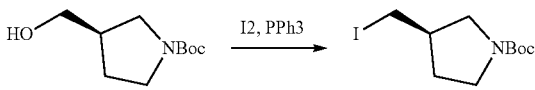 [SMILES: CC(C)(C)OC(=O)N1CC[C@@H](CO)C1 ; CC(C)(C)OC(=O)N1CC[C@@H](CI)C1]

To a solution of triphenylphosphine (5.11 g, 19.5 mmol) and 1H-imidazole (1.33 g, 19.5 mmol) in DCM (50 mL) at 0° C. was slowly added iodine (4.95 g, 19.5 mmol). The reaction was stirred at 0° C. for 30 mins, and then a solution of (R)-tert-butyl 3-(hydroxymethyl)pyrrolidine-1-carboxylate in DCM (10 mL) was added. The reaction was stirred at room temperature overnight, then diluted with water (50 mL) and extracted with DCM (30 mL×3). The combined organic layer was dried over Na₂SO₄, filtered and concentrated in vacuo. The residue was purified by silica gel column (pet ether:EtOAc 10:1) to give the desired product (R)-tert-butyl 3-(iodomethyl)pyrrolidine-1-carboxylate as a colorless oil (3.7 g). Yield 80%. (ESI 256 (M+H−56)⁺).

Step 2: (R)-((1-(tert-butoxycarbonyl)pyrrolidin-3-yl)methyl)triphenylphosphonium

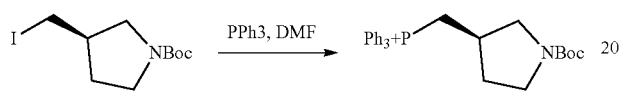

A solution of (R)-tert-butyl 3-(iodomethyl)pyrrolidine-1-carboxylate (3.7 g, 12 mmol) and triphenyl phosphine (4.1 g, 15.5 mmol) in DMF (50 mL) was stirred at room temperature overnight. Solvent was removed in vacuo, and the residue was purified by silica gel column (DCM:MeOH 10:1) to give the crude product. Diethyl ether (30 mL) was added to the crude product, and the mixture was stirred at room temperature for 30 mins. The solid was collected by filtration and dried under vacuum to give the desired product (R)-((1-(tert-butoxycarbonyl)pyrrolidin-3-yl)methyl)triphenylphosphonium as a white solid (5.6 g). Yield 84%. (ESI N/A).

Step 3: ethyl 4-(2-methyl-1,3-dioxolan-2-yl)butanoate

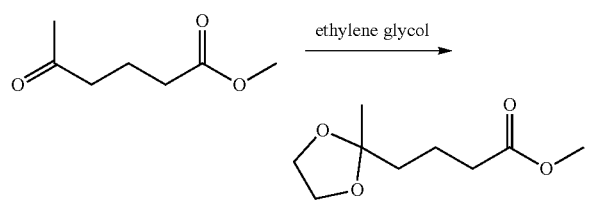

A solution of ethyl 5-oxohexanoate (2 g, 13.9 mmol), ethylene glycol (2.6 g, 42 mmol) and p-toluene sulfonic acid (478 mg, 2.78 mmol) in toluene (50 mL) was refluxed with a Dean-stark trap for 6 hours. Solvent was removed in vacuo, and the residue was purified by silica gel column (pet ether:EtOAc 10:1) to give the desired product ethyl 4-(2-methyl-1,3-dioxolan-2-yl)butanoate as a colourless oil (1.4 g, 50% yield). (ESI 203 (M+H)⁺).

Step 4: 4-(2-methyl-1,3-dioxolan-2-yl)butanal

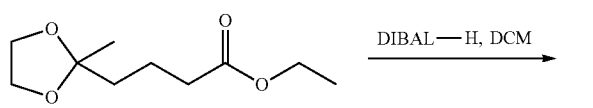

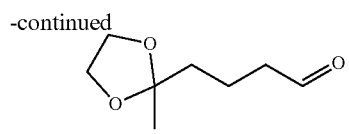

To a solution of ethyl 4-(2-methyl-1,3-dioxolan-2-yl)butanoate (500 mg, 2.48 mmol) in DCM (10 mL) at −78° C. under Ar was added slowly DIBAL-H (1 M, 3.7 mL, 3.7 mmol). The reaction was stirred at −78° C. for 30 mins, then quenched with 20 mL of water, warmed to room temperature and extracted with DCM (20 mL×3). The combined organic layer was dried over sodium sulfate, filtered and concentrated under vacuum. The residue was purified by silica gel column (pet ether:EtOAc 2:1) to give the desired product 4-(2-methyl-1,3-dioxolan-2-yl)butanal as a colorless oil (220 mg). Yield 56%. (ESI 159 (M+H)⁺).

Step 5: (S)-tert-butyl 3-(5-(2-methyl-1,3-dioxolan-2-yl)pent-1-enyl)pyrrolidine-1-carboxylate

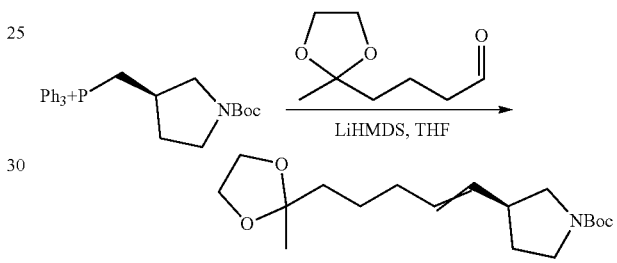

To a solution of (R)-((1-(tert-butoxycarbonyl)pyrrolidin-3-yl)methyl)triphenylphosphonium (2.0 g, 3.6 mmol) in DCM (30 mL) at 0° C. under nitrogen was added LiHMDS (1 M, 5.4 mL, 5.4 mmol). The mixture was stirred at 0° C. for 30 mins, and then 4-(2-methyl-1,3-dioxolan-2-yl)butanal (565 mg, 3.6 mmol) was added. The reaction was stirred at room temperate for 4 hours, then quenched with MeOH (20 mL). Solvent was removed in vacuo, and the residue was purified by silica gel column (pet ether:EtOAc 3:1) to give the desired product (S)-tert-butyl 3-(5-(2-methyl-1,3-dioxolan-2-yl)pent-1-enyl)pyrrolidine-1-carboxylate as a yellow oil (500 mg). Yield 43%. (ESI 226 (M+H−100)⁺).

Step 6: (R)-7-(pyrrolidin-3-yl)heptan-2-one

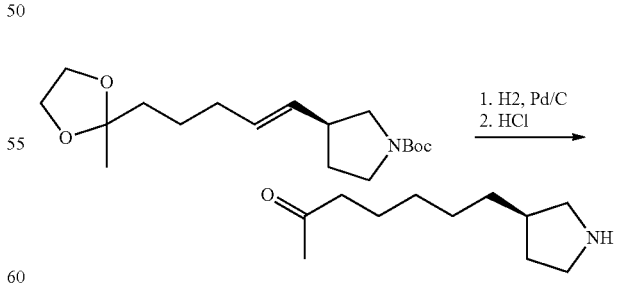

A mixture of (S)-tert-butyl 3-(5-(2-methyl-1,3-dioxolan-2-yl)pent-1-enyl)pyrrolidine-1-carboxylate (440 mg, 1.35 mmol) and Pd/C (10%, 40 mg) in EtOAc (20 mL) was stirred at 40° C. overnight under hydrogen. The reaction was filtered and concentrated in vacuo. The residue was treated with 5 mL of HCl in 1,4-dioxane solution (4M). The mixture was stirred at room temperature for 2 hours, then concentrated in vacuo to give the desired product (R)-7-(pyrrolidin-3-yl)heptan-2-one as a yellow oil. (220 mg). Yield 89%. (ESI 184 (M+H)$^+$).

Step 7: methyl 2-((R)-3-(6-oxoheptyl)pyrrolidin-1-yl)-2-phenylacetate

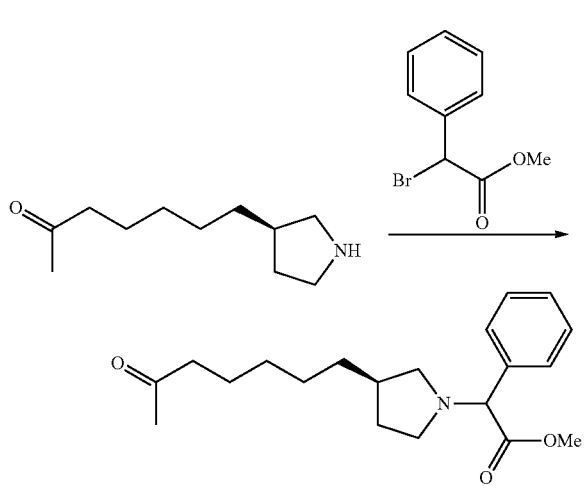

A mixture of (R)-7-(pyrrolidin-3-yl)heptan-2-one (210 mg, 1.15 mmol), methyl 2-bromo-2-phenylacetate (315 mg, 1.4 mmol) and K$_2$CO$_3$ (476 g, 3.45 mmol) in MeCN (10 mL) was stirred at 40° C. overnight. The reaction was filtered and concentrated in vacuo, and the residue was purified by silica gel column (DCM:MeOH=30:1) to give the desired product methyl 2-((R)-3-(6-oxoheptyl)pyrrolidin-1-yl)-2-phenylacetate as a yellow oil (260 g). Yield 68%. (ESI 331 (M+H)$^+$).

Step 8: methyl 2-((R)-3-(5-(1,8-naphthyridin-2-yl)pentyl)pyrrolidin-1-yl)-2-phenylacetate

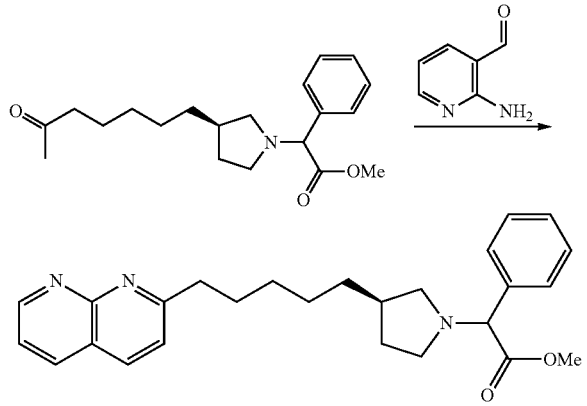

To a solution of methyl 2-((R)-3-(6-oxoheptyl)pyrrolidin-1-yl)-2-phenylacetate (260 mg, 0.78 mmol) in EtOH (10 mL), was added 2-aminonicotinaldehyde (144 mg, 1.18 mmol) and pyrrolidine (28 mg, 0.39 mmol). The reaction was heated to reflux overnight, then concentrated in vacuo, and the residue was purified by silica gel column (DCM:MeOH=20:1) to give the desired product methyl 2-((R)-3-(5-(1,8-naphthyridin-2-yl)pentyl)pyrrolidin-1-yl)-2-phenylacetate as a yellow oil (260 mg). Yield 78%. (ESI 418 (M+H)$^+$).

Step 9: methyl 2-phenyl-2-((R)-3-(5-(5,6,7,8-tetrahydro-1,8-naphthyridin-2-yl)pentyl)pyrrolidin-1-yl)acetate

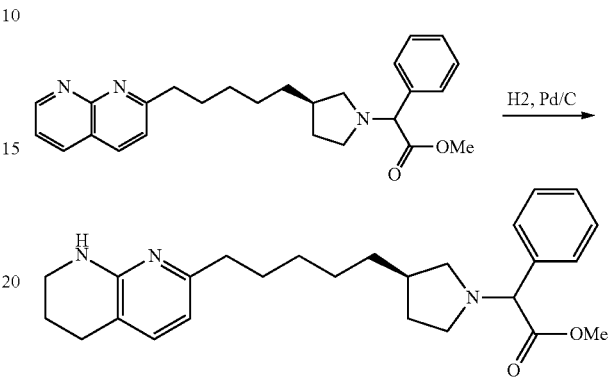

A mixture of methyl 2-((R)-3-(5-(1,8-naphthyridin-2-yl)pentyl)pyrrolidin-1-yl)-2-phenylacetate (260 mg, 0.62 mmol) and Pd/C (10%, 30 mg) in EtOAc (10 mL) was stirred at 40° C. overnight under hydrogen. The reaction was filtered and concentrated in vacuo to give the desired product methyl 2-phenyl-2-((R)-3-(5-(5,6,7,8-tetrahydro-1,8-naphthyridin-2-yl)pentyl)pyrrolidin-1-yl)acetate as a yellow oil (220 mg). Yield 84%. (ESI 422 (M+H)$^+$).

Step 10: 2-phenyl-2-((R)-3-(5-(5,6,7,8-tetrahydro-1,8-naphthyridin-2-yl)pentyl)pyrrolidin-1-yl)acetic acid (Compounds 131-E1 and 131-E2)

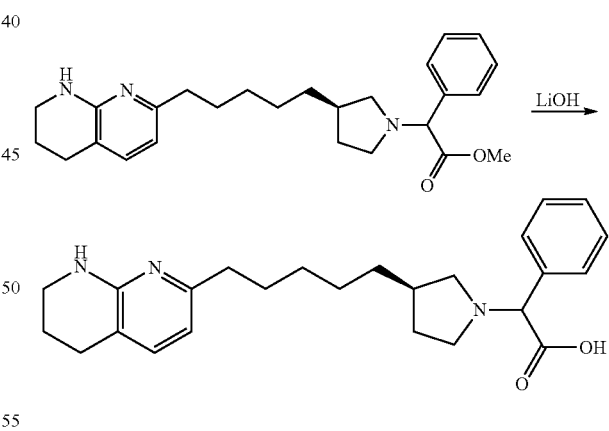

Methyl 2-phenyl-2-((R)-3-(5-(5,6,7,8-tetrahydro-1,8-naphthyridin-2-yl)pentyl)pyrrolidin-1-yl)acetate (200 mg, 0.49 mmol) was treated with LiOH—H$_2$O (83 mg, 1.97 mmol) in MeOH (10 mL) and H$_2$O (2 mL) at room temperature for 2 hours. Solvent was removed in vacuo, and the residue was purified by Prep-HPLC to give compound 131 as a white solid (120 mg, 62% yield). The racemic product was separated by Prep chiral SFC A to give enantiomeric products compound 131-E1 (35 mg) and compound 131-E2 (39 mg) as white solids.

Compound 131-E1 LC/MS ESI 408 (M+H)$^+$ 1H NMR (400 MHz, MeOD) δ 7.58-7.55 (m, 2H), 7.44-7.41 (m, 3H), 7.12 (d, J=7.2 Hz, 1H), 6.35 (d, J=7.2 Hz, 1H), 4.49 (s, 1H), 3.71-3.62 (m, 1H), 3.41-3.36 (m, 3H), 3.02-2.95 (m, 1H), 2.72-2.66 (m, 3H), 2.50 (t, J=7.2 Hz, 2H), 2.41-2.11 (m, 2H), 1.92-1.84 (m, 2H), 1.69-1.25 (m, 9H). Chiral SFC A (40% MeOH): ee 100%, Rt=2.04 min.

Compound 131-E2 LC/MS ESI 408 (M+H)+ 1H NMR (400 MHz, MeOD) δ 7.47-7.44 (m, 2H), 7.34-7.31 (m, 3H), 7.00 (d, J=7.2 Hz, 1H), 6.22 (d, J=7.2 Hz, 1H), 4.39 (s, 1H), 3.39-3.26 (m, 3H), 2.98-2.78 (m, 3H), 2.58 (t, J=6.4 Hz, 2H), 2.38 (t, J=7.6 Hz, 2H), 2.28-2.01 (m, 2H), 1.78-1.74 (m, 2H), 1.60-1.15 (m, 9H). Chiral SFC A (40% MeOH): ee 100%, Rt=3.86 min.

Example 32: Preparation of 2-(3-fluoro-3-(5-(5,6,7,8-tetrahydro-1,8-naphthyridin-2-yl)pentyl)pyrrolidin-1-yl)-2-phenylacetic acid (Compounds 132-E1 and 132-E2)

Step 1: tert-butyl 3-(4-(benzyloxy)butyl)-3-hydroxypyrrolidine-1-carboxylate

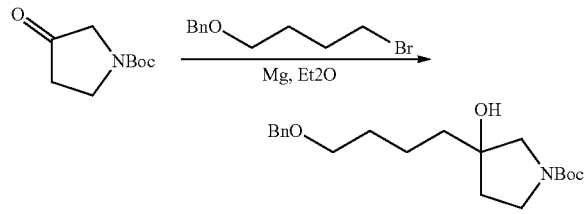

To a mixture of ((4-bromobutoxy)methyl)benzene (9.45 g, 38.87 mmol) and Mg (1.89 g, 77.74 mmol) in Et₂O (20 mL) was added 12 (202 mg, 1.09 mmol). The reaction mixture was stirred at 40° C. for 1 h. After cooled to room temperature, the mixture was added to a solution of tert-butyl 3-oxopyrrolidine-1-carboxylate (2.4 g, 12.96 mmol) in 30 mL of Et₂O at 5° C. The reaction was stirred at room temperature overnight, then quenched with aq. NH₄Cl (10 mL) and extracted with EtOAc (30 mL×3). The combined organic layer was dried over sodium sulfate, filtered and concentrated in vacuo. The residue was purified by silica gel column (pet ether:EtOAc 5:1-2:1) to give the desired product tert-butyl 3-(4-(benzyloxy)butyl)-3-hydroxypyrrolidine-1-carboxylate as a yellow oil (1.7 g). Yield 38% (ESI 294 (M+H−56)+).

Step 2: tert-butyl 3-(4-(benzyloxy)butyl)-3-fluoropyrrolidine-1-carboxylate

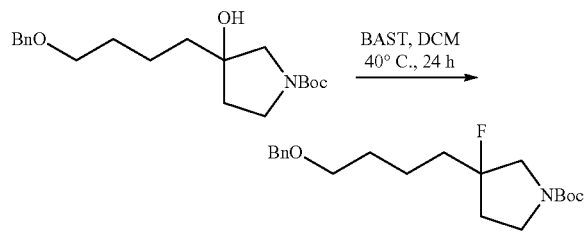

A mixture of tert-butyl 3-(4-(benzyloxy)butyl)-3-hydroxypyrrolidine-1-carboxylateas (1.7 g, 4.86 mmol) and BAST (10.76 g, 48.6 mmol) in DCM (30 mL) was stirred at 40° C. for 24 h.

The reaction was diluted with MeOH (2 mL), washed with water (20 mL), dried over sodium sulfate, filtered and concentrated in vacuo. The residue was purified by silica gel column (pet ether:EtOAc 20:1~10:1) to give the desired product tert-butyl 3-(4-(benzyloxy)butyl)-3-fluoropyrrolidine-1-carboxylate as a light yellow oil (1.1 g). Yield 64% (ESI 296 (M+H−56))

Step 3: (tert-butyl 3-fluoro-3-(4-hydroxybutyl)pyrrolidine-1-carboxylate

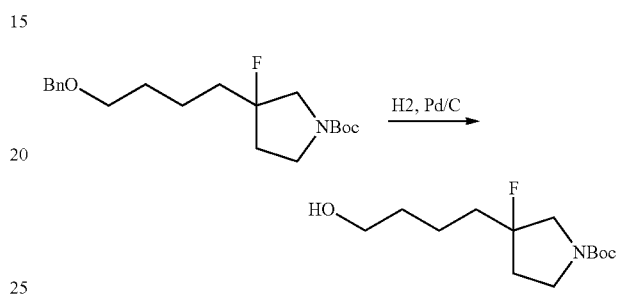

A mixture of tert-butyl 3-(4-(benzyloxy)butyl)-3-fluoropyrrolidine-1-carboxylate (1.1 g, 3.13 mmol) and Pd/C (5%, 1.1 g) in EtOAc (100 mL) was stirred under hydrogen at 45° C. overnight. The mixture was filtered and concentrated in vacuo to give the desired product tert-butyl 3-fluoro-3-(4-hydroxybutyl)pyrrolidine-1-carboxylate as a light yellow oil (780 mg). Yield 95% (ESI 206 (M+H−56)+).

Step 4: tert-butyl 3-fluoro-3-(4-iodobutyl)pyrrolidine-1-carboxylate

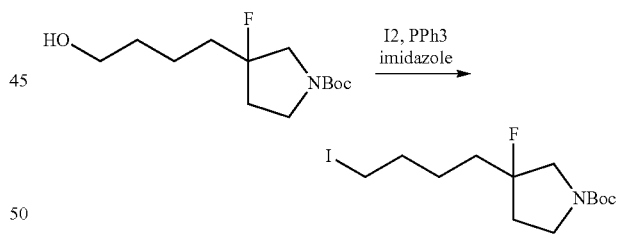

To a solution of triphenylphosphine (1.58 g, 6.04 mmol) and imidazole (411 mg, 6.04 mmol) in DCM (40 mL) at 5° C. was added 12 (835 mg, 3.29 mmol). The reaction mixture was stirred at 5° C. for 15 min, and then a solution of (tert-butyl 3-fluoro-3-(4-hydroxybutyl)pyrrolidine-1-carboxylate (780 mg, 2.99 mmol) in DCM (15 mL) was added. The reaction mixture was stirred at 5° C. for 1 h, then concentrated in vacuo at 15° C., and the residue was purified by silica gel column (pet ether:EtOAc 20:1-10:1) to give the desired product tert-butyl 3-fluoro-3-(4-iodobutyl)pyrrolidine-1-carboxylate as a light yellow oil (700 mg). Yield 63% (ESI 316 (M+H−56)+).

Step 5: tert-butyl 3-(5-(1,8-naphthyridin-2-yl)pentyl)-3-fluoropyrrolidine-1-carboxylate

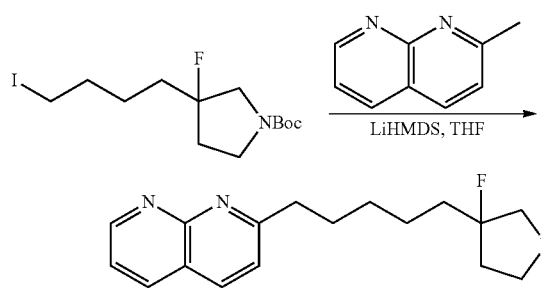

To a solution of (R)-tert-butyl 3-(1,1-difluoro-4-iodobutyl)pyrrolidine-1-carboxylate (700 mg, 1.88 mmol) and 2-methyl-1,8-naphthyridine (407 mg, 2.82 mmol) in THF (12 mL) at 0° C. was added LiHMDS (2.82 mL, 1M, 2.82 mmol). The reaction mixture was stirred at 0° C. for 3 h, then quenched with saturated ammonium chloride solution (6 mL), diluted with water (15 mL) and extracted with EtOAc (30 mL×2). The combined organic layers were dried over sodium sulfate, filtered and concentrated in vacuo. The residue was purified by prep-TLC to give the desired product tert-butyl 3-(5-(1,8-naphthyridin-2-yl)pentyl)-3-fluoropyrrolidine-1-carboxylate as a light yellow solid (350 mg). Yield 48% (ESI 388 (M+H)$^+$).

Step 6: 7-(5-(3-fluoropyrrolidin-3-yl)pentyl)-1,2,3,4-tetrahydro-1,8-naphthyridine

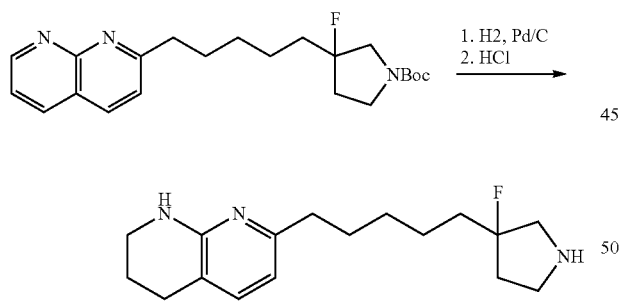

A mixture of 3-(5-(1,8-naphthyridin-2-yl)pentyl)-3-fluoropyrrolidine-1-carboxylate (200 mg, 0.516 mmol) and Pd/C (5%, 200 mg) in EtOAc (20 mL) under hydrogen was stirred at 45° C. overnight. The reaction mixture was filtered and concentrated in vacuo. To the residue was added 1,4-dioxane (2 mL) and HCl/dioxane (2 mL, 4 M) at room temperature. The reaction mixture was stirred at room temperature for 3 h, then concentrated in vacuo to give the desired product 7-(5-(3-fluoropyrrolidin-3-yl)pentyl)-1,2,3,4-tetrahydro-1,8-naphthyridine as a light yellow solid (140 mg). Yield 93% (ESI 292 (M+H)$^+$).

Step 7: 2-(3-fluoro-3-(5-(5,6,7,8-tetrahydro-1,8-naphthyridin-2-yl)pentyl)pyrrolidin-1-yl)-2-phenylacetic acid (Compounds 132-E1 and 132-E2)

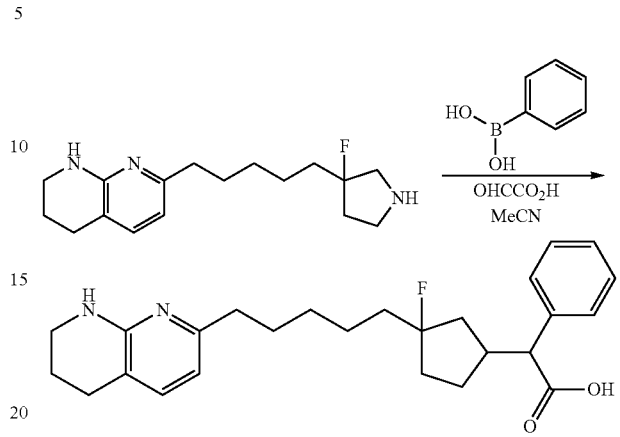

A mixture of 7-(5-(3-fluoropyrrolidin-3-yl)pentyl)-1,2,3,4-tetrahydro-1,8-naphthyridine (140 mg, 0.48 mmol), 2-oxoacetic acid (76.5 mg, 0.62 mmol) and phenylboronic acid (75.6 mg, 0.62 mmol) in MeCN (1.5 mL) was heated at 50° C. for 2 hours. Solvent was removed in vacuo, and the residue was purified by Prep-HPLC A to give compound 132 as a white solid (90 mg, 44% yield). The racemic product was separated by Prep chiral SFC A to give compound 132-E1 (41 mg) and compound 132-E2 (36 mg) as white solids.

Compound 132-E1 LC/MS ESI 426 (M+H)$^+$ 1H NMR (500 MHz, MeOD) δ 7.47-7.45 (m, 2H), 7.31-7.29 (m, 3H), 7.08 (d, J=7.5 Hz, 1H), 6.27 (d, J=7.5 Hz, 1H), 4.31 (d, 1H), 3.43-3.27 (m, 4H), 3.08-2.90 (m, 2H), 2.60 (t, J=6.0 Hz, 2H), 2.42 (t, J=8.5 Hz, 2H), 2.11-1.93 (m, 2H), 1.80-1.63 (m, 4H), 1.57-1.49 (m, 2H), 1.39-1.19 (m, 4H). Chiral SFC A (40% MeOH): ee 100%, Rt=2.45 min.

Compound 132-E2 LC/MS ESI 426 (M+H)$^+$ 1H NMR (500 MHz, MeOD) δ 7.59-7.57 (m, 2H), 7.42-7.38 (m, 3H), 7.22 (d, J=8.0 Hz, 1H), 6.40 (d, J=7.5 Hz, 1H), 4.33 (d, 1H), 3.46-3.30 (m, 4H), 3.16-2.93 (m, 2H), 2.72 (t, J=6.0 Hz, 2H), 2.55 (t, J=7.5 Hz, 2H), 2.25-2.05 (m, 2H), 1.91-1.87 (m, 2H), 1.85-1.73 (m, 2H), 1.68-1.62 (m, 2H), 1.48-1.31 (m, 4H). Chiral SFC A (40% MeOH): ee 98%, Rt=3.92, 4.42 min.

Example 33: Preparation of 2-(4-isopropoxypyridin-3-yl)-2-((R)-3-(4-(5,6,7,8-tetrahydro-1,8-naphthyridin-2-yl)butoxy)pyrrolidin-1-yl)acetic acid (Compound 133)

Step 1: 3-bromo-4-isopropoxypyridine

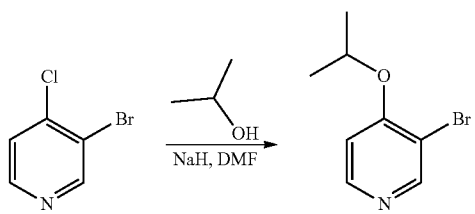

To a solution of i-PrOH (1.87 g, 31.2 mmol) in DMF (20 mL) at 0° C., was added NaH (60%, 1.25 g, 31.2 mmol). The mixture was stirred at room temperature for 1 h, and 3-bromo-4-chloropyridine (2 g, 10.4 mmol) was added. The reaction was stirred at 80° C. overnight, then cooled to room temperature, diluted with H₂O (20 mL) and extracted with EtOAc (20 mL×3). The combined organic layer was dried over sodium sulfate, filtered and concentrated in vacuo, and the residue was purified by silica gel column (pet ether: EtOAc 5:1) to give the desired product 3-bromo-4-isopropoxypyridine as a colorless oil (1.7 g). Yield 76% (ESI 216.0 (M+H)⁺).

Step 2: 4-isopropoxypyridin-3-ylboronic acid

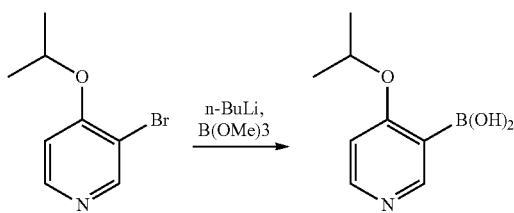

To a solution of 3-bromo-4-isopropoxypyridine (1 g, 4.63 mmol) in dry THF (20 mL) under Ar at −78° C., was added n-BuLi (2.5 M in Hexanes, 2.8 mL). The reaction was stirred at −78° C. for 1 hour, then trimethyl borate (722 mg, 6.95 mmol) was added. The reaction was stirred at room temperature overnight, then quenched with MeOH (5 mL) and concentrated in vacuo, and the residue was used directly in the next step.

Step 3: 2-(4-isopropoxypyridin-3-yl)-2-((R)-3-(4-(5,6,7,8-tetrahydro-1,8-naphthyridin-2-yl)butoxy)pyrrolidin-1-yl)acetic acid (Compound 133)

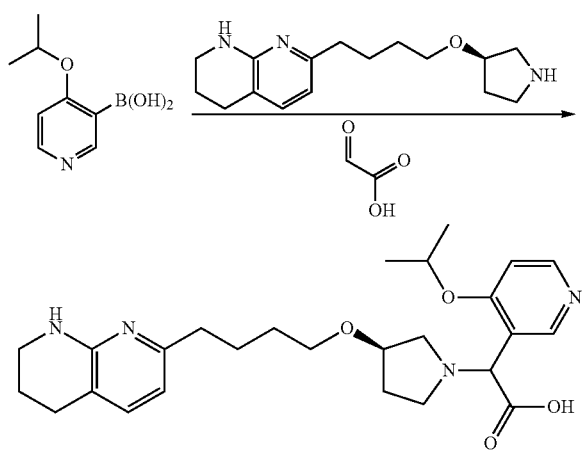

The above residue was diluted with MeCN (10 mL), (R)-7-(4-(pyrrolidin-3-yloxy)butyl)-1,2,3,4-tetrahydro-1,8-naphthyridine (150 mg, 0.54 mmol) and glyoxylic acid (50% in water, 161 mg, 1.08 mmol) were added. The reaction was stirred under reflux for 15 hours. Solvent was removed in vacuo, and the residue was purified by Prep-HPLC A (30-65% MeCN) to give compound 133 as a white solid (20 mg).

Compound 133 LC/MS ESI 469 (M+H)⁺ ¹H NMR (400 MHz, MeOD) δ 8.56 (s, 1H), 8.40 (d, J=6 Hz, 1H), 7.19-7.14 (m, 2H), 6.38 (d, J=7.2 Hz, 1H), 4.89-4.86 (m, 2H), 4.25-4.19 (m, 1H), 3.48-3.30 (m, 8H), 2.71 (t, J=6.4 Hz, 2H), 2.55 (t, J=7.6 Hz, 2H), 2.25-1.88 (m, 4H), 1.71-1.38 (m, 10H).

Additional Examples

Compounds 29-128 and 134-201 were prepared using general procedures based on the method used to prepare compounds 1-28 and 129-133.

2-(4-((4-((5,6,7,8-tetrahydro-1,8-naphthyridin-2-yl)methyl)piperidin-1-yl)methyl) piperidin-1-yl)acetic acid (Compound 29)

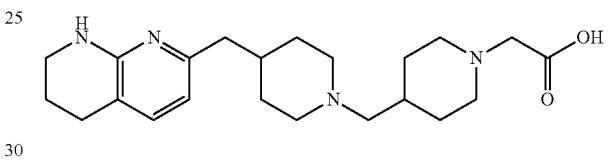

Compound 29 LC/MS A: 100% purity, UV=214 nm, Rt=1.18 min, ESI 387.2 (M+H)⁺. ¹H NMR (500 MHz, MeOD) δ 7.13 (d, J=7.3 Hz, 1H), 6.34 (d, J=7.3 Hz, 1H), 3.50-3.48 (m, 4H), 3.38 (dd, J=14.9, 9.3 Hz, 2H), 2.93 (d, J=11.5 Hz, 2H), 2.85 (t, J=11.8 Hz, 2H), 2.71 (t, J=6.2 Hz, 2H), 2.45 (d, J=7.0 Hz, 2H), 2.28 (d, J=7.0 Hz, 2H), 2.01-1.98 (m, 4H), 1.65-1.62 (m, 3H), 1.73-1.56 (m, 3H), 1.52-1.40 (m, 2H), 1.33 (dd, J=22.6, 10.5 Hz, 2H).

2-(2-oxo-4-(4-((5,6,7,8-tetrahydro-1,8-naphthyridin-2-yl)methyl)piperidine-1-carbonyl)piperidin-1-yl) acetic acid formic acid salt (Compound 30)

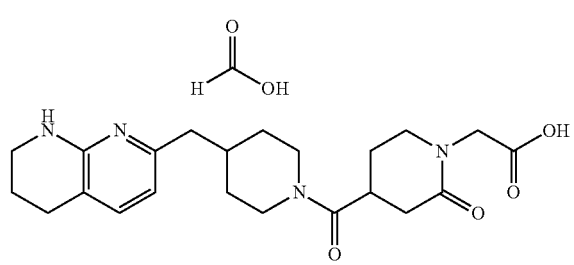

Compound 30 LC/MS D: 100% purity, UV=214 nm, Rt=1.427 min, ESI 415.1 (M+H)+. 1H NMR (400 MHz, DMSO-d6) δ 8.18 (0.73H, HCOOH), 7.03 (d, J=7.6 Hz, 1H), 6.41 (s, 1H), 6.23 (d, J=7.2 Hz, 1H), 4.36-4.33 (m, 1H), 4.08-4.03 (m, 1H), 3.92-3.78 (m, 2H), 3.39-3.15 (m, 5H), 2.98-2.92 (m, 1H), 2.62-2.59 (m, 2H), 2.50-2.23 (m, 5H), 1.88-1.85 (m, 2H), 1.76-1.72 (m, 3H), 1.68-1.59 (m, 2H), 1.13-0.96 (m, 2H).

2-(2-oxo-4-((2-(5,6,7,8-tetrahydro-1,8-naphthyridin-2-yl)ethyl)carbamoyl)piperidin-1-yl)acetic acid formic acid salt (Compound 31)

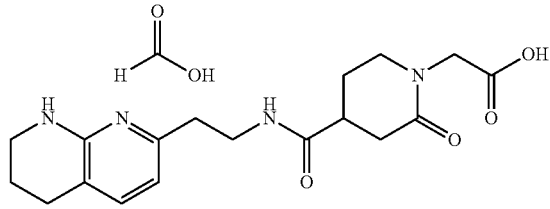

Compound 31 LC/MS D: 100% purity, UV=214 nm, Rt=1.290 min, ESI 361.0 (M+H)+. 1H NMR (400 MHz, DMSO-d6) δ 8.18 (1H, HCOOH), 7.98-7.95 (m, 1H), 7.04 (d, J=7.2 Hz, 1H), 6.41 (s, 1H), 6.24 (d, J=7.6 Hz, 1H), 4.12-4.07 (m, 1H), 3.78-3.74 (m, 1H), 3.33-3.24 (m, 5H), 2.62-2.53 (m, 6H), 2.32-2.29 (m, 2H), 1.90-1.87 (m, 1H), 1.77-1.72 (m, 3H).

2-(2-oxo-4-((2-(5,6,7,8-tetrahydro-1,8-naphthyridin-2-yl)ethyl)carbamoyl)piperazin-1-yl)acetic acid (Compound 32)

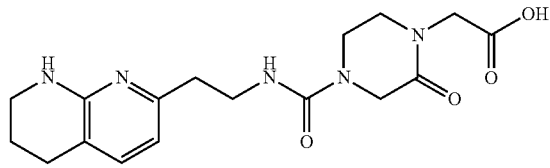 [SMILES: O=C(O)CN1CCN(C(=O)NCCc2ccc3c(n2)NCCC3)CC1=O]

Compound 32 LC/MS D: 97% purity, UV=214 nm, Rt=0.838 min, ESI 362.1 (M+H)+. 1H NMR (400 MHz, DMSO-d6) δ 7.06 (d, J=7.2 Hz, 1H), 6.72 (t, J=5.2 Hz, 1H), 6.49 (s, 1H), 6.26 (d, J=7.2 Hz, 1H), 4.02 (s, 2H), 3.93 (s, 2H), 3.56-3.53 (m, 2H), 3.36-3.33 (m, 2H), 3.29-3.24 (m, 4H), 2.62-2.57 (m, 4H), 1.78-1.72 (m, 2H).

2-(2-oxo-4-((3-(5,6,7,8-tetrahydro-1,8-naphthyridin-2-yl)propyl)carbamoyl) piperidin-1-yl)acetic acid compound formic acid salt (Compound 33)

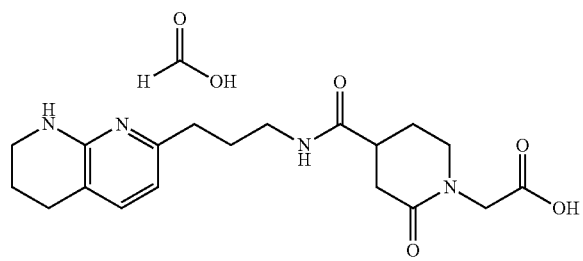

Compound 33 LC/MS D: 100% purity, UV=214 nm, Rt=1.353 min, ESI 375.1 (M+H)+. 1H NMR (400 MHz, DMSO-d6) δ 8.14 (0.27H, HCOOH), 7.97-7.94 (m, 1H), 7.37 (s, 1H), 7.26 (d, J=6.8 Hz, 1H), 6.40 (d, J=7.2 Hz, 1H), 3.97-3.86 (m, 2H), 3.39-3.29 (m, 4H), 3.10-3.04 (m, 2H), 2.66-2.63 (m, 3H), 2.50-2.48 (m, 2H), 2.38-2.34 (m, 2H), 1.90-1.68 (m, 6H).

2-(2-oxo-4-((3-(5,6,7,8-tetrahydro-1,8-naphthyridin-2-yl)propyl)carbamoyl) piperazin-1-yl)acetic acid (Compound 34)

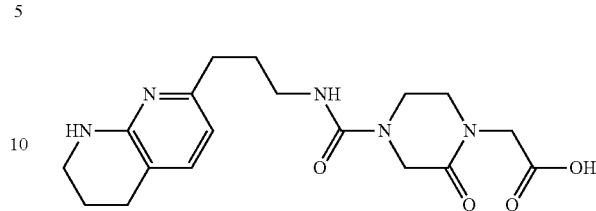

Compound 34 LC/MS B: 96% purity, UV=214 nm, Rt=1.285 min, ESI 376.3 (M+H)+. 1H NMR (400 MHz, CD3OD) δ 7.48 (d, J=7.6 Hz, 1H), 6.53 (d, J=7.6 Hz, 1H), 4.12 (s, 2H), 3.94 (s, 2H), 3.76-3.74 (m, 2H), 3.52-3.49 (m, 2H), 3.46-3.43 (m, 2H), 3.30-3.28 (m, 2H), 2.79-2.75 (m, 2H), 2.70-2.66 (m, 2H), 1.93-1.90 (m, 2H), 1.79-1.75 (m, 2H).

2-(2-oxo-4-((4-(5,6,7,8-tetrahydro-1,8-naphthyridin-2-yl)butyl)carbamoyl)piperidin-1-yl)acetic acid (Compound 35)

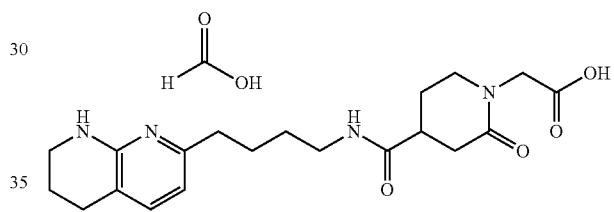

Compound 35 LC/MS C: 98% purity, UV=214 nm, Rt=1.378 min, ESI 389.1 (M+H)+. 1H NMR (400 MHz, DMSO-d6) δ 8.18 (0.37H, HCOOH), 7.89-7.86 (m, 1H), 7.07 (d, J=7.2 Hz, 1H), 6.87 (s, 1H), 6.27 (d, J=7.2 Hz, 1H), 4.01-3.97 (m, 1H), 3.85-3.80 (m, 1H), 3.32-3.29 (m, 2H), 3.27-3.20 (m, 2H), 3.08-3.03 (m, 2H), 2.64-2.59 (m, 3H), 2.46-2.38 (m, 2H), 2.38-2.31 (m, 2H), 1.91-1.87 (m, 1H), 1.80-1.73 (m, 3H), 1.58-1.53 (m, 2H), 1.43-1.37 (m, 2H).

2-(2-oxo-4-((4-(5,6,7,8-tetrahydro-1,8-naphthyridin-2-yl)butyl)carbamoyl)piperazin-1-yl)acetic acid (Compound 36)

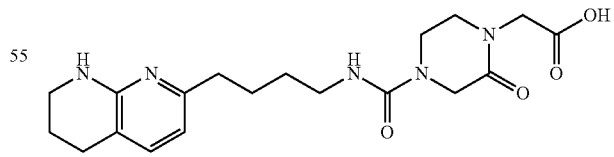

Compound 36 LC/MS D: 100% purity, UV=214 nm, Rt=0.999 min, ESI 390.3 (M+H)+. 1H NMR (400 MHz, CD3OD) δ 7.59 (d, J=7.2 Hz, 1H), 6.63 (d, J=7.6 Hz, 1H), 4.17 (s, 2H), 4.08 (s, 2H), 3.71-3.68 (m, 2H), 3.52-3.48 (m, 4H), 3.24-3.20 (m, 2H), 2.84-2.80 (m, 2H), 2.75-2.71 (m, 2H), 1.97-1.94 (m, 2H), 1.70 (d, J=7.6 Hz, 2H), 1.58 (d, J=7.6 Hz, 2H).

2-(4-((2-(5,6,7,8-tetrahydro-1,8-naphthyridin-2-yl)ethyl)carbamoyl)piperidin-1-yl)acetic acid (Compound 37)

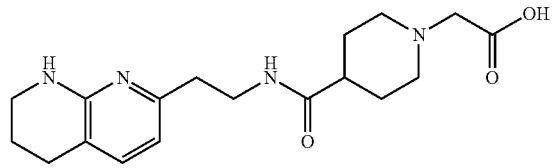 [SMILES: O=C(O)CN1CCC(C(=O)NCCc2ccc3c(n2)NCCC3)CC1]

Compound 37 LC/MS A: 96.8% purity, UV=214 nm, Rt=1.31 min, ESI 347.2 (M+H)+. 1H NMR (400 MHz, CD3OD) δ 7.17 (d, J=7.2 Hz, 1H), 6.38 (d, J=7.2 Hz, 1H), 3.62-3.57 (m, 4H), 3.48-3.36 (m, 4H), 3.03-2.96 (m, 2H), 2.73-2.69 (m, 4H), 2.50-2.44 (m, 1H), 2.02-1.86 (m, 6H).

2-(4-((2-(5,6,7,8-tetrahydro-1,8-naphthyridin-2-yl)ethyl)carbamoyl)piperazin-1-yl)acetic acid (Compound 38)

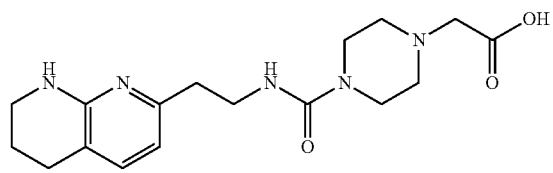 [SMILES: O=C(O)CN1CCN(C(=O)NCCc2ccc3c(n2)NCCC3)CC1]

Compound 38 LC/MS A: 99% purity, UV=214 nm, Rt=1.28 min, ESI 348.3 (M+H)+. 1H NMR (500 MHz, MeOD) δ 7.25 (d, J=7.3 Hz, 1H), 6.44 (d, J=7.3 Hz, 1H), 3.59-3.57 (m, 4H), 3.49-3.38 (m, 6H), 3.04-3.03 (m, 4H), 2.77-2.74 (m, 4H), 1.93-1.88 (m, 2H).

2-(4-((4-(5,6,7,8-tetrahydro-1,8-naphthyridin-2-yl)butyl)carbamoyl)piperidin-1-yl)acetic acid (Compound 39)

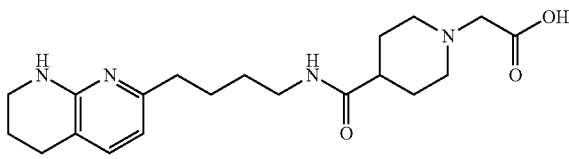 [SMILES: O=C(O)CN1CCC(C(=O)NCCCCc2ccc3c(n2)NCCC3)CC1]

Compound 39 LC/MS A: 97.4% purity, UV=214 nm, Rt=1.71 min, ESI 375.3 (M+H)+. 1H NMR (400 MHz, CD3OD) δ 7.03 (d, J=7.6 Hz, 1H), 6.26 (d, J=7.6 Hz, 1H), 3.52-3.45 (m, 4H), 3.27 (t, J=5.2 Hz, 2H), 3.09 (t, J=6.4 Hz, 2H), 2.92-2.85 (m, 2H), 2.59 (t, J=6.4 Hz, 2H), 2.44-2.35 (m, 3H), 1.92-1.74 (m, 6H), 1.56-1.39 (m, 4H).

2-(4-((4-(5,6,7,8-tetrahydro-1,8-naphthyridin-2-yl)butyl)carbamoyl)piperazin-1-yl)acetic acid (Compound 40)

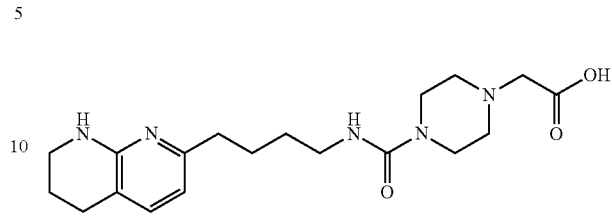

Compound 40 LC/MS B: 100% purity, UV=214 nm, Rt=0.82 min, ESI 376.0 (M+H)+. 1H NMR (400 MHz, MeOD) δ 7.32 (d, J=7.3 Hz, 1H), 6.45 (d, J=7.3 Hz, 1H), 3.54 (t, J=4. Hz, 4H), 3.42 (t, J=5.6 Hz, 2H), 3.37 (s, 2H), 3.21 (t, J=6.6 Hz, 2H), 2.98 (t, J=5.2 Hz, 2H), 2.75 (t, J=6.2 Hz, 2H), 2.61 (t, J=7.6 Hz, 2H), 1.98-1.83 (m, 2H), 1.75-1.48 (m, 4H).

(R)-2-(3-(hydroxymethyl)-2-oxo-4-((3-(5,6,7,8-tetrahydro-1,8-naphthyridin-2-yl)propyl)carbamoyl)piperazin-1-yl)acetic acid (Compound 41)

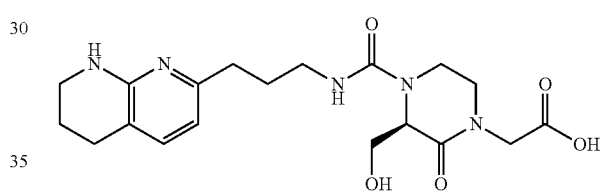

Compound 41 LC/MS B: 100% purity, UV=214 nm, Rt=1.01 min, ESI 406.2 (M+H)+. 1H NMR (400 MHz, CD3OD) δ 7.35 (d, J=7.2 Hz, 1H), 6.42 (d, J=7.2 Hz, 1H), 4.50 (brs, 1H), 4.40 (m, 1H), 4.00-3.95 (m, 2H), 3.83-3.79 (m, 1H), 3.66-3.51 (m, 2H), 3.36-3.30 (m, 4H), 3.15-3.07 (m, 2H), 2.68-2.49 (m, 4H), 1.85-1.63 (m, 4H).

2-(2,2-dimethyl-4-((3-(5,6,7,8-tetrahydro-1,8-naphthyridin-2-yl)propyl)carbamoyl) piperazin-1-yl)acetic acid (Compound 42)

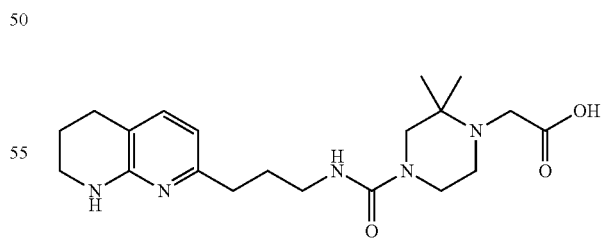

Compound 42 LC/MS B: 100% purity, UV=214 nm, Rt=1.12 min, ESI 390.2 (M+H)+. 1H NMR (400 MHz, CD3OD) δ 7.24 (d, J=7.6 Hz, 1H), 6.44 (d, J=7.6 Hz, 1H), 3.67-3.65 (m, 2H), 3.50 (s, 2H), 3.46 (s, 2H), 3.43-3.40 (m, 2H), 3.24-3.19 (m, 4H), 2.75-2.72 (m, 2H), 2.62-2.57 (m, 2H), 1.92-1.83 (m, 4H), 1.30 (s, 6H).

2-(3-((3-(5,6,7,8-tetrahydro-1,8-naphthyridin-2-yl)propyl)carbamoyl)-3,8-diazabicyclo[3.2.1]octan-8-yl)acetic acid (Compound 43)

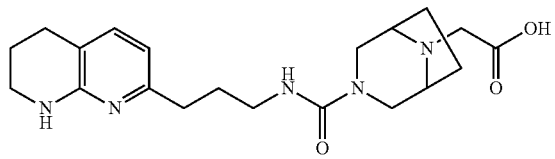 [SMILES: O=C(O)CN1C2CCC1CN(C(=O)NCCCc1ccc3c(n1)NCCC3)C2]

Compound 43 LC/MS A: 100% purity, UV=214 nm, Rt=1.12 min, ESI 387 (M+H)+. 1H NMR (500 MHz, MeOD) δ 7.19 (d, J=7.3 Hz, 1H), 6.42 (d, J=7.3 Hz, 1H), 3.98 (s, 2H), 3.88 (d, J=12.2 Hz, 2H), 3.52 (s, 2H), 3.43-3.34 (m, 4H), 3.22 (t, J=6.9 Hz, 2H), 2.73 (t, J=6.3 Hz, 2H), 2.57 (t, J=7.6 Hz, 2H), 2.24-2.12 (m, 2H), 1.98-1.79 (m, 6H).

2-(4-(4-(5,6,7,8-tetrahydro-1,8-naphthyridin-2-yl)butanamido)piperidin-1-yl)propanoic acid (Enantiomeric Compounds 44-E1 and 44-E2)

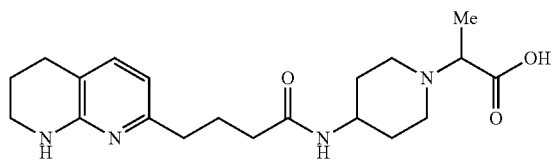 [SMILES: CC(C(=O)O)N1CCC(NC(=O)CCCc2ccc3c(n2)NCCC3)CC1]

Compound 44-E1 LC/MS A: 95% purity, UV=214 nm, Rt=1.377 min, ESI 374 (M+H)+. 1H NMR (500 MHz, MeOD) δ 7.16 (d, J=7.3 Hz, 1H), 6.39 (d, J=7.3 Hz, 1H), 3.97-3.86 (m, 1H), 3.56-3.37 (m, 5H), 3.14-3.04 (m, 2H), 2.71 (t, J=6.2 Hz, 2H), 2.56 (t, J=7.6 Hz, 2H), 2.23 (t, J=7.5 Hz, 2H), 2.23-2.08 (m, 2H), 1.98-1.78 (m, 6H), 1.51 (d, J=7.0 Hz, 3H). Chiral SFC A (45% MeOH): ee 100%, Rt=4.06 min.

Compound 44-E2 LC/MS A: 95% purity, UV=214 nm, Rt=1.386 min, ESI 374 (M+H)+. 1H NMR (500 MHz, MeOD) δ 7.16 (d, J=7.3 Hz, 1H), 6.39 (d, J=7.3 Hz, 1H), 3.97-3.86 (m, 1H), 3.56-3.37 (m, 5H), 3.14-3.04 (m, 2H), 2.71 (t, J=6.2 Hz, 2H), 2.56 (t, J=7.6 Hz, 2H), 2.23 (t, J=7.5 Hz, 2H), 2.23-2.08 (m, 2H), 1.98-1.78 (m, 6H), 1.51 (d, J=7.0 Hz, 3H). Chiral SFC A (45% MeOH): ee 100%, Rt=8.73 min.

2-phenyl-2-(3-(4-(5,6,7,8-tetrahydro-1,8-naphthyridin-2-yl)butanamido)azetidin-1-yl)acetic acid (Enantiomeric Compounds 45-E1 and 45-E2)

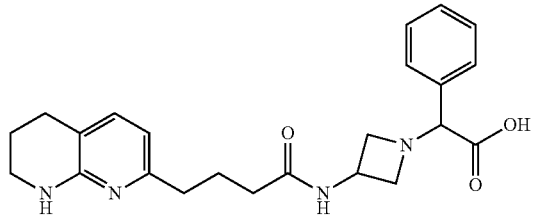 [SMILES: O=C(CCCc1ccc2c(n1)NCCC2)NC1CN(C(C(=O)O)c2ccccc2)C1]

Compound 45-E1 LC/MS A: 99% purity, UV=214 nm, Rt=1.44 min, ESI 409.4 (M+H)+. ¹H NMR (400 MHz, MeOD) δ 7.41-7.24 (m, 5H), 7.07 (d, J=7.3 Hz, 1H), 6.28 (d, J=7.2 Hz, 1H), 4.48 (s, 1H), 4.46-4.40 (m, 1H), 4.23 (t, J=8.8 Hz, 1H), 3.72-3.70 (m, 3H), 3.28-3.26 (m, 2H), 2.59 (t, J=6.2 Hz, 2H), 2.45 (t, J=7.2 Hz, 2H), 2.14-2.10 (m, 2H), 1.90-1.65 (m, 4H). Chiral SFC A (45% MeOH): ee 100%, Rt=1.65 min Compound 45-E2 LC/MS A: 99% purity, UV=214 nm, Rt=1.44 min, ESI 409.4 (M+H)+. ¹H NMR (400 MHz, MeOD) δ 7.41-7.24 (m, 5H), 7.07 (d, J=7.3 Hz, 1H), 6.28 (d, J=7.2 Hz, 1H), 4.48 (s, 1H), 4.46-4.40 (m, 1H), 4.23 (t, J=8.8 Hz, 1H), 3.72-3.70 (m, 3H), 3.28-3.26 (m, 2H), 2.59 (t, J=6.2 Hz, 2H), 2.45 (t, J=7.2 Hz, 2H), 2.14-2.10 (m, 2H), 1.90-1.65 (m, 4H). Chiral SFC A (45% MeOH): ee 100%, Rt=2.72 min 2-phenyl-2-(3-((4-(5,6,7,8-tetrahydro-1,8-naphthyridin-2-yl)butyl)carbamoyl) azetidin-1-yl)acetic acid (Enantiomeric Compounds 46-E1 and 46-E2)

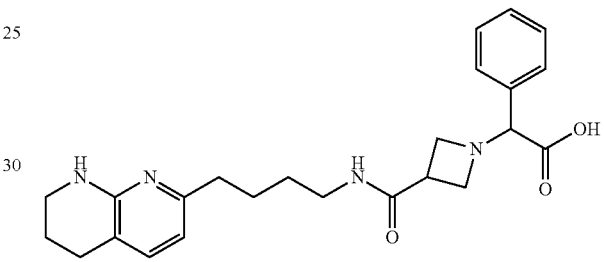

Compound 46-E1 LC/MS A: 96% purity, UV=214 nm, Rt=1.49 min, ESI 423.4 (M+H)+. 1H NMR (400 MHz, CD3OD) δ 7.51-7.48 (m, 2H), 7.44-7.41 (m, 3H), 7.18 (d, J=7.6 Hz, 1H), 6.38 (d, J=7.2 Hz, 1H), 4.70 (s, 1H), 4.20-4.18 (m, 1H), 4.08-4.03 (m, 1H), 3.99-3.94 (m, 1H), 3.81-3.76 (m, 1H), 3.50-3.46 (m, 1H), 3.39-3.36 (m, 2H), 3.25-3.21 (m, 1H), 2.72-2.69 (m, 2H), 2.57-2.53 (m, 2H), 1.90-1.84 (m, 2H), 1.68-1.62 (m, 2H), 1.57-1.52 (m, 2H). Chiral SFC A (45% MeOH): ee 100%, Rt=1.62 min.

Compound 46-E2 LC/MS A: 96% purity, UV=214 nm, Rt=1.49 min, ESI 423.3 (M+H)+. 1H NMR (400 MHz, CD3OD) δ 7.51-7.48 (m, 2H), 7.44-7.41 (m, 3H), 7.18 (d, J=7.6 Hz, 1H), 6.38 (d, J=7.2 Hz, 1H), 4.70 (s, 1H), 4.20-4.18 (m, 1H), 4.08-4.03 (m, 1H), 3.99-3.94 (m, 1H), 3.81-3.76 (m, 1H), 3.50-3.46 (m, 1H), 3.39-3.36 (m, 2H), 3.25-3.21 (m, 1H), 2.72-2.69 (m, 2H), 2.57-2.53 (m, 2H), 1.90-1.84 (m, 2H), 1.68-1.62 (m, 2H), 1.57-1.52 (m, 2H). Chiral SFC A (45% MeOH): ee 99%, Rt=3.17 min.

2-(3-(4-(5,6,7,8-tetrahydro-1,8-naphthyridin-2-yl)butanamido)azetidin-1-yl)propanoic acid (Compound 47)

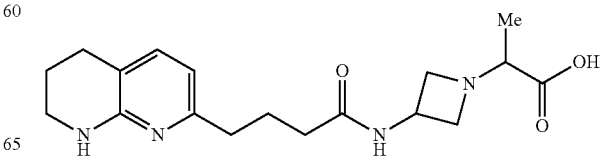

Compound 47 LC/MS A: 99% purity, UV=214 nm, Rt=1.37 min, ESI 347.4 (M+H)+. ¹H NMR (400 MHz, MeOD) δ 7.06 (d, J=7.1 Hz, 1H), 6.28 (d, J=7.2 Hz, 1H), 4.50-4.33 (m, 1H), 4.22 (s, 1H), 4.04 (s, 1H), 3.89-3.39 (m, 3H), 3.36-3.25 (m, 2H), 2.67-2.38 (m, 4H), 2.13 (t, J=7.3 Hz, 2H), 1.91-1.70 (m, 4H), 1.24 (d, J=6.8 Hz, 3H).

2-phenyl-2-(4-(5-(5,6,7,8-tetrahydro-1,8-naphthyridin-2-yl)pentanoyl)piperazin-1-yl)acetic acid (Enantiomeric Compounds 48-E1 and 48-E2)

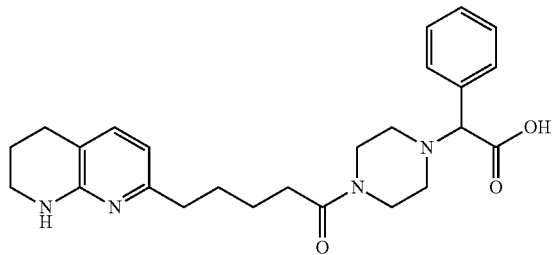 [SMILES: O=C(O)C(c1ccccc1)N1CCN(C(=O)CCCCc2ccc3c(n2)NCCC3)CC1]

Compound 48-E1 LC/MS A: 99% purity, UV=214 nm, Rt=1.46 min, ESI 437.4 (M+H)+. ¹H NMR (400 MHz, MeOD) δ 7.54 (d, J=7.0 Hz, 2H), 7.39-7.29 (m, 4H), 6.48 (d, J=7.3 Hz, 1H), 3.88 (s, 1H), 3.76-3.46 (m, 4H), 3.43-3.37 (m, 2H), 2.77-2.36 (m, 10H), 1.96-1.79 (m, 2H), 1.70-1.59 (m, 4H). Chiral SFC A (40% MeOH): ee 100%, Rt=3.55 min.

Compounds 48-E2 LC/MS A: 99% purity, UV=214 nm, Rt=1.46 min, ESI 437.4 (M+H)+. ¹H NMR (400 MHz, MeOD) δ 7.54 (d, J=7.0 Hz, 2H), 7.39-7.29 (m, 4H), 6.48 (d, J=7.3 Hz, 1H), 3.88 (s, 1H), 3.76-3.46 (m, 4H), 3.43-3.37 (m, 2H), 2.77-2.36 (m, 10H), 1.96-1.79 (m, 2H), 1.70-1.59 (m, 4H). Chiral SFC A (40% MeOH): ee 95%, Rt=4.31 min.

2-(2-oxo-4-(5-(5,6,7,8-tetrahydro-1,8-naphthyridin-2-yl)pentyl)piperazin-1-yl)-2-phenylacetic acid (Enantiomeric Compounds 49-E1 and 49-E2)

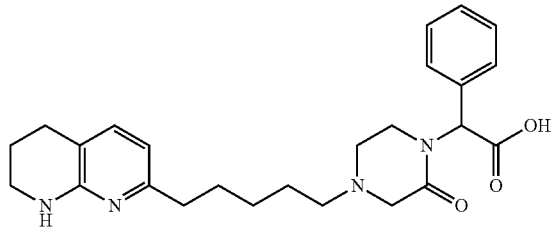 [SMILES: O=C(O)C(c1ccccc1)N1CCN(CCCCCc2ccc3c(n2)NCCC3)CC1=O]

Compound 49-E1 LC/MS A: 99% purity, UV=214 nm, Rt=1.53 min, ESI 437.4 (M+H)+. ¹H NMR (400 MHz, MeOD) δ 7.46 (d, J=7.3 Hz, 1H), 7.42-7.28 (m, 5H), 6.51 (d, J=7.3 Hz, 1H), 6.30 (s, 1H), 3.85-3.68 (m, 1H), 3.59-3.37 (m, 3H), 3.08-2.94 (m, 2H), 2.91-2.50 (m, 8H), 2.02-1.83 (m, 2H), 1.81-1.50 (m, 6H). Chiral SFC A (35% MeOH): ee 100%, Rt=3.5 min.

Compound 49-E2 LC/MS A: 96.8% purity, UV=214 nm, Rt=1.53 min, ESI 437.4 (M+H)+. ¹H NMR (400 MHz, MeOD) δ 7.46 (d, J=7.3 Hz, 1H), 7.42-7.28 (m, 5H), 6.51 (d, J=7.3 Hz, 1H), 6.30 (s, 1H), 3.85-3.68 (m, 1H), 3.59-3.37 (m, 3H), 3.08-2.94 (m, 2H), 2.91-2.50 (m, 8H), 2.02-1.83 (m, 2H), 1.81-1.50 (m, 6H). Chiral SFC A (35% MeOH): ee 97%, Rt=4.48 min.

2-(4-(5-(5,6,7,8-tetrahydro-1,8-naphthyridin-2-yl)pentyl)piperazin-1-yl)propanoic acid (Enantiomeric Compounds 50-E1 and 50-E2)

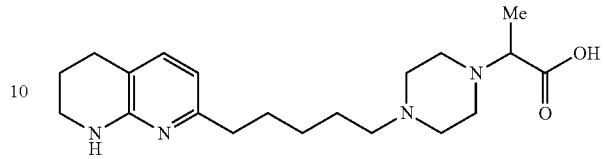

Compound 50-E1 LC/MS A: 100% purity, UV=214 nm, Rt=1.203 min, ESI 361.0 (M+H)+. 1H NMR (500 MHz, CD3OD) δ 7.13 (d, J=9.0 Hz, 1H), 6.35 (d, J=9.5 Hz, 1H), 3.39-3.36 (m, 2H), 3.27-3.25 (m, 1H), 3.03-2.68 (m, 9H), 2.56-2.51 (m, 4H), 1.89-1.86 (m, 2H), 1.69-1.56 (m, 4H), 1.39-1.34 (m, 6H). Chiral SFC B (40% MeOH): ee 100%, Rt=1.51 min Compound 50-E2 LC/MS A: 100% purity, UV=214 nm, Rt=1.203 min, ESI 361.0 (M+H)+. 1H NMR (500 MHz, CD3OD) δ 7.11 (d, J=9.0 Hz, 3H), 6.36 (d, J=9.5 Hz, 2H), 3.39-3.36 (m, 2H), 2.88 (q, J=6.8 Hz, 1H), 2.71-2.49 (m, 11H), 2.34 (t, J=8.0 Hz, 2H), 1.89-1.86 (m, 2H), 1.69-1.56 (m, 4H), 1.39-1.34 (m, 6H). Chiral SFC B (40% MeOH): ee 100%, Rt=3.47 min 2-(2-oxo-4-(5-(5,6,7,8-tetrahydro-1,8-naphthyridin-2-yl)pentyl)piperazin-1-yl)propanoic acid (Enantiomeric Compounds 51-E1 and 51-E2)

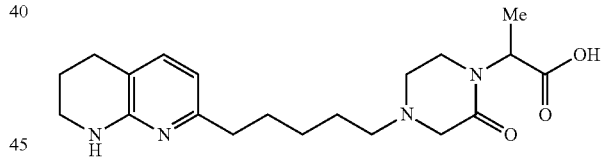

Compound 51-E1 LC/MS A: 97% purity, UV=214 nm, Rt=1.45 min, ESI 375.4 (M+H)+. ¹H NMR (400 MHz, MeOD) δ 7.42 (d, J=7.3 Hz, 1H), 6.48 (d, J=7.3 Hz, 1H), 5.01-4.9 (m, 1H), 3.71-3.56 (m, 1H), 3.53-3.34 (m, 4H), 3.23 (d, J=17.1 Hz, 1H), 3.10-3.05 (m, 9.4 Hz, 2H), 2.90-2.71 (m, 4H), 2.67-2.53 (m, 2H), 1.99-1.86 (m, 2H), 1.78-1.49 (m, 6H), 1.45-1.41 (m, 3H). Chiral SFC E (45% MeOH): ee 100%, Rt=3.36 min.

Compound 51-E2 LC/MS A: 96% purity, UV=214 nm, Rt=1.44 min, ESI 375.4 (M+H)+. ¹H NMR (400 MHz, MeOD) δ 7.42 (d, J=7.3 Hz, 1H), 6.48 (d, J=7.3 Hz, 1H), 5.01-4.9 (m, 1H), 3.71-3.56 (m, 1H), 3.53-3.34 (m, 4H), 3.23 (d, J=17.1 Hz, 1H), 3.10-3.05 (m, 9.4 Hz, 2H), 2.90-2.71 (m, 4H), 2.67-2.53 (m, 2H), 1.99-1.86 (m, 2H), 1.78-1.49 (m, 6H), 1.45-1.41 (m, 3H). Chiral SFC E (45% MeOH): ee 97%, Rt=5.29 min.

2-phenyl-2-(3-((5-(5,6,7,8-tetrahydro-1,8-naphthyridin-2-yl)pentyl)amino)azetidin-1-yl)acetic acid (Compound 52)

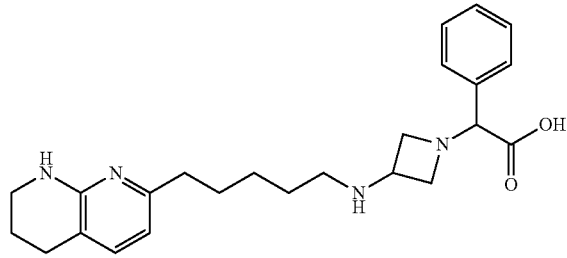 [SMILES: O=C(O)C(c1ccccc1)N1CC(NCCCCCc2ccc3c(n2)NCCC3)C1]

Compound 52 LC/MS A: 98.2% purity, UV=214 nm, Rt=1.55 min, ESI 409.2 (M+H)+. ¹H NMR (400 MHz, MeOD) δ 7.49-7.47 (m, 2H), 7.44-7.36 (m, 3H), 7.14 (d, J=7.3 Hz, 1H), 6.37 (d, J=7.3 Hz, 1H), 4.49 (s, 1H), 4.21-4.16 (m, 1H), 3.77-3.58 (m, 4H), 3.42-3.36 (m, 2H), 2.70 (t, J=6.3 Hz, 2H), 2.60 (t, J=7.2 Hz, 2H), 2.2 (t, J=7.6 Hz, 2H), 1.90-1.85 (m, 2H), 1.69-1.62 (m, 2H), 1.61-1.51 (m, 2H), 1.49-1.34 (m, 2H).

2-phenyl-2-(4-(4-((5,6,7,8-tetrahydro-1,8-naphthyridin-2-yl)methyl)piperidine-1-carbonyl)piperidin-1-yl)acetic acid (Enantiomeric Compounds 53-E1 and 53-E2)

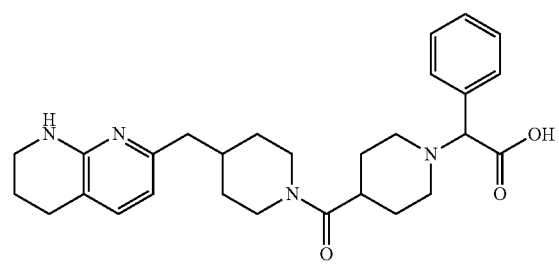 [SMILES: O=C(O)C(c1ccccc1)N1CCC(C(=O)N2CCC(Cc3ccc4c(n3)NCCC4)CC2)CC1]

Compound 53-E1 LC/MS A: 94% purity, UV=214 nm, Rt=1.56 min, ESI 477.4 (M+H)+. 1H NMR (400 MHz, MeOD) δ 7.58-7.56 (m, 2H), 7.46-7.44 (m, 3H), 7.14 (d, J=7.2 Hz, 1H), 6.36-6.33 (m, 1H), 4.57-4.40 (m, 2H), 4.07-3.69 (m, 2H), 3.46-3.35 (m, 2H), 3.16-2.79 (m, 5H), 2.71 (t, J=6.1 Hz, 2H), 2.58 (m, 1H), 2.45 (t, J=6.6 Hz, 2H), 2.17-1.59 (m, 9H), 1.26-1.00 (m, 2H). Chiral SFC D (25% MeOH): ee 96%, Rt=2.75 min.

Compound 53-E2 LC/MS A: 99% purity, UV=214 nm, Rt=1.56 min, ESI 477.4 (M+H)+. 1H NMR (400 MHz, MeOD) δ 7.58-7.56 (m, 2H), 7.46-7.44 (m, 3H), 7.14 (d, J=7.2 Hz, 1H), 6.36-6.33 (m, 1H), 4.57-4.40 (m, 2H), 4.07-3.69 (m, 2H), 3.46-3.35 (m, 2H), 3.16-2.79 (m, 5H), 2.71 (t, J=6.1 Hz, 2H), 2.58 (m, 1H), 2.45 (t, J=6.6 Hz, 2H), 2.17-1.59 (m, 9H), 1.26-1.00 (m, 2H). Chiral SFC D (25% MeOH): ee 100%, Rt=3.73 min.

2-phenyl-2-(4-((4-(5,6,7,8-tetrahydro-1,8-naphthyridin-2-yl)piperidin-1-yl)methyl) piperidin-1-yl)acetic acid (Enantiomeric Compounds 54-E1 and 54-E2)

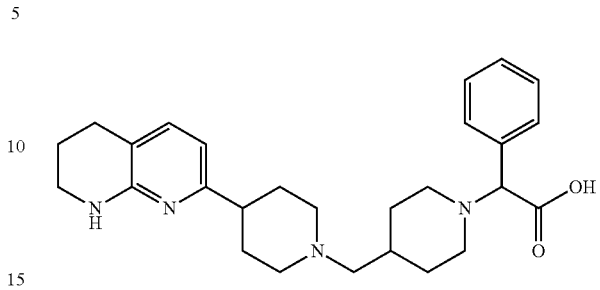

Compound 54-E1 LC/MS A: 100% purity, UV=214 nm, Rt=1.59 min, ESI 449.4 (M+H)+. 1H NMR (400 MHz, CD3OD) δ 7.59-7.55 (m, 2H), 7.45-7.42 (m, 3H), 7.15 (d, J=7.6 Hz, 1H), 6.36 (d, J=7.2 Hz, 1H), 4.35 (s, 1H), 3.69-3.65 (brs, 1H), 3.38-3.35 (m, 2H), 3.09-3.06 (m, 2H), 2.98-2.95 (m, 1H), 2.89-2.83 (m, 1H), 2.71-2.67 (m, 3H), 2.48-2.40 (m, 1H), 2.37-2.35 (m, 2H), 2.20-2.10 (m, 2H), 2.00-1.97 (m, 1H), 1.89-1.71 (m, 8H), 1.60-1.41 (m, 1H). Chiral SFC A (40% MeOH): ee 100%, Rt=2.51 min.

Compound 54-E2 LC/MS A: 100% purity, UV=214 nm, Rt=1.59 min, ESI 449.4 (M+H)+. 1H NMR (400 MHz, CD3OD) δ 7.59-7.55 (m, 2H), 7.44-7.41 (m, 3H), 7.14 (d, J=7.6 Hz, 1H), 6.37 (d, J=7.6 Hz, 1H), 4.35 (s, 1H), 3.70-3.69 (brs, 1H), 3.38-3.35 (m, 2H), 3.09-3.06 (m, 2H), 2.98-2.95 (m, 1H), 2.89-2.83 (m, 1H), 2.71-2.68 (m, 3H), 2.47-2.40 (m, 1H), 2.37-2.35 (m, 2H), 2.19-2.19 (m, 2H), 2.02-1.97 (m, 1H), 1.90-1.71 (m, 8H), 1.59-1.41 (m, 1H). Chiral SFC A (40% MeOH): ee 97%, Rt=3.75 min.

2-phenyl-2-(3-(4-(5,6,7,8-tetrahydro-1,8-naphthyridin-2-yl)piperidine-1-carbonyl) azetidin-1-yl)acetic acid (Enantiomeric Compounds 55-E1 and 55-E2)

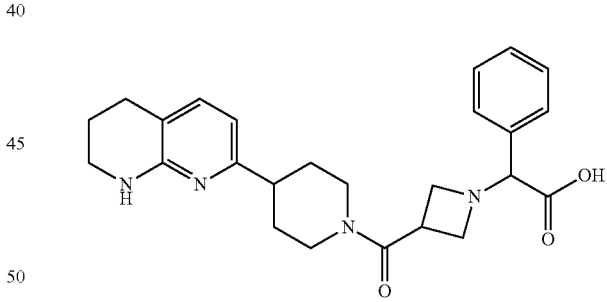

Compound 55-E1 LC/MS A: 97.7% purity, UV=214 nm, Rt=1.0 min, ESI 435.2 (M+H)+. 1H NMR (400 MHz, CD3OD) δ 7.42-7.40 (m, 2H), 7.35-7.32 (m, 3H), 7.04 (d, J=6.0 Hz, 1H), 6.26 (dd, J=7.2 Hz, 2.4 Hz, 1H), 4.59 (s, 1H), 4.52-4.50 (m, 1H), 4.24-4.22 (m, 1H), 4.11-4.07 (m, 1H), 4.00-3.93 (m, 1H), 3.83-3.76 (m, 2H), 3.59-3.56 (m, 1H), 3.28-3.26 (m, 2H), 3.06-3.01 (m, 1H), 2.68-2.56 (m, 4H), 1.77-1.75 (m, 4H), 1.54-1.45 (m, 2H). Chiral SFC A (40% MeOH): ee 100%, Rt=2.39 min Compound 55-E2 LC/MS A: 96.7% purity, UV=214 nm, Rt=1.0 min, ESI 435.2 (M+H)+. 1H NMR (400 MHz, CD3OD) δ 7.41-7.40 (m, 2H), 7.34-7.32 (m, 3H), 7.04 (d, J=6.0 Hz, 1H), 6.26 (dd, J=7.2 Hz, 1.6 Hz, 1H), 4.57 (s, 1H), 4.53-4.50 (m, 1H), 4.23-4.21 (m, 1H), 4.10-4.06 (m, 1H), 3.97-3.90 (m, 1H), 3.83-3.75 (m, 2H), 3.59-3.54 (m, 1H), 3.28-3.26 (m, 2H), 3.06-3.01 (m, 1H), 2.69-2.56 (m, 4H), 1.77-1.75 (m, 4H), 1.54-1.45 (m, 2H). Chiral SFC A (40% MeOH): ee 100%, Rt=4.37 min.

2-phenyl-2-(3-((4-((5,6,7,8-tetrahydro-1,8-naphthyridin-2-yl)methyl)piperidin-1-yl)methyl)azetidin-1-yl) acetic acid (Enantiomeric Compounds 56-E1 and 56-E2)

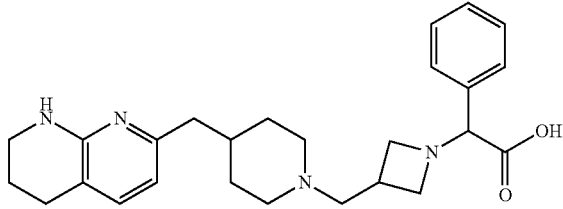 [SMILES: O=C(O)C(c1ccccc1)N1CC(CN2CCC(Cc3ccc4c(n3)NCCC4)CC2)C1]

Compound 56-E1 LC/MS A: 99% purity, UV=214 nm, Rt=1.53 min, ESI 435.4 (M+H)+. $^1$H NMR (400 MHz, MeOD) δ 7.55-7.33 (m, 5H), 7.12 (d, J=7.3 Hz, 1H), 6.32 (d, J=7.3 Hz, 1H), 4.59 (s, 1H), 4.17-4.13 (m, 1H), 3.70 (d, J=8.1 Hz, 2H), 3.53.57-3.39 (m, 1H), 3.44-3.34 (m, 2H), 3.02-2.98 (m, 1H), 2.84 (d, J=11.3 Hz, 2H), 2.74-2.61 (m, 4H), 2.42 (d, J=6.8 Hz, 2H), 2.03 (t, J=11.7 Hz, 2H), 1.93-1.80 (m, 2H), 1.67-1.61 (m, 3H), 1.32-1.26 (m, 2H). Chiral SFC A (45% MeOH): ee 51%, Rt=2.89 min Compound 56-E2 LC/MS A: 99% purity, UV=214 nm, Rt=1.53 min, ESI 435.4 (M+H)+. $^1$H NMR (400 MHz, MeOD) δ 7.55-7.33 (m, 5H), 7.12 (d, J=7.3 Hz, 1H), 6.32 (d, J=7.3 Hz, 1H), 4.59 (s, 1H), 4.17-4.13 (m, 1H), 3.70 (d, J=8.1 Hz, 2H), 3.53.57-3.39 (m, 1H), 3.44-3.34 (m, 2H), 3.02-2.98 (m, 1H), 2.84 (d, J=11.3 Hz, 2H), 2.74-2.61 (m, 4H), 2.42 (d, J=6.8 Hz, 2H), 2.03 (t, J=11.7 Hz, 2H), 1.93-1.80 (m, 2H), 1.67-1.61 (m, 3H), 1.32-1.26 (m, 2H). Chiral SFC A (45% MeOH): ee 100%, Rt=3.84 min 2-phenyl-2-((S)-3-((3-(5,6,7,8-tetrahydro-1,8-naphthyridin-2-yl)propyl)carbamoyl) pyrrolidin-1-yl) acetic acid (Compound 57)

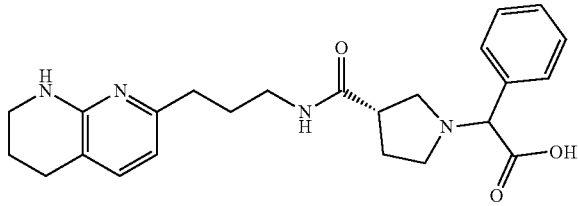 [SMILES: O=C(O)C(c1ccccc1)N1CC[C@H](C(=O)NCCCc2ccc3c(n2)NCCC3)C1]

Compound 57/MS B: 100% purity, UV=214 nm, Rt=1.22 min, ESI 423.3 (M+H)+. 1H NMR (400 MHz, CD3OD) δ 8.49 (s, 1.6H, formate), 7.58-7.43 (m, 6H), 6.52 (d, J=7.2 Hz, 1H), 4.70 (s, 0.6H), 4.56 (s, 0.4H), 3.65-3.56 (m, 1H), 3.47-3.39 (m, 3H), 3.29-3.01 (m, 5H), 2.77 (t, J=6 Hz, 2H), 2.67 (t, J=6 Hz, 2H), 2.36-2.10 (m, 2H), 1.95-1.82 (m, 4H).

2-phenyl-2-((R)-3-(4-(5,6,7,8-tetrahydro-1,8-naphthyridin-2-yl)piperidine-1-carbonyl)pyrrolidin-1-yl) acetic acid (Enantiomeric Compounds 58-E1 and 58-E2)

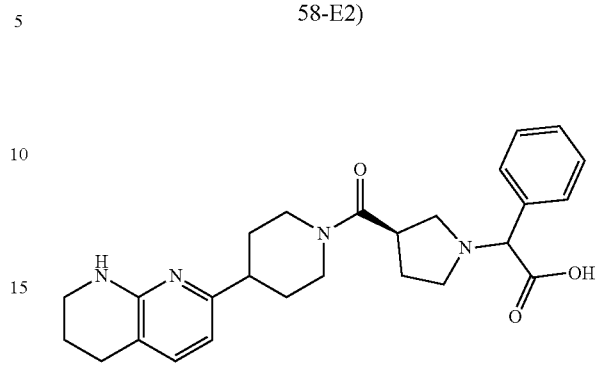

Compound 58-E1 LC/MS B: 97% purity, UV=214 nm, Rt=1.24 min, ESI 449.3 (M+H)+. $^1$H NMR (400 MHz, MeOD) δ 7.62-7.59 (m, 2H), 7.45-7.44 (m, 3H), 7.15 (d, J=7.4 Hz, 1H), 6.37 (t, J=7.0 Hz, 1H), 4.65-4.61 (m, 2H), 4.06 (d, J=13.3 Hz, 1H), 3.73-3.57 (m, 2H), 3.38 (t, J=5.6 Hz, 3H), 3.25-3.14 (m, 3H), 2.75-2.68 (m, 4H), 2.41-2.35 (m, 1H), 2.22-2.10 (m, 1H), 1.96-1.84 (m, 4H), 1.64-1.58 (m, 2H). Chiral SFC B (35% MeOH): ee 98%, Rt=2.15 min.

Compound 58-E2 LC/MS B: 93% purity, UV=214 nm, Rt=1.24 min, ESI 449.3 (M+H)+. $^1$H NMR (400 MHz, MeOD) δ 7.60-7.58 (m, 2H), 7.45-7.43 (m, 3H), 7.14 (d, J=7.2 Hz, 1H), 6.37 (dd, J$_1$=7.4 Hz, 3.1 Hz, 1H), 4.65-4.58 (m, 2H), 4.08 (d, J=13.0 Hz, 1H), 3.72-3.60 (m, 2H), 3.38 (t, J=5.6 Hz, 3H), 3.25-3.18 (m, 2H), 3.04-2.98 (m, 1H), 2.76-2.68 (m, 4H), 2.36-2.27 (m, 1H), 2.17-2.06 (m, 1H), 1.95-1.86 (m, 4H), 1.70-1.54 (m, 2H). Chiral SFC B (35% MeOH): ee 99%, Rt=3.15 min.

2-(3-fluoro-3-(4-((5,6,7,8-tetrahydro-1,8-naphthyridin-2-yl)methyl)piperidine-1-carbonyl)azetidin-1-yl) acetic acid (Compound 59)

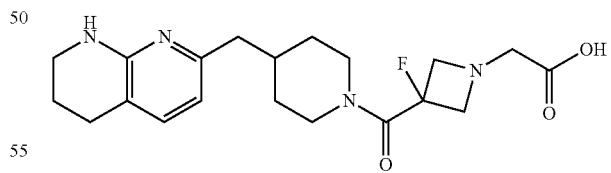

Compound 59 LC/MS B: 100% purity, UV=214 nm, Rt=1.05 min, ESI 391 (M+H)$^+$. $^1$H NMR (400 MHz, MeOD) δ 7.22 (d, J=7.3 Hz, 1H), 6.38 (d, J=7.3 Hz, 1H), 4.49-4.35 (m, 1H), 4.32-4.10 (m, 2H), 4.03-3.86 (m, 2H), 3.67 (m, 1H), 3.51-3.34 (m, 4H), 3.05 (t, J=15.4 Hz, 1H), 2.74-2.68 (m, 3H), 2.57-2.41 (m, 2H), 1.98-1.85 (m, 3H), 1.91-1.81 (m, 2H), 1.33-1.06 (m, 2H).

2-(3-((4-(5,6,7,8-tetrahydro-1,8-naphthyridin-2-yl)butyl)carbamoyl)azetidin-1-yl)acetic acid (Compound 60)

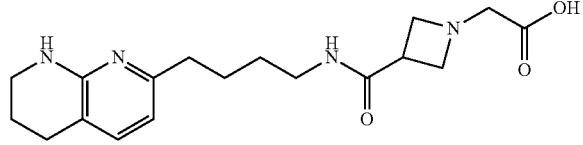 [SMILES: O=C(O)CN1CC(C(=O)NCCCCc2ccc3c(n2)NCCC3)C1]

Compound 60 LC/MS B: 100% purity, UV=214 nm, Rt=1.06 min, ESI 347.1 (M+H)+. ¹H NMR (500 MHz, Methanol-d₄) δ 8.47 (s, 1H), 7.45 (d, J=7.3 Hz, 1H), 6.53 (d, J=7.3 Hz, 1H), 4.36-4.27 (m, 4H), 3.82 (s, 2H), 3.64-3.54 (m, 1H), 3.50-3.43 (m, 2H), 3.30 (t, J=6.8 Hz, 2H), 2.82-2.76 (m, 2H), 2.73-2.65 (m, 2H), 1.98-1.89 (m, 2H), 1.78-1.66 (m, 2H), 1.65-1.54 (m, 2H).

2-(3-fluoro-3-((4-(5,6,7,8-tetrahydro-1,8-naphthyridin-2-yl)butyl)carbamoyl) azetidin-1-yl)acetic acid (Compound 61)

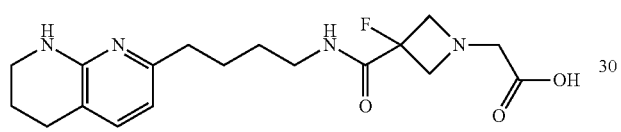

Compound 61 LC/MS A: 100% purity, UV=214 nm, Rt=1.49 min, ESI 365.2 (M+H)+. ¹H NMR (500 MHz, Methanol-d₄) δ 7.20 (d, J=7.3 Hz, 1H), 6.41 (d, J=7.2 Hz, 1H), 3.92 (dd, J=20.0, 10.4 Hz, 2H), 3.76 (dd, J=20.6, 10.3 Hz, 2H), 3.44-3.38 (m, 2H), 3.36-3.28 (m, 4H), 2.73 (t, J=6.3 Hz, 2H), 2.57 (t, J=7.6 Hz, 2H), 1.92-1.85 (m, 2H), 1.71-1.55 (m, 4H).

2-(3-(4-((5,6,7,8-tetrahydro-1,8-naphthyridin-2-yl)methyl)piperidine-1-carbonyl) pyrrolidin-1-yl)acetic acid (Enantiomeric Compounds 62-E1 and 62-E2)

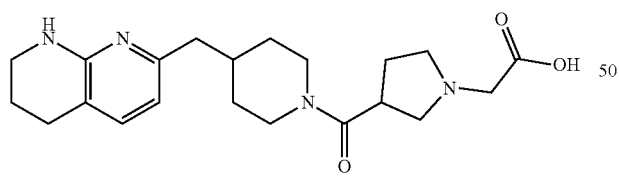

Compound 62-E1 LC/MS A: 100% purity, UV=214 nm, Rt=1.54 min, ESI 387.3 (M+H)+. ¹H NMR (500 MHz, Methanol-d₄) δ 7.16 (d, J=7.3 Hz, 1H), 6.37 (d, J=7.2 Hz, 1H), 4.53-4.45 (m, 1H), 4.02-3.94 (m, 1H), 3.85-3.65 (m, 4H), 3.58-3.36 (m, 5H), 3.14-3.06 (m, 1H), 2.74-2.61 (m, 3H), 2.45 (dd, J=34.6, 7.4 Hz, 3H), 2.18-2.04 (m, 1H), 2.01-1.85 (m, 3H), 1.79-1.66 (m, 2H), 1.26-1.11 (m, 2H). Chiral SFC B (40% MeOH): ee 95%, Rt=1.24 min.

Compound 62-E2 LC/MS A: 100% purity, UV=214 nm, Rt=1.54 min, ESI 387.3 (M+H)+. ¹H NMR (500 MHz, Methanol-d₄) δ 7.16 (d, J=7.3 Hz, 1H), 6.37 (d, J=7.1 Hz, 1H), 4.54-4.45 (m, 1H), 4.02-3.95 (m, 1H), 3.86-3.63 (m, 4H), 3.60-3.36 (m, 5H), 3.10 (td, J=13.3, 2.7 Hz, 1H), 2.76-2.59 (m, 3H), 2.51-2.34 (m, 3H), 2.20-2.06 (m, 1H), 2.02-1.83 (m, 3H), 1.80-1.66 (m, 2H), 1.28-1.08 (m, 2H). Chiral SFC B (40% MeOH): ee 96%, Rt=2.45 min

(R)-2-(3-((4-(5,6,7,8-tetrahydro-1,8-naphthyridin-2-yl)butyl)carbamoyl)pyrrolidin-1-yl)acetic acid (Compound 63)

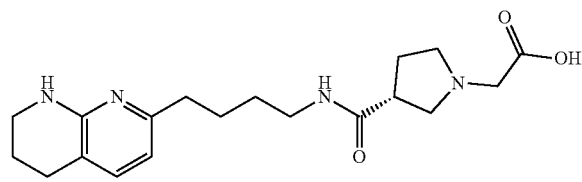 [SMILES: O=C(O)CN1CC[C@@H](C(=O)NCCCCc2ccc3c(n2)NCCC3)C1]

Compound 63 LC/MS A: 100% purity, UV=214 nm, Rt=1.43 min, ESI 361.4 (M+H)+. ¹H NMR (500 MHz, Methanol-d₄) δ 7.24 (d, J=7.3 Hz, 1H), 6.41 (d, J=7.3 Hz, 1H), 3.62 (d, J=15.8 Hz, 1H), 3.43-3.13 (m, 7H), 3.07-2.97 (m, 3H), 2.74 (t, J=6.3 Hz, 2H), 2.66-2.60 (m, 1H), 2.56-2.47 (m, 1H), 2.31-2.23 (m, 1H), 2.09-2.01 (m, 1H), 1.94-1.87 (m, 2H), 1.81-1.71 (m, 1H), 1.69-1.50 (m, 3H).

(S)-2-(3-((4-(5,6,7,8-tetrahydro-1,8-naphthyridin-2-yl)butyl)carbamoyl)pyrrolidin-1-yl)acetic acid (Compound 64)

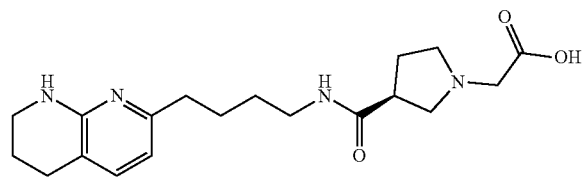 [SMILES: O=C(O)CN1CC[C@H](C(=O)NCCCCc2ccc3c(n2)NCCC3)C1]

Compound 64 LC/MS A: 100% purity, UV=214 nm, Rt=1.43 min, ESI 361.4 (M+H)+. ¹H NMR (500 MHz, Methanol-d₄) δ 7.26 (d, J=7.2 Hz, 1H), 6.42 (d, J=7.3 Hz, 1H), 3.69 (d, J=15.9 Hz, 1H), 3.52-3.38 (m, 4H), 3.38-3.28 (m, 2H), 3.22-3.13 (m, 1H), 3.10-3.01 (m, 3H), 2.77-2.71 (m, 2H), 2.68-2.61 (m, 1H), 2.57-2.48 (m, 1H), 2.36-2.25 (m, 1H), 2.12-2.03 (m, 1H), 1.96-1.86 (m, 2H), 1.83-1.71 (m, 1H), 1.69-1.51 (m, 3H).

2-(3-fluoro-3-(4-((5,6,7,8-tetrahydro-1,8-naphthyridin-2-yl)methyl)piperidine-1-carbonyl)pyrrolidin-1-yl)acetic acid (Compound 65)

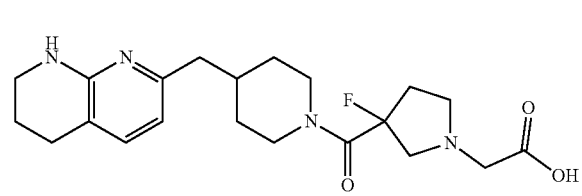 [SMILES: O=C(O)CN1CCC(F)(C(=O)N2CCC(Cc3ccc4c(n3)NCCC4)CC2)C1]

Compound 65 LC/MS A: 100% purity, UV=214 nm, Rt=1.45 min, ESI 405.2 (M+H)+. ¹H NMR (500 MHz, DMSO-d₆) δ 7.23 (d, J=7.3 Hz, 1H), 7.12 (s, 1H), 6.36 (d, J=7.3 Hz, 1H), 4.29 (d, J=12.8 Hz, 1H), 3.98 (d, J=13.4 Hz, 1H), 3.39-3.11 (m, 6H), 3.05-2.91 (m, 2H), 2.70-2.52 (m, 5H), 2.44 (d, J=7.2 Hz, 2H), 2.21-2.04 (m, 1H), 1.99-1.87 (m, 1H), 1.81-1.72 (m, 2H), 1.67-1.55 (m, 2H), 1.18-0.96 (m, 2H).

2-(3-fluoro-3-((4-(5,6,7,8-tetrahydro-1,8-naphthyridin-2-yl)butyl)carbamoyl) pyrrolidin-1-yl)acetic acid (Compound 66)

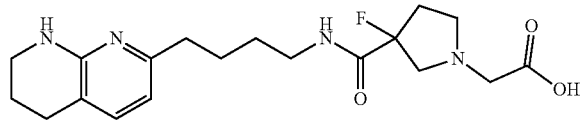 [SMILES: O=C(O)CN1CCC(F)(C(=O)NCCCCc2ccc3c(n2)NCCC3)C1]

Compound 66 LC/MS A: 100% purity, UV=214 nm, Rt=1.59 min, ESI 379.3 (M+H)+. 1H NMR (500 MHz, Methanol-d4) δ 7.37 (d, J=7.3 Hz, 1H), 6.47 (d, J=7.3 Hz, 1H), 3.59-3.50 (m, 2H), 3.48-3.40 (m, 3H), 3.38-3.30 (m, 1H), 3.26-3.05 (m, 4H), 2.79-2.68 (m, 3H), 2.61-2.42 (m, 2H), 2.32-2.19 (m, 1H), 1.95-1.89 (m, 2H), 1.85-1.54 (m, 4H).

2-(4-fluoro-4-(4-((5,6,7,8-tetrahydro-1,8-naphthyridin-2-yl)methyl)piperidine-1-carbonyl)piperidin-1-yl)acetic acid (Compound 67)

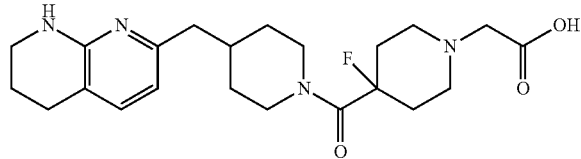 [SMILES: O=C(O)CN1CCC(F)(C(=O)N2CCC(Cc3ccc4c(n3)NCCC4)CC2)CC1]

Compound 67 LC/MS A: 100% purity, UV=214 nm, Rt=1.59 min, ESI 419.3 (M+H)+. 1H NMR (500 MHz, DMSO-d6) δ 7.13 (d, J=7.3 Hz, 1H), 6.33 (d, J=7.3 Hz, 1H), 4.32-4.13 (m, 2H), 3.42-3.25 (m, 6H), 3.08-2.97 (m, 3H), 2.68-2.60 (m, 3H), 2.43-2.27 (m, 4H), 2.21-2.08 (m, 2H), 1.94-1.84 (m, 1H), 1.81-1.72 (m, 2H), 1.68-1.59 (m, 2H), 1.19-0.99 (m, 2H).

2-((1R,3s,5S)-3-(4-((5,6,7,8-tetrahydro-1,8-naphthyridin-2-yl)methyl)piperidine-1-carbonyl)-8-azabicyclo[3.2.1]octan-8-yl)acetic acid (Compound 68)

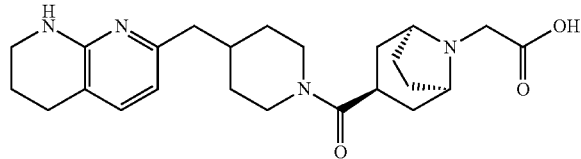 [SMILES: O=C(O)CN1[C@@H]2CC[C@H]1C[C@H](C(=O)N1CCC(Cc3ccc4c(n3)NCCC4)CC1)C2]

Compound 68 LC/MS B: 100% purity, UV=214 nm, Rt=1.05 min, ESI 427.0 (M+H)+. 1H NMR (400 MHz, Methanol-d4) δ 5.87 (d, J=7.3 Hz, 1H), 4.93 (d, J=7.3 Hz, 1H), 2.90 (d, J=13.3 Hz, 1H), 2.55-2.39 (m, 3H), 1.98 (s, 2H), 1.73-1.62 (m, 2H), 1.51 (t, J=12.6 Hz, 1H), 1.23-1.13 (m, 2H), 1.07-0.93 (m, 3H), 0.75-0.04 (m, 14H), −0.29--0.54 (m, 2H).

2-(4-(3-(2-(5,6,7,8-tetrahydro-1,8-naphthyridin-2-yl)ethyl)ureido)piperidin-1-yl)acetic acid (Compound 69)

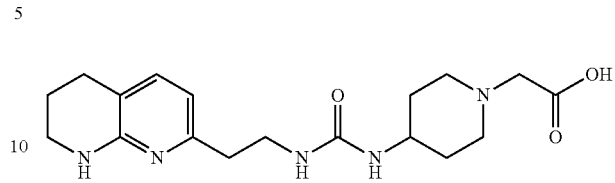

Compound 69 LC/MS A: 97% purity, UV=254 nm, Rt=1.34 min, ESI 362.2 (M+H)+. 1H NMR (500 MHz, Methanol-d4) δ 7.16 (d, J=7.3 Hz, 1H), 6.40 (d, J=7.3 Hz, 1H), 3.78-3.68 (m, 1H), 3.55 (s, 2H), 3.53-3.45 (m, 2H), 3.44-3.37 (m, 4H), 3.13-3.00 (m, 2H), 2.74-2.65 (m, 4H), 2.12-2.03 (m, 2H), 1.93-1.85 (m, 2H), 1.80-1.69 (m, 2H).

(R)-2-(3-((3-(5,6,7,8-tetrahydro-1,8-naphthyridin-2-yl)propyl)carbamoyl)pyrrolidin-1-yl)acetic acid (Compound 70)

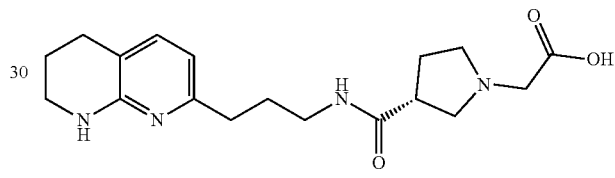

Compound 70 LC/MS A: 100% purity, UV=214 nm, Rt=1.46 min, ESI 347 (M+H)+. 1H NMR (400 MHz, MeOD) δ 7.19 (d, J=7.3 Hz, 1H), 6.41 (d, J=7.3 Hz, 1H), 3.66 (dd, J=35.1, 15.9 Hz, 2H), 3.56-3.31 (m, 5), 3.32-3.08 (m, 4H), 2.71 (t, J=6.2 Hz, 2H), 2.63-2.49 (m, 2H), 2.33 (m, 1H), 2.13 (m, 1H), 1.94-1.77 (m, 4H). Chiral SFC B (40% MeOH): ee 100%, Rt=2.12 min (S)-2-(3-((3-(5,6,7,8-tetrahydro-1,8-naphthyridin-2-yl)propyl)carbamoyl)pyrrolidin-1-yl)acetic acid (Compound 71)

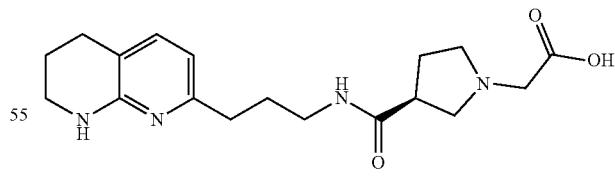

Compound 71 LC/MS A: 100% purity, UV=214 nm, Rt=1.45 min, ESI 347.2 (M+H)+. 1H NMR (500 MHz, Methanol-d4) δ 7.19 (d, J=7.3 Hz, 1H), 6.41 (d, J=7.3 Hz, 1H), 3.68 (d, J=15.9 Hz, 1H), 3.59 (d, J=15.9 Hz, 1H), 3.51-3.43 (m, 1H), 3.43-3.34 (m, 4H), 3.29-3.11 (m, 4H), 2.76-2.69 (m, 2H), 2.63-2.51 (m, 2H), 2.37-2.26 (m, 1H), 2.18-2.08 (m, 1H), 1.95-1.80 (m, 4H). Chiral SFC B (40% MeOH): ee 100%, Rt=1.77 min

2-(1-oxo-2-(3-(5,6,7,8-tetrahydro-1,8-naphthyridin-2-yl)propyl)-2,9-diazaspiro[5.5]undecan-9-yl)acetic acid (Compound 72)

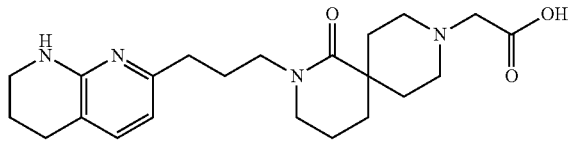 [SMILES: O=C(O)CN1CCC2(CCCN(CCCc3ccc4c(n3)NCCC4)C2=O)CC1]

Compound 72 LC/MS A: 100% purity, UV=214 nm, Rt=1.69 min, ESI 401.3 (M+H)+. 1H NMR (500 MHz, MeOD) δ 7.14 (d, J=7.3 Hz, 1H), 6.40 (d, J=7.3 Hz, 1H), 3.60 (d, J=16.7 Hz, 4H), 3.44-3.35 (m, 6H), 3.19 (s, 2H), 2.71 (t, J=6.2 Hz, 2H), 2.53 (t, J=7.7 Hz, 2H), 2.29 (s, 2H), 1.96-1.81 (m, 8H), 1.81-1.69 (m, 2H).

2-(3-(5-(5,6,7,8-tetrahydro-1,8-naphthyridin-2-yl)pentanamido)azetidin-1-yl)acetic acid (Compound 73)

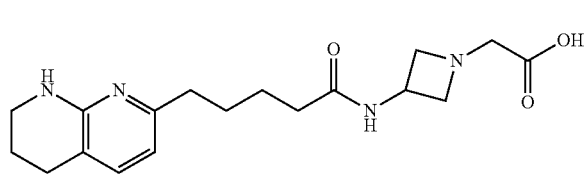 [SMILES: O=C(O)CN1CC(NC(=O)CCCCc2ccc3c(n2)NCCC3)C1]

Compound 73 LC/MS A: 100% purity, UV=214 nm, Rt=1.51 min, ESI 347.3 (M+H)+. $^1$H NMR (500 MHz, Methanol-$d_4$) δ 7.19 (d, J=7.3 Hz, 1H), 6.40 (d, J=7.3 Hz, 1H), 4.58 (p, J=7.4 Hz, 1H), 4.37-4.30 (m, 2H), 4.05-3.97 (m, 2H), 3.74 (s, 2H), 3.43-3.37 (m, 2H), 2.72 (t, J=6.3 Hz, 2H), 2.61-2.52 (m, 2H), 2.30-2.22 (m, 2H), 1.94-1.84 (m, 2H), 1.71-1.60 (m, 4H).

2-(3-(3-(2-(5,6,7,8-tetrahydro-1,8-naphthyridin-2-yl)ethyl)ureido)azetidin-1-yl)acetic acid (Compound 74)

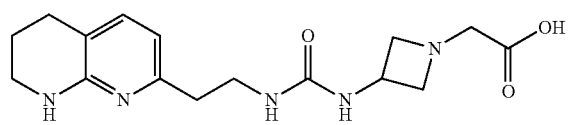 [SMILES: O=C(O)CN1CC(NC(=O)NCCc2ccc3c(n2)NCCC3)C1]

Compound 74 LC/MS A: 100% purity, UV=214 nm, Rt=1.34 min, ESI 334 (M+H)+. $^1$H NMR (500 MHz, MeOD) δ 7.21 (d, J=7.3 Hz, 1H), 6.43 (d, J=7.3 Hz, 1H), 4.52 (brs, 1H), 4.36 (t, J=8.6 Hz, 2H), 4.14-4.01 (m, 2H), 3.80 (s, 2H), 3.41 (d, J=7.0 Hz, 4H), 2.79-2.65 (m, 4H), 1.96-1.82 (m, 2H).

2-(3-(3-(3-(5,6,7,8-tetrahydro-1,8-naphthyridin-2-yl)propyl)ureido)azetidin-1-yl)acetic acid (Compound 75)

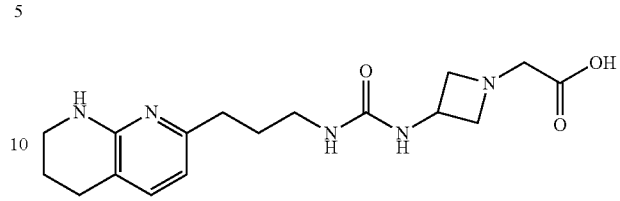

Compound 75 LC/MS C: 100% purity, UV=214 nm, Rt=1.49 min, ESI 348.2 (M+H)+. $^1$H NMR (400 MHz, MeOD) δ 7.15 (d, J=7.3 Hz, 1H), 6.39 (d, J=7.3 Hz, 1H), 4.54-4.45 (m, 1H), 4.23 (t, J=9.1 Hz, 2H), 3.89-3.80 (m, 2H), 3.64 (s, 2H), 3.42-3.36 (m, 2H), 3.14 (t, J=6.9 Hz, 2H), 2.71 (t, J=6.2 Hz, 2H), 2.59-2.49 (m, 2H), 1.90-1.78 (m, 4H),

2-(4-((3-(5,6,7,8-tetrahydro-1,8-naphthyridin-2-yl)propyl)carbamoyl)piperidin-1-yl)propanoic acid (Enantiomeric Compounds 76-E1 and 76-E2)

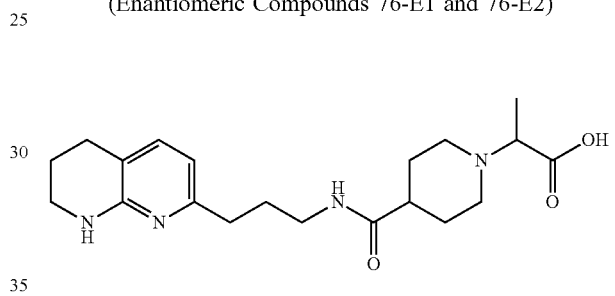

Compound 76-E1 LC/MS A: 96% purity, UV=214 nm, Rt=1.41 min, ESI 375.2 (M+H)+. $^1$H NMR (500 MHz, Methanol-$d_4$) δ 7.16 (d, J=7.3 Hz, 1H), 6.40 (d, J=7.3 Hz, 1H), 3.64-3.52 (m, 3H), 3.41-3.37 (m, 2H), 3.22 (t, J=6.9 Hz, 2H), 3.15-2.99 (m, 2H), 2.72 (t, J=6.4 Hz, 2H), 2.58-2.45 (m, 3H), 2.10-1.96 (m, 4H), 1.93-1.78 (m, 4H), 1.52 (d, J=7.1 Hz, 3H). Chiral SFC B (30% MeOH): ee 100%, Rt=1.98 min Compound 76-E2 LC/MS A: 100% purity, UV=214 nm, Rt=0.91 min, ESI 375.3 (M+H)+. $^1$H NMR (500 MHz, Methanol-$d_4$) δ 7.16 (d, J=7.2 Hz, 1H), 6.39 (d, J=7.4 Hz, 1H), 3.66-3.50 (m, 3H), 3.42-3.37 (m, 2H), 3.22 (t, J=7.0 Hz, 2H), 3.15-2.98 (m, 2H), 2.72 (t, J=6.3 Hz, 2H), 2.55 (t, J=7.7 Hz, 2H), 2.52-2.45 (m, 1H), 2.11-1.97 (m, 4H), 1.93-1.80 (m, 4H), 1.52 (d, J=7.2 Hz, 3H). Chiral SFC B (30% MeOH): ee 99%, Rt=3.36 min

2-(4-methyl-4-(4-((5,6,7,8-tetrahydro-1,8-naphthyridin-2-yl)methyl)piperidine-1-carbonyl)piperidin-1-yl)acetic acid (Compound 77)

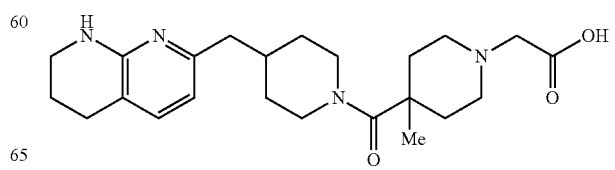

Compound 77 LC/MS A: 100% purity, UV=214 nm, Rt=1.61 min, ESI 415.3 (M+H)+. 1H NMR (500 MHz, Methanol-d4) δ 7.15 (d, J=7.3 Hz, 1H), 6.37 (d, J=7.1 Hz, 1H), 4.36 (d, J=12.9 Hz, 2H), 3.58 (s, 2H), 3.53-3.42 (m, 2H), 3.43-3.36 (m, 2H), 3.21-3.08 (m, 2H), 2.98-2.78 (m, 2H), 2.72 (t, J=6.3 Hz, 2H), 2.47 (d, J=7.2 Hz, 2H), 2.40 (d, J=15.0 Hz, 2H), 2.03-1.93 (m, 1H), 1.92-1.79 (m, 4H), 1.75-1.67 (m, 2H), 1.38 (s, 3H), 1.23-1.12 (m, 2H).

2-(4-hydroxy-4-(4-((5,6,7,8-tetrahydro-1,8-naphthyridin-2-yl)methyl)piperidine-1-carbonyl)piperidin-1-yl)acetic acid (Compound 78)

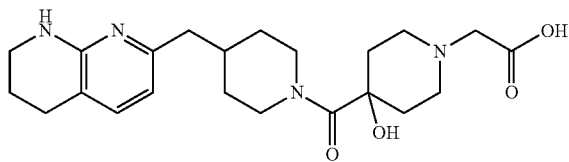 [SMILES: O=C(O)CN1CCC(O)(C(=O)N2CCC(Cc3ccc4c(n3)NCCC4)CC2)CC1]

Compound 78 LC/MS A: 100% purity, UV=214 nm, Rt=1.46 min, ESI 417 (M+H)+. 1H NMR (500 MHz, MeOD) δ 7.15 (d, J=7.3 Hz, 1H), 6.35 (d, J=7.3 Hz, 1H), 4.83 (s, 1H), 4.50 (brs, 1H), 3.53 (brs, 1H), 3.47-3.34 (m, 2H), 3.22 (m, 3H), 3.01 (s, 1H), 2.71 (t, J=6.1 Hz, 2H), 2.60 (brs, 1H), 2.46 (d, J=7.1 Hz, 2H), 2.33 (brs, 1H), 1.98 (d, J=14.6 Hz, 2H), 1.91-1.82 (m, 2H), 1.69 (d, J=11.9 Hz, 21H), 1.21 (brs, 2H).

2-(4-methyl-4-((3-(5,6,7,8-tetrahydro-1,8-naphthyridin-2-yl)propyl)carbamoyl) piperidin-1-yl)acetic acid (Compound 79)

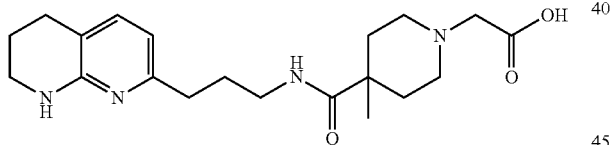

Compound 79 LC/MS A: 100% purity, UV=214 nm, Rt=1.41 min, ESI 375.4 (M+H)+. 1H NMR (500 MHz, Methanol-d4) δ 7.22 (d, J=7.3 Hz, 1H), 6.43 (d, J=7.3 Hz, 1H), 3.56 (s, 2H), 3.42-3.37 (m, 2H), 3.32-3.17 (m, 6H), 2.73 (t, J=6.3 Hz, 2H), 2.62-2.56 (m, 2H), 2.36-2.26 (m, 2H), 1.94-1.81 (m, 4H), 1.79-1.70 (m, 2H), 1.24 (s, 3H).

2-(3,3-difluoro-4-((3-(5,6,7,8-tetrahydro-1,8-naphthyridin-2-yl)propyl)carbamoyl)piperidin-1-yl)acetic acid (Compound 80)

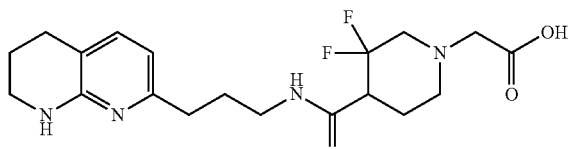

Compound 80 LC/MS A: 100% purity, UV=214 nm, Rt=1.48 min, ESI 397.2 (M+H)+. 1H NMR (500 MHz, Methanol-d4) δ 7.51 (d, J=7.3 Hz, 1H), 6.57 (d, J=7.3 Hz, 1H), 3.48 (t, J=5.6 Hz, 2H), 3.39-3.33 (m, 2H), 3.28-3.17 (m, 3H), 3.08-3.01 (m, 1H), 2.92-2.64 (m, 6H), 2.56 (t, J=11.1 Hz, 1H), 2.17-2.05 (m, 1H), 1.97-1.85 (m, 5H).

2-(2-propionamidophenyl)-2-(4-((3-(5,6,7,8-tetrahydro-1,8-naphthyridin-2-yl)propyl)carbamoyl)piperidin-1-yl)acetic acid (Compound 81)

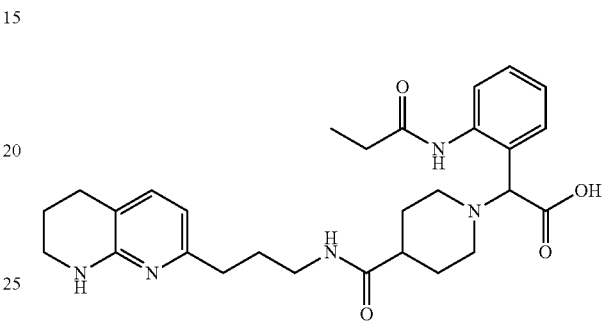

Compound 81 LC/MS A: 100% purity, UV=214 nm, Rt=1.46 min, ESI 508.4 (M+H)+. 1H NMR (500 MHz, MeOD) δ 8.40 (s, 1H), 7.69 (s, 1H), 7.55 (s, 1H), 7.42 (s, 2H), 7.29 (s, 1H), 6.54 (d, J=7.2 Hz, 1H), 3.66 (s, 1H), 3.49-3.40 (m, 2H), 3.26 (m, 4H), 2.96-2.25 (m, 9H), 2.15-1.69 (m, 8H), 1.29 (t, J=7.6 Hz, 3H).

2-(4-hydroxyphenyl)-2-(4-((3-(5,6,7,8-tetrahydro-1,8-naphthyridin-2-yl)propyl) carbamoyl)piperidin-1-yl)acetic acid (Compound 82)

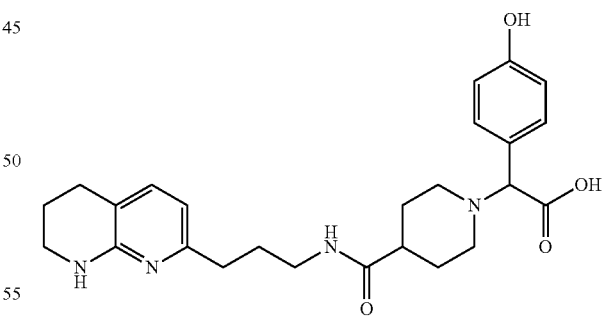

Compound 82 LC/MS A: 99% purity, UV=214 nm, Rt=1.45 min, ESI 453 (M+H)+. 1H NMR (500 MHz, MeOD) δ 7.39 (d, J=8.6 Hz, 2H), 7.15 (d, J=7.3 Hz, 1H), 6.85 (d, J=8.4 Hz, 2H), 6.38 (d, J=7.3 Hz, 1H), 4.37 (s, 1H), 3.72 (s, 1H), 3.42-3.37 (m, 2H), 3.20 (t, J=6.9 Hz, 2H), 3.10 (s, 1H), 2.95 (s, 1H), 2.71 (t, J=6.2 Hz, 3H), 2.57-2.51 (m, 2H), 2.43 (s, 1H), 2.05-1.80 (m, 8H).

211

2-(4-methoxyphenyl)-2-(4-((3-(5,6,7,8-tetrahydro-1,8-naphthyridin-2-yl)propyl) carbamoyl)piperidin-1-yl)acetic acid (Compound 83)

212

2-(6-aminopyridin-3-yl)-2-(4-((3-(5,6,7,8-tetrahydro-1,8-naphthyridin-2-yl)propyl)carbamoyl)piperidin-1-yl)acetic acid (Compound 85)

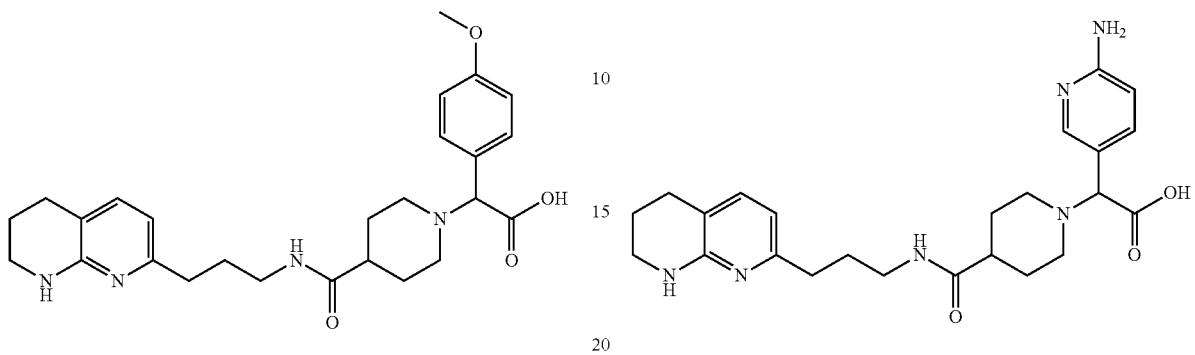

Compound 83 LC/MS A: 98% purity, UV=214 nm, Rt=1.49 min, ESI 467.2 (M+H)+. $^1$H NMR (500 MHz, Methanol-$d_4$) δ 7.49 (d, J=8.7 Hz, 2H), 7.16 (d, J=7.3 Hz, 1H), 6.99 (d, J=8.7 Hz, 2H), 6.38 (d, J=7.4 Hz, 1H), 4.38 (s, 1H), 3.82 (s, 3H), 3.76-3.68 (m, 1H), 3.40-3.35 (m, 2H), 3.20 (t, J=6.9 Hz, 2H), 3.12-3.02 (m, 1H), 2.95-2.84 (m, 1H), 2.81-2.72 (m, 1H), 2.70 (t, J=6.3 Hz, 2H), 2.54 (t, J=7.6 Hz, 2H), 2.47-2.39 (m, 1H), 2.08-1.77 (m, 8H).

Compound 85 LC/MS A: 100% purity, UV=214 nm, Rt=0.90 min, ESI 453 (M+H)+. $^1$H NMR (500 MHz, MeOD) δ 8.01 (d, J=1.4 Hz, 1H), 7.66 (dd, J=8.7, 2.2 Hz, 1H), 7.14 (d, J=7.2 Hz, 1H), 6.62 (d, J=8.8 Hz, 1H), 6.38 (d, J=7.3 Hz, 1H), 4.18 (s, 1H), 3.60 (brs, 1H), 3.44-3.35 (m, 2H), 3.20 (t, J=6.9 Hz, 2H), 3.07 (m, 1H), 2.83-2.65 (m, 3H), 2.58-2.49 (m, 2H), 2.41-2.31 (m, 1H), 2.03-1.76 (m, 8H).

3-(3-(ethylcarbamoyl)phenyl)-2-(4-((3-(5,6,7,8-tetrahydro-1,8-naphthyridin-2-yl)propyl)carbamoyl)piperidin-1-yl)propanoic acid (Compound 84)

2-(4-carbamoylphenyl)-2-(4-((3-(5,6,7,8-tetrahydro-1,8-naphthyridin-2-yl)propyl) carbamoyl)piperidin-1-yl)acetic acid (Compound 86)

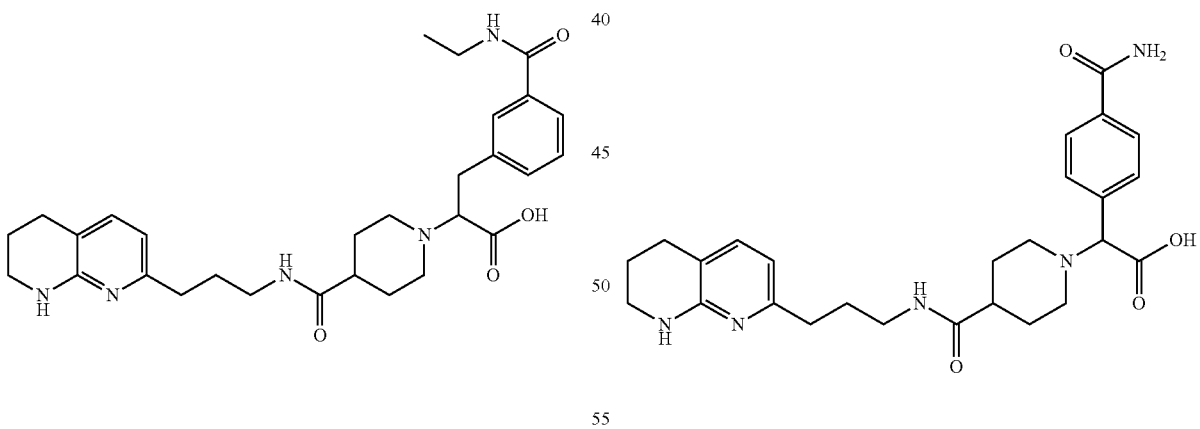

Compound 84 LC/MS A: 98% purity, UV=214 nm, Rt=1.45 min, ESI 522.0 (M+H)+. $^1$H NMR (500 MHz, Methanol-$d_4$) δ 7.74 (t, J=1.9 Hz, 1H), 7.71-7.66 (m, 1H), 7.52-7.48 (m, 1H), 7.43-7.38 (m, 1H), 7.23 (d, J=7.4 Hz, 1H), 6.43 (d, J=7.4 Hz, 1H), 3.67 (t, J=7.1 Hz, 1H), 3.59-3.46 (m, 2H), 3.45-3.37 (m, 4H), 3.26-3.20 (m, 4H), 3.02-2.91 (m, 2H), 2.73 (t, J=6.3 Hz, 2H), 2.58 (t, J=7.7 Hz, 2H), 2.49-2.38 (m, 1H), 2.00-1.78 (m, 8H), 1.25 (t, J=7.3 Hz, 3H).

Compound 86 LC/MS A: 100% purity, UV=214 nm, Rt=0.90 min, ESI 480 (M+H)+. $^1$H NMR (500 MHz, MeOD) δ 7.94 (d, J=8.3 Hz, 2H), 7.69 (d, J=8.3 Hz, 2H), 7.19 (d, J=7.3 Hz, 1H), 6.40 (d, J=7.3 Hz, 1H), 4.43 (s, 1H), 3.73 (brs, 1H), 3.44-3.35 (m, 2H), 3.21 (t, J=6.9 Hz, 2H), 3.12-2.97 (m, 1H), 2.87 (m, 1H), 2.79-2.67 (m, 3H), 2.62-2.49 (m, 2H), 2.43 (m, 1H), 2.11-1.92 (m, 3H), 1.88 (m, 3H), 1.82 (m, 2H).

2-(pyridin-2-yl)-2-(4-((3-(5,6,7,8-tetrahydro-1,8-naphthyridin-2-yl)propyl) carbamoyl)piperidin-1-yl) acetic acid (Compound 87)

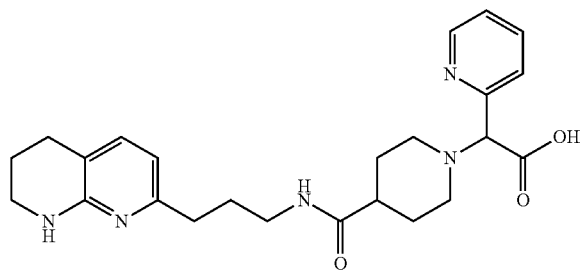 [SMILES: O=C(NCCCc1ccc2c(n1)NCCC2)C1CCN(C(C(=O)O)c2ccccn2)CC1]

Compound 87 LC/MS A: 100% purity, UV=214 nm, Rt=1.54 min, ESI 438 (M+H)+. 1H NMR (400 MHz, MeOD) δ 8.59 (d, J=4.3 Hz, 1H), 7.86 (td, J=7.7, 1.7 Hz, 1H), 7.67 (d, J=7.8 Hz, 1H), 7.41-7.37 (m, 1H), 7.25 (d, J=7.3 Hz, 1H), 6.42 (d, J=7.3 Hz, 1H), 4.48 (s, 1H), 3.66 (d, J=10.9 Hz, 1H), 3.45-3.38 (m, 2H), 3.20 (t, J=6.8 Hz, 2H), 3.07 (d, J=11.4 Hz, 1H), 2.76-2.52 (m, 6H), 2.44-2.36 (m, 1H), 1.97-1.79 (m, 8H).

2-(pyridin-3-yl)-2-(4-((3-(5,6,7,8-tetrahydro-1,8-naphthyridin-2-yl)propyl) carbamoyl)piperidin-1-yl) acetic acid (Compound 88)

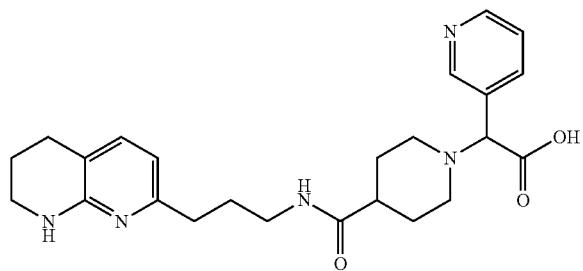 [SMILES: O=C(NCCCc1ccc2c(n1)NCCC2)C1CCN(C(C(=O)O)c2cccnc2)CC1]

Compound 88 LC/MS A: 100% purity, UV=214 nm, Rt=1.48 min, ESI 438 (M+H)+. 1H NMR (500 MHz, MeOD) δ 8.72 (s, 1H), 8.57 (d, J=4.2 Hz, 1H), 8.07 (d, J=8.0 Hz, 1H), 7.50 (dd, J=7.8, 4.9 Hz, 1H), 7.27 (d, J=7.3 Hz, 1H), 6.45 (d, J=7.3 Hz, 1H), 4.34 (s, 1H), 3.63 (s, 1H), 3.44-3.37 (m, 2H), 3.22 (t, J=6.8 Hz, 2H), 3.02 (d, J=11.6 Hz, 1H), 2.74 (t, J=6.2 Hz, 3H), 2.64-2.48 (m, 3H), 2.39 (dd, J=12.8, 8.5 Hz, 1H), 2.04-1.79 (m, 8H).

2-(pyridin-4-yl)-2-(4-((3-(5,6,7,8-tetrahydro-1,8-naphthyridin-2-yl)propyl) carbamoyl)piperidin-1-yl) acetic acid (Compound 89)

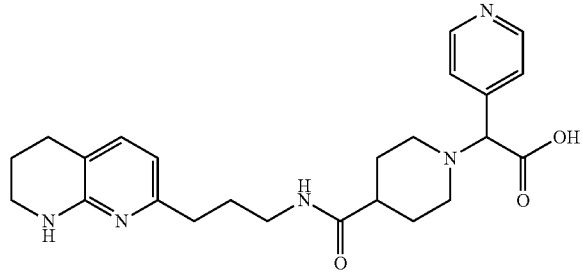 [SMILES: O=C(NCCCc1ccc2c(n1)NCCC2)C1CCN(C(C(=O)O)c2ccncc2)CC1]

Compound 89 LC/MS A: 100% purity, UV=214 nm, Rt=1.38 min, ESI 438 (M+H). 1H NMR (500 MHz, DMSO) δ 8.51 (d, J=5.3 Hz, 2H), 7.76 (t, J=5.3 Hz, 1H), 7.33 (d, J=5.0 Hz, 2H), 7.05 (d, J=7.3 Hz, 1H), 6.35 (s, 1H), 6.27 (d, J=7.2 Hz, 1H), 3.52 (s, 1H), 3.24 (s, 2H), 3.03 (dd, J=12.9, 6.9 Hz, 2H), 2.81 (d, J=10.0 Hz, 2H), 2.61 (dd, J=15.0, 8.9 Hz, 2H), 2.42 (t, J=7.6 Hz, 2H), 2.12-1.88 (m, 3H), 1.76-1.54 (m, 8H).

2-(2-chlorophenyl)-2-(4-((3-(5,6,7,8-tetrahydro-1,8-naphthyridin-2-yl)propyl) carbamoyl)piperidin-1-yl) acetic acid (Compound 90)

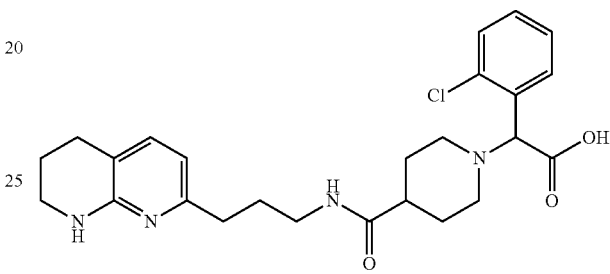

Compound 90 (500 MHz, Methanol-d4) δ 7.84-7.78 (m, 1H), 7.57-7.51 (m, 1H), 7.46-7.37 (m, 2H), 7.20 (d, J=7.3 Hz, 1H), 6.41 (d, J=7.3 Hz, 1H), 4.97 (s, 1H), 3.87-3.77 (m, 1H), 3.42-3.36 (m, 2H), 3.21 (t, J=6.9 Hz, 2H), 3.11-3.03 (m, 1H), 2.98-2.80 (m, 2H), 2.72 (t, J=6.3 Hz, 2H), 2.57 (t, J=7.7 Hz, 2H), 2.50-2.41 (m, 1H), 2.09-1.79 (m, 8H).

2-(3-chlorophenyl)-2-(4-((3-(5,6,7,8-tetrahydro-1,8-naphthyridin-2-yl)propyl) carbamoyl)piperidin-1-yl) acetic acid (Compound 91)

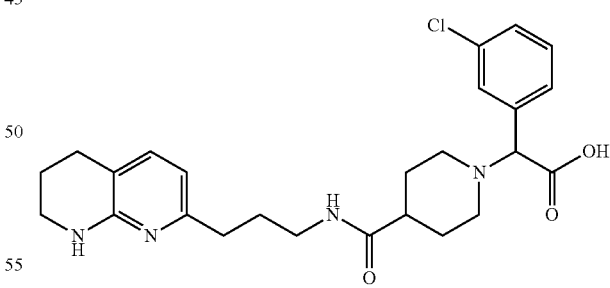

Compound 91 LC/MS A: 100% purity, UV=214 nm, Rt=1.68 min, ESI 471.3 (M+H)+. 1H NMR (500 MHz, Methanol-d4) δ 7.67 (s, 1H), 7.53-7.49 (m, 1H), 7.47-7.40 (m, 2H), 7.22 (d, J=7.3 Hz, 1H), 6.42 (d, J=7.3 Hz, 1H), 4.36 (d, J=3.6 Hz, 1H), 3.75-3.67 (m, 1H), 3.42-3.38 (m, 2H), 3.21 (t, J=6.9 Hz, 2H), 3.09-3.00 (m, 1H), 2.89-2.80 (m, 1H), 2.72 (t, J=6.3 Hz, 3H), 2.57 (t, J=7.7 Hz, 2H), 2.47-2.37 (m, 1H), 2.07-1.80 (m, 8H).

2-(4-chlorophenyl)-2-(4-((3-(5,6,7,8-tetrahydro-1,8-naphthyridin-2-yl)propyl)carbamoyl)piperidin-1-yl)acetic acid (Compound 92)

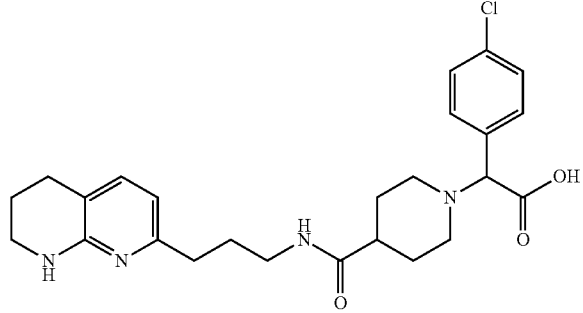 [SMILES: O=C(NCCCc1ccc2c(n1)NCCC2)C1CCN(C(C(=O)O)c2ccc(Cl)cc2)CC1]

Compound 92 LC/MS A: 99% purity, UV=214 nm, Rt=1.52 min, ESI 471.2 (M+H)+. $^1$H NMR (500 MHz, Methanol-$d_4$) δ 7.57 (d, J=8.5 Hz, 2H), 7.49-7.43 (m, 2H), 7.19 (d, J=7.3 Hz, 1H), 6.41 (d, J=7.3 Hz, 1H), 4.40 (s, 1H), 3.77-3.66 (m, 1H), 3.41-3.37 (m, 2H), 3.21 (t, J=6.9 Hz, 2H), 3.11-3.01 (m, 1H), 2.94-2.83 (m, 1H), 2.82-2.67 (m, 3H), 2.56 (t, J=7.6 Hz, 2H), 2.48-2.38 (m, 1H), 2.05-1.79 (m, 8H).

2-(3-carbamoylphenyl)-2-(4-((3-(5,6,7,8-tetrahydro-1,8-naphthyridin-2-yl)propyl)carbamoyl)piperidin-1-yl)acetic acid (Compound 93)

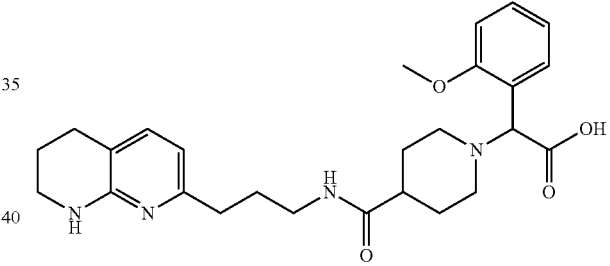

Compound 93 LC/MS A: 100% purity, UV=214 nm, Rt=1.09 min, ESI 480.2 (M+H)+. $^1$H NMR (500 MHz, Methanol-$d_4$) δ 8.07 (d, J=1.9 Hz, 1H), 7.91 (d, J=8.1 Hz, 1H), 7.76 (d, J=7.8 Hz, 1H), 7.58-7.51 (m, 1H), 7.18 (d, J=7.3 Hz, 1H), 6.40 (d, J=7.3 Hz, 1H), 4.42 (s, 1H), 3.79-3.67 (m, 1H), 3.42-3.37 (m, 2H), 3.20 (t, J=6.9 Hz, 2H), 3.09-3.01 (m, 1H), 2.91-2.82 (m, 1H), 2.71 (t, J=6.3 Hz, 3H), 2.55 (t, J=7.7 Hz, 2H), 2.46-2.36 (m, 1H), 2.08-1.80 (m, 8H).

2-(3-methoxyphenyl)-2-(4-((3-(5,6,7,8-tetrahydro-1,8-naphthyridin-2-yl)propyl) carbamoyl)piperidin-1-yl)acetic acid (Compound 94)

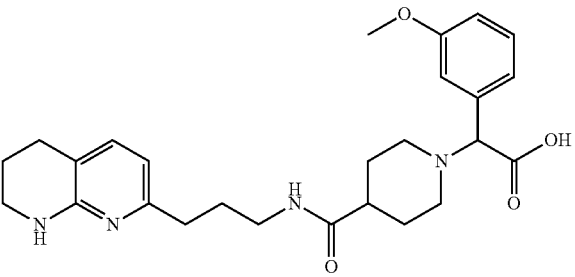 [SMILES: COc1cccc(C(C(=O)O)N2CCC(C(=O)NCCCc3ccc4c(n3)NCCC4)CC2)c1]

Compound 94 LC/MS A: 100% purity, UV=214 nm, Rt=1.50 min, ESI 467.2 (M+H)+. $^1$H NMR (500 MHz, MeOD) δ 7.35 (t, J=8.0 Hz, 1H), 7.21-7.11 (m, 3H), 7.00 (dd, J=8.3, 2.3 Hz, 1H), 6.39 (d, J=7.3 Hz, 1H), 4.38 (s, 1H), 3.75 (s, 1H), 3.46-3.34 (m, 2H), 3.20 (t, J=6.9 Hz, 2H), 3.06 (s, 1H), 2.93 (t, J=8.6 Hz, 1H), 2.82 (s, 1H), 2.71 (t, J=6.3 Hz, 2H), 2.60-2.51 (m, 2H), 2.45 (ddd, J=14.7, 10.4, 4.2 Hz, 1H), 2.20-1.76 (m, 8H).

2-(2-methoxyphenyl)-2-(4-((3-(5,6,7,8-tetrahydro-1,8-naphthyridin-2-yl)propyl) carbamoyl)piperidin-1-yl)acetic acid (Compound 95)

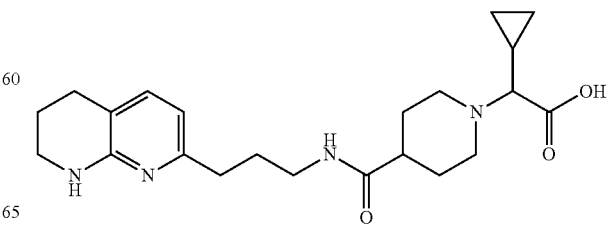

Compound 95 LC/MS A: 100% purity, UV=214 nm, Rt=1.49 min, ESI 467.2 (M+H)+. $^1$H NMR (500 MHz, MeOD) δ 7.56 (dd, J=7.7, 1.5 Hz, 1H), 7.50-7.43 (m, 1H), 7.13 (dd, J=9.7, 8.2 Hz, 2H), 7.05 (t, J=7.4 Hz, 1H), 6.38 (d, J=7.3 Hz, 1H), 4.97 (s, 1H), 3.92 (s, 3H), 3.43-3.34 (m, 2H), 3.21 (dd, J=15.7, 8.8 Hz, 3H), 3.02 (d, J=3.3 Hz, 1H), 2.72 (dd, J=18.3, 12.0 Hz, 2H), 2.59-2.50 (m, 2H), 2.45 (s, 1H), 2.14-1.69 (m, 8H).

2-cyclopropyl-2-(4-((3-(5,6,7,8-tetrahydro-1,8-naphthyridin-2-yl)propyl)carbamoyl) piperidin-1-yl)acetic acid (Compound 96)

Compound 96 LC/MS A: 98% purity, UV=214 nm, Rt=1.42 min, ESI 401.2 (M+H)+. ¹H NMR (500 MHz, Methanol-d₄) δ 7.16 (d, J=7.4 Hz, 1H), 6.40 (d, J=7.3 Hz, 1H), 3.87 (d, J=12.3 Hz, 1H), 3.59 (dd, J=10.2, 6.0 Hz, 1H), 3.42-3.37 (m, 2H), 3.22 (t, J=7.0 Hz, 2H), 3.10-2.96 (m, 2H), 2.84 (d, J=9.5 Hz, 1H), 2.71 (t, J=6.3 Hz, 2H), 2.58-2.53 (m, 2H), 2.53-2.45 (m, 1H), 2.10-1.97 (m, 4H), 1.92-1.79 (m, 4H), 1.18-1.07 (m, 1H), 0.88-0.76 (m, 1H), 0.76-0.64 (m, 2H), 0.62-0.54 (m, 1H).

2-(1H-indol-3-yl)-2-(4-((3-(5,6,7,8-tetrahydro-1,8-naphthyridin-2-yl)propyl) carbamoyl)piperidin-1-yl) acetic acid (Compound 97)

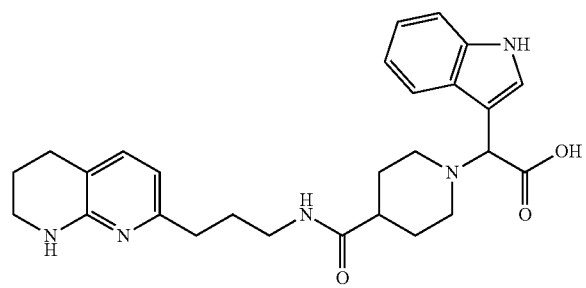 [SMILES: O=C(NCCCc1ccc2c(n1)NCCC2)C1CCN(C(C(=O)O)c2c[nH]c3ccccc23)CC1]

Compound 97 LC/MS A: 100% purity, UV=214 nm, Rt=1.52 min, ESI 476 (M+H)+. ¹H NMR (500 MHz, MeOD) δ 7.78 (d, J=7.9 Hz, 1H), 7.54 (s, 1H), 7.43 (d, J=8.1 Hz, 1H), 7.18 (t, J=7.3 Hz, 1H), 7.12 (t, J=6.9 Hz, 2H), 6.36 (d, J=7.3 Hz, 1H), 4.84 (s, 1H), 3.69 (s, 1H), 3.36 (d, J=5.6 Hz, 3H), 3.18 (t, J=6.9 Hz, 2H), 3.05 (t, J=10.8 Hz, 1H), 2.68 (t, J=6.2 Hz, 3H), 2.52 (t, J=7.6 Hz, 2H), 2.38 (s, 1H), 1.86 (ddt, J=21.9, 14.3, 11.8 Hz, 8H).

2-(1-oxo-2-(2-(5,6,7,8-tetrahydro-1,8-naphthyridin-2-yl)ethyl)-2,9-diazaspiro[5.5]undecan-9-yl)acetic acid (Compound 98)

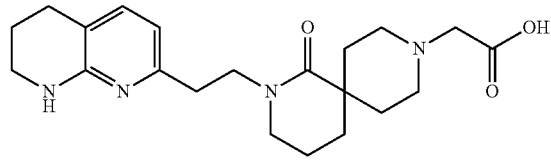 [SMILES: O=C(O)CN1CCC2(CCCN(CCc3ccc4c(n3)NCCC4)C2=O)CC1]

Compound 98 LC/MS A: 100% purity, UV=214 nm, Rt=1.41 min, ESI 387.2 (M+H)+. 1H NMR (500 MHz, MeOD) δ 7.30 (d, J=7.3 Hz, 1H), 6.47 (d, J=7.3 Hz, 1H), 3.70-3.57 (m, 4H), 3.54 (s, 2H), 3.48-3.41 (m, 2H), 3.19 (s, 4H), 2.83 (t, J=6.9 Hz, 2H), 2.76 (t, J=6.2 Hz, 2H), 2.13 (br, 2H), 1.96-1.89 (m, 2H), 1.84 (s, 2H), 1.78-1.69 (m, 2H).

2-(1-oxo-2-(2-(5,6,7,8-tetrahydro-1,8-naphthyridin-2-yl)ethyl)-2,8-diazaspiro[4.5] decan-8-yl)acetic acid (Compound 99)

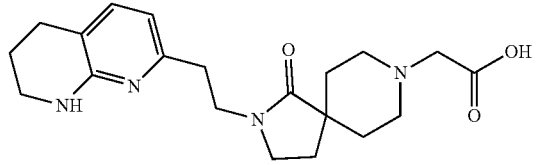 [SMILES: O=C(O)CN1CCC2(CC1)CCN(CCc1ccc3c(n1)NCCC3)C2=O]

Compound 99 LC/MS A: 100% purity, UV=214 nm, Rt=1.36 min, ESI 373.0 (M+H)+. 1H NMR (500 MHz, MeOD) δ 7.14 (d, J=7.3 Hz, 1H), 6.41 (d, J=7.3 Hz, 1H), 3.59 (m, 6H), 3.45-3.34 (m, 4H), 3.18 (s, 2H), 2.74 (dt, J=12.4, 6.5 Hz, 4H), 2.00 (d, J=6.8 Hz, 4H), 1.91-1.81 (m, 2H), 1.71 (d, J=14.1 Hz, 2H).

2-(4-((4-(pyridin-2-ylamino)butyl)carbamoyl)piperidin-1-yl)acetic acid (Compound 100)

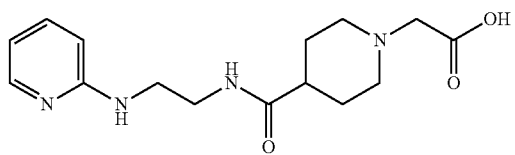 [SMILES: O=C(O)CN1CCC(C(=O)NCCNc2ccccn2)CC1]

Compound 100 LC/MS A: 100% purity, UV=214 nm, Rt=1.30 min, ESI 335.2 (M+H)+. ¹H NMR (500 MHz, MeOD) δ 7.90 (d, J=5.2 Hz, 1H), 7.50 (t, J=7.8 Hz, 1H), 6.60 (dd, J=12.3, 7.5 Hz, 2H), 4.95 (s, 2H), 3.74-3.58 (m, 4H), 3.25 (t, J=5.9 Hz, 2H), 3.07 (s, 2H), 2.57-2.46 (m, 1H), 2.10-1.97 (m, 4H), 1.64 (s, 4H).

2-(4-((3-(5,6,7,8-tetrahydro-1,8-naphthyridin-2-yl) butyl)carbamoyl)piperidin-1-yl)acetic acid (Compound 101)

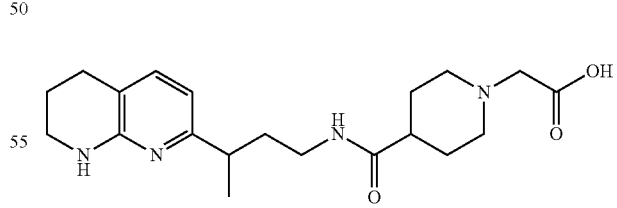

Compound 101 LC/MS B: 100% purity, UV=214 nm, Rt=1.44 min, ESI 375 (M+H). ¹H NMR (500 MHz, MeOD) δ 8.45 (s, 1H), 7.47 (d, J=7.4 Hz, 1H), 6.57 (d, J=7.4 Hz, 1H), 3.71 (t, J=11.2 Hz, 2H), 3.64 (s, 2H), 3.51-3.46 (m, 2H), 3.23-3.17 (m, 2H), 3.10 (s, 2H), 2.86-2.77 (m, 3H), 2.52 (s, 1H), 2.09-2.01 (m, 4H), 1.97-1.87 (m, 3H), 1.82-1.79 (m, 1H), 1.32 (d, J=7.0 Hz, 3H).

2-(4-(phenyl(3-(5,6,7,8-tetrahydro-1,8-naphthyridin-2-yl)propyl)carbamoyl) piperidin-1-yl)acetic acid (Compound 102)

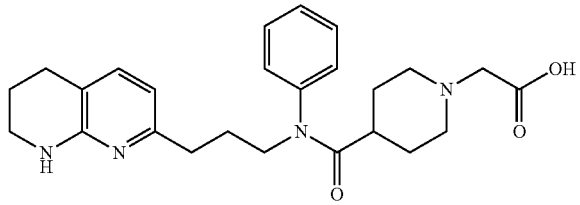 [SMILES: O=C(O)CN1CCC(C(=O)N(CCCc2ccc3c(n2)NCCC3)c2ccccc2)CC1]

Compound 102 LC/MS A: 100% purity, UV=254 nm, Rt=1.53 min, ESI 437 (M+H)+. $^1$H NMR (500 MHz, MeOD) δ 7.53 (dd, J=10.3, 4.7 Hz, 2H), 7.46 (t, J=7.4 Hz, 1H), 7.34 (d, J=7.3 Hz, 2H), 7.16 (d, J=7.3 Hz, 1H), 6.37 (d, J=7.3 Hz, 1H), 3.77-3.72 (m, 2H), 3.56 (d, J=12.6 Hz, 2H), 3.48 (s, 2H), 3.41-3.36 (m, 2H), 2.81-2.68 (m, 4H), 2.56-2.49 (m, 3H), 2.06 (dd, J=23.5, 11.1 Hz, 2H), 1.94-1.84 (m, 6H).

2-(3-((4-(5,6,7,8-tetrahydro-1,8-naphthyridin-2-yl)butyl)carbamoyl)azetidin-1-yl)propanoic acid (Compound 103)

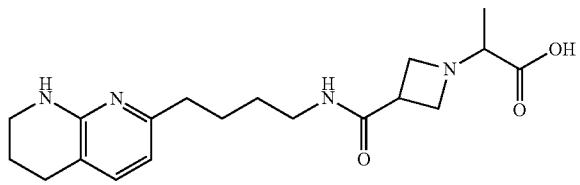 [SMILES: CC(C(=O)O)N1CC(C(=O)NCCCCc2ccc3c(n2)NCCC3)C1]

Compound 103 LC/MS A: 100% purity, UV=214 nm, Rt=1.51 min, ESI 361.3 (M+H)+. 1H NMR (500 MHz, MeOD) δ 7.16 (d, J=7.3 Hz, 1H), 6.38 (d, J=7.3 Hz, 1H), 4.36-4.15 (m, 2H), 4.09 (t, J=9.0 Hz, 2H), 3.74 (q, J=7.0 Hz, 1H), 3.50 (dt, J=16.2, 8.1 Hz, 1H), 3.44-3.36 (m, 2H), 3.25 (t, J=6.9 Hz, 2H), 2.72 (t, J=6.2 Hz, 2H), 2.55 (t, J=7.6 Hz, 2H), 1.95-1.78 (m, 2H), 1.75-1.60 (m, 2H), 1.56-1.39 (m, 2H), 1.39 (d, J=7.1 Hz, 3H).

2-(4-((3-(5,6,7,8-tetrahydro-1,8-naphthyridin-2-yl)propyl)carbamoyl)piperazin-1-yl)propanoic acid (Compound 104)

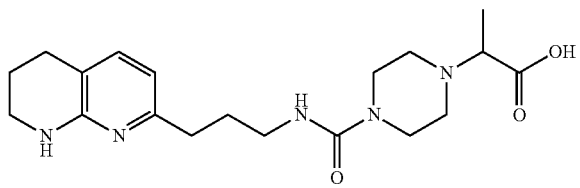 [SMILES: CC(C(=O)O)N1CCN(C(=O)NCCCc2ccc3c(n2)NCCC3)CC1]

Compound 104 LC/MS A: 100% purity, UV=214 nm, Rt=1.34 min, ESI 376 (M+H)+. $^1$H NMR (500 MHz, MeOD) δ 8.50 (s, 1H), 7.50 (d, J=7.3 Hz, 1H), 6.57 (d, J=7.3 Hz, 1H), 3.66 (m, 5H), 3.52-3.44 (m, 2H), 3.41-3.33 (m, 4H), 3.28 (t, J=6.3 Hz, 2H), 2.80 (t, J=6.1 Hz, 2H), 2.75-2.66 (m, 2H), 2.00-1.90 (m, 2H), 1.91-1.81 (m, 2H), 1.55 (d, J=7.2 Hz, 3H).

2-phenyl-2-(4-((3-(5,6,7,8-tetrahydro-1,8-naphthyridin-2-yl)propyl)carbamoyl) piperazin-1-yl)acetic acid (Compound 105)

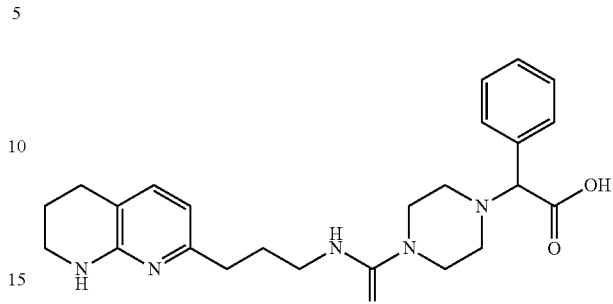

Compound 105 LC/MS A: 100% purity, UV=214 nm, Rt=1.42 min, ESI 438 (M+H)+. $^1$H NMR (500 MHz, MeOD) δ 7.55 (d, J=8.2 Hz, 2H), 7.42-7.29 (m, 4H), 6.49 (d, J=7.3 Hz, 1H), 4.01 (s, 1H), 3.55-3.44 (m, 3H), 3.43-3.38 (m, 3H), 3.22 (m, 2H), 2.79 (m, 4H), 2.63 (m, 4H), 1.95-1.79 (m, 4H).

2-(4-fluoro-4-((3-(5,6,7,8-tetrahydro-1,8-naphthyridin-2-yl)propyl)carbamoyl) piperidin-1-yl)propanoic acid (Compound 106)

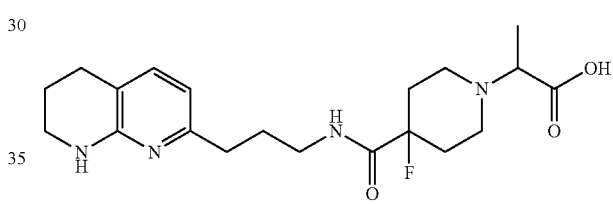

Compound 106 LC/MS A: 100% purity, UV=214 nm, Rt=1.41 min, ESI 393.2 (M+H)+. $^1$H NMR (500 MHz, Methanol-$d_4$) δ 7.17 (d, J=7.3 Hz, 1H), 6.41 (d, J=7.4 Hz, 1H), 3.56 (q, J=7.1 Hz, 1H), 3.52-3.44 (m, 2H), 3.41-3.36 (m, 2H), 3.28 (t, J=7.0 Hz, 2H), 3.24-3.09 (m, 2H), 2.72 (t, J=6.0 Hz, 2H), 2.57 (t, J=7.7 Hz, 2H), 2.53-2.38 (m, 2H), 2.15-2.03 (m, 2H), 1.93-1.83 (m, 4H), 1.51 (d, J=7.1 Hz, 3H).

2-(4-fluoro-4-((3-(5,6,7,8-tetrahydro-1,8-naphthyridin-2-yl)propyl)carbamoyl) piperidin-1-yl)-2-phenylacetic acid (Compound 107)

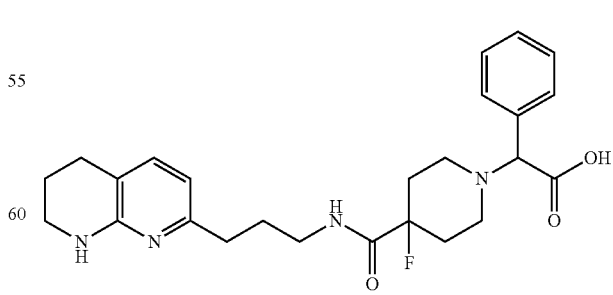

Compound 107 LC/MS A: 100% purity, UV=214 nm, Rt=1.50 min, ESI 455.3 (M+H)+. $^1$H NMR (500 MHz, Methanol-$d_4$) δ 7.63-7.54 (m, 2H), 7.46-7.37 (m, 3H), 7.24

(d, J=7.4 Hz, 1H), 6.43 (d, J=7.3 Hz, 1H), 4.34 (s, 1H), 3.67-3.57 (m, 1H), 3.41-3.37 (m, 2H), 3.26 (t, J=6.9 Hz, 2H), 3.06-2.96 (m, 1H), 2.94-2.87 (m, 1H), 2.85-2.75 (m, 1H), 2.72 (t, J=6.3 Hz, 2H), 2.58 (t, J=7.7 Hz, 2H), 2.54-2.30 (m, 2H), 2.09-2.00 (m, 1H), 1.95-1.81 (m, 5H).

2-(4-methyl-4-((3-(5,6,7,8-tetrahydro-1,8-naphthyridin-2-yl)propyl)carbamoyl) piperidin-1-yl)propanoic acid (Compound 108)

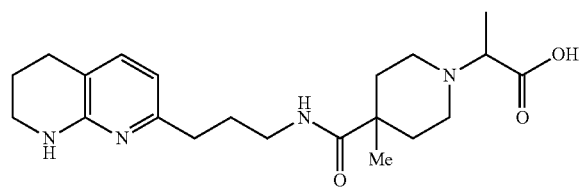 [SMILES: CC(C(=O)O)N1CCC(C)(C(=O)NCCCc2ccc3c(n2)NCCC3)CC1]

Compound 108 LC/MS A: 100% purity, UV=214 nm, Rt=1.41 min, ESI 389.2 (M+H)+. 1H NMR (500 MHz, MeOD) δ 7.23 (d, J=7.3 Hz, 1H), 6.44 (d, J=7.3 Hz, 1H), 3.52 (d, J=7.2 Hz, 1H), 3.44-3.38 (m, 2H), 3.31-3.15 (m, 6H), 2.73 (t, J=6.2 Hz, 2H), 2.64-2.56 (m, 2H), 2.31 (d, J=12.2 Hz, 2H), 1.88 (ddd, J=22.2, 13.4, 6.9 Hz, 4H), 1.73 (ddd, J=19.4, 13.3, 3.9 Hz, 4H), 1.47 (d, J=7.2 Hz, 3H), 1.24 (s, 3H).

2-(4-methyl-4-((3-(5,6,7,8-tetrahydro-1,8-naphthyridin-2-yl)propyl)carbamoyl) piperidin-1-yl)-2-phenylacetic acid (Compound 109)

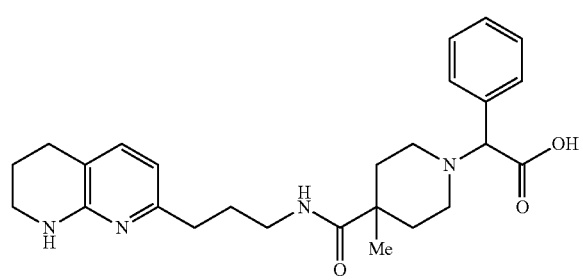 [SMILES: CC1(C(=O)NCCCc2ccc3c(n2)NCCC3)CCN(C(C(=O)O)c2ccccc2)CC1]

Compound 109 LC/MS A: 100% purity, UV=214 nm, Rt=1.49 min, ESI 451.2 (M+H)+. 1H NMR (500 MHz, MeOD) δ 7.55 (dd, J=7.3, 2.1 Hz, 2H), 7.47-7.37 (m, 3H), 7.22 (d, J=7.3 Hz, 1H), 6.43 (d, J=7.3 Hz, 1H), 4.51 (s, 1H), 3.43-3.37 (m, 2H), 3.26 (td, J=6.6, 3.3 Hz, 3H), 2.99 (s, 3H), 2.73 (t, J=6.2 Hz, 2H), 2.58 (dd, J=14.6, 7.2 Hz, 2H), 2.24 (d, J=13.1 Hz, 2H), 1.96-1.65 (m, 6H), 1.22 (s, 3H).

2-(4-hydroxy-4-((3-(5,6,7,8-tetrahydro-1,8-naphthyridin-2-yl)propyl)carbamoyl) piperidin-1-yl)propanoic acid (Compound 110)

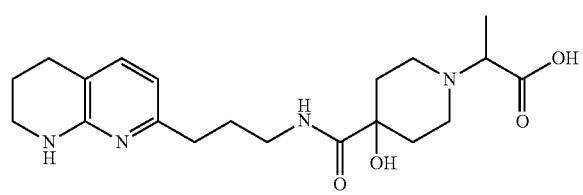 [SMILES: CC(C(=O)O)N1CCC(O)(C(=O)NCCCc2ccc3c(n2)NCCC3)CC1]

Compound 110 LC/MS A: 100% purity, UV=214 nm, Rt=1.38 min, ESI 391 (M+H)+. 1H NMR (500 MHz, MeOD) δ 7.15 (d, J=7.3 Hz, 1H), 6.40 (d, J=7.3 Hz, 1H), 3.62 (q, J=7.1 Hz, 1H), 3.54-3.46 (m, 2H), 3.43-3.37 (m, 2H), 3.33-3.23 (m, 4H), 2.72 (t, J=6.3 Hz, 2H), 2.57 (t, J=7.6 Hz, 2H), 2.40 (td, J=14.6, 4.2 Hz, 2H), 1.92-1.80 (m, 6H), 1.54 (d, J=7.1 Hz, 3H).

2-(4-hydroxy-4-((3-(5,6,7,8-tetrahydro-1,8-naphthyridin-2-yl)propyl)carbamoyl) piperidin-1-yl)-2-phenylacetic acid (Compound 111)

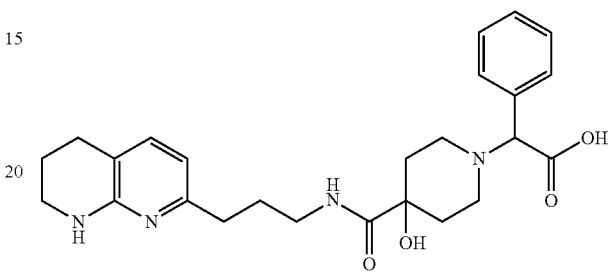

(Compound 111) LC/MS A: 98% purity, UV=214 nm, Rt=1.46 min, ESI 453 (M+H)+. 1H NMR (500 MHz, MeOD) δ 7.61 (dd, J=6.6, 2.9 Hz, 2H), 7.48-7.42 (m, 3H), 7.15 (d, J=7.3 Hz, 1H), 6.39 (d, J=7.3 Hz, 1H), 4.53 (s, 1H), 3.71 (s, 1H), 3.42-3.36 (m, 2H), 3.24 (t, J=6.9 Hz, 3H), 3.01 (d, J=54.4 Hz, 2H), 2.71 (t, J=6.3 Hz, 2H), 2.55 (t, J=7.5 Hz, 2H), 2.45 (t, J=12.3 Hz, 1H), 2.34 (dd, J=19.3, 8.9 Hz, 1H), 1.90-1.78 (m, 5H), 1.69 (d, J=12.8 Hz, 1H).

2-(4-fluoro-4-((3-(5,6,7,8-tetrahydro-1,8-naphthyridin-2-yl)propyl)carbamoyl) piperidin-1-yl)acetic acid (Compound 112)

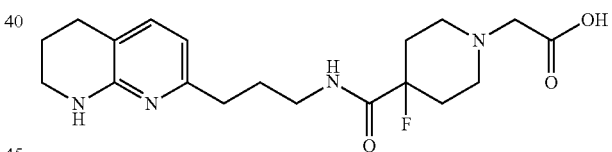

Compound 112 LC/MS A: 100% purity, UV=214 nm, Rt=1.40 min, ESI 379.1 (M+H)+. 1H NMR (500 MHz, Methanol-d4) δ 7.19 (d, J=7.3 Hz, 1H), 6.42 (d, J=7.4 Hz, 1H), 3.48 (s, 2H), 3.46-3.38 (m, 4H), 3.28 (t, J=6.9 Hz, 2H), 3.05-2.95 (m, 2H), 2.72 (t, J=6.2 Hz, 2H), 2.57 (t, J=7.6 Hz, 2H), 2.52-2.36 (m, 2H), 2.06-1.97 (m, 2H), 1.92-1.83 (m, 4H).

2-(4-hydroxy-4-((3-(5,6,7,8-tetrahydro-1,8-naphthyridin-2-yl)propyl)carbamoyl) piperidin-1-yl)acetic acid (Compound 113)

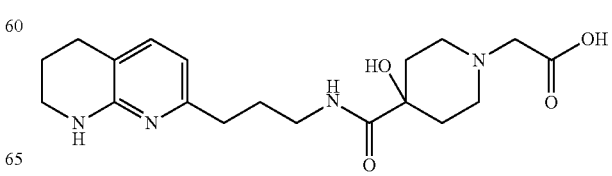

Compound 113 LC/MS A: 100% purity, UV=214 nm, Rt=1.38 min, ESI 377 (M+H)+. 1H NMR (500 MHz, MeOD) δ 7.15 (d, J=7.3 Hz, 1H), 6.40 (d, J=7.3 Hz, 1H), 3.64 (s, 2H), 3.56 (d, J=12.4 Hz, 2H), 3.42-3.37 (m, 2H), 3.27 (dd, J=16.8, 9.9 Hz, 4H), 2.72 (t, J=6.3 Hz, 2H), 2.59-2.53 (m, 2H), 2.39 (td, J=14.5, 4.3 Hz, 2H), 1.92-1.78 (m, 6H).

2-(2-chlorophenyl)-2-((1R,5S,6r)-6-((3-(5,6,7,8-tetrahydro-1,8-naphthyridin-2-yl)propyl)carbamoyl)-3-azabicyclo[3.1.0]hexan-3-yl)acetic acid (Compound 114)

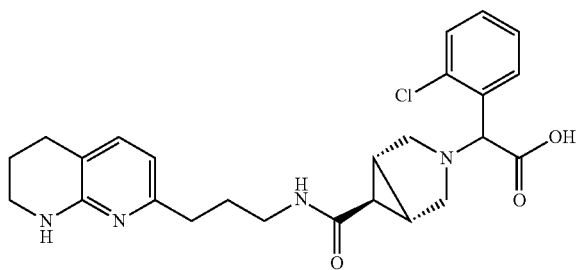 [SMILES: O=C(O)C(c1ccccc1Cl)N1C[C@@H]2[C@H](C1)[C@H]2C(=O)NCCCc1ccc2c(n1)NCCC2]

Compound 114 LC/MS A: 100% purity, UV=214 nm, Rt=1.51 min, ESI 469 (M+H)+. 1H NMR (500 MHz, MeOD) δ 7.76-7.70 (m, 1H), 7.42 (d, J=7.5 Hz, 1H), 7.37 (d, J=7.2 Hz, 1H), 7.34-7.25 (m, 2H), 6.51 (d, J=7.3 Hz, 1H), 4.72 (s, 1H), 3.43 (dd, J=12.2, 7.0 Hz, 3H), 3.22 (t, J=6.7 Hz, 2H), 2.95 (d, J=7.0 Hz, 1H), 2.87 (d, J=9.8 Hz, 1H), 2.76 (t, J=6.1 Hz, 3H), 2.63 (t, J=7.5 Hz, 2H), 2.09 (s, 1H), 2.03-1.97 (m, 1H), 1.92 (dt, J=12.0, 5.8 Hz, 3H), 1.85 (dd, J=14.4, 7.2 Hz, 2H).

2-(4-((3-(5,6,7,8-tetrahydro-1,8-naphthyridin-2-yl)propyl)carbamoyl)piperidin-1-yl)propanoic acid (Compound 115)

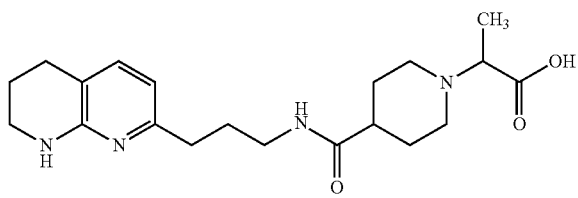 [SMILES: CC(C(=O)O)N1CCC(C(=O)NCCCc2ccc3c(n2)NCCC3)CC1]

Compound 115 LC/MS F: 97% purity, UV 254 nm, Rt=1.896, ESI 375.2 (M+H). 1H NMR (400 MHz, DMSO-d6) δ7.8-7.75 (m, 1H), 7.03 (d, J=7.2 Hz, 1H), 6.34 (bs, 1H), 6.26 (d, 1H), 3.27-3.21 (m, 3H), 3.11-2.99 (m, 4H), 2.62-2.53 (m, 3H), 2.41 (m, 2H), 2.16 (m, 3H), 1.78-1.59 (m, 8H), 1.21 (d, J=7.2 Hz, 3H) 3-methoxy-2-(4-((3-(5,6,7,8-tetrahydro-1,8-naphthyridin-2-yl)propyl)carbamoyl) piperidin-1-yl)propanoic acid (Compound 116)

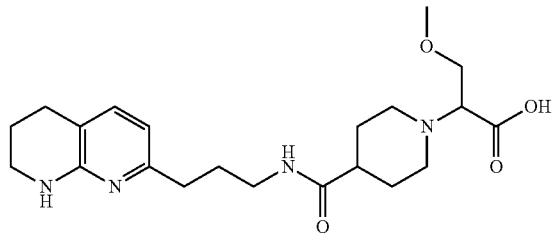 [SMILES: COCC(C(=O)O)N1CCC(C(=O)NCCCc2ccc3c(n2)NCCC3)CC1]

Compound 116 LC/MS F: 96% purity, UV 254 nm, Rt=1.842, ESI 437.2 (M+H). 1H NMR (400 MHz, DMSO-d6) δ7.72 (t, 1H), 7.02 (d, 1H), 6.28 (bs, 1H), 6.24 (d, J=7.24, 1H), 3.68-3.64 (m, 1H), 3.61-3.57 (m, 1H), 3.34 (t, 1H) 3.26-3.21 (q, 5H), 3.05-2.98 (m, 4H), 2.62-2.55 (m, 3H), 2.43-2.37 (m, 2H), 2.17-2.09 (m, 2H), 1.79-1.59 (m, 8H) 3-phenyl-2-(4-((3-(5,6,7,8-tetrahydro-1,8-naphthyridin-2-yl)propyl)carbamoyl) piperidin-1-yl)propanoic acid (Compound 117)

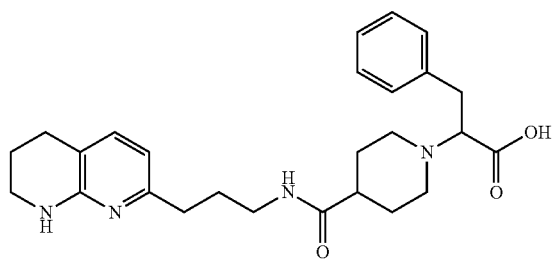 [SMILES: O=C(NCCCc1ccc2c(n1)NCCC2)C1CCN(C(Cc2ccccc2)C(=O)O)CC1]

Compound 117 LC/MS F: 96% purity, UV 254 nm, Rt=3.123 min, ESI 451.2 (M+H). 1H NMR 1H NMR (400 MHz, DMSO-d6) δ 7.66 (t, J=5.6 Hz, 1H), 7.31-7.12 (m, 4H), 6.95 (d, J=7.2 Hz, 1H), 6.21-6.14 (m, 2H), 3.72 (dd, J=10.5, 5.3 Hz, 2H), 3.20-3.12 (m, 2H), 3.08-2.90 (m, 5H), 2.86 (m, 1H), 2.53 (t, J=6.3 Hz, 2H), 2.37 (t, J=6.5 Hz, 2H), 2.14-1.87 (m, 3H), 1.74-1.35 (m, 8H)

2-(4-(N-(3-(5,6,7,8-tetrahydro-1,8-naphthyridin-2-yl)propyl)sulfamoyl)piperidin-1-yl)acetic acid (Compound 118)

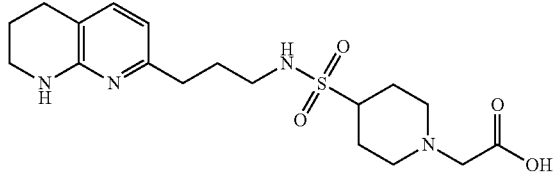 [SMILES: O=C(O)CN1CCC(S(=O)(=O)NCCCc2ccc3c(n2)NCCC3)CC1]

Compound 118 LC/MS F: 96% purity, UV 254 nm ESI 397.2 (M+H). 1H NMR (400 MHz, DMSO-d6) δ 7.04 (t, J=5.7 Hz, 1H), 6.96 (d, J=7.2 Hz, 1H), 6.22-6.15 (m, 2H), 3.21-3.12 (m, 2H), 3.09 (s, 2H), 2.99-2.78 (m, 5H), 2.53 (t, J=6.3 Hz, 2H), 2.42-2.33 (m, 2H), 2.29-2.18 (m, 2H), 1.85 (m, 2H), 1.71-1.52 (m, 6H)

2-((1R,5S,6s)-6-((3-(5,6,7,8-tetrahydro-1,8-naphthyridin-2-yl)propyl)carbamoyl)-3-azabicyclo[3.1.0]hexan-3-yl)acetic acid (Compound 119)

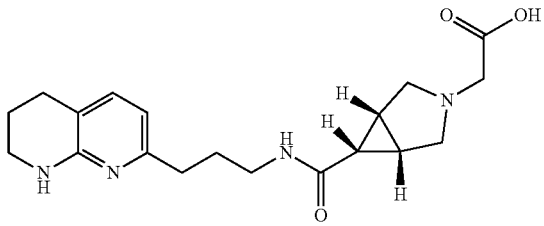 [SMILES: O=C(O)CN1C[C@@H]2[C@H](C1)[C@@H]2C(=O)NCCCc1ccc2c(n1)NCCC2]

Compound 119 LC/MS F: 95% purity, UV 254 nm, Rt=2.78 min, ESI 359.2 (M+H). 1H NMR (400 MHz, DMSO-d$_6$) δ 8.67 (t, J=5.5 Hz, 1H), 7.05-6.98 (d, J=7.2 Hz, 1H), 6.67 (bs, 1H), 6.23 (d, J=7.2 Hz, 1H), 3.38 (d, J=10.7 Hz, 2H), 3.28 (s, 2H) 3.22-3.14 (m, 2H), 3.09-2.92 (m, 4H), 2.54 (t, J=6.3 Hz, 2H), 2.43-2.28 (m, 2H), 1.93-1.85 (m, 2H), 1.74-1.54 (m, 5H).

2-(4-((3-(5,6,7,8-tetrahydro-1,8-naphthyridin-2-yl)propyl)amino)piperidin-1-yl)acetic acid (Compound 120)

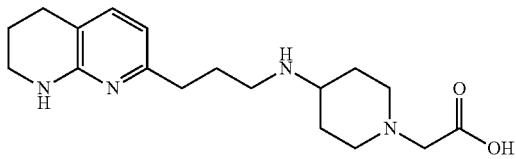 [SMILES: O=C(O)CN1CCC(NCCCc2ccc3c(n2)NCCC3)CC1]

Compound 120 LC/MS F: 95% purity, UV 254 nm ESI 333.2 (M+H). 1H NMR (400 MHz, DMSO-d$_6$) δ 7.04 (d, J=7.3 Hz, 1H), 6.31-6.22 (m, 2H), 3.26-3.22 (m, 2H), 3.15 (s, 2H), 3.09-3.02 (m, 2H), 2.74-2.65 (m, 2H), 2.61 (t, J=6.3 Hz, 2H), 2.50-2.42 (m, 3H), 1.93-1.84 (m, 2H), 1.83-1.7 (m, 4H), 1.56-1.42 (m, 2H).

2-((1R,5S,6r)-6-((3-(5,6,7,8-tetrahydro-1,8-naphthyridin-2-yl)propyl)carbamoyl)-3-azabicyclo[3.1.0]hexan-3-yl)acetic acid (Compound 121)

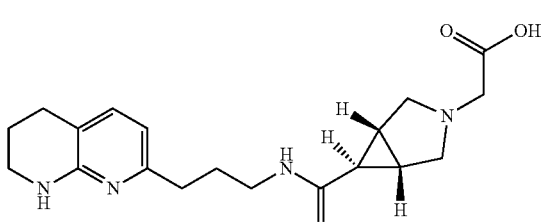

Compound 121 LC/MS F: 95% purity, UV 254 nm, Rt=2.586, ESI 359.2 (M+H). 1H NMR (400 MHz, D2O) δ 7.46 (d, J=7.4 Hz, 1H), 6.52 (d, J=7.3 Hz, 1H), 3.72 (m, 4H), 3.52 (bs, 2H), 3.43-3.35 (m, 2H), 3.18 (t, J=6.6 Hz, 2H), 2.71 (t, J=6.3 Hz, 2H), 2.63 (t, J=7.4 Hz, 2H), 2.19 (t, J=3.1 Hz, 2H), 1.91-1.81 (m, 4H), 1.78 (t, J=3.4 Hz, 1H).

2-phenyl-2-(4-((3-(5,6,7,8-tetrahydro-1,8-naphthyridin-2-yl)propyl)amino)piperidin-1-yl)acetic acid (Compound 122)

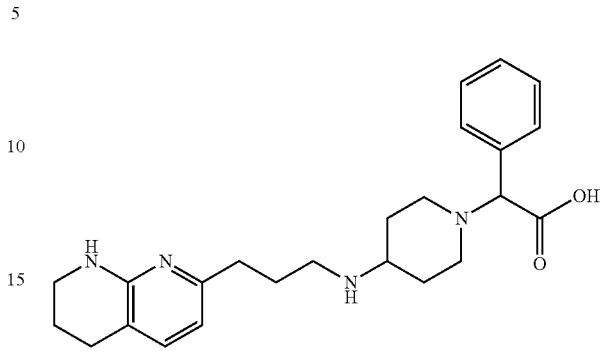

Compound 122 LC/MS F: 98% purity, UV 254 nm, Rt=1.315 min, ESI 409.3 (M+H). 1H NMR (400 MHz, DMSO-d$_6$) δ 7.45-7.28 (m, 5H), 7.06 (d, J=7.3 Hz, 1H), 6.33-6.26 (m, 2H), 4.03 (s, 1H), 3.3-3.22 (m, 2H), 3.07-3.01 (m, 1H), 2.96-2.81 (m, 3H), 2.78-2.73 (m, 1H), 2.62 (t, J=6.2 Hz, 2H), 2.48 (t, J=6.2 Hz, 2H), 2.27-2.2 (m, 1H), 2.09-1.86 (m, 5H), 1.82-1.71 (m, 2H), 1.68-1.54 (m, 2H).

2-(4-((4-methyl-3-(5,6,7,8-tetrahydro-1,8-naphthyridin-2-yl)phenyl)carbamoyl) piperidin-1-yl)acetic acid (Compound 123)

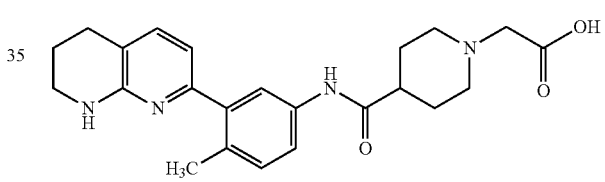

Compound 123 LC/MS F: 97% purity, UV 254 nm, Rt=3.218 min, ESI 409.2 (M+H). 1H NMR (400 MHz, DMSO-d$_6$) δ 9.84 (s, 1H), 7.57 (d, J=2.3 Hz, 1H), 7.45 (dd, J=8.2, 2.3 Hz, 1H), 7.23-7.16 (m, 1H), 7.12 (d, J=8.3 Hz, 1H), 6.45 (d, J=7.3 Hz, 1H), 6.39 (s, 1H), 3.33-3.26 (m, 2H), 3.22 (s, 2H), 3.19-3.13 (m, 2H), 2.69 (t, J=6.2 Hz, 2H), 2.55-2.51 (m, J=3.6 Hz, 2H), 2.43-2.35 (m, 1H), 2.24 (s, 3H), 1.86-1.74 (m, 6H)

2-(4-((4-methyl-3-(5,6,7,8-tetrahydro-1,8-naphthyridin-2-yl)phenyl)carbamoyl) piperidin-1-yl)propanoic acid (Compound 124)

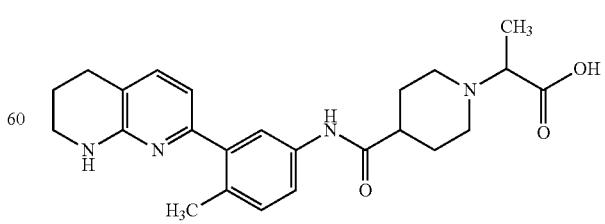

Compound 124 LC/MS F: 99% purity, UV 254 nm, Rt=3.232 min, ESI 423.2 (M+H). 1H NMR (400 MHz, DMSO-d$_6$) δ 9.80 (s, 1H), 7.57 (d, J=2.4 Hz, 1H), 7.44 (dd, J=8.2, 2.4 Hz, 1H), 7.20 (d, J=7.4 Hz, 1H), 7.12 (d, J=8.2 Hz, 1H), 6.45 (d, J=7.3 Hz, 1H), 6.38 (s, 1H), 3.30-3.20 (m, 3H), 3.06 (m, 2H), 2.69 (t, J=6.2 Hz, 2H), 2.59-2.49 (m, 2H), 2.43-2.31 (m, 2H), 2.24 (s, 3H), 1.86-1.65 (m, 6H), 1.21 (d, J=7.0 Hz, 3H).

2-(4-((4-methyl-3-(5,6,7,8-tetrahydro-1,8-naphthyridin-2-yl)phenyl)carbamoyl) piperidin-1-yl)-2-phenylacetic acid (Compound 125)

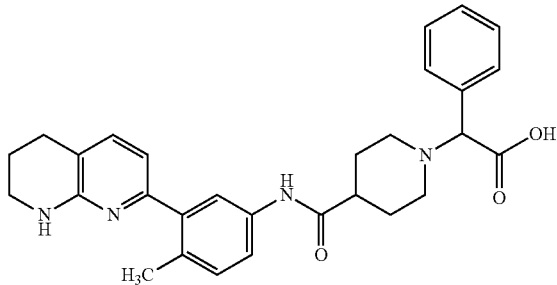 [SMILES: Cc1ccc(NC(=O)C2CCN(C(C(=O)O)c3ccccc3)CC2)cc1-c1ccc2c(n1)NCCC2]

Compound 125 LC/MS F: 95% purity, UV 254 nm, Rt=3.399 min, ESI 485.2 (M+H). 1H NMR (400 MHz, DMSO-d$_6$) δ 9.80 (s, 1H), 7.56 (d, J=2.3 Hz, 1H), 7.48-7.25 (m, 6H), 7.19 (d, J=7.4 Hz, 1H), 7.11 (d, J=8.3 Hz, 1H), 6.45 (d, J=7.2 Hz, 1H), 6.38 (bs, 1H), 3.31-3.26 (s, 4H), 3.22-3.18 (m, 1H), 2.79-3.72 (m, 1H), 2.69 (t, J=6.3 Hz, 2H), 2.43-2.32 (m, 1H), 2.25-2.13 (m, 4H), 1.84-1.70 (m, 6H).

2-(4-(N-(3-(5,6,7,8-tetrahydro-1,8-naphthyridin-2-yl)propyl)sulfamoyl)piperidin-1-yl)propanoic acid (Compound 126)

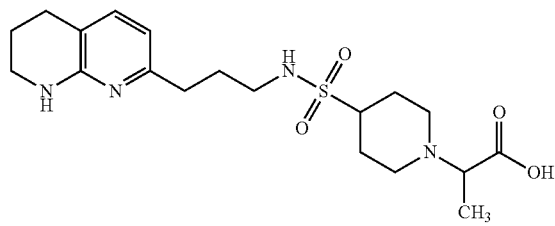 [SMILES: CC(C(=O)O)N1CCC(S(=O)(=O)NCCCc2ccc3c(n2)NCCC3)CC1]

Compound 126 LC/MS F: 99% purity, UV 254 nm, Rt=2.929 min, ESI 411.2 (M+H). 1H NMR (400 MHz, DMSO-d$_6$) δ 7.56-7.49 (d, 7.3 Hz, 1H), 7.36 (t, J=5.8 Hz, 1H), 6.57 (d, J=7.3 Hz, 1H), 3.71-3.61 (m, 1H), 3.42-3.36 (m, 2H), 3.31-3.15 (m, 3H), 3.01-2.95 (m, 2H), 2.9-2.8 (m, 2H), 2.75-2.64 (m, 4H), 2.12-2.03 (m, 2H), 1.94-1.75 (m, 6H), 1.34 (d, J=7.2, 3H).

2-(4-((4-methyl-3-(5,6,7,8-tetrahydro-1,8-naphthyridin-2-yl)benzyl)carbamoyl) piperidin-1-yl)acetic acid (Compound 127)

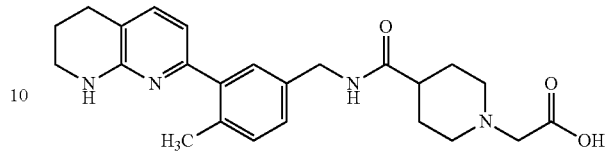

Compound 127 LC/MS F: 97% purity, UV 254 nm, Rt=3.216 min, ESI 423.2 (M+H). 1H NMR (400 MHz, DMSO-d$_6$) δ 8.30 (t, J=5.9 Hz, 1H), 7.23-7.12 (m, 3H), 7.08 (dd, J=7.8, 1.9 Hz, 1H), 6.45 (d, J=7.3 Hz, 1H), 6.38 (s, 1H), 4.23 (d, J=5.9 Hz, 2H), 3.27 (m, 2H), 3.17 (s, 2H), 3.14-3.06 (m, 2H), 2.69 (t, J=6.3 Hz, 2H), 2.50-2.42 (m, 2H), 2.2-2.17 (m, 4H), 1.84-1.67 (m, 6H).

2-(4-((4-methyl-3-(5,6,7,8-tetrahydro-1,8-naphthyridin-2-yl)benzyl)carbamoyl) piperidin-1-yl)propanoic acid (Compound 128)

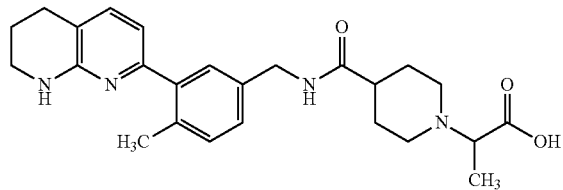 [SMILES: Cc1ccc(CNC(=O)C2CCN(C(C)C(=O)O)CC2)cc1-c1ccc2c(n1)NCCC2]

Compound 128 LC/MS F: 99% purity, UV 254 nm, Rt=3.226 min, ESI 437.2 (M+H). $^1$H NMR (400 MHz, DMSO-d$_6$) δ 8.29 (t, J=5.9 Hz, 1H), 7.23-7.12 (m, 3H), 7.08 (dd, J=7.8, 1.9 Hz, 1H), 6.48-6.38 (m, 2H), 4.23 (d, J=5.9 Hz, 2H), 3.33-3.21 (m, 3H), 3.05 (t, J=13.3 Hz, 2H), 2.69 (t, J=6.3 Hz, 2H), 2.58-2.51 (m, 2H), 2.28-2.21 (m, 4H), 1.83-1.65 (m, 6H), 1.20 (d, J=7.1 Hz, 3H).

Compounds 134-201 were prepared using analogous methods to those used for the preparation of compounds 1-28 and 129-133 according to the general procedures.

2-phenyl-2-(3-(4-(5,6,7,8-tetrahydro-1,8-naphthyridin-2-yl)butoxy)azetidin-1-yl)acetic acid (Enantiomeric Compounds 134-E1 and 134-E2)

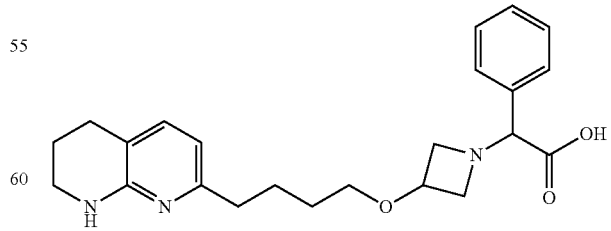

Compound 134-E1 LC/MS ESI 396 (M+H)$^+$ $^1$H NMR (400 MHz, MeOD) δ 7.56-7.35 (m, 5H), 7.15 (d, J=7.3 Hz, 1H), 6.37 (d, J=7.3 Hz, 1H), 4.65 (s, 1H), 4.30-4.28 (m, 2H), 3.93-3.91 (m, 2H), 3.75-3.71 (m, 1H), 3.47-3.36 (m, 4H), 2.70 (t, J=6.3 Hz, 2H), 2.54 (t, J=7.5 Hz, 2H), 1.96-1.81 (m, 2H), 1.76-1.64 (m, 2H), 1.59-1.55 (m, 2H). Chiral SFC B (30% MeOH): ee 100%, Rt=1.06 min Compound 134-E2 LC/MS ESI 396 (M+H)+ $^1$H NMR (400 MHz, MeOD) δ 7.56-7.35 (m, 5H), 7.15 (d, J=7.3 Hz, 1H), 6.37 (d, J=7.3 Hz, 1H), 4.65 (s, 1H), 4.30-4.28 (m, 2H), 3.93-3.91 (m, 2H), 3.75-3.71 (m, 1H), 3.47-3.36 (m, 4H), 2.70 (t, J=6.3 Hz, 2H), 2.54 (t, J=7.5 Hz, 2H), 1.96-1.81 (m, 2H), 1.76-1.64 (m, 2H), 1.59-1.55 (m, 2H). Chiral SFC B (30% MeOH): ee 99.5%, Rt=2.58 min 2-phenyl-2-(3-(5-(5,6,7,8-tetrahydro-1,8-naphthyridin-2-yl)pentyl)azetidin-1-yl)acetic acid (enantiomeric compounds 135-E1 and 135-E2

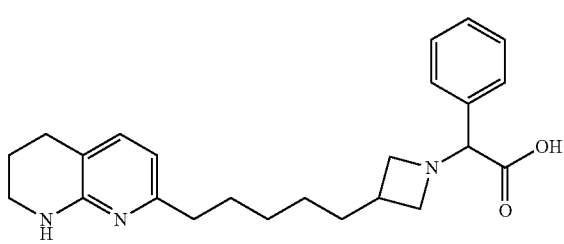 [SMILES: O=C(O)C(c1ccccc1)N1CC(CCCCCc2ccc3c(n2)NCCC3)C1]

Compound 135-E1 LC/MS ESI 394.2 (M+H)+. $^1$H NMR (400 MHz, MeOD) δ 7.51-7.41 (m, 5H), 7.11 (d, J=7.2 Hz, 1H), 6.34 (d, J=7.2 Hz, 1H), 4.67 (s, 1H), 4.22 (s, 1H), 3.77-3.33 (m, 5H), 2.79-2.68 (m, 3H), 2.49 (t, J=7.6 Hz, 2H), 1.92-1.84 (m, 2H), 1.66-1.58 (m, 4H), 1.34-1.22 (m, 4H). Chiral SFC A (40% MeOH): ee 98%, Rt=1.96 min.

Compound 135-E2 LC/MS ESI 394.2 (M+H)+. $^1$H NMR (400 MHz, MeOD) δ 7.40-7.31 (m, 5H), 7.003 (d, J=7.2 Hz, 1H), 6.231 (d, J=7.2 Hz, 1H), 4.55 (s, 1H), 4.10 (s, 1H), 3.63-3.20 (m, 5H), 2.68-2.56 (m, 3H), 2.38 (t, J=7.6 Hz, 2H), 1.80-1.73 (m, 2H), 1.55-1.47 (m, 4H), 1.22-1.11 (m, 4H). Chiral SFC A (40% MeOH): ee 98%, Rt=3.63 min.

2-phenyl-2-((R)-3-(4-((5,6,7,8-tetrahydro-1,8-naphthyridin-2-yl)methyl)piperidine-1-carbonyl)pyrrolidin-1-yl)acetic acid (Diastereomeric Compounds 136-E1 and 136-E2)

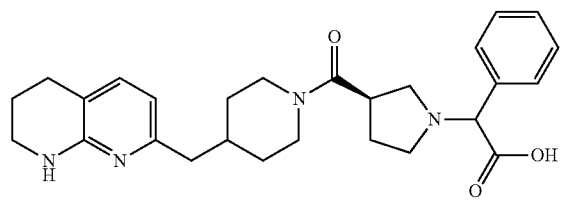 [SMILES: O=C(O)C(c1ccccc1)N1CC[C@@H](C(=O)N2CCC(Cc3ccc4c(n3)NCCC4)CC2)C1]

Compound 136-E1 LC/MS ESI 463.2 (M+H)+. $^1$H NMR (500 MHz, MeOD) δ 7.59-7.56 (m, 2H), 7.44-7.43 (m, 3H), 7.12 (d, J=7.3 Hz, 1H), 6.35 (m, J=5.5 Hz, 1H), 4.46 (m, 2H), 3.94 (d, J=13.5 Hz, 1H), 3.67 (m, 2H), 3.39-3.35 (m, 3H), 3.09-3.02 (m, 3H), 2.69 (m, 3H), 2.46 (m, 2H), 2.43 (m, 1H), 2.11-2.09 (m, 1H), 1.96-1.83 (m, 3H), 1.84-1.65 (m, 2H), 1.19-1.09 (m, 2H). Chiral SFC A (45% MeOH): ee 100%, Rt=2.16 min.

Compound 136-E2 LC/MS ESI 463.2 (M+H)+. $^1$H NMR (500 MHz, MeOD) δ 7.59-7.56 (m, 2H), 7.44-7.43 (m, 3H), 7.12 (d, J=7.3 Hz, 1H), 6.35 (m, J=5.5 Hz, 1H), 4.46 (m, 2H), 3.94 (d, J=13.5 Hz, 1H), 3.67 (m, 2H), 3.39-3.35 (m, 3H), 3.09-3.02 (m, 3H), 2.69 (m, 3H), 2.46 (m, 2H), 2.43 (m, 1H), 2.11-2.09 (m, 1H), 1.96-1.83 (m, 3H), 1.84-1.65 (m, 2H), 1.19-1.09 (m, 2H). Chiral SFC A (45% MeOH): ee 97%, Rt=3.68 min.

2-phenyl-2-((S)-3-(4-((5,6,7,8-tetrahydro-1,8-naphthyridin-2-yl)methyl)piperidine-1-carbonyl)pyrrolidin-1-yl)acetic acid (Diastereomeric Compounds 137-E1 and 137-E2)

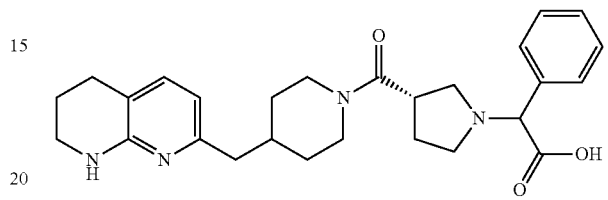

Compound 137-E1 LC/MS ESI 463.2 (M+H)+. $^1$H NMR (500 MHz, MeOD) δ 7.59-7.52 (m, 2H), 7.45-7.37 (m, 3H), 7.12 (d, J=7.3 Hz, 1H), 6.35 (t, J=5.5 Hz, 1H), 4.46 (d, J=13.8 Hz, 2H), 3.91 (d, J=13.5 Hz, 1H), 3.54 (s, 3H), 3.39-3.35 (m, 2H), 3.09-3.02 (m, 3H), 2.69 (t, J=6.2 Hz, 2H), 2.64-2.60 (m, 1H), 2.43 (t, J=7.1 Hz, 2H), 2.30 (d, J=6.7 Hz, 1H), 2.11-2.09 (m, 1H), 1.96-1.83 (m, 3H), 1.73-1.65 (m, 2H), 1.20-1.04 (m, 2H). Chiral SFC A (45% MeOH): ee 100%, Rt=2.41 min Compound 137-E2 LC/MS ESI 463.2 (M+H)+. $^1$H NMR (500 MHz, MeOD) δ 7.59-7.52 (m, 2H), 7.46-7.38 (m, 3H), 7.13 (d, J=7.1 Hz, 1H), 6.33 (d, J=7.3 Hz, 1H), 4.59 (s, 1H), 4.46 (d, J=12.3 Hz, 1H), 3.92 (d, J=13.4 Hz, 1H), 3.63 (s, 2H), 3.39-3.35 (m, 3H), 3.16 (br, 1H), 3.10-3.00 (m, 2H), 2.69 (t, J=6.3 Hz, 2H), 2.61 (t, J=13.3 Hz, 1H), 2.44 (d, J=7.1 Hz, 2H), 2.28 (d, J=18.9 Hz, 1H), 2.11-2.00 (m, 1H), 1.92 (s, 1H), 1.89-1.84 (m, 2H), 1.73-1.65 (m, 2H), 1.20-1.04 (m, 2H). Chiral SFC A (45% MeOH): ee 100%, Rt=3.43 min 2-phenyl-2-((R)-3-(4-(5,6,7,8-tetrahydro-1,8-naphthyridin-2-yl)butylamino)pyrrolidin-1-yl)acetic acid (Diastereomeric Compounds 138-E1 and 138-E2)

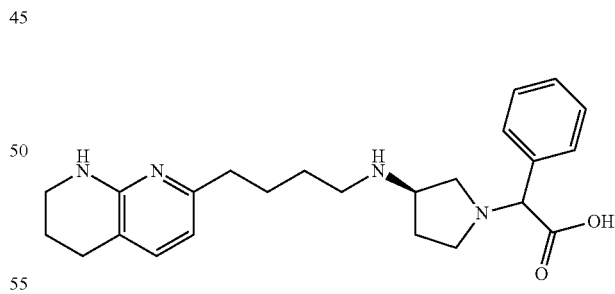

Compound 138-E1 LC/MS ESI 409.2 (M+H)+. $^1$H NMR (500 MHz, MeOD) δ 7.50 (d, J=6.9 Hz, 2H), 7.34-7.29 (m, 3H), 7.18 (d, J=7.3 Hz, 1H), 6.41 (d, J=7.3 Hz, 1H), 3.86 (s, 1H), 3.56 (s, 1H), 3.42-3.38 (m, 2H), 3.32-3.26 (m, 1H), 2.97-2.90 (m, 1H), 2.85-2.80 (m, 1H), 2.75-2.69 (m, 3H), 2.59 (t, J=7.1 Hz, 2H), 2.37-2.30 (m, 2H), 2.25-2.20 (m, 1H), 2.09-2.07 (m, 2H), 2.01-1.94 (m, 1H), 1.92-1.86 (m, 2H), 1.77-1.66 (m, 4H). Chiral SFC F (45% MeOH): ee 100%, Rt=3.6 min.

Compound 138-E2 LC/MS ESI 409.2 (M+H)+. $^1$H NMR (500 MHz, MeOD) δ 7.50 (d, J=6.9 Hz, 2H), 7.34-7.30 (m, 3H), 7.18 (d, J=7.3 Hz, 1H), 6.43 (d, J=7.3 Hz, 1H), 3.86 (s, 1H), 3.56 (s, 1H), 3.45-3.38 (m, 2H), 3.36-3.26 (m, 1H), 2.98-2.90 (m, 1H), 2.83-2.80 (m, 1H), 2.75-2.69 (m, 3H), 2.59 (t, J=7.1 Hz, 2H), 2.35-2.30 (m, 2H), 2.24-2.20 (m, 1H), 2.08-2.07 (m, 2H), 2.02-1.94 (m, 1H), 1.93-1.86 (m, 2H), 1.79-1.66 (m, 4H). Chiral SFC F (45% MeOH): ee 100%, Rt=5.6 min.

2-(2-methoxyphenyl)-2-(4-(4-(5,6,7,8-tetrahydro-1,8-naphthyridin-2-yl)butanamido)piperidin-1-yl)acetic acid (Enantiomeric Compounds 139-E1 and 139-E2)

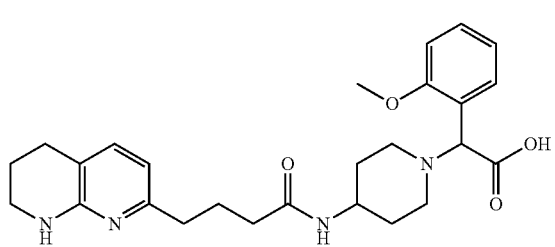 [SMILES: COc1ccccc1C(C(=O)O)N1CCC(NC(=O)CCCc2ccc3c(n2)NCCC3)CC1]

Compound 139-E1 LC/MS ESI 467.1 (M+H)+. 1H NMR (500 MHz, MeOD) δ 7.56 (d, J=7.7 Hz, 1H), 7.47-7.42 (m, 1H), 7.15-7.11 (m, 2H), 7.04 (t, J=7.5 Hz, 1H), 6.37 (d, J=7.3 Hz, 1H), 4.97 (s, 1H), 3.92 (s, 3H), 3.89 (s, 1H), 3.72 (br, 1H), 3.39 (t, J=6 Hz, 2H), 3.17 (s, 1H), 3.09 (t, J=11.2 Hz, 2H), 2.71 (t, J=6.2 Hz, 2H), 2.53 (t, J=7.5 Hz, 2H), 2.20 (t, J=7.5 Hz, 2H), 2.06-2.02 (m, 2H), 1.95-1.84 (m, 6H). Chiral SFC A (45% MeOH): ee 100%, Rt=2.35 min.

Compound 139-E2 LC/MS ESI 467.1 (M+H)+. 1H NMR (500 MHz, MeOD) δ 7.56 (dd, J=7.6 Hz, 1H), 7.47-7.41 (m, 1H), 7.15-7.11 (m, 2H), 7.04 (t, J=7.5 Hz, 1H), 6.37 (d, J=7.3 Hz, 1H), 4.97 (s, 1H), 3.92 (s, 3H), 3.88 (s, 1H), 3.71 (br, 1H), 3.39 (t, J=6 Hz, 2H), 3.16 (s, 1H), 3.08 (t, J=11.3 Hz, 2H), 2.71 (t, J=6.3 Hz, 2H), 2.53 (t, J=7.6 Hz, 2H), 2.20 (t, J=7.5 Hz, 2H), 2.05 (t, J=16.2 Hz, 2H), 1.95-1.76 (m, 6H). Chiral SFC A (45% MeOH): ee 100%, Rt=3.03 min.

2-phenyl-2-((R)-3-(4-(5,6,7,8-tetrahydro-1,8-naphthyridin-2-yl)butanamido)pyrrolidin-1-yl)acetic acid (Diastereomeric Compounds 140-E1 and 140-E2)

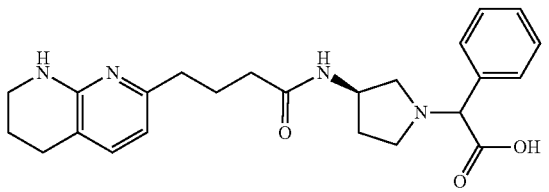 [SMILES: O=C(CCCc1ccc2c(n1)NCCC2)N[C@@H]1CCN(C(C(=O)O)c2ccccc2)C1]

Compound 140-E1 LC/MS ESI 423.2 (M+H)+. 1H NMR (500 MHz, MeOD) δ 7.55 (m, 2H), 7.43-7.39 (m, 3H), 7.24 (d, J=9.0 Hz, 1H), 6.42 (d, J=7.3 Hz, 1H), 4.47 (s, 1H), 4.33 (s, 1H), 3.60-3.44 (m, 4H), 2.99 (s, 2H), 2.74-2.71 (t, J=15.5 Hz, 2H), 2.59-2.55 (t, J=19.3 Hz, 2H), 2.30-2.20 (m, 3H), 2.04-1.85 (m, 5H). Chiral SFC A (45% MeOH): ee 100%, Rt=2.15 min Compound 140-E2 LC/MS ESI 423.2 (M+H)+. 1H NMR (500 MHz, MeOD) δ 7.55 (m, 2H), 7.43-7.39 (m, 3H), 7.24 (d, J=9.0 Hz, 1H), 6.42 (d, J=7.3 Hz, 1H), 4.47 (s, 1H), 4.33 (s, 1H), 3.60-3.44 (m, 4H), 2.99 (s, 2H), 2.74-2.71 (t, J=15.5 Hz, 2H), 2.59-2.55 (t, J=19.3 Hz, 2H), 2.30-2.20 (m, 3H), 2.04-1.85 (m, 5H). Chiral SFC A (45% MeOH): ee 100%, Rt=4.59 min 2-phenyl-2-((R)-3-(4-(2-(5,6,7,8-tetrahydro-1,8-naphthyridin-2-yl)ethyl)oxazol-2-yl)pyrrolidin-1-yl)acetic acid (Diastereomeric Compounds 141-E1 and 141-E2)

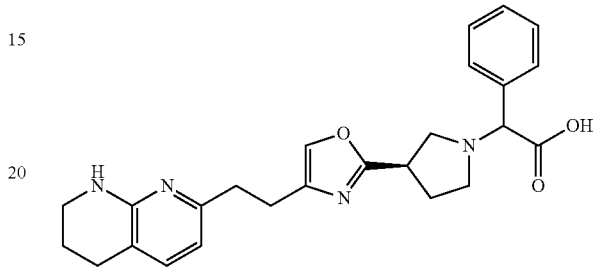

Compound 141-E1 LC/MS ESI 433 (M+H)+ 1H NMR (400 MHz, MeOD) δ 7.60-7.57 (m, 2H), 7.49 (s, 1H), 7.40-7.37 (m, 3H), 7.11 (d, J=7.6 Hz, 1H), 6.34 (d, J=7.2 Hz, 1H), 4.34 (s, 1H), 3.69-3.67 (m, 1H), 3.50-3.23 (m, 5H), 3.03-3.00 (m, 1H), 2.82-2.80 (m, 4H), 2.71-2.68 (m, 2H), 2.39-2.37 (m, 1H), 2.28-2.25 (m, 1H), 1.89-1.86 (m, 2H).

Compound 141-E2 LC/MS ESI 433 (M+H)+ 1H NMR (400 MHz, MeOD) δ 7.60-7.57 (m, 2H), 7.51-7.50 (m, 1H), 7.43-7.38 (m, 3H), 7.16 (d, J=7.2 Hz, 1H), 6.37 (d, J=7.2 Hz, 1H), 4.45 (s, 1H), 3.78-3.75 (m, 2H), 3.39-3.23 (m, 7H), 3.03-3.00 (m, 1H), 2.85-2.83 (m, 4H), 2.71-2.68 (m, 2H), 2.39-2.37 (m, 1H), 2.28-2.25 (m, 1H), 1.89-1.83 (m, 2H).

2-(4-chlorophenyl)-2-(4-((5,6,7,8-tetrahydro-1,8-naphthyridin-2-yl)methyl)-1,4'-bipiperidin-1'-yl)acetic acid (Compound 142)

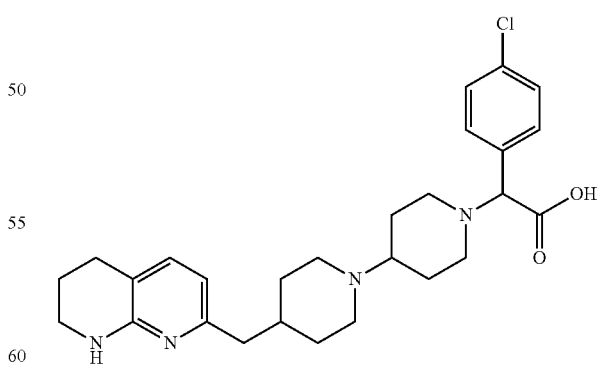

Compound 142 LC/MS ESI 483 (M+H)+. 1H NMR (400 MHz, MeOD) δ 7.50 (d, J=8.8, 2H), 7.32 (d, J=8.4, 2H), 7.14 (d, J=7.2 Hz, 1H), 6.35 (d, J=7.2 Hz, 1H), 3.80 (s, 1H), 3.49-3.31 (m, 5H), 2.95-2.69 (m, 6H), 2.47 (d, J=9.2 Hz, 2H), 2.37-1.67 (m, 11H), 1.51 5-1.38 (m, 2H).

2-(3-chlorophenyl)-2-(4-((5,6,7,8-tetrahydro-1,8-naphthyridin-2-yl)methyl)-1,4'-bipiperidin-1'-yl)acetic acid (Compound 143)

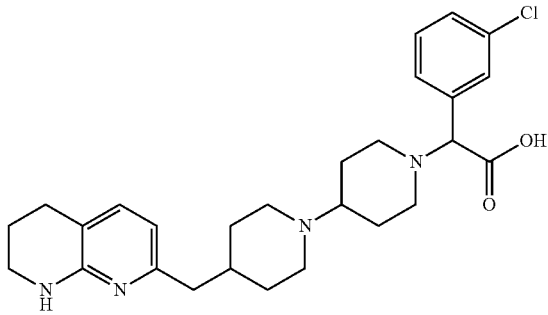 [SMILES: O=C(O)C(c1cccc(Cl)c1)N1CCC(N2CCC(Cc3ccc4c(n3)NCCC4)CC2)CC1]

Compound 143 LC/MS ESI 483.2 (M+H)⁺. ¹H NMR (500 MHz, MeOD) δ 7.61 (s, 1H), 7.44-7.42 (m, 1H), 7.32-7.29 (m, 2H), 7.16 (d, J=7.0 Hz, 1H), 6.38 (d, J=7.3 Hz, 1H), 3.86 (s, 1H), 3.46-3.37 (m, 6H), 3.01 (m, 1H), 2.85 (m, 2H), 2.79 (t, J=6.2 Hz, 2H), 2.51 (t, J=7.5 Hz, 2H), 2.25 (s, 2H), 2.04 (m, 1H), 1.97-1.84 (m, 8H), 1.77 (m, 1H), 1.65 (m, 2H).

2-(2-chlorophenyl)-2-(4-((5,6,7,8-tetrahydro-1,8-naphthyridin-2-yl)methyl)-1,4'-bipiperidin-1'-yl)acetic acid (Enantiomeric Compounds 144-E1 and 144-E2)

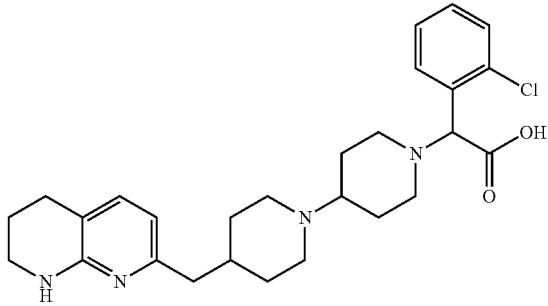 [SMILES: O=C(O)C(c1ccccc1Cl)N1CCC(N2CCC(Cc3ccc4c(n3)NCCC4)CC2)CC1]

Compound 144-E1 LC/MS ESI 483 (M+H)⁺. ¹H NMR (500 MHz, MeOD) δ 7.82 (dd, J=7.7, 1.8 Hz, 1H), 7.41 (dd, J=7.8, 1.3 Hz, 1H), 7.32-7.15 (m, 2H), 7.16 (d, J=7.3 Hz, 1H), 6.37 (d, J=7.3 Hz, 1H), 4.52 (s, 1H), 3.48 (d, J=10.5 Hz, 1H), 3.43-3.35 (m, 4H), 2.99 (s, 1H), 2.88-2.74 (m, 3H), 2.72 (t, J=6.2 Hz, 2H), 2.49 (d, J=6.9 Hz, 2H), 2.37 (s, 1H), 2.22 (s, 1H), 2.04 (d, J=12.0 Hz, 1H), 1.93-1.85 (m, 7H), 1.77-1.67 (m, 1H), 1.51-1.38 (m, 2H). Chiral SFC I (50% EtOH): ee 100%, Rt=8.05 min.

Compound 144-E2 LC/MS ESI 483 (M+H)⁺. ¹H NMR (500 MHz, MeOD) δ 7.82 (dd, J=7.6, 1.8 Hz, 1H), 7.41 (dd, J=7.8, 1.2 Hz, 1H), 7.32-7.15 (m, 2H), 7.16 (d, J=7.3 Hz, 1H), 6.37 (d, J=7.3 Hz, 1H), 4.52 (s, 1H), 3.47 (d, J=9.3 Hz, 1H), 3.42-3.35 (m, 4H), 2.99 (s, 1H), 2.87-2.74 (m, 3H), 2.72 (t, J=6.2 Hz, 2H), 2.49 (d, J=6.9 Hz, 2H), 2.37 (s, 1H), 2.22 (s, 1H), 2.04 (d, J=12.7 Hz, 1H), 1.94-1.82 (m, 7H), 1.76-1.68 (m, 1H), 1.49-1.42 (m, 2H). Chiral SFC I (50% EtOH): ee 100%, Rt=11.00 min.

2-phenyl-2-((3R,3'R)-3-(2-(5,6,7,8-tetrahydro-1,8-naphthyridin-2-yl)ethyl)-1,3'-bipyrrolidin-1'-yl)acetic acid (Compound 145)

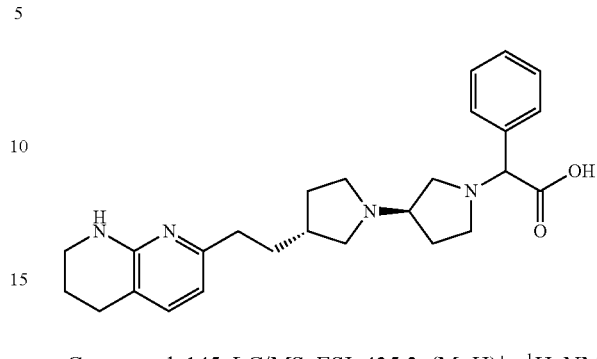

Compound 145 LC/MS ESI 435.2 (M+H)⁺. ¹H NMR (500 MHz, MeOD) δ 7.45-7.40 (m, 2H), 7.25-7.18 (m, 3H), 7.03-7.01 (m, 1H), 6.27 (t, J=7.5 Hz, 1H), 3.78-3.74 (m, 1H), 3.30-3.25 (m, 2H), 3.15-2.90 (m, 2H), 2.85-1.85 (m, 16H), 1.80-1.44 (m, 6H).

2-(3-chlorophenyl)-2-((R)-3-(4-(5,6,7,8-tetrahydro-1,8-naphthyridin-2-yl)butoxy)pyrrolidin-1-yl)acetic acid (Diastereomeric Compounds 146-E1 and 146-E2)

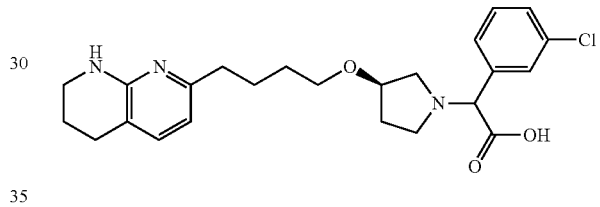

Compound 146-E1 LC/MS ESI 375.2 (M+H)⁺. ¹H NMR (500 MHz, MeOD) δ 7.61 (s, 1H), 7.48-7.39 (m, 3H), 7.20 (d, J=9.0 Hz, 1H), 6.41 (d, J=9.0 Hz, 1H), 4.42 (s, 1H), 4.16 (s, 1H), 3.47-3.37 (m, 5H), 3.13 (m, 1H), 2.98 (m, 1H), 2.73 (t, J=8.0 Hz, 2H), 2.58 (t, J=9.5 Hz, 2H), 2.09 (s, 2H), 1.90-1.88 (m, 2H), 1.74-1.59 (m, 5H). Chiral SFC A (35% MeOH): ee 100%, Rt=2.81 min.

Compound 146-E2 LC/MS ESI 375.2 (M+H)⁺. ¹H NMR (500 MHz, MeOD) δ 7.62 (s, 1H), 7.48-7.39 (m, 3H), 7.20 (d, J=9.0 Hz, 1H), 6.41 (d, J=9.0 Hz, 1H), 4.33 (s, 1H), 4.15 (s, 1H), 3.47-3.37 (m, 4H), 3.27 (m, 2H), 3.05 (m, 2H), 2.73 (t, J=8.0 Hz, 2H), 2.58 (m, 2H), 2.09 (s, 1H), 1.90-1.88 (m, 2H), 1.74 (m, 2H), 1.61 (m, 2H). Chiral SFC A (35% MeOH): ee 100%, Rt=5.23 min.

2-(4-chlorophenyl)-2-((R)-3-(4-(5,6,7,8-tetrahydro-1,8-naphthyridin-2-yl)butoxy)pyrrolidin-1-yl)acetic acid (Diastereomeric Compounds 147-E1 and 147-E2)

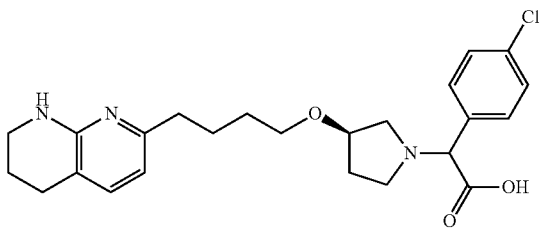 [SMILES: O=C(O)C(c1ccc(Cl)cc1)N1CC[C@@H](OCCCCc2ccc3c(n2)NCCC3)C1]

Compound 147-E1 LC/MS ESI 444 (M+H)+. 1H NMR (400 MHz, MeOD) δ 7.51 (d, J=8.8, 2H), 7.42 (d, J=8.8, 2H), 7.19 (d, J=7.6 Hz, 1H), 6.40 (d, J=7.6 Hz, 1H), 4.49-4.47 (m, 1H), 4.17 (s, 1H), 3.49-3.31 (m, 5H), 3.25-2.91 (m, 3H), 2.98 (t, J=5.6 Hz, 2H), 2.56 (t, J=8.0 Hz, 2H), 2.11-1.61 (m, 8H). Chiral SFC A (40% MeOH): ee 100%, Rt=2.21 min Compound 147-E2 LC/MS ESI 444 (M+H)+. 1H NMR (400 MHz, MeOD) δ 7.51 (d, J=8.8, 2H), 7.42 (d, J=8.8, 2H), 7.19 (d, J=7.6 Hz, 1H), 6.40 (d, J=7.6 Hz, 1H), 4.41-4.37 (m, 1H), 4.18 (s, 1H), 3.49-3.31 (m, 4H), 3.25-2.95 (m, 4H), 2.71 (t, J=6.4 Hz, 2H), 2.65-2.56 (m, 2H), 2.15-1.55 (m, 8H). Chiral SFC A (40% MeOH): ee 100%, Rt=4.29 min 2-(2-chlorophenyl)-2-((R)-3-(4-(5,6,7,8-tetrahydro-1,8-naphthyridin-2-yl)butoxy)pyrrolidin-1-yl)acetic acid (Diastereomeric Compounds 148-E1 and 148-E2)

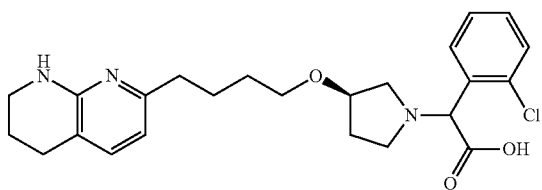 [SMILES: O=C(O)C(c1ccccc1Cl)N1CC[C@@H](OCCCCc2ccc3c(n2)NCCC3)C1]

Compound 148-E1 LC/MS ESI 444 (M+H)+. 1H NMR (400 MHz, MeOD) δ 7.81-7.39 (m, 4H), 7.19 (d, J=7.2 Hz, 1H), 6.40 (d, J=7.6 Hz, 1H), 5.03 (s, 1H), 4.16 (s, 1H), 3.49-3.31 (m, 5H), 3.22-3.05 (m, 3H), 2.73-2.55 (m, 4H), 2.25-1.55 (m, 8H). Chiral SFC F (45% MeOH): ee 100%, Rt=5.41 min.

Compound 148-E2 LC/MS ESI 444 (M+H)+. 1H NMR (400 MHz, MeOD) δ 7.81-7.39 (m, 4H), 7.19 (d, J=7.2 Hz, 1H), 6.40 (d, J=7.6 Hz, 1H), 5.16 (s, 1H), 4.18 (s, 1H), 3.49-3.31 (m, 5H), 3.22-3.05 (m, 3H), 2.73-2.55 (m, 4H), 2.25-1.55 (m, 8H). Chiral SFC F (45% MeOH): ee 100%, Rt=7.48 min.

2-(3-chlorophenyl)-2-((R)-3-(4-(5,6,7,8-tetrahydro-1,8-naphthyridin-2-yl)piperidine-1-carbonyl)pyrrolidin-1-yl)acetic acid (Diastereomeric Compounds 149-E1 and 149-E2)

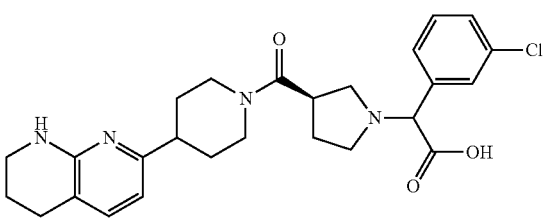 [SMILES: O=C(O)C(c1cccc(Cl)c1)N1CC[C@@H](C(=O)N2CCC(c3ccc4c(n3)NCCC4)CC2)C1]

Compound 149-E1 LC/MS ESI 483.2 (M+H)+. 1H NMR (400 MHz, MeOD) δ 7.56 (s, 1H), 7.52-7.41 (m, 3H), 7.17-7.14 (m, 1H), 6.38 (d, J=7.2 Hz, 1H), 4.63 (d, J=11.6 Hz, 1H), 4.53 (s, 1H), 4.08 (d, J=12.8 Hz, 1H), 3.71-3.58 (m, 2H), 3.40-2.98 (m, 6H), 2.80-2.68 (m, 4H), 2.38-1.85 (m, 6H), 1.73-1.55 (m, 2H). Chiral SFC A (45% MeOH): ee 100%, Rt=1.89 min Compound 149-E2 LC/MS ESI 483.2 (M+H)+. 1H NMR (400 MHz, MeOD) δ 7.56 (s, 1H), 7.52-7.41 (m, 3H), 7.05 (d, J=7.6 Hz, 1H), 6.26 (t, J=7.2 Hz, 1H), 4.53 (d, J=12.4 Hz, 1H), 4.36 (s, 1H), 3.95 (d, J=14.0 Hz, 1H), 3.51-3.38 (m, 5H), 3.18-2.84 (m, 3H), 2.68-2.55 (m, 4H), 2.31-1.75 (m, 6H), 1.60-1.45 (m, 2H). Chiral SFC A (45% MeOH): ee 100%, Rt=3.40 min 2-(2-chlorophenyl)-2-((R)-3-(4-(5,6,7,8-tetrahydro-1,8-naphthyridin-2-yl)piperidine-1-carbonyl)pyrrolidin-1-yl)acetic acid (Compound 150)

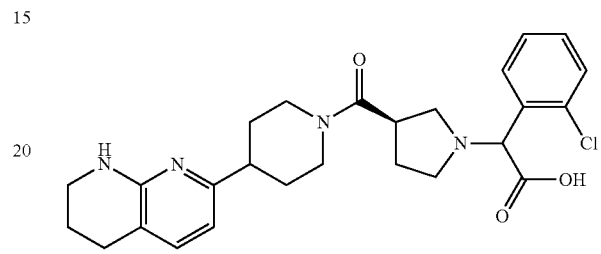

Compound 150 LC/MS ESI 483.2 (M+H)+. 1H NMR (400 MHz, MeOD) δ 7.81-7.75 (m, 1H), 7.58-7.38 (m, 3H), 7.16 (d, J=7.2 Hz, 1H), 6.40-6.35 (m, 1H), 5.24-5.10 (m, 1H), 4.65-4.61 (m, 1H), 4.10-4.06 (m, 1H), 3.71-2.98 (m, 8H), 2.80-2.68 (m, 4H), 2.38-1.81 (m, 6H), 1.75-1.55 (m, 2H).

2-(4-chlorophenyl)-2-((R)-3-(4-(5,6,7,8-tetrahydro-1,8-naphthyridin-2-yl)piperidine-1-carbonyl)pyrrolidin-1-yl)acetic acid (Diastereomeric Compounds 151-E1 and 151-E2)

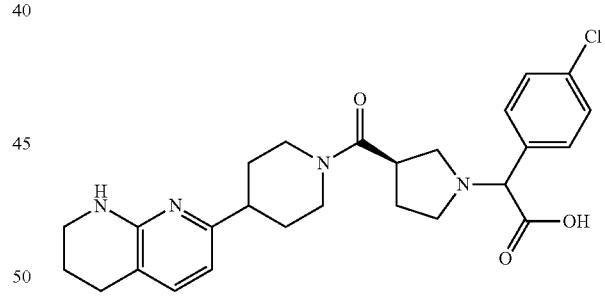

Compound 151-E1 LC/MS ESI 483.2 (M+H)+. 1H NMR (400 MHz, MeOD) δ 7.58 (d, J=7.4 Hz, 2H), 7.45 (d, J=7.4 Hz, 2H), 7.19-7.14 (m, 1H), 6.39-6.36 (m, 1H), 4.65-4.60 (m, 2H), 4.08 (d, J=12.4 Hz, 1H), 3.75-3.58 (m, 2H), 3.40-2.91 (m, 6H), 2.79-2.65 (m, 4H), 2.38-1.82 (m, 6H), 1.72-1.55 (m, 2H). Chiral SFC A (45% MeOH): ee 100%, Rt=1.96 min.

Compound 151-E2 LC/MS ESI 483.2 (M+H)+. 1H NMR (400 MHz, MeOD) δ 7.48-7.45 (m, 2H), 7.33 (d, J=8.4 Hz, 2H), 7.04 (d, J=7.2 Hz, 1H), 6.26 (t, J=7.2 Hz, 1H), 4.50 (d, J=13.2 Hz, 1H), 4.39 (s, 1H), 3.95 (d, J=13.2 Hz, 1H), 3.55-3.31 (m, 5H), 3.18-2.85 (m, 3H), 2.70-2.55 (m, 4H), 2.31-1.72 (m, 6H), 1.60-1.41 (m, 2H). Chiral SFC A (45% MeOH): ee 100%, Rt=3.71 min.

237

2-((R)-3-(4-(5,6,7,8-tetrahydro-1,8-naphthyridin-2-yl)piperidine-1-carbonyl)pyrrolidin-1-yl)-2-(4-(trifluoromethyl)phenyl)acetic acid (Diastereomeric Compounds 152-E1 and 152-E2)

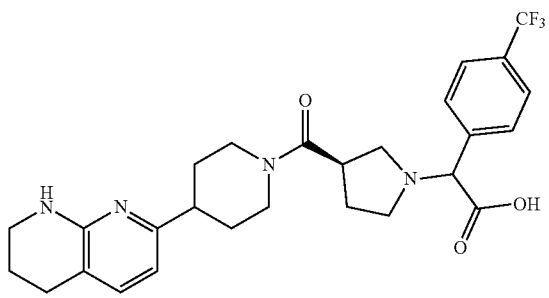 [SMILES: O=C(O)C(c1ccc(C(F)(F)F)cc1)N1CC[C@@H](C(=O)N2CCC(c3ccc4c(n3)NCCC4)CC2)C1]

Compound 152-E1 LC/MS ESI 517 (M+H)+. $^1$H NMR (400 MHz, MeOD) δ 7.80-7.74 (m, 4H), 7.18 (t, J=6.4 Hz, 1H), 6.39 (d, J=7.2 Hz, 1H), 4.71-4.63 (m, 2H), 4.08 (d, J=13.2 Hz, 1H), 3.76-3.58 (m, 2H), 3.42-2.91 (m, 6H), 2.79-2.65 (m, 4H), 2.38-1.82 (m, 6H), 1.72-1.55 (m, 2H). Chiral SFC A (35% MeOH): ee 100%, Rt=2.47 min.

Compound 152-E2 LC/MS ESI 517 (M+H)+. $^1$H NMR (400 MHz, MeOD) δ 7.68-7.56 (m, 4H), 7.03 (d, J=6.8 Hz, 1H), 6.28-6.23 (m, 1H), 4.52 (d, J=12.8 Hz, 1H), 4.23-4.19 (m, 1H), 3.99-3.96 (m, 1H), 3.45-2.65 (m, 8H), 2.62-2.55 (m, 4H), 2.21-1.72 (m, 6H), 1.59-1.42 (m, 2H). Chiral SFC A (35% MeOH): ee 100%, Rt=3.81 min.

2-(4-ethylphenyl)-2-((R)-3-(4-(5,6,7,8-tetrahydro-1,8-naphthyridin-2-yl)butoxy)pyrrolidin-1-yl)acetic acid (Diastereomeric Compounds 153-E1 and 153-E2)

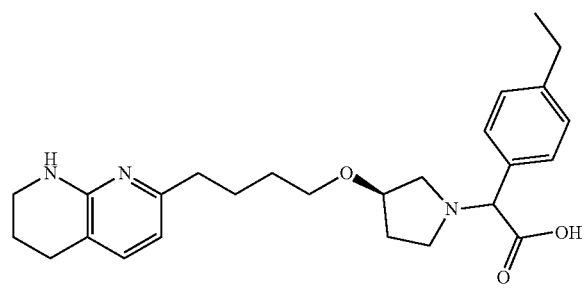 [SMILES: CCc1ccc(C(C(=O)O)N2CC[C@@H](OCCCCc3ccc4c(n3)NCCC4)C2)cc1]

Compound 153-E1 LC/MS ESI 438 (M+H)+ 1H NMR (400 MHz, MeOD) δ 7.43 (d, J=8.4, 2H), 7.26 (d, J=8.0, 2H), 7.15 (d, J=7.2 Hz, 1H), 6.38 (d, J=7.2 Hz, 1H), 4.46 (s, 1H), 4.18 (s, 1H), 3.55-2.95 (m, 8H), 2.73-2.53 (m, 6H), 2.18-1.56 (m, 8H), 1.23 (t, J=7.6 Hz, 3H). Chiral SFC A (35% MeOH): ee 100%, Rt=2.86 min.

Compound 153-E1 LC/MS ESI 438 (M+H)+ $^1$H NMR (400 MHz, MeOD) δ 7.43 (d, J=8.4, 2H), 7.26 (d, J=8.0, 2H), 7.15 (d, J=7.2 Hz, 1H), 6.38 (d, J=7.2 Hz, 1H), 4.34 (s, 1H), 4.05 (s, 1H), 3.41-2.95 (m, 8H), 2.61-2.38 (m, 6H), 2.10-1.46 (m, 8H), 1.13 (t, J=7.6 Hz, 3H). Chiral SFC A (35% MeOH): ee 100%, Rt=4.99 min.

238

2-(3-ethylphenyl)-2-((R)-3-(4-(5,6,7,8-tetrahydro-1,8-naphthyridin-2-yl)butoxy)pyrrolidin-1-yl)acetic acid (Diastereomeric Compounds 154-E1 and 154-E2)

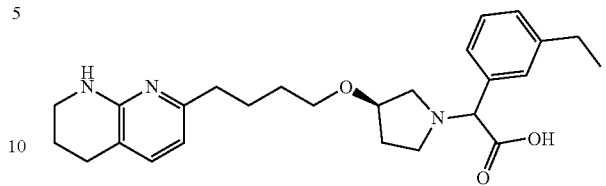

Compound 154-E1 LC/MS ESI 438 (M+H)+ $^1$H NMR (400 MHz, MeOD) δ 7.40-7.25 (m, 4H), 7.14 (d, J=7.2 Hz, 1H), 6.38 (d, J=7.2 Hz, 1H), 4.45 (s, 1H), 4.18 (s, 1H), 3.53-2.95 (m, 8H), 2.72-2.52 (m, 6H), 2.15-1.56 (m, 8H), 1.35 (t, 3H). Chiral SFC A (40% MeOH): ee 100%, Rt=1.88 min.

Compound 154-E2 LC/MS ESI 438 (M+H)+ $^1$H NMR (400 MHz, MeOD) δ 7.30-7.14 (m, 4H), 7.04 (d, J=7.2 Hz, 1H), 6.28 (d, J=7.2 Hz, 1H), 4.34 (s, 1H), 4.06 (s, 1H), 3.43-2.99 (m, 8H), 2.62-2.42 (m, 6H), 2.15-1.46 (m, 8H), 1.25 (t, 3H). Chiral SFC A (40% MeOH): ee 100%, Rt=3.59 min.

2-(2-ethylphenyl)-2-((R)-3-(4-(5,6,7,8-tetrahydro-1,8-naphthyridin-2-yl)butoxy)pyrrolidin-1-yl)acetic acid (Diastereomeric Compounds 155-E1 and 155-E2)

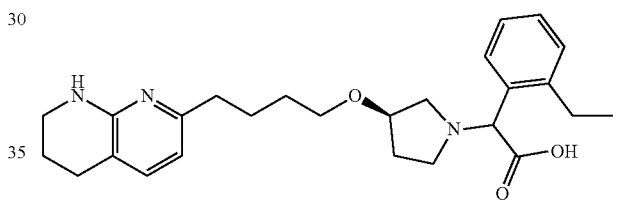

Compound 155-E1 LC/MS ESI 438 (M+H)+ $^1$H NMR (400 MHz, MeOD) δ 7.62 (d, J=7.6, 1H), 7.32-7.14 (m, 4H), 6.38 (d, J=7.2 Hz, 1H), 4.83 (s, 1H), 4.15 (s, 1H), 3.53-3.15 (m, 8H), 2.91-2.53 (m, 6H), 2.18-1.56 (m, 8H), 1.35 (t, 3H). Chiral SFC F (30% MeOH): ee 100%, Rt=3.28 min.

Compound 155-E2 LC/MS ESI 438 (M+H)+ 1H NMR (400 MHz, MeOD) δ 7.62 (d, J=7.6, 1H), 7.32-7.14 (m, 4H), 6.38 (d, J=7.2 Hz, 1H), 4.73 (s, 1H), 4.15 (s, 1H), 3.53-3.15 (m, 8H), 2.91-2.53 (m, 6H), 2.18-1.56 (m, 8H), 1.35 (t, 3H). Chiral SFC F (30% MeOH): ee 100%, Rt=6.54 min.

2-((R)-3-(4-(5,6,7,8-tetrahydro-1,8-naphthyridin-2-yl)butoxy)pyrrolidin-1-yl)-2-(4-(trifluoromethyl)phenyl)acetic acid (Diastereomeric Compounds 156-E1 and 156-E2)

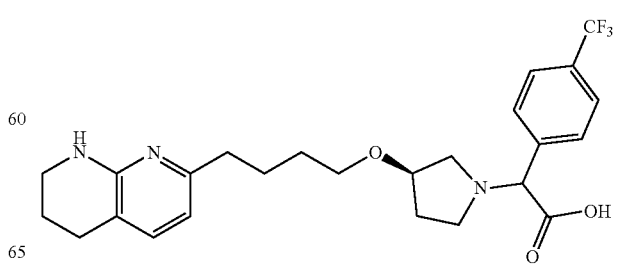

Compound 156-E1 LC/MS ESI 478 (M+H)+ 1H NMR (400 MHz, MeOD) δ 7.75-7.70 (m, 4H), 7.20 (d, J=7.2 Hz, 1H), 6.41 (d, J=7.2 Hz, 1H), 4.42 (s, 1H), 4.15 (s, 1H), 3.51-2.95 (m, 8H), 2.74-2.53 (m, 4H), 2.18-1.56 (m, 8H). Chiral SFC A (35% MeOH): ee 100%, Rt=1.73 min Compound 156-E2 LC/MS ESI 478 (M+H)+ 1H NMR (400 MHz, MeOD) δ 7.75-7.70 (m, 4H), 7.22 (d, J=7.6 Hz, 1H), 6.42 (d, J=7.2 Hz, 1H), 4.53 (s, 1H), 4.16 (s, 1H), 3.51-2.95 (m, 8H), 2.74-2.53 (m, 4H), 2.18-1.56 (m, 8H). Chiral SFC A (35% MeOH): ee 100%, Rt=2.72 min 2-((R)-3-(4-(5,6,7,8-tetrahydro-1,8-naphthyridin-2-yl)butoxy)pyrrolidin-1-yl)-2-(3-(trifluoromethyl)phenyl)acetic acid (Diastereomeric Compounds 157-E1 and 157-E2)

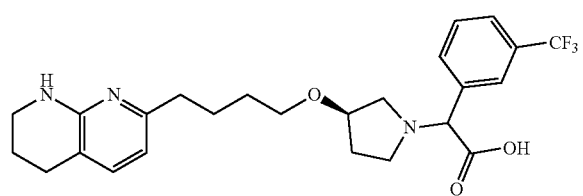 [SMILES: O=C(O)C(c1cccc(C(F)(F)F)c1)N1CC[C@@H](OCCCCc2ccc3c(n2)NCCC3)C1]

Compound 157-E1 LC/MS ESI 478 (M+H)+ 1H NMR (400 MHz, MeOD) δ 7.91 (s, 1H), 7.80 (d, J=7.6 Hz, 1H), 7.61-7.50 (m, 2H), 7.15 (d, J=7.6 Hz, 1H), 6.37 (d, J=7.6 Hz, 1H), 4.10-4.04 (m, 2H), 3.49-2.85 (m, 5H), 2.75-2.51 (m, 7H), 2.18-1.56 (m, 8H). Chiral SFC A (25% MeOH): ee 100%, Rt=3.28 min Compound 157-E2 LC/MS ESI 478 (M+H)+ 1H NMR (400 MHz, MeOD) δ 7.93 (s, 1H), 7.80 (d, J=7.6 Hz, 1H), 7.61-7.50 (m, 2H), 7.21 (d, J=7.2 Hz, 1H), 6.41 (d, J=7.6 Hz, 1H), 4.38 (s, 1H), 4.15 (s, 1H), 3.50-2.95 (m, 8H), 2.73-2.51 (m, 4H), 2.18-1.56 (m, 8H). Chiral SFC A (25% MeOH): ee 100%, Rt=4.83 min 2-((R)-3-(4-(5,6,7,8-tetrahydro-1,8-naphthyridin-2-yl)butoxy)pyrrolidin-1-yl)-2-(2-(trifluoromethyl)phenyl)acetic acid (Diastereomeric Compounds 158-E1 and 158-E2)

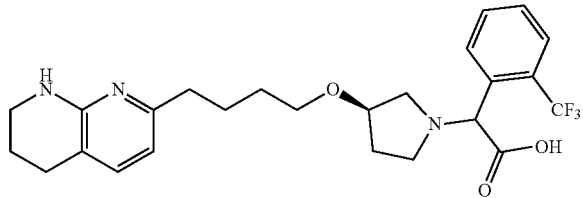 [SMILES: O=C(O)C(c1ccccc1C(F)(F)F)N1CC[C@@H](OCCCCc2ccc3c(n2)NCCC3)C1]

Compound 158-E1 LC/MS ESI 478 (M+H)+ 1H NMR (400 MHz, MeOD) δ 8.01 (d, J=8.0 Hz, 1H), 7.76 (d, J=7.6 Hz, 1H), 7.67 (t, J=7.2 Hz, 1H), 7.54 (t, J=7.6 Hz, 1H), 7.19 (d, J=7.2 Hz, 1H), 6.40 (d, J=7.2 Hz, 1H), 4.62 (s, 1H), 4.13 (s, 1H), 3.49-2.85 (m, 8H), 2.73-2.55 (m, 4H), 2.16-1.56 (m, 8H).

Compound 158-E2 LC/MS ESI 478 (M+H)+ 1H NMR (400 MHz, MeOD) δ 8.01 (d, J=8.0 Hz, 1H), 7.76 (d, J=7.6 Hz, 1H), 7.67 (t, J=7.2 Hz, 1H), 7.54 (t, J=7.6 Hz, 1H), 7.19 (d, J=7.2 Hz, 1H), 6.40 (d, J=7.2 Hz, 1H), 4.73 (s, 1H), 4.13 (s, 1H), 3.49-2.85 (m, 8H), 2.73-2.55 (m, 4H), 2.16-1.56 (m, 8H).

2-((3R)-3-(4-(7-methyl-5,6,7,8-tetrahydro-1,8-naphthyridin-2-yl)butoxy)pyrrolidin-1-yl)-2-phenylacetic acid (Diastereomeric Compounds 159-E1 and 159-E2)

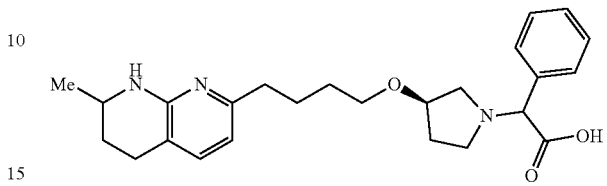

Compound 159-E1 LC/MS ESI 424 (M+H)+ 1H NMR (400 MHz, MeOD) δ 7.76-7.53 (m, 2H), 7.42-7.40 (m, 3H), 7.19 (d, J=7.2 Hz, 1H), 6.40 (d, J=7.2 Hz, 1H), 4.48 (s, 1H), 4.18-4.16 (m, 1H), 3.55-3.24 (m, 5H), 3.16-2.98 (m, 2H), 2.75-2.53 (m, 4H), 2.16-1.45 (m, 8H), 1.22 (d, J=7.2 Hz, 3H). Chiral SFC A (30% MeOH): ee 100%, Rt=2.50 min.

Compound 159-E2 LC/MS ESI 424 (M+H)+ 1H NMR (400 MHz, MeOD) δ 7.76-7.53 (m, 2H), 7.42-7.40 (m, 3H), 7.19 (d, J=7.2 Hz, 1H), 6.40 (d, J=7.2 Hz, 1H), 4.39 (s, 1H), 4.18-4.16 (m, 1H), 3.65-3.20 (m, 5H), 3.18-3.02 (m, 2H), 2.75-2.53 (m, 4H), 2.21-1.45 (m, 8H), 1.22 (d, J=7.2 Hz, 3H). Chiral SFC A (30% MeOH): ee 100%, Rt=4.40 min.

2-((3R)-3-(4-(6-methyl-5,6,7,8-tetrahydro-1,8-naphthyridin-2-yl)butoxy)pyrrolidin-1-yl)-2-phenylacetic acid (Diastereomeric Compounds 160-E1 and 160-E2)

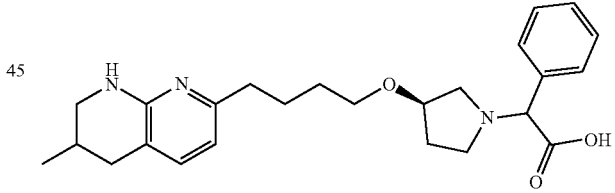

Compound 160-E1 LC/MS ESI 424 (M+H)+ 1H NMR (400 MHz, MeOD) δ 7.55-7.53 (m, 2H), 7.42-7.40 (m, 3H), 7.16 (d, J=7.2 Hz, 1H), 6.38 (d, J=7.2 Hz, 1H), 4.46 (s, 1H), 4.18-4.16 (m, 1H), 3.58-3.24 (m, 5H), 3.16-2.91 (m, 3H), 2.78-2.35 (m, 4H), 2.16-1.45 (m, 7H), 1.04 (d, J=6.4 Hz, 3H). Chiral SFC A (40% MeOH): ee 100%, Rt=1.83 min.

Compound 160-E2 LC/MS ESI 424 (M+H)+ 1H NMR (400 MHz, MeOD) δ 7.55-7.53 (m, 2H), 7.42-7.40 (m, 3H), 7.16 (d, J=7.2 Hz, 1H), 6.38 (d, J=7.2 Hz, 1H), 4.44 (s, 1H), 4.18-4.16 (m, 1H), 3.48-3.24 (m, 5H), 3.16-2.91 (m, 3H), 2.78-2.35 (m, 4H), 2.16-1.90 (m, 4H), 1.75-1.50 (m, 3H), 1.04 (d, J=6.4 Hz, 3H). Chiral SFC A (40% MeOH): ee 100%, Rt=2.84 min.

2-((3R)-3-(4-(5-methyl-5,6,7,8-tetrahydro-1,8-naphthyridin-2-yl)butoxy)pyrrolidin-1-yl)-2-phenylacetic acid (Diastereomeric Compounds 161-E1 and 161-E2)

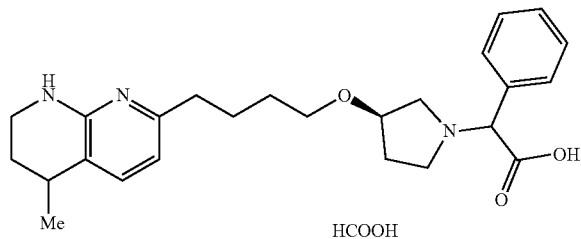 [SMILES: CC1CCNc2nc(CCCCO[C@@H]3CCN(C(C(=O)O)c4ccccc4)C3)ccc21 ; "HCOOH"]

HCOOH

Compound 161-E1 LC/MS ESI 424 (M+H)+ 1H NMR (400 MHz, MeOD) δ 8.54 (s, 1H), 7.58-7.57 (m, 3H), 7.45-7.43 (m, 3H), 6.57 (d, J=7.6 Hz, 1H), 4.62 (s, 1H), 4.21-4.19 (m, 1H), 3.51-3.40 (m, 6H), 3.27-3.21 (m, 2H), 2.95-2.91 (m, 1H), 2.72-2.68 (m, 2H), 2.16-2.14 (m, 2H), 1.96-1.94 (m, 1H), 1.71-1.63 (m, 5H), 1.30 (d, J=6.8 Hz, 1H).

Compound 161-E2 LC/MS ESI 424 (M+H)+ ¹H NMR (400 MHz, MeOD) δ 8.53 (s, 1H), 7.57-7.55 (m, 3H), 7.46-7.44 (m, 3H), 6.56 (d, J=7.2 Hz, 1H), 4.67 (s, 1H), 4.21-4.19 (m, 1H), 3.51-3.40 (m, 5H), 3.11-3.09 (m, 1H), 2.93-2.91 (m, 1H), 2.72-2.65 (m, 2H), 2.16-2.14 (m, 1H), 1.96-1.94 (m, 1H), 1.71-1.63 (m, 5H), 1.30 (d, J=6.8 Hz, 1H).

2-phenyl-2-((R)-3-((1r,4R)-4-(5,6,7,8-tetrahydro-1,8-naphthyridin-2-yl)cyclohexyloxy)pyrrolidin-1-yl)acetic acid (Diastereomeric Compounds 162-E1 and 162-E2)

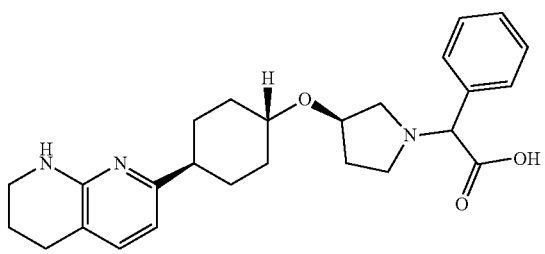 [SMILES: O=C(O)C(c1ccccc1)N1CC[C@@H](O[C@H]2CC[C@H](c3ccc4c(n3)NCCC4)CC2)C1]

Compound 162-E1 LC/MS ESI 436.2 (M+H)+. 1H NMR (500 MHz, CD3OD) δ 7.59-7.58 (m, 2H), 7.45-7.44 (m, 3H), 7.14 (d, J=7.5 Hz, 1H), 6.37 (d, J=7.5 Hz, 1H), 4.46-4.42 (m, 2H), 3.40-3.33 (m, 4H), 3.19-3.17 (m, 2H), 2.72-2.69 (m, 2H), 2.42-2.38 (m, 1H), 2.26-2.22 (m, 1H), 2.14-2.12 (m, 3H), 1.94-1.86 (m, 4H), 1.54-1.52 (m, 2H) 1.43-1.30 (m, 3H). Chiral SFC B (40% MeOH): ee 100%, Rt=1.83 min.

Compound 162-E2 LC/MS ESI 436.2 (M+H)+. 1H NMR (500 MHz, CD3OD) δ 7.59-7.57 (m, 2H), 7.47-7.44 (m, 3H), 7.14 (d, J=8.0 Hz, 1H), 6.38 (d, J=8.0 Hz, 1H), 4.47-4.44 (m, 2H), 3.61-3.59 (m, 1H), 3.36-3.33 (m, 3H), 3.06-2.99 (m, 1H), 2.72-2.69 (m, 2H), 2.43-2.38 (m, 1H), 2.18-2.07 (m, 4H), 1.94-1.86 (m, 4H), 1.46-1.38 (m, 2H) 1.31-1.16 (m, 3H). Chiral SFC B (40% MeOH): ee 95.0%, Rt=3.14 min.

2-(4-cyclopropoxyphenyl)-2-((R)-3-(4-(5,6,7,8-tetrahydro-1,8-naphthyridin-2-yl)butoxy)pyrrolidin-1-yl)acetic acid (Diastereomeric Compounds 163-E1 and 163-E2)

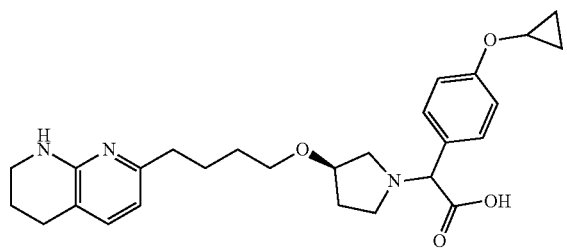 [SMILES: O=C(O)C(c1ccc(OC2CC2)cc1)N1CC[C@@H](OCCCCc2ccc3c(n2)NCCC3)C1]

Compound 163-E1 LC/MS ESI 466.3 (M+H)+. ¹H NMR (400 MHz, MeOD) δ 7.47-7.45 (m, 2H), 7.16-7.07 (m, 3H), 6.383 (d, J=7.6 Hz, 1H), 4.456 (s, 1H), 4.19 (s, 1H), 3.82-3.78 (m, 1H), 3.46-3.31 (m, 6H), 3.21-3.15 (m, 2H), 2.70-2.68 (m, 2H), 2.55-2.53 (m, 2H), 2.22-2.16 (m, 2H), 1.95-1.91 (m, 2H), 1.88-1.55 (m, 4H), 0.81-0.79 (m, 2H), 0.69-0.68 (m, 2H).

Compound 163-E2 LC/MS ESI 466.3 (M+H)+. ¹H NMR (400 MHz, MeOD) δ 7.462-7.44 (m, 2H), 7.16-7.08 (m, 3H), 6.387 (d, J=7.2 Hz, 1H), 4.462 (s, 1H), 4.19 (s, 1H), 3.82-3.78 (m, 1H), 3.46-3.31 (m, 6H), 3.21-3.15 (m, 2H), 2.72-2.69 (m, 2H), 2.56-2.53 (m, 2H), 2.2-2.00 (m, 2H), 1.89-1.86 (m, 2H), 1.78-1.60 (m, 4H), 0.81-0.79 (m, 2H), 0.69-0.68 (m, 2H).

2-((R)-3-(4-(4-methyl-5,6,7,8-tetrahydro-1,8-naphthyridin-2-yl)butoxy)pyrrolidin-1-yl)-2-phenylacetic acid (Diastereomeric Compounds 164-E1 and 164-E2)

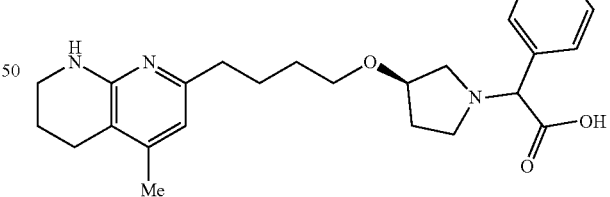

Compound 164-E1 LC/MS ESI 424.3 (M+H)+. ¹H NMR (400 MHz, MeOD) δ 7.54-7.41 (m, 5H), 6.37 (s, 1H), 4.45 (s, 1H), 4.17 (s, 1H), 3.45-2.91 (m, 8H), 2.68-2.52 (m 4H), 2.17 (s, 3H), 2.15-1.55 (m, 8H). Chiral SFC B (30% MeOH): ee 100%, Rt=1.48 min.

Compound 164-E2 LC/MS ESI 424.3 (M+H)+. ¹H NMR (400 MHz, MeOD) δ 7.55-7.41 (m, 5H), 6.37 (s, 1H), 4.41 (s, 1H), 4.16 (s, 1H), 3.45-3.05 (m, 8H), 2.68-2.52 (m 4H), 2.17 (s, 3H), 2.15-1.55 (m, 8H). Chiral SFC B (30% MeOH): ee 100%, Rt=2.66 min.

2-((R)-3-(4-(3-methyl-5,6,7,8-tetrahydro-1,8-naphthyridin-2-yl)butoxy)pyrrolidin-1-yl)-2-phenylacetic acid (Diastereomeric Compounds 165-E1 and 165-E2)

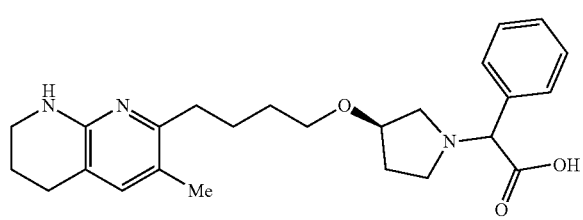 [SMILES: Cc1cc2c(nc1CCCCO[C@@H]1CCN(C(C(=O)O)c3ccccc3)C1)NCCC2]

Compound 165-E1 LC/MS ESI 424.1 (M+H)⁺. ¹H NMR (500 MHz, MeOD) δ 7.54 (s, 2H), 7.41 (m, 3H), 7.08 (s, 1H), 4.44 (s, 1H), 4.16 (s, 1H), 3.45 (m, 3H), 3.21 (m, 2H), 3.18 (m, 2H), 2.98 (m, 1H), 2.77-2.58 (m 4H), 2.09 (s, 5H), 1.88 (m, 2H), 1.67 (m, 4H). Chiral SFC A (40% MeOH): ee 100%, Rt=2.36 min.

Compound 165-E2 LC/MS ESI 424.1 (M+H)⁺. ¹H NMR (500 MHz, MeOD) δ 7.54 (s, 2H), 7.41 (m, 3H), 7.06 (s, 1H), 4.40 (s, 1H), 4.19 (s, 1H), 3.45 (m, 6H), 3.18 (m, 2H), 2.77-2.58 (m 4H), 2.09 (m, 5H), 1.88 (m, 2H), 1.67 (m, 4H). Chiral SFC A (40% MeOH): ee 99%, Rt=3.55 min.

2-(2-isopropoxyphenyl)-2-((R)-3-(4-(5,6,7,8-tetrahydro-1,8-naphthyridin-2-yl)butoxy)pyrrolidin-1-yl)acetic acid (Diastereomeric Compounds 166-P1 and 166-P2)

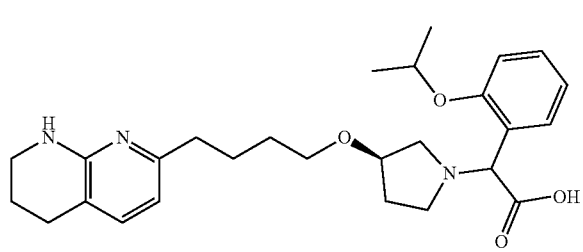 [SMILES: CC(C)Oc1ccccc1C(C(=O)O)N1CC[C@@H](OCCCCc2ccc3c(n2)NCCC3)C1]

Compound 166-P1 LC/MS ESI 468.3 (M+H)⁺. ¹H NMR (400 MHz, MeOD) δ 7.55 (d, J=6.4 Hz, 1H), 7.38-7.35 (m, 1H), 7.15-6.95 (m, 3H), 6.37 (d, J=7.6 Hz, 1H), 4.99 (s, 1H), 4.89-4.72 (m, 1H), 4.19 (s, 1H), 3.64-3.36 (m, 6H), 3.24-3.20 (m, 2H), 2.72-2.68 (m, 2H), 2.55-2.51 (m, 2H), 2.14-2.11 (m, 2H), 1.89-1.86 (m, 2H), 1.71-1.56 (m, 4H), 1.38-1.35 (m, 6H).

Compound 166-P2 LC/MS ESI 468.3 (M+H)⁺. ¹H NMR (400 MHz, MeOD) δ 7.51 (d, J=6.8 Hz, 1H), 7.38-7.35 (m, 1H), 7.15-6.95 (m, 3H), 6.37 (d, J=6.8 Hz, 1H), 5.06 (s, 1H), 4.74-4.71 (m, 1H), 4.18 (s, 1H), 3.64-3.36 (m, 6H), 3.24-3.05 (m, 2H), 2.72-2.68 (m, 2H), 2.55-2.51 (m, 2H), 2.20-2.00 (m, 2H), 1.89-1.86 (m, 2H), 1.71-1.56 (m, 4H), 1.38-1.35 (m, 6H).

2-(2,3-dihydrobenzofuran-7-yl)-2-((R)-3-(4-(5,6,7,8-tetrahydro-1,8-naphthyridin-2-yl)butoxy)pyrrolidin-1-yl)acetic acid (Diastereomeric Compounds 167-P1 and 167-P2)

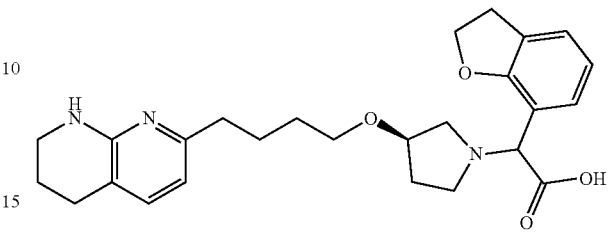

Compound 167-P1 LC/MS ESI 452 (M+H)⁺ ¹H NMR (400 MHz, MeOD) δ 7.26 (d, J=7.6 Hz, 2H), 7.15 (d, J=7.2 Hz, 1H), 6.88 (t, J=7.6 Hz, 1H), 6.38 (d, J=7.2 Hz, 1H), 4.83 (s, 1H), 4.56 (t, J=7.6 Hz, 2H), 4.15 (s, 1H), 3.55-3.15 (m, 10H), 2.71-2.52 (m, 4H), 2.20-1.56 (m, 8H). Chiral SFC C (25% MeOH): ee 100%, Rt=0.97 min.

Compound 167-P2 LC/MS ESI 452 (M+H)⁺ ¹H NMR (400 MHz, MeOD) δ 7.30-7.25 (m, 2H), 7.15 (d, J=7.2 Hz, 1H), 6.88 (t, J=7.6 Hz, 1H), 6.38 (d, J=7.2 Hz, 1H), 4.78 (s, 1H), 4.60 (t, J=8.4 Hz, 2H), 4.15 (s, 1H), 3.55-3.15 (m, 10H), 2.71-2.52 (m, 4H), 2.20-1.56 (m, 8H). Chiral SFC C (25% MeOH): ee 100%, Rt=1.73 min.

2-(2-methoxyphenyl)-2-((R)-3-(4-(5,6,7,8-tetrahydro-1,8-naphthyridin-2-yl)butoxy)pyrrolidin-1-yl)acetic acid (Compound 168)

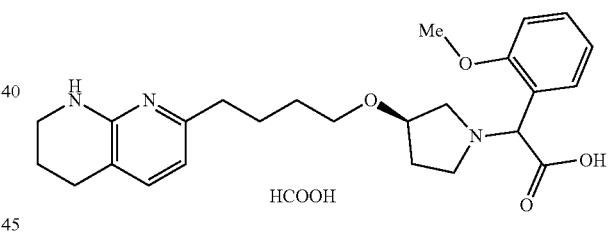

Compound 168 LC/MS ESI 440 (M+H)⁺ 1H NMR (400 MHz, MeOD) δ 8.38 (s, 1H), 7.41-7.33 (m, 3H), 7.02-6.92 (m, 2H), 6.48-6.44 (m, 1H), 4.94-4.79 (m, 1H), 4.20-4.15 (m, 1H), 3.77-2.95 (m, 11H), 2.58-2.50 (m, 4H), 2.15-1.49 (m, 8H).

2-(2-ethoxyphenyl)-2-((R)-3-(4-(5,6,7,8-tetrahydro-1,8-naphthyridin-2-yl)butoxy)pyrrolidin-1-yl)acetic acid (Compound 169)

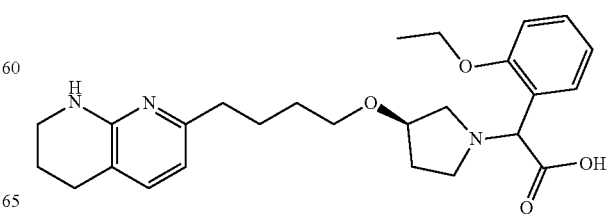

Compound 169 LC/MS ESI 454 (M+H)+ 1H NMR (400 MHz, MeOD) δ 7.52 (t, J=4.8 Hz, 1H), 7.41 (t, J=4.8 Hz, 1H), 7.15-6.98 (m, 3H), 6.39-6.35 (m, 1H), 5.09-5.02 (m, 1H), 4.17-4.10 (m, 3H), 3.55-3.11 (m, 8H), 2.72-2.50 (m, 4H), 2.15-1.38 (m, 11H).

2-(2,3-dihydrobenzofuran-4-yl)-2-((R)-3-(4-(5,6,7,8-tetrahydro-1,8-naphthyridin-2-yl)butoxy)pyrrolidin-1-yl)acetic acid (Diastereomeric Compounds 170-E1 and 170-E2)

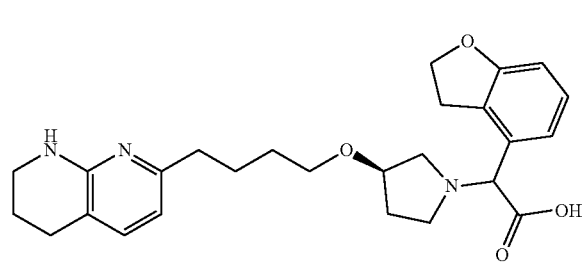 [SMILES: O=C(O)C(c1cccc2c1CCO2)N1CC[C@@H](OCCCCc2ccc3c(n2)NCCC3)C1]

Compound 170-E1 LC/MS ESI 452.2 (M+H)+. 1H NMR (500 MHz, CD3OD) δ 7.18-7.15 (m, 2H), 7.08-7.04 (m, 1H), 6.77 (d, J=8.0 Hz, 1H), 6.41-6.38 (m, 1H), 4.59-4.52 (m, 3H), 4.21-4.19 (m, 1H), 3.54-3.38 (m, 6H), 3.29-3.20 (m, 3H), 3.11-3.07 (m, 1H), 2.72 (t, J=6.0 Hz, 2H), 2.56 (t, J=7.0 Hz, 2H), 2.17-2.07 (m, 2H), 1.92-1.88 (m, 2H), 1.76-1.71 (m, 2H), 1.70-1.59 (m, 2H). Chiral SFC A (40% MeOH): ee 41.7%, Rt=2.55 min.

Compound 170-E2 LC/MS ESI 452.2 (M+H)+. 1H NMR (500 MHz, CD3OD) δ 7.18-7.15 (m, 2H), 7.08-7.04 (m, 1H), 6.77 (d, J=8.0 Hz, 1H), 6.41-6.39 (m, 1H), 4.59-4.52 (m, 3H), 4.20-4.18 (m, 1H), 3.54-3.36 (m, 6H), 3.30-3.09 (m, 4H), 2.72 (t, J=6.5 Hz, 2H), 2.60-2.53 (m, 2H), 2.20-2.18 (m, 2H), 1.91-1.87 (m, 2H), 1.76-1.65 (m, 2H), 1.63-1.59 (m, 2H). Chiral SFC A (40% MeOH): ee 57.7%, Rt=4.22 min.

2-(2-methoxyphenyl)-2-((R)-3-(5-(5,6,7,8-tetrahydro-1,8-naphthyridin-2-yl)pentyl)pyrrolidin-1-yl)acetic acid (Diastereomeric Compounds 171-E1 and 171-E2)

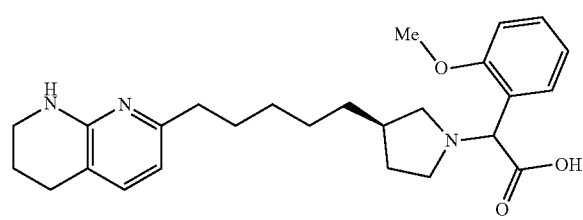 [SMILES: COc1ccccc1C(C(=O)O)N1CC[C@@H](CCCCCc2ccc3c(n2)NCCC3)C1]

Compound 171-E1 LC/MS ESI 438.3 (M+H)+. 1H NMR (400 MHz, MeOD) δ 7.50-7.43 (m, 3H), 7.12-7.03 (m, 2H), 6.52 (d, J=7.6 Hz, 1H), 5.01 (s, 1H), 3.91 (s, 3H), 3.47-3.43 (m, 3H), 3.33-3.00 (m, 3H), 2.80-2.77 (m, 2H), 2.65-2.62 (m, 2H), 2.40-2.10 (m, 2H), 1.95-1.85 (m, 2H), 1.75-1.68 (m, 3H), 1.52-1.24 (m, 6H).

Compound 171-E2 LC/MS ESI 438.3 (M+H)+. 1H NMR (400 MHz, MeOD) δ 7.55-7.43 (m, 3H), 7.12-7.03 (m, 2H), 6.52 (d, J=7.2 Hz, 1H), 5.04 (s, 1H), 3.91 (s, 3H), 3.47-3.43 (m, 4H), 3.21-3.11 (m, 1H), 2.80-2.63 (m, 5H), 2.45-2.12 (m, 2H), 1.94-1.91 (m, 2H), 1.68-1.65 (m, 3H), 1.52-1.24 (m, 6H).

2-(4-ethoxyphenyl)-2-((R)-3-(4-(5,6,7,8-tetrahydro-1,8-naphthyridin-2-yl)butoxy)pyrrolidin-1-yl)acetic acid (Diastereomeric Compounds 172-E1 and 172-E2)

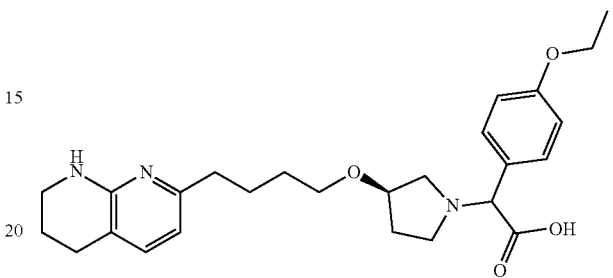

Compound 172-E1 LC/MS ESI 454 (M+H)+ 1H NMR (400 MHz, MeOD) δ 7.46 (d, J=8.4 Hz, 2H), 7.17 (d, J=7.2 Hz, 1H), 6.93 (d, J=8.4 Hz, 2H), 6.37 (d, J=7.2 Hz, 1H), 4.42 (s, 1H), 4.16 (s, 1H), 4.04 (q, J=6.8 Hz, 2H), 3.50-3.11 (m, 8H), 2.72-2.52 (m, 4H), 2.20-1.55 (m, 8H), 1.38 (t, J=6.8 Hz, 3H). Chiral SFC B (30% MeOH): ee 100%, Rt=1.59 min.

Compound 172-E2 LC/MS ESI 454 (M+H)+ 1H NMR (400 MHz, MeOD) δ 7.46 (d, J=8.4 Hz, 2H), 7.17 (d, J=7.2 Hz, 1H), 6.93 (d, J=8.4 Hz, 2H), 6.37 (d, J=7.2 Hz, 1H), 4.39 (s, 1H), 4.17 (s, 1H), 4.04 (q, J=6.8 Hz, 2H), 3.50-2.95 (m, 8H), 2.70 (t, J=6.0 Hz, 2H), 2.54 (t, J=7.2 Hz, 2H), 2.10-1.45 (m, 8H), 1.38 (t, J=6.8 Hz, 3H). Chiral SFC B (30% MeOH): ee 100%, Rt=4.18 min 2-(2-methoxy-4-(trifluoromethyl)phenyl)-2-((R)-3-(4-(5,6,7,8-tetrahydro-1,8-naphthyridin-2-yl)butoxy)pyrrolidin-1-yl)acetic acid (Diastereomeric Compounds 173-E1 and 173-E2)

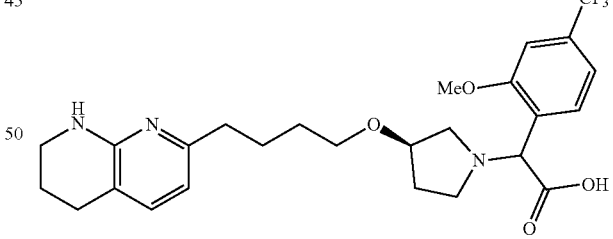

Compound 173-E1 LC/MS ESI 508 (M+H)+ 1H NMR (400 MHz, MeOD) δ 7.67 (d, J=7.9 Hz, 1H), 7.32 (d, J=10.7 Hz, 2H), 7.17 (d, J=7.3 Hz, 1H), 6.40 (d, J=7.3 Hz, 1H), 5.05 (s, 1H), 4.19 (s, 1H), 3.95 (s, 3H), 3.70-3.32 (m, 6H), 3.12-3.08 (m, 2H), 2.64-2.54 (m, 4H), 2.13-1.49 (m, 8H). Chiral SFC A (35% MeOH): ee 100%, Rt=2.34 min.

Compound 173-E2 LC/MS ESI 508 (M+H)+ 1H NMR (400 MHz, MeOD) δ 7.67 (d, J=7.9 Hz, 1H), 7.32 (d, J=10.7 Hz, 2H), 7.17 (d, J=7.3 Hz, 1H), 6.40 (d, J=7.3 Hz, 1H), 5.08 (s, 1H), 4.21 (s, 1H), 3.95 (s, 3H), 3.70-3.32 (m, 6H), 3.12-3.08 (m, 2H), 2.64-2.54 (m, 4H), 2.13-1.49 (m, 8H). Chiral SFC A (35% MeOH): ee 100%, Rt=3.25 min.

2-(4-tert-butoxyphenyl)-2-((R)-3-(4-(5,6,7,8-tetra-hydro-1,8-naphthyridin-2-yl)butoxy)pyrrolidin-1-yl) acetic acid (Compound 174)

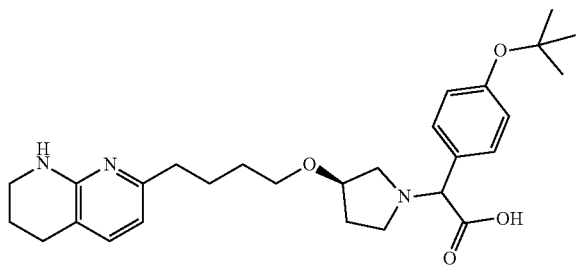 [SMILES: CC(C)(C)Oc1ccc(C(C(=O)O)N2CC[C@@H](OCCCCc3ccc4c(n3)NCCC4)C2)cc1]

Compound 174 LC/MS ESI 482 (M+H)+ 1H NMR (400 MHz, MeOD) δ 7.45 (d, J=8.4 Hz, 2H), 7.15 (d, J=7.6 Hz, 1H), 7.03 (d, J=8.4 Hz, 2H), 6.39 (d, J=7.6 Hz, 1H), 4.47 (s, 1H), 4.19 (s, 1H), 3.55-3.32 (m, 6H), 3.20-3.05 (m, 2H), 2.75-2.54 (m, 4H), 2.20-1.58 (m, 8H), 1.36 (s, 9H).

2-(4-cyanophenyl)-2-((R)-3-(4-(5,6,7,8-tetrahydro-1, 8-naphthyridin-2-yl)butoxy)pyrrolidin-1-yl)acetic acid (Diastereomeric Compounds 175-E1 and 175-E2)

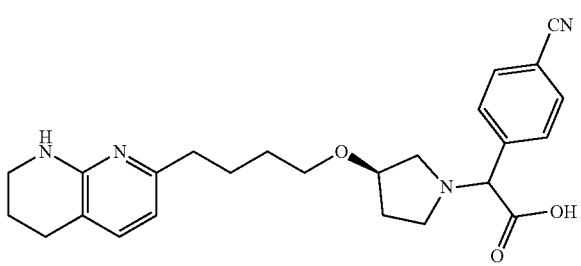 [SMILES: N#Cc1ccc(C(C(=O)O)N2CC[C@@H](OCCCCc3ccc4c(n3)NCCC4)C2)cc1]

Compound 175-E1 LC/MS ESI 435 (M+H)+ 1H NMR (400 MHz, MeOD) δ 7.77-7.71 (m, 4H), 7.26 (d, J=7.6 Hz, 1H), 6.44 (d, J=7.6 Hz, 1H), 4.31 (s, 1H), 4.16-4.11 (m, 1H), 3.51-3.29 (m, 5H), 3.20-2.97 (m, 3H), 2.75-2.59 (m, 4H), 2.22-1.65 (m, 8H). Chiral SFC B (30% MeOH): ee 100%, Rt=1.26 min.

Compound 175-E2 LC/MS ESI 435 (M+H)+ 1H NMR (400 MHz, MeOD) δ 7.77-7.71 (m, 4H), 7.26 (d, J=7.6 Hz, 1H), 6.44 (d, J=7.6 Hz, 1H), 4.48 (s, 1H), 4.16-4.11 (m, 1H), 3.51-3.15 (m, 7H), 2.85-2.57 (m, 5H), 2.15-1.55 (m, 8H). Chiral SFC B (30% MeOH): ee 100%, Rt=3.06 min.

2-((R)-3-(3-(5,6,7,8-tetrahydro-1,8-naphthyridin-2-yl)propoxy)pyrrolidin-1-yl)-2-(4-(trifluoromethyl) phenyl)acetic acid (Diastereomeric Compounds 176-E1 and 176-E2)

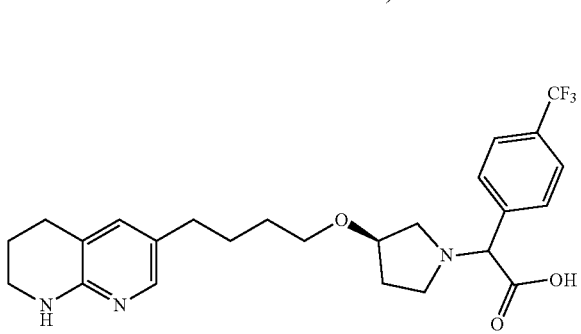

Compound 176-E1 LC/MS ESI 464 (M+H)+ 1H NMR (400 MHz, MeOD) δ 7.76 (d, J=8.4 Hz, 2H), 7.69 (d, J=8.0 Hz, 2H), 7.17 (d, J=7.2 Hz, 1H), 6.39 (d, J=7.2 Hz, 1H), 4.30 (s, 1H), 4.12 (s, 1H), 3.44-3.37 (m, 4H), 3.20-2.89 (m, 4H), 2.72-2.59 (m, 4H), 2.20-1.85 (m, 6H). Chiral SFC B (35% MeOH): ee 100%, Rt=0.79 min Compound 176-E2 LC/MS ESI 464 (M+H)+ 1H NMR (400 MHz, MeOD) δ 7.76 (d, J=8.4 Hz, 2H), 7.69 (d, J=8.0 Hz, 2H), 7.17 (d, J=7.2 Hz, 1H), 6.39 (d, J=7.2 Hz, 1H), 4.20 (s, 1H), 4.11 (s, 1H), 3.44-3.28 (m, 5H), 3.09-2.95 (m, 1H), 2.78-2.55 (m, 6H), 2.10-1.85 (m, 6H). Chiral SFC B (35% MeOH): ee 90%, Rt=2.65 min 2-(3,5-dimethylphenyl)-2-((R)-3-(4-(5,6,7,8-tetra-hydro-1,8-naphthyridin-2-yl)butoxy)pyrrolidin-1-yl) acetic acid (Diastereomeric Compounds 177-E1 and 177-E2)

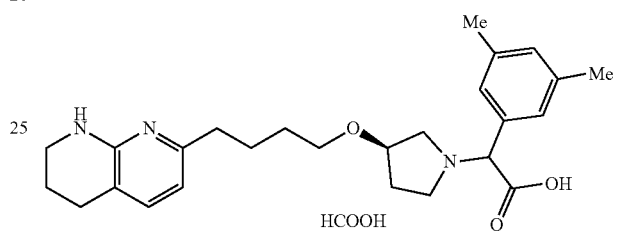

Compound 177-E1 LC/MS ESI 438 (M+H)+ 1H NMR (400 MHz, MeOD) δ 8.51 (s, 1H), 7.49 (d, J=7.6 Hz, 1H), 7.18 (s, 2H), 7.08 (s, 1H), 6.55 (d, J=7.2 Hz, 1H), 4.55 (s, 1H), 4.19 (s, 1H), 3.52-3.24 (m, 9H), 2.80-2.69 (m, 4H), 2.31-2.15 (m, 8H), 1.93-1.65 (m, 6H).

Compound 177-E2 LC/MS ESI 438 (M+H)+ 1H NMR (400 MHz, MeOD) δ 8.51 (s, 1H), 7.49 (d, J=7.6 Hz, 1H), 7.18 (s, 2H), 7.08 (s, 1H), 6.55 (d, J=7.2 Hz, 1H), 4.59 (s, 1H), 4.20 (s, 1H), 3.50-3.10 (m, 9H), 2.80-2.68 (m, 4H), 2.31-2.15 (m, 8H), 1.93-1.65 (m, 6H).

2-phenyl-2-(3-(4-((5,6,7,8-tetrahydro-1,8-naphthyri-din-2-yl)methyl)piperidine-1-carbonyl)azetidin-1-yl) acetic acid (Enantiomeric Compounds 178-E1 and 178-E2)

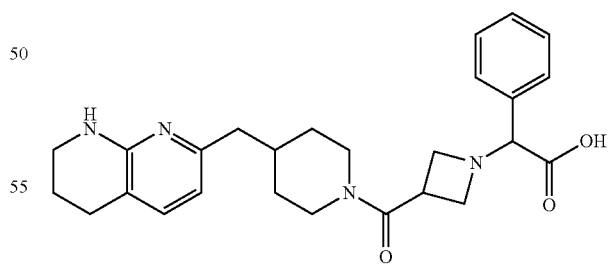

Compound 178-E1 LC/MS ESI 449.1 (M+H)+. 1H NMR (500 MHz, MeOD) δ 7.51 (d, J=7.6 Hz, 2H), 7.41 (d, J=6.5 Hz, 3H), 7.15 (d, J=7.1 Hz, 1H), 6.35 (d, J=7.3 Hz, 1H), 4.47 (d, J=13.4 Hz, 2H), 4.19 (s, 1H), 3.86 (M, 4H), 3.64-3.54 (m, 1H), 3.43-3.37 (m, 2H), 2.98 (t, J=13.2 Hz, 1H), 2.68 (M, 3H), 2.52-2.38 (m, 2H), 1.96-1.82 (m, 3H), 1.68 (d, J=13.0 Hz, 2H), 1.12 (M, 2H). Chiral SFC A (45% MeOH): ee 100%, Rt=2.12 min.

Compound 178-E2 LC/MS ESI 449.1 (M+H)⁺. ¹H NMR (500 MHz, MeOD) δ 7.51 (d, J=7.6 Hz, 2H), 7.41 (d, J=6.5 Hz, 3H), 7.15 (d, J=7.1 Hz, 1H), 6.51 (d, J=7.3 Hz, 1H), 4.47 (d, J=13.4 Hz, 2H), 4.19 (s, 1H), 3.86 (M, 4H), 3.64-3.54 (m, 1H), 3.42-3.37 (m, 2H), 2.98 (t, J=13.2 Hz, 1H), 2.68 (M, 3H), 2.62-2.38 (m, 2H), 1.96-1.82 (m, 3H), 1.68 (d, J=13.0 Hz, 2H), 1.12 (M, 2H). Chiral SFC A (45% MeOH): ee 100%, Rt=3.57 min.

2-(4-(methyl(4-(5,6,7,8-tetrahydro-1,8-naphthyridin-2-yl)butyl)amino)piperidin-1-yl)acetic acid (Compound 179)

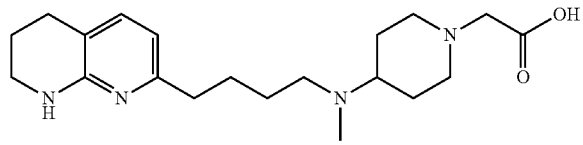 [SMILES: CN(CCCCc1ccc2c(n1)NCCC2)C1CCN(CC(=O)O)CC1]

Compound 179 LC/MS ESI 361 (M+H)⁺. 1H NMR (500 MHz, MeOD) δ 7.15 (d, J=7.3 Hz, 1H), 6.39 (d, J=7.3 Hz, 1H), 3.41-3.37 (m, 2H), 3.24 (s, 2H), 2.78-2.63 (m, 6H), 2.58-2.48 (m, 4H), 2.39 (s, 3H), 1.90 (dd, J=11.1, 6.5 Hz, 4H), 1.83-1.55 (m, 7H).

2-(2,4-dimethoxyphenyl)-2-(4-(3-(5,6,7,8-tetrahydro-1,8-naphthyridin-2-yl)propylcarbamoyl)piperidin-1-yl)acetic acid (Compound 180)

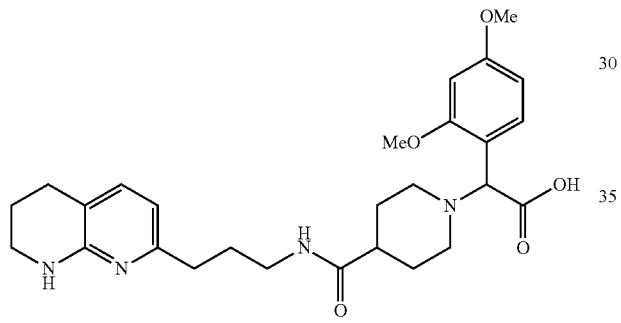

Compound 180 LC/MS ESI 497 (M+H)⁺. 1H NMR (500 MHz, MeOD) 1H NMR (500 MHz, MeOD) δ 7.49 (d, J=8.4 Hz, 1H), 7.13 (d, J=7.3 Hz, 1H), 6.65-6.51 (m, 2H), 6.38 (t, J=6.3 Hz, 1H), 4.71 (s, 1H), 3.87 (s, 3H), 3.82 (d, J=6.3 Hz, 3H), 3.40-3.36 (m, 2H), 3.19 (t, J=7.0 Hz, 2H), 3.13 (s, 1H), 2.71 (dd, J=18.0, 11.8 Hz, 3H), 2.57-2.49 (m, 2H), 2.35 (s, 1H), 2.00 (dd, J=22.2, 11.0 Hz, 1H), 1.98-1.73 (m, 8H).

2-(2-isopropoxyphenyl)-2-(4-((3-(5,6,7,8-tetrahydro-1,8-naphthyridin-2-yl)propyl) carbamoyl)piperidin-1-yl)acetic acid (Enantiomeric Compounds 181-E1 and 181-E2)

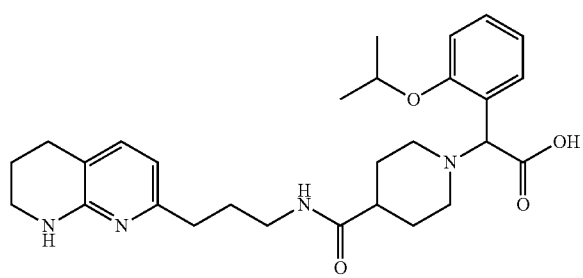 [SMILES: CC(C)Oc1ccccc1C(C(=O)O)N1CCC(C(=O)NCCCc2ccc3c(n2)NCCC3)CC1]

Compound 181-E1 LC/MS ESI 495 (M+H)⁺. ¹H NMR (500 MHz, MeOD) δ 7.56 (dd, J=7.7, 1.4 Hz, 1H), 7.45-7.36 (m, 1H), 7.12 (dd, J=18.8, 7.8 Hz, 2H), 7.00 (t, J=7.5 Hz, 1H), 6.38 (d, J=7.3 Hz, 1H), 4.96 (s, 1H), 4.75 (dt, J=12.1, 6.0 Hz, 1H), 3.71 (s, 1H), 3.45-3.35 (m, 2H), 3.33-3.25 (m, 2H), 3.19 (t, J=6.9 Hz, 2H), 2.96 (s, 2H), 2.70 (t, J=6.2 Hz, 2H), 2.57-2.49 (m, 2H), 2.44 (d, J=4.6 Hz, 1H), 1.95 (d, J=4.7 Hz, 4H), 1.91-1.70 (m, 4H), 1.42 (d, J=6.0 Hz, 6H). Chiral SFC F (45% MeOH): ee 97%, Rt=5.83 min.

Compound 181-E2 LC/MS ESI 495 (M+H)⁺. ¹H NMR (500 MHz, MeOD) δ 7.56 (dd, J=7.7, 1.5 Hz, 1H), 7.41 (dd, J=12.4, 5.1 Hz, 1H), 7.12 (dd, J=16.5, 7.8 Hz, 2H), 7.01 (t, J=7.5 Hz, 1H), 6.38 (d, J=7.3 Hz, 1H), 4.98 (s, 1H), 4.76 (dt, J=12.1, 6.0 Hz, 1H), 3.41-3.35 (m, 2H), 3.20 (t, J=7.0 Hz, 2H), 2.99 (t, J=10.5 Hz, 1H), 2.72 (dd, J=18.3, 12.0 Hz, 2H), 2.57-2.50 (m, 2H), 2.45 (s, 1H), 2.12-1.92 (m, 4H), 1.91-1.73 (m, 4H), 1.42 (d, J=6.0 Hz, 6H). Chiral SFC F (45% MeOH): ee 94%, Rt=13.18 min.

2-(2-isopropoxyphenyl)-2-(3-(4-((5,6,7,8-tetrahydro-1,8-naphthyridin-2-yl)methyl)piperidine-1-carbonyl)azetidin-1-yl)acetic acid (Enantiomeric Compounds 182-E1 and 182-E2)

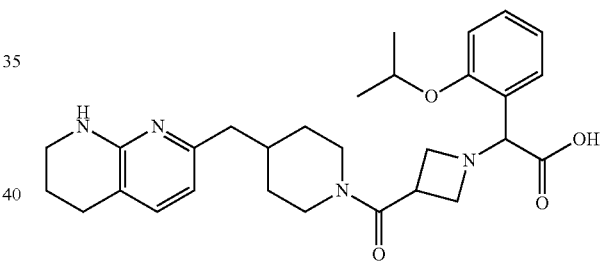

Compound 182-E1 LC/MS ESI 507.2 (M+H)⁺. ¹H NMR (500 MHz, MeOD) δ 7.42-7.38 (m, 2H), 7.14-7.09 (m, 2H), 6.99 (t, J=7.5 Hz, 2H), 6.35-6.33 (m, 1H), 5.13 (d, J=9 Hz, 1H), 4.78-4.52 (m, 1H), 4.75-4.40 (m, 2H), 4.21-4.14 (m, 2H), 3.89-3.86 (m, 2H), 3.57 (d, J=15 Hz, 1H), 3.39 (t, J=5.5 Hz, 2H), 3.03-2.98 (m, 1H), 2.78-2.60 (m, 3H), 2.46-2.45 (m, 2H), 2.00-1.83 (m, 3H), 1.71-1.68 (m, 2H), 1.48-1.37 (m, 6H), 1.14 (s, 2H). Chiral HPLC L (70% EtOH): ee 100%, Rt=17.25 min.

Compound 182-E2 LC/MS ESI 507.2 (M+H)⁺. ¹H NMR (500 MHz, MeOD) δ 7.43-7.38 (m, 2H), 7.15-7.10 (m, 2H), 6.99 (t, J=7.5 Hz, 2H), 6.35-6.33 (m, 1H), 5.14 (d, J=9 Hz, 1H), 4.79-4.52 (m, 1H), 4.76-4.40 (m, 2H), 4.21-4.13 (m, 2H), 3.91-3.88 (m, 2H), 3.57 (d, J=15 Hz, 1H), 3.39 (t, J=5.5 Hz, 2H), 3.03-2.98 (m, 1H), 2.79-2.60 (m, 3H), 2.46-2.45 (m, 2H), 2.00-1.83 (m, 3H), 1.71-1.68 (m, 2H), 1.48-1.37 (m, 6H), 1.14 (s, 2H). Chiral HPLC L (70% EtOH): ee 100%, Rt=22.66 min.

2-(2-chlorophenyl)-2-(3-(4-((5,6,7,8-tetrahydro-1,8-naphthyridin-2-yl)methyl)piperidine-1-carbonyl)azetidin-1-yl)acetic acid (Enantiomeric Compounds 183-E1 and 183-E2)

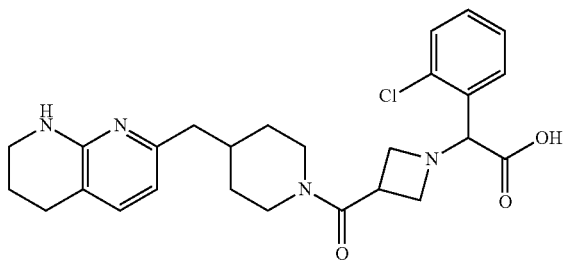

Compound 183-E1 LC/MS ESI 483.1 (M+H)⁺. ¹H NMR (500 MHz, MeOD) δ 7.63-7.57 (m, 1H), 7.55-7.50 (m, 1H), 7.42-7.35 (m, 2H), 7.24 (t, J=7.7 Hz, 1H), 6.39 (d, J=7.3 Hz, 1H), 5.13 (d, J=27.2 Hz, 1H), 4.47 (d, J=12.6 Hz, 1H), 4.25 (s, 1H), 4.08-3.73 (m, 4H), 3.60 (s, 1H), 3.45-3.37 (m, 2H), 3.04-2.95 (m, 1H), 2.73 (t, J=6.2 Hz, 2H), 2.68-2.42 (m, 3H), 2.00-1.85 (m, 3H), 1.79-1.62 (m, 2H), 1.23-1.05 (m, 2H). Chiral HPLC K (50% EtOH): ee 100%, Rt=12.44 min.

Compound 183-E2 LC/MS ESI 483.1 (M+H)⁺. ¹H NMR (500 MHz, MeOD) δ 7.64-7.58 (m, 1H), 7.55-7.50 (m, 1H), 7.42-7.35 (m, 2H), 7.25 (t, J 7.7 Hz, 1H), 6.39 (d, J 7.3 Hz, 1H), 5.13 (d, J 27.2 Hz, 1H), 4.48 (d, J 12.6 Hz, 1H), 4.27 (s, 1H), 4.09-3.75 (m, 4H), 3.62 (s, 1H), 3.45-3.37 (m, 2H), 3.04-2.95 (m, 1H), 2.73 (t, J 6.2 Hz, 2H), 2.68-2.42 (m, 3H), 2.00-1.85 (m, 3H), 1.79-1.62 (m, 2H), 1.23-1.05 (m, 2H). Chiral HPLC K (50% EtOH): ee 100%, Rt=22.79 min.

2-(2-cyclopropoxyphenyl)-2-(3-(4-((5,6,7,8-tetrahydro-1,8-naphthyridin-2-yl)methyl) piperidine-1-carbonyl)azetidin-1-yl)acetic acid (Enantiomeric Compounds 184-E1 and 184-E2)

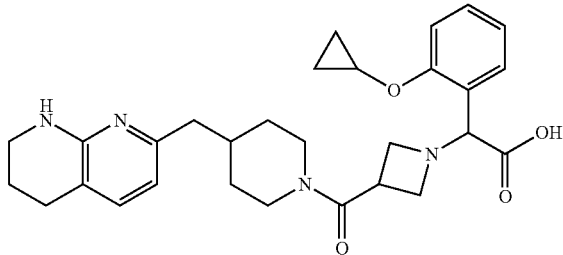 [SMILES: O=C(O)C(c1ccccc1OC1CC1)N1CC(C(=O)N2CCC(Cc3ccc4c(n3)NCCC4)CC2)C1]

Compound 184-E1 LC/MS ESI 505 (M+H)⁺. ¹H NMR (500 MHz, MeOD) δ 7.41 (d, J=13.0 Hz, 3H), 7.14 (d, J=7.3 Hz, 1H), 7.05 (s, 1H), 6.35 (d, J=7.2 Hz, 1H), 5.00 (s, 1H), 4.50-3.84 (m, 7H), 3.55 (s, 1H), 3.39 (dd, J=11.4, 5.7 Hz, 2H), 3.00 (t, J=13.2 Hz, 1H), 2.70 (dd, J=18.7, 12.5 Hz, 3H), 2.46 (d, J=7.0 Hz, 2H), 1.99-1.85 (m, 3H), 1.69 (d, J=12.6 Hz, 2H), 1.15 (d, J=11.2 Hz, 2H), 1.04-0.75 (m, 4H). Chiral H (45% MeOH): ee 100%, Rt=17.33 min.

Compound 184-E2 LC/MS ESI 505 (M+H)⁺. ¹H NMR (500 MHz, MeOD) δ 7.41 (t, J=6.1 Hz, 3H), 7.14 (d, J=7.3 Hz, 1H), 7.05 (d, J=5.6 Hz, 1H), 6.35 (d, J=7.2 Hz, 1H), 4.98 (s, 1H), 4.49-3.82 (m, 7H), 3.57 (s, 1H), 3.39 (dd, J=11.2, 5.5 Hz, 2H), 3.00 (s, 1H), 2.70 (dd, J=19.2, 13.0 Hz, 3H), 2.46 (d, J=7.1 Hz, 2H), 2.02-1.84 (m, 3H), 1.69 (d, J=12.6 Hz, 2H), 1.14 (d, J=12.4 Hz, 2H), 0.99-0.74 (m, 4H). Chiral H (45% MeOH): ee 99%, Rt=22.42 min.

2-(2-isopropoxyphenyl)-2-((R)-3-(4-((5,6,7,8-tetrahydro-1,8-naphthyridin-2-yl)methyl)piperidine-1-carbonyl)pyrrolidin-1-yl)acetic acid (Diasteromeric Compounds 185-E1 and 185-E2)

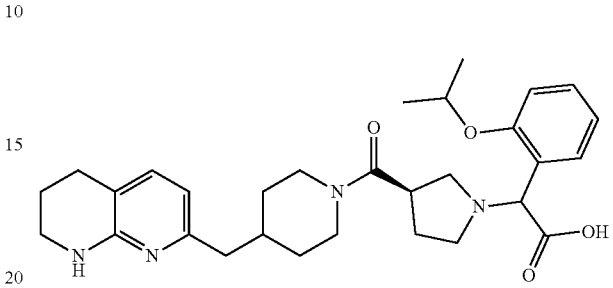

Compound 185-E1 LC/MS ESI 521.2 (M+H)⁺. ¹H NMR (500 MHz, MeOD) δ 7.53 (d, J=7.6 Hz, 1H), 7.45-7.37 (m, 1H), 7.14 (d, J=7.3 Hz, 1H), 7.12-7.07 (m, 1H), 7.04-6.95 (m, 1H), 6.35 (dd, J=7.3, 3.1 Hz, 1H), 5.03 (s, 1H), 4.81-4.72 (m, 1H), 4.60 (s, 1H), 4.48 (d, J=13.3 Hz, 1H), 3.95-3.85 (t, J=23.5 Hz, 2H), 3.61 (s, 1H), 3.43-3.37 (m, 2H), 3.28-3.17 (m, 2H), 3.07 (t, J=13.2 Hz, 1H), 2.72 (t, J=6.2 Hz, 2H), 2.68-2.56 (m, 1H), 2.50-2.31 (m, 3H), 2.15-2.02 (m, 1H), 2.00-1.85 (m, 3H), 1.78-1.64 (m, 2H), 1.48-1.38 (m, 6H), 1.25-1.07 (m, 2H). Chiral HPLC K (70% EtOH): ee 100%, Rt=13.9 min Compound 185-E2 LC/MS ESI 521.2 (M+H)⁺. ¹H NMR (500 MHz, MeOD) δ 7.51 (d, J=7.0 Hz, 1H), 7.40 (t, J=7.9 Hz, 1H), 7.14 (d, J=7.2 Hz, 1H), 7.09 (d, J=8.2 Hz, 1H), 7.00 (t, J=7.5 Hz, 1H), 6.35 (dd, J=7.3, 3.8 Hz, 1H), 5.09 (s, 1H), 4.81-4.71 (m, 1H), 4.50 (d, J=13.2 Hz, 1H), 3.94 (d, J=13.3 Hz, 1H), 3.66 (s, 1H), 3.53-3.37 (m, 4H), 3.19 (s, 1H), 3.08 (t, J=12.9 Hz, 1H), 2.72 (t, J=6.2 Hz, 2H), 2.69-2.59 (m, 1H), 2.51-2.31 (m, 3H), 2.16-2.03 (m, 1H), 2.01-1.84 (m, 3H), 1.79-1.65 (m, 2H), 1.48-1.35 (m, 6H), 1.26-1.08 (m, 2H). Chiral HPLC K (70% EtOH): ee 100%, Rt=25.5 min

2-(2-chlorophenyl)-2-(3-(4-((5,6,7,8-tetrahydro-1,8-naphthyridin-2-yl)methyl)piperidine-1-carbonyl)azetidin-1-yl)acetic acid (Diasteromeric Compounds 186-E1 and 186-E2)

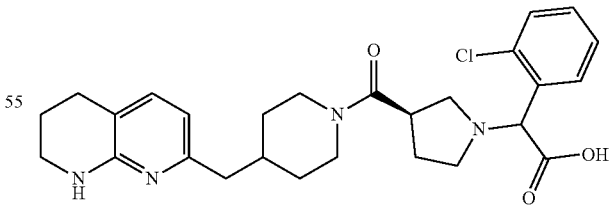

Compound 186-E1 LC/MS ESI 497.1 (M+H)⁺. ¹H NMR (500 MHz, MeOD) δ 7.65 (s, 1H), 7.42 (s, 1H), 7.30 (d, J=3.9 Hz, 2H), 7.04 (d, J=7.3 Hz, 1H), 6.24 (dd, J=7.2, 2.8 Hz, 1H), 5.02 (s, 1H), 4.35 (d, J=11.8 Hz, 1H), 3.83 (d, J=12.9 Hz, 1H), 3.48 (s, 3H), 3.32-3.26 (m, 2H), 3.15-2.88 (m, 3H), 2.60 (t, J=6.1 Hz, 2H), 2.57-2.46 (m, 1H), 2.34 (d, J=3.5 Hz, 2H), 2.29-2.17 (m, 1H), 2.05-1.92 (m, 1H), 1.88-1.74 (m, 3H), 1.65-1.51 (m, 2H), 1.12-0.96 (m, 2H). Chiral SFC B (40% MeOH): ee 100%, Rt=1.13 min.

Compound 186-E2 LC/MS ESI 497.1 (M+H)⁺. ¹H NMR (500 MHz, MeOD) δ 7.78 (d, J=3.7 Hz, 1H), 7.52 (d, J=3.9 Hz, 1H), 7.43-7.38 (m, 2H), 7.15 (d, J=7.3 Hz, 1H), 6.36 (d, J=7.2 Hz, 1H), 5.18 (s, 1H), 4.49 (d, J=12.8 Hz, 1H), 3.98 (d, J=12.8 Hz, 1H), 3.64 (s, 3H), 3.44-3.37 (m, 2H), 3.14-2.98 (m, 3H), 2.72 (t, J=6.2 Hz, 2H), 2.64 (t, J=12.7 Hz, 1H), 2.47 (d, J=7.1 Hz, 2H), 2.35-2.21 (m, 1H), 2.17-2.04 (m, 1H), 1.99-1.86 (m, 3H), 1.78-1.65 (m, 2H), 1.26-1.09 (m, 2H). Chiral SFC B (40% MeOH): ee 86%, Rt=2.44 min.

2-(2-isopropoxyphenyl)-2-((R)-3-((R)-3-(2-(5,6,7,8-tetrahydro-1,8-naphthridin-2-yl)ethyl)pyrrolidine-1-carbonyl)pyrrolidin-1-yl)acetic acid (Diastereomeric Compounds 187-E1 and 187-E2)

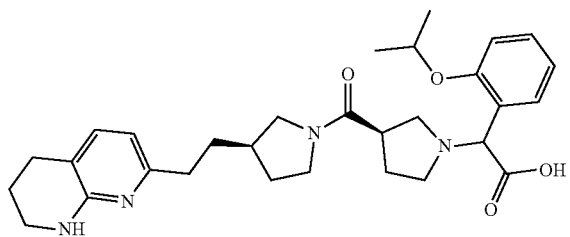 [SMILES: CC(C)Oc1ccccc1C(C(=O)O)N1CC[C@@H](C(=O)N2CC[C@@H](CCc3ccc4c(n3)NCCC4)C2)C1]

Compound 187-E1 LC/MS ESI 521.2 (M+H)⁺. ¹H NMR (500 MHz, MeOD) δ 7.54 (d, J=7.6 Hz, 1H), 7.40 (t, J=7.3 Hz, 1H), 7.15 (dd, J=7.3, 4.3 Hz, 1H), 7.10 (d, J=8.4 Hz, 1H), 7.00 (t, J=7.5 Hz, 1H), 6.40 (dd, J=7.3, 2.6 Hz, 1H), 5.03 (s, 1H), 4.81-4.72 (m, 1H), 3.88-3.59 (m, 3H), 3.55-3.37 (m, 4H), 3.30-3.22 (m, 2H), 3.15-2.95 (m, 1H), 2.71 (t, J=6.2 Hz, 2H), 2.62-2.53 (m, 2H), 2.40 (td, J=15.8, 8.1 Hz, 1H), 2.30-2.06 (m, 3H), 1.92-1.85 (m, 2H), 1.75 (dd, J=14.9, 7.4 Hz, 2H), 1.69-1.51 (m, 1H), 1.44 (dd, J=10.7, 6.0 Hz, 6H). Chiral SFC F (40% EtOH): ee 95%, Rt=7.8 min.

Compound 187-E2 LC/MS ESI 521.2 (M+H)⁺. ¹H NMR (500 MHz, MeOD) δ 7.43 (d, J=7.5 Hz, 1H), 7.35-7.30 (m, 1H), 7.09-7.05 (m, 1H), 7.01 (d, J=8.3 Hz, 1H), 6.92 (t, J=7.5 Hz, 1H), 6.32 (dd, J=7.3, 1.5 Hz, 1H), 4.99 (s, 1H), 4.68 (dt, J=12.1, 6.0 Hz, 1H), 3.67-3.51 (m, 3H), 3.46-3.29 (m, 5H), 3.21-2.86 (m, 2H), 2.64 (t, J=6.2 Hz, 2H), 2.55-2.46 (m, 2H), 2.32 (s, 1H), 2.23-1.98 (m, 3H), 1.84-1.77 (m, 2H), 1.68 (dd, J=14.9, 7.3 Hz, 2H), 1.63-1.45 (m, 1H), 1.35 (dd, J=12.9, 6.0 Hz, 6H). Chiral SFC F (40% EtOH): ee 100%, Rt=9.6 min.

2-(2-isopropoxyphenyl)-2-(3-((R)-3-(2-(5,6,7,8-tetrahydro-1,8-naphthridin-2-yl)ethyl)pyrrolidine-1-carbonyl)azetidin-1-yl)acetic acid (Diastereomeric Compounds 188-E1 and 188-E2)

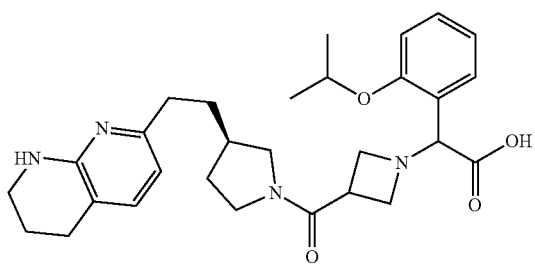 [SMILES: CC(C)Oc1ccccc1C(C(=O)O)N1CC(C(=O)N2CC[C@@H](CCc3ccc4c(n3)NCCC4)C2)C1]

Compound 188-E1 LC/MS ESI 507.2 (M+H)⁺. ¹H NMR (500 MHz, MeOD) δ 7.33 (dd, J=16.8, 7.8 Hz, 2H), 7.07 (d, J=7.3 Hz, 1H), 7.03 (d, J=8.4 Hz, 1H), 6.92 (t, J=7.5 Hz, 1H), 6.32 (dd, J=7.3, 1.8 Hz, 1H), 5.08 (s, 1H), 4.69 (dt, J=12.1, 6.0 Hz, 1H), 4.40-4.06 (m, 3H), 3.86 (s, 1H), 3.76-3.69 (m, 1H), 3.58-3.40 (m, 2H), 3.31 (dt, J=12.8, 4.8 Hz, 3H), 2.97-2.89 (m, 1H), 2.64 (t, J=5.7 Hz, 2H), 2.52-2.46 (m, 2H), 2.18-1.99 (m, 2H), 1.85-1.78 (m, 2H), 1.70-1.64 (m, 2H), 1.61-1.44 (m, 1H), 1.40-1.34 (m, 6H). Chiral SFC F (40% EtOH): ee 100%, Rt=9.14 min Compound 188-E2 LC/MS ESI 507.2 (M+H)⁺. ¹H NMR (500 MHz, MeOD) δ 7.33 (dd, J=14.6, 7.7 Hz, 2H), 7.08 (d, J=4.7 Hz, 1H), 7.03 (d, J=8.3 Hz, 1H), 6.92 (t, J=7.5 Hz, 1H), 6.33 (d, J=6.1 Hz, 1H), 5.09 (s, 1H), 4.72-4.67 (m, 1H), 4.39-4.07 (m, 3H), 3.90-3.43 (m, 4H), 3.34-3.26 (m, 3H), 2.98-2.90 (m, 1H), 2.64 (t, J=6.1 Hz, 2H), 2.49 (d, J=5.9 Hz, 2H), 2.11 (d, J=39.5 Hz, 2H), 1.82 (s, 2H), 1.73-1.65 (m, 2H), 1.53 (d, J=38.0 Hz, 1H), 1.37 (dd, J=16.7, 6.0 Hz, 6H). Chiral SFC F (40% EtOH): ee 96%, Rt=11.57 min 2-((R)-3-(4-(2-(5,6,7,8-tetrahydro-1,8-naphthridin-2-yl)ethyl)piperidin-1-yl)-2-(4-(trifluoromethyl)phenyl)acetic acid (Diastereomeric Compounds 189-E1 and 189-E2)

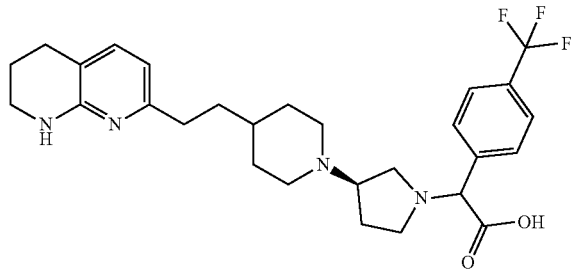 [SMILES: O=C(O)C(c1ccc(C(F)(F)F)cc1)N1CC[C@@H](N2CCC(CCc3ccc4c(n3)NCCC4)CC2)C1]

Compound 189-E1 LC/MS ESI 517.0 (M+H)⁺. ¹H NMR (500 MHz, MeOD) δ 7.63 (d, J=8.2 Hz, 2H), 7.55 (d, J=8.2 Hz, 2H), 7.08 (d, J=7.5 Hz, 1H), 6.32 (d, J=7.3 Hz, 1H), 3.87 (s, 1H), 3.50 (s, 2H), 3.34-3.26 (m, 3H), 3.19-3.12 (m, 1H), 2.64 (dd, J=15.8, 9.5 Hz, 6H), 2.54-2.39 (m, 3H), 2.12 (s, 1H), 1.91 (s, 3H), 1.80 (dt, J=12.1, 6.1 Hz, 2H), 1.46 (m, J=92.1 Hz, 5H). Chiral SFC F (45% EtOH): ee 100%, Rt=9.14 min.

Compound 189-E2 LC/MS ESI 517.0 (M+H)⁺. ¹H NMR (500 MHz, MeOD) δ 7.63 (d, J=8.2 Hz, 2H), 7.56 (d, J=8.2 Hz, 2H), 7.07 (d, J=7.3 Hz, 1H), 6.31 (d, J=7.3 Hz, 1H), 3.89 (s, 1H), 3.41 (s, 2H), 3.34-3.28 (m, 2H), 3.19 (s, 1H), 3.00 (s, 1H), 2.64 (dd, J=19.8, 13.7 Hz, 6H), 2.50-2.40 (m, 3H), 2.14 (dd, J=13.5, 4.9 Hz, 1H), 1.96 (dd, J=23.8, 16.9 Hz, 3H), 1.84-1.77 (m, 2H), 1.55 (dd, J=14.9, 6.8 Hz, 2H), 1.37 (dd, J=41.3, 26.8 Hz, 3H). Chiral SFC F (45% EtOH): ee 100%, Rt=9.14 min.

2-(3-(3-(5,6,7,8-tetrahydro-1,8-naphthyridin-2-yl)propyl)-1,3'-biazetidin-1'-yl)-2-(4-(trifluoromethyl)phenyl)acetic acid (Enantiomeric Compounds 190-E1 and 190-E2)

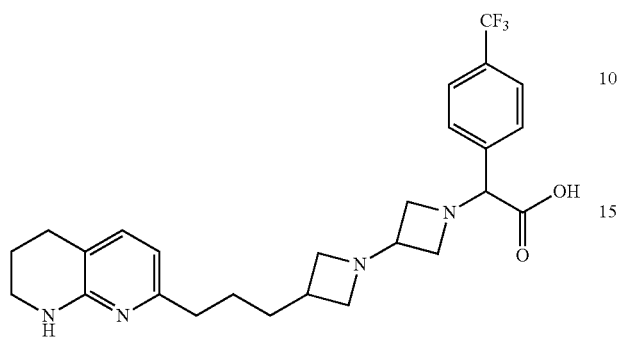

Compound 190-E1 LC/MS ESI 489.1 (M+H)+. 1H NMR (500 MHz, MeOD) δ 7.62 (s, 4H), 7.28 (d, J=7.3 Hz, 1H), 6.43 (d, J=7.3 Hz, 1H), 4.26 (s, 2H), 3.83 (s, 1H), 3.70-3.48 (m, 4H), 3.39 (dd, J=12.3, 6.7 Hz, 3H), 3.28 (s, 1H), 3.14 (s, 1H), 2.73 (t, J=6.2 Hz, 3H), 2.64-2.52 (m, 2H), 1.92-1.85 (m, 2H), 1.71-1.58 (m, 4H). Chiral SFC B (40% MeOH): ee 100%, Rt=0.73 min.

Compound 190-E2 LC/MS ESI 489.1 (M+H)+. 1H NMR (500 MHz, MeOD) δ 7.66 (s, 4H), 7.18 (d, J=7.6 Hz, 1H), 6.39 (d, J=7.3 Hz, 1H), 4.29 (s, 1H), 3.67 (d, J=45.8 Hz, 4H), 3.53-3.37 (m, 4H), 3.23 (s, 3H), 2.72 (t, J=6.2 Hz, 2H), 2.63 (s, 1H), 2.53 (t, J=6.7 Hz, 2H), 1.93-1.84 (m, 2H), 1.61 (s, 4H). Chiral SFC B (40% MeOH): ee 100%, Rt=1.85 min.

2-((R)-3-(3-(2-(5,6,7,8-tetrahydro-1,8-naphthyridin-2-yl)ethyl)azetidine-1-carbonyl)pyrrolidin-1-yl)-2-(4-(trifluoromethyl)phenyl)acetic acid (Diastereomeric compounds 191-E1 and 191-E2)

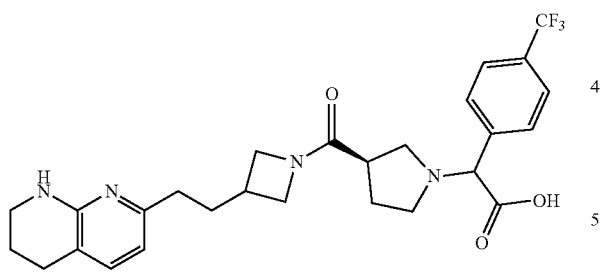

Compound 191-E1 LC/MS ESI 517.2 (M+H)+. 1H NMR (500 MHz, MeOD) δ 7.76-7.71 (m, 4H), 7.20-7.18 (m, 1H), 6.40-6.38 (m, 1H), 4.41 (s, 1H), 4.31-4.24 (m, 1H), 4.07-4.00 (m, 1H), 3.93 (d, J=31.7 Hz, 1H), 3.59-3.53 (m, 1H), 3.48-3.34 (m, 3H), 3.17 (d, J=19.1 Hz, 2H), 2.98 (d, J=41.3 Hz, 2H), 2.72 (t, J=6.1 Hz, 2H), 2.68-2.59 (m, 1H), 2.56-2.48 (m, 2H), 2.24 (d, J=7.2 Hz, 1H), 2.08 (s, 1H), 1.96-1.90 (m, 4H). Chiral HPLC J (30% EtOH): ee 100%, Rt=13.53 min.

Compound 191-E2 LC/MS ESI 517.2 (M+H)+. 1H NMR (500 MHz, MeOD) δ 7.79-7.72 (m, 4H), 7.22-7.18 (m, 1H), 6.43-6.38 (m, 1H), 4.42 (s, 1H), 4.33-4.24 (m, 1H), 4.08-4.00 (m, 1H), 3.94 (d, J=31.7 Hz, 1H), 3.62-3.53 (m, 1H), 3.49-3.34 (m, 3H), 3.18 (d, J=19.1 Hz, 2H), 2.99 (d, J=41.3 Hz, 2H), 2.73 (t, J=6.1 Hz, 2H), 2.69-2.59 (m, 1H), 2.57-2.48 (m, 2H), 2.24 (d, J=7.2 Hz, 1H), 2.09 (s, 1H), 1.97-1.90 (m, 4H). Chiral HPLC J (30% EtOH): ee 100%, Rt=24.12 min.

2-((R)-3-(4-((5,6,7,8-tetrahydro-1,8-naphthyridin-2-yl)methyl)piperidine-1-carbonyl)pyrrolidin-1-yl)-2-(4-(trifluoromethyl)phenyl)acetic acid (Diastereomeric compounds 192-E1 and 192-E2)

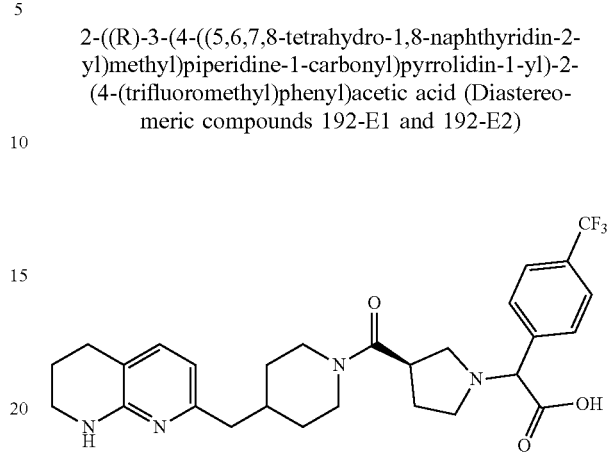

Compound 192-E1 LC/MS ESI 531.1 (M+H)+. 1H NMR (500 MHz, MeOD) δ 7.74 (t, J=7.6 Hz, 2H), 7.64-7.57 (m, 2H), 7.12 (t, J=6.8 Hz, 1H), 6.33 (dd, J=16.2, 7.3 Hz, 1H), 4.46 (d, J=12.6 Hz, 1H), 3.97 (d, J=12.5 Hz, 1H), 3.82 (d, J=12.1 Hz, 1H), 3.42-3.37 (m, 2H), 3.15 (s, 1H), 3.04-2.93 (m, 1H), 2.77-2.72 (m, 3H), 2.57 (dd, J=23.6, 12.7 Hz, 1H), 2.49-2.36 (m, 4H), 2.15-2.01 (m, 3H), 1.89 (dd, J=11.3, 5.8 Hz, 3H), 1.72-1.61 (m, 2H), 1.20-0.99 (m, 2H). Chiral SFC B (35% MeOH): ee 100%, Rt=1.27 min.

Compound 192-E2 LC/MS ESI 531.1 (M+H)+. 1H NMR (500 MHz, MeOD) δ 7.73 (s, 2H), 7.62-7.57 (m, 2H), 7.14 (d, J=7.7 Hz, 1H), 6.35 (t, J=6.7 Hz, 1H), 4.49 (s, 1H), 4.04 (d, J=13.9 Hz, 1H), 3.79 (d, J=5.7 Hz, 1H), 3.39 (dd, J=11.7, 6.0 Hz, 3H), 3.19 (s, 1H), 3.05 (s, 1H), 2.72 (t, J=6.1 Hz, 2H), 2.63-2.52 (m, 2H), 2.45 (t, J=7.6 Hz, 4H), 2.02 (s, 2H), 1.96 (s, 1H), 1.92-1.87 (m, 2H), 1.68 (d, J=16.6 Hz, 2H), 1.12 (s, 2H). Chiral SFC B (35% MeOH): ee 100%, Rt=4.19 min.

2-(3-(4-((5,6,7,8-tetrahydro-1,8-naphthyridin-2-yl)methyl)piperidine-1-carbonyl)azetidin-1-yl)-2-(4-(trifluoromethyl)phenyl)acetic acid (enantiomeric compounds 193-E1 and 193-E2)

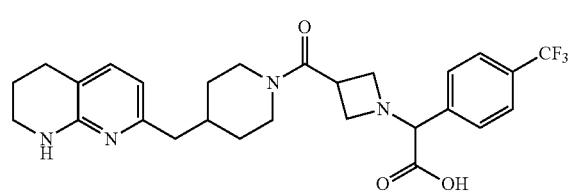 [SMILES: O=C(O)C(c1ccc(C(F)(F)F)cc1)N1CC(C(=O)N2CCC(Cc3ccc4c(n3)NCCC4)CC2)C1]

Compound 193-E1 LC/MS ESI 517.1 (M+H)+. 1H NMR (500 MHz, MeOD) δ 7.72 (dd, J=20.3, 8.1 Hz, 4H), 7.26 (d, J=6.2 Hz, 1H), 6.41 (d, J=7.2 Hz, 1H), 4.64 (s, 1H), 4.49 (d, J=13.1 Hz, 1H), 4.22 (s, 1H), 3.91 (d, J=67.7 Hz, 4H), 3.61 (d, J=12.8 Hz, 1H), 3.41 (s, 2H), 3.00 (t, J=13.1 Hz, 1H), 2.74 (t, J=6.2 Hz, 2H), 2.65 (t, J=11.7 Hz, 1H), 2.57-2.46 (m, 2H), 1.98-1.87 (m, 3H), 1.69 (d, J=10.7 Hz, 2H), 1.16 (d, J=11.3 Hz, 2H). Chiral SFC B (35% MeOH): ee 100%, Rt=0.93 min Compound 193-E2 LC/MS ESI 517.1 (M+H)+. 1H NMR (500 MHz, MeOD) δ 7.72 (dd, J=19.2, 8.2 Hz, 4H), 7.26 (s, 1H), 6.42 (d, J=7.3 Hz, 1H), 4.62 (s, 1H), 4.49 (d, J=13.0 Hz, 1H), 4.20 (s, 1H), 3.83 (s, 4H), 3.61 (d, J=13.8 Hz, 1H), 3.42 (s, 2H), 3.00 (t, J=13.0 Hz, 1H), 2.75 (t, J=6.2 Hz, 2H), 2.65 (t, J=11.7 Hz, 1H), 2.51 (d, J=7.0 Hz, 2H), 1.99-1.87 (m, 3H), 1.70 (s, 2H), 1.17 (d, J=11.8 Hz, 2H). Chiral SFC B (35% MeOH): ee 100%, Rt=3.78 min 2-((R)-3-(5-(5,6,7,8-tetrahydro-1,8-naphthyridin-2-yl)pentyloxy)pyrrolidin-1-yl)-2-(4-(trifluoromethyl)phenyl)acetic acid (Diastereomeric Compounds 194-E1 and 194-E2)

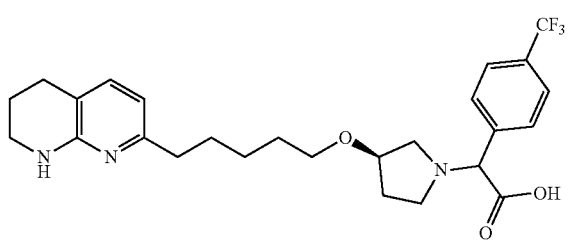 [SMILES: O=C(O)C(c1ccc(C(F)(F)F)cc1)N1CC[C@@H](OCCCCCc2ccc3c(n2)NCCC3)C1]

Compound 194-E1 LC/MS ESI 492.1 (M+H)+. 1H NMR (500 MHz, MeOD) δ 7.81-7.69 (m, 4H), 7.22 (d, J 7.3 Hz, 1H), 6.42 (d, J 7.3 Hz, 1H), 4.54 (s, 1H), 4.17 (s, 1H), 3.49-3.36 (m, 5H), 3.21 (s, 1H), 3.12 (s, 1H), 2.93 (s, 1H), 2.72 (t, J 6.2 Hz, 2H), 2.58 (t, J 7.8 Hz, 2H), 2.13-2.08 (m, 2H), 1.93-1.85 (m, 2H), 1.78-1.56 (m, 4H), 1.54-1.39 (m, 2H).
Compound 194-E2 LC/MS ESI 492.1 (M+H)+. 1H NMR (500 MHz, MeOD) δ 7.81-7.70 (m, 4H), 7.31 (d, J 7.1 Hz, 1H), 6.45 (d, J=7.2 Hz, 2H), 4.19-4.12 (m, 2H), 3.53-3.37 (m, 5H), 2.90 (s, 1H), 2.81-2.67 (m, 5H), 2.64-2.53 (m, 1H), 2.31-2.17 (m, 1H), 2.00-1.85 (m, 3H), 1.84-1.62 (m, 3H), 1.60-1.41 (m, 3H).

2-(3-chlorophenyl-2-((R)-3-(5-(5,6,7,8-tetrahydro-1,8-naphthridin-2-yl)pentyloxy)pyrrolidin-1-yl)acetic acid (Diastereomeric Compounds 195-E1 and 195-E2)

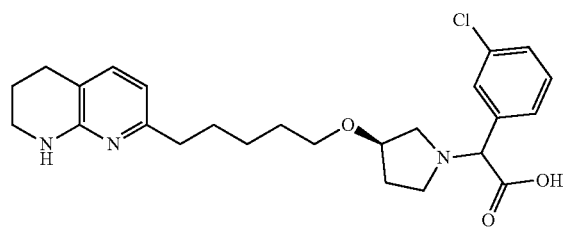 [SMILES: O=C(O)C(c1cccc(Cl)c1)N1CC[C@@H](OCCCCCc2ccc3c(n2)NCCC3)C1]

Compound 195-E1 LC/MS ESI 458.1 (M+H)+. 1H NMR (500 MHz, MeOD) δ 7.52 (s, 1H), 7.37 (dd, J=6.7, 1.9 Hz, 1H), 7.35-7.30 (m, 2H), 7.09 (d, J=7.3 Hz, 1H), 6.29 (d, J=7.3 Hz, 1H), 4.35 (s, 1H), 4.06 (s, 1H), 3.32 (ddd, J=29.1, 13.4, 8.3 Hz, 5H), 3.15 (d, J=9.0 Hz, 1H), 3.00 (d, J=12.2 Hz, 1H), 2.90-2.81 (m, 1H), 2.61 (t, J=6.2 Hz, 2H), 2.45 (t, J=7.7 Hz, 2H), 1.99 (dd, J=12.0, 8.5 Hz, 2H), 1.82-1.74 (m, 2H), 1.63-1.48 (m, 4H), 1.39-1.28 (m, 2H).
Compound 195-E2 LC/MS ESI 458.1 (M+H)+. 1H NMR (500 MHz, MeOD) δ 7.56 (s, 1H), 7.39 (dd, J=5.3, 2.4 Hz, 1H), 7.28 (dd, J=4.8, 1.4 Hz, 2H), 7.17 (d, J=7.4 Hz, 1H), 6.32 (d, J=7.3 Hz, 1H), 4.03 (d, J=17.6 Hz, 2H), 3.39-3.26 (m, 5H), 2.76 (d, J=65.3 Hz, 3H), 2.65-2.52 (m, 3H), 2.50-2.43 (m, 1H), 2.12 (dd, J=13.8, 6.8 Hz, 1H), 1.88 (s, 1H), 1.77 (dd, J=11.4, 6.1 Hz, 2H), 1.70-1.50 (m, 3H), 1.49-1.29 (m, 3H).

2-(2-ethylphenyl-2-((R)-3-(5-(5,6,7,8-tetrahydro-1,8-naphthridin-2-yl)pentyloxy)pyrrolidin-1-yl)acetic acid (Diastereomeric Compounds 196-E1 and 196-E2)

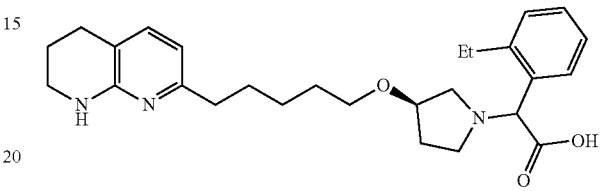

Compound 196-E1 LC/MS ESI 452.2.1 (M+H)+. 1H NMR (500 MHz, MeOD) δ 7.51 (d, J=7.7 Hz, 1H), 7.26-7.21 (m, 2H), 7.19-7.13 (m, 1H), 7.03 (d, J=7.3 Hz, 1H), 6.27 (d, J=7.3 Hz, 1H), 4.11 (s, 1H), 3.51-3.36 (m, 3H), 3.31-3.26 (m, 2H), 3.16 (d, J=12.6 Hz, 1H), 2.94 (s, 2H), 2.76 (ddd, J=14.9, 7.4, 2.9 Hz, 2H), 2.60 (t, J=6.3 Hz, 2H), 2.44 (t, J=7.5 Hz, 2H), 2.07-1.90 (m, 2H), 1.78 (dt, J=12.3, 6.2 Hz, 2H), 1.60-1.32 (m, 7H), 1.23 (t, J=7.6 Hz, 3H).
Compound 196-E2 LC/MS ESI 452.2.1 (M+H)+. 1H NMR (500 MHz, MeOD) δ 7.56 (d, J=7.8 Hz, 1H), 7.22 (q, J=5.2 Hz, 2H), 7.18-7.14 (m, 1H), 7.07 (d, J=7.3 Hz, 1H), 6.28 (d, J=7.3 Hz, 1H), 4.67 (s, 1H), 4.05 (s, 1H), 3.43-3.26 (m, 5H), 3.15-3.00 (m, 3H), 2.79 (ddt, J=22.1, 14.7, 7.3 Hz, 2H), 2.61 (t, J=6.3 Hz, 2H), 2.50-2.41 (m, 2H), 2.05 (s, 2H), 1.82-1.75 (m, 2H), 1.63-1.46 (m, 4H), 1.35 (dd, J=14.7, 8.2 Hz, 2H), 1.22 (t, J=7.6 Hz, 3H).

2-(2-methoxyphenyl)-2-((R)-3-(5-(5,6,7,8-tetrahydro-1,8-naphthridin-2-yl)pentyloxy)pyrrolidin-1-yl)acetic acid (Diastereomeric Compounds 197-E1 and 197-E2)

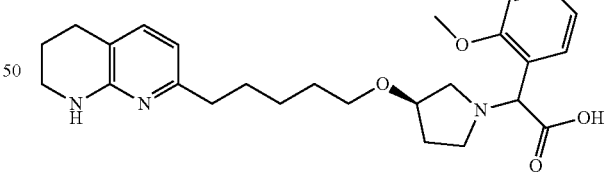

Compound 197-E1 LC/MS ESI 454.2.1 (M+H)+. 1H NMR (500 MHz, MeOD) δ 7.41 (d, J=7.3 Hz, 1H), 7.35 (ddd, J=8.4, 7.5, 1.7 Hz, 1H), 7.03 (dd, J=13.5, 7.7 Hz, 2H), 6.97-6.93 (m, 1H), 6.29 (d, J=7.3 Hz, 1H), 4.94 (s, 1H), 4.10 (s, 1H), 3.82 (d, J=4.0 Hz, 3H), 3.54-3.28 (m, 5H), 3.17 (d, J=13.0 Hz, 1H), 3.00 (ddd, J=11.5, 8.1, 3.5 Hz, 1H), 2.61 (t, J=6.3 Hz, 2H), 2.45 (dd, J=8.2, 6.3 Hz, 2H), 2.07-1.93 (m, 2H), 1.83-1.75 (m, 2H), 1.58 (ddd, J=14.0, 12.9, 7.5 Hz, 4H), 1.39-1.30 (m, 2H)). Chiral SFC F (45% EtOH): ee 100%, Rt=2.41 min.
Compound 197-E2 LC/MS ESI 454.2.1 (M+H)+. 1H NMR (500 MHz, MeOD) δ 7.45 (d, J=7.5 Hz, 1H), 7.36-

7.29 (m, 1H), 7.06 (d, J=7.3 Hz, 1H), 7.01 (d, J=8.2 Hz, 1H), 6.93 (t, J=7.5 Hz, 1H), 6.29 (d, J=7.3 Hz, 1H), 4.87 (s, 1H), 4.07 (s, 1H), 3.80 (d, J=10.1 Hz, 3H), 3.48-3.26 (m, 6H), 3.17-3.05 (m, 2H), 2.61 (t, J=6.2 Hz, 2H), 2.50-2.41 (m, 2H), 2.14-1.97 (m, 2H), 1.82-1.76 (m, 2H), 1.62-1.46 (m, 4H), 1.40-1.28 (m, 2H). Chiral SFC F (45% EtOH): ee 99%, Rt=3.8 min.

2-(2-ethylphenyl)-2-(3-(4-(5,6,7,8-tetrahydro-1,8-naphthyridin-2-yl)butoxy)azetidin-1-yl)acetic acid (Enantiomeric Compounds 198-E1 and 198-E2)

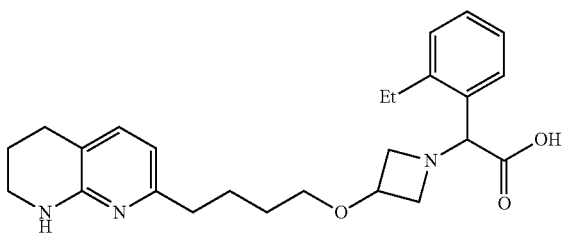 [SMILES: CCc1ccccc1C(C(=O)O)N1CC(OCCCCc2ccc3c(n2)NCCC3)C1]

Compound 198-E1 LC/MS ESI 424.1 (M+H)⁺. ¹H NMR (500 MHz, MeOD) δ 7.43 (d, J=7.7 Hz, 1H), 7.32 (dd, J=7.3, 5.5 Hz, 2H), 7.26-7.21 (m, 1H), 7.17 (d, J=7.3 Hz, 1H), 6.39 (d, J=7.3 Hz, 1H), 5.01 (s, 1H), 4.29 (d, J=4.8 Hz, 2H), 3.97 (s, 1H), 3.81 (s, 1H), 3.62 (s, 1H), 3.46-3.40 (m, 4H), 2.97-2.92 (m, 2H), 2.72 (t, J=6.2 Hz, 2H), 2.56 (t, J=7.6 Hz, 2H), 1.92-1.86 (m, 2H), 1.76-1.70 (m, 2H), 1.64-1.57 (m, 2H), 1.34 (t, J=7.6 Hz, 3H). Chiral HPLC K (50% EtOH): ee 100%, Rt=5.40 min.

Compound 198-E2 LC/MS ESI 424.1 (M+H)⁺. ¹H NMR (500 MHz, MeOD) δ 7.44 (d, J=7.8 Hz, 1H), 7.34-7.28 (m, 2H), 7.25-7.16 (m, 2H), 6.39 (d, J=7.3 Hz, 1H), 4.99 (s, 1H), 4.28 (d, J=5.2 Hz, 2H), 3.95 (s, 1H), 3.76 (d, J=4.8 Hz, 1H), 3.56 (d, J=9.5 Hz, 1H), 3.45-3.40 (m, 4H), 2.96-2.90 (m, 2H), 2.71 (t, J=6.2 Hz, 2H), 2.56 (t, J=7.6 Hz, 2H), 1.91-1.83 (m, 2H), 1.75-1.65 (m, 2H), 1.64-1.54 (m, 2H), 1.34 (t, J=7.6 Hz, 3H). Chiral HPLC K (50% EtOH): ee 100%, Rt=7.56 min.

2-(2-ethyl-4-fluorophenyl)-2-(3-(4-(5,6,7,8-tetrahydro-1,8-naphthyridin-2-yl)butoxy)azetidin-1-yl) acetic acid (Enantiomeric Compounds 199-E1 and 199-E2)

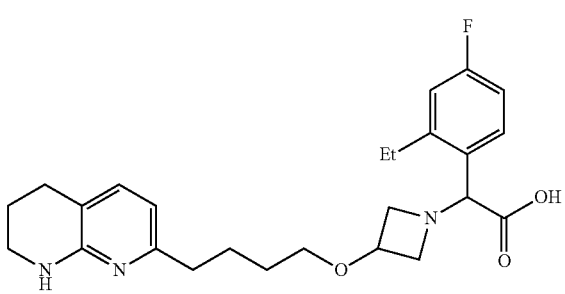 [SMILES: CCc1cc(F)ccc1C(C(=O)O)N1CC(OCCCCc2ccc3c(n2)NCCC3)C1]

Compound 199-E1 LC/MS ESI 442.3 (M+H)⁺. ¹H NMR (500 MHz, MeOD) δ 7.47 (dd, J=8.5, 5.9 Hz, 1H), 7.18 (d, J=7.3 Hz, 1H), 7.06 (dd, J=10.2, 2.4 Hz, 1H), 6.99-6.91 (m, 1H), 6.39 (d, J=7.3 Hz, 1H), 4.87 (s, 1H), 4.30-4.17 (m, 2H), 3.89 (s, 1H), 3.69 (d, J=5.4 Hz, 1H), 3.52 (s, 1H), 3.45-3.40 (m, 4H), 2.95-2.90 (m, 2H), 2.71 (t, J=6.2 Hz, 2H), 2.56 (t, J=7.6 Hz, 2H), 1.91-1.84 (m, 2H), 1.75-1.67 (m, 2H), 1.62-1.55 (m, 2H), 1.33 (t, J=7.5 Hz, 3H). Chiral SFC B (20% MeOH): ee 100%, Rt=1.96 min Compound 199-E2 LC/MS ESI 442.3 (M+H)⁺. ¹H NMR (500 MHz, MeOD) δ 7.49 (dd, J=8.5, 5.9 Hz, 1H), 7.20 (d, J=7.3 Hz, 1H), 7.08 (dd, J=10.2, 2.4 Hz, 1H), 7.01-6.91 (m, 1H), 6.39 (d, J=7.3 Hz, 1H), 4.89 (s, 1H), 4.35-4.19 (m, 2H), 3.90 (s, 1H), 3.72 (d, J=5.4 Hz, 1H), 3.52 (s, 1H), 3.45-3.42 (m, 4H), 2.98-2.90 (m, 2H), 2.74 (t, J=6.2 Hz, 2H), 2.57 (t, J=7.6 Hz, 2H), 1.93-1.84 (m, 2H), 1.79-1.67 (m, 2H), 1.68-1.55 (m, 2H), 1.35 (t, J=7.5 Hz, 3H). Chiral SFC B (20% MeOH): ee 100%, Rt=3.19 min.

2-(2-ethylphenyl)-2-(3-(5-(5,6,7,8-tetrahydro-1,8-naphthridin-2-yl)pentyloxy)azetidin-1-yl)acetic acid (Enantiomeric Compounds 200-E1 and 200-E2)

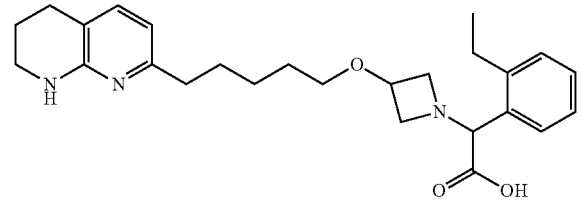 [SMILES: CCc1ccccc1C(C(=O)O)N1CC(OCCCCCc2ccc3c(n2)NCCC3)C1]

Compound 200-E1 LC/MS ESI 438.3 (M+H)⁺. 1H NMR (500 MHz, MeOD) δ 7.33 (d, J=7.7 Hz, 1H), 7.28-7.24 (m, 2H), 7.18-7.14 (m, 1H), 7.06 (d, J=7.3 Hz, 1H), 6.28 (d, J=7.3 Hz, 1H), 4.98 (s, 1H), 4.23 (s, 2H), 3.93 (s, 1H), 3.76 (s, 1H), 3.60 (s, 1H), 3.37-3.32 (m, 2H), 3.32-3.29 (m, 2H), 2.90-2.82 (m, 2H), 2.62 (d, J=6.2 Hz, 2H), 2.44 (t, J=7.6 Hz, 2H), 1.83-1.77 (m, 2H), 1.61-1.51 (m, 4H), 1.37-1.32 (m, 2H), 1.27 (t, J=7.6 Hz, 3H). Chiral SFC F (60% MeOH): ee 100%, Rt=2.96 min.

Compound 200-E2 LC/MS ESI 438.3 (M+H)⁺. 1H NMR (500 MHz, MeOD) δ 7.33 (d, J=7.7 Hz, 1H), 7.28-7.24 (m, 2H), 7.18-7.13 (m, 1H), 7.06 (d, J=7.3 Hz, 1H), 6.28 (d, J=7.3 Hz, 1H), 4.97 (s, 1H), 4.22 (dd, J=11.2, 5.7 Hz, 2H), 3.93 (d, J=10.4 Hz, 1H), 3.75 (d, J=6.4 Hz, 1H), 3.59 (d, J=10.6 Hz, 1H), 3.38-3.27 (m, 4H), 2.84 (dq, J=22.2, 7.4 Hz, 2H), 2.62 (t, J=6.3 Hz, 2H), 2.44 (t, J=7.7 Hz, 2H), 1.84-1.76 (m, 2H), 1.60-1.49 (m, 4H), 1.33 (dd, J=15.4, 8.2 Hz, 2H), 1.27 (t, J=7.6 Hz, 3H). Chiral SFC F (60% MeOH): ee 98%, Rt=4.89 min.

2-((R)-3-(methyl(5-(5,6,7,8-tetrahydro-1,8-naphthyridin-2-yl)pentyl)amino)pyrrolidin-1-yl)-2-phenylacetic acid (Diastereomeric Compounds 201-E1 and 201-E2)

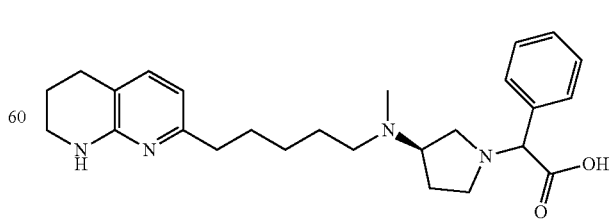

Compound 201-E1 LC/MS ESI 437.1 (M+H)⁺. ¹H NMR (500 MHz, MeOD) δ 7.53 (d, J=6.6 Hz, 2H), 7.37-7.30 (m, 3H), 7.17 (d, J=7.3 Hz, 1H), 6.39 (d, J=7.3 Hz, 1H), 4.05 (s, 1H), 3.48-3.42 (m, 1H), 3.41-3.37 (m, 2H), 3.19 (s, 1H), 2.91 (s, 1H), 2.78 (d, J=6.8 Hz, 2H), 2.71 (dd, J=16.2, 10.0 Hz, 3H), 2.62-2.49 (m, 6H), 2.16 (dd, J=13.3, 5.1 Hz, 1H), 2.00 (dd, J=13.5, 5.9 Hz, 1H), 1.92-1.86 (m, 2H), 1.71-1.59 (m, 4H), 1.38 (dt, J=14.2, 7.3 Hz, 2H).

Compound 201-E2 LC/MS ESI 437.1 (M+H)$^+$. $^1$H NMR (500 MHz, MeOD) δ 7.55 (d, J=6.5 Hz, 2H), 7.39-7.31 (m, 3H), 7.19 (d, J=7.3 Hz, 1H), 6.39 (d, J=7.3 Hz, 1H), 4.05 (s, 1H), 3.43 (d, J=6.3 Hz, 1H), 3.40-3.36 (m, 2H), 3.19 (s, 1H), 2.79 (s, 4H), 2.72 (t, J=6.2 Hz, 2H), 2.65-2.59 (m, 1H), 2.56 (t, J=7.7 Hz, 2H), 2.46 (s, 3H), 2.13 (dd, J=13.3, 7.7 Hz, 1H), 1.96-1.85 (m, 3H), 1.74-1.56 (m, 4H), 1.41 (p, J=7.4 Hz, 2H).

Example 34: Fluorescence Polarization Assays of Compounds for αvβ6 Binding

Fluorescence Polarization (FP) assays were used to measure compound activity through binding competition with the fluorescein-labeled peptide GRGDLGRL. In the assay, 10 nM of integrin αvβ6 was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. The assays were run in 384-well plates. For both assay versions, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. IC$_{50}$ values were determined by nonlinear regression, 4-parameter curve fitting (FIG. 1).

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound of formula (I):

A-B—C    (I)

wherein:
A is

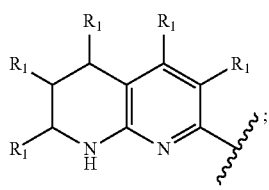

B is -alkylene-C(O)N(R)—;

C is

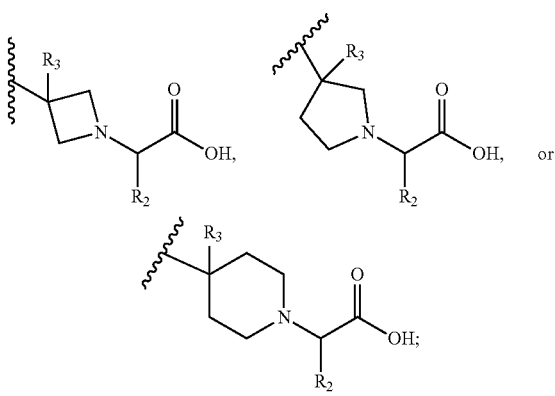

R is H;
R$_1$ is H;
R$_2$ is H, alkyl, substituted or unsubstituted aryl, substituted or unsubstituted heteroaryl, cycloalkyl, -alkylene-alkoxy, alkylene-aryl, or heterocycloalkyl; and
R$_3$ is H;
or a pharmaceutically acceptable salt thereof.

2. The compound of claim 1, wherein R$_2$ is H, (C$_1$-C$_4$) alkyl, cyclopropyl, CH$_2$OMe, phenyl, —CH$_2$Ph, pyridinyl, or indolyl.

3. The compound of claim 1, wherein R$_2$ is unsubstituted phenyl.

4. The compound of claim 1, wherein R$_2$ is substituted phenyl.

5. The compound of claim 4, wherein the substituted phenyl is substituted with one or more independent instances of alkoxy, OH, halide, —N(H)C(O)alkyl, —C(O)NH$_2$, or —C(O)alkyl.

6. The compound of claim 5, wherein the substituted phenyl is substituted with at least one halide.

7. The compound of claim 6, wherein the halide is Cl.

8. The compound of claim 1, wherein the compound is selected from the group consisting of:

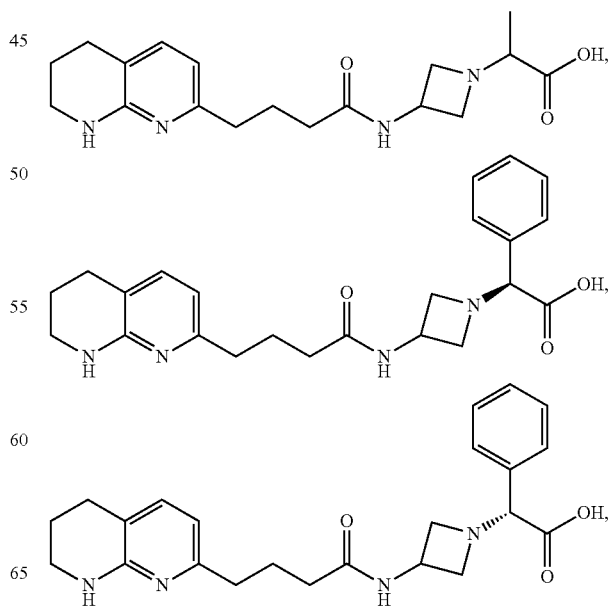

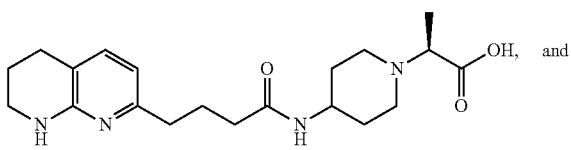
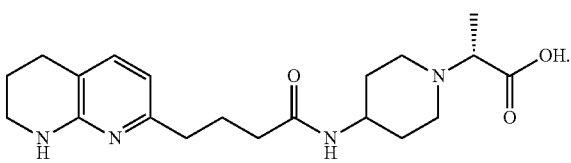
9. The compound of claim 1, wherein the compound is:
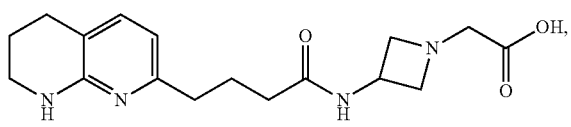
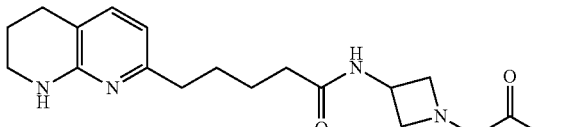
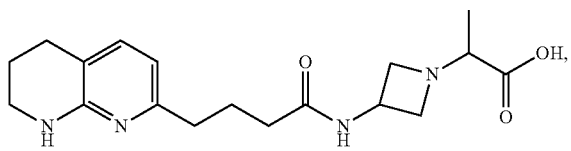
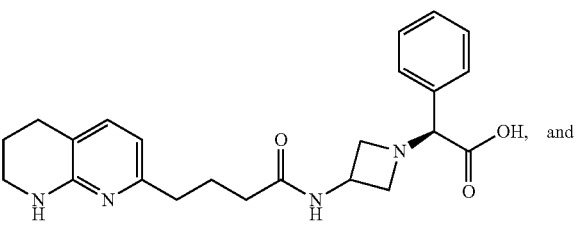
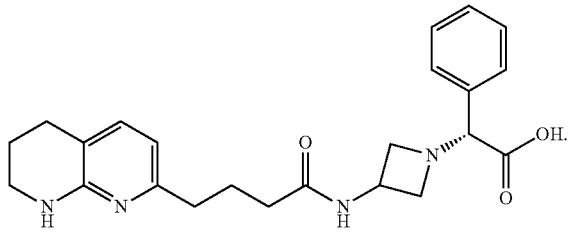 [SMILES: O=C(CCCc1ccc2c(n1)NCCC2)NC1CN([C@@H](C(=O)O)c2ccccc2)C1]
10. The compound of claim 1, wherein the compound is selected from the group consisting of:
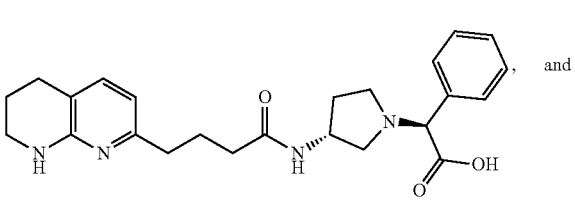
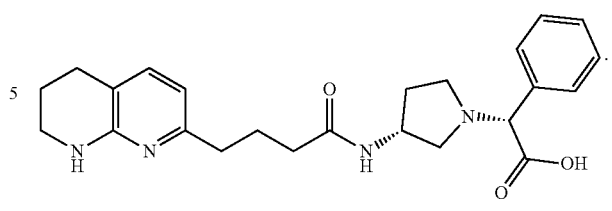
11. The compound of claim 1, wherein the compound is:
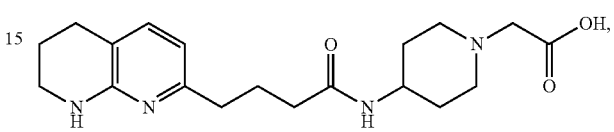
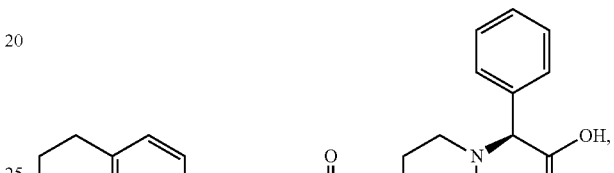
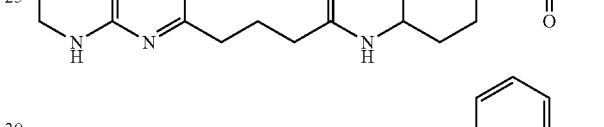
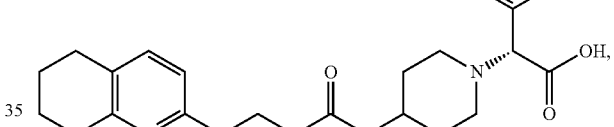
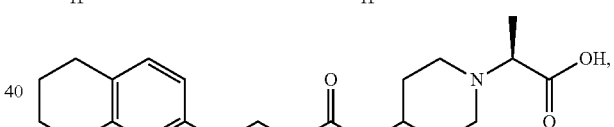
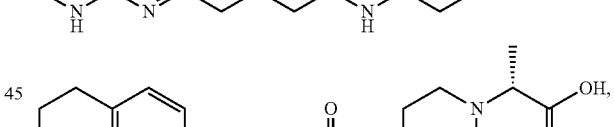
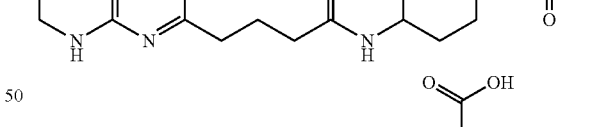
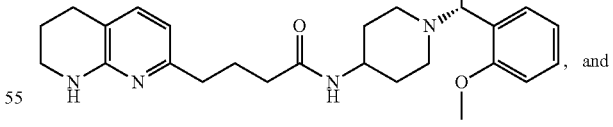
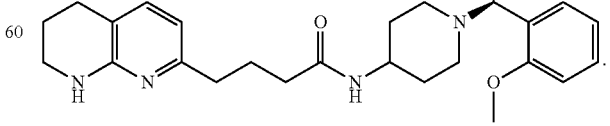
12. The compound of claim 1, wherein the compound is selected from the group:

13. The compound of claim 1, wherein the compound is:

14. The compound of claim 1, wherein
a. alkylene in B is n-propyl or n-butyl; and
b. R₂ is selected from unsubstituted phenyl, or phenyl substituted with one or more of alkoxy, alkyl, cycloalkyl, or halide.

15. The compound of claim 1, wherein R₂ is H.

16. The compound of claim 1, wherein the compound is:

17. The compound of claim 1, wherein the compound is:

18. The compound of claim 1, wherein R₂ is selected from H, Me, unsubstituted phenyl, or phenyl substituted with one or more of alkoxy, alkyl, cycloalkyl, or halide.

19. The compound of claim 1, wherein R₂ is H, alkyl, substituted or unsubstituted aryl, or substituted or unsubstituted heteroaryl.

20. The compound of claim 1, wherein R₂ is selected from H, Me, unsubstituted phenyl, or phenyl substituted with one or more of methoxy, methyl, cyclopropyl, or halide.

21. The compound of claim 1, wherein alkylene in B is propyl or butyl.

22. The compound of claim 1, wherein alkylene in B is n-propyl or n-butyl.

23. The compound of claim 1, wherein C is

24. The compound of claim 23, wherein R₂ is H, alkyl, or aryl.

25. The compound of claim 24, wherein alkylene in B is propyl or butyl.

26. The compound of claim 24, wherein R₂ is H, methyl or unsubstituted phenyl and alkylene in B is n-propyl or n-butyl.

27. The compound of claim 1, wherein alkylene in B is n-propyl or n-butyl.

28. The compound of claim 1, wherein C is

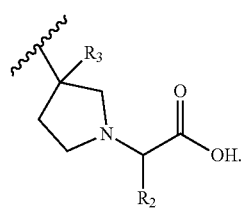

29. The compound of claim 28, wherein $R_2$ is H, alkyl, or aryl.

30. The compound of claim 28, wherein $R_2$ is unsubstituted phenyl and alkylene in B is n-propyl or n-butyl.

31. The compound of claim 1, wherein C is

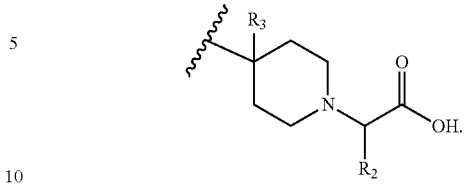

32. The compound of claim 31, wherein $R_2$ is H, alkyl, or aryl.

33. The compound of claim 32, wherein alkylene in B is propyl or butyl.

34. The compound of claim 31, wherein $R_2$ is unsubstituted phenyl or phenyl substituted with alkoxy, alkyl or halogen, and the alkylene in B is n-propyl or n-butyl.

35. The compound of claim 34, wherein $R_2$ is unsubstituted phenyl or phenyl substituted with methoxy, and alkylene in B is n-propyl.

* * * * *